United States Patent
Cheetham et al.

(10) Patent No.: US 8,124,392 B2
(45) Date of Patent: *Feb. 28, 2012

(54) CRYSTAL STRUCTURE OF AURORA-2 PROTEIN AND BINDING POCKETS THEREOF

(75) Inventors: Graham Cheetham, Abingdon (GB); Ronald Knegtel, Abingdon (GB); Lovorka Swenson, Belmont, MA (US); Joyce T. Coll, Westborough, MA (US); Suzanne Renwick, Sunbury on Thames (GB); Peter Weber, Abingdon (GB)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/890,826

(22) Filed: Sep. 27, 2010

(65) Prior Publication Data

US 2011/0104782 A1 May 5, 2011

Related U.S. Application Data

(60) Division of application No. 12/070,054, filed on Feb. 13, 2008, now Pat. No. 7,809,541, which is a division of application No. 10/979,375, filed on Nov. 1, 2004, now Pat. No. 7,361,492, which is a continuation of application No. PCT/US03/13605, filed on May 1, 2003.

(60) Provisional application No. 60/377,510, filed on May 1, 2002.

(51) Int. Cl.
*C12N 9/12* (2006.01)
*G01N 31/00* (2006.01)

(52) U.S. Cl. .......................... 435/194; 436/4
(58) Field of Classification Search .................. None
See application file for complete search history.

(56) References Cited

U.S. PATENT DOCUMENTS

| | | | |
|---|---|---|---|
| 4,886,646 | A | 12/1989 | Carter et al. |
| 5,096,676 | A | 3/1992 | McPherson et al. |
| 5,130,105 | A | 7/1992 | Carter et al. |
| 5,221,410 | A | 6/1993 | Kushner |
| 5,400,741 | A | 3/1995 | DeTitta et al. |
| 5,884,230 | A | 3/1999 | Srinivasan et al. |
| 7,214,518 | B2 | 5/2007 | Anderson et al. |

FOREIGN PATENT DOCUMENTS

| WO | WO 02/22602 | 3/2002 |
|---|---|---|
| WO | WO 03/031606 | 4/2003 |

OTHER PUBLICATIONS

Owen et al., "Two structures of the catalytic domain of phosphorylase kinase: an active protein kinase complexed with substrate analogue and product.", Structure 1995, 3:467-482.*

DaliLite v.3 Results—Run on May 13, 2011 < http://ekhidna.biocenter.helsinki.fi/dali_server/results/20110513-0110-60ff9fa378b6de85e1c797b6922f4b75/index. html >.*

Appendix A—Figure of 1 MUD VS. 1 FIN. Created in Swis-spdbviewer, v. 3.7 with the output files from DaliLite. No date.

Appendix B—Figure of 1 MUO vs. 1 JST. Created in Swis-spdbviewer, v. 3.7 with the output files from DaliLite. No date.

Balbes et al., "A Perspective of Modern Methods in Computer-Aided Drug Design", *Rev. in Comp. Chem.*, 5: 337-379 (1994).

Bartlett et al., "Caveat: A Program to Facilitate the Structure-Derived Design of Biologically Active Molecules", *Mol. Recog. in Chem. and Biol. Prob.*, 78: 182-196 (1989).

Bayliss, et al., "Structural Basis of Aurora-A Activation by TPX2 at the Mitotic Spindle", *Mol. Cell*, 12: 851-862 (2003).

Bellon, et al., "The Structure of Phosphorylated P38γ is Monomeric and Reveals a Conserved Activation-Loop Conformation", *Structure*, 7: 1057-1065 (1999).

Blundell et al., "Knowledge-Based Prediction of Protein Structures and the Design of Novel Molecules", *Nature*, 326: 347-352 (1987).

Böhm, "The Computer Program LUDI: A New Method for the De Novo Design of Enzyme Inhibitors", *J. Comp. Aid. Molec. Design*, 6: 61-78 (1992).

Brown, et al., "Effects of Phosphorylation of Threonine 160 on Cyclin-Dependent Kinase 2 Structure and Activity", *J. Biol. Chem.*, 274: 8746-8756 (1999).

Brönger et al.,"Crystallography & NMR System: A New Software Suite for Macromolecular Structure Determination", *Acta Cryst.*, D54: 905-921 (1998).

Carson, "Ribbons 2.0", *J. Appl. Cryst.*, 24: 958-961 (1991).

Chayen, "A Novel Technique to Control the Rate of Vapour Diffusion, Giving Larger Protein Crystals", *J. Appl. Cryst.*, 30: 198-202 (1997).

Chayen, "The Role of Oil in Macromolecular Crystallization", *Structure*, 5: 1269-1274 (1997).

Chayen, "Comparative Studies of Protein Crystallization by Vapour-Diffusion and Microbatch Techniques", *Acta Cryst.*, D54: 8-15 (1998).

Cheetam et al., "Crystal Structure of Aurora-2, an Oncogenic Serine/Threonine Kinase", *J. Biol. Chem.*, 277: 42419-42422 (2002).

Cohen et al., "Molecular Modeling Software and Methods for Medicinal Chemistry", *J. Med. Chem*, 33: 883-894 (1990).

DaliLite (www.ebi.ac.uk/dali/) Results of Structure Comparison, 1 MUO vs. 1 FIN. No date.

(Continued)

*Primary Examiner* — Suzanne M Noakes
(74) *Attorney, Agent, or Firm* — Ropes & Gray LLP; James F. Haley, Jr.; Raymond M. Doss

(57) ABSTRACT

The present invention provides crystalline molecules or molecular complexes which comprise binding pockets of Aurora-2 or its homologues. The invention also provides crystals comprising Aurora-2. The present invention also relates to a computer comprising a data storage medium encoded with the structural coordinates of Aurora-2 binding pockets and methods of using a computer to evaluate the ability of a compound to bind to the molecule or molecular complex. This invention also provides methods of using the structure coordinates to solve the structure of homologous proteins or protein complexes. In addition, this invention provides methods of using the structure coordinates to screen for and design compounds, including inhibitory compounds, that bind to Aurora-2 or homologues thereof.

4 Claims, 141 Drawing Sheets

OTHER PUBLICATIONS

DaliLite (www.ebi.ac.uk/dali/) Results of Structure Comparison, 1 MUO vs. 1JST. No date.
D'Arcy et al., "A Novel Approach to Crystallising Proteins Under Oil", *J. Cryst. Growth*, 168: 175-180 (1996).
Drenth, "Principles of Protein X-Ray Crystallography", 2nd Edition, 1999 Springer-Verlag New York Inc., Chapter 1, p. 1-21.
Eisen et al., "Hook: a Program for Finding Novel Molecular Architectures that Satisfy the Chemical and Steric Requirements of a Macromolecule Binding Site", *Proteins Struct. Funct. Genet.*, 19: 199-221 (1994).
Fetrow et al., "New Programs for Protein Tertiary Structure Prediction", *Bio/Technology*, 11: 479-484 (1993).
Fox et al., "A Single Amino Acid Substitution Makes ERK2 Susceptible to Pyridinyl Imidazole Inhibitors of p38 MAP Kinase" *Protein Sci.*, 7: 2249-2255 (1998).
Gerstein et al., "Average Core Structures and Variability Measures for Protein Families: Application to the Immunoglobulins", *J. Mol. Biol.*, 251: 161-175 (1995).
Giege et al. Crystallogenesis of Biological Macromolecules: Facts and Perspectives, Acta Cryst., D50:339-350 (1994).
Giet et al., "Aurora/Ipl1p-Related Kinases, a New Oncogenic Family of Mitotic Serine-Threonine Kinases", *J. Cell Science*, 112: 3591-3601 (1999).
Gillet et al., "Sprout: A Program for Structure Generation", *J. Comp. Aid. Molec. Design*, 7: 127-153 (1993).
Goepfert et al., "The Centrosome-Associated Aurora/Ipl-Like Kinase Family", *Curr. Top. Dev. Biol.*, 49: 331-342 (2000).
Goodford, "A Computational Procedure for Determining Energetically Favorable Binding Sites on Biologically Important Macromolecules", *J. Med. Chem.*, 28: 849-857 (1985).
Goodsell et al., "Automated Docking of Substrates to Proteins by Simulated Annealing", *Proteins Struct. Funct. Genet.*, 8: 195-202 (1990).
Greer, "Comparative Modeling of Homologous Proteins", *Methods in Enzymol.*, 202: 239-253 (1991).
Guex et al., "Swiss-Model and the SwissPdb Viewer: An Environment for Comparative Protein Modeling", Electrophoresis, 18: 2714-2723 (1997).
Guida, "Software for Structure-Based Drug Design", *Curr. Opin. Struct. Biol.*, 4: 777-781 (1994).
Hanks et al., "The Protein Kinase Family: Conserved Features and Deduced Phylogeny of the Catalytic Domains", *Science*, 241: 42-52 (1988).
Hanks et al., "Protein Kinase Catalytic Domain Sequence Database: Identification of Conserved Features of Primary Structure and Classification of Family Members", *Methods in Enzymol.*, 200: 38-62 (1991).
Higgins et al., "Using Clustal for Multiple Sequence Alignments", *Methods in Enzymol.*, 266: 383-402 (1996).
Jeffrey et al., Mechanism of CDK Activation Revealed by the Structure of a Cyclin A-CDK *Complex. Nature.*, 376:313-320. (1995).
Johnson Et al., "Knowledge-Based Protein Modeling", *Crit. Rev. Biochem. Mol. Biol.*, 29: 1-68 (1994).
Jones et al., "Improved Methods for Building Protein Models in Electron Density Maps and the Location of Errors in these Models", *Acta Cryst.*, A47: 110-119 (1991).
Kuntz et al., "A Geometric Approach to Macromolecule-Ligand Interactions", *J. Mol. Biol.*, 161: 269-288 (1982).
Kundrot, "Which Strategy for a Protein Crystallization Project?," Cellular Molecular Life Science, 61:525-536 (2004).
Lattman, "Use of the Rotation and Translation Functions", *Methods in Enzymol.*, 115: 55-77 (1985).
Lauri et al., "Caveat: A Program to Facilitate the Design of Organic Molecules", *J. Comput. Aided Mol. Des.*, 8: 51-66 (1994).
Leslie, "Integration of Macromolecular Diffraction Data", *Acta Cryst.*, D55: 1696-1702 (1999).
Martin, "3D Database Searching in Drug Design", *J. Med. Chem.*, 35: 2145-2154 (1992).
Mcpherson, "A. Current Approaches to Macromolecular Crystallization, " European Journal of Biochemistry, 189:1-23 (1990).
Meng et al., "Automated Docking with Grid-Based Energy Evaluation", J. Comp. Chem., 13: 505-524 (1992).
Miranker et al., "Functionality Maps of Binding Sites: A Multiple Copy Simultaneous Search Method", *Proteins Struct. Funct. Genet.*, 11: 29-34 (1991).
Miyoshi et al., "Association of Centrosomal Kinase *STK15/BTAK* MRNA Expression with Chromosomal Instability in Human Breast Cancers", *Int. J. Cancer*, 92: 370-373 (2001).
Navaza, "*AmoRe*: An Automated Package for Molecular Replacement" *Acta Cryst.*, A50: 157-163 (1994).
Navia et al., "Use of Structural Information in Drug Design", *Curr. Opin. Struct. Biol.*, 2: 202-210 (1992).
Nishibata et al., "Automatic Creation of Drug Candidate Structures Based on Receptor Structure. Starting Point for Artificial Lead Generation", *Tetrahedron*, 47: 8985-8990 (1991).
Nowakowski et al., "Structures of the Cancer-Related Aurora-A, FAK, and EphA2 Protein Kinases from Nanovolume Crystallography", *Structure*, 10: 1659-1667 (2002).
Pay et al., "Microtube Batch Protein Crystallization: Applications to Human Immunodeficiency Virus Type 2 (HIV-2) Protease and Human Renin", *Proteins Struct. Funct. Genet.*, 20: 98-102 (1994).
Schnare et al., "Comprehensive Comparison of Structural Characteristics in Eukaryotic Cytoplasmic Large Subunit (23 S-like) Ribosomal RNA", *J. Mol. Biol.*, 256: 701-719 (1996).
Russo et al., Structural Basis of Cyclin-Dependent Kinase Activation by Phosphorylation, Nature Structure Biology, 3(8):696-700 (1996).
Smith et al., "Comparison of Biosequences", *Adv. in App. Math.*, 2: 482-489 (1981).
Szklarz et al., "Use of Homology Modeling in Conjunction with Site-Directed Mutagenesis for Analysis of Structure-Function Relationships of Mammalian Cytochromes P450", *Life Sci.*, 61: 2507-2520 (1997).
Tainer et al., "The Reactivity of Anti-Peptide Antibodies is a Function of the Atomic Mobility of Sites in a Protein", *Nature*, 312: 127-134 (1984).
Ter Haar et al., "Structure of GSKβ Reveals a Primed Phosphorylation Mechanism" *Nat. Struct. Biol.* 8: 593-596 (2001).
Wang et al., "The Structure of Mitogen-Activated Protein Kinase p38 at 2.1-Å Resolution", *Proc. Natl. Acad. Sci. USA*, 94: 2327-2332 (1997).
Weber, "Overview of Crystallization Methods," Methods in Enzymology, 276:13-22 (1997).
Wilson et al., "Crystal Structure of P38 Mitogen-Activated Protein Kinase", *J. Biol. Chem.*, 271: 27696-27700 (1996).
Wishart et al., "Constrained Multiple Sequence Alignment Using Xalign", *Comput. Appl. Biosci.*, 10: 687-688 (1994).
Xie et al., "Crystal Structure of JNK3: A Kinase Implicated in Neuronal Apoptosis" *Structure*, 6: 983-991 (1998).
Zhang et al., "Atomic Structure of the MAP Kinase ERK2 at 2.3 Å Resolution", *Nature*, 367: 704-711 (1994).
"The *CCP4* Suite: Programs for Protein Crystallography", Collaborative Computational Project, No. 4, *Acta. Cryst.*, D50: 760-763 (1994).

* cited by examiner

Figure 1A

| Atom | Type | Resid | # | X | Y | Z | Occ | B | Mol | |
|---|---|---|---|---|---|---|---|---|---|---|
| ATOM | 1 | CB | GLN A 127 | 0.325 | 21.296 | 18.772 | 1.00 | 127.88 | A | C |
| ATOM | 2 | CG | GLN A 127 | -1.046 | 21.256 | 19.422 | 1.00 | 128.33 | A | C |
| ATOM | 3 | CD | GLN A 127 | -1.726 | 22.612 | 19.427 | 1.00 | 128.40 | A | C |
| ATOM | 4 | OE1 | GLN A 127 | -2.899 | 22.730 | 19.780 | 1.00 | 127.91 | A | O |
| ATOM | 5 | NE2 | GLN A 127 | -0.990 | 23.647 | 19.034 | 1.00 | 127.78 | A | N |
| ATOM | 6 | C | GLN A 127 | 2.235 | 20.064 | 17.748 | 1.00 | 125.78 | A | C |
| ATOM | 7 | O | GLN A 127 | 2.597 | 19.151 | 17.005 | 1.00 | 125.94 | A | O |
| ATOM | 8 | N | GLN A 127 | 1.319 | 19.351 | 19.941 | 1.00 | 126.48 | A | N |
| ATOM | 9 | CA | GLN A 127 | 0.982 | 19.925 | 18.604 | 1.00 | 127.22 | A | C |
| ATOM | 10 | N | TRP A 128 | 2.876 | 21.224 | 17.851 | 1.00 | 122.47 | A | N |
| ATOM | 11 | CA | TRP A 128 | 4.112 | 21.520 | 17.137 | 1.00 | 116.88 | A | C |
| ATOM | 12 | CB | TRP A 128 | 5.143 | 20.425 | 17.416 | 1.00 | 115.02 | A | C |
| ATOM | 13 | CG | TRP A 128 | 5.203 | 20.045 | 18.870 | 1.00 | 113.98 | A | C |
| ATOM | 14 | CD2 | TRP A 128 | 4.931 | 20.893 | 19.998 | 1.00 | 114.80 | A | C |
| ATOM | 15 | CE2 | TRP A 128 | 5.069 | 20.101 | 21.158 | 1.00 | 114.55 | A | C |
| ATOM | 16 | CE3 | TRP A 128 | 4.570 | 22.241 | 20.139 | 1.00 | 117.38 | A | C |
| ATOM | 17 | CD1 | TRP A 128 | 5.500 | 18.817 | 19.380 | 1.00 | 113.92 | A | C |
| ATOM | 18 | NE1 | TRP A 128 | 5.421 | 18.840 | 20.755 | 1.00 | 114.05 | A | N |
| ATOM | 19 | CZ2 | TRP A 128 | 4.875 | 20.615 | 22.444 | 1.00 | 116.69 | A | C |
| ATOM | 20 | CZ3 | TRP A 128 | 4.375 | 22.750 | 21.417 | 1.00 | 118.82 | A | C |
| ATOM | 21 | CH2 | TRP A 128 | 4.522 | 21.935 | 22.552 | 1.00 | 118.90 | A | C |
| ATOM | 22 | C | TRP A 128 | 3.997 | 21.765 | 15.640 | 1.00 | 113.95 | A | C |
| ATOM | 23 | O | TRP A 128 | 3.608 | 20.896 | 14.857 | 1.00 | 110.45 | A | O |
| ATOM | 24 | N | ALA A 129 | 4.352 | 22.991 | 15.281 | 1.00 | 111.97 | A | N |
| ATOM | 25 | CA | ALA A 129 | 4.370 | 23.502 | 13.921 | 1.00 | 113.78 | A | C |
| ATOM | 26 | CB | ALA A 129 | 3.018 | 24.104 | 13.558 | 1.00 | 113.78 | A | C |
| ATOM | 27 | C | ALA A 129 | 5.412 | 24.594 | 14.095 | 1.00 | 111.90 | A | C |
| ATOM | 28 | O | ALA A 129 | 5.480 | 25.205 | 15.161 | 1.00 | 110.75 | A | O |
| ATOM | 29 | N | LEU A 130 | 6.234 | 24.841 | 13.084 | 1.00 | 113.37 | A | N |
| ATOM | 30 | CA | LEU A 130 | 7.266 | 25.861 | 13.224 | 1.00 | 114.76 | A | C |
| ATOM | 31 | CB | LEU A 130 | 7.958 | 26.119 | 11.885 | 1.00 | 112.78 | A | C |
| ATOM | 32 | CG | LEU A 130 | 9.132 | 27.100 | 11.973 | 1.00 | 111.35 | A | C |
| ATOM | 33 | CD1 | LEU A 130 | 10.120 | 26.630 | 13.032 | 1.00 | 110.44 | A | C |
| ATOM | 34 | CD2 | LEU A 130 | 9.810 | 27.212 | 10.618 | 1.00 | 112.52 | A | C |
| ATOM | 35 | C | LEU A 130 | 6.733 | 27.178 | 13.788 | 1.00 | 116.59 | A | C |
| ATOM | 36 | O | LEU A 130 | 7.501 | 27.999 | 14.290 | 1.00 | 117.26 | A | O |
| ATOM | 37 | N | GLU A 131 | 5.420 | 27.372 | 13.717 | 1.00 | 117.84 | A | N |
| ATOM | 38 | CA | GLU A 131 | 4.801 | 28.597 | 14.214 | 1.00 | 117.92 | A | C |
| ATOM | 39 | CB | GLU A 131 | 3.329 | 28.660 | 13.801 | 1.00 | 122.28 | A | C |
| ATOM | 40 | CG | GLU A 131 | 2.698 | 30.027 | 14.020 | 1.00 | 129.95 | A | C |
| ATOM | 41 | CD | GLU A 131 | 1.184 | 29.976 | 14.066 | 1.00 | 134.06 | A | C |
| ATOM | 42 | OE1 | GLU A 131 | 0.573 | 29.459 | 13.108 | 1.00 | 135.96 | A | O |
| ATOM | 43 | OE2 | GLU A 131 | 0.606 | 30.458 | 15.063 | 1.00 | 135.89 | A | O- |
| ATOM | 44 | C | GLU A 131 | 4.884 | 28.741 | 15.732 | 1.00 | 115.10 | A | C |
| ATOM | 45 | O | GLU A 131 | 5.359 | 29.756 | 16.242 | 1.00 | 114.82 | A | O |
| ATOM | 46 | N | ASP A 132 | 4.416 | 27.720 | 16.444 | 1.00 | 111.27 | A | N |
| ATOM | 47 | CA | ASP A 132 | 4.404 | 27.718 | 17.905 | 1.00 | 106.88 | A | C |
| ATOM | 48 | CB | ASP A 132 | 4.003 | 26.336 | 18.431 | 1.00 | 106.57 | A | C |
| ATOM | 49 | CG | ASP A 132 | 2.959 | 25.660 | 17.568 | 1.00 | 106.64 | A | C |
| ATOM | 50 | OD1 | ASP A 132 | 3.274 | 25.329 | 16.406 | 1.00 | 105.58 | A | O |
| ATOM | 51 | OD2 | ASP A 132 | 1.825 | 25.458 | 18.050 | 1.00 | 107.73 | A | O |
| ATOM | 52 | C | ASP A 132 | 5.736 | 28.097 | 18.541 | 1.00 | 103.44 | A | C |
| ATOM | 53 | O | ASP A 132 | 5.832 | 28.192 | 19.765 | 1.00 | 101.89 | A | O |
| ATOM | 54 | N | PHE A 133 | 6.764 | 28.315 | 17.728 | 1.00 | 99.34 | A | N |
| ATOM | 55 | CA | PHE A 133 | 8.063 | 28.642 | 18.290 | 1.00 | 96.10 | A | C |
| ATOM | 56 | CB | PHE A 133 | 9.041 | 27.501 | 18.012 | 1.00 | 93.17 | A | C |
| ATOM | 57 | CG | PHE A 133 | 8.600 | 26.190 | 18.586 | 1.00 | 90.32 | A | C |
| ATOM | 58 | CD1 | PHE A 133 | 7.596 | 25.451 | 17.969 | 1.00 | 87.81 | A | C |

Figure 1B

| ATOM | 59 | CD2 | PHE | A | 133 | 9.146 | 25.719 | 19.773 | 1.00 | 91.26 | A | C |
| --- | --- | --- | --- | --- | --- | --- | --- | --- | --- | --- | --- | --- |
| ATOM | 60 | CE1 | PHE | A | 133 | 7.139 | 24.265 | 18.528 | 1.00 | 87.69 | A | C |
| ATOM | 61 | CE2 | PHE | A | 133 | 8.696 | 24.533 | 20.342 | 1.00 | 91.81 | A | C |
| ATOM | 62 | CZ | PHE | A | 133 | 7.690 | 23.806 | 19.718 | 1.00 | 89.39 | A | C |
| ATOM | 63 | C | PHE | A | 133 | 8.698 | 29.964 | 17.897 | 1.00 | 95.70 | A | C |
| ATOM | 64 | O | PHE | A | 133 | 8.702 | 30.368 | 16.735 | 1.00 | 95.61 | A | O |
| ATOM | 65 | N | GLU | A | 134 | 9.236 | 30.624 | 18.915 | 1.00 | 94.54 | A | N |
| ATOM | 66 | CA | GLU | A | 134 | 9.921 | 31.899 | 18.788 | 1.00 | 92.75 | A | C |
| ATOM | 67 | CB | GLU | A | 134 | 9.547 | 32.774 | 19.989 | 1.00 | 96.03 | A | C |
| ATOM | 68 | CG | GLU | A | 134 | 9.973 | 34.219 | 19.905 | 1.00 | 100.91 | A | C |
| ATOM | 69 | CD | GLU | A | 134 | 9.406 | 35.063 | 21.033 | 1.00 | 104.28 | A | C |
| ATOM | 70 | OE1 | GLU | A | 134 | 8.193 | 34.954 | 21.307 | 1.00 | 107.44 | A | O |
| ATOM | 71 | OE2 | GLU | A | 134 | 10.169 | 35.843 | 21.640 | 1.00 | 105.04 | A | O |
| ATOM | 72 | C | GLU | A | 134 | 11.391 | 31.487 | 18.853 | 1.00 | 89.51 | A | C |
| ATOM | 73 | O | GLU | A | 134 | 11.829 | 30.964 | 19.873 | 1.00 | 89.68 | A | O |
| ATOM | 74 | N | ILE | A | 135 | 12.149 | 31.698 | 17.779 | 1.00 | 85.75 | A | N |
| ATOM | 75 | CA | ILE | A | 135 | 13.554 | 31.289 | 17.775 | 1.00 | 85.62 | A | C |
| ATOM | 76 | CB | ILE | A | 135 | 13.880 | 30.431 | 16.517 | 1.00 | 86.50 | A | C |
| ATOM | 77 | CG2 | ILE | A | 135 | 12.664 | 29.588 | 16.145 | 1.00 | 86.30 | A | C |
| ATOM | 78 | CG1 | ILE | A | 135 | 14.263 | 31.321 | 15.330 | 1.00 | 86.14 | A | C |
| ATOM | 79 | CD1 | ILE | A | 135 | 14.720 | 30.544 | 14.106 | 1.00 | 81.51 | A | C |
| ATOM | 80 | C | ILE | A | 135 | 14.554 | 32.443 | 17.881 | 1.00 | 84.38 | A | C |
| ATOM | 81 | O | ILE | A | 135 | 14.418 | 33.467 | 17.211 | 1.00 | 83.97 | A | O |
| ATOM | 82 | N | GLY | A | 136 | 15.562 | 32.260 | 18.729 | 1.00 | 83.40 | A | N |
| ATOM | 83 | CA | GLY | A | 136 | 16.565 | 33.291 | 18.928 | 1.00 | 85.07 | A | C |
| ATOM | 84 | C | GLY | A | 136 | 17.894 | 33.051 | 18.236 | 1.00 | 87.82 | A | C |
| ATOM | 85 | O | GLY | A | 136 | 17.980 | 33.076 | 17.008 | 1.00 | 91.47 | A | O |
| ATOM | 86 | N | ARG | A | 137 | 18.932 | 32.813 | 19.032 | 1.00 | 88.84 | A | N |
| ATOM | 87 | CA | ARG | A | 137 | 20.281 | 32.591 | 18.518 | 1.00 | 88.46 | A | C |
| ATOM | 88 | CB | ARG | A | 137 | 21.311 | 32.931 | 19.594 | 1.00 | 89.82 | A | C |
| ATOM | 89 | CG | ARG | A | 137 | 20.773 | 33.763 | 20.745 | 1.00 | 92.84 | A | C |
| ATOM | 90 | CD | ARG | A | 137 | 21.693 | 33.648 | 21.942 | 1.00 | 93.88 | A | C |
| ATOM | 91 | NE | ARG | A | 137 | 23.072 | 33.982 | 21.598 | 1.00 | 94.43 | A | N |
| ATOM | 92 | CZ | ARG | A | 137 | 24.136 | 33.517 | 22.246 | 1.00 | 95.05 | A | C |
| ATOM | 93 | NH1 | ARG | A | 137 | 25.357 | 33.875 | 21.868 | 1.00 | 94.11 | A | N |
| ATOM | 94 | NH2 | ARG | A | 137 | 23.981 | 32.682 | 23.265 | 1.00 | 93.59 | A | N |
| ATOM | 95 | C | ARG | A | 137 | 20.530 | 31.156 | 18.059 | 1.00 | 87.21 | A | C |
| ATOM | 96 | O | ARG | A | 137 | 19.937 | 30.212 | 18.581 | 1.00 | 87.20 | A | O |
| ATOM | 97 | N | PRO | A | 138 | 21.426 | 30.978 | 17.075 | 1.00 | 87.47 | A | N |
| ATOM | 98 | CD | PRO | A | 138 | 22.013 | 32.055 | 16.256 | 1.00 | 88.32 | A | C |
| ATOM | 99 | CA | PRO | A | 138 | 21.779 | 29.662 | 16.532 | 1.00 | 88.68 | A | C |
| ATOM | 100 | CB | PRO | A | 138 | 22.296 | 30.001 | 15.139 | 1.00 | 87.16 | A | C |
| ATOM | 101 | CG | PRO | A | 138 | 22.987 | 31.305 | 15.371 | 1.00 | 89.17 | A | C |
| ATOM | 102 | C | PRO | A | 138 | 22.844 | 28.983 | 17.399 | 1.00 | 89.44 | A | C |
| ATOM | 103 | O | PRO | A | 138 | 23.982 | 28.798 | 16.968 | 1.00 | 92.83 | A | O |
| ATOM | 104 | N | LEU | A | 139 | 22.455 | 28.620 | 18.620 | 1.00 | 86.94 | A | N |
| ATOM | 105 | CA | LEU | A | 139 | 23.339 | 27.974 | 19.592 | 1.00 | 82.18 | A | C |
| ATOM | 106 | CB | LEU | A | 139 | 22.554 | 26.950 | 20.415 | 1.00 | 76.92 | A | C |
| ATOM | 107 | CG | LEU | A | 139 | 21.300 | 27.449 | 21.136 | 1.00 | 75.64 | A | C |
| ATOM | 108 | CD1 | LEU | A | 139 | 20.653 | 26.287 | 21.876 | 1.00 | 78.04 | A | C |
| ATOM | 109 | CD2 | LEU | A | 139 | 21.664 | 28.566 | 22.104 | 1.00 | 75.94 | A | C |
| ATOM | 110 | C | LEU | A | 139 | 24.585 | 27.298 | 19.027 | 1.00 | 82.77 | A | C |
| ATOM | 111 | O | LEU | A | 139 | 25.701 | 27.589 | 19.459 | 1.00 | 82.01 | A | O |
| ATOM | 112 | N | GLY | A | 140 | 24.398 | 26.390 | 18.074 | 1.00 | 83.56 | A | N |
| ATOM | 113 | CA | GLY | A | 140 | 25.535 | 25.697 | 17.496 | 1.00 | 85.06 | A | C |
| ATOM | 114 | C | GLY | A | 140 | 25.410 | 25.446 | 16.007 | 1.00 | 87.56 | A | C |
| ATOM | 115 | O | GLY | A | 140 | 24.315 | 25.495 | 15.449 | 1.00 | 86.09 | A | O |
| ATOM | 116 | N | LYS | A | 141 | 26.539 | 25.168 | 15.365 | 1.00 | 91.22 | A | N |
| ATOM | 117 | CA | LYS | A | 141 | 26.565 | 24.912 | 13.930 | 1.00 | 95.38 | A | C |
| ATOM | 118 | CB | LYS | A | 141 | 27.998 | 25.026 | 13.402 | 1.00 | 97.20 | A | C |
| ATOM | 123 | C | LYS | A | 141 | 26.600 | 23.541 | 13.581 | 1.00 | 98.12 | A | C |

Figure 1C

```
ATOM    124  O    LYS A 141      25.228  22.959  14.344  1.00   99.43      A  O
ATOM    125  N    GLY A 142      26.393  23.032  12.417  1.00  100.94      A  N
ATOM    126  CA   GLY A 142      25.919  21.736  11.976  1.00  104.98      A  C
ATOM    127  C    GLY A 142      25.548  21.730  10.507  1.00  108.77      A  C
ATOM    128  O    GLY A 142      24.573  22.364  10.103  1.00  108.88      A  O
ATOM    129  N    LYS A 143      26.334  21.024   9.700  1.00  112.43      A  N
ATOM    130  CA   LYS A 143      26.062  20.935   8.272  1.00  113.18      A  C
ATOM    131  CB   LYS A 143      26.998  19.917   7.615  1.00  112.94      A  C
ATOM    136  C    LYS A 143      24.617  20.487   8.113  1.00  113.43      A  C
ATOM    137  O    LYS A 143      23.772  21.224   7.604  1.00  112.42      A  O
ATOM    138  N    PHE A 144      24.347  19.269   8.566  1.00  112.92      A  N
ATOM    139  CA   PHE A 144      23.014  18.687   8.512  1.00  111.42      A  C
ATOM    140  CB   PHE A 144      22.961  17.481   9.448  1.00  109.06      A  C
ATOM    141  CG   PHE A 144      23.264  17.829  10.872  1.00  107.42      A  C
ATOM    142  CD1  PHE A 144      22.254  17.858  11.824  1.00  107.19      A  C
ATOM    143  CD2  PHE A 144      24.543  18.232  11.240  1.00  104.89      A  C
ATOM    144  CE1  PHE A 144      22.510  18.291  13.115  1.00  106.53      A  C
ATOM    145  CE2  PHE A 144      24.806  18.667  12.527  1.00  104.75      A  C
ATOM    146  CZ   PHE A 144      23.786  18.699  13.465  1.00  106.91      A  C
ATOM    147  C    PHE A 144      21.989  19.730   8.955  1.00  110.35      A  C
ATOM    148  O    PHE A 144      21.012  19.989   8.255  1.00  109.93      A  O
ATOM    149  N    GLY A 145      22.226  20.327  10.120  1.00  109.25      A  N
ATOM    150  CA   GLY A 145      21.317  21.328  10.646  1.00  109.11      A  C
ATOM    151  C    GLY A 145      21.840  21.997  11.902  1.00  109.43      A  C
ATOM    152  O    GLY A 145      22.520  21.370  12.717  1.00  108.80      A  O
ATOM    153  N    ASN A 146      21.509  23.274  12.061  1.00  108.86      A  N
ATOM    154  CA   ASN A 146      21.953  24.055  13.208  1.00  104.91      A  C
ATOM    155  CB   ASN A 146      22.130  25.518  12.798  1.00  105.52      A  C
ATOM    156  CG   ASN A 146      22.632  25.669  11.377  1.00  106.13      A  C
ATOM    157  OD1  ASN A 146      23.696  25.161  11.023  1.00  106.74      A  O
ATOM    158  ND2  ASN A 146      21.864  26.370  10.552  1.00  105.37      A  N
ATOM    159  C    ASN A 146      20.965  23.986  14.366  1.00  102.25      A  C
ATOM    160  O    ASN A 146      19.814  23.581  14.198  1.00  101.20      A  O
ATOM    161  N    VAL A 147      21.429  24.385  15.545  1.00   99.56      A  N
ATOM    162  CA   VAL A 147      20.593  24.407  16.736  1.00   99.53      A  C
ATOM    163  CB   VAL A 147      21.335  23.850  17.963  1.00  102.12      A  C
ATOM    164  CG1  VAL A 147      20.466  23.995  19.202  1.00  104.13      A  C
ATOM    165  CG2  VAL A 147      21.697  22.394  17.735  1.00  105.72      A  C
ATOM    166  C    VAL A 147      20.248  25.865  17.000  1.00   96.66      A  C
ATOM    167  O    VAL A 147      21.136  26.714  17.060  1.00   96.10      A  O
ATOM    168  N    TYR A 148      18.961  26.157  17.149  1.00   95.42      A  N
ATOM    169  CA   TYR A 148      18.522  27.526  17.391  1.00   94.17      A  C
ATOM    170  CB   TYR A 148      17.627  28.011  16.243  1.00   98.41      A  C
ATOM    171  CG   TYR A 148      18.156  27.733  14.852  1.00  102.75      A  C
ATOM    172  CD1  TYR A 148      17.353  27.112  13.895  1.00  104.82      A  C
ATOM    173  CE1  TYR A 148      17.825  26.858  12.610  1.00  106.48      A  C
ATOM    174  CD2  TYR A 148      19.452  28.096  14.487  1.00  103.82      A  C
ATOM    175  CE2  TYR A 148      19.935  27.846  13.201  1.00  105.10      A  C
ATOM    176  CZ   TYR A 148      19.116  27.226  12.270  1.00  106.26      A  C
ATOM    177  OH   TYR A 148      19.589  26.964  11.005  1.00  105.49      A  O
ATOM    178  C    TYR A 148      17.738  27.637  18.692  1.00   88.98      A  C
ATOM    179  O    TYR A 148      16.700  26.995  18.848  1.00   86.31      A  O
ATOM    180  N    LEU A 149      18.226  28.449  19.624  1.00   85.38      A  N
ATOM    181  CA   LEU A 149      17.513  28.629  20.880  1.00   84.60      A  C
ATOM    182  CB   LEU A 149      18.177  29.713  21.728  1.00   79.30      A  C
ATOM    183  CG   LEU A 149      17.530  29.958  23.093  1.00   74.32      A  C
ATOM    184  CD1  LEU A 149      17.948  28.864  24.068  1.00   70.70      A  C
ATOM    185  CD2  LEU A 149      17.951  31.321  23.612  1.00   74.22      A  C
ATOM    186  C    LEU A 149      16.109  29.074  20.494  1.00   86.75      A  C
ATOM    187  O    LEU A 149      15.929  29.733  19.470  1.00   88.87      A  O
ATOM    188  N    ALA A 150      15.116  28.712  21.296  1.00   88.09      A  N
```

Figure 1D

```
ATOM    189  CA   ALA A 150      13.747  29.093  20.981  1.00  88.79      A    C
ATOM    190  CB   ALA A 150      13.295  28.388  19.708  1.00  88.44      A    C
ATOM    191  C    ALA A 150      12.763  28.810  22.106  1.00  90.35      A    C
ATOM    192  O    ALA A 150      12.983  27.935  22.943  1.00  90.99      A    O
ATOM    193  N    ARG A 151      11.670  29.564  22.106  1.00  91.73      A    N
ATOM    194  CA   ARG A 151      10.622  29.430  23.108  1.00  92.12      A    C
ATOM    195  CB   ARG A 151      10.369  30.771  23.804  1.00  90.75      A    C
ATOM    196  CG   ARG A 151      11.464  31.291  24.715  1.00  90.18      A    C
ATOM    197  CD   ARG A 151      11.110  32.710  25.145  1.00  90.72      A    C
ATOM    198  NE   ARG A 151      11.878  33.180  26.294  1.00  93.83      A    N
ATOM    199  CZ   ARG A 151      12.417  34.392  26.384  1.00  96.26      A    C
ATOM    200  NH1  ARG A 151      12.281  35.258  25.388  1.00  97.00      A    N
ATOM    201  NH2  ARG A 151      13.082  34.743  27.475  1.00  96.06      A    N
ATOM    202  C    ARG A 151       9.310  29.003  22.466  1.00  93.41      A    C
ATOM    203  O    ARG A 151       9.085  29.240  21.279  1.00  91.28      A    O
ATOM    204  N    GLU A 152       8.451  28.365  23.253  1.00  96.78      A    N
ATOM    205  CA   GLU A 152       7.134  27.983  22.767  1.00 102.06      A    C
ATOM    206  CB   GLU A 152       6.616  26.722  23.461  1.00 104.07      A    C
ATOM    207  CG   GLU A 152       5.128  26.495  23.223  1.00 108.42      A    C
ATOM    208  CD   GLU A 152       4.577  25.298  23.967  1.00 110.39      A    C
ATOM    209  OE1  GLU A 152       5.123  24.954  25.035  1.00 111.04      A    O
ATOM    210  OE2  GLU A 152       3.583  24.711  23.492  1.00 112.78      A    O
ATOM    211  C    GLU A 152       6.294  29.181  23.185  1.00 104.27      A    C
ATOM    212  O    GLU A 152       6.618  29.843  24.170  1.00 103.44      A    O
ATOM    213  N    LYS A 153       5.221  29.469  22.460  1.00 107.77      A    N
ATOM    214  CA   LYS A 153       4.407  30.627  22.800  1.00 110.31      A    C
ATOM    215  CB   LYS A 153       3.713  31.159  21.546  1.00 112.39      A    C
ATOM    216  CG   LYS A 153       4.692  31.558  20.457  1.00 115.61      A    C
ATOM    217  CD   LYS A 153       3.990  32.201  19.277  1.00 120.65      A    C
ATOM    218  CE   LYS A 153       4.954  33.071  18.491  1.00 124.59      A    C
ATOM    219  NZ   LYS A 153       4.245  34.041  17.616  1.00 128.43      A    N
ATOM    220  C    LYS A 153       3.390  30.475  23.927  1.00 110.30      A    C
ATOM    221  O    LYS A 153       3.176  31.421  24.685  1.00 110.14      A    O
ATOM    222  N    GLN A 154       2.762  29.310  24.055  1.00 109.62      A    N
ATOM    223  CA   GLN A 154       1.775  29.135  25.118  1.00 107.71      A    C
ATOM    224  CB   GLN A 154       0.840  27.959  24.817  1.00 110.66      A    C
ATOM    225  CG   GLN A 154       1.582  26.597  24.758  1.00 116.23      A    C
ATOM    226  CD   GLN A 154       0.489  25.468  24.814  1.00 118.82      A    C
ATOM    227  OE1  GLN A 154      -0.639  25.610  24.342  1.00 120.66      A    O
ATOM    228  NE2  GLN A 154       0.890  24.338  25.383  1.00 118.54      A    N
ATOM    229  C    GLN A 154       2.403  28.946  26.493  1.00 105.48      A    C
ATOM    230  O    GLN A 154       1.808  29.311  27.507  1.00 103.81      A    O
ATOM    231  N    SER A 155       3.601  28.374  26.531  1.00 103.19      A    N
ATOM    232  CA   SER A 155       4.287  28.162  27.799  1.00 100.54      A    C
ATOM    233  CB   SER A 155       4.843  26.738  27.877  1.00 102.21      A    C
ATOM    234  OG   SER A 155       5.873  26.541  26.924  1.00 102.53      A    O
ATOM    235  C    SER A 155       5.426  29.162  27.936  1.00  98.13      A    C
ATOM    236  O    SER A 155       6.034  29.281  29.000  1.00  96.44      A    O
ATOM    237  N    LYS A 156       5.707  29.882  26.854  1.00  95.92      A    N
ATOM    238  CA   LYS A 156       6.787  30.861  26.852  1.00  94.57      A    C
ATOM    239  CB   LYS A 156       6.459  32.019  27.798  1.00  93.51      A    C
ATOM    244  C    LYS A 156       8.050  30.150  27.317  1.00  95.02      A    C
ATOM    245  O    LYS A 156       9.059  30.781  27.631  1.00  95.60      A    O
ATOM    246  N    PHE A 157       7.977  28.823  27.350  1.00  93.90      A    N
ATOM    247  CA   PHE A 157       9.087  27.990  27.784  1.00  92.28      A    C
ATOM    248  CB   PHE A 157       8.686  26.515  27.729  1.00  90.68      A    C
ATOM    249  CG   PHE A 157       9.401  25.663  28.732  1.00  91.96      A    C
ATOM    250  CD1  PHE A 157       8.918  25.551  30.031  1.00  93.69      A    C
ATOM    251  CD2  PHE A 157      10.566  24.990  28.390  1.00  91.93      A    C
ATOM    252  CE1  PHE A 157       9.587  24.785  30.976  1.00  93.65      A    C
ATOM    253  CE2  PHE A 157      11.245  24.220  29.329  1.00  92.82      A    C
```

Figure 1E

```
ATOM    254  CZ  PHE A 157      10.753  24.117  30.625  1.00  93.45      A    C
ATOM    255  C   PHE A 157      10.317  28.220  26.916  1.00  92.26      A    C
ATOM    256  O   PHE A 157      10.204  28.503  25.726  1.00  92.77      A    O
ATOM    257  N   ILE A 158      11.491  28.092  27.525  1.00  91.24      A    N
ATOM    258  CA  ILE A 158      12.763  28.285  26.833  1.00  90.72      A    C
ATOM    259  CB  ILE A 158      13.770  29.003  27.763  1.00  88.82      A    C
ATOM    260  CG2 ILE A 158      13.986  28.182  29.025  1.00  89.43      A    C
ATOM    261  CG1 ILE A 158      15.085  29.264  27.027  1.00  88.63      A    C
ATOM    262  CD1 ILE A 158      15.009  30.401  26.022  1.00  84.57      A    C
ATOM    263  C   ILE A 158      13.322  26.924  26.410  1.00  91.05      A    C
ATOM    264  O   ILE A 158      13.485  26.028  27.238  1.00  92.86      A    O
ATOM    265  N   LEU A 159      13.622  26.768  25.123  1.00  89.70      A    N
ATOM    266  CA  LEU A 159      14.130  25.493  24.627  1.00  87.20      A    C
ATOM    267  CB  LEU A 159      12.956  24.603  24.211  1.00  86.64      A    C
ATOM    268  CG  LEU A 159      11.853  24.378  25.244  1.00  86.69      A    C
ATOM    269  CD1 LEU A 159      10.590  23.890  24.557  1.00  85.40      A    C
ATOM    270  CD2 LEU A 159      12.330  23.377  26.277  1.00  84.76      A    C
ATOM    271  C   LEU A 159      15.107  25.572  23.460  1.00  84.72      A    C
ATOM    272  O   LEU A 159      15.270  26.613  22.824  1.00  85.39      A    O
ATOM    273  N   ALA A 160      15.755  24.440  23.201  1.00  81.50      A    N
ATOM    274  CA  ALA A 160      16.699  24.296  22.103  1.00  77.15      A    C
ATOM    275  CB  ALA A 160      17.901  23.464  22.540  1.00  75.91      A    C
ATOM    276  C   ALA A 160      15.914  23.566  21.021  1.00  74.93      A    C
ATOM    277  O   ALA A 160      15.073  22.722  21.327  1.00  74.12      A    O
ATOM    278  N   LEU A 161      16.181  23.890  19.761  1.00  74.67      A    N
ATOM    279  CA  LEU A 161      15.468  23.265  18.654  1.00  75.02      A    C
ATOM    280  CB  LEU A 161      14.383  24.223  18.150  1.00  75.06      A    C
ATOM    281  CG  LEU A 161      13.510  23.833  16.956  1.00  75.02      A    C
ATOM    282  CD1 LEU A 161      12.142  24.475  17.106  1.00  75.75      A    C
ATOM    283  CD2 LEU A 161      14.171  24.267  15.657  1.00  76.38      A    C
ATOM    284  C   LEU A 161      16.418  22.883  17.526  1.00  76.40      A    C
ATOM    285  O   LEU A 161      17.018  23.747  16.886  1.00  76.89      A    O
ATOM    286  N   LYS A 162      16.544  21.582  17.282  1.00  78.13      A    N
ATOM    287  CA  LYS A 162      17.436  21.082  16.243  1.00  79.57      A    C
ATOM    288  CB  LYS A 162      17.920  19.673  16.599  1.00  77.96      A    C
ATOM    289  CG  LYS A 162      19.271  19.310  15.999  1.00  78.55      A    C
ATOM    290  CD  LYS A 162      19.860  18.076  16.665  1.00  82.07      A    C
ATOM    291  CE  LYS A 162      21.252  17.781  16.135  1.00  81.82      A    C
ATOM    292  NZ  LYS A 162      21.706  16.406  16.474  1.00  78.96      A    N
ATOM    293  C   LYS A 162      16.785  21.063  14.866  1.00  82.47      A    C
ATOM    294  O   LYS A 162      15.653  20.607  14.702  1.00  85.49      A    O
ATOM    295  N   VAL A 163      17.517  21.563  13.878  1.00  84.02      A    N
ATOM    296  CA  VAL A 163      17.039  21.606  12.504  1.00  86.85      A    C
ATOM    297  CB  VAL A 163      17.271  23.003  11.883  1.00  87.17      A    C
ATOM    298  CG1 VAL A 163      17.521  22.883  10.386  1.00  88.25      A    C
ATOM    299  CG2 VAL A 163      16.061  23.886  12.137  1.00  86.04      A    C
ATOM    300  C   VAL A 163      17.760  20.559  11.661  1.00  88.50      A    C
ATOM    301  O   VAL A 163      18.978  20.425  11.740  1.00  89.12      A    O
ATOM    302  N   LEU A 164      16.998  19.816  10.863  1.00  90.00      A    N
ATOM    303  CA  LEU A 164      17.564  18.785   9.997  1.00  91.35      A    C
ATOM    304  CB  LEU A 164      17.208  17.383  10.510  1.00  88.34      A    C
ATOM    305  CG  LEU A 164      17.406  16.974  11.976  1.00  87.99      A    C
ATOM    306  CD1 LEU A 164      18.884  16.918  12.304  1.00  84.24      A    C
ATOM    307  CD2 LEU A 164      16.686  17.951  12.891  1.00  88.71      A    C
ATOM    308  C   LEU A 164      16.996  18.950   8.589  1.00  94.98      A    C
ATOM    309  O   LEU A 164      15.802  18.743   8.373  1.00  96.48      A    O
ATOM    310  N   PHE A 165      17.840  19.329   7.633  1.00  98.57      A    N
ATOM    311  CA  PHE A 165      17.381  19.501   6.258  1.00 101.54      A    C
ATOM    312  CB  PHE A 165      18.355  20.380   5.464  1.00 104.88      A    C
ATOM    313  CG  PHE A 165      18.512  21.769   6.023  1.00 108.26      A    C
ATOM    314  CD1 PHE A 165      19.573  22.078   6.867  1.00 109.01      A    C
```

Figure 1F

| | | | | | | | | | | | |
|---|---|---|---|---|---|---|---|---|---|---|---|
| ATOM | 315 | CD2 | PHE | A | 165 | 17.583 | 22.763 | 5.730 | 1.00 | 109.20 | A C |
| ATOM | 316 | CE1 | PHE | A | 165 | 19.709 | 23.353 | 7.414 | 1.00 | 110.42 | A C |
| ATOM | 317 | CE2 | PHE | A | 165 | 17.709 | 24.043 | 6.272 | 1.00 | 108.75 | A C |
| ATOM | 318 | CZ | PHE | A | 165 | 18.775 | 24.337 | 7.116 | 1.00 | 109.79 | A C |
| ATOM | 319 | C | PHE | A | 165 | 17.240 | 18.134 | 5.593 | 1.00 | 101.63 | A C |
| ATOM | 320 | O | PHE | A | 165 | 18.218 | 17.401 | 5.445 | 1.00 | 101.61 | A O |
| ATOM | 321 | N | LYS | A | 166 | 16.016 | 17.799 | 5.195 | 1.00 | 101.72 | A N |
| ATOM | 322 | CA | LYS | A | 166 | 15.728 | 16.513 | 4.570 | 1.00 | 103.84 | A C |
| ATOM | 323 | CB | LYS | A | 166 | 14.256 | 16.449 | 4.155 | 1.00 | 103.58 | A C |
| ATOM | 324 | CG | LYS | A | 166 | 13.313 | 16.422 | 5.345 | 1.00 | 103.85 | A C |
| ATOM | 325 | CD | LYS | A | 166 | 12.105 | 15.538 | 5.102 | 1.00 | 103.86 | A C |
| ATOM | 326 | CE | LYS | A | 166 | 11.354 | 15.280 | 6.401 | 1.00 | 104.05 | A C |
| ATOM | 327 | NZ | LYS | A | 166 | 10.261 | 14.281 | 6.250 | 1.00 | 103.60 | A N |
| ATOM | 328 | C | LYS | A | 166 | 16.616 | 16.129 | 3.392 | 1.00 | 105.93 | A C |
| ATOM | 329 | O | LYS | A | 166 | 17.011 | 14.970 | 3.267 | 1.00 | 104.96 | A O |
| ATOM | 330 | N | ALA | A | 167 | 16.925 | 17.087 | 2.524 | 1.00 | 109.33 | A N |
| ATOM | 331 | CA | ALA | A | 167 | 17.784 | 16.797 | 1.381 | 1.00 | 112.33 | A C |
| ATOM | 332 | CB | ALA | A | 167 | 18.082 | 18.073 | 0.607 | 1.00 | 112.98 | A C |
| ATOM | 333 | C | ALA | A | 167 | 19.075 | 16.193 | 1.919 | 1.00 | 113.44 | A C |
| ATOM | 334 | O | ALA | A | 167 | 19.243 | 14.974 | 1.941 | 1.00 | 113.65 | A O |
| ATOM | 335 | N | GLN | A | 168 | 19.975 | 17.062 | 2.367 | 1.00 | 114.18 | A N |
| ATOM | 336 | CA | GLN | A | 168 | 21.256 | 16.648 | 2.925 | 1.00 | 115.44 | A C |
| ATOM | 337 | CB | GLN | A | 168 | 21.851 | 17.795 | 3.746 | 1.00 | 120.15 | A C |
| ATOM | 338 | CG | GLN | A | 168 | 21.906 | 19.121 | 3.002 | 1.00 | 125.55 | A C |
| ATOM | 339 | CD | GLN | A | 168 | 22.068 | 20.312 | 3.930 | 1.00 | 129.43 | A C |
| ATOM | 340 | OE1 | GLN | A | 168 | 21.962 | 21.462 | 3.504 | 1.00 | 131.74 | A O |
| ATOM | 341 | NE2 | GLN | A | 168 | 22.320 | 20.042 | 5.205 | 1.00 | 129.67 | A N |
| ATOM | 342 | C | GLN | A | 168 | 21.058 | 15.428 | 3.821 | 1.00 | 113.54 | A C |
| ATOM | 343 | O | GLN | A | 168 | 21.986 | 14.653 | 4.044 | 1.00 | 112.20 | A O |
| ATOM | 344 | N | LEU | A | 169 | 19.839 | 15.269 | 4.329 | 1.00 | 111.68 | A N |
| ATOM | 345 | CA | LEU | A | 169 | 19.503 | 14.155 | 5.206 | 1.00 | 111.81 | A C |
| ATOM | 346 | CB | LEU | A | 169 | 18.168 | 14.420 | 5.906 | 1.00 | 110.14 | A C |
| ATOM | 350 | C | LEU | A | 169 | 19.432 | 12.824 | 4.464 | 1.00 | 112.82 | A C |
| ATOM | 351 | O | LEU | A | 169 | 20.195 | 11.905 | 4.761 | 1.00 | 112.78 | A O |
| ATOM | 352 | N | GLU | A | 170 | 18.516 | 12.714 | 3.505 | 1.00 | 114.18 | A N |
| ATOM | 353 | CA | GLU | A | 170 | 18.387 | 11.471 | 2.755 | 1.00 | 115.81 | A C |
| ATOM | 354 | CB | GLU | A | 170 | 16.981 | 11.325 | 2.170 | 1.00 | 114.91 | A C |
| ATOM | 355 | CG | GLU | A | 170 | 16.630 | 9.882 | 1.847 | 1.00 | 113.07 | A C |
| ATOM | 356 | CD | GLU | A | 170 | 15.182 | 9.697 | 1.448 | 1.00 | 113.39 | A C |
| ATOM | 357 | OE1 | GLU | A | 170 | 14.294 | 9.947 | 2.291 | 1.00 | 112.40 | A O |
| ATOM | 358 | OE2 | GLU | A | 170 | 14.933 | 9.296 | 0.293 | 1.00 | 111.79 | A O |
| ATOM | 359 | C | GLU | A | 170 | 19.434 | 11.395 | 1.649 | 1.00 | 117.12 | A C |
| ATOM | 360 | O | GLU | A | 170 | 19.692 | 10.324 | 1.099 | 1.00 | 118.53 | A O |
| ATOM | 361 | N | LYS | A | 171 | 20.028 | 12.539 | 1.322 | 1.00 | 117.88 | A N |
| ATOM | 362 | CA | LYS | A | 171 | 21.085 | 12.589 | 0.320 | 1.00 | 117.42 | A C |
| ATOM | 363 | CB | LYS | A | 171 | 21.267 | 14.011 | -0.213 | 1.00 | 116.45 | A C |
| ATOM | 368 | C | LYS | A | 171 | 22.314 | 12.162 | 1.110 | 1.00 | 117.53 | A C |
| ATOM | 369 | O | LYS | A | 171 | 23.454 | 12.469 | 0.758 | 1.00 | 115.71 | A O |
| ATOM | 370 | N | ALA | A | 172 | 22.036 | 11.456 | 2.202 | 1.00 | 118.51 | A N |
| ATOM | 371 | CA | ALA | A | 172 | 23.042 | 10.936 | 3.114 | 1.00 | 118.89 | A C |
| ATOM | 372 | CB | ALA | A | 172 | 23.190 | 11.867 | 4.311 | 1.00 | 118.79 | A C |
| ATOM | 373 | C | ALA | A | 172 | 22.584 | 9.557 | 3.578 | 1.00 | 118.84 | A C |
| ATOM | 374 | O | ALA | A | 172 | 23.232 | 8.926 | 4.412 | 1.00 | 119.39 | A O |
| ATOM | 375 | N | GLY | A | 173 | 21.457 | 9.103 | 3.032 | 1.00 | 118.85 | A N |
| ATOM | 376 | CA | GLY | A | 173 | 20.914 | 7.804 | 3.392 | 1.00 | 119.82 | A C |
| ATOM | 377 | C | GLY | A | 173 | 21.031 | 7.520 | 4.875 | 1.00 | 120.01 | A C |
| ATOM | 378 | O | GLY | A | 173 | 21.780 | 6.633 | 5.284 | 1.00 | 119.19 | A O |
| ATOM | 379 | N | VAL | A | 174 | 20.292 | 8.271 | 5.686 | 1.00 | 120.83 | A N |
| ATOM | 380 | CA | VAL | A | 174 | 20.341 | 8.087 | 7.131 | 1.00 | 121.86 | A C |
| ATOM | 381 | CB | VAL | A | 174 | 21.270 | 9.125 | 7.788 | 1.00 | 122.57 | A C |
| ATOM | 384 | C | VAL | A | 174 | 18.976 | 8.176 | 7.802 | 1.00 | 122.18 | A C |

Figure 1G

| ATOM | 385 | O | VAL A 174 | 18.854 | 7.927 | 9.002 | 1.00 | 122.36 | A | O |
|---|---|---|---|---|---|---|---|---|---|---|
| ATOM | 386 | N | GLU A 175 | 17.954 | 8.527 | 7.027 | 1.00 | 121.37 | A | N |
| ATOM | 387 | CA | GLU A 175 | 16.597 | 8.651 | 7.551 | 1.00 | 120.75 | A | C |
| ATOM | 388 | CB | GLU A 175 | 15.588 | 8.630 | 6.396 | 1.00 | 121.34 | A | C |
| ATOM | 389 | CG | GLU A 175 | 14.128 | 8.728 | 6.821 | 1.00 | 124.85 | A | C |
| ATOM | 390 | CD | GLU A 175 | 13.453 | 7.373 | 6.926 | 1.00 | 127.13 | A | C |
| ATOM | 391 | OE1 | GLU A 175 | 13.987 | 6.486 | 7.625 | 1.00 | 128.98 | A | O |
| ATOM | 392 | OE2 | GLU A 175 | 12.384 | 7.194 | 6.305 | 1.00 | 127.07 | A | O |
| ATOM | 393 | C | GLU A 175 | 16.274 | 7.545 | 8.554 | 1.00 | 120.20 | A | C |
| ATOM | 394 | O | GLU A 175 | 15.357 | 7.679 | 9.364 | 1.00 | 119.19 | A | O |
| ATOM | 395 | N | HIS A 176 | 17.037 | 6.457 | 8.500 | 1.00 | 120.40 | A | N |
| ATOM | 396 | CA | HIS A 176 | 16.832 | 5.331 | 9.404 | 1.00 | 120.81 | A | C |
| ATOM | 397 | CB | HIS A 176 | 17.754 | 4.165 | 9.020 | 1.00 | 125.34 | A | C |
| ATOM | 398 | CG | HIS A 176 | 19.212 | 4.461 | 9.191 | 1.00 | 130.03 | A | C |
| ATOM | 399 | CD2 | HIS A 176 | 20.153 | 3.883 | 9.975 | 1.00 | 131.97 | A | C |
| ATOM | 400 | ND1 | HIS A 176 | 19.850 | 5.483 | 8.521 | 1.00 | 131.52 | A | N |
| ATOM | 401 | CE1 | HIS A 176 | 21.119 | 5.522 | 8.885 | 1.00 | 131.98 | A | C |
| ATOM | 402 | NE2 | HIS A 176 | 21.329 | 4.561 | 9.767 | 1.00 | 132.95 | A | N |
| ATOM | 403 | C | HIS A 176 | 17.078 | 5.725 | 10.860 | 1.00 | 119.03 | A | C |
| ATOM | 404 | O | HIS A 176 | 16.142 | 5.794 | 11.656 | 1.00 | 117.35 | A | O |
| ATOM | 405 | N | GLN A 177 | 18.339 | 5.985 | 11.196 | 1.00 | 117.92 | A | N |
| ATOM | 406 | CA | GLN A 177 | 18.730 | 6.368 | 12.547 | 1.00 | 117.37 | A | C |
| ATOM | 407 | CB | GLN A 177 | 20.099 | 7.053 | 12.523 | 1.00 | 116.13 | A | C |
| ATOM | 412 | C | GLN A 177 | 17.702 | 7.302 | 13.167 | 1.00 | 117.97 | A | C |
| ATOM | 413 | O | GLN A 177 | 17.348 | 7.163 | 14.337 | 1.00 | 120.44 | A | O |
| ATOM | 414 | N | LEU A 178 | 17.223 | 8.249 | 12.368 | 1.00 | 116.97 | A | N |
| ATOM | 415 | CA | LEU A 178 | 16.235 | 9.216 | 12.823 | 1.00 | 115.33 | A | C |
| ATOM | 416 | CB | LEU A 178 | 15.685 | 9.998 | 11.629 | 1.00 | 112.40 | A | C |
| ATOM | 417 | CG | LEU A 178 | 15.569 | 11.515 | 11.790 | 1.00 | 110.53 | A | C |
| ATOM | 418 | CD1 | LEU A 178 | 16.951 | 12.118 | 12.009 | 1.00 | 109.48 | A | C |
| ATOM | 419 | CD2 | LEU A 178 | 14.928 | 12.110 | 10.547 | 1.00 | 110.78 | A | C |
| ATOM | 420 | C | LEU A 178 | 15.092 | 8.514 | 13.552 | 1.00 | 115.18 | A | C |
| ATOM | 421 | O | LEU A 178 | 14.961 | 8.628 | 14.768 | 1.00 | 115.78 | A | O |
| ATOM | 422 | N | ARG A 179 | 14.278 | 7.777 | 12.802 | 1.00 | 112.96 | A | N |
| ATOM | 423 | CA | ARG A 179 | 13.142 | 7.059 | 13.372 | 1.00 | 110.82 | A | C |
| ATOM | 424 | CB | ARG A 179 | 12.510 | 6.158 | 12.306 | 1.00 | 113.18 | A | C |
| ATOM | 425 | CG | ARG A 179 | 11.912 | 6.940 | 11.148 | 1.00 | 114.39 | A | C |
| ATOM | 426 | CD | ARG A 179 | 11.344 | 6.043 | 10.062 | 1.00 | 113.13 | A | C |
| ATOM | 427 | NE | ARG A 179 | 10.649 | 6.833 | 9.049 | 1.00 | 108.98 | A | N |
| ATOM | 428 | CZ | ARG A 179 | 10.168 | 6.344 | 7.910 | 1.00 | 104.95 | A | C |
| ATOM | 429 | NH1 | ARG A 179 | 9.549 | 7.145 | 7.053 | 1.00 | 101.10 | A | N |
| ATOM | 430 | NH2 | ARG A 179 | 10.309 | 5.057 | 7.624 | 1.00 | 103.56 | A | N |
| ATOM | 431 | C | ARG A 179 | 13.508 | 6.233 | 14.603 | 1.00 | 108.63 | A | C |
| ATOM | 432 | O | ARG A 179 | 12.708 | 6.102 | 15.529 | 1.00 | 108.15 | A | O |
| ATOM | 433 | N | ARG A 180 | 14.716 | 5.681 | 14.614 | 1.00 | 107.15 | A | N |
| ATOM | 434 | CA | ARG A 180 | 15.166 | 4.875 | 15.743 | 1.00 | 107.25 | A | C |
| ATOM | 435 | CB | ARG A 180 | 16.386 | 4.042 | 15.345 | 1.00 | 111.18 | A | C |
| ATOM | 436 | CG | ARG A 180 | 16.097 | 2.999 | 14.282 | 1.00 | 117.87 | A | C |
| ATOM | 437 | CD | ARG A 180 | 17.375 | 2.340 | 13.798 | 1.00 | 123.14 | A | C |
| ATOM | 438 | NE | ARG A 180 | 17.141 | 1.505 | 12.624 | 1.00 | 126.86 | A | N |
| ATOM | 439 | CZ | ARG A 180 | 18.104 | 0.947 | 11.898 | 1.00 | 128.62 | A | C |
| ATOM | 440 | NH1 | ARG A 180 | 17.796 | 0.203 | 10.845 | 1.00 | 127.65 | A | N |
| ATOM | 441 | NH2 | ARG A 180 | 19.377 | 1.134 | 12.222 | 1.00 | 130.30 | A | N |
| ATOM | 442 | C | ARG A 180 | 15.518 | 5.757 | 16.937 | 1.00 | 105.77 | A | C |
| ATOM | 443 | O | ARG A 180 | 14.850 | 5.713 | 17.970 | 1.00 | 104.05 | A | O |
| ATOM | 444 | N | GLU A 181 | 16.568 | 6.556 | 16.784 | 1.00 | 106.19 | A | N |
| ATOM | 445 | CA | GLU A 181 | 17.023 | 7.449 | 17.843 | 1.00 | 106.68 | A | C |
| ATOM | 446 | CB | GLU A 181 | 18.198 | 8.291 | 17.342 | 1.00 | 109.26 | A | C |
| ATOM | 447 | CG | GLU A 181 | 19.412 | 7.472 | 16.933 | 1.00 | 115.60 | A | C |
| ATOM | 448 | CD | GLU A 181 | 20.500 | 8.318 | 16.303 | 1.00 | 119.11 | A | C |
| ATOM | 449 | OE1 | GLU A 181 | 20.184 | 9.097 | 15.379 | 1.00 | 119.89 | A | O |

Figure 1H

```
ATOM   450  OE2 GLU A 181      21.669   8.204  16.729  1.00  122.34  A  O
ATOM   451  C   GLU A 181      15.899   8.362  18.319  1.00  105.66  A  C
ATOM   452  O   GLU A 181      15.689   8.526  19.521  1.00  103.30  A  O
ATOM   453  N   VAL A 182      15.180   8.957  17.374  1.00  105.89  A  N
ATOM   454  CA  VAL A 182      14.077   9.843  17.717  1.00  105.51  A  C
ATOM   455  CB  VAL A 182      13.305  10.303  16.464  1.00  102.41  A  C
ATOM   456  CG1 VAL A 182      11.964  10.901  16.865  1.00  101.98  A  C
ATOM   457  CG2 VAL A 182      14.125  11.328  15.702  1.00  101.95  A  C
ATOM   458  C   VAL A 182      13.107   9.131  18.646  1.00  107.04  A  C
ATOM   459  O   VAL A 182      12.672   9.692  19.648  1.00  105.25  A  O
ATOM   460  N   GLU A 183      12.777   7.888  18.311  1.00  110.60  A  N
ATOM   461  CA  GLU A 183      11.849   7.117  19.122  1.00  113.53  A  C
ATOM   462  CB  GLU A 183      11.296   5.936  18.322  1.00  117.52  A  C
ATOM   463  CG  GLU A 183      10.121   5.274  19.007  1.00  123.07  A  C
ATOM   464  CD  GLU A 183       9.146   6.294  19.561  1.00  124.93  A  C
ATOM   465  OE1 GLU A 183       8.186   6.654  18.848  1.00  127.33  A  O
ATOM   466  OE2 GLU A 183       9.351   6.750  20.706  1.00  123.54  A  O
ATOM   467  C   GLU A 183      12.474   6.615  20.418  1.00  112.55  A  C
ATOM   468  O   GLU A 183      11.798   6.525  21.442  1.00  110.65  A  O
ATOM   469  N   ILE A 184      13.762   6.288  20.375  1.00  112.82  A  N
ATOM   470  CA  ILE A 184      14.454   5.801  21.564  1.00  114.40  A  C
ATOM   471  CB  ILE A 184      15.855   5.243  21.217  1.00  112.70  A  C
ATOM   472  CG2 ILE A 184      16.563   4.785  22.486  1.00  113.24  A  C
ATOM   473  CG1 ILE A 184      15.723   4.077  20.234  1.00  109.31  A  C
ATOM   474  CD1 ILE A 184      17.035   3.388  19.907  1.00  105.27  A  C
ATOM   475  C   ILE A 184      14.611   6.920  22.590  1.00  115.99  A  C
ATOM   476  O   ILE A 184      14.585   6.674  23.796  1.00  115.91  A  O
ATOM   477  N   GLN A 185      14.772   8.148  22.108  1.00  117.10  A  N
ATOM   478  CA  GLN A 185      14.929   9.289  22.999  1.00  117.42  A  C
ATOM   479  CB  GLN A 185      15.741  10.391  22.319  1.00  118.18  A  C
ATOM   480  CG  GLN A 185      16.473  11.298  23.297  1.00  119.65  A  C
ATOM   481  CD  GLN A 185      17.301  12.358  22.601  1.00  120.49  A  C
ATOM   482  OE1 GLN A 185      18.076  13.075  23.237  1.00  120.60  A  O
ATOM   483  NE2 GLN A 185      17.137  12.468  21.289  1.00  121.39  A  N
ATOM   484  C   GLN A 185      13.553   9.815  23.391  1.00  116.72  A  C
ATOM   485  O   GLN A 185      13.345  10.244  24.525  1.00  115.14  A  O
ATOM   486  N   SER A 186      12.619   9.784  22.443  1.00  115.77  A  N
ATOM   487  CA  SER A 186      11.256  10.230  22.702  1.00  114.36  A  C
ATOM   488  CB  SER A 186      10.460  10.326  21.399  1.00  115.38  A  C
ATOM   489  OG  SER A 186       9.102  10.639  21.657  1.00  118.46  A  O
ATOM   490  C   SER A 186      10.623   9.190  23.612  1.00  112.50  A  C
ATOM   491  O   SER A 186       9.688   8.489  23.223  1.00  112.76  A  O
ATOM   492  N   HIS A 187      11.159   9.094  24.824  1.00  110.43  A  N
ATOM   493  CA  HIS A 187      10.694   8.140  25.820  1.00  109.09  A  C
ATOM   494  CB  HIS A 187      10.635   6.733  25.220  1.00  109.59  A  C
ATOM   495  CG  HIS A 187       9.376   5.991  25.540  1.00  111.95  A  C
ATOM   496  CD2 HIS A 187       9.171   4.817  26.182  1.00  112.80  A  C
ATOM   497  ND1 HIS A 187       8.130   6.447  25.168  1.00  112.91  A  N
ATOM   498  CE1 HIS A 187       7.211   5.585  25.566  1.00  113.02  A  C
ATOM   499  NE2 HIS A 187       7.816   4.587  26.184  1.00  113.92  A  N
ATOM   500  C   HIS A 187      11.714   8.163  26.949  1.00  107.62  A  C
ATOM   501  O   HIS A 187      11.394   8.511  28.086  1.00  110.36  A  O
ATOM   502  N   LEU A 188      12.946   7.793  26.608  1.00  104.43  A  N
ATOM   503  CA  LEU A 188      14.060   7.756  27.550  1.00  100.63  A  C
ATOM   504  CB  LEU A 188      15.382   7.788  26.779  1.00   98.13  A  C
ATOM   505  CG  LEU A 188      16.639   7.244  27.459  1.00   96.18  A  C
ATOM   506  CD1 LEU A 188      16.426   5.788  27.850  1.00   94.54  A  C
ATOM   507  CD2 LEU A 188      17.818   7.370  26.506  1.00   96.27  A  C
ATOM   508  C   LEU A 188      13.961   8.957  28.484  1.00   99.02  A  C
ATOM   509  O   LEU A 188      14.381  10.063  28.143  1.00   99.73  A  O
ATOM   510  N   ARG A 189      13.400   8.725  29.665  1.00   96.00  A  N
```

Figure 1I

```
ATOM   511  CA   ARG A 189      13.199    9.780   30.650  1.00   92.28      A    C
ATOM   512  CB   ARG A 189      11.752    9.707   31.151  1.00   93.53      A    C
ATOM   513  CG   ARG A 189      11.181   10.992   31.728  1.00   99.54      A    C
ATOM   514  CD   ARG A 189       9.692   11.072   31.406  1.00  106.53      A    C
ATOM   515  NE   ARG A 189       9.007   12.161   32.095  1.00  112.84      A    N
ATOM   516  CZ   ARG A 189       7.751   12.525   31.849  1.00  115.31      A    C
ATOM   517  NH1  ARG A 189       7.042   11.889   30.924  1.00  115.96      A    N
ATOM   518  NH2  ARG A 189       7.200   13.521   32.529  1.00  117.03      A    N
ATOM   519  C    ARG A 189      14.183    9.650   31.812  1.00   87.52      A    C
ATOM   520  O    ARG A 189      13.991    8.836   32.717  1.00   86.75      A    O
ATOM   521  N    HIS A 190      15.237   10.460   31.776  1.00   81.53      A    N
ATOM   522  CA   HIS A 190      16.266   10.447   32.812  1.00   77.41      A    C
ATOM   523  CB   HIS A 190      17.364    9.448   32.437  1.00   79.03      A    C
ATOM   524  CG   HIS A 190      18.377    9.227   33.516  1.00   81.08      A    C
ATOM   525  CD2  HIS A 190      19.573    9.817   33.748  1.00   81.13      A    C
ATOM   526  ND1  HIS A 190      18.191    8.323   34.539  1.00   80.28      A    N
ATOM   527  CE1  HIS A 190      19.229    8.365   35.356  1.00   79.22      A    C
ATOM   528  NE2  HIS A 190      20.082    9.263   34.898  1.00   80.19      A    N
ATOM   529  C    HIS A 190      16.869   11.847   32.963  1.00   74.62      A    C
ATOM   530  O    HIS A 190      16.960   12.599   31.992  1.00   73.28      A    O
ATOM   531  N    PRO A 191      17.289   12.212   34.186  1.00   73.43      A    N
ATOM   532  CD   PRO A 191      17.178   11.421   35.424  1.00   72.98      A    C
ATOM   533  CA   PRO A 191      17.885   13.524   34.469  1.00   73.07      A    C
ATOM   534  CB   PRO A 191      18.084   13.491   35.986  1.00   73.23      A    C
ATOM   535  CG   PRO A 191      18.256   12.030   36.275  1.00   74.76      A    C
ATOM   536  C    PRO A 191      19.176   13.863   33.719  1.00   72.34      A    C
ATOM   537  O    PRO A 191      19.333   14.983   33.233  1.00   71.62      A    O
ATOM   538  N    ASN A 192      20.098   12.909   33.623  1.00   71.67      A    N
ATOM   539  CA   ASN A 192      21.362   13.160   32.934  1.00   69.74      A    C
ATOM   540  CB   ASN A 192      22.492   12.373   33.604  1.00   66.25      A    C
ATOM   541  CG   ASN A 192      22.459   12.480   35.120  1.00   63.30      A    C
ATOM   542  OD1  ASN A 192      21.757   11.723   35.790  1.00   60.29      A    O
ATOM   543  ND2  ASN A 192      23.211   13.430   35.666  1.00   63.08      A    N
ATOM   544  C    ASN A 192      21.301   12.827   31.441  1.00   68.30      A    C
ATOM   545  O    ASN A 192      22.330   12.717   30.774  1.00   69.72      A    O
ATOM   546  N    ILE A 193      20.083   12.671   30.930  1.00   64.40      A    N
ATOM   547  CA   ILE A 193      19.847   12.375   29.521  1.00   60.95      A    C
ATOM   548  CB   ILE A 193      19.162   11.001   29.333  1.00   58.46      A    C
ATOM   549  CG2  ILE A 193      18.485   10.930   27.965  1.00   54.49      A    C
ATOM   550  CG1  ILE A 193      20.193    9.883   29.503  1.00   58.79      A    C
ATOM   551  CD1  ILE A 193      19.627    8.487   29.347  1.00   58.61      A    C
ATOM   552  C    ILE A 193      18.930   13.461   28.980  1.00   62.13      A    C
ATOM   553  O    ILE A 193      17.788   13.591   29.420  1.00   64.50      A    O
ATOM   554  N    LEU A 194      19.434   14.245   28.033  1.00   62.31      A    N
ATOM   555  CA   LEU A 194      18.647   15.322   27.449  1.00   63.77      A    C
ATOM   556  CB   LEU A 194      19.384   15.941   26.262  1.00   57.37      A    C
ATOM   557  CG   LEU A 194      18.800   17.255   25.743  1.00   51.42      A    C
ATOM   558  CD1  LEU A 194      19.649   18.415   26.242  1.00   43.33      A    C
ATOM   559  CD2  LEU A 194      18.776   17.243   24.229  1.00   53.35      A    C
ATOM   560  C    LEU A 194      17.304   14.776   26.979  1.00   66.99      A    C
ATOM   561  O    LEU A 194      17.249   13.778   26.260  1.00   66.89      A    O
ATOM   562  N    ARG A 195      16.223   15.430   27.386  1.00   69.52      A    N
ATOM   563  CA   ARG A 195      14.890   14.992   26.999  1.00   75.05      A    C
ATOM   564  CB   ARG A 195      13.846   15.659   27.893  1.00   80.25      A    C
ATOM   565  CG   ARG A 195      12.658   14.770   28.184  1.00   86.65      A    C
ATOM   566  CD   ARG A 195      11.599   15.493   28.980  1.00   89.95      A    C
ATOM   567  NE   ARG A 195      10.312   14.819   28.863  1.00   94.47      A    N
ATOM   568  CZ   ARG A 195       9.140   15.407   29.071  1.00   96.89      A    C
ATOM   569  NH1  ARG A 195       8.018   14.713   28.940  1.00   97.23      A    N
ATOM   570  NH2  ARG A 195       9.089   16.690   29.402  1.00   99.86      A    N
ATOM   571  C    ARG A 195      14.632   15.329   25.528  1.00   75.32      A    C
```

Figure 1J

```
ATOM    572  O   ARG A 195      15.397  16.076  24.919  1.00  72.66      A    O
ATOM    573  N   LEU A 196      13.558  14.782  24.961  1.00  79.34      A    N
ATOM    574  CA  LEU A 196      13.231  15.018  23.554  1.00  84.04      A    C
ATOM    575  CB  LEU A 196      13.534  13.754  22.742  1.00  88.38      A    C
ATOM    576  CG  LEU A 196      13.309  13.793  21.228  1.00  89.46      A    C
ATOM    577  CD1 LEU A 196      13.868  15.081  20.645  1.00  89.95      A    C
ATOM    578  CD2 LEU A 196      13.969  12.582  20.592  1.00  92.11      A    C
ATOM    579  C   LEU A 196      11.780  15.451  23.326  1.00  85.72      A    C
ATOM    580  O   LEU A 196      11.100  14.953  22.430  1.00  86.79      A    O
ATOM    581  N   TYR A 197      11.331  16.401  24.139  1.00  86.16      A    N
ATOM    582  CA  TYR A 197       9.976  16.946  24.090  1.00  86.47      A    C
ATOM    583  CB  TYR A 197      10.037  18.463  24.278  1.00  83.34      A    C
ATOM    584  CG  TYR A 197      10.640  18.880  25.600  1.00  82.62      A    C
ATOM    585  CD1 TYR A 197      11.781  19.679  25.646  1.00  83.09      A    C
ATOM    586  CE1 TYR A 197      12.348  20.051  26.861  1.00  83.11      A    C
ATOM    587  CD2 TYR A 197      10.077  18.464  26.807  1.00  83.87      A    C
ATOM    588  CE2 TYR A 197      10.638  18.834  28.027  1.00  85.48      A    C
ATOM    589  CZ  TYR A 197      11.772  19.625  28.045  1.00  83.57      A    C
ATOM    590  OH  TYR A 197      12.335  19.983  29.247  1.00  80.52      A    O
ATOM    591  C   TYR A 197       9.080  16.630  22.890  1.00  88.41      A    C
ATOM    592  O   TYR A 197       7.969  16.134  23.074  1.00  90.29      A    O
ATOM    593  N   GLY A 198       9.533  16.914  21.670  1.00  90.68      A    N
ATOM    594  CA  GLY A 198       8.675  16.648  20.525  1.00  92.01      A    C
ATOM    595  C   GLY A 198       9.297  16.310  19.182  1.00  91.88      A    C
ATOM    596  O   GLY A 198      10.497  16.056  19.079  1.00  92.62      A    O
ATOM    597  N   TYR A 199       8.460  16.315  18.146  1.00  91.47      A    N
ATOM    598  CA  TYR A 199       8.884  15.995  16.784  1.00  92.91      A    C
ATOM    599  CB  TYR A 199       9.073  14.467  16.656  1.00  94.40      A    C
ATOM    600  CG  TYR A 199       9.186  13.880  15.247  1.00  98.95      A    C
ATOM    601  CD1 TYR A 199       9.171  12.496  15.053  1.00 101.21      A    C
ATOM    602  CE1 TYR A 199       9.259  11.940  13.770  1.00 103.34      A    C
ATOM    603  CD2 TYR A 199       9.296  14.692  14.116  1.00 102.24      A    C
ATOM    604  CE2 TYR A 199       9.383  14.147  12.834  1.00 104.38      A    C
ATOM    605  CZ  TYR A 199       9.365  12.775  12.667  1.00 103.79      A    C
ATOM    606  OH  TYR A 199       9.453  12.251  11.396  1.00 102.20      A    O
ATOM    607  C   TYR A 199       7.860  16.494  15.760  1.00  94.83      A    C
ATOM    608  O   TYR A 199       6.657  16.287  15.914  1.00  97.00      A    O
ATOM    609  N   PHE A 200       8.354  17.166  14.724  1.00  96.16      A    N
ATOM    610  CA  PHE A 200       7.515  17.662  13.637  1.00  99.75      A    C
ATOM    611  CB  PHE A 200       6.739  18.921  14.047  1.00 101.18      A    C
ATOM    612  CG  PHE A 200       7.603  20.083  14.448  1.00 101.76      A    C
ATOM    613  CD1 PHE A 200       8.280  20.081  15.663  1.00 100.54      A    C
ATOM    614  CD2 PHE A 200       7.699  21.204  13.629  1.00 101.45      A    C
ATOM    615  CE1 PHE A 200       9.035  21.183  16.059  1.00  98.76      A    C
ATOM    616  CE2 PHE A 200       8.451  22.309  14.016  1.00  98.84      A    C
ATOM    617  CZ  PHE A 200       9.119  22.299  15.234  1.00  98.18      A    C
ATOM    618  C   PHE A 200       8.396  17.948  12.425  1.00 102.64      A    C
ATOM    619  O   PHE A 200       9.603  18.143  12.565  1.00 105.53      A    O
ATOM    620  N   HIS A 201       7.796  17.965  11.238  1.00 105.71      A    N
ATOM    621  CA  HIS A 201       8.556  18.197  10.012  1.00 109.97      A    C
ATOM    622  CB  HIS A 201       9.073  16.858   9.478  1.00 115.72      A    C
ATOM    623  CG  HIS A 201       8.001  15.826   9.299  1.00 122.37      A    C
ATOM    624  CD2 HIS A 201       7.729  14.695   9.992  1.00 124.07      A    C
ATOM    625  ND1 HIS A 201       7.032  15.917   8.323  1.00 125.11      A    N
ATOM    626  CE1 HIS A 201       6.209  14.889   8.423  1.00 126.58      A    C
ATOM    627  NE2 HIS A 201       6.610  14.132   9.429  1.00 126.42      A    N
ATOM    628  C   HIS A 201       7.783  18.908   8.905  1.00 110.12      A    C
ATOM    629  O   HIS A 201       6.665  18.517   8.571  1.00 109.61      A    O
ATOM    630  N   ASP A 202       8.383  19.949   8.334  1.00 112.18      A    N
ATOM    631  CA  ASP A 202       7.745  20.677   7.242  1.00 115.14      A    C
ATOM    632  CB  ASP A 202       8.037  22.185   7.322  1.00 115.18      A    C
```

Figure 1K

```
ATOM    633  CG  ASP A 202       9.496  22.527   7.047  1.00 115.61      A    C
ATOM    634  OD1 ASP A 202      10.117  21.880   6.177  1.00 115.07      A    O
ATOM    635  OD2 ASP A 202      10.018  23.462   7.690  1.00 116.37      A    O
ATOM    636  C   ASP A 202       8.282  20.113   5.932  1.00 116.67      A    C
ATOM    637  O   ASP A 202       9.098  19.190   5.937  1.00 117.19      A    O
ATOM    638  N   ALA A 203       7.829  20.670   4.815  1.00 116.52      A    N
ATOM    639  CA  ALA A 203       8.270  20.214   3.503  1.00 115.43      A    C
ATOM    640  CB  ALA A 203       7.798  21.185   2.430  1.00 114.36      A    C
ATOM    641  C   ALA A 203       9.789  20.062   3.439  1.00 116.09      A    C
ATOM    642  O   ALA A 203      10.304  18.965   3.217  1.00 114.35      A    O
ATOM    643  N   THR A 204      10.500  21.167   3.644  1.00 117.33      A    N
ATOM    644  CA  THR A 204      11.960  21.169   3.595  1.00 116.73      A    C
ATOM    645  CB  THR A 204      12.515  22.613   3.622  1.00 116.90      A    C
ATOM    646  OG1 THR A 204      11.976  23.355   2.521  1.00 117.88      A    O
ATOM    647  CG2 THR A 204      14.036  22.605   3.521  1.00 115.80      A    C
ATOM    648  C   THR A 204      12.620  20.382   4.725  1.00 115.79      A    C
ATOM    649  O   THR A 204      12.906  19.193   4.585  1.00 115.16      A    O
ATOM    650  N   ARG A 205      12.863  21.057   5.843  1.00 114.12      A    N
ATOM    651  CA  ARG A 205      13.514  20.445   6.995  1.00 112.83      A    C
ATOM    652  CB  ARG A 205      14.253  21.521   7.803  1.00 114.63      A    C
ATOM    653  CG  ARG A 205      13.529  22.867   7.902  1.00 120.69      A    C
ATOM    654  CD  ARG A 205      13.746  23.713   6.647  1.00 125.29      A    C
ATOM    655  NE  ARG A 205      13.063  25.007   6.690  1.00 132.52      A    N
ATOM    656  CZ  ARG A 205      13.315  25.969   7.573  1.00 136.85      A    C
ATOM    657  NH1 ARG A 205      14.240  25.796   8.508  1.00 139.64      A    N
ATOM    658  NH2 ARG A 205      12.644  27.113   7.518  1.00 139.70      A    N
ATOM    659  C   ARG A 205      12.594  19.664   7.928  1.00 110.90      A    C
ATOM    660  O   ARG A 205      11.419  19.443   7.635  1.00 110.68      A    O
ATOM    661  N   VAL A 206      13.167  19.233   9.048  1.00 108.69      A    N
ATOM    662  CA  VAL A 206      12.451  18.497  10.083  1.00 104.24      A    C
ATOM    663  CB  VAL A 206      12.845  16.998  10.109  1.00 102.24      A    C
ATOM    664  CG1 VAL A 206      13.162  16.523   8.710  1.00 103.73      A    C
ATOM    665  CG2 VAL A 206      14.027  16.773  11.030  1.00  98.51      A    C
ATOM    666  C   VAL A 206      12.914  19.158  11.374  1.00 102.88      A    C
ATOM    667  O   VAL A 206      13.982  19.768  11.403  1.00 103.16      A    O
ATOM    668  N   TYR A 207      12.132  19.048  12.441  1.00 101.75      A    N
ATOM    669  CA  TYR A 207      12.535  19.681  13.687  1.00 100.09      A    C
ATOM    670  CB  TYR A 207      11.733  20.962  13.921  1.00 101.19      A    C
ATOM    671  CG  TYR A 207      11.733  21.931  12.761  1.00 101.88      A    C
ATOM    672  CD1 TYR A 207      10.804  21.812  11.727  1.00 101.47      A    C
ATOM    673  CE1 TYR A 207      10.789  22.712  10.666  1.00 104.18      A    C
ATOM    674  CD2 TYR A 207      12.654  22.977  12.703  1.00 104.04      A    C
ATOM    675  CE2 TYR A 207      12.649  23.882  11.645  1.00 106.21      A    C
ATOM    676  CZ  TYR A 207      11.713  23.744  10.632  1.00 106.59      A    C
ATOM    677  OH  TYR A 207      11.699  24.638   9.587  1.00 113.08      A    O
ATOM    678  C   TYR A 207      12.429  18.813  14.929  1.00  98.20      A    C
ATOM    679  O   TYR A 207      11.399  18.191  15.194  1.00  97.21      A    O
ATOM    680  N   LEU A 208      13.515  18.795  15.691  1.00  96.15      A    N
ATOM    681  CA  LEU A 208      13.583  18.046  16.932  1.00  93.59      A    C
ATOM    682  CB  LEU A 208      14.911  17.286  17.029  1.00  94.10      A    C
ATOM    683  CG  LEU A 208      15.261  16.275  15.931  1.00  94.01      A    C
ATOM    684  CD1 LEU A 208      16.726  15.882  16.050  1.00  95.81      A    C
ATOM    685  CD2 LEU A 208      14.367  15.052  16.044  1.00  91.99      A    C
ATOM    686  C   LEU A 208      13.492  19.070  18.059  1.00  91.52      A    C
ATOM    687  O   LEU A 208      14.293  20.002  18.125  1.00  92.03      A    O
ATOM    688  N   ILE A 209      12.495  18.917  18.922  1.00  87.28      A    N
ATOM    689  CA  ILE A 209      12.325  19.823  20.050  1.00  82.44      A    C
ATOM    690  CB  ILE A 209      10.841  20.067  20.351  1.00  81.18      A    C
ATOM    691  CG2 ILE A 209      10.699  20.947  21.583  1.00  83.06      A    C
ATOM    692  CG1 ILE A 209      10.173  20.722  19.142  1.00  79.11      A    C
ATOM    693  CD1 ILE A 209       8.681  20.878  19.285  1.00  77.41      A    C
```

Figure 1L

```
ATOM    694  C   ILE A 209      12.974  19.141  21.242  1.00  80.66      A    C
ATOM    695  O   ILE A 209      12.519  18.086  21.679  1.00  83.60      A    O
ATOM    696  N   LEU A 210      14.032  19.742  21.772  1.00  78.81      A    N
ATOM    697  CA  LEU A 210      14.735  19.130  22.889  1.00  76.80      A    C
ATOM    698  CB  LEU A 210      16.107  18.644  22.434  1.00  76.48      A    C
ATOM    699  CG  LEU A 210      16.200  17.966  21.071  1.00  74.49      A    C
ATOM    700  CD1 LEU A 210      16.408  19.001  19.978  1.00  73.14      A    C
ATOM    701  CD2 LEU A 210      17.359  17.014  21.091  1.00  74.20      A    C
ATOM    702  C   LEU A 210      14.932  20.012  24.104  1.00  74.81      A    C
ATOM    703  O   LEU A 210      14.777  21.233  24.045  1.00  74.93      A    O
ATOM    704  N   GLU A 211      15.279  19.365  25.212  1.00  72.58      A    N
ATOM    705  CA  GLU A 211      15.545  20.067  26.453  1.00  72.94      A    C
ATOM    706  CB  GLU A 211      15.865  19.069  27.573  1.00  76.08      A    C
ATOM    707  CG  GLU A 211      17.052  19.455  28.445  1.00  80.00      A    C
ATOM    708  CD  GLU A 211      17.078  18.715  29.767  1.00  78.72      A    C
ATOM    709  OE1 GLU A 211      16.820  17.494  29.778  1.00  79.83      A    O
ATOM    710  OE2 GLU A 211      17.365  19.358  30.798  1.00  73.80      A    O
ATOM    711  C   GLU A 211      16.738  20.972  26.188  1.00  72.77      A    C
ATOM    712  O   GLU A 211      17.553  20.696  25.311  1.00  70.47      A    O
ATOM    713  N   TYR A 212      16.834  22.054  26.948  1.00  74.66      A    N
ATOM    714  CA  TYR A 212      17.917  23.010  26.783  1.00  76.39      A    C
ATOM    715  CB  TYR A 212      17.323  24.416  26.665  1.00  78.44      A    C
ATOM    716  CG  TYR A 212      18.323  25.532  26.813  1.00  80.65      A    C
ATOM    717  CD1 TYR A 212      19.355  25.703  25.892  1.00  78.59      A    C
ATOM    718  CE1 TYR A 212      20.280  26.733  26.033  1.00  78.55      A    C
ATOM    719  CD2 TYR A 212      18.240  26.420  27.882  1.00  81.53      A    C
ATOM    720  CE2 TYR A 212      19.156  27.450  28.034  1.00  79.55      A    C
ATOM    721  CZ  TYR A 212      20.173  27.602  27.108  1.00  78.83      A    C
ATOM    722  OH  TYR A 212      21.078  28.627  27.262  1.00  78.92      A    O
ATOM    723  C   TYR A 212      18.926  22.950  27.931  1.00  76.64      A    C
ATOM    724  O   TYR A 212      18.547  22.798  29.092  1.00  76.15      A    O
ATOM    725  N   ALA A 213      20.210  23.062  27.594  1.00  76.47      A    N
ATOM    726  CA  ALA A 213      21.290  23.036  28.582  1.00  77.42      A    C
ATOM    727  CB  ALA A 213      22.148  21.789  28.393  1.00  77.65      A    C
ATOM    728  C   ALA A 213      22.145  24.297  28.422  1.00  78.28      A    C
ATOM    729  O   ALA A 213      22.960  24.392  27.506  1.00  75.08      A    O
ATOM    730  N   PRO A 214      21.968  25.275  29.326  1.00  80.20      A    N
ATOM    731  CD  PRO A 214      20.990  25.179  30.425  1.00  80.42      A    C
ATOM    732  CA  PRO A 214      22.661  26.570  29.371  1.00  80.88      A    C
ATOM    733  CB  PRO A 214      21.876  27.333  30.436  1.00  80.64      A    C
ATOM    734  CG  PRO A 214      21.465  26.252  31.374  1.00  80.40      A    C
ATOM    735  C   PRO A 214      24.173  26.633  29.624  1.00  80.54      A    C
ATOM    736  O   PRO A 214      24.775  27.696  29.469  1.00  82.40      A    O
ATOM    737  N   LEU A 215      24.795  25.523  30.008  1.00  77.95      A    N
ATOM    738  CA  LEU A 215      26.232  25.545  30.275  1.00  74.18      A    C
ATOM    739  CB  LEU A 215      26.538  24.798  31.572  1.00  76.09      A    C
ATOM    740  CG  LEU A 215      26.427  25.661  32.833  1.00  79.15      A    C
ATOM    741  CD1 LEU A 215      26.323  24.772  34.053  1.00  80.09      A    C
ATOM    742  CD2 LEU A 215      27.631  26.591  32.933  1.00  81.98      A    C
ATOM    743  C   LEU A 215      27.106  25.011  29.149  1.00  72.14      A    C
ATOM    744  O   LEU A 215      28.332  24.979  29.268  1.00  71.05      A    O
ATOM    745  N   GLY A 216      26.476  24.592  28.057  1.00  70.26      A    N
ATOM    746  CA  GLY A 216      27.227  24.091  26.921  1.00  67.90      A    C
ATOM    747  C   GLY A 216      27.677  22.647  27.022  1.00  65.44      A    C
ATOM    748  O   GLY A 216      27.056  21.834  27.705  1.00  64.26      A    O
ATOM    749  N   THR A 217      28.766  22.327  26.334  1.00  62.90      A    N
ATOM    750  CA  THR A 217      29.296  20.971  26.341  1.00  62.07      A    C
ATOM    751  CB  THR A 217      29.828  20.586  24.955  1.00  58.21      A    C
ATOM    752  OG1 THR A 217      30.927  21.440  24.614  1.00  56.12      A    O
ATOM    753  CG2 THR A 217      28.733  20.736  23.909  1.00  55.88      A    C
ATOM    754  C   THR A 217      30.431  20.819  27.343  1.00  64.73      A    C
```

Figure 1M

```
ATOM    755  O    THR A 217      31.143  21.779  27.637  1.00  65.23      A    O
ATOM    756  N    VAL A 218      30.600  19.607  27.863  1.00  65.76      A    N
ATOM    757  CA   VAL A 218      31.666  19.344  28.819  1.00  65.75      A    C
ATOM    758  CB   VAL A 218      31.628  17.886  29.333  1.00  62.46      A    C
ATOM    759  CG1  VAL A 218      32.718  17.673  30.378  1.00  59.39      A    C
ATOM    760  CG2  VAL A 218      30.264  17.578  29.926  1.00  61.71      A    C
ATOM    761  C    VAL A 218      32.997  19.582  28.114  1.00  68.91      A    C
ATOM    762  O    VAL A 218      33.993  19.933  28.744  1.00  70.76      A    O
ATOM    763  N    TYR A 219      32.999  19.394  26.797  1.00  70.27      A    N
ATOM    764  CA   TYR A 219      34.198  19.588  25.994  1.00  71.74      A    C
ATOM    765  CB   TYR A 219      33.912  19.288  24.519  1.00  70.23      A    C
ATOM    766  CG   TYR A 219      35.098  19.539  23.614  1.00  70.80      A    C
ATOM    767  CD1  TYR A 219      36.367  19.078  23.960  1.00  72.10      A    C
ATOM    768  CE1  TYR A 219      37.465  19.303  23.138  1.00  74.02      A    C
ATOM    769  CD2  TYR A 219      34.955  20.233  22.413  1.00  72.83      A    C
ATOM    770  CE2  TYR A 219      36.050  20.462  21.580  1.00  74.82      A    C
ATOM    771  CZ   TYR A 219      37.300  19.994  21.951  1.00  76.33      A    C
ATOM    772  OH   TYR A 219      38.385  20.218  21.138  1.00  76.92      A    O
ATOM    773  C    TYR A 219      34.749  21.002  26.118  1.00  74.36      A    C
ATOM    774  O    TYR A 219      35.940  21.190  26.367  1.00  74.47      A    O
ATOM    775  N    ARG A 220      33.885  21.996  25.942  1.00  77.38      A    N
ATOM    776  CA   ARG A 220      34.326  23.380  26.029  1.00  81.83      A    C
ATOM    777  CB   ARG A 220      33.210  24.341  25.626  1.00  86.64      A    C
ATOM    778  CG   ARG A 220      33.751  25.720  25.309  1.00  92.65      A    C
ATOM    779  CD   ARG A 220      32.695  26.804  25.317  1.00  97.88      A    C
ATOM    780  NE   ARG A 220      33.266  28.069  24.864  1.00  98.55      A    N
ATOM    781  CZ   ARG A 220      32.647  29.242  24.926  1.00  95.81      A    C
ATOM    782  NH1  ARG A 220      31.422  29.325  25.427  1.00  94.05      A    N
ATOM    783  NH2  ARG A 220      33.255  30.333  24.485  1.00  93.24      A    N
ATOM    784  C    ARG A 220      34.804  23.727  27.431  1.00  82.37      A    C
ATOM    785  O    ARG A 220      35.895  24.265  27.604  1.00  83.73      A    O
ATOM    786  N    GLU A 221      33.984  23.425  28.431  1.00  83.07      A    N
ATOM    787  CA   GLU A 221      34.351  23.707  29.813  1.00  85.35      A    C
ATOM    788  CB   GLU A 221      33.195  23.360  30.753  1.00  87.33      A    C
ATOM    789  CG   GLU A 221      33.535  23.482  32.231  1.00  90.73      A    C
ATOM    790  CD   GLU A 221      33.298  24.871  32.790  1.00  92.50      A    C
ATOM    791  OE1  GLU A 221      32.207  25.430  32.551  1.00  95.78      A    O
ATOM    792  OE2  GLU A 221      34.196  25.402  33.478  1.00  90.48      A    O
ATOM    793  C    GLU A 221      35.582  22.884  30.181  1.00  85.57      A    C
ATOM    794  O    GLU A 221      36.188  23.089  31.233  1.00  86.94      A    O
ATOM    795  N    LEU A 222      35.941  21.947  29.309  1.00  85.47      A    N
ATOM    796  CA   LEU A 222      37.107  21.101  29.535  1.00  85.07      A    C
ATOM    797  CB   LEU A 222      36.867  19.694  28.969  1.00  86.86      A    C
ATOM    798  CG   LEU A 222      37.979  18.651  29.129  1.00  89.01      A    C
ATOM    799  CD1  LEU A 222      38.431  18.588  30.578  1.00  90.45      A    C
ATOM    800  CD2  LEU A 222      37.475  17.292  28.662  1.00  89.40      A    C
ATOM    801  C    LEU A 222      38.328  21.726  28.874  1.00  84.81      A    C
ATOM    802  O    LEU A 222      39.425  21.706  29.431  1.00  84.04      A    O
ATOM    803  N    GLN A 223      38.133  22.290  27.686  1.00  87.70      A    N
ATOM    804  CA   GLN A 223      39.229  22.919  26.962  1.00  92.05      A    C
ATOM    805  CB   GLN A 223      38.860  23.117  25.484  1.00  95.24      A    C
ATOM    806  CG   GLN A 223      37.703  24.068  25.205  1.00  99.72      A    C
ATOM    807  CD   GLN A 223      37.346  24.120  23.727  1.00 100.63      A    C
ATOM    808  OE1  GLN A 223      36.403  24.804  23.324  1.00 101.42      A    O
ATOM    809  NE2  GLN A 223      38.101  23.392  22.911  1.00 100.32      A    N
ATOM    810  C    GLN A 223      39.634  24.247  27.593  1.00  92.42      A    C
ATOM    811  O    GLN A 223      40.729  24.751  27.346  1.00  93.09      A    O
ATOM    812  N    LYS A 224      38.751  24.807  28.415  1.00  93.18      A    N
ATOM    813  CA   LYS A 224      39.027  26.072  29.091  1.00  93.04      A    C
ATOM    814  CB   LYS A 224      37.717  26.775  29.463  1.00  95.71      A    C
ATOM    815  CG   LYS A 224      36.700  26.896  28.331  1.00  98.55      A    C
```

Figure 1N

```
ATOM   816  CD   LYS A 224      37.159  27.860  27.244  1.00  98.21      A  C
ATOM   817  CE   LYS A 224      36.455  27.596  25.913  1.00  97.94      A  C
ATOM   818  NZ   LYS A 224      36.265  28.846  25.120  1.00  93.95      A  N
ATOM   819  C    LYS A 224      39.804  25.764  30.366  1.00  90.14      A  C
ATOM   820  O    LYS A 224      40.856  26.347  30.636  1.00  90.33      A  O
ATOM   821  N    LEU A 225      39.260  24.833  31.141  1.00  85.73      A  N
ATOM   822  CA   LEU A 225      39.847  24.413  32.405  1.00  82.95      A  C
ATOM   823  CB   LEU A 225      38.767  23.768  33.278  1.00  79.91      A  C
ATOM   824  CG   LEU A 225      38.272  24.583  34.478  1.00  79.40      A  C
ATOM   825  CD1  LEU A 225      37.987  26.023  34.074  1.00  80.68      A  C
ATOM   826  CD2  LEU A 225      37.030  23.923  35.048  1.00  77.55      A  C
ATOM   827  C    LEU A 225      41.029  23.460  32.248  1.00  83.25      A  C
ATOM   828  O    LEU A 225      41.665  23.091  33.234  1.00  84.26      A  O
ATOM   829  N    SER A 226      41.316  23.061  31.013  1.00  83.25      A  N
ATOM   830  CA   SER A 226      42.435  22.165  30.733  1.00  81.93      A  C
ATOM   831  CB   SER A 226      43.710  22.715  31.385  1.00  83.49      A  C
ATOM   832  OG   SER A 226      44.755  22.856  30.440  1.00  86.13      A  O
ATOM   833  C    SER A 226      42.175  20.738  31.221  1.00  80.46      A  C
ATOM   834  O    SER A 226      42.008  19.819  30.418  1.00  80.71      A  O
ATOM   835  N    LYS A 227      42.143  20.561  32.538  1.00  78.84      A  N
ATOM   836  CA   LYS A 227      41.907  19.253  33.143  1.00  79.61      A  C
ATOM   837  CB   LYS A 227      43.227  18.659  33.646  1.00  78.81      A  C
ATOM   838  CG   LYS A 227      43.068  17.407  34.499  1.00  83.08      A  C
ATOM   839  CD   LYS A 227      44.237  17.252  35.455  1.00  83.38      A  C
ATOM   840  CE   LYS A 227      43.894  16.305  36.593  1.00  83.21      A  C
ATOM   841  NZ   LYS A 227      44.864  16.411  37.717  1.00  82.39      A  N
ATOM   842  C    LYS A 227      40.930  19.373  34.310  1.00  80.74      A  C
ATOM   843  O    LYS A 227      40.794  20.441  34.907  1.00  82.85      A  O
ATOM   844  N    PHE A 228      40.256  18.272  34.630  1.00  81.37      A  N
ATOM   845  CA   PHE A 228      39.298  18.246  35.731  1.00  81.27      A  C
ATOM   846  CB   PHE A 228      38.068  17.400  35.370  1.00  77.46      A  C
ATOM   847  CG   PHE A 228      37.222  17.973  34.265  1.00  73.67      A  C
ATOM   848  CD1  PHE A 228      37.273  19.327  33.951  1.00  70.30      A  C
ATOM   849  CD2  PHE A 228      36.345  17.154  33.556  1.00  71.19      A  C
ATOM   850  CE1  PHE A 228      36.463  19.860  32.950  1.00  68.60      A  C
ATOM   851  CE2  PHE A 228      35.530  17.676  32.555  1.00  67.99      A  C
ATOM   852  CZ   PHE A 228      35.589  19.032  32.251  1.00  67.14      A  C
ATOM   853  C    PHE A 228      39.920  17.658  36.993  1.00  84.23      A  C
ATOM   854  O    PHE A 228      40.832  16.835  36.917  1.00  85.49      A  O
ATOM   855  N    ASP A 229      39.424  18.086  38.152  1.00  87.03      A  N
ATOM   856  CA   ASP A 229      39.912  17.561  39.422  1.00  87.98      A  C
ATOM   857  CB   ASP A 229      39.641  18.543  40.569  1.00  92.20      A  C
ATOM   858  CG   ASP A 229      38.162  18.813  40.773  1.00  94.47      A  C
ATOM   859  OD1  ASP A 229      37.538  19.438  39.889  1.00  93.40      A  O
ATOM   860  OD2  ASP A 229      37.620  18.395  41.817  1.00  97.35      A  O
ATOM   861  C    ASP A 229      39.149  16.262  39.659  1.00  85.99      A  C
ATOM   862  O    ASP A 229      38.124  16.021  39.022  1.00  82.28      A  O
ATOM   863  N    GLU A 230      39.637  15.428  40.571  1.00  87.00      A  N
ATOM   864  CA   GLU A 230      38.981  14.155  40.844  1.00  90.39      A  C
ATOM   865  CB   GLU A 230      39.850  13.295  41.768  1.00  93.88      A  C
ATOM   866  CG   GLU A 230      40.984  14.025  42.463  1.00  99.69      A  C
ATOM   867  CD   GLU A 230      42.343  13.474  42.067  1.00 102.31      A  C
ATOM   868  OE1  GLU A 230      42.465  12.238  41.938  1.00 101.27      A  O
ATOM   869  OE2  GLU A 230      43.288  14.271  41.890  1.00 104.60      A  O
ATOM   870  C    GLU A 230      37.562  14.242  41.406  1.00  91.31      A  C
ATOM   871  O    GLU A 230      36.814  13.267  41.349  1.00  90.26      A  O
ATOM   872  N    GLN A 231      37.185  15.400  41.941  1.00  93.98      A  N
ATOM   873  CA   GLN A 231      35.841  15.573  42.492  1.00  95.14      A  C
ATOM   874  CB   GLN A 231      35.803  16.742  43.479  1.00  97.54      A  C
ATOM   875  CG   GLN A 231      36.579  16.516  44.765  1.00  99.92      A  C
ATOM   876  CD   GLN A 231      38.025  16.144  44.519  1.00 101.11      A  C
```

Figure 10

```
ATOM   877  OE1 GLN A 231      38.341  14.989  44.231  1.00  105.38      A  O
ATOM   878  NE2 GLN A 231      38.913  17.125  44.619  1.00   98.87      A  N
ATOM   879  C   GLN A 231      34.852  15.839  41.365  1.00   94.23      A  C
ATOM   880  O   GLN A 231      33.724  15.350  41.378  1.00   92.43      A  O
ATOM   881  N   ARG A 232      35.281  16.630  40.392  1.00   93.32      A  N
ATOM   882  CA  ARG A 232      34.432  16.950  39.258  1.00   91.45      A  C
ATOM   883  CB  ARG A 232      35.032  18.111  38.467  1.00   92.28      A  C
ATOM   884  CG  ARG A 232      34.190  18.540  37.289  1.00   95.39      A  C
ATOM   885  CD  ARG A 232      34.513  19.955  36.871  1.00   96.89      A  C
ATOM   886  NE  ARG A 232      33.645  20.375  35.779  1.00  101.97      A  N
ATOM   887  CZ  ARG A 232      33.613  21.600  35.271  1.00  104.47      A  C
ATOM   888  NH1 ARG A 232      34.405  22.550  35.753  1.00  104.97      A  N
ATOM   889  NH2 ARG A 232      32.778  21.874  34.281  1.00  104.96      A  N
ATOM   890  C   ARG A 232      34.314  15.719  38.372  1.00   90.04      A  C
ATOM   891  O   ARG A 232      33.221  15.348  37.940  1.00   88.50      A  O
ATOM   892  N   THR A 233      35.452  15.086  38.117  1.00   89.90      A  N
ATOM   893  CA  THR A 233      35.500  13.893  37.286  1.00   88.96      A  C
ATOM   894  CB  THR A 233      36.953  13.425  37.069  1.00   88.59      A  C
ATOM   895  OG1 THR A 233      37.739  14.512  36.565  1.00   86.45      A  O
ATOM   896  CG2 THR A 233      36.996  12.273  36.075  1.00   86.30      A  C
ATOM   897  C   THR A 233      34.711  12.742  37.903  1.00   88.42      A  C
ATOM   898  O   THR A 233      33.755  12.248  37.308  1.00   87.03      A  O
ATOM   899  N   ALA A 234      35.112  12.322  39.099  1.00   88.51      A  N
ATOM   900  CA  ALA A 234      34.454  11.213  39.780  1.00   86.27      A  C
ATOM   901  CB  ALA A 234      35.125  10.952  41.125  1.00   87.18      A  C
ATOM   902  C   ALA A 234      32.947  11.377  39.966  1.00   85.58      A  C
ATOM   903  O   ALA A 234      32.250  10.394  40.214  1.00   85.70      A  O
ATOM   904  N   THR A 235      32.437  12.602  39.858  1.00   84.56      A  N
ATOM   905  CA  THR A 235      31.000  12.811  40.007  1.00   84.21      A  C
ATOM   906  CB  THR A 235      30.665  14.102  40.776  1.00   83.98      A  C
ATOM   907  OG1 THR A 235      29.245  14.184  40.961  1.00   86.69      A  O
ATOM   908  CG2 THR A 235      31.138  15.322  40.009  1.00   82.48      A  C
ATOM   909  C   THR A 235      30.349  12.872  38.633  1.00   82.82      A  C
ATOM   910  O   THR A 235      29.142  12.685  38.500  1.00   80.06      A  O
ATOM   911  N   TYR A 236      31.150  13.162  37.612  1.00   82.22      A  N
ATOM   912  CA  TYR A 236      30.633  13.185  36.253  1.00   80.40      A  C
ATOM   913  CB  TYR A 236      31.614  13.868  35.298  1.00   81.31      A  C
ATOM   914  CG  TYR A 236      31.411  15.368  35.185  1.00   82.36      A  C
ATOM   915  CD1 TYR A 236      30.368  16.011  35.861  1.00   82.98      A  C
ATOM   916  CE1 TYR A 236      30.168  17.386  35.740  1.00   85.13      A  C
ATOM   917  CD2 TYR A 236      32.248  16.143  34.385  1.00   84.39      A  C
ATOM   918  CE2 TYR A 236      32.055  17.517  34.257  1.00   87.07      A  C
ATOM   919  CZ  TYR A 236      31.016  18.131  34.936  1.00   88.40      A  C
ATOM   920  OH  TYR A 236      30.829  19.489  34.810  1.00   90.84      A  O
ATOM   921  C   TYR A 236      30.470  11.713  35.923  1.00   77.82      A  C
ATOM   922  O   TYR A 236      29.543  11.318  35.216  1.00   73.41      A  O
ATOM   923  N   ILE A 237      31.394  10.908  36.441  1.00   78.17      A  N
ATOM   924  CA  ILE A 237      31.314   9.466  36.290  1.00   78.47      A  C
ATOM   925  CB  ILE A 237      32.637   8.772  36.634  1.00   76.30      A  C
ATOM   926  CG2 ILE A 237      32.514   7.278  36.376  1.00   71.32      A  C
ATOM   927  CG1 ILE A 237      33.767   9.361  35.784  1.00   73.49      A  C
ATOM   928  CD1 ILE A 237      33.516   9.309  34.286  1.00   76.49      A  C
ATOM   929  C   ILE A 237      30.286   9.240  37.387  1.00   82.65      A  C
ATOM   930  O   ILE A 237      30.469   9.690  38.515  1.00   82.70      A  O
ATOM   931  N   THR A 238      29.214   8.547  37.032  1.00   85.03      A  N
ATOM   932  CA  THR A 238      28.043   8.315  37.875  1.00   85.40      A  C
ATOM   933  CB  THR A 238      28.188   8.852  39.328  1.00   88.03      A  C
ATOM   934  OG1 THR A 238      27.275   8.152  40.182  1.00   92.44      A  O
ATOM   935  CG2 THR A 238      27.871  10.342  39.402  1.00   91.64      A  C
ATOM   936  C   THR A 238      27.264   9.297  37.012  1.00   83.02      A  C
ATOM   937  O   THR A 238      27.866   9.857  36.102  1.00   82.96      A  O
```

Figure 1P

```
ATOM    938  N    GLU A 239      25.990   9.567  37.263  1.00  79.97      A    N
ATOM    939  CA   GLU A 239      25.282  10.461  36.344  1.00  78.88      A    C
ATOM    940  CB   GLU A 239      25.994  11.817  36.183  1.00  77.01      A    C
ATOM    941  CG   GLU A 239      25.859  12.792  37.350  1.00  76.68      A    C
ATOM    942  CD   GLU A 239      25.890  14.250  36.896  1.00  73.09      A    C
ATOM    943  OE1  GLU A 239      26.064  15.146  37.750  1.00  69.24      A    O
ATOM    944  OE2  GLU A 239      25.729  14.501  35.684  1.00  70.34      A    O
ATOM    945  C    GLU A 239      25.381   9.688  35.025  1.00  78.47      A    C
ATOM    946  O    GLU A 239      24.427   9.041  34.598  1.00  79.87      A    O
ATOM    947  N    LEU A 240      26.554   9.760  34.396  1.00  77.02      A    N
ATOM    948  CA   LEU A 240      26.830   9.038  33.160  1.00  74.70      A    C
ATOM    949  CB   LEU A 240      28.308   9.162  32.776  1.00  70.36      A    C
ATOM    950  CG   LEU A 240      28.768  10.233  31.791  1.00  64.42      A    C
ATOM    951  CD1  LEU A 240      30.251  10.045  31.516  1.00  58.25      A    C
ATOM    952  CD2  LEU A 240      27.975  10.121  30.500  1.00  59.32      A    C
ATOM    953  C    LEU A 240      26.524   7.568  33.398  1.00  73.98      A    C
ATOM    954  O    LEU A 240      25.578   7.022  32.838  1.00  74.52      A    O
ATOM    955  N    ALA A 241      27.333   6.938  34.245  1.00  72.15      A    N
ATOM    956  CA   ALA A 241      27.175   5.526  34.568  1.00  70.75      A    C
ATOM    957  CB   ALA A 241      28.177   5.122  35.641  1.00  67.24      A    C
ATOM    958  C    ALA A 241      25.761   5.172  35.018  1.00  72.13      A    C
ATOM    959  O    ALA A 241      25.379   4.003  35.002  1.00  73.99      A    O
ATOM    960  N    ASN A 242      24.985   6.174  35.421  1.00  72.05      A    N
ATOM    961  CA   ASN A 242      23.620   5.923  35.864  1.00  70.46      A    C
ATOM    962  CB   ASN A 242      23.271   6.817  37.055  1.00  73.99      A    C
ATOM    963  CG   ASN A 242      21.859   6.590  37.554  1.00  79.17      A    C
ATOM    964  OD1  ASN A 242      21.334   5.478  37.486  1.00  83.57      A    O
ATOM    965  ND2  ASN A 242      21.239   7.644  38.072  1.00  80.38      A    N
ATOM    966  C    ASN A 242      22.609   6.119  34.740  1.00  67.08      A    C
ATOM    967  O    ASN A 242      21.574   5.453  34.705  1.00  63.26      A    O
ATOM    968  N    ALA A 243      22.904   7.037  33.825  1.00  64.69      A    N
ATOM    969  CA   ALA A 243      22.020   7.275  32.691  1.00  65.11      A    C
ATOM    970  CB   ALA A 243      22.338   8.609  32.042  1.00  60.99      A    C
ATOM    971  C    ALA A 243      22.339   6.142  31.735  1.00  69.67      A    C
ATOM    972  O    ALA A 243      21.557   5.800  30.848  1.00  71.13      A    O
ATOM    973  N    LEU A 244      23.516   5.567  31.949  1.00  73.41      A    N
ATOM    974  CA   LEU A 244      24.027   4.466  31.152  1.00  74.63      A    C
ATOM    975  CB   LEU A 244      25.539   4.365  31.359  1.00  73.56      A    C
ATOM    976  CG   LEU A 244      26.467   4.485  30.147  1.00  70.75      A    C
ATOM    977  CD1  LEU A 244      25.703   4.959  28.920  1.00  71.94      A    C
ATOM    978  CD2  LEU A 244      27.593   5.453  30.490  1.00  66.59      A    C
ATOM    979  C    LEU A 244      23.343   3.177  31.585  1.00  74.67      A    C
ATOM    980  O    LEU A 244      22.914   2.379  30.752  1.00  76.93      A    O
ATOM    981  N    SER A 245      23.250   2.982  32.896  1.00  73.64      A    N
ATOM    982  CA   SER A 245      22.605   1.802  33.449  1.00  75.44      A    C
ATOM    983  CB   SER A 245      22.765   1.773  34.969  1.00  75.61      A    C
ATOM    984  OG   SER A 245      22.575   0.463  35.474  1.00  79.33      A    O
ATOM    985  C    SER A 245      21.131   1.878  33.083  1.00  76.58      A    C
ATOM    986  O    SER A 245      20.578   0.948  32.494  1.00  76.07      A    O
ATOM    987  N    TYR A 246      20.502   2.996  33.439  1.00  76.96      A    N
ATOM    988  CA   TYR A 246      19.096   3.211  33.127  1.00  78.83      A    C
ATOM    989  CB   TYR A 246      18.680   4.642  33.473  1.00  75.97      A    C
ATOM    990  CG   TYR A 246      17.390   5.068  32.809  1.00  79.29      A    C
ATOM    991  CD1  TYR A 246      16.154   4.647  33.299  1.00  79.17      A    C
ATOM    992  CE1  TYR A 246      14.966   4.997  32.656  1.00  81.13      A    C
ATOM    993  CD2  TYR A 246      17.409   5.854  31.660  1.00  81.72      A    C
ATOM    994  CE2  TYR A 246      16.231   6.209  31.011  1.00  80.64      A    C
ATOM    995  CZ   TYR A 246      15.015   5.778  31.511  1.00  80.96      A    C
ATOM    996  OH   TYR A 246      13.856   6.120  30.853  1.00  76.16      A    O
ATOM    997  C    TYR A 246      18.922   2.971  31.635  1.00  81.66      A    C
ATOM    998  O    TYR A 246      17.874   2.509  31.186  1.00  82.82      A    O
```

Figure 1Q

```
ATOM    999  N   CYS A 247      19.959   3.299  30.871  1.00  84.18      A   N
ATOM   1000  CA  CYS A 247      19.934   3.096  29.430  1.00  86.69      A   C
ATOM   1001  CB  CYS A 247      21.069   3.866  28.752  1.00  85.41      A   C
ATOM   1002  SG  CYS A 247      20.539   5.359  27.886  1.00  89.36      A   S
ATOM   1003  C   CYS A 247      20.081   1.610  29.139  1.00  87.79      A   C
ATOM   1004  O   CYS A 247      19.401   1.070  28.268  1.00  85.88      A   O
ATOM   1005  N   HIS A 248      20.974   0.956  29.877  1.00  91.06      A   N
ATOM   1006  CA  HIS A 248      21.208  -0.472  29.706  1.00  93.69      A   C
ATOM   1007  CB  HIS A 248      22.320  -0.964  30.643  1.00  95.80      A   C
ATOM   1008  CG  HIS A 248      23.705  -0.612  30.192  1.00  96.43      A   C
ATOM   1009  CD2 HIS A 248      24.886  -0.625  30.854  1.00  94.27      A   C
ATOM   1010  ND1 HIS A 248      23.996  -0.244  28.896  1.00  95.60      A   N
ATOM   1011  CE1 HIS A 248      25.297  -0.046  28.779  1.00  93.15      A   C
ATOM   1012  NE2 HIS A 248      25.861  -0.271  29.952  1.00  92.81      A   N
ATOM   1013  C   HIS A 248      19.942  -1.281  29.972  1.00  93.26      A   C
ATOM   1014  O   HIS A 248      19.685  -2.276  29.295  1.00  93.78      A   O
ATOM   1015  N   SER A 249      19.155  -0.854  30.957  1.00  91.12      A   N
ATOM   1016  CA  SER A 249      17.924  -1.555  31.312  1.00  88.77      A   C
ATOM   1017  CB  SER A 249      17.309  -0.957  32.578  1.00  85.88      A   C
ATOM   1018  OG  SER A 249      16.590   0.229  32.290  1.00  82.36      A   O
ATOM   1019  C   SER A 249      16.898  -1.492  30.191  1.00  88.21      A   C
ATOM   1020  O   SER A 249      16.431  -2.521  29.703  1.00  90.86      A   O
ATOM   1021  N   LYS A 250      16.543  -0.276  29.789  1.00  86.52      A   N
ATOM   1022  CA  LYS A 250      15.567  -0.084  28.726  1.00  86.28      A   C
ATOM   1023  CB  LYS A 250      15.301   1.409  28.521  1.00  86.17      A   C
ATOM   1028  C   LYS A 250      16.040  -0.707  27.415  1.00  86.56      A   C
ATOM   1029  O   LYS A 250      15.423  -0.510  26.368  1.00  84.67      A   O
ATOM   1030  N   ARG A 251      17.135  -1.459  27.480  1.00  88.16      A   N
ATOM   1031  CA  ARG A 251      17.698  -2.118  26.305  1.00  89.43      A   C
ATOM   1032  CB  ARG A 251      16.636  -2.986  25.620  1.00  90.20      A   C
ATOM   1039  C   ARG A 251      18.251  -1.109  25.307  1.00  89.95      A   C
ATOM   1040  O   ARG A 251      18.017  -1.220  24.104  1.00  90.39      A   O
ATOM   1041  N   VAL A 252      18.991  -0.126  25.810  1.00  90.42      A   N
ATOM   1042  CA  VAL A 252      19.574   0.899  24.954  1.00  91.68      A   C
ATOM   1043  CB  VAL A 252      18.933   2.283  25.210  1.00  88.89      A   C
ATOM   1044  CG1 VAL A 252      19.637   3.345  24.372  1.00  88.48      A   C
ATOM   1045  CG2 VAL A 252      17.452   2.244  24.869  1.00  86.55      A   C
ATOM   1046  C   VAL A 252      21.078   1.036  25.145  1.00  95.55      A   C
ATOM   1047  O   VAL A 252      21.540   1.589  26.143  1.00  97.78      A   O
ATOM   1048  N   ILE A 253      21.839   0.527  24.181  1.00  97.48      A   N
ATOM   1049  CA  ILE A 253      23.292   0.620  24.226  1.00  96.69      A   C
ATOM   1050  CB  ILE A 253      23.974  -0.616  23.587  1.00  95.60      A   C
ATOM   1051  CG2 ILE A 253      25.486  -0.449  23.627  1.00  96.66      A   C
ATOM   1052  CG1 ILE A 253      23.570  -1.896  24.328  1.00  92.70      A   C
ATOM   1053  CD1 ILE A 253      22.235  -2.475  23.897  1.00  90.25      A   C
ATOM   1054  C   ILE A 253      23.674   1.861  23.421  1.00  97.77      A   C
ATOM   1055  O   ILE A 253      23.788   1.801  22.197  1.00  98.28      A   O
ATOM   1056  N   HIS A 254      23.857   2.983  24.112  1.00  97.86      A   N
ATOM   1057  CA  HIS A 254      24.210   4.241  23.459  1.00  97.97      A   C
ATOM   1058  CB  HIS A 254      23.833   5.421  24.358  1.00  99.21      A   C
ATOM   1059  CG  HIS A 254      22.892   6.392  23.715  1.00 105.22      A   C
ATOM   1060  CD2 HIS A 254      21.629   6.755  24.041  1.00 107.77      A   C
ATOM   1061  ND1 HIS A 254      23.224   7.116  22.592  1.00 108.31      A   N
ATOM   1062  CE1 HIS A 254      22.204   7.886  22.252  1.00 110.97      A   C
ATOM   1063  NE2 HIS A 254      21.225   7.686  23.114  1.00 111.77      A   N
ATOM   1064  C   HIS A 254      25.693   4.315  23.114  1.00  96.74      A   C
ATOM   1065  O   HIS A 254      26.154   3.641  22.191  1.00  95.57      A   O
ATOM   1066  N   ARG A 255      26.422   5.149  23.854  1.00  94.48      A   N
ATOM   1067  CA  ARG A 255      27.862   5.346  23.682  1.00  94.14      A   C
ATOM   1068  CB  ARG A 255      28.522   4.112  23.052  1.00  91.58      A   C
ATOM   1075  C   ARG A 255      28.253   6.587  22.885  1.00  95.07      A   C
```

Figure 1R

| ATOM | 1076 | O   | ARG | A | 255 | 27.500 | 7.561  | 22.814 | 1.00 | 91.67  | A | O |
|------|------|-----|-----|---|-----|--------|--------|--------|------|--------|---|---|
| ATOM | 1077 | N   | ASP | A | 256 | 29.437 | 6.521  | 22.277 | 1.00 | 97.41  | A | N |
| ATOM | 1078 | CA  | ASP | A | 256 | 30.020 | 7.626  | 21.522 | 1.00 | 94.96  | A | C |
| ATOM | 1079 | CB  | ASP | A | 256 | 29.500 | 7.707  | 20.087 | 1.00 | 97.08  | A | C |
| ATOM | 1080 | CG  | ASP | A | 256 | 30.518 | 8.346  | 19.143 | 1.00 | 98.93  | A | C |
| ATOM | 1081 | OD1 | ASP | A | 256 | 31.440 | 9.039  | 19.629 | 1.00 | 95.83  | A | O |
| ATOM | 1082 | OD2 | ASP | A | 256 | 30.399 | 8.156  | 17.915 | 1.00 | 101.47 | A | O |
| ATOM | 1083 | C   | ASP | A | 256 | 29.718 | 8.911  | 22.262 | 1.00 | 92.06  | A | C |
| ATOM | 1084 | O   | ASP | A | 256 | 29.588 | 9.987  | 21.675 | 1.00 | 88.97  | A | O |
| ATOM | 1085 | N   | ILE | A | 257 | 29.564 | 8.756  | 23.571 | 1.00 | 89.62  | A | N |
| ATOM | 1086 | CA  | ILE | A | 257 | 29.340 | 9.865  | 24.467 | 1.00 | 85.97  | A | C |
| ATOM | 1087 | CB  | ILE | A | 257 | 28.961 | 9.383  | 25.880 | 1.00 | 81.37  | A | C |
| ATOM | 1088 | CG2 | ILE | A | 257 | 27.495 | 8.971  | 25.926 | 1.00 | 81.99  | A | C |
| ATOM | 1089 | CG1 | ILE | A | 257 | 29.873 | 8.214  | 26.271 | 1.00 | 77.22  | A | C |
| ATOM | 1090 | CD1 | ILE | A | 257 | 30.242 | 8.157  | 27.734 | 1.00 | 73.68  | A | C |
| ATOM | 1091 | C   | ILE | A | 257 | 30.768 | 10.371 | 24.508 | 1.00 | 87.10  | A | C |
| ATOM | 1092 | O   | ILE | A | 257 | 31.689 | 9.632  | 24.161 | 1.00 | 91.22  | A | O |
| ATOM | 1093 | N   | LYS | A | 258 | 30.954 | 11.615 | 24.919 | 1.00 | 83.96  | A | N |
| ATOM | 1094 | CA  | LYS | A | 258 | 32.279 | 12.208 | 25.015 | 1.00 | 78.70  | A | C |
| ATOM | 1095 | CB  | LYS | A | 258 | 33.169 | 11.812 | 23.818 | 1.00 | 73.98  | A | C |
| ATOM | 1096 | CG  | LYS | A | 258 | 32.542 | 11.903 | 22.430 | 1.00 | 72.21  | A | C |
| ATOM | 1097 | CD  | LYS | A | 258 | 33.399 | 11.130 | 21.423 | 1.00 | 72.30  | A | C |
| ATOM | 1098 | CE  | LYS | A | 258 | 33.288 | 11.680 | 20.007 | 1.00 | 69.20  | A | C |
| ATOM | 1099 | NZ  | LYS | A | 258 | 34.457 | 11.286 | 19.164 | 1.00 | 70.94  | A | N |
| ATOM | 1100 | C   | LYS | A | 258 | 32.119 | 13.711 | 25.095 | 1.00 | 77.42  | A | C |
| ATOM | 1101 | O   | LYS | A | 258 | 31.096 | 14.253 | 24.680 | 1.00 | 75.43  | A | O |
| ATOM | 1102 | N   | PRO | A | 259 | 33.127 | 14.406 | 25.642 | 1.00 | 77.43  | A | N |
| ATOM | 1103 | CD  | PRO | A | 259 | 34.496 | 13.904 | 25.867 | 1.00 | 77.13  | A | C |
| ATOM | 1104 | CA  | PRO | A | 259 | 33.086 | 15.861 | 25.780 | 1.00 | 77.33  | A | C |
| ATOM | 1105 | CB  | PRO | A | 259 | 34.551 | 16.244 | 25.631 | 1.00 | 77.11  | A | C |
| ATOM | 1106 | CG  | PRO | A | 259 | 35.225 | 15.137 | 26.373 | 1.00 | 77.96  | A | C |
| ATOM | 1107 | C   | PRO | A | 259 | 32.181 | 16.552 | 24.762 | 1.00 | 76.08  | A | C |
| ATOM | 1108 | O   | PRO | A | 259 | 31.202 | 17.201 | 25.128 | 1.00 | 77.45  | A | O |
| ATOM | 1109 | N   | GLU | A | 260 | 32.500 | 16.376 | 23.485 | 1.00 | 74.03  | A | N |
| ATOM | 1110 | CA  | GLU | A | 260 | 31.749 | 16.992 | 22.396 | 1.00 | 73.63  | A | C |
| ATOM | 1111 | CB  | GLU | A | 260 | 32.343 | 16.561 | 21.050 | 1.00 | 76.31  | A | C |
| ATOM | 1112 | CG  | GLU | A | 260 | 33.860 | 16.651 | 20.984 | 1.00 | 80.27  | A | C |
| ATOM | 1113 | CD  | GLU | A | 260 | 34.533 | 15.298 | 21.126 | 1.00 | 82.34  | A | C |
| ATOM | 1114 | OE1 | GLU | A | 260 | 35.646 | 15.240 | 21.688 | 1.00 | 81.73  | A | O |
| ATOM | 1115 | OE2 | GLU | A | 260 | 33.955 | 14.293 | 20.663 | 1.00 | 85.70  | A | O |
| ATOM | 1116 | C   | GLU | A | 260 | 30.241 | 16.733 | 22.376 | 1.00 | 71.66  | A | C |
| ATOM | 1117 | O   | GLU | A | 260 | 29.480 | 17.571 | 21.897 | 1.00 | 73.66  | A | O |
| ATOM | 1118 | N   | ASN | A | 261 | 29.802 | 15.587 | 22.889 | 1.00 | 67.69  | A | N |
| ATOM | 1119 | CA  | ASN | A | 261 | 28.376 | 15.261 | 22.872 | 1.00 | 65.95  | A | C |
| ATOM | 1120 | CB  | ASN | A | 261 | 28.164 | 13.921 | 22.159 | 1.00 | 67.65  | A | C |
| ATOM | 1121 | CG  | ASN | A | 261 | 28.806 | 13.885 | 20.783 | 1.00 | 70.09  | A | C |
| ATOM | 1122 | OD1 | ASN | A | 261 | 28.497 | 14.706 | 19.919 | 1.00 | 72.78  | A | O |
| ATOM | 1123 | ND2 | ASN | A | 261 | 29.707 | 12.931 | 20.575 | 1.00 | 70.72  | A | N |
| ATOM | 1124 | C   | ASN | A | 261 | 27.702 | 15.227 | 24.244 | 1.00 | 64.57  | A | C |
| ATOM | 1125 | O   | ASN | A | 261 | 26.623 | 14.654 | 24.399 | 1.00 | 64.11  | A | O |
| ATOM | 1126 | N   | LEU | A | 262 | 28.332 | 15.845 | 25.236 | 1.00 | 63.53  | A | N |
| ATOM | 1127 | CA  | LEU | A | 262 | 27.771 | 15.875 | 26.582 | 1.00 | 64.28  | A | C |
| ATOM | 1128 | CB  | LEU | A | 262 | 28.715 | 15.170 | 27.556 | 1.00 | 62.90  | A | C |
| ATOM | 1129 | CG  | LEU | A | 262 | 28.917 | 13.670 | 27.318 | 1.00 | 59.58  | A | C |
| ATOM | 1130 | CD1 | LEU | A | 262 | 30.129 | 13.197 | 28.097 | 1.00 | 55.63  | A | C |
| ATOM | 1131 | CD2 | LEU | A | 262 | 27.671 | 12.897 | 27.730 | 1.00 | 57.08  | A | C |
| ATOM | 1132 | C   | LEU | A | 262 | 27.513 | 17.311 | 27.038 | 1.00 | 64.94  | A | C |
| ATOM | 1133 | O   | LEU | A | 262 | 28.437 | 18.118 | 27.142 | 1.00 | 65.55  | A | O |
| ATOM | 1134 | N   | LEU | A | 263 | 26.250 | 17.622 | 27.310 | 1.00 | 63.24  | A | N |
| ATOM | 1135 | CA  | LEU | A | 263 | 25.871 | 18.962 | 27.737 | 1.00 | 62.23  | A | C |
| ATOM | 1136 | CB  | LEU | A | 263 | 24.546 | 19.358 | 27.079 | 1.00 | 63.99  | A | C |

Figure 1S

```
ATOM   1137  CG   LEU A 263      24.519  19.344  25.546  1.00  62.68      A    C
ATOM   1138  CD1  LEU A 263      23.095  19.572  25.066  1.00  63.40      A    C
ATOM   1139  CD2  LEU A 263      25.454  20.415  24.992  1.00  59.47      A    C
ATOM   1140  C    LEU A 263      25.755  19.088  29.252  1.00  61.46      A    C
ATOM   1141  O    LEU A 263      25.645  18.092  29.965  1.00  60.18      A    O
ATOM   1142  N    LEU A 264      25.782  20.326  29.734  1.00  62.60      A    N
ATOM   1143  CA   LEU A 264      25.683  20.599  31.162  1.00  66.05      A    C
ATOM   1144  CB   LEU A 264      26.950  21.311  31.643  1.00  62.69      A    C
ATOM   1145  CG   LEU A 264      28.259  20.571  31.349  1.00  62.68      A    C
ATOM   1146  CD1  LEU A 264      29.441  21.501  31.555  1.00  61.04      A    C
ATOM   1147  CD2  LEU A 264      28.368  19.345  32.241  1.00  63.10      A    C
ATOM   1148  C    LEU A 264      24.459  21.464  31.446  1.00  71.25      A    C
ATOM   1149  O    LEU A 264      24.304  22.544  30.875  1.00  72.79      A    O
ATOM   1150  N    GLY A 265      23.592  20.981  32.330  1.00  74.49      A    N
ATOM   1151  CA   GLY A 265      22.386  21.716  32.668  1.00  77.02      A    C
ATOM   1152  C    GLY A 265      22.623  22.958  33.509  1.00  80.14      A    C
ATOM   1153  O    GLY A 265      23.671  23.597  33.411  1.00  79.51      A    O
ATOM   1154  N    SER A 266      21.641  23.297  34.339  1.00  82.00      A    N
ATOM   1155  CA   SER A 266      21.729  24.471  35.201  1.00  84.92      A    C
ATOM   1156  CB   SER A 266      20.334  24.871  35.689  1.00  84.90      A    C
ATOM   1157  OG   SER A 266      19.472  25.160  34.601  1.00  90.15      A    O
ATOM   1158  C    SER A 266      22.638  24.228  36.401  1.00  87.00      A    C
ATOM   1159  O    SER A 266      23.466  25.072  36.742  1.00  90.66      A    O
ATOM   1160  N    ALA A 267      22.482  23.074  37.040  1.00  86.96      A    N
ATOM   1161  CA   ALA A 267      23.293  22.736  38.204  1.00  87.35      A    C
ATOM   1162  CB   ALA A 267      22.523  21.792  39.115  1.00  88.52      A    C
ATOM   1163  C    ALA A 267      24.612  22.095  37.792  1.00  87.15      A    C
ATOM   1164  O    ALA A 267      25.231  21.376  38.573  1.00  87.84      A    O
ATOM   1165  N    GLY A 268      25.047  22.360  36.566  1.00  85.80      A    N
ATOM   1166  CA   GLY A 268      26.287  21.769  36.101  1.00  83.82      A    C
ATOM   1167  C    GLY A 268      26.122  20.267  35.969  1.00  82.41      A    C
ATOM   1168  O    GLY A 268      27.097  19.533  35.810  1.00  82.61      A    O
ATOM   1169  N    GLU A 269      24.875  19.810  36.045  1.00  80.23      A    N
ATOM   1170  CA   GLU A 269      24.567  18.390  35.923  1.00  81.12      A    C
ATOM   1171  CB   GLU A 269      23.108  18.123  36.315  1.00  84.16      A    C
ATOM   1172  CG   GLU A 269      22.304  19.373  36.648  1.00  88.34      A    C
ATOM   1173  CD   GLU A 269      21.110  19.568  35.731  1.00  89.21      A    C
ATOM   1174  OE1  GLU A 269      20.270  18.649  35.639  1.00  91.10      A    O
ATOM   1175  OE2  GLU A 269      21.008  20.645  35.106  1.00  85.80      A    O
ATOM   1176  C    GLU A 269      24.807  17.936  34.489  1.00  81.41      A    C
ATOM   1177  O    GLU A 269      24.502  18.662  33.544  1.00  81.45      A    O
ATOM   1178  N    LEU A 270      25.363  16.739  34.329  1.00  82.53      A    N
ATOM   1179  CA   LEU A 270      25.636  16.204  33.002  1.00  85.63      A    C
ATOM   1180  CB   LEU A 270      26.484  14.932  33.097  1.00  87.10      A    C
ATOM   1181  CG   LEU A 270      27.981  15.088  32.820  1.00  86.77      A    C
ATOM   1182  CD1  LEU A 270      28.715  13.802  33.169  1.00  86.80      A    C
ATOM   1183  CD2  LEU A 270      28.181  15.433  31.353  1.00  86.46      A    C
ATOM   1184  C    LEU A 270      24.355  15.898  32.244  1.00  86.17      A    C
ATOM   1185  O    LEU A 270      23.266  15.881  32.814  1.00  89.09      A    O
ATOM   1186  N    LYS A 271      24.506  15.663  30.947  1.00  84.70      A    N
ATOM   1187  CA   LYS A 271      23.392  15.341  30.067  1.00  85.02      A    C
ATOM   1188  CB   LYS A 271      22.634  16.605  29.646  1.00  80.67      A    C
ATOM   1189  CG   LYS A 271      21.963  17.402  30.755  1.00  78.60      A    C
ATOM   1190  CD   LYS A 271      20.652  16.785  31.212  1.00  78.50      A    C
ATOM   1191  CE   LYS A 271      19.659  17.870  31.620  1.00  78.81      A    C
ATOM   1192  NZ   LYS A 271      19.404  17.896  33.089  1.00  85.61      A    N
ATOM   1193  C    LYS A 271      24.014  14.727  28.822  1.00  89.00      A    C
ATOM   1194  O    LYS A 271      25.011  15.242  28.315  1.00  89.64      A    O
ATOM   1195  N    ILE A 272      23.446  13.628  28.335  1.00  94.42      A    N
ATOM   1196  CA   ILE A 272      23.964  13.009  27.120  1.00  98.28      A    C
ATOM   1197  CB   ILE A 272      24.049  11.454  27.220  1.00  96.97      A    C
```

Figure 1T

```
ATOM   1198  CG2 ILE A 272      24.325  11.037  28.657  1.00  96.63      A   C
ATOM   1199  CG1 ILE A 272      22.753  10.809  26.724  1.00  94.52      A   C
ATOM   1200  CD1 ILE A 272      22.980   9.676  25.736  1.00  90.80      A   C
ATOM   1201  C   ILE A 272      23.012  13.390  25.991  1.00  99.75      A   C
ATOM   1202  O   ILE A 272      21.837  13.675  26.228  1.00  98.91      A   O
ATOM   1203  N   ALA A 273      23.527  13.409  24.768  1.00 100.92      A   N
ATOM   1204  CA  ALA A 273      22.720  13.759  23.607  1.00 101.66      A   C
ATOM   1205  CB  ALA A 273      22.537  15.265  23.542  1.00 100.28      A   C
ATOM   1206  C   ALA A 273      23.399  13.250  22.342  1.00 103.46      A   C
ATOM   1207  O   ALA A 273      24.553  13.583  22.072  1.00 103.70      A   O
ATOM   1208  N   ASP A 274      22.675  12.454  21.560  1.00 104.59      A   N
ATOM   1209  CA  ASP A 274      23.232  11.880  20.341  1.00 103.89      A   C
ATOM   1210  CB  ASP A 274      23.296  10.358  20.480  1.00  97.97      A   C
ATOM   1211  CG  ASP A 274      24.596   9.886  21.093  1.00  95.56      A   C
ATOM   1212  OD1 ASP A 274      25.621   9.898  20.379  1.00  95.42      A   O
ATOM   1213  OD2 ASP A 274      24.598   9.508  22.283  1.00  93.78      A   O
ATOM   1214  C   ASP A 274      22.557  12.232  19.016  1.00 106.91      A   C
ATOM   1215  O   ASP A 274      22.713  13.339  18.501  1.00 108.26      A   O
ATOM   1216  N   PHE A 275      21.800  11.273  18.484  1.00 108.56      A   N
ATOM   1217  CA  PHE A 275      21.117  11.401  17.198  1.00 108.63      A   C
ATOM   1218  CB  PHE A 275      19.749  12.104  17.338  1.00 108.66      A   C
ATOM   1219  CG  PHE A 275      19.718  13.212  18.348  1.00 111.57      A   C
ATOM   1220  CD1 PHE A 275      19.592  12.937  19.707  1.00 112.94      A   C
ATOM   1221  CD2 PHE A 275      19.814  14.534  17.938  1.00 111.92      A   C
ATOM   1222  CE1 PHE A 275      19.569  13.967  20.640  1.00 112.27      A   C
ATOM   1223  CE2 PHE A 275      19.792  15.566  18.863  1.00 112.32      A   C
ATOM   1224  CZ  PHE A 275      19.668  15.280  20.216  1.00 112.23      A   C
ATOM   1225  C   PHE A 275      21.995  12.082  16.145  1.00 107.62      A   C
ATOM   1226  O   PHE A 275      21.513  12.791  15.260  1.00 106.19      A   O
ATOM   1227  N   GLY A 276      23.298  11.826  16.269  1.00 107.26      A   N
ATOM   1228  CA  GLY A 276      24.313  12.343  15.361  1.00 105.49      A   C
ATOM   1229  C   GLY A 276      24.299  13.802  14.948  1.00 106.32      A   C
ATOM   1230  O   GLY A 276      23.305  14.294  14.413  1.00 103.73      A   O
ATOM   1231  N   TRP A 277      25.411  14.498  15.185  1.00 109.28      A   N
ATOM   1232  CA  TRP A 277      25.510  15.901  14.801  1.00 113.03      A   C
ATOM   1233  CB  TRP A 277      24.597  16.764  15.687  1.00 116.38      A   C
ATOM   1234  CG  TRP A 277      25.106  17.152  17.047  1.00 119.83      A   C
ATOM   1235  CD2 TRP A 277      24.380  17.069  18.279  1.00 120.48      A   C
ATOM   1236  CE2 TRP A 277      25.176  17.672  19.278  1.00 120.99      A   C
ATOM   1237  CE3 TRP A 277      23.128  16.553  18.634  1.00 119.93      A   C
ATOM   1238  CD1 TRP A 277      26.286  17.773  17.341  1.00 120.79      A   C
ATOM   1239  NE1 TRP A 277      26.335  18.092  18.681  1.00 119.88      A   N
ATOM   1240  CZ2 TRP A 277      24.761  17.767  20.609  1.00 122.14      A   C
ATOM   1241  CZ3 TRP A 277      22.716  16.648  19.955  1.00 121.05      A   C
ATOM   1242  CH2 TRP A 277      23.530  17.253  20.926  1.00 123.58      A   C
ATOM   1243  C   TRP A 277      26.919  16.495  14.761  1.00 113.86      A   C
ATOM   1244  O   TRP A 277      27.898  15.860  15.158  1.00 112.61      A   O
ATOM   1245  N   SER A 278      26.993  17.729  14.268  1.00 114.18      A   N
ATOM   1246  CA  SER A 278      28.243  18.469  14.134  1.00 111.58      A   C
ATOM   1247  CB  SER A 278      28.062  19.590  13.105  1.00 108.42      A   C
ATOM   1248  OG  SER A 278      29.254  20.333  12.917  1.00 102.59      A   O
ATOM   1249  C   SER A 278      28.682  19.056  15.473  1.00 111.28      A   C
ATOM   1250  O   SER A 278      29.069  20.222  15.557  1.00 109.28      A   O
ATOM   1251  N   CYS A 290      42.402  12.691  15.198  1.00 109.15      A   N
ATOM   1252  CA  CYS A 290      41.980  11.295  15.190  1.00 109.38      A   C
ATOM   1253  CB  CYS A 290      43.138  10.393  15.619  1.00 112.80      A   C
ATOM   1254  SG  CYS A 290      44.588  10.476  14.546  1.00 116.21      A   S
ATOM   1255  C   CYS A 290      40.807  11.096  16.141  1.00 107.53      A   C
ATOM   1256  O   CYS A 290      40.578   9.993  16.637  1.00 107.57      A   O
ATOM   1257  N   GLY A 291      40.067  12.174  16.384  1.00 105.63      A   N
ATOM   1258  CA  GLY A 291      38.930  12.122  17.287  1.00 103.04      A   C
```

Figure 1U

```
ATOM   1259  C    GLY A 291      37.801  11.188  16.893  1.00  99.11      A  C
ATOM   1260  O    GLY A 291      36.746  11.190  17.529  1.00  99.15      A  O
ATOM   1261  N    THR A 292      38.009  10.392  15.848  1.00  95.20      A  N
ATOM   1262  CA   THR A 292      36.992   9.450  15.391  1.00  89.55      A  C
ATOM   1263  CB   THR A 292      37.013   9.291  13.855  1.00  87.32      A  C
ATOM   1264  OG1  THR A 292      38.240   8.668  13.456  1.00  87.47      A  O
ATOM   1265  CG2  THR A 292      36.892  10.648  13.173  1.00  84.15      A  C
ATOM   1266  C    THR A 292      37.218   8.075  16.020  1.00  86.28      A  C
ATOM   1267  O    THR A 292      36.278   7.445  16.502  1.00  86.04      A  O
ATOM   1268  N    LEU A 293      38.466   7.615  16.013  1.00  80.57      A  N
ATOM   1269  CA   LEU A 293      38.811   6.314  16.587  1.00  72.64      A  C
ATOM   1270  CB   LEU A 293      40.112   5.777  15.977  1.00  70.14      A  C
ATOM   1271  CG   LEU A 293      40.152   5.118  14.599  1.00  72.57      A  C
ATOM   1272  CD1  LEU A 293      41.548   4.554  14.395  1.00  69.12      A  C
ATOM   1273  CD2  LEU A 293      39.122   4.009  14.537  1.00  73.26      A  C
ATOM   1274  C    LEU A 293      38.997   6.370  18.102  1.00  70.44      A  C
ATOM   1275  O    LEU A 293      38.763   5.387  18.802  1.00  70.20      A  O
ATOM   1276  N    ASP A 294      39.419   7.530  18.593  1.00  70.63      A  N
ATOM   1277  CA   ASP A 294      39.703   7.749  20.010  1.00  68.26      A  C
ATOM   1278  CB   ASP A 294      39.928   9.241  20.268  1.00  65.94      A  C
ATOM   1279  CG   ASP A 294      41.374   9.648  20.079  1.00  66.75      A  C
ATOM   1280  OD1  ASP A 294      41.778   9.924  18.930  1.00  66.44      A  O
ATOM   1281  OD2  ASP A 294      42.110   9.675  21.087  1.00  70.87      A  O
ATOM   1282  C    ASP A 294      38.797   7.199  21.112  1.00  66.91      A  C
ATOM   1283  O    ASP A 294      39.234   7.104  22.257  1.00  62.67      A  O
ATOM   1284  N    TYR A 295      37.553   6.847  20.809  1.00  69.98      A  N
ATOM   1285  CA   TYR A 295      36.680   6.318  21.855  1.00  72.30      A  C
ATOM   1286  CB   TYR A 295      35.536   7.296  22.146  1.00  73.70      A  C
ATOM   1287  CG   TYR A 295      35.936   8.450  23.044  1.00  73.37      A  C
ATOM   1288  CD1  TYR A 295      36.924   9.354  22.654  1.00  75.69      A  C
ATOM   1289  CE1  TYR A 295      37.302  10.411  23.483  1.00  75.51      A  C
ATOM   1290  CD2  TYR A 295      35.334   8.630  24.291  1.00  69.24      A  C
ATOM   1291  CE2  TYR A 295      35.705   9.683  25.127  1.00  70.87      A  C
ATOM   1292  CZ   TYR A 295      36.688  10.568  24.717  1.00  74.03      A  C
ATOM   1293  OH   TYR A 295      37.052  11.609  25.537  1.00  77.13      A  O
ATOM   1294  C    TYR A 295      36.121   4.938  21.542  1.00  71.27      A  C
ATOM   1295  O    TYR A 295      35.519   4.290  22.401  1.00  70.55      A  O
ATOM   1296  N    LEU A 296      36.330   4.489  20.310  1.00  66.62      A  N
ATOM   1297  CA   LEU A 296      35.858   3.179  19.890  1.00  62.00      A  C
ATOM   1298  CB   LEU A 296      36.080   2.995  18.390  1.00  59.67      A  C
ATOM   1299  CG   LEU A 296      35.424   4.017  17.464  1.00  57.94      A  C
ATOM   1300  CD1  LEU A 296      35.794   3.706  16.025  1.00  59.45      A  C
ATOM   1301  CD2  LEU A 296      33.916   3.985  17.651  1.00  58.03      A  C
ATOM   1302  C    LEU A 296      36.620   2.097  20.642  1.00  62.36      A  C
ATOM   1303  O    LEU A 296      37.834   2.193  20.818  1.00  60.84      A  O
ATOM   1304  N    PRO A 297      35.916   1.056  21.109  1.00  62.57      A  N
ATOM   1305  CD   PRO A 297      34.467   0.797  21.025  1.00  62.94      A  C
ATOM   1306  CA   PRO A 297      36.594  -0.019  21.834  1.00  59.56      A  C
ATOM   1307  CB   PRO A 297      35.439  -0.769  22.480  1.00  59.60      A  C
ATOM   1308  CG   PRO A 297      34.374  -0.662  21.432  1.00  58.84      A  C
ATOM   1309  C    PRO A 297      37.355  -0.881  20.834  1.00  59.80      A  C
ATOM   1310  O    PRO A 297      37.229  -0.692  19.624  1.00  60.49      A  O
ATOM   1311  N    PRO A 298      38.163  -1.833  21.322  1.00  60.93      A  N
ATOM   1312  CD   PRO A 298      38.693  -1.987  22.689  1.00  61.40      A  C
ATOM   1313  CA   PRO A 298      38.904  -2.677  20.383  1.00  60.77      A  C
ATOM   1314  CB   PRO A 298      39.782  -3.522  21.302  1.00  58.81      A  C
ATOM   1315  CG   PRO A 298      40.061  -2.586  22.433  1.00  58.46      A  C
ATOM   1316  C    PRO A 298      38.008  -3.534  19.488  1.00  63.91      A  C
ATOM   1317  O    PRO A 298      38.336  -3.769  18.325  1.00  61.30      A  O
ATOM   1318  N    GLU A 299      36.873  -3.983  20.019  1.00  68.47      A  N
ATOM   1319  CA   GLU A 299      35.975  -4.835  19.245  1.00  72.05      A  C
```

Figure 1V

```
ATOM   1320  CB   GLU A 299      34.887  -5.459  20.138  1.00  75.53      A    C
ATOM   1321  CG   GLU A 299      33.970  -4.502  20.885  1.00  79.40      A    C
ATOM   1322  CD   GLU A 299      34.429  -4.256  22.306  1.00  81.50      A    C
ATOM   1323  OE1  GLU A 299      33.574  -4.247  23.217  1.00  83.14      A    O
ATOM   1324  OE2  GLU A 299      35.646  -4.067  22.511  1.00  81.72      A    O
ATOM   1325  C    GLU A 299      35.324  -4.219  18.008  1.00  72.43      A    C
ATOM   1326  O    GLU A 299      35.037  -4.939  17.053  1.00  72.29      A    O
ATOM   1327  N    MET A 300      35.082  -2.909  17.999  1.00  75.36      A    N
ATOM   1328  CA   MET A 300      34.468  -2.308  16.815  1.00  79.51      A    C
ATOM   1329  CB   MET A 300      33.671  -1.044  17.152  1.00  86.80      A    C
ATOM   1330  CG   MET A 300      32.578  -0.759  16.111  1.00  98.28      A    C
ATOM   1331  SD   MET A 300      32.363   0.967  15.636  1.00 110.98      A    S
ATOM   1332  CE   MET A 300      33.232   0.986  14.045  1.00 106.30      A    C
ATOM   1333  C    MET A 300      35.500  -1.958  15.751  1.00  77.49      A    C
ATOM   1334  O    MET A 300      35.314  -2.271  14.577  1.00  80.56      A    O
ATOM   1335  N    ILE A 301      36.583  -1.300  16.151  1.00  73.12      A    N
ATOM   1336  CA   ILE A 301      37.615  -0.934  15.190  1.00  73.24      A    C
ATOM   1337  CB   ILE A 301      38.836  -0.274  15.870  1.00  73.32      A    C
ATOM   1338  CG2  ILE A 301      38.367   0.738  16.899  1.00  73.00      A    C
ATOM   1339  CG1  ILE A 301      39.714  -1.336  16.536  1.00  74.96      A    C
ATOM   1340  CD1  ILE A 301      41.045  -0.806  17.027  1.00  71.37      A    C
ATOM   1341  C    ILE A 301      38.074  -2.212  14.503  1.00  73.93      A    C
ATOM   1342  O    ILE A 301      38.520  -2.191  13.356  1.00  71.39      A    O
ATOM   1343  N    GLU A 302      37.948  -3.322  15.225  1.00  76.64      A    N
ATOM   1344  CA   GLU A 302      38.341  -4.634  14.729  1.00  77.44      A    C
ATOM   1345  CB   GLU A 302      38.755  -5.527  15.904  1.00  75.82      A    C
ATOM   1346  CG   GLU A 302      40.258  -5.565  16.138  1.00  77.10      A    C
ATOM   1347  CD   GLU A 302      40.630  -6.124  17.495  1.00  77.22      A    C
ATOM   1348  OE1  GLU A 302      40.044  -7.148  17.899  1.00  75.06      A    O
ATOM   1349  OE2  GLU A 302      41.517  -5.542  18.154  1.00  76.89      A    O
ATOM   1350  C    GLU A 302      37.255  -5.320  13.901  1.00  78.88      A    C
ATOM   1351  O    GLU A 302      37.541  -6.254  13.154  1.00  77.29      A    O
ATOM   1352  N    GLY A 303      36.014  -4.858  14.033  1.00  82.09      A    N
ATOM   1353  CA   GLY A 303      34.920  -5.435  13.267  1.00  81.95      A    C
ATOM   1354  C    GLY A 303      34.081  -6.461  14.005  1.00  82.32      A    C
ATOM   1355  O    GLY A 303      32.934  -6.720  13.633  1.00  83.26      A    O
ATOM   1356  N    ARG A 304      34.654  -7.046  15.050  1.00  82.72      A    N
ATOM   1357  CA   ARG A 304      33.971  -8.056  15.853  1.00  82.93      A    C
ATOM   1358  CB   ARG A 304      34.820  -8.398  17.079  1.00  84.98      A    C
ATOM   1359  CG   ARG A 304      36.199  -8.944  16.743  1.00  91.84      A    C
ATOM   1360  CD   ARG A 304      37.177  -8.724  17.885  1.00 100.66      A    C
ATOM   1361  NE   ARG A 304      38.418  -9.470  17.699  1.00 111.07      A    N
ATOM   1362  CZ   ARG A 304      39.408  -9.504  18.585  1.00 114.58      A    C
ATOM   1363  NH1  ARG A 304      40.500 -10.212  18.333  1.00 116.75      A    N
ATOM   1364  NH2  ARG A 304      39.313  -8.820  19.718  1.00 113.67      A    N
ATOM   1365  C    ARG A 304      32.581  -7.611  16.301  1.00  81.93      A    C
ATOM   1366  O    ARG A 304      32.138  -6.506  15.998  1.00  78.99      A    O
ATOM   1367  N    MET A 305      31.901  -8.480  17.044  1.00  82.97      A    N
ATOM   1368  CA   MET A 305      30.558  -8.190  17.530  1.00  85.52      A    C
ATOM   1369  CB   MET A 305      29.726  -9.476  17.560  1.00  86.07      A    C
ATOM   1373  C    MET A 305      30.555  -7.547  18.915  1.00  88.79      A    C
ATOM   1374  O    MET A 305      30.855  -8.195  19.918  1.00  86.40      A    O
ATOM   1375  N    HIS A 306      30.211  -6.264  18.953  1.00  94.28      A    N
ATOM   1376  CA   HIS A 306      30.143  -5.495  20.193  1.00  99.57      A    C
ATOM   1377  CB   HIS A 306      30.321  -4.011  19.887  1.00 103.72      A    C
ATOM   1378  CG   HIS A 306      29.182  -3.428  19.108  1.00 107.47      A    C
ATOM   1379  CD2  HIS A 306      28.265  -2.488  19.436  1.00 108.68      A    C
ATOM   1380  ND1  HIS A 306      28.860  -3.852  17.837  1.00 108.46      A    N
ATOM   1381  CE1  HIS A 306      27.791  -3.198  17.415  1.00 107.45      A    C
ATOM   1382  NE2  HIS A 306      27.411  -2.366  18.366  1.00 108.27      A    N
ATOM   1383  C    HIS A 306      28.753  -5.697  20.784  1.00 101.39      A    C
```

Figure 1W

```
ATOM   1384  O    HIS A 306      27.893  -6.295  20.138  1.00  103.87      A    O
ATOM   1385  N    ASP A 307      28.536  -5.192  21.998  1.00  101.02      A    N
ATOM   1386  CA   ASP A 307      27.233  -5.291  22.652  1.00   98.62      A    C
ATOM   1387  CB   ASP A 307      26.618  -6.677  22.436  1.00  107.40      A    C
ATOM   1388  CG   ASP A 307      25.143  -6.610  22.088  1.00  113.35      A    C
ATOM   1389  OD1  ASP A 307      24.815  -6.166  20.966  1.00  113.31      A    O
ATOM   1390  OD2  ASP A 307      24.312  -6.995  22.936  1.00  116.92      A    O
ATOM   1391  C    ASP A 307      27.226  -4.991  24.147  1.00   92.83      A    C
ATOM   1392  O    ASP A 307      27.757  -5.762  24.947  1.00   89.55      A    O
ATOM   1393  N    GLU A 308      26.621  -3.864  24.512  1.00   87.84      A    N
ATOM   1394  CA   GLU A 308      26.485  -3.470  25.912  1.00   84.64      A    C
ATOM   1395  CB   GLU A 308      25.673  -4.546  26.645  1.00   84.79      A    C
ATOM   1396  CG   GLU A 308      25.769  -4.523  28.160  1.00   85.31      A    C
ATOM   1397  CD   GLU A 308      26.179  -5.874  28.723  1.00   86.21      A    C
ATOM   1398  OE1  GLU A 308      25.559  -6.895  28.351  1.00   86.01      A    O
ATOM   1399  OE2  GLU A 308      27.123  -5.917  29.539  1.00   87.12      A    O
ATOM   1400  C    GLU A 308      27.778  -3.179  26.686  1.00   82.84      A    C
ATOM   1401  O    GLU A 308      27.778  -2.328  27.576  1.00   81.84      A    O
ATOM   1402  N    LYS A 309      28.853  -3.875  26.359  1.00   81.92      A    N
ATOM   1403  CA   LYS A 309      30.112  -3.669  27.068  1.00   79.59      A    C
ATOM   1404  CB   LYS A 309      30.992  -4.918  26.963  1.00   80.41      A    C
ATOM   1405  CG   LYS A 309      30.671  -5.953  28.028  1.00   83.88      A    C
ATOM   1406  CD   LYS A 309      30.609  -5.281  29.397  1.00   88.76      A    C
ATOM   1407  CE   LYS A 309      30.083  -6.206  30.485  1.00   91.71      A    C
ATOM   1408  NZ   LYS A 309      31.157  -6.822  31.309  1.00   90.42      A    N
ATOM   1409  C    LYS A 309      30.913  -2.450  26.645  1.00   76.97      A    C
ATOM   1410  O    LYS A 309      31.588  -1.829  27.465  1.00   77.18      A    O
ATOM   1411  N    VAL A 310      30.836  -2.105  25.367  1.00   74.98      A    N
ATOM   1412  CA   VAL A 310      31.567  -0.959  24.846  1.00   74.68      A    C
ATOM   1413  CB   VAL A 310      31.032  -0.548  23.463  1.00   74.56      A    C
ATOM   1414  CG1  VAL A 310      31.131  -1.719  22.502  1.00   74.14      A    C
ATOM   1415  CG2  VAL A 310      29.594  -0.076  23.585  1.00   75.32      A    C
ATOM   1416  C    VAL A 310      31.505   0.259  25.765  1.00   75.81      A    C
ATOM   1417  O    VAL A 310      32.489   0.985  25.904  1.00   78.46      A    O
ATOM   1418  N    ASP A 311      30.354   0.476  26.395  1.00   75.34      A    N
ATOM   1419  CA   ASP A 311      30.177   1.625  27.278  1.00   73.08      A    C
ATOM   1420  CB   ASP A 311      28.745   1.669  27.812  1.00   80.08      A    C
ATOM   1421  CG   ASP A 311      27.734   1.958  26.722  1.00   85.72      A    C
ATOM   1422  OD1  ASP A 311      28.044   2.778  25.832  1.00   89.31      A    O
ATOM   1423  OD2  ASP A 311      26.631   1.376  26.754  1.00   89.18      A    O
ATOM   1424  C    ASP A 311      31.163   1.703  28.437  1.00   67.57      A    C
ATOM   1425  O    ASP A 311      31.651   2.783  28.762  1.00   63.00      A    O
ATOM   1426  N    LEU A 312      31.451   0.571  29.070  1.00   65.08      A    N
ATOM   1427  CA   LEU A 312      32.404   0.565  30.174  1.00   63.29      A    C
ATOM   1428  CB   LEU A 312      32.509  -0.833  30.789  1.00   63.28      A    C
ATOM   1429  CG   LEU A 312      31.480  -1.177  31.872  1.00   61.20      A    C
ATOM   1430  CD1  LEU A 312      31.879  -0.520  33.184  1.00   62.60      A    C
ATOM   1431  CD2  LEU A 312      30.098  -0.721  31.439  1.00   60.06      A    C
ATOM   1432  C    LEU A 312      33.763   1.014  29.652  1.00   63.07      A    C
ATOM   1433  O    LEU A 312      34.557   1.608  30.383  1.00   65.54      A    O
ATOM   1434  N    TRP A 313      34.018   0.728  28.379  1.00   62.33      A    N
ATOM   1435  CA   TRP A 313      35.268   1.114  27.737  1.00   64.42      A    C
ATOM   1436  CB   TRP A 313      35.447   0.339  26.426  1.00   68.18      A    C
ATOM   1437  CG   TRP A 313      36.593   0.816  25.578  1.00   70.13      A    C
ATOM   1438  CD2  TRP A 313      37.915   0.266  25.530  1.00   69.22      A    C
ATOM   1439  CE2  TRP A 313      38.658   1.039  24.609  1.00   69.11      A    C
ATOM   1440  CE3  TRP A 313      38.545  -0.807  26.174  1.00   69.93      A    C
ATOM   1441  CD1  TRP A 313      36.587   1.872  24.711  1.00   71.92      A    C
ATOM   1442  NE1  TRP A 313      37.825   2.012  24.124  1.00   70.63      A    N
ATOM   1443  CZ2  TRP A 313      40.001   0.775  24.320  1.00   67.64      A    C
ATOM   1444  CZ3  TRP A 313      39.884  -1.069  25.884  1.00   67.83      A    C
```

Figure 1X

```
ATOM   1445  CH2 TRP A 313      40.594  -0.280  24.964  1.00  63.35      A    C
ATOM   1446  C   TRP A 313      35.237   2.613  27.470  1.00  65.74      A    C
ATOM   1447  O   TRP A 313      36.124   3.350  27.903  1.00  64.60      A    O
ATOM   1448  N   SER A 314      34.211   3.058  26.752  1.00  67.32      A    N
ATOM   1449  CA  SER A 314      34.057   4.472  26.449  1.00  66.80      A    C
ATOM   1450  CB  SER A 314      32.686   4.728  25.825  1.00  69.36      A    C
ATOM   1451  OG  SER A 314      32.582   4.074  24.574  1.00  76.05      A    O
ATOM   1452  C   SER A 314      34.185   5.225  27.764  1.00  64.67      A    C
ATOM   1453  O   SER A 314      35.058   6.077  27.926  1.00  61.27      A    O
ATOM   1454  N   LEU A 315      33.312   4.888  28.706  1.00  64.39      A    N
ATOM   1455  CA  LEU A 315      33.324   5.503  30.025  1.00  62.14      A    C
ATOM   1456  CB  LEU A 315      32.335   4.777  30.941  1.00  61.30      A    C
ATOM   1457  CG  LEU A 315      32.143   5.295  32.367  1.00  61.14      A    C
ATOM   1458  CD1 LEU A 315      31.630   6.726  32.338  1.00  62.79      A    C
ATOM   1459  CD2 LEU A 315      31.161   4.396  33.100  1.00  59.71      A    C
ATOM   1460  C   LEU A 315      34.731   5.425  30.613  1.00  60.98      A    C
ATOM   1461  O   LEU A 315      35.088   6.198  31.499  1.00  60.23      A    O
ATOM   1462  N   GLY A 316      35.527   4.485  30.111  1.00  60.42      A    N
ATOM   1463  CA  GLY A 316      36.885   4.326  30.599  1.00  60.05      A    C
ATOM   1464  C   GLY A 316      37.805   5.387  30.036  1.00  60.12      A    C
ATOM   1465  O   GLY A 316      38.661   5.923  30.740  1.00  60.16      A    O
ATOM   1466  N   VAL A 317      37.625   5.692  28.757  1.00  58.47      A    N
ATOM   1467  CA  VAL A 317      38.433   6.698  28.089  1.00  58.01      A    C
ATOM   1468  CB  VAL A 317      38.157   6.709  26.584  1.00  56.62      A    C
ATOM   1469  CG1 VAL A 317      39.250   7.475  25.864  1.00  56.39      A    C
ATOM   1470  CG2 VAL A 317      38.052   5.293  26.067  1.00  53.04      A    C
ATOM   1471  C   VAL A 317      38.078   8.069  28.639  1.00  59.78      A    C
ATOM   1472  O   VAL A 317      38.946   8.914  28.853  1.00  61.19      A    O
ATOM   1473  N   LEU A 318      36.785   8.278  28.852  1.00  59.83      A    N
ATOM   1474  CA  LEU A 318      36.278   9.536  29.374  1.00  60.59      A    C
ATOM   1475  CB  LEU A 318      34.758   9.439  29.540  1.00  64.41      A    C
ATOM   1476  CG  LEU A 318      33.926  10.717  29.419  1.00  65.10      A    C
ATOM   1477  CD1 LEU A 318      34.502  11.605  28.326  1.00  63.64      A    C
ATOM   1478  CD2 LEU A 318      32.481  10.353  29.108  1.00  64.53      A    C
ATOM   1479  C   LEU A 318      36.948   9.827  30.714  1.00  60.86      A    C
ATOM   1480  O   LEU A 318      37.613  10.853  30.882  1.00  62.50      A    O
ATOM   1481  N   CYS A 319      36.780   8.902  31.656  1.00  61.28      A    N
ATOM   1482  CA  CYS A 319      37.357   9.034  32.988  1.00  63.73      A    C
ATOM   1483  CB  CYS A 319      37.259   7.702  33.740  1.00  68.60      A    C
ATOM   1484  SG  CYS A 319      37.322   7.844  35.544  1.00  74.58      A    S
ATOM   1485  C   CYS A 319      38.816   9.462  32.877  1.00  62.69      A    C
ATOM   1486  O   CYS A 319      39.316  10.220  33.708  1.00  62.36      A    O
ATOM   1487  N   TYR A 320      39.490   8.976  31.838  1.00  64.27      A    N
ATOM   1488  CA  TYR A 320      40.890   9.310  31.597  1.00  68.69      A    C
ATOM   1489  CB  TYR A 320      41.480   8.427  30.495  1.00  70.97      A    C
ATOM   1490  CG  TYR A 320      42.957   8.662  30.253  1.00  71.15      A    C
ATOM   1491  CD1 TYR A 320      43.921   7.933  30.947  1.00  67.85      A    C
ATOM   1492  CE1 TYR A 320      45.281   8.163  30.748  1.00  66.84      A    C
ATOM   1493  CD2 TYR A 320      43.392   9.632  29.350  1.00  73.18      A    C
ATOM   1494  CE2 TYR A 320      44.751   9.870  29.145  1.00  73.75      A    C
ATOM   1495  CZ  TYR A 320      45.688   9.132  29.848  1.00  69.70      A    C
ATOM   1496  OH  TYR A 320      47.032   9.364  29.657  1.00  62.02      A    O
ATOM   1497  C   TYR A 320      41.015  10.764  31.162  1.00  69.87      A    C
ATOM   1498  O   TYR A 320      41.527  11.605  31.901  1.00  71.42      A    O
ATOM   1499  N   GLU A 321      40.547  11.042  29.948  1.00  70.58      A    N
ATOM   1500  CA  GLU A 321      40.601  12.384  29.376  1.00  70.66      A    C
ATOM   1501  CB  GLU A 321      39.588  12.519  28.238  1.00  72.38      A    C
ATOM   1502  CG  GLU A 321      40.199  12.946  26.915  1.00  80.40      A    C
ATOM   1503  CD  GLU A 321      39.308  13.900  26.145  1.00  84.47      A    C
ATOM   1504  OE1 GLU A 321      38.095  13.630  26.041  1.00  88.10      A    O
ATOM   1505  OE2 GLU A 321      39.821  14.921  25.640  1.00  86.17      A    O
```

Figure 1Y

```
ATOM   1506  C   GLU A 321      40.324  13.460  30.418  1.00  71.15      A    C
ATOM   1507  O   GLU A 321      41.074  14.430  30.537  1.00  69.71      A    O
ATOM   1508  N   PHE A 322      39.243  13.288  31.170  1.00  70.29      A    N
ATOM   1509  CA  PHE A 322      38.877  14.253  32.198  1.00  68.50      A    C
ATOM   1510  CB  PHE A 322      37.722  13.725  33.056  1.00  59.21      A    C
ATOM   1511  CG  PHE A 322      36.389  13.705  32.360  1.00  51.02      A    C
ATOM   1512  CD1 PHE A 322      36.146  14.513  31.253  1.00  46.80      A    C
ATOM   1513  CD2 PHE A 322      35.355  12.910  32.847  1.00  49.96      A    C
ATOM   1514  CE1 PHE A 322      34.893  14.531  30.646  1.00  47.66      A    C
ATOM   1515  CE2 PHE A 322      34.098  12.923  32.247  1.00  48.76      A    C
ATOM   1516  CZ  PHE A 322      33.868  13.735  31.144  1.00  49.16      A    C
ATOM   1517  C   PHE A 322      40.038  14.597  33.125  1.00  71.37      A    C
ATOM   1518  O   PHE A 322      40.192  15.747  33.535  1.00  74.60      A    O
ATOM   1519  N   LEU A 323      40.852  13.599  33.452  1.00  72.30      A    N
ATOM   1520  CA  LEU A 323      41.970  13.794  34.368  1.00  71.37      A    C
ATOM   1521  CB  LEU A 323      42.111  12.562  35.270  1.00  71.27      A    C
ATOM   1522  CG  LEU A 323      40.842  12.093  35.992  1.00  69.94      A    C
ATOM   1523  CD1 LEU A 323      41.061  10.710  36.591  1.00  72.65      A    C
ATOM   1524  CD2 LEU A 323      40.467  13.097  37.072  1.00  70.46      A    C
ATOM   1525  C   LEU A 323      43.322  14.102  33.726  1.00  70.63      A    C
ATOM   1526  O   LEU A 323      44.339  14.115  34.417  1.00  72.87      A    O
ATOM   1527  N   VAL A 324      43.350  14.355  32.421  1.00  69.48      A    N
ATOM   1528  CA  VAL A 324      44.620  14.643  31.758  1.00  69.28      A    C
ATOM   1529  CB  VAL A 324      45.261  13.352  31.201  1.00  67.56      A    C
ATOM   1530  CG1 VAL A 324      46.655  13.648  30.668  1.00  68.29      A    C
ATOM   1531  CG2 VAL A 324      45.331  12.296  32.289  1.00  65.20      A    C
ATOM   1532  C   VAL A 324      44.492  15.652  30.621  1.00  72.55      A    C
ATOM   1533  O   VAL A 324      45.468  16.304  30.245  1.00  73.88      A    O
ATOM   1534  N   GLY A 325      43.288  15.781  30.073  1.00  72.69      A    N
ATOM   1535  CA  GLY A 325      43.076  16.719  28.987  1.00  73.78      A    C
ATOM   1536  C   GLY A 325      43.001  16.049  27.629  1.00  74.19      A    C
ATOM   1537  O   GLY A 325      42.417  16.595  26.692  1.00  80.44      A    O
ATOM   1538  N   LYS A 326      43.589  14.864  27.516  1.00  69.35      A    N
ATOM   1539  CA  LYS A 326      43.575  14.131  26.255  1.00  65.10      A    C
ATOM   1540  CB  LYS A 326      44.908  14.330  25.515  1.00  64.07      A    C
ATOM   1541  CG  LYS A 326      46.136  13.996  26.333  1.00  64.20      A    C
ATOM   1542  CD  LYS A 326      47.407  14.299  25.549  1.00  66.30      A    C
ATOM   1543  CE  LYS A 326      48.658  13.904  26.320  1.00  68.72      A    C
ATOM   1544  NZ  LYS A 326      48.688  14.456  27.701  1.00  70.08      A    N
ATOM   1545  C   LYS A 326      43.316  12.642  26.471  1.00  63.47      A    C
ATOM   1546  O   LYS A 326      43.547  12.112  27.560  1.00  59.38      A    O
ATOM   1547  N   PRO A 327      42.816  11.951  25.432  1.00  61.80      A    N
ATOM   1548  CD  PRO A 327      42.361  12.523  24.153  1.00  59.30      A    C
ATOM   1549  CA  PRO A 327      42.516  10.514  25.490  1.00  61.39      A    C
ATOM   1550  CB  PRO A 327      41.880  10.238  24.128  1.00  60.42      A    C
ATOM   1551  CG  PRO A 327      41.277  11.557  23.754  1.00  56.17      A    C
ATOM   1552  C   PRO A 327      43.781   9.682  25.711  1.00  61.60      A    C
ATOM   1553  O   PRO A 327      44.891  10.167  25.502  1.00  61.65      A    O
ATOM   1554  N   PRO A 328      43.629   8.417  26.135  1.00  62.94      A    N
ATOM   1555  CD  PRO A 328      42.400   7.768  26.627  1.00  62.32      A    C
ATOM   1556  CA  PRO A 328      44.793   7.557  26.371  1.00  66.12      A    C
ATOM   1557  CB  PRO A 328      44.232   6.478  27.288  1.00  66.21      A    C
ATOM   1558  CG  PRO A 328      42.838   6.326  26.778  1.00  64.07      A    C
ATOM   1559  C   PRO A 328      45.459   6.955  25.131  1.00  69.10      A    C
ATOM   1560  O   PRO A 328      46.579   6.448  25.215  1.00  69.99      A    O
ATOM   1561  N   PHE A 329      44.785   7.009  23.986  1.00  70.96      A    N
ATOM   1562  CA  PHE A 329      45.341   6.428  22.767  1.00  73.93      A    C
ATOM   1563  CB  PHE A 329      44.436   5.291  22.295  1.00  73.09      A    C
ATOM   1564  CG  PHE A 329      43.981   4.393  23.407  1.00  67.14      A    C
ATOM   1565  CD1 PHE A 329      44.893   3.607  24.103  1.00  62.52      A    C
ATOM   1566  CD2 PHE A 329      42.647   4.372  23.795  1.00  66.77      A    C
```

Figure 1Z

```
ATOM   1567  CE1 PHE A 329      44.482   2.814  25.171  1.00  61.94      A  C
ATOM   1568  CE2 PHE A 329      42.227   3.582  24.862  1.00  63.91      A  C
ATOM   1569  CZ  PHE A 329      43.147   2.803  25.552  1.00  64.00      A  C
ATOM   1570  C   PHE A 329      45.550   7.440  21.647  1.00  77.92      A  C
ATOM   1571  O   PHE A 329      45.856   7.070  20.512  1.00  80.68      A  O
ATOM   1572  N   GLU A 330      45.381   8.718  21.970  1.00  81.78      A  N
ATOM   1573  CA  GLU A 330      45.576   9.784  20.996  1.00  84.46      A  C
ATOM   1574  CB  GLU A 330      45.333  11.144  21.658  1.00  85.13      A  C
ATOM   1575  CG  GLU A 330      45.868  12.340  20.885  1.00  87.63      A  C
ATOM   1576  CD  GLU A 330      45.631  13.651  21.611  1.00  88.70      A  C
ATOM   1577  OE1 GLU A 330      44.505  14.182  21.525  1.00  91.66      A  O
ATOM   1578  OE2 GLU A 330      46.567  14.148  22.273  1.00  88.30      A  O
ATOM   1579  C   GLU A 330      47.003   9.700  20.466  1.00  86.04      A  C
ATOM   1580  O   GLU A 330      47.937   9.454  21.230  1.00  82.26      A  O
ATOM   1581  N   ALA A 331      47.174   9.900  19.162  1.00  89.59      A  N
ATOM   1582  CA  ALA A 331      48.504   9.825  18.571  1.00  93.10      A  C
ATOM   1583  CB  ALA A 331      48.970   8.376  18.544  1.00  93.91      A  C
ATOM   1584  C   ALA A 331      48.625  10.425  17.175  1.00  95.06      A  C
ATOM   1585  O   ALA A 331      47.699  11.053  16.658  1.00  92.91      A  O
ATOM   1586  N   ASN A 332      49.794  10.211  16.580  1.00  99.10      A  N
ATOM   1587  CA  ASN A 332      50.116  10.699  15.248  1.00 102.47      A  C
ATOM   1588  CB  ASN A 332      51.632  10.860  15.120  1.00 103.56      A  C
ATOM   1589  CG  ASN A 332      52.385   9.625  15.579  1.00 105.59      A  C
ATOM   1590  OD1 ASN A 332      52.379   9.285  16.763  1.00 104.67      A  O
ATOM   1591  ND2 ASN A 332      53.033   8.942  14.641  1.00 106.76      A  N
ATOM   1592  C   ASN A 332      49.614   9.751  14.164  1.00 104.90      A  C
ATOM   1593  O   ASN A 332      50.368   8.909  13.684  1.00 105.73      A  O
ATOM   1594  N   THR A 333      48.341   9.905  13.798  1.00 105.87      A  N
ATOM   1595  CA  THR A 333      47.664   9.110  12.765  1.00 106.12      A  C
ATOM   1596  CB  THR A 333      48.645   8.594  11.674  1.00 109.36      A  C
ATOM   1597  OG1 THR A 333      47.951   8.495  10.425  1.00 113.09      A  O
ATOM   1598  CG2 THR A 333      49.186   7.211  12.034  1.00 110.86      A  C
ATOM   1599  C   THR A 333      46.877   7.920  13.312  1.00 102.49      A  C
ATOM   1600  O   THR A 333      47.179   7.397  14.384  1.00 103.44      A  O
ATOM   1601  N   TYR A 334      45.866   7.505  12.552  1.00  97.46      A  N
ATOM   1602  CA  TYR A 334      45.000   6.388  12.920  1.00  93.45      A  C
ATOM   1603  CB  TYR A 334      43.896   6.210  11.879  1.00  94.80      A  C
ATOM   1604  CG  TYR A 334      42.917   7.354  11.769  1.00  98.46      A  C
ATOM   1605  CD1 TYR A 334      42.078   7.690  12.830  1.00 101.64      A  C
ATOM   1606  CE1 TYR A 334      41.142   8.715  12.709  1.00 106.33      A  C
ATOM   1607  CD2 TYR A 334      42.801   8.075  10.583  1.00 101.48      A  C
ATOM   1608  CE2 TYR A 334      41.871   9.100  10.451  1.00 104.51      A  C
ATOM   1609  CZ  TYR A 334      41.043   9.413  11.515  1.00 106.06      A  C
ATOM   1610  OH  TYR A 334      40.108  10.413  11.378  1.00 106.62      A  O
ATOM   1611  C   TYR A 334      45.732   5.057  13.069  1.00  91.47      A  C
ATOM   1612  O   TYR A 334      45.391   4.264  13.945  1.00  92.73      A  O
ATOM   1613  N   GLN A 335      46.705   4.797  12.198  1.00  89.49      A  N
ATOM   1614  CA  GLN A 335      47.471   3.552  12.261  1.00  89.06      A  C
ATOM   1615  CB  GLN A 335      48.719   3.643  11.383  1.00  90.33      A  C
ATOM   1616  CG  GLN A 335      48.424   3.760   9.891  1.00  92.09      A  C
ATOM   1617  CD  GLN A 335      47.509   4.926   9.558  1.00  93.60      A  C
ATOM   1618  OE1 GLN A 335      46.292   4.844   9.722  1.00  91.71      A  O
ATOM   1619  NE2 GLN A 335      48.096   6.023   9.094  1.00  97.59      A  N
ATOM   1620  C   GLN A 335      47.848   3.354  13.718  1.00  88.56      A  C
ATOM   1621  O   GLN A 335      47.610   2.289  14.294  1.00  90.18      A  O
ATOM   1622  N   GLU A 336      48.440   4.389  14.310  1.00  85.02      A  N
ATOM   1623  CA  GLU A 336      48.770   4.364  15.729  1.00  81.44      A  C
ATOM   1624  CB  GLU A 336      49.471   5.657  16.148  1.00  81.66      A  C
ATOM   1625  CG  GLU A 336      50.907   5.813  15.668  1.00  87.82      A  C
ATOM   1626  CD  GLU A 336      51.869   4.874  16.371  1.00  94.22      A  C
ATOM   1627  OE1 GLU A 336      52.146   3.781  15.833  1.00  97.25      A  O
```

Figure 1AA

| | | | | | | | | | | |
|---|---|---|---|---|---|---|---|---|---|---|
| ATOM | 1628 | OE2 | GLU | A | 336 | 52.340 | 5.228 | 17.473 | 1.00 | 97.60 | A | O |
| ATOM | 1629 | C | GLU | A | 336 | 47.347 | 4.347 | 16.276 | 1.00 | 79.60 | A | C |
| ATOM | 1630 | O | GLU | A | 336 | 46.460 | 3.832 | 15.613 | 1.00 | 84.36 | A | O |
| ATOM | 1631 | N | THR | A | 337 | 47.099 | 4.920 | 17.446 | 1.00 | 73.12 | A | N |
| ATOM | 1632 | CA | THR | A | 337 | 45.734 | 4.926 | 17.976 | 1.00 | 70.19 | A | C |
| ATOM | 1633 | CB | THR | A | 337 | 44.820 | 5.847 | 17.135 | 1.00 | 68.05 | A | C |
| ATOM | 1634 | OG1 | THR | A | 337 | 45.557 | 7.006 | 16.728 | 1.00 | 66.16 | A | O |
| ATOM | 1635 | CG2 | THR | A | 337 | 43.613 | 6.295 | 17.951 | 1.00 | 66.43 | A | C |
| ATOM | 1636 | C | THR | A | 337 | 45.184 | 3.497 | 17.940 | 1.00 | 70.77 | A | C |
| ATOM | 1637 | O | THR | A | 337 | 45.052 | 2.860 | 18.979 | 1.00 | 71.10 | A | O |
| ATOM | 1638 | N | TYR | A | 338 | 44.854 | 3.002 | 16.747 | 1.00 | 70.08 | A | N |
| ATOM | 1639 | CA | TYR | A | 338 | 44.366 | 1.634 | 16.592 | 1.00 | 66.84 | A | C |
| ATOM | 1640 | CB | TYR | A | 338 | 44.287 | 1.245 | 15.109 | 1.00 | 72.87 | A | C |
| ATOM | 1641 | CG | TYR | A | 338 | 43.705 | -0.135 | 14.853 | 1.00 | 81.75 | A | C |
| ATOM | 1642 | CD1 | TYR | A | 338 | 42.515 | -0.288 | 14.145 | 1.00 | 85.69 | A | C |
| ATOM | 1643 | CE1 | TYR | A | 338 | 41.954 | -1.547 | 13.934 | 1.00 | 85.27 | A | C |
| ATOM | 1644 | CD2 | TYR | A | 338 | 44.327 | -1.285 | 15.342 | 1.00 | 84.66 | A | C |
| ATOM | 1645 | CE2 | TYR | A | 338 | 43.774 | -2.549 | 15.137 | 1.00 | 87.13 | A | C |
| ATOM | 1646 | CZ | TYR | A | 338 | 42.587 | -2.668 | 14.433 | 1.00 | 86.38 | A | C |
| ATOM | 1647 | OH | TYR | A | 338 | 42.017 | -3.903 | 14.243 | 1.00 | 86.81 | A | O |
| ATOM | 1648 | C | TYR | A | 338 | 45.412 | 0.771 | 17.278 | 1.00 | 62.62 | A | C |
| ATOM | 1649 | O | TYR | A | 338 | 45.110 | 0.008 | 18.196 | 1.00 | 64.08 | A | O |
| ATOM | 1650 | N | LYS | A | 339 | 46.650 | 0.915 | 16.819 | 1.00 | 55.79 | A | N |
| ATOM | 1651 | CA | LYS | A | 339 | 47.769 | 0.173 | 17.371 | 1.00 | 50.23 | A | C |
| ATOM | 1652 | CB | LYS | A | 339 | 49.086 | 0.816 | 16.929 | 1.00 | 48.02 | A | C |
| ATOM | 1653 | CG | LYS | A | 339 | 50.331 | 0.108 | 17.446 | 1.00 | 49.73 | A | C |
| ATOM | 1654 | CD | LYS | A | 339 | 51.586 | 0.544 | 16.686 | 1.00 | 52.62 | A | C |
| ATOM | 1655 | CE | LYS | A | 339 | 51.542 | 0.052 | 15.242 | 1.00 | 55.54 | A | C |
| ATOM | 1656 | NZ | LYS | A | 339 | 52.769 | 0.372 | 14.451 | 1.00 | 58.93 | A | N |
| ATOM | 1657 | C | LYS | A | 339 | 47.685 | 0.137 | 18.893 | 1.00 | 49.93 | A | C |
| ATOM | 1658 | O | LYS | A | 339 | 47.578 | -0.935 | 19.488 | 1.00 | 47.91 | A | O |
| ATOM | 1659 | N | ARG | A | 340 | 47.708 | 1.311 | 19.517 | 1.00 | 52.40 | A | N |
| ATOM | 1660 | CA | ARG | A | 340 | 47.646 | 1.408 | 20.972 | 1.00 | 54.39 | A | C |
| ATOM | 1661 | CB | ARG | A | 340 | 48.125 | 2.789 | 21.424 | 1.00 | 60.69 | A | C |
| ATOM | 1662 | CG | ARG | A | 340 | 49.573 | 3.076 | 21.055 | 1.00 | 74.59 | A | C |
| ATOM | 1663 | CD | ARG | A | 340 | 49.972 | 4.494 | 21.407 | 1.00 | 86.78 | A | C |
| ATOM | 1664 | NE | ARG | A | 340 | 51.129 | 4.927 | 20.628 | 1.00 | 99.96 | A | N |
| ATOM | 1665 | CZ | ARG | A | 340 | 51.521 | 6.191 | 20.511 | 1.00 | 105.56 | A | C |
| ATOM | 1666 | NH1 | ARG | A | 340 | 50.850 | 7.156 | 21.126 | 1.00 | 107.00 | A | N |
| ATOM | 1667 | NH2 | ARG | A | 340 | 52.576 | 6.493 | 19.767 | 1.00 | 108.09 | A | N |
| ATOM | 1668 | C | ARG | A | 340 | 46.260 | 1.123 | 21.549 | 1.00 | 51.73 | A | C |
| ATOM | 1669 | O | ARG | A | 340 | 46.131 | 0.835 | 22.738 | 1.00 | 50.86 | A | O |
| ATOM | 1670 | N | ILE | A | 341 | 45.225 | 1.209 | 20.718 | 1.00 | 50.26 | A | N |
| ATOM | 1671 | CA | ILE | A | 341 | 43.870 | 0.930 | 21.182 | 1.00 | 50.94 | A | C |
| ATOM | 1672 | CB | ILE | A | 341 | 42.792 | 1.497 | 20.220 | 1.00 | 52.17 | A | C |
| ATOM | 1673 | CG2 | ILE | A | 341 | 41.492 | 0.716 | 20.379 | 1.00 | 52.54 | A | C |
| ATOM | 1674 | CG1 | ILE | A | 341 | 42.549 | 2.983 | 20.506 | 1.00 | 50.97 | A | C |
| ATOM | 1675 | CD1 | ILE | A | 341 | 41.540 | 3.637 | 19.572 | 1.00 | 44.72 | A | C |
| ATOM | 1676 | C | ILE | A | 341 | 43.688 | -0.580 | 21.271 | 1.00 | 51.79 | A | C |
| ATOM | 1677 | O | ILE | A | 341 | 43.248 | -1.104 | 22.292 | 1.00 | 49.99 | A | O |
| ATOM | 1678 | N | SER | A | 342 | 44.034 | -1.272 | 20.190 | 1.00 | 55.69 | A | N |
| ATOM | 1679 | CA | SER | A | 342 | 43.911 | -2.723 | 20.133 | 1.00 | 59.70 | A | C |
| ATOM | 1680 | CB | SER | A | 342 | 44.051 | -3.210 | 18.688 | 1.00 | 56.71 | A | C |
| ATOM | 1681 | OG | SER | A | 342 | 45.312 | -2.858 | 18.148 | 1.00 | 56.64 | A | O |
| ATOM | 1682 | C | SER | A | 342 | 44.947 | -3.412 | 21.015 | 1.00 | 63.35 | A | C |
| ATOM | 1683 | O | SER | A | 342 | 44.754 | -4.555 | 21.426 | 1.00 | 64.45 | A | O |
| ATOM | 1684 | N | ARG | A | 343 | 46.050 | -2.724 | 21.297 | 1.00 | 66.96 | A | N |
| ATOM | 1685 | CA | ARG | A | 343 | 47.089 | -3.293 | 22.149 | 1.00 | 69.51 | A | C |
| ATOM | 1686 | CB | ARG | A | 343 | 48.484 | -3.021 | 21.576 | 1.00 | 75.49 | A | C |
| ATOM | 1687 | CG | ARG | A | 343 | 48.938 | -3.987 | 20.491 | 1.00 | 81.68 | A | C |
| ATOM | 1688 | CD | ARG | A | 343 | 50.448 | -3.918 | 20.325 | 1.00 | 85.52 | A | C |

Figure 1BB

```
ATOM  1689  NE   ARG A 343      50.859  -3.974  18.925  1.00  87.10      A    N
ATOM  1690  CZ   ARG A 343      51.889  -3.300  18.422  1.00  89.22      A    C
ATOM  1691  NH1  ARG A 343      52.193  -3.411  17.135  1.00  91.00      A    N
ATOM  1692  NH2  ARG A 343      52.612  -2.508  19.203  1.00  89.19      A    N
ATOM  1693  C    ARG A 343      46.987  -2.686  23.541  1.00  69.20      A    C
ATOM  1694  O    ARG A 343      47.829  -2.943  24.402  1.00  71.36      A    O
ATOM  1695  N    VAL A 344      45.954  -1.875  23.747  1.00  69.00      A    N
ATOM  1696  CA   VAL A 344      45.726  -1.225  25.030  1.00  68.61      A    C
ATOM  1697  CB   VAL A 344      45.112  -2.216  26.046  1.00  67.63      A    C
ATOM  1698  CG1  VAL A 344      44.741  -1.492  27.328  1.00  68.26      A    C
ATOM  1699  CG2  VAL A 344      43.887  -2.884  25.442  1.00  69.64      A    C
ATOM  1700  C    VAL A 344      47.045  -0.680  25.575  1.00  70.76      A    C
ATOM  1701  O    VAL A 344      47.479  -1.036  26.672  1.00  69.87      A    O
ATOM  1702  N    GLU A 345      47.680   0.184  24.790  1.00  72.52      A    N
ATOM  1703  CA   GLU A 345      48.954   0.778  25.176  1.00  77.62      A    C
ATOM  1704  CB   GLU A 345      49.910   0.796  23.977  1.00  77.44      A    C
ATOM  1705  CG   GLU A 345      49.795  -0.435  23.087  1.00  73.64      A    C
ATOM  1706  CD   GLU A 345      51.064  -0.740  22.314  1.00  71.14      A    C
ATOM  1707  OE1  GLU A 345      51.631   0.178  21.687  1.00  67.47      A    O
ATOM  1708  OE2  GLU A 345      51.493  -1.912  22.331  1.00  68.43      A    O
ATOM  1709  C    GLU A 345      48.739   2.197  25.694  1.00  81.79      A    C
ATOM  1710  O    GLU A 345      48.894   3.170  24.955  1.00  82.61      A    O
ATOM  1711  N    PHE A 346      48.378   2.304  26.969  1.00  88.75      A    N
ATOM  1712  CA   PHE A 346      48.131   3.599  27.592  1.00  96.38      A    C
ATOM  1713  CB   PHE A 346      46.624   3.792  27.801  1.00  99.32      A    C
ATOM  1714  CG   PHE A 346      46.040   2.923  28.883  1.00 101.61      A    C
ATOM  1715  CD1  PHE A 346      46.016   3.357  30.205  1.00 100.34      A    C
ATOM  1716  CD2  PHE A 346      45.508   1.674  28.581  1.00 103.01      A    C
ATOM  1717  CE1  PHE A 346      45.475   2.561  31.211  1.00 104.40      A    C
ATOM  1718  CE2  PHE A 346      44.964   0.868  29.581  1.00 103.77      A    C
ATOM  1719  CZ   PHE A 346      44.945   1.315  30.898  1.00 104.44      A    C
ATOM  1720  C    PHE A 346      48.865   3.706  28.928  1.00  99.33      A    C
ATOM  1721  O    PHE A 346      49.012   2.714  29.642  1.00  99.78      A    O
ATOM  1722  N    THR A 347      49.323   4.911  29.260  1.00 100.36      A    N
ATOM  1723  CA   THR A 347      50.039   5.144  30.512  1.00 103.94      A    C
ATOM  1724  CB   THR A 347      51.564   5.201  30.267  1.00 105.34      A    C
ATOM  1725  OG1  THR A 347      52.249   5.229  31.524  1.00 106.68      A    O
ATOM  1726  CG2  THR A 347      51.934   6.429  29.456  1.00 105.74      A    C
ATOM  1727  C    THR A 347      49.559   6.437  31.189  1.00 103.53      A    C
ATOM  1728  O    THR A 347      49.003   7.316  30.531  1.00 103.60      A    O
ATOM  1729  N    PHE A 348      49.782   6.547  32.499  1.00 103.30      A    N
ATOM  1730  CA   PHE A 348      49.332   7.702  33.289  1.00 102.41      A    C
ATOM  1731  CB   PHE A 348      48.846   7.236  34.661  1.00 101.42      A    C
ATOM  1732  CG   PHE A 348      47.704   6.281  34.611  1.00  97.86      A    C
ATOM  1733  CD1  PHE A 348      46.432   6.714  34.262  1.00  97.29      A    C
ATOM  1734  CD2  PHE A 348      47.898   4.942  34.924  1.00  98.42      A    C
ATOM  1735  CE1  PHE A 348      45.369   5.826  34.229  1.00  96.46      A    C
ATOM  1736  CE2  PHE A 348      46.844   4.045  34.894  1.00  98.86      A    C
ATOM  1737  CZ   PHE A 348      45.577   4.485  34.545  1.00  96.44      A    C
ATOM  1738  C    PHE A 348      50.317   8.835  33.550  1.00 102.01      A    C
ATOM  1739  O    PHE A 348      51.436   8.600  34.002  1.00 103.96      A    O
ATOM  1740  N    PRO A 349      49.893  10.089  33.317  1.00 100.57      A    N
ATOM  1741  CD   PRO A 349      48.539  10.559  32.976  1.00  99.87      A    C
ATOM  1742  CA   PRO A 349      50.788  11.222  33.561  1.00  99.02      A    C
ATOM  1743  CB   PRO A 349      49.932  12.427  33.181  1.00  96.96      A    C
ATOM  1744  CG   PRO A 349      48.551  11.969  33.518  1.00  97.63      A    C
ATOM  1745  C    PRO A 349      51.160  11.203  35.043  1.00  99.44      A    C
ATOM  1746  O    PRO A 349      50.388  10.727  35.875  1.00  98.79      A    O
ATOM  1747  N    ASP A 350      52.336  11.723  35.366  1.00  99.90      A    N
ATOM  1748  CA   ASP A 350      52.841  11.733  36.733  1.00  99.38      A    C
ATOM  1749  CB   ASP A 350      54.246  12.343  36.734  1.00 103.18      A    C
```

Figure 1CC

```
ATOM  1750  CG   ASP A 350      55.134   11.767   37.818  1.00  107.14      A    C
ATOM  1751  OD1  ASP A 350      55.163   10.527   37.963  1.00  110.05      A    O
ATOM  1752  OD2  ASP A 350      55.810   12.549   38.519  1.00  107.17      A    O
ATOM  1753  C    ASP A 350      51.985   12.431   37.797  1.00   97.22      A    C
ATOM  1754  O    ASP A 350      52.241   13.589   38.127  1.00   96.30      A    O
ATOM  1755  N    PHE A 351      50.978   11.729   38.326  1.00   94.00      A    N
ATOM  1756  CA   PHE A 351      50.116   12.264   39.390  1.00   91.51      A    C
ATOM  1757  CB   PHE A 351      49.916   13.783   39.234  1.00   90.18      A    C
ATOM  1758  CG   PHE A 351      49.014   14.176   38.099  1.00   88.37      A    C
ATOM  1759  CD1  PHE A 351      47.636   14.014   38.198  1.00   87.54      A    C
ATOM  1760  CD2  PHE A 351      49.541   14.716   36.931  1.00   89.42      A    C
ATOM  1761  CE1  PHE A 351      46.796   14.382   37.154  1.00   88.78      A    C
ATOM  1762  CE2  PHE A 351      48.708   15.089   35.879  1.00   89.04      A    C
ATOM  1763  CZ   PHE A 351      47.332   14.921   35.992  1.00   89.27      A    C
ATOM  1764  C    PHE A 351      48.749   11.597   39.565  1.00   90.32      A    C
ATOM  1765  O    PHE A 351      48.100   11.783   40.596  1.00   92.13      A    O
ATOM  1766  N    VAL A 352      48.303   10.830   38.576  1.00   87.82      A    N
ATOM  1767  CA   VAL A 352      47.002   10.171   38.675  1.00   87.40      A    C
ATOM  1768  CB   VAL A 352      46.738    9.251   37.463  1.00   85.41      A    C
ATOM  1769  CG1  VAL A 352      45.338    8.650   37.555  1.00   81.11      A    C
ATOM  1770  CG2  VAL A 352      46.887   10.043   36.177  1.00   86.93      A    C
ATOM  1771  C    VAL A 352      46.880    9.346   39.952  1.00   87.82      A    C
ATOM  1772  O    VAL A 352      47.753    8.539   40.271  1.00   88.33      A    O
ATOM  1773  N    THR A 353      45.789    9.559   40.680  1.00   88.01      A    N
ATOM  1774  CA   THR A 353      45.544    8.841   41.924  1.00   89.73      A    C
ATOM  1775  CB   THR A 353      44.197    9.252   42.551  1.00   93.08      A    C
ATOM  1776  OG1  THR A 353      43.845    8.323   43.584  1.00   97.32      A    O
ATOM  1777  CG2  THR A 353      43.107    9.276   41.495  1.00   94.79      A    C
ATOM  1778  C    THR A 353      45.528    7.335   41.704  1.00   87.39      A    C
ATOM  1779  O    THR A 353      44.955    6.848   40.729  1.00   83.88      A    O
ATOM  1780  N    GLU A 354      46.167    6.601   42.618  1.00   87.16      A    N
ATOM  1781  CA   GLU A 354      46.197    5.148   42.516  1.00   87.36      A    C
ATOM  1782  CB   GLU A 354      46.901    4.545   43.740  1.00   91.80      A    C
ATOM  1783  CG   GLU A 354      46.642    3.054   43.963  1.00  100.66      A    C
ATOM  1784  CD   GLU A 354      47.563    2.448   45.010  1.00  105.03      A    C
ATOM  1785  OE1  GLU A 354      47.932    3.162   45.966  1.00  107.78      A    O
ATOM  1786  OE2  GLU A 354      47.909    1.253   44.883  1.00  107.92      A    O
ATOM  1787  C    GLU A 354      44.756    4.660   42.433  1.00   85.09      A    C
ATOM  1788  O    GLU A 354      44.497    3.511   42.084  1.00   88.33      A    O
ATOM  1789  N    GLY A 355      43.822    5.549   42.752  1.00   81.49      A    N
ATOM  1790  CA   GLY A 355      42.415    5.201   42.699  1.00   79.11      A    C
ATOM  1791  C    GLY A 355      41.890    5.262   41.279  1.00   79.21      A    C
ATOM  1792  O    GLY A 355      41.165    4.373   40.836  1.00   79.18      A    O
ATOM  1793  N    ALA A 356      42.251    6.319   40.560  1.00   79.61      A    N
ATOM  1794  CA   ALA A 356      41.813    6.469   39.179  1.00   80.14      A    C
ATOM  1795  CB   ALA A 356      42.093    7.881   38.690  1.00   80.26      A    C
ATOM  1796  C    ALA A 356      42.568    5.459   38.327  1.00   81.05      A    C
ATOM  1797  O    ALA A 356      42.001    4.837   37.427  1.00   80.61      A    O
ATOM  1798  N    ARG A 357      43.853    5.301   38.629  1.00   81.02      A    N
ATOM  1799  CA   ARG A 357      44.719    4.375   37.913  1.00   80.85      A    C
ATOM  1800  CB   ARG A 357      46.097    4.331   38.583  1.00   81.00      A    C
ATOM  1801  CG   ARG A 357      46.998    5.502   38.213  1.00   84.22      A    C
ATOM  1802  CD   ARG A 357      48.106    5.720   39.235  1.00   84.92      A    C
ATOM  1803  NE   ARG A 357      49.194    6.523   38.683  1.00   85.32      A    N
ATOM  1804  CZ   ARG A 357      50.012    6.105   37.721  1.00   85.13      A    C
ATOM  1805  NH1  ARG A 357      49.868    4.890   37.210  1.00   83.70      A    N
ATOM  1806  NH2  ARG A 357      50.970    6.901   37.264  1.00   82.39      A    N
ATOM  1807  C    ARG A 357      44.139    2.968   37.816  1.00   80.46      A    C
ATOM  1808  O    ARG A 357      44.192    2.345   36.756  1.00   81.00      A    O
ATOM  1809  N    ASP A 358      43.581    2.467   38.912  1.00   80.63      A    N
ATOM  1810  CA   ASP A 358      43.009    1.127   38.902  1.00   85.31      A    C
```

Figure 1DD

```
ATOM   1811  CB   ASP A 358      43.140    0.483   40.284  1.00   90.08      A    C
ATOM   1812  CG   ASP A 358      42.324    1.195   41.338  1.00   95.10      A    C
ATOM   1813  OD1  ASP A 358      42.327    2.440   41.349  1.00   97.84      A    O
ATOM   1814  OD2  ASP A 358      41.685    0.509   42.162  1.00   99.78      A    O
ATOM   1815  C    ASP A 358      41.548    1.147   38.470  1.00   85.66      A    C
ATOM   1816  O    ASP A 358      41.017    0.135   38.014  1.00   84.97      A    O
ATOM   1817  N    LEU A 359      40.902    2.299   38.613  1.00   85.76      A    N
ATOM   1818  CA   LEU A 359      39.506    2.430   38.225  1.00   88.71      A    C
ATOM   1819  CB   LEU A 359      38.917    3.726   38.794  1.00   88.21      A    C
ATOM   1820  CG   LEU A 359      37.480    4.117   38.421  1.00   87.42      A    C
ATOM   1821  CD1  LEU A 359      37.485    4.978   37.167  1.00   87.71      A    C
ATOM   1822  CD2  LEU A 359      36.627    2.866   38.233  1.00   84.26      A    C
ATOM   1823  C    LEU A 359      39.376    2.415   36.709  1.00   89.80      A    C
ATOM   1824  O    LEU A 359      38.428    1.853   36.165  1.00   93.70      A    O
ATOM   1825  N    ILE A 360      40.335    3.030   36.027  1.00   89.63      A    N
ATOM   1826  CA   ILE A 360      40.305    3.081   34.574  1.00   89.46      A    C
ATOM   1827  CB   ILE A 360      41.064    4.312   34.050  1.00   88.57      A    C
ATOM   1828  CG2  ILE A 360      42.506    4.259   34.503  1.00   85.73      A    C
ATOM   1829  CG1  ILE A 360      40.983    4.362   32.526  1.00   87.34      A    C
ATOM   1830  CD1  ILE A 360      41.597    5.600   31.931  1.00   86.28      A    C
ATOM   1831  C    ILE A 360      40.912    1.824   33.965  1.00   88.13      A    C
ATOM   1832  O    ILE A 360      40.408    1.301   32.971  1.00   87.68      A    O
ATOM   1833  N    SER A 361      41.993    1.341   34.566  1.00   84.60      A    N
ATOM   1834  CA   SER A 361      42.656    0.143   34.074  1.00   80.91      A    C
ATOM   1835  CB   SER A 361      43.913   -0.139   34.894  1.00   79.16      A    C
ATOM   1836  OG   SER A 361      45.067   -0.042   34.078  1.00   75.11      A    O
ATOM   1837  C    SER A 361      41.706   -1.042   34.146  1.00   79.71      A    C
ATOM   1838  O    SER A 361      41.827   -1.999   33.380  1.00   80.94      A    O
ATOM   1839  N    ARG A 362      40.760   -0.965   35.075  1.00   75.83      A    N
ATOM   1840  CA   ARG A 362      39.768   -2.014   35.246  1.00   74.19      A    C
ATOM   1841  CB   ARG A 362      39.096   -1.889   36.616  1.00   74.56      A    C
ATOM   1842  CG   ARG A 362      38.181   -3.051   36.956  1.00   79.80      A    C
ATOM   1843  CD   ARG A 362      38.828   -3.986   37.963  1.00   84.13      A    C
ATOM   1844  NE   ARG A 362      38.581   -3.550   39.335  1.00   85.30      A    N
ATOM   1845  CZ   ARG A 362      37.395   -3.616   39.932  1.00   86.23      A    C
ATOM   1846  NH1  ARG A 362      36.348   -4.101   39.278  1.00   86.36      A    N
ATOM   1847  NH2  ARG A 362      37.253   -3.201   41.183  1.00   84.60      A    N
ATOM   1848  C    ARG A 362      38.721   -1.855   34.143  1.00   72.90      A    C
ATOM   1849  O    ARG A 362      38.140   -2.833   33.678  1.00   72.79      A    O
ATOM   1850  N    LEU A 363      38.490   -0.612   33.728  1.00   71.80      A    N
ATOM   1851  CA   LEU A 363      37.515   -0.315   32.681  1.00   70.72      A    C
ATOM   1852  CB   LEU A 363      37.079    1.151   32.762  1.00   64.76      A    C
ATOM   1853  CG   LEU A 363      36.158    1.555   33.915  1.00   60.12      A    C
ATOM   1854  CD1  LEU A 363      36.021    3.069   33.978  1.00   56.35      A    C
ATOM   1855  CD2  LEU A 363      34.803    0.907   33.716  1.00   52.11      A    C
ATOM   1856  C    LEU A 363      38.068   -0.590   31.290  1.00   72.44      A    C
ATOM   1857  O    LEU A 363      37.393   -1.184   30.446  1.00   70.48      A    O
ATOM   1858  N    LEU A 364      39.300   -0.151   31.060  1.00   76.73      A    N
ATOM   1859  CA   LEU A 364      39.949   -0.324   29.770  1.00   81.33      A    C
ATOM   1860  CB   LEU A 364      40.978    0.790   29.556  1.00   84.37      A    C
ATOM   1861  CG   LEU A 364      40.379    2.192   29.398  1.00   85.33      A    C
ATOM   1862  CD1  LEU A 364      41.489    3.202   29.169  1.00   86.20      A    C
ATOM   1863  CD2  LEU A 364      39.401    2.209   28.230  1.00   81.47      A    C
ATOM   1864  C    LEU A 364      40.608   -1.686   29.585  1.00   80.71      A    C
ATOM   1865  O    LEU A 364      41.825   -1.825   29.714  1.00   79.90      A    O
ATOM   1866  N    LYS A 365      39.792   -2.688   29.280  1.00   79.64      A    N
ATOM   1867  CA   LYS A 365      40.287   -4.036   29.052  1.00   78.35      A    C
ATOM   1868  CB   LYS A 365      39.772   -4.986   30.136  1.00   77.82      A    C
ATOM   1869  CG   LYS A 365      40.702   -5.055   31.338  1.00   80.03      A    C
ATOM   1870  CD   LYS A 365      40.021   -5.574   32.591  1.00   83.87      A    C
ATOM   1871  CE   LYS A 365      40.989   -5.516   33.764  1.00   86.11      A    C
```

Figure 1EE

```
ATOM   1872  NZ  LYS A 365      40.345  -5.793  35.075  1.00  85.44      A    N
ATOM   1873  C   LYS A 365      39.875  -4.519  27.670  1.00  80.50      A    C
ATOM   1874  O   LYS A 365      38.705  -4.445  27.292  1.00  78.83      A    O
ATOM   1875  N   HIS A 366      40.859  -5.000  26.918  1.00  83.28      A    N
ATOM   1876  CA  HIS A 366      40.636  -5.495  25.567  1.00  84.31      A    C
ATOM   1877  CB  HIS A 366      41.879  -6.235  25.068  1.00  87.07      A    C
ATOM   1878  CG  HIS A 366      41.815  -6.617  23.622  1.00  92.58      A    C
ATOM   1879  CD2 HIS A 366      40.986  -7.455  22.956  1.00  95.01      A    C
ATOM   1880  ND1 HIS A 366      42.674  -6.097  22.677  1.00  97.09      A    N
ATOM   1881  CE1 HIS A 366      42.377  -6.599  21.492  1.00  98.44      A    C
ATOM   1882  NE2 HIS A 366      41.356  -7.425  21.633  1.00  97.38      A    N
ATOM   1883  C   HIS A 366      39.435  -6.428  25.520  1.00  83.89      A    C
ATOM   1884  O   HIS A 366      38.633  -6.373  24.590  1.00  80.13      A    O
ATOM   1885  N   ASN A 367      39.312  -7.279  26.532  1.00  87.01      A    N
ATOM   1886  CA  ASN A 367      38.213  -8.231  26.594  1.00  90.31      A    C
ATOM   1887  CB  ASN A 367      38.675  -9.499  27.316  1.00  94.38      A    C
ATOM   1888  CG  ASN A 367      38.396 -10.755  26.516  1.00  99.40      A    C
ATOM   1889  OD1 ASN A 367      38.540 -10.766  25.293  1.00  98.07      A    O
ATOM   1890  ND2 ASN A 367      38.009 -11.825  27.202  1.00 102.68      A    N
ATOM   1891  C   ASN A 367      36.992  -7.637  27.293  1.00  89.33      A    C
ATOM   1892  O   ASN A 367      37.070  -7.216  28.447  1.00  88.68      A    O
ATOM   1893  N   PRO A 368      35.844  -7.593  26.593  1.00  89.38      A    N
ATOM   1894  CD  PRO A 368      35.626  -8.089  25.224  1.00  86.96      A    C
ATOM   1895  CA  PRO A 368      34.602  -7.046  27.148  1.00  91.53      A    C
ATOM   1896  CB  PRO A 368      33.591  -7.269  26.023  1.00  89.15      A    C
ATOM   1897  CG  PRO A 368      34.438  -7.278  24.785  1.00  86.98      A    C
ATOM   1898  C   PRO A 368      34.213  -7.803  28.410  1.00  94.64      A    C
ATOM   1899  O   PRO A 368      33.976  -7.214  29.464  1.00  96.41      A    O
ATOM   1900  N   SER A 369      34.156  -9.123  28.273  1.00  97.36      A    N
ATOM   1901  CA  SER A 369      33.805 -10.018  29.364  1.00 101.06      A    C
ATOM   1902  CB  SER A 369      34.152 -11.457  28.974  1.00 102.60      A    C
ATOM   1903  OG  SER A 369      34.268 -12.285  30.117  1.00 108.96      A    O
ATOM   1904  C   SER A 369      34.500  -9.667  30.676  1.00 102.42      A    C
ATOM   1905  O   SER A 369      33.939  -9.873  31.751  1.00 103.45      A    O
ATOM   1906  N   GLN A 370      35.716  -9.134  30.589  1.00 103.21      A    N
ATOM   1907  CA  GLN A 370      36.474  -8.780  31.787  1.00 103.35      A    C
ATOM   1908  CB  GLN A 370      37.979  -8.864  31.513  1.00 101.24      A    C
ATOM   1909  CG  GLN A 370      38.497 -10.257  31.195  1.00  99.41      A    C
ATOM   1910  CD  GLN A 370      40.014 -10.335  31.243  1.00  99.54      A    C
ATOM   1911  OE1 GLN A 370      40.629 -11.136  30.539  1.00 103.93      A    O
ATOM   1912  NE2 GLN A 370      40.623  -9.509  32.087  1.00  98.34      A    N
ATOM   1913  C   GLN A 370      36.159  -7.396  32.345  1.00 103.55      A    C
ATOM   1914  O   GLN A 370      36.649  -7.032  33.415  1.00 104.91      A    O
ATOM   1915  N   ARG A 371      35.349  -6.626  31.628  1.00 101.46      A    N
ATOM   1916  CA  ARG A 371      34.998  -5.280  32.067  1.00  97.63      A    C
ATOM   1917  CB  ARG A 371      34.549  -4.438  30.870  1.00  95.62      A    C
ATOM   1924  C   ARG A 371      33.906  -5.273  33.135  1.00  95.93      A    C
ATOM   1925  O   ARG A 371      32.894  -5.962  33.008  1.00  95.32      A    O
ATOM   1926  N   PRO A 372      34.099  -4.479  34.202  1.00  94.85      A    N
ATOM   1927  CD  PRO A 372      35.209  -3.530  34.394  1.00  95.12      A    C
ATOM   1928  CA  PRO A 372      33.135  -4.374  35.300  1.00  95.00      A    C
ATOM   1929  CB  PRO A 372      33.820  -3.413  36.268  1.00  95.57      A    C
ATOM   1930  CG  PRO A 372      34.610  -2.533  35.357  1.00  96.16      A    C
ATOM   1931  C   PRO A 372      31.777  -3.861  34.832  1.00  94.75      A    C
ATOM   1932  O   PRO A 372      31.646  -3.352  33.719  1.00  97.12      A    O
ATOM   1933  N   MET A 373      30.771  -3.998  35.687  1.00  92.10      A    N
ATOM   1934  CA  MET A 373      29.426  -3.554  35.349  1.00  92.05      A    C
ATOM   1935  CB  MET A 373      28.412  -4.660  35.656  1.00  93.38      A    C
ATOM   1936  CG  MET A 373      27.438  -4.948  34.519  1.00  96.77      A    C
ATOM   1937  SD  MET A 373      26.501  -3.495  34.006  1.00 102.02      A    S
ATOM   1938  CE  MET A 373      25.407  -4.195  32.770  1.00  92.68      A    C
```

Figure 1FF

```
ATOM   1939  C   MET A 373      29.048  -2.286  36.106  1.00  91.70      A    C
ATOM   1940  O   MET A 373      29.842  -1.739  36.871  1.00  91.12      A    O
ATOM   1941  N   LEU A 374      27.821  -1.834  35.876  1.00  91.98      A    N
ATOM   1942  CA  LEU A 374      27.265  -0.637  36.492  1.00  93.17      A    C
ATOM   1943  CB  LEU A 374      25.747  -0.640  36.281  1.00  92.14      A    C
ATOM   1944  CG  LEU A 374      25.059  -2.007  36.417  1.00  89.07      A    C
ATOM   1945  CD1 LEU A 374      24.547  -2.208  37.832  1.00  86.18      A    C
ATOM   1946  CD2 LEU A 374      23.901  -2.092  35.441  1.00  86.52      A    C
ATOM   1947  C   LEU A 374      27.592  -0.434  37.973  1.00  95.60      A    C
ATOM   1948  O   LEU A 374      28.374   0.450  38.327  1.00  95.97      A    O
ATOM   1949  N   ARG A 375      26.994  -1.257  38.828  1.00  95.21      A    N
ATOM   1950  CA  ARG A 375      27.182  -1.170  40.274  1.00  92.13      A    C
ATOM   1951  CB  ARG A 375      26.447  -2.323  40.960  1.00  90.79      A    C
ATOM   1958  C   ARG A 375      28.634  -1.153  40.740  1.00  91.00      A    C
ATOM   1959  O   ARG A 375      28.958  -0.527  41.751  1.00  90.97      A    O
ATOM   1960  N   GLU A 376      29.506  -1.843  40.012  1.00  90.15      A    N
ATOM   1961  CA  GLU A 376      30.917  -1.898  40.378  1.00  90.23      A    C
ATOM   1962  CB  GLU A 376      31.780  -2.709  39.342  1.00  89.46      A    C
ATOM   1967  C   GLU A 376      31.510  -0.497  40.493  1.00  90.92      A    C
ATOM   1968  O   GLU A 376      31.945  -0.083  41.567  1.00  90.38      A    O
ATOM   1969  N   VAL A 377      31.521   0.228  39.380  1.00  93.10      A    N
ATOM   1970  CA  VAL A 377      32.061   1.582  39.350  1.00  94.36      A    C
ATOM   1971  CB  VAL A 377      32.093   2.133  37.910  1.00  94.04      A    C
ATOM   1974  C   VAL A 377      31.235   2.529  40.214  1.00  95.21      A    C
ATOM   1975  O   VAL A 377      31.769   3.463  40.810  1.00  96.50      A    O
ATOM   1976  N   LEU A 378      29.932   2.279  40.276  1.00  95.05      A    N
ATOM   1977  CA  LEU A 378      29.021   3.102  41.061  1.00  94.61      A    C
ATOM   1978  CB  LEU A 378      27.578   2.819  40.633  1.00  88.14      A    C
ATOM   1979  CG  LEU A 378      26.811   3.947  39.934  1.00  83.74      A    C
ATOM   1980  CD1 LEU A 378      27.761   4.860  39.169  1.00  80.09      A    C
ATOM   1981  CD2 LEU A 378      25.771   3.336  39.005  1.00  82.05      A    C
ATOM   1982  C   LEU A 378      29.177   2.876  42.562  1.00  96.93      A    C
ATOM   1983  O   LEU A 378      28.501   3.515  43.369  1.00  97.72      A    O
ATOM   1984  N   GLU A 379      30.074   1.965  42.928  1.00  97.82      A    N
ATOM   1985  CA  GLU A 379      30.339   1.649  44.329  1.00  96.52      A    C
ATOM   1986  CB  GLU A 379      29.540   0.415  44.754  1.00  96.06      A    C
ATOM   1991  C   GLU A 379      31.832   1.386  44.516  1.00  94.69      A    C
ATOM   1992  O   GLU A 379      32.254   0.782  45.503  1.00  97.69      A    O
ATOM   1993  N   HIS A 380      32.619   1.850  43.551  1.00  91.51      A    N
ATOM   1994  CA  HIS A 380      34.068   1.685  43.558  1.00  91.22      A    C
ATOM   1995  CB  HIS A 380      34.604   1.930  42.141  1.00  90.28      A    C
ATOM   1996  CG  HIS A 380      36.098   1.952  42.046  1.00  87.98      A    C
ATOM   1997  CD2 HIS A 380      36.970   1.060  41.521  1.00  86.19      A    C
ATOM   1998  ND1 HIS A 380      36.858   2.990  42.537  1.00  87.48      A    N
ATOM   1999  CE1 HIS A 380      38.137   2.737  42.318  1.00  85.91      A    C
ATOM   2000  NE2 HIS A 380      38.232   1.573  41.704  1.00  86.00      A    N
ATOM   2001  C   HIS A 380      34.739   2.625  44.563  1.00  91.71      A    C
ATOM   2002  O   HIS A 380      34.252   3.724  44.819  1.00  89.07      A    O
ATOM   2003  N   PRO A 381      35.867   2.197  45.154  1.00  93.36      A    N
ATOM   2004  CD  PRO A 381      36.509   0.881  44.999  1.00  93.32      A    C
ATOM   2005  CA  PRO A 381      36.596   3.009  46.134  1.00  95.25      A    C
ATOM   2006  CB  PRO A 381      37.728   2.081  46.579  1.00  94.28      A    C
ATOM   2007  CG  PRO A 381      37.925   1.181  45.397  1.00  92.08      A    C
ATOM   2008  C   PRO A 381      37.108   4.370  45.657  1.00  96.97      A    C
ATOM   2009  O   PRO A 381      37.861   5.030  46.372  1.00  97.79      A    O
ATOM   2010  N   TRP A 382      36.712   4.792  44.458  1.00  98.24      A    N
ATOM   2011  CA  TRP A 382      37.143   6.093  43.956  1.00 100.14      A    C
ATOM   2012  CB  TRP A 382      37.956   5.959  42.669  1.00 102.98      A    C
ATOM   2013  CG  TRP A 382      38.809   7.168  42.412  1.00 106.14      A    C
ATOM   2014  CD2 TRP A 382      38.634   8.143  41.376  1.00 106.96      A    C
ATOM   2015  CE2 TRP A 382      39.646   9.116  41.541  1.00 108.81      A    C
```

Figure 1GG

```
ATOM  2016  CE3  TRP A 382      37.715    8.294   40.329  1.00  105.08   A    C
ATOM  2017  CD1  TRP A 382      39.892    7.574   43.139  1.00  108.44   A    C
ATOM  2018  NE1  TRP A 382      40.401    8.745   42.622  1.00  110.49   A    N
ATOM  2019  CZ2  TRP A 382      39.770   10.220   40.692  1.00  107.72   A    C
ATOM  2020  CZ3  TRP A 382      37.839    9.394   39.483  1.00  106.37   A    C
ATOM  2021  CH2  TRP A 382      38.858   10.344   39.674  1.00  106.62   A    C
ATOM  2022  C    TRP A 382      35.932    6.987   43.715  1.00  100.57   A    C
ATOM  2023  O    TRP A 382      35.994    8.195   43.951  1.00   98.78   A    O
ATOM  2024  N    ILE A 383      34.838    6.403   43.231  1.00  101.81   A    N
ATOM  2025  CA   ILE A 383      33.617    7.176   43.022  1.00  104.81   A    C
ATOM  2026  CB   ILE A 383      32.452    6.309   42.481  1.00  106.59   A    C
ATOM  2027  CG2  ILE A 383      32.459    4.942   43.139  1.00  104.66   A    C
ATOM  2028  CG1  ILE A 383      31.119    7.022   42.733  1.00  108.98   A    C
ATOM  2029  CD1  ILE A 383      29.893    6.146   42.554  1.00  109.51   A    C
ATOM  2030  C    ILE A 383      33.261    7.648   44.422  1.00  106.17   A    C
ATOM  2031  O    ILE A 383      32.991    8.828   44.651  1.00  106.49   A    O
ATOM  2032  N    THR A 384      33.273    6.699   45.353  1.00  108.25   A    N
ATOM  2033  CA   THR A 384      32.996    6.970   46.754  1.00  109.45   A    C
ATOM  2034  CB   THR A 384      32.741    5.660   47.537  1.00  110.60   A    C
ATOM  2035  OG1  THR A 384      33.891    4.809   47.441  1.00  110.98   A    O
ATOM  2036  CG2  THR A 384      31.530    4.927   46.971  1.00  109.33   A    C
ATOM  2037  C    THR A 384      34.254    7.649   47.285  1.00  109.77   A    C
ATOM  2038  O    THR A 384      35.353    7.115   47.142  1.00  109.57   A    O
ATOM  2039  N    ALA A 385      34.071    8.826   47.882  1.00  110.37   A    N
ATOM  2040  CA   ALA A 385      35.141    9.666   48.432  1.00  112.53   A    C
ATOM  2041  CB   ALA A 385      36.474    8.913   48.501  1.00  111.99   A    C
ATOM  2042  C    ALA A 385      35.258   10.860   47.491  1.00  113.04   A    C
ATOM  2043  O    ALA A 385      34.446   11.783   47.559  1.00  115.94   A    O
ATOM  2044  N    ASN A 386      36.253   10.840   46.609  1.00  111.79   A    N
ATOM  2045  CA   ASN A 386      36.425   11.929   45.654  1.00  109.04   A    C
ATOM  2046  CB   ASN A 386      37.598   11.647   44.710  1.00  104.45   A    C
ATOM  2047  CG   ASN A 386      38.936   11.658   45.417  1.00  104.48   A    C
ATOM  2048  OD1  ASN A 386      39.279   12.618   46.106  1.00  103.93   A    O
ATOM  2049  ND2  ASN A 386      39.706   10.590   45.243  1.00  106.22   A    N
ATOM  2050  C    ASN A 386      35.150   12.066   44.830  1.00  109.99   A    C
ATOM  2051  O    ASN A 386      34.628   11.076   44.316  1.00  110.65   A    O
ATOM  2052  N    SER A 387      34.648   13.292   44.719  1.00  110.34   A    N
ATOM  2053  CA   SER A 387      33.439   13.571   43.949  1.00  111.41   A    C
ATOM  2054  CB   SER A 387      33.621   13.116   42.504  1.00  111.26   A    C
ATOM  2056  C    SER A 387      32.181   12.927   44.517  1.00  112.05   A    C
ATOM  2057  O    SER A 387      32.088   11.703   44.628  1.00  112.03   A    O
ATOM  2058  N    SER A 388      31.212   13.774   44.852  1.00  112.96   A    N
ATOM  2059  CA   SER A 388      29.931   13.357   45.414  1.00  114.75   A    C
ATOM  2060  CB   SER A 388      28.847   14.367   45.031  1.00  112.67   A    C
ATOM  2061  OG   SER A 388      27.597   14.013   45.596  1.00  114.44   A    O
ATOM  2062  C    SER A 388      29.466   11.958   45.018  1.00  117.30   A    C
ATOM  2063  O    SER A 388      29.737   11.482   43.914  1.00  115.65   A    O
ATOM  2064  N    LYS A 389      28.746   11.319   45.935  1.00  121.30   A    N
ATOM  2065  CA   LYS A 389      28.216    9.975   45.736  1.00  125.05   A    C
ATOM  2066  CB   LYS A 389      27.800    9.389   47.089  1.00  122.77   A    C
ATOM  2071  C    LYS A 389      27.020    9.990   44.778  1.00  128.15   A    C
ATOM  2072  O    LYS A 389      26.569   11.057   44.358  1.00  129.66   A    O
ATOM  2073  N    PRO A 390      26.492    8.803   44.420  1.00  128.94   A    N
ATOM  2074  CD   PRO A 390      26.918    7.463   44.867  1.00  128.63   A    C
ATOM  2075  CA   PRO A 390      25.347    8.695   43.509  1.00  128.53   A    C
ATOM  2076  CB   PRO A 390      24.858    7.274   43.754  1.00  126.83   A    C
ATOM  2077  CG   PRO A 390      26.134    6.539   43.951  1.00  126.18   A    C
ATOM  2078  C    PRO A 390      24.257    9.734   43.757  1.00  129.34   A    C
ATOM  2079  O    PRO A 390      24.289   10.765   43.051  1.00  129.66   A    O
TER   2081       PRO A 390                                              A
ATOM  2082  C1   216 B   1      27.070   23.338   20.180  1.00   93.97   B    C
```

Figure 1HH

```
ATOM  2083  C2   216 B   1      25.733  23.364  20.566  1.00   93.18  B   C
ATOM  2084  C3   216 B   1      24.767  22.820  19.732  1.00   92.55  B   C
ATOM  2085  C4   216 B   1      25.128  22.260  18.505  1.00   92.63  B   C
ATOM  2086  CS5  216 B   1      26.469  22.237  18.117  1.00   94.07  B   C
ATOM  2087  C6   216 B   1      27.443  22.780  18.955  1.00   94.54  B   C
ATOM  2088  C7   216 B   1      24.625  25.148  24.180  1.00   95.50  B   C
ATOM  2089  C9   216 B   1      25.796  25.550  23.500  1.00   96.00  B   C
ATOM  2090  N    216 B   1      26.152  24.948  22.310  1.00   93.73  B   N
ATOM  2091  C14  216 B   1      25.370  23.950  21.770  1.00   92.76  B   C
ATOM  2092  N2   216 B   1      24.229  23.566  22.443  1.00   92.60  B   N
ATOM  2093  C17  216 B   1      23.838  24.138  23.634  1.00   94.87  B   C
ATOM  2094  C8   216 B   1      21.062  20.844  23.065  1.00  100.05  B   C
ATOM  2095  C10  216 B   1      22.140  21.767  23.054  1.00   97.29  B   C
ATOM  2096  C12  216 B   1      21.776  22.769  23.932  1.00   94.91  B   C
ATOM  2097  N4   216 B   1      20.479  22.633  24.356  1.00   91.80  B   N
ATOM  2098  N3   216 B   1      19.999  21.500  23.741  1.00   95.15  B   N
ATOM  2099  C15  216 B   1      21.052  19.595  22.496  1.00  104.55  B   C
ATOM  2100  C11  216 B   1      24.268  25.768  25.380  1.00   95.89  B   C
ATOM  2101  C13  216 B   1      25.069  26.790  25.909  1.00   96.79  B   C
ATOM  2102  C16  216 B   1      26.233  27.189  25.238  1.00   98.64  B   C
ATOM  2103  C5   216 B   1      26.594  26.568  24.035  1.00   98.25  B   C
ATOM  2104  N6   216 B   1      22.682  23.749  24.277  1.00   96.61  B   N
ATOM  2105  C18  216 B   1      20.263  19.429  21.331  1.00  105.53  B   C
ATOM  2106  C19  216 B   1      19.797  18.949  22.583  1.00  107.33  B   C
TER   2107       216 B   1                                             B
END
```

Figure 2A

| Atom | Type | Resid | # | X | Y | Z | Occ | B | Mol | |
|---|---|---|---|---|---|---|---|---|---|---|
| ATOM | 1 | CB | ASN A 120 | -25.184 | 17.387 | 17.980 | 1.00 | 134.47 | A | C |
| ATOM | 5 | C | ASN A 120 | -23.201 | 15.983 | 17.367 | 1.00 | 139.87 | A | C |
| ATOM | 6 | O | ASN A 120 | -22.523 | 17.000 | 17.516 | 1.00 | 141.64 | A | O |
| ATOM | 7 | N | ASN A 120 | -25.010 | 15.048 | 18.805 | 1.00 | 137.11 | A | N |
| ATOM | 8 | CA | ASN A 120 | -24.696 | 15.967 | 17.672 | 1.00 | 139.34 | A | C |
| ATOM | 9 | N | GLU A 121 | -22.716 | 14.819 | 16.953 | 1.00 | 143.53 | A | N |
| ATOM | 10 | CA | GLU A 121 | -21.332 | 14.556 | 16.564 | 1.00 | 145.36 | A | C |
| ATOM | 11 | CB | GLU A 121 | -21.265 | 14.440 | 15.038 | 1.00 | 148.03 | A | C |
| ATOM | 16 | C | GLU A 121 | -20.142 | 15.404 | 17.024 | 1.00 | 145.17 | A | C |
| ATOM | 17 | O | GLU A 121 | -19.788 | 15.422 | 18.205 | 1.00 | 147.49 | A | O |
| ATOM | 18 | N | GLU A 122 | -19.531 | 16.080 | 16.049 | 1.00 | 142.16 | A | N |
| ATOM | 19 | CA | GLU A 122 | -18.316 | 16.885 | 16.203 | 1.00 | 138.66 | A | C |
| ATOM | 20 | CB | GLU A 122 | -18.059 | 17.310 | 17.653 | 1.00 | 138.41 | A | C |
| ATOM | 25 | C | GLU A 122 | -17.328 | 15.809 | 15.806 | 1.00 | 133.45 | A | C |
| ATOM | 26 | O | GLU A 122 | -16.478 | 16.014 | 14.931 | 1.00 | 134.51 | A | O |
| ATOM | 27 | N | SER A 123 | -17.484 | 14.650 | 16.454 | 1.00 | 128.27 | A | N |
| ATOM | 28 | CA | SER A 123 | -16.674 | 13.471 | 16.172 | 1.00 | 122.12 | A | C |
| ATOM | 29 | CB | SER A 123 | -17.429 | 12.213 | 16.618 | 1.00 | 120.57 | A | C |
| ATOM | 31 | C | SER A 123 | -16.496 | 13.499 | 14.650 | 1.00 | 117.73 | A | C |
| ATOM | 32 | O | SER A 123 | -17.391 | 13.117 | 13.887 | 1.00 | 116.68 | A | O |
| ATOM | 33 | N | LYS A 124 | -15.333 | 13.978 | 14.226 | 1.00 | 114.78 | A | N |
| ATOM | 34 | CA | LYS A 124 | -15.039 | 14.147 | 12.816 | 1.00 | 111.29 | A | C |
| ATOM | 35 | CB | LYS A 124 | -14.153 | 15.380 | 12.657 | 1.00 | 108.44 | A | C |
| ATOM | 40 | C | LYS A 124 | -14.407 | 12.972 | 12.072 | 1.00 | 110.56 | A | C |
| ATOM | 41 | O | LYS A 124 | -13.623 | 13.184 | 11.154 | 1.00 | 111.66 | A | O |
| ATOM | 42 | N | LYS A 125 | -14.775 | 11.744 | 12.416 | 1.00 | 110.30 | A | N |
| ATOM | 43 | CA | LYS A 125 | -14.185 | 10.568 | 11.772 | 1.00 | 109.56 | A | C |
| ATOM | 44 | CB | LYS A 125 | -14.239 | 9.399 | 12.764 | 1.00 | 106.61 | A | C |
| ATOM | 49 | C | LYS A 125 | -14.699 | 10.084 | 10.383 | 1.00 | 109.28 | A | C |
| ATOM | 50 | O | LYS A 125 | -14.010 | 9.317 | 9.715 | 1.00 | 113.16 | A | O |
| ATOM | 51 | N | ARG A 126 | -15.874 | 10.547 | 9.949 | 1.00 | 104.45 | A | N |
| ATOM | 52 | CA | ARG A 126 | -16.553 | 10.151 | 8.683 | 1.00 | 98.84 | A | C |
| ATOM | 53 | CB | ARG A 126 | -17.682 | 11.156 | 8.404 | 1.00 | 94.42 | A | C |
| ATOM | 60 | C | ARG A 126 | -15.854 | 9.859 | 7.330 | 1.00 | 94.87 | A | C |
| ATOM | 61 | O | ARG A 126 | -14.821 | 9.181 | 7.258 | 1.00 | 93.08 | A | O |
| ATOM | 62 | N | GLN A 127 | -16.510 | 10.340 | 6.263 | 1.00 | 93.82 | A | N |
| ATOM | 63 | CA | GLN A 127 | -16.082 | 10.229 | 4.852 | 1.00 | 91.47 | A | C |
| ATOM | 64 | CB | GLN A 127 | -16.553 | 8.893 | 4.254 | 1.00 | 89.98 | A | C |
| ATOM | 69 | C | GLN A 127 | -16.709 | 11.418 | 4.074 | 1.00 | 89.31 | A | C |
| ATOM | 70 | O | GLN A 127 | -17.539 | 11.248 | 3.172 | 1.00 | 89.46 | A | O |
| ATOM | 71 | N | TRP A 128 | -16.281 | 12.619 | 4.455 | 1.00 | 87.24 | A | N |
| ATOM | 72 | CA | TRP A 128 | -16.748 | 13.901 | 3.927 | 1.00 | 83.92 | A | C |
| ATOM | 73 | CB | TRP A 128 | -15.728 | 14.968 | 4.300 | 1.00 | 86.41 | A | C |
| ATOM | 74 | CG | TRP A 128 | -15.199 | 14.741 | 5.655 | 1.00 | 92.37 | A | C |
| ATOM | 75 | CD2 | TRP A 128 | -15.930 | 14.831 | 6.882 | 1.00 | 94.67 | A | C |
| ATOM | 76 | CE2 | TRP A 128 | -15.048 | 14.464 | 7.922 | 1.00 | 96.00 | A | C |
| ATOM | 77 | CE3 | TRP A 128 | -17.243 | 15.185 | 7.202 | 1.00 | 93.59 | A | C |
| ATOM | 78 | CD1 | TRP A 128 | -13.940 | 14.338 | 5.986 | 1.00 | 95.29 | A | C |
| ATOM | 79 | NE1 | TRP A 128 | -13.841 | 14.168 | 7.350 | 1.00 | 97.00 | A | N |
| ATOM | 80 | CZ2 | TRP A 128 | -15.438 | 14.440 | 9.263 | 1.00 | 95.88 | A | C |
| ATOM | 81 | CZ3 | TRP A 128 | -17.631 | 15.159 | 8.532 | 1.00 | 94.85 | A | C |
| ATOM | 82 | CH2 | TRP A 128 | -16.729 | 14.788 | 9.550 | 1.00 | 95.78 | A | C |
| ATOM | 83 | C | TRP A 128 | -17.141 | 14.102 | 2.466 | 1.00 | 81.09 | A | C |
| ATOM | 84 | O | TRP A 128 | -16.633 | 13.447 | 1.552 | 1.00 | 79.39 | A | O |
| ATOM | 85 | N | ALA A 129 | -18.053 | 15.058 | 2.290 | 1.00 | 78.26 | A | N |
| ATOM | 86 | CA | ALA A 129 | -18.587 | 15.477 | 1.001 | 1.00 | 76.01 | A | C |
| ATOM | 87 | CB | ALA A 129 | -19.874 | 14.727 | 0.693 | 1.00 | 74.48 | A | C |
| ATOM | 88 | C | ALA A 129 | -18.881 | 16.966 | 1.165 | 1.00 | 75.27 | A | C |

Figure 2B

```
ATOM   89  O    ALA A 129    -19.232  17.405   2.265  1.00  74.01  A  O
ATOM   90  N    LEU A 130    -18.741  17.746   0.093  1.00  74.72  A  N
ATOM   91  CA   LEU A 130    -19.016  19.172   0.187  1.00  72.32  A  C
ATOM   92  CB   LEU A 130    -18.910  19.849  -1.180  1.00  66.69  A  C
ATOM   93  CG   LEU A 130    -19.205  21.360  -1.201  1.00  62.03  A  C
ATOM   94  CD1  LEU A 130    -18.330  22.068  -0.158  1.00  57.90  A  C
ATOM   95  CD2  LEU A 130    -18.931  21.938  -2.593  1.00  59.55  A  C
ATOM   96  C    LEU A 130    -20.420  19.347   0.738  1.00  74.13  A  C
ATOM   97  O    LEU A 130    -20.712  20.325   1.429  1.00  74.05  A  O
ATOM   98  N    GLU A 131    -21.288  18.384   0.448  1.00  75.10  A  N
ATOM   99  CA   GLU A 131    -22.663  18.463   0.924  1.00  75.77  A  C
ATOM  100  CB   GLU A 131    -23.483  17.255   0.468  1.00  79.06  A  C
ATOM  101  CG   GLU A 131    -24.975  17.453   0.710  1.00  87.95  A  C
ATOM  102  CD   GLU A 131    -25.740  16.155   0.902  1.00  93.25  A  C
ATOM  103  OE1  GLU A 131    -25.653  15.270   0.024  1.00  95.69  A  O
ATOM  104  OE2  GLU A 131    -26.440  16.025   1.935  1.00  96.56  A  O
ATOM  105  C    GLU A 131    -22.760  18.557   2.441  1.00  74.18  A  C
ATOM  106  O    GLU A 131    -23.487  19.400   2.950  1.00  76.86  A  O
ATOM  107  N    ASP A 132    -22.032  17.692   3.151  1.00  72.20  A  N
ATOM  108  CA   ASP A 132    -22.050  17.650   4.626  1.00  69.11  A  C
ATOM  109  CB   ASP A 132    -21.021  16.633   5.150  1.00  67.71  A  C
ATOM  110  CG   ASP A 132    -21.232  15.235   4.592  1.00  67.05  A  C
ATOM  111  OD1  ASP A 132    -21.251  15.100   3.358  1.00  70.79  A  O
ATOM  112  OD2  ASP A 132    -21.373  14.270   5.377  1.00  62.87  A  O
ATOM  113  C    ASP A 132    -21.808  18.969   5.372  1.00  66.16  A  C
ATOM  114  O    ASP A 132    -21.774  18.970   6.597  1.00  60.94  A  O
ATOM  115  N    PHE A 133    -21.655  20.084   4.660  1.00  65.23  A  N
ATOM  116  CA   PHE A 133    -21.363  21.355   5.327  1.00  60.63  A  C
ATOM  117  CB   PHE A 133    -19.865  21.676   5.187  1.00  59.10  A  C
ATOM  118  CG   PHE A 133    -18.953  20.607   5.730  1.00  54.10  A  C
ATOM  119  CD1  PHE A 133    -18.756  19.431   5.029  1.00  49.91  A  C
ATOM  120  CD2  PHE A 133    -18.299  20.789   6.951  1.00  54.44  A  C
ATOM  121  CE1  PHE A 133    -17.925  18.447   5.519  1.00  49.64  A  C
ATOM  122  CE2  PHE A 133    -17.462  19.820   7.462  1.00  54.13  A  C
ATOM  123  CZ   PHE A 133    -17.267  18.635   6.746  1.00  51.78  A  C
ATOM  124  C    PHE A 133    -22.140  22.575   4.878  1.00  58.23  A  C
ATOM  125  O    PHE A 133    -22.522  22.675   3.729  1.00  58.80  A  O
ATOM  126  N    GLU A 134    -22.347  23.507   5.805  1.00  57.80  A  N
ATOM  127  CA   GLU A 134    -23.036  24.774   5.531  1.00  57.26  A  C
ATOM  128  CB   GLU A 134    -24.039  25.086   6.639  1.00  49.36  A  C
ATOM  133  C    GLU A 134    -21.945  25.848   5.491  1.00  59.26  A  C
ATOM  134  O    GLU A 134    -21.188  26.020   6.446  1.00  60.67  A  O
ATOM  135  N    ILE A 135    -21.845  26.570   4.390  1.00  60.17  A  N
ATOM  136  CA   ILE A 135    -20.783  27.548   4.292  1.00  62.37  A  C
ATOM  137  CB   ILE A 135    -20.202  27.605   2.854  1.00  59.94  A  C
ATOM  138  CG2  ILE A 135    -19.541  26.277   2.509  1.00  56.04  A  C
ATOM  139  CG1  ILE A 135    -21.319  27.926   1.862  1.00  61.70  A  C
ATOM  140  CD1  ILE A 135    -20.858  28.594   0.569  1.00  60.25  A  C
ATOM  141  C    ILE A 135    -21.167  28.953   4.706  1.00  66.13  A  C
ATOM  142  O    ILE A 135    -22.229  29.456   4.331  1.00  68.81  A  O
ATOM  143  N    GLY A 136    -20.282  29.580   5.478  1.00  68.37  A  N
ATOM  144  CA   GLY A 136    -20.495  30.944   5.922  1.00  67.99  A  C
ATOM  145  C    GLY A 136    -19.749  31.913   5.018  1.00  66.99  A  C
ATOM  146  O    GLY A 136    -19.551  31.619   3.842  1.00  68.95  A  O
ATOM  147  N    ARG A 137    -19.338  33.058   5.562  1.00  65.08  A  N
ATOM  148  CA   ARG A 137    -18.611  34.075   4.799  1.00  64.58  A  C
ATOM  149  CB   ARG A 137    -18.516  35.369   5.612  1.00  64.24  A  C
ATOM  150  CG   ARG A 137    -17.245  35.491   6.489  1.00  61.36  A  C
ATOM  151  CD   ARG A 137    -17.508  36.256   7.792  1.00  62.13  A  C
ATOM  152  NE   ARG A 137    -16.265  36.433   8.541  1.00  72.52  A  N
ATOM  153  CZ   ARG A 137    -16.173  36.502   9.868  1.00  75.05  A  C
```

Figure 2C

| ATOM | 154 | NH1 | ARG | A | 137 | -14.986 | 36.664 | 10.449 | 1.00 | 74.71 | A | N |
|------|-----|-----|-----|---|-----|---------|--------|--------|------|-------|---|---|
| ATOM | 155 | NH2 | ARG | A | 137 | -17.257 | 36.399 | 10.617 | 1.00 | 75.04 | A | N |
| ATOM | 156 | C | ARG | A | 137 | -17.204 | 33.593 | 4.514 | 1.00 | 65.94 | A | C |
| ATOM | 157 | O | ARG | A | 137 | -16.818 | 32.513 | 4.942 | 1.00 | 66.67 | A | O |
| ATOM | 158 | N | PRO | A | 138 | -16.429 | 34.369 | 3.749 | 1.00 | 68.43 | A | N |
| ATOM | 159 | CD | PRO | A | 138 | -16.934 | 35.337 | 2.762 | 1.00 | 71.71 | A | C |
| ATOM | 160 | CA | PRO | A | 138 | -15.040 | 33.996 | 3.430 | 1.00 | 68.44 | A | C |
| ATOM | 161 | CB | PRO | A | 138 | -14.818 | 34.626 | 2.059 | 1.00 | 68.50 | A | C |
| ATOM | 162 | CG | PRO | A | 138 | -15.651 | 35.852 | 2.132 | 1.00 | 72.38 | A | C |
| ATOM | 163 | C | PRO | A | 138 | -14.102 | 34.582 | 4.501 | 1.00 | 69.30 | A | C |
| ATOM | 164 | O | PRO | A | 138 | -13.894 | 35.807 | 4.568 | 1.00 | 71.18 | A | O |
| ATOM | 165 | N | LEU | A | 139 | -13.551 | 33.709 | 5.341 | 1.00 | 68.08 | A | N |
| ATOM | 166 | CA | LEU | A | 139 | -12.676 | 34.149 | 6.402 | 1.00 | 66.00 | A | C |
| ATOM | 167 | CB | LEU | A | 139 | -12.226 | 32.962 | 7.246 | 1.00 | 60.44 | A | C |
| ATOM | 168 | CG | LEU | A | 139 | -13.366 | 32.246 | 7.995 | 1.00 | 56.97 | A | C |
| ATOM | 169 | CD1 | LEU | A | 139 | -12.791 | 31.129 | 8.881 | 1.00 | 58.44 | A | C |
| ATOM | 170 | CD2 | LEU | A | 139 | -14.150 | 33.250 | 8.856 | 1.00 | 55.72 | A | C |
| ATOM | 171 | C | LEU | A | 139 | -11.474 | 34.937 | 5.917 | 1.00 | 69.54 | A | C |
| ATOM | 172 | O | LEU | A | 139 | -10.885 | 35.680 | 6.701 | 1.00 | 70.82 | A | O |
| ATOM | 173 | N | GLY | A | 140 | -11.121 | 34.803 | 4.639 | 1.00 | 72.38 | A | N |
| ATOM | 174 | CA | GLY | A | 140 | -9.987 | 35.548 | 4.116 | 1.00 | 76.78 | A | C |
| ATOM | 175 | C | GLY | A | 140 | -9.433 | 35.075 | 2.780 | 1.00 | 80.16 | A | C |
| ATOM | 176 | O | GLY | A | 140 | -9.590 | 33.904 | 2.426 | 1.00 | 80.45 | A | O |
| ATOM | 177 | N | LYS | A | 141 | -8.772 | 35.974 | 2.046 | 1.00 | 82.86 | A | N |
| ATOM | 178 | CA | LYS | A | 141 | -8.198 | 35.639 | 0.742 | 1.00 | 88.14 | A | C |
| ATOM | 179 | CB | LYS | A | 141 | -7.649 | 36.899 | 0.067 | 1.00 | 84.53 | A | C |
| ATOM | 184 | C | LYS | A | 141 | -7.094 | 34.569 | 0.788 | 1.00 | 92.85 | A | C |
| ATOM | 185 | O | LYS | A | 141 | -6.452 | 34.360 | 1.820 | 1.00 | 95.88 | A | O |
| ATOM | 186 | N | GLY | A | 142 | -6.873 | 33.899 | -0.341 | 1.00 | 96.31 | A | N |
| ATOM | 187 | CA | GLY | A | 142 | -5.851 | 32.867 | -0.391 | 1.00 | 99.27 | A | C |
| ATOM | 188 | C | GLY | A | 142 | -5.416 | 32.479 | -1.793 | 1.00 | 102.36 | A | C |
| ATOM | 189 | O | GLY | A | 142 | -4.659 | 31.516 | -1.950 | 1.00 | 101.58 | A | O |
| ATOM | 190 | N | LYS | A | 143 | -5.896 | 33.232 | -2.790 | 1.00 | 105.52 | A | N |
| ATOM | 191 | CA | LYS | A | 143 | -5.597 | 33.040 | -4.222 | 1.00 | 106.84 | A | C |
| ATOM | 192 | CB | LYS | A | 143 | -4.193 | 33.581 | -4.553 | 1.00 | 108.45 | A | C |
| ATOM | 193 | CG | LYS | A | 143 | -3.903 | 33.731 | -6.047 | 1.00 | 109.75 | A | C |
| ATOM | 194 | CD | LYS | A | 143 | -2.518 | 34.328 | -6.297 | 1.00 | 110.63 | A | C |
| ATOM | 195 | CE | LYS | A | 143 | -2.229 | 34.527 | -7.790 | 1.00 | 112.22 | A | C |
| ATOM | 196 | NZ | LYS | A | 143 | -3.041 | 35.612 | -8.427 | 1.00 | 111.69 | A | N |
| ATOM | 197 | C | LYS | A | 143 | -5.733 | 31.587 | -4.696 | 1.00 | 106.80 | A | C |
| ATOM | 198 | O | LYS | A | 143 | -6.361 | 31.317 | -5.727 | 1.00 | 106.21 | A | O |
| ATOM | 199 | N | PHE | A | 144 | -5.123 | 30.665 | -3.950 | 1.00 | 106.27 | A | N |
| ATOM | 200 | CA | PHE | A | 144 | -5.194 | 29.236 | -4.236 | 1.00 | 101.88 | A | C |
| ATOM | 201 | CB | PHE | A | 144 | -4.263 | 28.461 | -3.301 | 1.00 | 102.76 | A | C |
| ATOM | 202 | CG | PHE | A | 144 | -2.980 | 28.022 | -3.944 | 1.00 | 105.27 | A | C |
| ATOM | 203 | CD1 | PHE | A | 144 | -1.924 | 27.560 | -3.166 | 1.00 | 106.66 | A | C |
| ATOM | 204 | CD2 | PHE | A | 144 | -2.830 | 28.044 | -5.326 | 1.00 | 104.58 | A | C |
| ATOM | 205 | CE1 | PHE | A | 144 | -0.739 | 27.126 | -3.754 | 1.00 | 104.82 | A | C |
| ATOM | 206 | CE2 | PHE | A | 144 | -1.650 | 27.611 | -5.925 | 1.00 | 103.14 | A | C |
| ATOM | 207 | CZ | PHE | A | 144 | -0.603 | 27.151 | -5.136 | 1.00 | 103.53 | A | C |
| ATOM | 208 | C | PHE | A | 144 | -6.630 | 28.858 | -3.931 | 1.00 | 98.80 | A | C |
| ATOM | 209 | O | PHE | A | 144 | -7.278 | 28.125 | -4.680 | 1.00 | 97.75 | A | O |
| ATOM | 210 | N | GLY | A | 145 | -7.116 | 29.388 | -2.815 | 1.00 | 95.65 | A | N |
| ATOM | 211 | CA | GLY | A | 145 | -8.471 | 29.122 | -2.392 | 1.00 | 91.96 | A | C |
| ATOM | 212 | C | GLY | A | 145 | -8.787 | 29.798 | -1.075 | 1.00 | 89.29 | A | C |
| ATOM | 213 | O | GLY | A | 145 | -7.974 | 29.774 | -0.141 | 1.00 | 90.14 | A | O |
| ATOM | 214 | N | ASN | A | 146 | -9.968 | 30.411 | -1.009 | 1.00 | 85.63 | A | N |
| ATOM | 215 | CA | ASN | A | 146 | -10.423 | 31.091 | 0.195 | 1.00 | 80.37 | A | C |
| ATOM | 216 | CB | ASN | A | 146 | -11.774 | 31.761 | -0.031 | 1.00 | 77.72 | A | C |
| ATOM | 217 | CG | ASN | A | 146 | -11.845 | 32.497 | -1.333 | 1.00 | 75.55 | A | C |
| ATOM | 218 | OD1 | ASN | A | 146 | -10.953 | 33.272 | -1.662 | 1.00 | 73.48 | A | O |

Figure 2D

| ATOM | 219 | ND2 | ASN | A | 146 | -12.915 | 32.271 | -2.085 | 1.00 | 74.52 | A | N |
|---|---|---|---|---|---|---|---|---|---|---|---|---|
| ATOM | 220 | C | ASN | A | 146 | -10.615 | 30.074 | 1.295 | 1.00 | 79.12 | A | C |
| ATOM | 221 | O | ASN | A | 146 | -10.521 | 28.861 | 1.079 | 1.00 | 78.35 | A | O |
| ATOM | 222 | N | VAL | A | 147 | -10.884 | 30.582 | 2.487 | 1.00 | 77.60 | A | N |
| ATOM | 223 | CA | VAL | A | 147 | -11.155 | 29.724 | 3.620 | 1.00 | 77.24 | A | C |
| ATOM | 224 | CB | VAL | A | 147 | -10.133 | 29.889 | 4.739 | 1.00 | 77.88 | A | C |
| ATOM | 225 | CG1 | VAL | A | 147 | -10.391 | 28.840 | 5.832 | 1.00 | 78.34 | A | C |
| ATOM | 226 | CG2 | VAL | A | 147 | -8.735 | 29.750 | 4.183 | 1.00 | 82.13 | A | C |
| ATOM | 227 | C | VAL | A | 147 | -12.487 | 30.241 | 4.082 | 1.00 | 76.51 | A | C |
| ATOM | 228 | O | VAL | A | 147 | -12.604 | 31.405 | 4.447 | 1.00 | 76.88 | A | O |
| ATOM | 229 | N | TYR | A | 148 | -13.501 | 29.388 | 4.035 | 1.00 | 77.03 | A | N |
| ATOM | 230 | CA | TYR | A | 148 | -14.830 | 29.816 | 4.442 | 1.00 | 76.02 | A | C |
| ATOM | 231 | CB | TYR | A | 148 | -15.890 | 29.344 | 3.448 | 1.00 | 77.00 | A | C |
| ATOM | 232 | CG | TYR | A | 148 | -15.725 | 29.863 | 2.049 | 1.00 | 75.64 | A | C |
| ATOM | 233 | CD1 | TYR | A | 148 | -14.756 | 29.327 | 1.196 | 1.00 | 73.17 | A | C |
| ATOM | 234 | CE1 | TYR | A | 148 | -14.617 | 29.782 | -0.098 | 1.00 | 72.40 | A | C |
| ATOM | 235 | CD2 | TYR | A | 148 | -16.548 | 30.876 | 1.571 | 1.00 | 74.33 | A | C |
| ATOM | 236 | CE2 | TYR | A | 148 | -16.415 | 31.339 | 0.280 | 1.00 | 75.51 | A | C |
| ATOM | 237 | CZ | TYR | A | 148 | -15.449 | 30.787 | -0.553 | 1.00 | 74.23 | A | C |
| ATOM | 238 | OH | TYR | A | 148 | -15.342 | 31.240 | -1.846 | 1.00 | 74.52 | A | O |
| ATOM | 239 | C | TYR | A | 148 | -15.240 | 29.316 | 5.801 | 1.00 | 73.10 | A | C |
| ATOM | 240 | O | TYR | A | 148 | -14.793 | 28.257 | 6.242 | 1.00 | 73.57 | A | O |
| ATOM | 241 | N | LEU | A | 149 | -16.097 | 30.093 | 6.458 | 1.00 | 69.73 | A | N |
| ATOM | 242 | CA | LEU | A | 149 | -16.628 | 29.695 | 7.744 | 1.00 | 69.52 | A | C |
| ATOM | 243 | CB | LEU | A | 149 | -17.522 | 30.779 | 8.314 | 1.00 | 70.25 | A | C |
| ATOM | 244 | CG | LEU | A | 149 | -17.076 | 31.433 | 9.620 | 1.00 | 69.99 | A | C |
| ATOM | 245 | CD1 | LEU | A | 149 | -18.310 | 32.028 | 10.272 | 1.00 | 72.54 | A | C |
| ATOM | 246 | CD2 | LEU | A | 149 | -16.421 | 30.433 | 10.556 | 1.00 | 67.04 | A | C |
| ATOM | 247 | C | LEU | A | 149 | -17.479 | 28.507 | 7.363 | 1.00 | 69.47 | A | C |
| ATOM | 248 | O | LEU | A | 149 | -18.012 | 28.457 | 6.254 | 1.00 | 68.87 | A | O |
| ATOM | 249 | N | ALA | A | 150 | -17.616 | 27.544 | 8.255 | 1.00 | 68.72 | A | N |
| ATOM | 250 | CA | ALA | A | 150 | -18.419 | 26.387 | 7.909 | 1.00 | 64.76 | A | C |
| ATOM | 251 | CB | ALA | A | 150 | -17.606 | 25.449 | 7.014 | 1.00 | 65.19 | A | C |
| ATOM | 252 | C | ALA | A | 150 | -18.955 | 25.633 | 9.108 | 1.00 | 63.39 | A | C |
| ATOM | 253 | O | ALA | A | 150 | -18.427 | 25.723 | 10.217 | 1.00 | 60.48 | A | O |
| ATOM | 254 | N | ARG | A | 151 | -20.003 | 24.864 | 8.858 | 1.00 | 64.44 | A | N |
| ATOM | 255 | CA | ARG | A | 151 | -20.647 | 24.078 | 9.906 | 1.00 | 65.91 | A | C |
| ATOM | 256 | CB | ARG | A | 151 | -21.959 | 24.743 | 10.324 | 1.00 | 66.85 | A | C |
| ATOM | 257 | CG | ARG | A | 151 | -22.059 | 25.117 | 11.786 | 1.00 | 65.08 | A | C |
| ATOM | 258 | CD | ARG | A | 151 | -23.363 | 25.889 | 12.056 | 1.00 | 63.90 | A | C |
| ATOM | 259 | NE | ARG | A | 151 | -23.338 | 26.527 | 13.367 | 1.00 | 64.48 | A | N |
| ATOM | 260 | CZ | ARG | A | 151 | -23.704 | 27.784 | 13.589 | 1.00 | 64.89 | A | C |
| ATOM | 261 | NH1 | ARG | A | 151 | -24.126 | 28.540 | 12.592 | 1.00 | 63.05 | A | N |
| ATOM | 262 | NH2 | ARG | A | 151 | -23.627 | 28.286 | 14.817 | 1.00 | 65.98 | A | N |
| ATOM | 263 | C | ARG | A | 151 | -20.967 | 22.684 | 9.420 | 1.00 | 65.57 | A | C |
| ATOM | 264 | O | ARG | A | 151 | -21.399 | 22.506 | 8.281 | 1.00 | 63.56 | A | O |
| ATOM | 265 | N | GLU | A | 152 | -20.745 | 21.683 | 10.260 | 1.00 | 67.29 | A | N |
| ATOM | 266 | CA | GLU | A | 152 | -21.124 | 20.341 | 9.843 | 1.00 | 70.72 | A | C |
| ATOM | 267 | CB | GLU | A | 152 | -20.341 | 19.246 | 10.573 | 1.00 | 74.84 | A | C |
| ATOM | 268 | CG | GLU | A | 152 | -20.963 | 17.885 | 10.243 | 1.00 | 84.84 | A | C |
| ATOM | 269 | CD | GLU | A | 152 | -20.157 | 16.696 | 10.704 | 1.00 | 91.77 | A | C |
| ATOM | 270 | OE1 | GLU | A | 152 | -19.836 | 16.611 | 11.911 | 1.00 | 96.51 | A | O |
| ATOM | 271 | OE2 | GLU | A | 152 | -19.859 | 15.833 | 9.853 | 1.00 | 96.32 | A | O |
| ATOM | 272 | C | GLU | A | 152 | -22.623 | 20.202 | 10.159 | 1.00 | 70.47 | A | C |
| ATOM | 273 | O | GLU | A | 152 | -23.034 | 20.229 | 11.329 | 1.00 | 70.01 | A | O |
| ATOM | 274 | N | ALA | A | 153 | -23.434 | 20.059 | 9.112 | 1.00 | 69.74 | A | N |
| ATOM | 275 | CA | ALA | A | 153 | -24.886 | 19.934 | 9.274 | 1.00 | 68.06 | A | C |
| ATOM | 276 | CB | ALA | A | 153 | -25.517 | 19.440 | 7.962 | 1.00 | 67.15 | A | C |
| ATOM | 277 | C | ALA | A | 153 | -25.338 | 19.047 | 10.453 | 1.00 | 65.26 | A | C |
| ATOM | 278 | O | ALA | A | 153 | -26.289 | 19.377 | 11.142 | 1.00 | 64.34 | A | O |
| ATOM | 279 | N | ALA | A | 154 | -24.646 | 17.938 | 10.684 | 1.00 | 62.32 | A | N |

Figure 2E

| ATOM | 280 | CA  | ALA | A | 154 | -24.982 | 17.005 | 11.758 | 1.00 | 59.92 | A | C |
| --- | --- | --- | --- | --- | --- | --- | --- | --- | --- | --- | --- | --- |
| ATOM | 281 | CB  | ALA | A | 154 | -24.254 | 15.694 | 11.537 | 1.00 | 56.94 | A | C |
| ATOM | 282 | C   | ALA | A | 154 | -24.634 | 17.542 | 13.138 | 1.00 | 60.87 | A | C |
| ATOM | 283 | O   | ALA | A | 154 | -25.507 | 17.822 | 13.962 | 1.00 | 61.89 | A | O |
| ATOM | 284 | N   | SER | A | 155 | -23.339 | 17.682 | 13.383 | 1.00 | 61.32 | A | N |
| ATOM | 285 | CA  | SER | A | 155 | -22.850 | 18.171 | 14.664 | 1.00 | 61.35 | A | C |
| ATOM | 286 | CB  | SER | A | 155 | -21.357 | 17.879 | 14.777 | 1.00 | 64.23 | A | C |
| ATOM | 287 | OG  | SER | A | 155 | -20.645 | 18.518 | 13.729 | 1.00 | 63.27 | A | O |
| ATOM | 288 | C   | SER | A | 155 | -23.072 | 19.651 | 14.896 | 1.00 | 59.60 | A | C |
| ATOM | 289 | O   | SER | A | 155 | -22.881 | 20.124 | 16.001 | 1.00 | 59.22 | A | O |
| ATOM | 290 | N   | ALA | A | 156 | -23.465 | 20.376 | 13.856 | 1.00 | 58.53 | A | N |
| ATOM | 291 | CA  | ALA | A | 156 | -23.663 | 21.822 | 13.943 | 1.00 | 60.56 | A | C |
| ATOM | 292 | CB  | ALA | A | 156 | -24.820 | 22.150 | 14.872 | 1.00 | 58.68 | A | C |
| ATOM | 293 | C   | ALA | A | 156 | -22.373 | 22.469 | 14.453 | 1.00 | 63.19 | A | C |
| ATOM | 294 | O   | ALA | A | 156 | -22.373 | 23.612 | 14.916 | 1.00 | 63.12 | A | O |
| ATOM | 295 | N   | PHE | A | 157 | -21.278 | 21.714 | 14.360 | 1.00 | 65.85 | A | N |
| ATOM | 296 | CA  | PHE | A | 157 | -19.947 | 22.161 | 14.800 | 1.00 | 63.55 | A | C |
| ATOM | 297 | CB  | PHE | A | 157 | -18.977 | 20.978 | 14.870 | 1.00 | 61.20 | A | C |
| ATOM | 298 | CG  | PHE | A | 157 | -17.677 | 21.309 | 15.528 | 1.00 | 61.88 | A | C |
| ATOM | 299 | CD1 | PHE | A | 157 | -17.651 | 21.769 | 16.845 | 1.00 | 65.01 | A | C |
| ATOM | 300 | CD2 | PHE | A | 157 | -16.478 | 21.165 | 14.849 | 1.00 | 61.24 | A | C |
| ATOM | 301 | CE1 | PHE | A | 157 | -16.447 | 22.086 | 17.479 | 1.00 | 65.15 | A | C |
| ATOM | 302 | CE2 | PHE | A | 157 | -15.263 | 21.479 | 15.478 | 1.00 | 63.94 | A | C |
| ATOM | 303 | CZ  | PHE | A | 157 | -15.253 | 21.942 | 16.796 | 1.00 | 65.83 | A | C |
| ATOM | 304 | C   | PHE | A | 157 | -19.367 | 23.200 | 13.859 | 1.00 | 62.39 | A | C |
| ATOM | 305 | O   | PHE | A | 157 | -19.182 | 22.933 | 12.670 | 1.00 | 62.00 | A | O |
| ATOM | 306 | N   | ILE | A | 158 | -19.073 | 24.380 | 14.399 | 1.00 | 61.09 | A | N |
| ATOM | 307 | CA  | ILE | A | 158 | -18.518 | 25.481 | 13.605 | 1.00 | 59.33 | A | C |
| ATOM | 308 | CB  | ILE | A | 158 | -18.603 | 26.789 | 14.406 | 1.00 | 59.98 | A | C |
| ATOM | 309 | CG2 | ILE | A | 158 | -18.432 | 26.460 | 15.904 | 1.00 | 61.02 | A | C |
| ATOM | 310 | CG1 | ILE | A | 158 | -17.545 | 27.793 | 13.944 | 1.00 | 61.79 | A | C |
| ATOM | 311 | CD1 | ILE | A | 158 | -17.545 | 28.077 | 12.462 | 1.00 | 61.05 | A | C |
| ATOM | 312 | C   | ILE | A | 158 | -17.074 | 25.153 | 13.244 | 1.00 | 59.03 | A | C |
| ATOM | 313 | O   | ILE | A | 158 | -16.275 | 24.828 | 14.108 | 1.00 | 60.97 | A | O |
| ATOM | 314 | N   | LEU | A | 159 | -16.762 | 25.230 | 11.955 | 1.00 | 56.83 | A | N |
| ATOM | 315 | CA  | LEU | A | 159 | -15.431 | 24.917 | 11.453 | 1.00 | 54.91 | A | C |
| ATOM | 316 | CB  | LEU | A | 159 | -15.437 | 23.487 | 10.922 | 1.00 | 55.64 | A | C |
| ATOM | 317 | CG  | LEU | A | 159 | -15.477 | 22.455 | 12.044 | 1.00 | 56.96 | A | C |
| ATOM | 318 | CD1 | LEU | A | 159 | -15.798 | 21.058 | 11.503 | 1.00 | 59.38 | A | C |
| ATOM | 319 | CD2 | LEU | A | 159 | -14.126 | 22.503 | 12.755 | 1.00 | 54.02 | A | C |
| ATOM | 320 | C   | LEU | A | 159 | -14.908 | 25.859 | 10.367 | 1.00 | 53.75 | A | C |
| ATOM | 321 | O   | LEU | A | 159 | -15.453 | 26.926 | 10.142 | 1.00 | 50.62 | A | O |
| ATOM | 322 | N   | ALA | A | 160 | -13.834 | 25.450 | 9.704  | 1.00 | 54.03 | A | N |
| ATOM | 323 | CA  | ALA | A | 160 | -13.255 | 26.239 | 8.635  | 1.00 | 55.56 | A | C |
| ATOM | 324 | CB  | ALA | A | 160 | -11.939 | 26.887 | 9.080  | 1.00 | 55.30 | A | C |
| ATOM | 325 | C   | ALA | A | 160 | -13.019 | 25.309 | 7.460  | 1.00 | 57.12 | A | C |
| ATOM | 326 | O   | ALA | A | 160 | -12.603 | 24.174 | 7.634  | 1.00 | 61.53 | A | O |
| ATOM | 327 | N   | LEU | A | 161 | -13.282 | 25.782 | 6.257  | 1.00 | 55.41 | A | N |
| ATOM | 328 | CA  | LEU | A | 161 | -13.110 | 24.922 | 5.106  | 1.00 | 55.58 | A | C |
| ATOM | 329 | CB  | LEU | A | 161 | -14.489 | 24.635 | 4.498  | 1.00 | 55.19 | A | C |
| ATOM | 330 | CG  | LEU | A | 161 | -14.672 | 23.619 | 3.364  | 1.00 | 53.85 | A | C |
| ATOM | 331 | CD1 | LEU | A | 161 | -16.142 | 23.133 | 3.258  | 1.00 | 51.55 | A | C |
| ATOM | 332 | CD2 | LEU | A | 161 | -14.258 | 24.308 | 2.069  | 1.00 | 55.87 | A | C |
| ATOM | 333 | C   | LEU | A | 161 | -12.149 | 25.589 | 4.116  | 1.00 | 58.99 | A | C |
| ATOM | 334 | O   | LEU | A | 161 | -12.431 | 26.650 | 3.540  | 1.00 | 60.39 | A | O |
| ATOM | 335 | N   | LYS | A | 162 | -10.976 | 24.987 | 3.969  | 1.00 | 57.69 | A | N |
| ATOM | 336 | CA  | LYS | A | 162 | -9.991  | 25.532 | 3.071  | 1.00 | 55.73 | A | C |
| ATOM | 337 | CB  | LYS | A | 162 | -8.593  | 25.159 | 3.519  | 1.00 | 49.05 | A | C |
| ATOM | 342 | C   | LYS | A | 162 | -10.269 | 24.949 | 1.711  | 1.00 | 59.22 | A | C |
| ATOM | 343 | O   | LYS | A | 162 | -10.331 | 23.731 | 1.550  | 1.00 | 59.62 | A | O |
| ATOM | 344 | N   | VAL | A | 163 | -10.484 | 25.835 | 0.749  | 1.00 | 63.45 | A | N |

Figure 2F

```
ATOM   345  CA   VAL A 163     -10.734   25.455   -0.625  1.00   67.46      A  C
ATOM   346  CB   VAL A 163     -11.755   26.413   -1.284  1.00   67.92      A  C
ATOM   347  CG1  VAL A 163     -11.318   26.733   -2.710  1.00   70.55      A  C
ATOM   348  CG2  VAL A 163     -13.153   25.789   -1.284  1.00   66.29      A  C
ATOM   349  C    VAL A 163      -9.398   25.564   -1.358  1.00   70.60      A  C
ATOM   350  O    VAL A 163      -8.682   26.560   -1.221  1.00   69.61      A  O
ATOM   351  N    LEU A 164      -9.058   24.528   -2.117  1.00   74.32      A  N
ATOM   352  CA   LEU A 164      -7.821   24.499   -2.901  1.00   76.23      A  C
ATOM   353  CB   LEU A 164      -6.860   23.440   -2.362  1.00   72.97      A  C
ATOM   354  CG   LEU A 164      -6.278   23.613   -0.960  1.00   68.75      A  C
ATOM   355  CD1  LEU A 164      -5.484   24.907   -0.909  1.00   66.02      A  C
ATOM   356  CD2  LEU A 164      -7.395   23.609    0.072  1.00   70.05      A  C
ATOM   357  C    LEU A 164      -8.195   24.132   -4.324  1.00   80.27      A  C
ATOM   358  O    LEU A 164      -8.792   23.082   -4.545  1.00   81.88      A  O
ATOM   359  N    PHE A 165      -7.851   24.976   -5.294  1.00   82.77      A  N
ATOM   360  CA   PHE A 165      -8.195   24.674   -6.686  1.00   84.62      A  C
ATOM   361  CB   PHE A 165      -8.334   25.961   -7.495  1.00   85.97      A  C
ATOM   362  CG   PHE A 165      -9.628   26.671   -7.264  1.00   89.67      A  C
ATOM   363  CD1  PHE A 165      -9.940   27.189   -6.011  1.00   90.31      A  C
ATOM   364  CD2  PHE A 165     -10.555   26.799   -8.288  1.00   92.81      A  C
ATOM   365  CE1  PHE A 165     -11.160   27.824   -5.787  1.00   91.32      A  C
ATOM   366  CE2  PHE A 165     -11.778   27.433   -8.072  1.00   93.88      A  C
ATOM   367  CZ   PHE A 165     -12.082   27.943   -6.824  1.00   92.30      A  C
ATOM   368  C    PHE A 165      -7.245   23.724   -7.397  1.00   86.65      A  C
ATOM   369  O    PHE A 165      -6.030   23.762   -7.192  1.00   87.81      A  O
ATOM   370  N    LYS A 166      -7.814   22.859   -8.230  1.00   89.07      A  N
ATOM   371  CA   LYS A 166      -7.024   21.901   -8.996  1.00   90.60      A  C
ATOM   372  CB   LYS A 166      -7.940   21.010   -9.842  1.00   89.27      A  C
ATOM   377  C    LYS A 166      -6.100   22.691   -9.911  1.00   92.14      A  C
ATOM   378  O    LYS A 166      -4.884   22.521   -9.883  1.00   91.22      A  O
ATOM   379  N    ALA A 167      -6.701   23.567  -10.710  1.00   94.87      A  N
ATOM   380  CA   ALA A 167      -5.964   24.402  -11.647  1.00   96.69      A  C
ATOM   381  CB   ALA A 167      -6.861   25.536  -12.153  1.00   96.62      A  C
ATOM   382  C    ALA A 167      -4.704   24.972  -10.999  1.00   97.46      A  C
ATOM   383  O    ALA A 167      -3.583   24.644  -11.398  1.00   98.79      A  O
ATOM   384  N    GLN A 168      -4.888   25.825  -10.000  1.00   97.12      A  N
ATOM   385  CA   GLN A 168      -3.758   26.421   -9.318  1.00   97.80      A  C
ATOM   386  CB   GLN A 168      -4.243   27.185   -8.096  1.00  101.53      A  C
ATOM   387  CG   GLN A 168      -5.454   28.057   -8.365  1.00  106.90      A  C
ATOM   388  CD   GLN A 168      -5.208   29.094   -9.433  1.00  110.01      A  C
ATOM   389  OE1  GLN A 168      -4.892   28.762  -10.580  1.00  112.17      A  O
ATOM   390  NE2  GLN A 168      -5.330   30.364   -9.063  1.00  110.01      A  N
ATOM   391  C    GLN A 168      -2.792   25.326   -8.891  1.00   96.74      A  C
ATOM   392  O    GLN A 168      -1.612   25.355   -9.235  1.00   94.27      A  O
ATOM   393  N    LEU A 169      -3.303   24.356   -8.142  1.00   97.32      A  N
ATOM   394  CA   LEU A 169      -2.480   23.249   -7.666  1.00   98.86      A  C
ATOM   395  CB   LEU A 169      -3.353   22.190   -6.981  1.00   97.16      A  C
ATOM   399  C    LEU A 169      -1.713   22.621   -8.828  1.00  100.16      A  C
ATOM   400  O    LEU A 169      -0.561   22.213   -8.672  1.00  102.12      A  O
ATOM   401  N    GLU A 170      -2.356   22.558   -9.993  1.00  100.84      A  N
ATOM   402  CA   GLU A 170      -1.747   21.984  -11.193  1.00  100.44      A  C
ATOM   403  CB   GLU A 170      -2.824   21.698  -12.245  1.00   98.56      A  C
ATOM   408  C    GLU A 170      -0.690   22.918  -11.789  1.00  100.25      A  C
ATOM   409  O    GLU A 170       0.458   22.517  -11.993  1.00   99.86      A  O
ATOM   410  N    LYS A 171      -1.088   24.160  -12.064  1.00   99.04      A  N
ATOM   411  CA   LYS A 171      -0.190   25.164  -12.635  1.00   96.37      A  C
ATOM   412  CB   LYS A 171      -0.980   26.426  -13.018  1.00   94.50      A  C
ATOM   417  C    LYS A 171       0.925   25.538  -11.660  1.00   94.44      A  C
ATOM   418  O    LYS A 171       1.276   26.715  -11.523  1.00   94.15      A  O
ATOM   419  N    ALA A 172       1.473   24.530  -10.985  1.00   91.81      A  N
ATOM   420  CA   ALA A 172       2.537   24.738  -10.021  1.00   90.59      A  C
```

Figure 2G

```
ATOM    421  CB  ALA A 172       2.193  25.887  -9.087  1.00  90.72      A    C
ATOM    422  C   ALA A 172       2.752  23.473  -9.215  1.00  89.71      A    C
ATOM    423  O   ALA A 172       2.423  23.427  -8.023  1.00  89.62      A    O
ATOM    424  N   GLY A 173       3.297  22.454  -9.867  1.00  88.62      A    N
ATOM    425  CA  GLY A 173       3.564  21.205  -9.188  1.00  87.20      A    C
ATOM    426  C   GLY A 173       3.749  21.429  -7.702  1.00  86.57      A    C
ATOM    427  O   GLY A 173       4.781  21.941  -7.254  1.00  85.87      A    O
ATOM    428  N   VAL A 174       2.711  21.084  -6.946  1.00  86.85      A    N
ATOM    429  CA  VAL A 174       2.711  21.217  -5.492  1.00  86.05      A    C
ATOM    430  CB  VAL A 174       2.037  22.538  -5.028  1.00  86.56      A    C
ATOM    433  C   VAL A 174       1.922  20.043  -4.939  1.00  84.87      A    C
ATOM    434  O   VAL A 174       2.130  19.638  -3.802  1.00  84.57      A    O
ATOM    435  N   GLU A 175       1.010  19.508  -5.753  1.00  83.91      A    N
ATOM    436  CA  GLU A 175       0.204  18.362  -5.353  1.00  85.21      A    C
ATOM    437  CB  GLU A 175      -0.301  17.609  -6.592  1.00  85.17      A    C
ATOM    442  C   GLU A 175       1.101  17.452  -4.515  1.00  86.96      A    C
ATOM    443  O   GLU A 175       0.641  16.760  -3.607  1.00  88.04      A    O
ATOM    444  N   HIS A 176       2.391  17.474  -4.833  1.00  89.02      A    N
ATOM    445  CA  HIS A 176       3.378  16.684  -4.114  1.00  91.29      A    C
ATOM    446  CB  HIS A 176       4.710  16.652  -4.889  1.00  89.92      A    C
ATOM    452  C   HIS A 176       3.576  17.340  -2.750  1.00  93.41      A    C
ATOM    453  O   HIS A 176       3.376  16.703  -1.710  1.00  94.69      A    O
ATOM    454  N   GLN A 177       3.980  18.613  -2.756  1.00  93.26      A    N
ATOM    455  CA  GLN A 177       4.179  19.366  -1.505  1.00  90.02      A    C
ATOM    456  CB  GLN A 177       4.295  20.874  -1.778  1.00  85.72      A    C
ATOM    461  C   GLN A 177       2.941  19.098  -0.657  1.00  87.75      A    C
ATOM    462  O   GLN A 177       3.039  18.804   0.539  1.00  87.33      A    O
ATOM    463  N   LEU A 178       1.777  19.188  -1.303  1.00  86.24      A    N
ATOM    464  CA  LEU A 178       0.507  18.936  -0.646  1.00  82.79      A    C
ATOM    465  CB  LEU A 178      -0.642  19.222  -1.613  1.00  79.26      A    C
ATOM    466  CG  LEU A 178      -1.783  20.087  -1.067  1.00  72.68      A    C
ATOM    467  CD1 LEU A 178      -2.424  20.859  -2.195  1.00  69.47      A    C
ATOM    468  CD2 LEU A 178      -2.791  19.212  -0.345  1.00  71.05      A    C
ATOM    469  C   LEU A 178       0.561  17.466  -0.253  1.00  84.70      A    C
ATOM    470  O   LEU A 178       1.632  16.871  -0.301  1.00  83.02      A    O
ATOM    471  N   ARG A 179      -0.562  16.866   0.119  1.00  86.50      A    N
ATOM    472  CA  ARG A 179      -0.526  15.466   0.540  1.00  91.77      A    C
ATOM    473  CB  ARG A 179      -0.078  14.552  -0.603  1.00  96.19      A    C
ATOM    474  CG  ARG A 179      -1.166  14.101  -1.553  1.00 106.72      A    C
ATOM    475  CD  ARG A 179      -0.796  12.738  -2.136  1.00 116.36      A    C
ATOM    476  NE  ARG A 179      -1.691  12.311  -3.209  1.00 123.85      A    N
ATOM    477  CZ  ARG A 179      -1.775  12.908  -4.395  1.00 125.37      A    C
ATOM    478  NH1 ARG A 179      -2.619  12.451  -5.317  1.00 123.70      A    N
ATOM    479  NH2 ARG A 179      -1.013  13.963  -4.661  1.00 127.09      A    N
ATOM    480  C   ARG A 179       0.491  15.352   1.675  1.00  93.28      A    C
ATOM    481  O   ARG A 179       0.129  15.168   2.833  1.00  95.60      A    O
ATOM    482  N   ARG A 180       1.765  15.453   1.314  1.00  93.39      A    N
ATOM    483  CA  ARG A 180       2.876  15.399   2.251  1.00  95.31      A    C
ATOM    484  CB  ARG A 180       4.103  16.072   1.616  1.00  96.64      A    C
ATOM    485  CG  ARG A 180       5.456  15.712   2.231  1.00  98.53      A    C
ATOM    486  CD  ARG A 180       5.951  14.312   1.815  1.00  98.96      A    C
ATOM    487  NE  ARG A 180       6.277  14.194   0.390  1.00  99.36      A    N
ATOM    488  CZ  ARG A 180       7.159  14.955  -0.255  1.00  99.72      A    C
ATOM    489  NH1 ARG A 180       7.382  14.762  -1.549  1.00  97.63      A    N
ATOM    490  NH2 ARG A 180       7.816  15.914   0.385  1.00 100.37      A    N
ATOM    491  C   ARG A 180       2.471  16.130   3.537  1.00  96.04      A    C
ATOM    492  O   ARG A 180       2.382  15.515   4.609  1.00  94.73      A    O
ATOM    493  N   GLU A 181       2.207  17.434   3.428  1.00  96.50      A    N
ATOM    494  CA  GLU A 181       1.800  18.221   4.596  1.00  95.99      A    C
ATOM    495  CB  GLU A 181       1.555  19.690   4.227  1.00 100.69      A    C
ATOM    496  CG  GLU A 181       2.649  20.359   3.414  1.00 107.20      A    C
```

Figure 2H

```
ATOM    497  CD   GLU A 181       2.598  21.883   3.494  1.00 109.29      A    C
ATOM    498  OE1  GLU A 181       1.486  22.457   3.504  1.00 109.80      A    O
ATOM    499  OE2  GLU A 181       3.679  22.509   3.536  1.00 111.33      A    O
ATOM    500  C    GLU A 181       0.505  17.635   5.158  1.00  93.01      A    C
ATOM    501  O    GLU A 181       0.386  17.389   6.361  1.00  90.72      A    O
ATOM    502  N    VAL A 182      -0.462  17.424   4.271  1.00  90.73      A    N
ATOM    503  CA   VAL A 182      -1.750  16.860   4.647  1.00  88.08      A    C
ATOM    504  CB   VAL A 182      -2.503  16.303   3.417  1.00  85.35      A    C
ATOM    505  CG1  VAL A 182      -3.623  15.388   3.870  1.00  84.70      A    C
ATOM    506  CG2  VAL A 182      -3.067  17.449   2.583  1.00  81.53      A    C
ATOM    507  C    VAL A 182      -1.577  15.734   5.652  1.00  87.40      A    C
ATOM    508  O    VAL A 182      -1.852  15.902   6.837  1.00  85.59      A    O
ATOM    509  N    GLU A 183      -1.115  14.585   5.167  1.00  87.45      A    N
ATOM    510  CA   GLU A 183      -0.906  13.422   6.018  1.00  86.73      A    C
ATOM    511  CB   GLU A 183      -0.107  12.355   5.271  1.00  89.56      A    C
ATOM    512  CG   GLU A 183       0.112  11.102   6.091  1.00  93.22      A    C
ATOM    513  CD   GLU A 183      -1.197  10.475   6.526  1.00  94.60      A    C
ATOM    514  OE1  GLU A 183      -1.869   9.856   5.676  1.00  94.65      A    O
ATOM    515  OE2  GLU A 183      -1.559  10.617   7.717  1.00  96.69      A    O
ATOM    516  C    GLU A 183      -0.196  13.779   7.320  1.00  86.17      A    C
ATOM    517  O    GLU A 183      -0.573  13.279   8.372  1.00  86.48      A    O
ATOM    518  N    ILE A 184       0.832  14.628   7.247  1.00  86.63      A    N
ATOM    519  CA   ILE A 184       1.565  15.057   8.445  1.00  88.15      A    C
ATOM    520  CB   ILE A 184       2.702  16.032   8.093  1.00  87.30      A    C
ATOM    521  CG2  ILE A 184       3.432  16.454   9.360  1.00  86.63      A    C
ATOM    522  CG1  ILE A 184       3.667  15.376   7.108  1.00  84.31      A    C
ATOM    523  CD1  ILE A 184       4.786  16.281   6.654  1.00  81.32      A    C
ATOM    524  C    ILE A 184       0.596  15.776   9.389  1.00  90.70      A    C
ATOM    525  O    ILE A 184       0.433  15.397  10.545  1.00  87.30      A    O
ATOM    526  N    GLN A 185      -0.046  16.826   8.887  1.00  93.30      A    N
ATOM    527  CA   GLN A 185      -1.014  17.566   9.682  1.00  95.37      A    C
ATOM    528  CB   GLN A 185      -1.590  18.722   8.862  1.00  97.61      A    C
ATOM    529  CG   GLN A 185      -0.547  19.770   8.538  1.00 103.35      A    C
ATOM    530  CD   GLN A 185      -0.039  20.441   9.793  1.00 106.52      A    C
ATOM    531  OE1  GLN A 185       1.035  21.042   9.795  1.00 107.64      A    O
ATOM    532  NE2  GLN A 185      -0.821  20.360  10.871  1.00 107.24      A    N
ATOM    533  C    GLN A 185      -2.115  16.589  10.066  1.00  94.94      A    C
ATOM    534  O    GLN A 185      -2.561  16.564  11.217  1.00  95.32      A    O
ATOM    535  N    SER A 186      -2.541  15.796   9.082  1.00  97.07      A    N
ATOM    536  CA   SER A 186      -3.571  14.777   9.248  1.00  97.57      A    C
ATOM    537  CB   SER A 186      -3.864  14.104   7.900  1.00  97.40      A    C
ATOM    538  OG   SER A 186      -4.753  13.010   8.050  1.00  99.43      A    O
ATOM    539  C    SER A 186      -3.028  13.751  10.230  1.00  97.37      A    C
ATOM    540  O    SER A 186      -2.768  12.603   9.867  1.00  97.45      A    O
ATOM    541  N    HIS A 187      -2.859  14.193  11.472  1.00  96.71      A    N
ATOM    542  CA   HIS A 187      -2.319  13.385  12.558  1.00  96.67      A    C
ATOM    543  CB   HIS A 187      -1.038  12.674  12.100  1.00  99.07      A    C
ATOM    544  CG   HIS A 187      -1.015  11.207  12.404  1.00 104.64      A    C
ATOM    545  CD2  HIS A 187      -0.018  10.401  12.845  1.00 106.54      A    C
ATOM    546  ND1  HIS A 187      -2.114  10.392  12.227  1.00 106.15      A    N
ATOM    547  CE1  HIS A 187      -1.796   9.150  12.547  1.00 106.73      A    C
ATOM    548  NE2  HIS A 187      -0.530   9.127  12.925  1.00 106.81      A    N
ATOM    549  C    HIS A 187      -1.985  14.390  13.658  1.00  95.21      A    C
ATOM    550  O    HIS A 187      -2.706  14.512  14.653  1.00  96.74      A    O
ATOM    551  N    LEU A 188      -0.891  15.116  13.455  1.00  89.19      A    N
ATOM    552  CA   LEU A 188      -0.432  16.130  14.392  1.00  82.17      A    C
ATOM    553  CB   LEU A 188       0.147  17.321  13.619  1.00  79.40      A    C
ATOM    554  CG   LEU A 188       1.560  17.775  14.014  1.00  75.97      A    C
ATOM    555  CD1  LEU A 188       2.523  16.635  13.805  1.00  72.51      A    C
ATOM    556  CD2  LEU A 188       1.976  18.971  13.176  1.00  76.13      A    C
ATOM    557  C    LEU A 188      -1.562  16.613  15.292  1.00  77.90      A    C
```

Figure 2I

```
ATOM    558  O   LEU A 188      -2.454  17.325  14.838  1.00  78.03      A    O
ATOM    559  N   ARG A 189      -1.531  16.210  16.556  1.00  72.06      A    N
ATOM    560  CA  ARG A 189      -2.549  16.611  17.521  1.00  67.92      A    C
ATOM    561  CB  ARG A 189      -3.229  15.367  18.103  1.00  73.90      A    C
ATOM    562  CG  ARG A 189      -4.597  15.566  18.786  1.00  78.66      A    C
ATOM    563  CD  ARG A 189      -5.498  14.400  18.364  1.00  85.49      A    C
ATOM    564  NE  ARG A 189      -6.684  14.185  19.194  1.00  91.19      A    N
ATOM    565  CZ  ARG A 189      -7.548  13.186  19.005  1.00  91.51      A    C
ATOM    566  NH1 ARG A 189      -7.357  12.321  18.012  1.00  93.38      A    N
ATOM    567  NH2 ARG A 189      -8.588  13.032  19.815  1.00  87.51      A    N
ATOM    568  C   ARG A 189      -1.858  17.406  18.624  1.00  60.47      A    C
ATOM    569  O   ARG A 189      -1.084  16.863  19.421  1.00  59.30      A    O
ATOM    570  N   HIS A 190      -2.111  18.704  18.656  1.00  54.86      A    N
ATOM    571  CA  HIS A 190      -1.497  19.541  19.671  1.00  50.95      A    C
ATOM    572  CB  HIS A 190      -0.066  19.933  19.252  1.00  51.83      A    C
ATOM    573  CG  HIS A 190       0.678  20.679  20.313  1.00  56.16      A    C
ATOM    574  CD2 HIS A 190       0.602  21.973  20.712  1.00  58.65      A    C
ATOM    575  ND1 HIS A 190       1.554  20.064  21.181  1.00  59.30      A    N
ATOM    576  CE1 HIS A 190       1.981  20.946  22.074  1.00  59.95      A    C
ATOM    577  NE2 HIS A 190       1.415  22.114  21.810  1.00  57.34      A    N
ATOM    578  C   HIS A 190      -2.326  20.795  19.907  1.00  49.69      A    C
ATOM    579  O   HIS A 190      -2.845  21.390  18.970  1.00  47.67      A    O
ATOM    580  N   PRO A 191      -2.435  21.228  21.169  1.00  47.55      A    N
ATOM    581  CD  PRO A 191      -1.833  20.635  22.376  1.00  47.91      A    C
ATOM    582  CA  PRO A 191      -3.215  22.429  21.492  1.00  45.35      A    C
ATOM    583  CB  PRO A 191      -3.045  22.579  23.008  1.00  42.47      A    C
ATOM    584  CG  PRO A 191      -1.783  21.809  23.316  1.00  46.75      A    C
ATOM    585  C   PRO A 191      -2.785  23.673  20.738  1.00  44.79      A    C
ATOM    586  O   PRO A 191      -3.617  24.499  20.376  1.00  48.53      A    O
ATOM    587  N   ASN A 192      -1.490  23.814  20.493  1.00  45.28      A    N
ATOM    588  CA  ASN A 192      -1.010  24.981  19.788  1.00  42.05      A    C
ATOM    589  CB  ASN A 192       0.196  25.557  20.519  1.00  46.05      A    C
ATOM    590  CG  ASN A 192      -0.169  26.091  21.909  1.00  49.31      A    C
ATOM    591  OD1 ASN A 192       0.510  25.815  22.906  1.00  51.60      A    O
ATOM    592  ND2 ASN A 192      -1.236  26.862  21.975  1.00  49.16      A    N
ATOM    593  C   ASN A 192      -0.727  24.753  18.301  1.00  40.78      A    C
ATOM    594  O   ASN A 192       0.022  25.531  17.664  1.00  39.75      A    O
ATOM    595  N   ILE A 193      -1.357  23.716  17.738  1.00  39.81      A    N
ATOM    596  CA  ILE A 193      -1.218  23.429  16.306  1.00  38.68      A    C
ATOM    597  CB  ILE A 193      -0.504  22.106  16.073  1.00  37.03      A    C
ATOM    598  CG2 ILE A 193      -0.627  21.684  14.631  1.00  35.39      A    C
ATOM    599  CG1 ILE A 193       0.979  22.295  16.403  1.00  36.80      A    C
ATOM    600  CD1 ILE A 193       1.856  21.084  16.162  1.00  40.43      A    C
ATOM    601  C   ILE A 193      -2.610  23.417  15.628  1.00  39.73      A    C
ATOM    602  O   ILE A 193      -3.563  22.815  16.147  1.00  41.98      A    O
ATOM    603  N   LEU A 194      -2.763  24.070  14.484  1.00  40.12      A    N
ATOM    604  CA  LEU A 194      -4.083  24.056  13.925  1.00  45.02      A    C
ATOM    605  CB  LEU A 194      -4.251  25.138  12.850  1.00  40.58      A    C
ATOM    606  CG  LEU A 194      -5.744  25.360  12.537  1.00  36.62      A    C
ATOM    607  CD1 LEU A 194      -6.365  26.215  13.662  1.00  34.79      A    C
ATOM    608  CD2 LEU A 194      -5.921  26.063  11.181  1.00  37.83      A    C
ATOM    609  C   LEU A 194      -4.408  22.661  13.373  1.00  50.26      A    C
ATOM    610  O   LEU A 194      -3.865  22.234  12.335  1.00  52.67      A    O
ATOM    611  N   ARG A 195      -5.308  21.968  14.070  1.00  52.68      A    N
ATOM    612  CA  ARG A 195      -5.708  20.623  13.695  1.00  55.93      A    C
ATOM    613  CB  ARG A 195      -6.722  20.079  14.711  1.00  62.40      A    C
ATOM    614  CG  ARG A 195      -7.098  18.616  14.480  1.00  74.73      A    C
ATOM    615  CD  ARG A 195      -7.982  18.045  15.599  1.00  83.65      A    C
ATOM    616  NE  ARG A 195      -8.294  16.628  15.376  1.00  87.43      A    N
ATOM    617  CZ  ARG A 195      -9.033  15.878  16.190  1.00  88.90      A    C
ATOM    618  NH1 ARG A 195      -9.253  14.598  15.899  1.00  89.95      A    N
```

Figure 2J

| ATOM | 619 | NH2 | ARG | A | 195 | -9.552 | 16.408 | 17.294 | 1.00 | 87.25 | A | N |
|---|---|---|---|---|---|---|---|---|---|---|---|---|
| ATOM | 620 | C | ARG | A | 195 | -6.291 | 20.522 | 12.294 | 1.00 | 55.88 | A | C |
| ATOM | 621 | O | ARG | A | 195 | -6.790 | 21.490 | 11.757 | 1.00 | 50.34 | A | O |
| ATOM | 622 | N | LEU | A | 196 | -6.209 | 19.336 | 11.698 | 1.00 | 58.92 | A | N |
| ATOM | 623 | CA | LEU | A | 196 | -6.758 | 19.109 | 10.358 | 1.00 | 60.64 | A | C |
| ATOM | 624 | CB | LEU | A | 196 | -5.641 | 18.794 | 9.361 | 1.00 | 62.65 | A | C |
| ATOM | 625 | CG | LEU | A | 196 | -6.067 | 18.246 | 7.987 | 1.00 | 63.74 | A | C |
| ATOM | 626 | CD1 | LEU | A | 196 | -7.235 | 19.049 | 7.422 | 1.00 | 65.54 | A | C |
| ATOM | 627 | CD2 | LEU | A | 196 | -4.889 | 18.300 | 7.034 | 1.00 | 65.02 | A | C |
| ATOM | 628 | C | LEU | A | 196 | -7.767 | 17.960 | 10.375 | 1.00 | 60.32 | A | C |
| ATOM | 629 | O | LEU | A | 196 | -7.497 | 16.895 | 9.856 | 1.00 | 63.33 | A | O |
| ATOM | 630 | N | TYR | A | 197 | -8.937 | 18.196 | 10.954 | 1.00 | 57.84 | A | N |
| ATOM | 631 | CA | TYR | A | 197 | -9.969 | 17.172 | 11.056 | 1.00 | 55.75 | A | C |
| ATOM | 632 | CB | TYR | A | 197 | -11.332 | 17.813 | 11.335 | 1.00 | 53.02 | A | C |
| ATOM | 633 | CG | TYR | A | 197 | -11.358 | 18.736 | 12.512 | 1.00 | 50.75 | A | C |
| ATOM | 634 | CD1 | TYR | A | 197 | -11.619 | 20.084 | 12.337 | 1.00 | 52.00 | A | C |
| ATOM | 635 | CE1 | TYR | A | 197 | -11.645 | 20.952 | 13.408 | 1.00 | 53.28 | A | C |
| ATOM | 636 | CD2 | TYR | A | 197 | -11.126 | 18.266 | 13.803 | 1.00 | 50.67 | A | C |
| ATOM | 637 | CE2 | TYR | A | 197 | -11.158 | 19.132 | 14.890 | 1.00 | 54.83 | A | C |
| ATOM | 638 | CZ | TYR | A | 197 | -11.417 | 20.484 | 14.679 | 1.00 | 55.28 | A | C |
| ATOM | 639 | OH | TYR | A | 197 | -11.440 | 21.388 | 15.718 | 1.00 | 56.06 | A | O |
| ATOM | 640 | C | TYR | A | 197 | -10.111 | 16.253 | 9.833 | 1.00 | 56.90 | A | C |
| ATOM | 641 | O | TYR | A | 197 | -10.370 | 15.057 | 9.978 | 1.00 | 58.41 | A | O |
| ATOM | 642 | N | GLY | A | 198 | -9.973 | 16.793 | 8.633 | 1.00 | 56.06 | A | N |
| ATOM | 643 | CA | GLY | A | 198 | -10.142 | 15.925 | 7.489 | 1.00 | 55.27 | A | C |
| ATOM | 644 | C | GLY | A | 198 | -9.947 | 16.587 | 6.159 | 1.00 | 56.71 | A | C |
| ATOM | 645 | O | GLY | A | 198 | -9.712 | 17.782 | 6.072 | 1.00 | 56.62 | A | O |
| ATOM | 646 | N | TYR | A | 199 | -10.065 | 15.791 | 5.111 | 1.00 | 60.94 | A | N |
| ATOM | 647 | CA | TYR | A | 199 | -9.866 | 16.275 | 3.756 | 1.00 | 65.84 | A | C |
| ATOM | 648 | CB | TYR | A | 199 | -8.364 | 16.186 | 3.412 | 1.00 | 74.72 | A | C |
| ATOM | 649 | CG | TYR | A | 199 | -7.996 | 15.390 | 2.163 | 1.00 | 83.56 | A | C |
| ATOM | 650 | CD1 | TYR | A | 199 | -7.325 | 14.158 | 2.253 | 1.00 | 82.92 | A | C |
| ATOM | 651 | CE1 | TYR | A | 199 | -6.942 | 13.454 | 1.088 | 1.00 | 83.87 | A | C |
| ATOM | 652 | CD2 | TYR | A | 199 | -8.281 | 15.894 | 0.880 | 1.00 | 87.81 | A | C |
| ATOM | 653 | CE2 | TYR | A | 199 | -7.909 | 15.201 | -0.278 | 1.00 | 86.53 | A | C |
| ATOM | 654 | CZ | TYR | A | 199 | -7.243 | 13.990 | -0.171 | 1.00 | 84.97 | A | C |
| ATOM | 655 | OH | TYR | A | 199 | -6.885 | 13.333 | -1.326 | 1.00 | 81.59 | A | O |
| ATOM | 656 | C | TYR | A | 199 | -10.686 | 15.465 | 2.767 | 1.00 | 65.66 | A | C |
| ATOM | 657 | O | TYR | A | 199 | -10.855 | 14.241 | 2.921 | 1.00 | 63.27 | A | O |
| ATOM | 658 | N | PHE | A | 200 | -11.204 | 16.163 | 1.760 | 1.00 | 66.20 | A | N |
| ATOM | 659 | CA | PHE | A | 200 | -11.977 | 15.527 | 0.698 | 1.00 | 69.20 | A | C |
| ATOM | 660 | CB | PHE | A | 200 | -13.464 | 15.395 | 1.064 | 1.00 | 66.91 | A | C |
| ATOM | 661 | CG | PHE | A | 200 | -14.151 | 16.694 | 1.335 | 1.00 | 62.69 | A | C |
| ATOM | 662 | CD1 | PHE | A | 200 | -14.056 | 17.293 | 2.585 | 1.00 | 58.08 | A | C |
| ATOM | 663 | CD2 | PHE | A | 200 | -14.959 | 17.282 | 0.363 | 1.00 | 62.80 | A | C |
| ATOM | 664 | CE1 | PHE | A | 200 | -14.761 | 18.446 | 2.864 | 1.00 | 56.62 | A | C |
| ATOM | 665 | CE2 | PHE | A | 200 | -15.673 | 18.442 | 0.637 | 1.00 | 60.26 | A | C |
| ATOM | 666 | CZ | PHE | A | 200 | -15.577 | 19.026 | 1.892 | 1.00 | 57.41 | A | C |
| ATOM | 667 | C | PHE | A | 200 | -11.810 | 16.314 | -0.588 | 1.00 | 69.75 | A | C |
| ATOM | 668 | O | PHE | A | 200 | -11.216 | 17.381 | -0.580 | 1.00 | 69.79 | A | O |
| ATOM | 669 | N | HIS | A | 201 | -12.319 | 15.790 | -1.697 | 1.00 | 73.90 | A | N |
| ATOM | 670 | CA | HIS | A | 201 | -12.149 | 16.489 | -2.960 | 1.00 | 81.60 | A | C |
| ATOM | 671 | CB | HIS | A | 201 | -10.754 | 16.210 | -3.512 | 1.00 | 86.89 | A | C |
| ATOM | 672 | CG | HIS | A | 201 | -10.470 | 14.753 | -3.714 | 1.00 | 91.24 | A | C |
| ATOM | 673 | CD2 | HIS | A | 201 | -9.564 | 13.930 | -3.131 | 1.00 | 92.97 | A | C |
| ATOM | 674 | ND1 | HIS | A | 201 | -11.183 | 13.971 | -4.597 | 1.00 | 91.80 | A | N |
| ATOM | 675 | CE1 | HIS | A | 201 | -10.730 | 12.731 | -4.549 | 1.00 | 94.28 | A | C |
| ATOM | 676 | NE2 | HIS | A | 201 | -9.747 | 12.679 | -3.667 | 1.00 | 94.89 | A | N |
| ATOM | 677 | C | HIS | A | 201 | -13.149 | 16.124 | -4.030 | 1.00 | 84.24 | A | C |
| ATOM | 678 | O | HIS | A | 201 | -13.518 | 14.966 | -4.175 | 1.00 | 85.37 | A | O |
| ATOM | 679 | N | ASP | A | 202 | -13.586 | 17.123 | -4.783 | 1.00 | 86.70 | A | N |

Figure 2K

| ATOM | 680 | CA | ASP | A | 202 | -14.492 | 16.871 | -5.887 | 1.00 | 89.01 | A | C |
|---|---|---|---|---|---|---|---|---|---|---|---|---|
| ATOM | 681 | CB | ASP | A | 202 | -15.638 | 17.891 | -5.918 | 1.00 | 90.40 | A | C |
| ATOM | 682 | CG | ASP | A | 202 | -15.156 | 19.316 | -6.030 | 1.00 | 90.77 | A | C |
| ATOM | 683 | OD1 | ASP | A | 202 | -14.206 | 19.561 | -6.794 | 1.00 | 93.69 | A | O |
| ATOM | 684 | OD2 | ASP | A | 202 | -15.742 | 20.196 | -5.365 | 1.00 | 91.09 | A | O |
| ATOM | 685 | C | ASP | A | 202 | -13.614 | 16.988 | -7.135 | 1.00 | 90.09 | A | C |
| ATOM | 686 | O | ASP | A | 202 | -12.388 | 17.068 | -7.024 | 1.00 | 89.07 | A | O |
| ATOM | 687 | N | ALA | A | 203 | -14.226 | 16.998 | -8.312 | 1.00 | 91.58 | A | N |
| ATOM | 688 | CA | ALA | A | 203 | -13.472 | 17.098 | -9.556 | 1.00 | 92.91 | A | C |
| ATOM | 689 | CB | ALA | A | 203 | -14.426 | 17.079 | -10.742 | 1.00 | 92.83 | A | C |
| ATOM | 690 | C | ALA | A | 203 | -12.594 | 18.345 | -9.616 | 1.00 | 94.23 | A | C |
| ATOM | 691 | O | ALA | A | 203 | -11.363 | 18.261 | -9.575 | 1.00 | 95.32 | A | O |
| ATOM | 692 | N | THR | A | 204 | -13.240 | 19.502 | -9.706 | 1.00 | 95.48 | A | N |
| ATOM | 693 | CA | THR | A | 204 | -12.549 | 20.785 | -9.799 | 1.00 | 95.58 | A | C |
| ATOM | 694 | CB | THR | A | 204 | -13.535 | 21.902 | -10.195 | 1.00 | 95.40 | A | C |
| ATOM | 695 | OG1 | THR | A | 204 | -12.928 | 23.177 | -9.955 | 1.00 | 98.51 | A | O |
| ATOM | 696 | CG2 | THR | A | 204 | -14.819 | 21.795 | -9.391 | 1.00 | 94.84 | A | C |
| ATOM | 697 | C | THR | A | 204 | -11.749 | 21.289 | -8.586 | 1.00 | 93.13 | A | C |
| ATOM | 698 | O | THR | A | 204 | -10.637 | 21.794 | -8.746 | 1.00 | 94.45 | A | O |
| ATOM | 699 | N | ARG | A | 205 | -12.300 | 21.158 | -7.385 | 1.00 | 88.53 | A | N |
| ATOM | 700 | CA | ARG | A | 205 | -11.625 | 21.662 | -6.187 | 1.00 | 81.26 | A | C |
| ATOM | 701 | CB | ARG | A | 205 | -12.401 | 22.864 | -5.646 | 1.00 | 82.44 | A | C |
| ATOM | 702 | CG | ARG | A | 205 | -13.898 | 22.665 | -5.707 | 1.00 | 85.01 | A | C |
| ATOM | 703 | CD | ARG | A | 205 | -14.642 | 23.956 | -5.501 | 1.00 | 88.56 | A | C |
| ATOM | 704 | NE | ARG | A | 205 | -16.049 | 23.808 | -5.850 | 1.00 | 91.44 | A | N |
| ATOM | 705 | CZ | ARG | A | 205 | -16.966 | 24.755 | -5.672 | 1.00 | 93.46 | A | C |
| ATOM | 706 | NH1 | ARG | A | 205 | -16.619 | 25.926 | -5.143 | 1.00 | 93.93 | A | N |
| ATOM | 707 | NH2 | ARG | A | 205 | -18.228 | 24.533 | -6.028 | 1.00 | 92.05 | A | N |
| ATOM | 708 | C | ARG | A | 205 | -11.415 | 20.657 | -5.067 | 1.00 | 76.60 | A | C |
| ATOM | 709 | O | ARG | A | 205 | -12.091 | 19.629 | -5.001 | 1.00 | 76.13 | A | O |
| ATOM | 710 | N | VAL | A | 206 | -10.462 | 20.969 | -4.193 | 1.00 | 71.44 | A | N |
| ATOM | 711 | CA | VAL | A | 206 | -10.138 | 20.127 | -3.046 | 1.00 | 67.56 | A | C |
| ATOM | 712 | CB | VAL | A | 206 | -8.638 | 19.789 | -3.023 | 1.00 | 63.79 | A | C |
| ATOM | 713 | CG1 | VAL | A | 206 | -7.941 | 20.550 | -4.112 | 1.00 | 61.96 | A | C |
| ATOM | 714 | CG2 | VAL | A | 206 | -8.036 | 20.096 | -1.669 | 1.00 | 58.59 | A | C |
| ATOM | 715 | C | VAL | A | 206 | -10.534 | 20.858 | -1.770 | 1.00 | 67.52 | A | C |
| ATOM | 716 | O | VAL | A | 206 | -10.688 | 22.070 | -1.785 | 1.00 | 68.61 | A | O |
| ATOM | 717 | N | TYR | A | 207 | -10.710 | 20.120 | -0.674 | 1.00 | 68.01 | A | N |
| ATOM | 718 | CA | TYR | A | 207 | -11.113 | 20.731 | 0.586 | 1.00 | 66.54 | A | C |
| ATOM | 719 | CB | TYR | A | 207 | -12.617 | 20.595 | 0.788 | 1.00 | 66.72 | A | C |
| ATOM | 720 | CG | TYR | A | 207 | -13.428 | 21.030 | -0.394 | 1.00 | 72.29 | A | C |
| ATOM | 721 | CD1 | TYR | A | 207 | -13.700 | 20.145 | -1.441 | 1.00 | 72.58 | A | C |
| ATOM | 722 | CE1 | TYR | A | 207 | -14.478 | 20.527 | -2.515 | 1.00 | 75.07 | A | C |
| ATOM | 723 | CD2 | TYR | A | 207 | -13.952 | 22.316 | -0.463 | 1.00 | 76.04 | A | C |
| ATOM | 724 | CE2 | TYR | A | 207 | -14.734 | 22.711 | -1.539 | 1.00 | 77.50 | A | C |
| ATOM | 725 | CZ | TYR | A | 207 | -14.995 | 21.806 | -2.557 | 1.00 | 76.66 | A | C |
| ATOM | 726 | OH | TYR | A | 207 | -15.808 | 22.169 | -3.598 | 1.00 | 82.13 | A | O |
| ATOM | 727 | C | TYR | A | 207 | -10.440 | 20.235 | 1.855 | 1.00 | 67.58 | A | C |
| ATOM | 728 | O | TYR | A | 207 | -10.345 | 19.022 | 2.128 | 1.00 | 67.06 | A | O |
| ATOM | 729 | N | LEU | A | 208 | -10.007 | 21.203 | 2.651 | 1.00 | 67.63 | A | N |
| ATOM | 730 | CA | LEU | A | 208 | -9.385 | 20.926 | 3.923 | 1.00 | 67.84 | A | C |
| ATOM | 731 | CB | LEU | A | 208 | -8.108 | 21.747 | 4.074 | 1.00 | 70.80 | A | C |
| ATOM | 732 | CG | LEU | A | 208 | -6.930 | 21.460 | 3.129 | 1.00 | 73.43 | A | C |
| ATOM | 733 | CD1 | LEU | A | 208 | -5.944 | 22.616 | 3.225 | 1.00 | 74.66 | A | C |
| ATOM | 734 | CD2 | LEU | A | 208 | -6.264 | 20.115 | 3.469 | 1.00 | 68.68 | A | C |
| ATOM | 735 | C | LEU | A | 208 | -10.381 | 21.309 | 5.008 | 1.00 | 65.82 | A | C |
| ATOM | 736 | O | LEU | A | 208 | -10.803 | 22.464 | 5.106 | 1.00 | 66.83 | A | O |
| ATOM | 737 | N | ILE | A | 209 | -10.786 | 20.328 | 5.802 | 1.00 | 62.12 | A | N |
| ATOM | 738 | CA | ILE | A | 209 | -11.690 | 20.582 | 6.896 | 1.00 | 57.67 | A | C |
| ATOM | 739 | CB | ILE | A | 209 | -12.392 | 19.319 | 7.336 | 1.00 | 57.85 | A | C |
| ATOM | 740 | CG2 | ILE | A | 209 | -13.350 | 19.636 | 8.484 | 1.00 | 59.56 | A | C |

Figure 2L

| ATOM | 741 | CG1 | ILE | A | 209 | -13.144 | 18.716 | 6.165 | 1.00 | 58.82 | A | C |
|---|---|---|---|---|---|---|---|---|---|---|---|---|
| ATOM | 742 | CD1 | ILE | A | 209 | -13.902 | 17.497 | 6.543 | 1.00 | 59.20 | A | C |
| ATOM | 743 | C | ILE | A | 209 | -10.776 | 20.999 | 8.013 | 1.00 | 54.58 | A | C |
| ATOM | 744 | O | ILE | A | 209 | -9.939 | 20.207 | 8.430 | 1.00 | 55.70 | A | O |
| ATOM | 745 | N | LEU | A | 210 | -10.938 | 22.211 | 8.527 | 1.00 | 49.77 | A | N |
| ATOM | 746 | CA | LEU | A | 210 | -10.039 | 22.668 | 9.576 | 1.00 | 47.70 | A | C |
| ATOM | 747 | CB | LEU | A | 210 | -9.002 | 23.627 | 8.972 | 1.00 | 49.91 | A | C |
| ATOM | 748 | CG | LEU | A | 210 | -7.898 | 23.099 | 8.039 | 1.00 | 49.59 | A | C |
| ATOM | 749 | CD1 | LEU | A | 210 | -8.214 | 23.467 | 6.603 | 1.00 | 51.49 | A | C |
| ATOM | 750 | CD2 | LEU | A | 210 | -6.548 | 23.722 | 8.440 | 1.00 | 48.94 | A | C |
| ATOM | 751 | C | LEU | A | 210 | -10.601 | 23.326 | 10.843 | 1.00 | 46.77 | A | C |
| ATOM | 752 | O | LEU | A | 210 | -11.682 | 23.947 | 10.839 | 1.00 | 47.63 | A | O |
| ATOM | 753 | N | GLU | A | 211 | -9.828 | 23.192 | 11.923 | 1.00 | 43.80 | A | N |
| ATOM | 754 | CA | GLU | A | 211 | -10.157 | 23.810 | 13.191 | 1.00 | 41.15 | A | C |
| ATOM | 755 | CB | GLU | A | 211 | -8.994 | 23.661 | 14.160 | 1.00 | 46.41 | A | C |
| ATOM | 756 | CG | GLU | A | 211 | -9.065 | 24.461 | 15.447 | 1.00 | 49.38 | A | C |
| ATOM | 757 | CD | GLU | A | 211 | -7.943 | 24.064 | 16.419 | 1.00 | 50.81 | A | C |
| ATOM | 758 | OE1 | GLU | A | 211 | -7.009 | 23.367 | 15.983 | 1.00 | 53.42 | A | O |
| ATOM | 759 | OE2 | GLU | A | 211 | -7.972 | 24.447 | 17.601 | 1.00 | 50.30 | A | O |
| ATOM | 760 | C | GLU | A | 211 | -10.389 | 25.281 | 12.879 | 1.00 | 40.72 | A | C |
| ATOM | 761 | O | GLU | A | 211 | -9.761 | 25.841 | 11.998 | 1.00 | 42.48 | A | O |
| ATOM | 762 | N | TYR | A | 212 | -11.312 | 25.906 | 13.589 | 1.00 | 40.45 | A | N |
| ATOM | 763 | CA | TYR | A | 212 | -11.611 | 27.296 | 13.346 | 1.00 | 36.06 | A | C |
| ATOM | 764 | CB | TYR | A | 212 | -13.125 | 27.543 | 13.286 | 1.00 | 33.34 | A | C |
| ATOM | 765 | CG | TYR | A | 212 | -13.426 | 29.011 | 13.240 | 1.00 | 34.48 | A | C |
| ATOM | 766 | CD1 | TYR | A | 212 | -12.992 | 29.777 | 12.177 | 1.00 | 40.29 | A | C |
| ATOM | 767 | CE1 | TYR | A | 212 | -13.160 | 31.135 | 12.149 | 1.00 | 42.24 | A | C |
| ATOM | 768 | CD2 | TYR | A | 212 | -14.054 | 29.648 | 14.285 | 1.00 | 36.96 | A | C |
| ATOM | 769 | CE2 | TYR | A | 212 | -14.234 | 31.031 | 14.270 | 1.00 | 40.03 | A | C |
| ATOM | 770 | CZ | TYR | A | 212 | -13.777 | 31.762 | 13.198 | 1.00 | 39.86 | A | C |
| ATOM | 771 | OH | TYR | A | 212 | -13.901 | 33.143 | 13.153 | 1.00 | 42.95 | A | O |
| ATOM | 772 | C | TYR | A | 212 | -11.032 | 28.088 | 14.491 | 1.00 | 37.10 | A | C |
| ATOM | 773 | O | TYR | A | 212 | -11.235 | 27.744 | 15.678 | 1.00 | 37.85 | A | O |
| ATOM | 774 | N | ALA | A | 213 | -10.304 | 29.139 | 14.121 | 1.00 | 36.19 | A | N |
| ATOM | 775 | CA | ALA | A | 213 | -9.681 | 29.998 | 15.089 | 1.00 | 37.02 | A | C |
| ATOM | 776 | CB | ALA | A | 213 | -8.188 | 30.053 | 14.855 | 1.00 | 37.96 | A | C |
| ATOM | 777 | C | ALA | A | 213 | -10.322 | 31.372 | 14.933 | 1.00 | 40.53 | A | C |
| ATOM | 778 | O | ALA | A | 213 | -10.062 | 32.103 | 13.960 | 1.00 | 38.10 | A | O |
| ATOM | 779 | N | PRO | A | 214 | -11.182 | 31.729 | 15.904 | 1.00 | 45.35 | A | N |
| ATOM | 780 | CD | PRO | A | 214 | -11.658 | 30.789 | 16.933 | 1.00 | 46.36 | A | C |
| ATOM | 781 | CA | PRO | A | 214 | -11.936 | 32.974 | 15.993 | 1.00 | 44.49 | A | C |
| ATOM | 782 | CB | PRO | A | 214 | -12.975 | 32.669 | 17.062 | 1.00 | 46.90 | A | C |
| ATOM | 783 | CG | PRO | A | 214 | -12.278 | 31.717 | 17.932 | 1.00 | 44.61 | A | C |
| ATOM | 784 | C | PRO | A | 214 | -11.246 | 34.286 | 16.258 | 1.00 | 45.02 | A | C |
| ATOM | 785 | O | PRO | A | 214 | -11.831 | 35.334 | 15.974 | 1.00 | 48.98 | A | O |
| ATOM | 786 | N | LEU | A | 215 | -10.030 | 34.285 | 16.778 | 1.00 | 44.72 | A | N |
| ATOM | 787 | CA | LEU | A | 215 | -9.431 | 35.586 | 17.059 | 1.00 | 45.19 | A | C |
| ATOM | 788 | CB | LEU | A | 215 | -8.744 | 35.568 | 18.425 | 1.00 | 45.00 | A | C |
| ATOM | 789 | CG | LEU | A | 215 | -9.851 | 35.667 | 19.482 | 1.00 | 45.94 | A | C |
| ATOM | 790 | CD1 | LEU | A | 215 | -9.318 | 35.460 | 20.905 | 1.00 | 50.35 | A | C |
| ATOM | 791 | CD2 | LEU | A | 215 | -10.491 | 37.031 | 19.349 | 1.00 | 45.10 | A | C |
| ATOM | 792 | C | LEU | A | 215 | -8.522 | 36.094 | 15.972 | 1.00 | 46.43 | A | C |
| ATOM | 793 | O | LEU | A | 215 | -7.909 | 37.171 | 16.097 | 1.00 | 47.38 | A | O |
| ATOM | 794 | N | GLY | A | 216 | -8.460 | 35.318 | 14.894 | 1.00 | 45.89 | A | N |
| ATOM | 795 | CA | GLY | A | 216 | -7.667 | 35.714 | 13.742 | 1.00 | 44.64 | A | C |
| ATOM | 796 | C | GLY | A | 216 | -6.149 | 35.565 | 13.809 | 1.00 | 44.96 | A | C |
| ATOM | 797 | O | GLY | A | 216 | -5.570 | 34.830 | 14.634 | 1.00 | 45.47 | A | O |
| ATOM | 798 | N | THR | A | 217 | -5.501 | 36.307 | 12.933 | 1.00 | 44.73 | A | N |
| ATOM | 799 | CA | THR | A | 217 | -4.064 | 36.248 | 12.802 | 1.00 | 46.75 | A | C |
| ATOM | 800 | CB | THR | A | 217 | -3.734 | 36.445 | 11.329 | 1.00 | 47.56 | A | C |
| ATOM | 801 | OG1 | THR | A | 217 | -2.913 | 35.359 | 10.901 | 1.00 | 53.23 | A | O |

Figure 2M

```
ATOM    802  CG2 THR A 217      -3.052  37.766  11.103  1.00  49.62       A    C
ATOM    803  C   THR A 217      -3.168  37.148  13.690  1.00  46.71       A    C
ATOM    804  O   THR A 217      -3.446  38.317  13.920  1.00  48.33       A    O
ATOM    805  N   VAL A 218      -2.097  36.571  14.205  1.00  46.45       A    N
ATOM    806  CA  VAL A 218      -1.166  37.332  15.029  1.00  47.22       A    C
ATOM    807  CB  VAL A 218      -0.012  36.441  15.519  1.00  47.68       A    C
ATOM    808  CG1 VAL A 218       1.239  37.266  15.791  1.00  47.53       A    C
ATOM    809  CG2 VAL A 218      -0.454  35.741  16.776  1.00  47.53       A    C
ATOM    810  C   VAL A 218      -0.632  38.500  14.216  1.00  46.92       A    C
ATOM    811  O   VAL A 218      -0.361  39.565  14.748  1.00  46.99       A    O
ATOM    812  N   TYR A 219      -0.517  38.297  12.909  1.00  48.89       A    N
ATOM    813  CA  TYR A 219      -0.049  39.348  12.034  1.00  48.66       A    C
ATOM    814  CB  TYR A 219      -0.204  38.949  10.579  1.00  49.72       A    C
ATOM    815  CG  TYR A 219       0.161  40.052   9.603  1.00  57.49       A    C
ATOM    816  CD1 TYR A 219       1.450  40.591   9.575  1.00  61.63       A    C
ATOM    817  CE1 TYR A 219       1.821  41.532   8.618  1.00  61.98       A    C
ATOM    818  CD2 TYR A 219      -0.758  40.503   8.655  1.00  60.63       A    C
ATOM    819  CE2 TYR A 219      -0.399  41.444   7.697  1.00  63.54       A    C
ATOM    820  CZ  TYR A 219       0.896  41.946   7.679  1.00  63.29       A    C
ATOM    821  OH  TYR A 219       1.276  42.812   6.677  1.00  63.78       A    O
ATOM    822  C   TYR A 219      -0.904  40.573  12.295  1.00  49.45       A    C
ATOM    823  O   TYR A 219      -0.376  41.685  12.440  1.00  50.30       A    O
ATOM    824  N   ARG A 220      -2.223  40.347  12.346  1.00  49.53       A    N
ATOM    825  CA  ARG A 220      -3.201  41.398  12.582  1.00  53.27       A    C
ATOM    826  CB  ARG A 220      -4.612  40.900  12.257  1.00  56.83       A    C
ATOM    827  CG  ARG A 220      -4.851  40.670  10.766  1.00  69.43       A    C
ATOM    828  CD  ARG A 220      -4.982  41.985  10.008  1.00  75.60       A    C
ATOM    829  NE  ARG A 220      -4.866  41.820   8.559  1.00  83.49       A    N
ATOM    830  CZ  ARG A 220      -5.621  41.003   7.828  1.00  88.43       A    C
ATOM    831  NH1 ARG A 220      -5.437  40.928   6.516  1.00  90.26       A    N
ATOM    832  NH2 ARG A 220      -6.555  40.254   8.402  1.00  91.97       A    N
ATOM    833  C   ARG A 220      -3.180  41.974  13.994  1.00  56.03       A    C
ATOM    834  O   ARG A 220      -3.171  43.187  14.153  1.00  59.37       A    O
ATOM    835  N   GLU A 221      -3.170  41.134  15.020  1.00  58.09       A    N
ATOM    836  CA  GLU A 221      -3.147  41.683  16.364  1.00  60.51       A    C
ATOM    837  CB  GLU A 221      -3.063  40.581  17.414  1.00  57.61       A    C
ATOM    838  CG  GLU A 221      -4.395  40.306  18.102  1.00  59.70       A    C
ATOM    839  CD  GLU A 221      -4.847  41.450  19.023  1.00  62.45       A    C
ATOM    840  OE1 GLU A 221      -4.826  42.626  18.575  1.00  65.90       A    O
ATOM    841  OE2 GLU A 221      -5.233  41.172  20.196  1.00  60.04       A    O
ATOM    842  C   GLU A 221      -1.938  42.581  16.452  1.00  63.48       A    C
ATOM    843  O   GLU A 221      -2.017  43.738  16.879  1.00  64.26       A    O
ATOM    844  N   LEU A 222      -0.820  42.033  15.995  1.00  67.70       A    N
ATOM    845  CA  LEU A 222       0.460  42.722  15.987  1.00  67.87       A    C
ATOM    846  CB  LEU A 222       1.515  41.885  15.244  1.00  67.58       A    C
ATOM    847  CG  LEU A 222       2.946  42.415  15.346  1.00  65.18       A    C
ATOM    848  CD1 LEU A 222       3.175  42.970  16.758  1.00  64.68       A    C
ATOM    849  CD2 LEU A 222       3.942  41.303  15.025  1.00  62.50       A    C
ATOM    850  C   LEU A 222       0.340  44.094  15.357  1.00  67.72       A    C
ATOM    851  O   LEU A 222       0.791  45.075  15.944  1.00  69.85       A    O
ATOM    852  N   GLN A 223      -0.260  44.186  14.179  1.00  66.51       A    N
ATOM    853  CA  GLN A 223      -0.408  45.502  13.571  1.00  67.39       A    C
ATOM    854  CB  GLN A 223      -0.768  45.376  12.086  1.00  66.06       A    C
ATOM    855  CG  GLN A 223      -2.046  44.668  11.795  1.00  67.20       A    C
ATOM    856  CD  GLN A 223      -2.305  44.601  10.305  1.00  68.41       A    C
ATOM    857  OE1 GLN A 223      -3.366  44.139   9.854  1.00  70.58       A    O
ATOM    858  NE2 GLN A 223      -1.335  45.063   9.527  1.00  67.38       A    N
ATOM    859  C   GLN A 223      -1.426  46.412  14.305  1.00  67.84       A    C
ATOM    860  O   GLN A 223      -1.327  47.636  14.240  1.00  67.50       A    O
ATOM    861  N   LYS A 224      -2.385  45.818  15.017  1.00  69.61       A    N
ATOM    862  CA  LYS A 224      -3.366  46.597  15.764  1.00  70.41       A    C
```

Figure 2N

```
ATOM    863  CB  LYS A 224      -4.636  45.767  16.050  1.00  70.62      A    C
ATOM    864  CG  LYS A 224      -5.663  45.788  14.895  1.00  68.80      A    C
ATOM    865  CD  LYS A 224      -6.855  44.854  15.124  1.00  68.86      A    C
ATOM    866  CE  LYS A 224      -7.685  45.273  16.327  1.00  69.95      A    C
ATOM    867  NZ  LYS A 224      -8.809  44.344  16.620  1.00  68.17      A    N
ATOM    868  C   LYS A 224      -2.743  47.109  17.063  1.00  70.17      A    C
ATOM    869  O   LYS A 224      -2.878  48.285  17.392  1.00  73.67      A    O
ATOM    870  N   LEU A 225      -2.056  46.249  17.806  1.00  66.47      A    N
ATOM    871  CA  LEU A 225      -1.416  46.710  19.038  1.00  61.45      A    C
ATOM    872  CB  LEU A 225      -1.322  45.570  20.060  1.00  58.57      A    C
ATOM    873  CG  LEU A 225      -2.506  45.483  21.039  1.00  57.64      A    C
ATOM    874  CD1 LEU A 225      -3.781  45.256  20.257  1.00  58.81      A    C
ATOM    875  CD2 LEU A 225      -2.295  44.364  22.056  1.00  55.79      A    C
ATOM    876  C   LEU A 225      -0.020  47.312  18.799  1.00  60.75      A    C
ATOM    877  O   LEU A 225       0.642  47.729  19.731  1.00  60.05      A    O
ATOM    878  N   SER A 226       0.409  47.369  17.545  1.00  61.40      A    N
ATOM    879  CA  SER A 226       1.724  47.895  17.189  1.00  62.37      A    C
ATOM    880  CB  SER A 226       1.899  49.318  17.733  1.00  65.25      A    C
ATOM    881  OG  SER A 226       2.870  50.050  16.986  1.00  66.92      A    O
ATOM    882  C   SER A 226       2.870  47.005  17.708  1.00  62.22      A    C
ATOM    883  O   SER A 226       3.716  46.520  16.941  1.00  62.39      A    O
ATOM    884  N   LYS A 227       2.874  46.786  19.016  1.00  59.86      A    N
ATOM    885  CA  LYS A 227       3.905  45.986  19.655  1.00  58.85      A    C
ATOM    886  CB  LYS A 227       4.986  46.933  20.203  1.00  60.81      A    C
ATOM    887  CG  LYS A 227       5.810  46.364  21.313  1.00  70.18      A    C
ATOM    888  CD  LYS A 227       6.349  47.457  22.246  1.00  74.56      A    C
ATOM    889  CE  LYS A 227       6.895  46.838  23.554  1.00  75.22      A    C
ATOM    890  NZ  LYS A 227       6.781  47.751  24.730  1.00  75.08      A    N
ATOM    891  C   LYS A 227       3.257  45.208  20.784  1.00  59.37      A    C
ATOM    892  O   LYS A 227       2.288  45.683  21.339  1.00  63.91      A    O
ATOM    893  N   PHE A 228       3.763  44.021  21.121  1.00  57.55      A    N
ATOM    894  CA  PHE A 228       3.198  43.247  22.237  1.00  54.42      A    C
ATOM    895  CB  PHE A 228       3.139  41.748  21.931  1.00  46.81      A    C
ATOM    896  CG  PHE A 228       2.318  41.393  20.732  1.00  38.81      A    C
ATOM    897  CD1 PHE A 228       1.317  42.233  20.282  1.00  35.93      A    C
ATOM    898  CD2 PHE A 228       2.512  40.173  20.095  1.00  36.88      A    C
ATOM    899  CE1 PHE A 228       0.518  41.880  19.227  1.00  37.85      A    C
ATOM    900  CE2 PHE A 228       1.721  39.791  19.039  1.00  34.85      A    C
ATOM    901  CZ  PHE A 228       0.709  40.658  18.596  1.00  38.71      A    C
ATOM    902  C   PHE A 228       4.047  43.401  23.497  1.00  56.35      A    C
ATOM    903  O   PHE A 228       5.280  43.424  23.422  1.00  56.01      A    O
ATOM    904  N   ASP A 229       3.389  43.474  24.650  1.00  60.32      A    N
ATOM    905  CA  ASP A 229       4.087  43.595  25.932  1.00  62.60      A    C
ATOM    906  CB  ASP A 229       3.100  43.752  27.096  1.00  66.99      A    C
ATOM    907  CG  ASP A 229       2.098  42.606  27.160  1.00  69.72      A    C
ATOM    908  OD1 ASP A 229       1.103  42.651  26.392  1.00  69.32      A    O
ATOM    909  OD2 ASP A 229       2.317  41.660  27.950  1.00  70.81      A    O
ATOM    910  C   ASP A 229       4.842  42.307  26.147  1.00  61.76      A    C
ATOM    911  O   ASP A 229       4.682  41.356  25.396  1.00  60.08      A    O
ATOM    912  N   GLU A 230       5.622  42.274  27.214  1.00  62.08      A    N
ATOM    913  CA  GLU A 230       6.427  41.128  27.560  1.00  65.64      A    C
ATOM    914  CB  GLU A 230       7.422  41.553  28.619  1.00  68.09      A    C
ATOM    915  CG  GLU A 230       8.259  42.727  28.153  1.00  76.32      A    C
ATOM    916  CD  GLU A 230       9.484  42.918  29.002  1.00  80.67      A    C
ATOM    917  OE1 GLU A 230      10.125  41.895  29.343  1.00  82.99      A    O
ATOM    918  OE2 GLU A 230       9.804  44.084  29.310  1.00  80.88      A    O
ATOM    919  C   GLU A 230       5.663  39.892  28.017  1.00  69.18      A    C
ATOM    920  O   GLU A 230       6.123  38.759  27.826  1.00  69.91      A    O
ATOM    921  N   GLN A 231       4.503  40.101  28.628  1.00  73.90      A    N
ATOM    922  CA  GLN A 231       3.685  38.988  29.097  1.00  75.17      A    C
ATOM    923  CB  GLN A 231       2.467  39.520  29.863  1.00  79.55      A    C
```

Figure 20

```
ATOM    924  CG  GLN A 231      2.798  40.367  31.089  1.00  89.47      A  C
ATOM    925  CD  GLN A 231      1.549  40.957  31.744  1.00  96.98      A  C
ATOM    926  OE1 GLN A 231      1.576  41.407  32.898  1.00 100.89      A  O
ATOM    927  NE2 GLN A 231      0.447  40.965  31.002  1.00  99.51      A  N
ATOM    928  C   GLN A 231      3.219  38.166  27.890  1.00  72.65      A  C
ATOM    929  O   GLN A 231      3.584  36.998  27.727  1.00  72.45      A  O
ATOM    930  N   ARG A 232      2.429  38.803  27.035  1.00  68.15      A  N
ATOM    931  CA  ARG A 232      1.879  38.170  25.846  1.00  63.38      A  C
ATOM    932  CB  ARG A 232      1.044  39.207  25.107  1.00  63.50      A  C
ATOM    933  CG  ARG A 232      0.215  38.677  23.969  1.00  65.53      A  C
ATOM    934  CD  ARG A 232     -0.748  39.766  23.568  1.00  67.35      A  C
ATOM    935  NE  ARG A 232     -1.432  39.509  22.304  1.00  70.97      A  N
ATOM    936  CZ  ARG A 232     -2.307  40.354  21.777  1.00  72.33      A  C
ATOM    937  NH1 ARG A 232     -2.586  41.485  22.418  1.00  69.71      A  N
ATOM    938  NH2 ARG A 232     -2.884  40.079  20.613  1.00  73.23      A  N
ATOM    939  C   ARG A 232      2.921  37.540  24.902  1.00  60.23      A  C
ATOM    940  O   ARG A 232      2.745  36.416  24.414  1.00  58.38      A  O
ATOM    941  N   THR A 233      4.004  38.272  24.648  1.00  55.56      A  N
ATOM    942  CA  THR A 233      5.070  37.794  23.781  1.00  48.72      A  C
ATOM    943  CB  THR A 233      6.149  38.859  23.610  1.00  39.44      A  C
ATOM    944  OG1 THR A 233      7.351  38.260  23.119  1.00  35.31      A  O
ATOM    945  CG2 THR A 233      6.443  39.475  24.921  1.00  38.09      A  C
ATOM    946  C   THR A 233      5.716  36.561  24.366  1.00  51.20      A  C
ATOM    947  O   THR A 233      5.943  35.583  23.669  1.00  52.51      A  O
ATOM    948  N   ALA A 234      5.989  36.605  25.665  1.00  53.14      A  N
ATOM    949  CA  ALA A 234      6.638  35.496  26.349  1.00  49.87      A  C
ATOM    950  CB  ALA A 234      7.074  35.921  27.742  1.00  52.72      A  C
ATOM    951  C   ALA A 234      5.779  34.260  26.445  1.00  48.45      A  C
ATOM    952  O   ALA A 234      6.292  33.154  26.392  1.00  47.78      A  O
ATOM    953  N   THR A 235      4.472  34.419  26.610  1.00  49.37      A  N
ATOM    954  CA  THR A 235      3.659  33.218  26.686  1.00  51.73      A  C
ATOM    955  CB  THR A 235      2.315  33.447  27.481  1.00  51.82      A  C
ATOM    956  OG1 THR A 235      1.261  32.688  26.884  1.00  58.83      A  O
ATOM    957  CG2 THR A 235      1.947  34.912  27.554  1.00  48.59      A  C
ATOM    958  C   THR A 235      3.460  32.688  25.271  1.00  52.58      A  C
ATOM    959  O   THR A 235      3.381  31.475  25.070  1.00  52.21      A  O
ATOM    960  N   TYR A 236      3.427  33.587  24.283  1.00  54.10      A  N
ATOM    961  CA  TYR A 236      3.297  33.143  22.883  1.00  53.71      A  C
ATOM    962  CB  TYR A 236      3.162  34.328  21.906  1.00  53.73      A  C
ATOM    963  CG  TYR A 236      1.750  34.812  21.663  1.00  61.66      A  C
ATOM    964  CD1 TYR A 236      0.652  34.070  22.074  1.00  66.38      A  C
ATOM    965  CE1 TYR A 236     -0.653  34.525  21.874  1.00  70.18      A  C
ATOM    966  CD2 TYR A 236      1.513  36.023  21.035  1.00  66.15      A  C
ATOM    967  CE2 TYR A 236      0.210  36.494  20.827  1.00  69.63      A  C
ATOM    968  CZ  TYR A 236     -0.871  35.739  21.252  1.00  70.75      A  C
ATOM    969  OH  TYR A 236     -2.164  36.202  21.067  1.00  69.03      A  O
ATOM    970  C   TYR A 236      4.554  32.342  22.518  1.00  52.18      A  C
ATOM    971  O   TYR A 236      4.488  31.341  21.792  1.00  51.78      A  O
ATOM    972  N   ILE A 237      5.695  32.779  23.041  1.00  50.58      A  N
ATOM    973  CA  ILE A 237      6.941  32.104  22.770  1.00  45.21      A  C
ATOM    974  CB  ILE A 237      8.137  32.957  23.271  1.00  41.69      A  C
ATOM    975  CG2 ILE A 237      9.415  32.140  23.281  1.00  39.89      A  C
ATOM    976  CG1 ILE A 237      8.312  34.160  22.349  1.00  38.56      A  C
ATOM    977  CD1 ILE A 237      8.430  33.772  20.858  1.00  35.28      A  C
ATOM    978  C   ILE A 237      6.951  30.698  23.381  1.00  45.03      A  C
ATOM    979  O   ILE A 237      7.433  29.749  22.767  1.00  43.50      A  O
ATOM    980  N   THR A 238      6.401  30.550  24.582  1.00  45.32      A  N
ATOM    981  CA  THR A 238      6.362  29.226  25.196  1.00  49.64      A  C
ATOM    982  CB  THR A 238      6.024  29.329  26.683  1.00  52.31      A  C
ATOM    983  OG1 THR A 238      5.180  28.233  27.077  1.00  57.19      A  O
ATOM    984  CG2 THR A 238      5.352  30.650  26.964  1.00  51.31      A  C
```

Figure 2P

```
ATOM    985  C   THR A 238       5.359  28.304  24.490  1.00  50.52      A  C
ATOM    986  O   THR A 238       5.621  27.115  24.297  1.00  48.52      A  O
ATOM    987  N   GLU A 239       4.216  28.857  24.092  1.00  53.64      A  N
ATOM    988  CA  GLU A 239       3.205  28.074  23.399  1.00  56.73      A  C
ATOM    989  CB  GLU A 239       1.983  28.929  23.068  1.00  57.03      A  C
ATOM    990  CG  GLU A 239       1.204  29.373  24.280  1.00  58.12      A  C
ATOM    991  CD  GLU A 239      -0.106  30.015  23.931  1.00  55.27      A  C
ATOM    992  OE1 GLU A 239      -0.843  30.341  24.877  1.00  54.36      A  O
ATOM    993  OE2 GLU A 239      -0.400  30.198  22.729  1.00  52.64      A  O
ATOM    994  C   GLU A 239       3.800  27.574  22.111  1.00  57.95      A  C
ATOM    995  O   GLU A 239       3.616  26.425  21.726  1.00  60.77      A  O
ATOM    996  N   LEU A 240       4.528  28.471  21.457  1.00  57.89      A  N
ATOM    997  CA  LEU A 240       5.166  28.180  20.183  1.00  57.54      A  C
ATOM    998  CB  LEU A 240       5.773  29.470  19.648  1.00  56.34      A  C
ATOM    999  CG  LEU A 240       5.551  29.768  18.179  1.00  56.65      A  C
ATOM   1000  CD1 LEU A 240       4.307  29.072  17.672  1.00  55.80      A  C
ATOM   1001  CD2 LEU A 240       5.459  31.276  18.027  1.00  56.33      A  C
ATOM   1002  C   LEU A 240       6.236  27.097  20.305  1.00  57.23      A  C
ATOM   1003  O   LEU A 240       6.254  26.125  19.536  1.00  56.19      A  O
ATOM   1004  N   ALA A 241       7.122  27.269  21.280  1.00  57.00      A  N
ATOM   1005  CA  ALA A 241       8.192  26.307  21.509  1.00  57.21      A  C
ATOM   1006  CB  ALA A 241       9.040  26.743  22.700  1.00  56.49      A  C
ATOM   1007  C   ALA A 241       7.641  24.889  21.734  1.00  57.20      A  C
ATOM   1008  O   ALA A 241       8.243  23.909  21.303  1.00  58.21      A  O
ATOM   1009  N   ASN A 242       6.493  24.779  22.397  1.00  56.93      A  N
ATOM   1010  CA  ASN A 242       5.917  23.465  22.633  1.00  56.45      A  C
ATOM   1011  CB  ASN A 242       4.750  23.563  23.614  1.00  61.22      A  C
ATOM   1012  CG  ASN A 242       5.190  23.981  25.002  1.00  65.81      A  C
ATOM   1013  OD1 ASN A 242       4.386  24.011  25.931  1.00  69.34      A  O
ATOM   1014  ND2 ASN A 242       6.477  24.311  25.152  1.00  67.04      A  N
ATOM   1015  C   ASN A 242       5.436  22.858  21.314  1.00  54.08      A  C
ATOM   1016  O   ASN A 242       5.776  21.713  20.980  1.00  51.81      A  O
ATOM   1017  N   ALA A 243       4.646  23.630  20.573  1.00  50.33      A  N
ATOM   1018  CA  ALA A 243       4.121  23.154  19.302  1.00  48.11      A  C
ATOM   1019  CB  ALA A 243       3.379  24.285  18.548  1.00  47.57      A  C
ATOM   1020  C   ALA A 243       5.311  22.686  18.496  1.00  46.61      A  C
ATOM   1021  O   ALA A 243       5.252  21.705  17.783  1.00  45.43      A  O
ATOM   1022  N   LEU A 244       6.395  23.429  18.616  1.00  48.76      A  N
ATOM   1023  CA  LEU A 244       7.617  23.081  17.930  1.00  51.97      A  C
ATOM   1024  CB  LEU A 244       8.608  24.233  18.065  1.00  47.46      A  C
ATOM   1025  CG  LEU A 244       8.958  25.044  16.820  1.00  43.86      A  C
ATOM   1026  CD1 LEU A 244       8.169  24.584  15.577  1.00  41.27      A  C
ATOM   1027  CD2 LEU A 244       8.723  26.506  17.148  1.00  40.03      A  C
ATOM   1028  C   LEU A 244       8.178  21.791  18.571  1.00  57.31      A  C
ATOM   1029  O   LEU A 244       8.430  20.781  17.877  1.00  58.25      A  O
ATOM   1030  N   SER A 245       8.337  21.817  19.897  1.00  59.32      A  N
ATOM   1031  CA  SER A 245       8.868  20.662  20.600  1.00  58.93      A  C
ATOM   1032  CB  SER A 245       8.845  20.870  22.095  1.00  58.15      A  C
ATOM   1033  OG  SER A 245       9.385  19.715  22.705  1.00  63.44      A  O
ATOM   1034  C   SER A 245       8.098  19.400  20.262  1.00  60.89      A  C
ATOM   1035  O   SER A 245       8.697  18.345  20.051  1.00  58.79      A  O
ATOM   1036  N   TYR A 246       6.771  19.507  20.219  1.00  65.62      A  N
ATOM   1037  CA  TYR A 246       5.937  18.372  19.852  1.00  69.78      A  C
ATOM   1038  CB  TYR A 246       4.451  18.676  20.080  1.00  67.46      A  C
ATOM   1039  CG  TYR A 246       3.526  17.734  19.329  1.00  68.67      A  C
ATOM   1040  CD1 TYR A 246       2.973  16.611  19.949  1.00  70.54      A  C
ATOM   1041  CE1 TYR A 246       2.177  15.706  19.227  1.00  71.87      A  C
ATOM   1042  CD2 TYR A 246       3.259  17.934  17.972  1.00  70.37      A  C
ATOM   1043  CE2 TYR A 246       2.476  17.049  17.247  1.00  71.97      A  C
ATOM   1044  CZ  TYR A 246       1.936  15.932  17.877  1.00  72.29      A  C
ATOM   1045  OH  TYR A 246       1.179  15.051  17.133  1.00  70.95      A  O
```

Figure 2Q

```
ATOM  1046  C    TYR A 246       6.175  18.075  18.362  1.00  73.83      A  C
ATOM  1047  O    TYR A 246       5.937  16.953  17.895  1.00  77.90      A  O
ATOM  1048  N    CYS A 247       6.635  19.067  17.605  1.00  73.82      A  N
ATOM  1049  CA   CYS A 247       6.871  18.826  16.193  1.00  73.88      A  C
ATOM  1050  CB   CYS A 247       6.821  20.133  15.400  1.00  71.94      A  C
ATOM  1051  SG   CYS A 247       5.157  20.515  14.790  1.00  74.34      A  S
ATOM  1052  C    CYS A 247       8.196  18.118  15.971  1.00  76.59      A  C
ATOM  1053  O    CYS A 247       8.332  17.311  15.054  1.00  77.68      A  O
ATOM  1054  N    HIS A 248       9.170  18.417  16.821  1.00  79.02      A  N
ATOM  1055  CA   HIS A 248      10.472  17.794  16.713  1.00  82.34      A  C
ATOM  1056  CB   HIS A 248      11.474  18.501  17.637  1.00  83.92      A  C
ATOM  1057  CG   HIS A 248      12.012  19.784  17.080  1.00  87.69      A  C
ATOM  1058  CD2  HIS A 248      13.201  20.406  17.264  1.00  88.71      A  C
ATOM  1059  ND1  HIS A 248      11.285  20.592  16.231  1.00  88.91      A  N
ATOM  1060  CE1  HIS A 248      12.004  21.655  15.915  1.00  88.73      A  C
ATOM  1061  NE2  HIS A 248      13.170  21.566  16.528  1.00  88.38      A  N
ATOM  1062  C    HIS A 248      10.378  16.298  17.052  1.00  84.20      A  C
ATOM  1063  O    HIS A 248      10.631  15.457  16.191  1.00  85.73      A  O
ATOM  1064  N    SER A 249      10.003  15.968  18.290  1.00  84.96      A  N
ATOM  1065  CA   SER A 249       9.904  14.565  18.713  1.00  86.31      A  C
ATOM  1066  CB   SER A 249       9.087  14.440  20.000  1.00  85.00      A  C
ATOM  1067  OG   SER A 249       7.723  14.705  19.746  1.00  84.45      A  O
ATOM  1068  C    SER A 249       9.262  13.678  17.651  1.00  87.78      A  C
ATOM  1069  O    SER A 249       9.759  12.590  17.346  1.00  87.49      A  O
ATOM  1070  N    LYS A 250       8.153  14.153  17.098  1.00  89.35      A  N
ATOM  1071  CA   LYS A 250       7.422  13.427  16.074  1.00  91.23      A  C
ATOM  1072  CB   LYS A 250       5.997  13.989  16.040  1.00  93.29      A  C
ATOM  1073  CG   LYS A 250       5.180  13.766  14.786  1.00 101.85      A  C
ATOM  1074  CD   LYS A 250       5.425  14.865  13.746  1.00 108.05      A  C
ATOM  1075  CE   LYS A 250       5.897  16.189  14.372  1.00 109.23      A  C
ATOM  1076  NZ   LYS A 250       5.059  16.669  15.508  1.00 111.44      A  N
ATOM  1077  C    LYS A 250       8.159  13.532  14.727  1.00  91.14      A  C
ATOM  1078  O    LYS A 250       7.638  13.186  13.664  1.00  90.16      A  O
ATOM  1079  N    ARG A 251       9.405  13.986  14.813  1.00  91.81      A  N
ATOM  1080  CA   ARG A 251      10.300  14.162  13.672  1.00  92.21      A  C
ATOM  1081  CB   ARG A 251      10.901  12.816  13.245  1.00  98.53      A  C
ATOM  1082  CG   ARG A 251      12.150  12.454  14.052  1.00 108.16      A  C
ATOM  1083  CD   ARG A 251      12.892  11.236  13.510  1.00 114.93      A  C
ATOM  1084  NE   ARG A 251      14.198  11.105  14.158  1.00 121.78      A  N
ATOM  1085  CZ   ARG A 251      15.045  10.097  13.966  1.00 124.87      A  C
ATOM  1086  NH1  ARG A 251      14.731   9.110  13.136  1.00 127.26      A  N
ATOM  1087  NH2  ARG A 251      16.213  10.081  14.601  1.00 125.17      A  N
ATOM  1088  C    ARG A 251       9.762  14.900  12.456  1.00  88.57      A  C
ATOM  1089  O    ARG A 251       9.643  14.345  11.369  1.00  87.62      A  O
ATOM  1090  N    VAL A 252       9.462  16.174  12.663  1.00  86.18      A  N
ATOM  1091  CA   VAL A 252       8.974  17.052  11.611  1.00  84.70      A  C
ATOM  1092  CB   VAL A 252       7.431  17.182  11.635  1.00  82.24      A  C
ATOM  1093  CG1  VAL A 252       6.995  18.381  10.816  1.00  80.36      A  C
ATOM  1094  CG2  VAL A 252       6.797  15.922  11.072  1.00  79.35      A  C
ATOM  1095  C    VAL A 252       9.605  18.402  11.908  1.00  85.34      A  C
ATOM  1096  O    VAL A 252       9.631  18.836  13.057  1.00  87.08      A  O
ATOM  1097  N    ILE A 253      10.149  19.046  10.886  1.00  85.65      A  N
ATOM  1098  CA   ILE A 253      10.770  20.343  11.078  1.00  87.22      A  C
ATOM  1099  CB   ILE A 253      12.216  20.371  10.588  1.00  89.79      A  C
ATOM  1100  CG2  ILE A 253      12.711  21.797  10.593  1.00  91.38      A  C
ATOM  1101  CG1  ILE A 253      13.106  19.505  11.485  1.00  91.78      A  C
ATOM  1102  CD1  ILE A 253      12.836  18.010  11.380  1.00  91.55      A  C
ATOM  1103  C    ILE A 253       9.998  21.393  10.312  1.00  87.67      A  C
ATOM  1104  O    ILE A 253       9.975  21.378   9.080  1.00  87.82      A  O
ATOM  1105  N    HIS A 254       9.368  22.306  11.049  1.00  86.39      A  N
ATOM  1106  CA   HIS A 254       8.571  23.363  10.442  1.00  85.51      A  C
```

Figure 2R

```
ATOM   1107  CB   HIS A 254       7.451  23.827  11.389  1.00  80.51      A    C
ATOM   1108  CG   HIS A 254       6.110  23.251  11.063  1.00  82.33      A    C
ATOM   1109  CD2  HIS A 254       5.222  22.573  11.825  1.00  84.09      A    C
ATOM   1110  ND1  HIS A 254       5.557  23.323   9.801  1.00  84.07      A    N
ATOM   1111  CE1  HIS A 254       4.386  22.711   9.800  1.00  86.17      A    C
ATOM   1112  NE2  HIS A 254       4.160  22.246  11.016  1.00  86.48      A    N
ATOM   1113  C    HIS A 254       9.400  24.566  10.062  1.00  86.59      A    C
ATOM   1114  O    HIS A 254      10.525  24.455   9.543  1.00  86.38      A    O
ATOM   1115  N    ARG A 255       8.803  25.714  10.366  1.00  88.55      A    N
ATOM   1116  CA   ARG A 255       9.338  27.037  10.116  1.00  87.88      A    C
ATOM   1117  CB   ARG A 255      10.523  26.987   9.138  1.00  88.00      A    C
ATOM   1124  C    ARG A 255       8.156  27.794   9.504  1.00  87.48      A    C
ATOM   1125  O    ARG A 255       6.991  27.403   9.685  1.00  83.80      A    O
ATOM   1126  N    ASP A 256       8.454  28.865   8.773  1.00  85.49      A    N
ATOM   1127  CA   ASP A 256       7.415  29.674   8.163  1.00  79.91      A    C
ATOM   1128  CB   ASP A 256       6.572  28.839   7.200  1.00  77.83      A    C
ATOM   1132  C    ASP A 256       6.516  30.226   9.261  1.00  76.92      A    C
ATOM   1133  O    ASP A 256       5.643  31.036   8.969  1.00  80.83      A    O
ATOM   1134  N    ILE A 257       6.731  29.796  10.508  1.00  68.19      A    N
ATOM   1135  CA   ILE A 257       5.915  30.247  11.625  1.00  57.62      A    C
ATOM   1136  CB   ILE A 257       6.280  29.551  12.973  1.00  53.48      A    C
ATOM   1137  CG2  ILE A 257       5.820  28.118  12.979  1.00  54.94      A    C
ATOM   1138  CG1  ILE A 257       7.770  29.661  13.232  1.00  49.61      A    C
ATOM   1139  CD1  ILE A 257       8.119  30.548  14.383  1.00  43.70      A    C
ATOM   1140  C    ILE A 257       5.959  31.744  11.878  1.00  54.17      A    C
ATOM   1141  O    ILE A 257       6.230  32.175  12.982  1.00  55.38      A    O
ATOM   1142  N    LYS A 258       5.680  32.531  10.856  1.00  49.16      A    N
ATOM   1143  CA   LYS A 258       5.649  33.971  10.991  1.00  46.30      A    C
ATOM   1144  CB   LYS A 258       6.128  34.630   9.691  1.00  47.36      A    C
ATOM   1145  CG   LYS A 258       5.575  33.995   8.448  1.00  48.03      A    C
ATOM   1146  CD   LYS A 258       6.122  34.644   7.196  1.00  47.79      A    C
ATOM   1147  CE   LYS A 258       7.598  34.477   7.051  1.00  48.62      A    C
ATOM   1148  NZ   LYS A 258       7.892  34.598   5.596  1.00  58.33      A    N
ATOM   1149  C    LYS A 258       4.229  34.420  11.333  1.00  45.88      A    C
ATOM   1150  O    LYS A 258       3.285  33.653  11.212  1.00  46.55      A    O
ATOM   1151  N    PRO A 259       4.068  35.677  11.761  1.00  45.68      A    N
ATOM   1152  CD   PRO A 259       5.118  36.704  11.817  1.00  46.78      A    C
ATOM   1153  CA   PRO A 259       2.775  36.253  12.132  1.00  45.43      A    C
ATOM   1154  CB   PRO A 259       3.077  37.740  12.180  1.00  46.00      A    C
ATOM   1155  CG   PRO A 259       4.473  37.754  12.674  1.00  46.05      A    C
ATOM   1156  C    PRO A 259       1.624  35.921  11.172  1.00  44.45      A    C
ATOM   1157  O    PRO A 259       0.495  35.659  11.581  1.00  41.11      A    O
ATOM   1158  N    GLU A 260       1.944  35.955   9.889  1.00  46.37      A    N
ATOM   1159  CA   GLU A 260       1.007  35.685   8.833  1.00  46.16      A    C
ATOM   1160  CB   GLU A 260       1.756  35.684   7.497  1.00  46.91      A    C
ATOM   1161  CG   GLU A 260       2.573  36.965   7.163  1.00  47.60      A    C
ATOM   1162  CD   GLU A 260       3.594  37.349   8.231  1.00  51.56      A    C
ATOM   1163  OE1  GLU A 260       3.944  38.549   8.333  1.00  49.95      A    O
ATOM   1164  OE2  GLU A 260       4.061  36.465   8.972  1.00  56.64      A    O
ATOM   1165  C    GLU A 260       0.387  34.310   9.057  1.00  48.99      A    C
ATOM   1166  O    GLU A 260      -0.809  34.113   8.877  1.00  51.12      A    O
ATOM   1167  N    ASN A 261       1.210  33.360   9.483  1.00  52.67      A    N
ATOM   1168  CA   ASN A 261       0.745  31.985   9.648  1.00  52.53      A    C
ATOM   1169  CB   ASN A 261       1.806  31.011   9.092  1.00  53.47      A    C
ATOM   1170  CG   ASN A 261       2.308  31.417   7.710  1.00  53.07      A    C
ATOM   1171  OD1  ASN A 261       1.526  31.794   6.832  1.00  50.76      A    O
ATOM   1172  ND2  ASN A 261       3.620  31.334   7.513  1.00  52.27      A    N
ATOM   1173  C    ASN A 261       0.351  31.562  11.042  1.00  49.79      A    C
ATOM   1174  O    ASN A 261       0.018  30.403  11.261  1.00  52.25      A    O
ATOM   1175  N    LEU A 262       0.392  32.495  11.984  1.00  46.23      A    N
ATOM   1176  CA   LEU A 262       0.016  32.171  13.339  1.00  42.90      A    C
```

Figure 2S

```
ATOM   1177  CB   LEU A  262       1.026  32.782  14.319  1.00  42.14      A    C
ATOM   1178  CG   LEU A  262       2.503  32.370  14.139  1.00  38.18      A    C
ATOM   1179  CD1  LEU A  262       3.305  33.014  15.238  1.00  34.58      A    C
ATOM   1180  CD2  LEU A  262       2.675  30.845  14.216  1.00  33.80      A    C
ATOM   1181  C    LEU A  262      -1.402  32.693  13.598  1.00  40.82      A    C
ATOM   1182  O    LEU A  262      -1.691  33.875  13.350  1.00  41.46      A    O
ATOM   1183  N    LEU A  263      -2.300  31.825  14.061  1.00  39.36      A    N
ATOM   1184  CA   LEU A  263      -3.669  32.261  14.325  1.00  43.05      A    C
ATOM   1185  CB   LEU A  263      -4.648  31.375  13.568  1.00  43.53      A    C
ATOM   1186  CG   LEU A  263      -4.681  31.451  12.040  1.00  43.00      A    C
ATOM   1187  CD1  LEU A  263      -5.699  30.417  11.435  1.00  38.01      A    C
ATOM   1188  CD2  LEU A  263      -5.106  32.848  11.703  1.00  46.40      A    C
ATOM   1189  C    LEU A  263      -4.012  32.254  15.815  1.00  45.66      A    C
ATOM   1190  O    LEU A  263      -3.360  31.589  16.620  1.00  47.95      A    O
ATOM   1191  N    LEU A  264      -5.039  32.993  16.203  1.00  48.56      A    N
ATOM   1192  CA   LEU A  264      -5.377  33.026  17.618  1.00  50.80      A    C
ATOM   1193  CB   LEU A  264      -5.425  34.490  18.074  1.00  52.52      A    C
ATOM   1194  CG   LEU A  264      -4.151  35.277  17.752  1.00  53.11      A    C
ATOM   1195  CD1  LEU A  264      -4.343  36.772  17.933  1.00  54.84      A    C
ATOM   1196  CD2  LEU A  264      -3.033  34.768  18.639  1.00  56.84      A    C
ATOM   1197  C    LEU A  264      -6.684  32.277  17.971  1.00  52.77      A    C
ATOM   1198  O    LEU A  264      -7.637  32.220  17.184  1.00  54.59      A    O
ATOM   1199  N    GLY A  265      -6.704  31.691  19.163  1.00  54.07      A    N
ATOM   1200  CA   GLY A  265      -7.877  30.952  19.615  1.00  55.88      A    C
ATOM   1201  C    GLY A  265      -8.780  31.761  20.540  1.00  57.02      A    C
ATOM   1202  O    GLY A  265      -8.523  32.942  20.799  1.00  56.82      A    O
ATOM   1203  N    SER A  266      -9.844  31.111  21.015  1.00  59.39      A    N
ATOM   1204  CA   SER A  266     -10.832  31.695  21.922  1.00  62.78      A    C
ATOM   1205  CB   SER A  266     -11.621  30.585  22.623  1.00  65.55      A    C
ATOM   1206  OG   SER A  266     -12.199  29.660  21.715  1.00  65.97      A    O
ATOM   1207  C    SER A  266     -10.128  32.531  22.980  1.00  65.41      A    C
ATOM   1208  O    SER A  266     -10.269  33.749  23.022  1.00  70.21      A    O
ATOM   1209  N    ALA A  267      -9.365  31.861  23.830  1.00  64.66      A    N
ATOM   1210  CA   ALA A  267      -8.630  32.512  24.895  1.00  63.74      A    C
ATOM   1211  CB   ALA A  267      -8.088  31.470  25.837  1.00  62.31      A    C
ATOM   1212  C    ALA A  267      -7.486  33.368  24.371  1.00  65.69      A    C
ATOM   1213  O    ALA A  267      -6.794  34.031  25.137  1.00  65.00      A    O
ATOM   1214  N    GLY A  268      -7.272  33.352  23.065  1.00  66.78      A    N
ATOM   1215  CA   GLY A  268      -6.187  34.142  22.517  1.00  62.93      A    C
ATOM   1216  C    GLY A  268      -4.927  33.308  22.483  1.00  61.09      A    C
ATOM   1217  O    GLY A  268      -3.819  33.834  22.564  1.00  61.62      A    O
ATOM   1218  N    GLU A  269      -5.128  32.000  22.354  1.00  58.70      A    N
ATOM   1219  CA   GLU A  269      -4.063  31.012  22.315  1.00  58.24      A    C
ATOM   1220  CB   GLU A  269      -4.595  29.676  22.828  1.00  60.49      A    C
ATOM   1221  CG   GLU A  269      -6.118  29.559  22.749  1.00  65.14      A    C
ATOM   1222  CD   GLU A  269      -6.584  28.250  22.140  1.00  69.20      A    C
ATOM   1223  OE1  GLU A  269      -6.008  27.183  22.467  1.00  72.44      A    O
ATOM   1224  OE2  GLU A  269      -7.542  28.295  21.335  1.00  69.75      A    O
ATOM   1225  C    GLU A  269      -3.511  30.839  20.907  1.00  57.55      A    C
ATOM   1226  O    GLU A  269      -4.253  30.880  19.912  1.00  56.54      A    O
ATOM   1227  N    LEU A  270      -2.207  30.607  20.831  1.00  58.50      A    N
ATOM   1228  CA   LEU A  270      -1.546  30.455  19.552  1.00  59.98      A    C
ATOM   1229  CB   LEU A  270      -0.040  30.479  19.754  1.00  59.88      A    C
ATOM   1230  CG   LEU A  270       0.700  30.847  18.479  1.00  63.72      A    C
ATOM   1231  CD1  LEU A  270       0.101  32.116  17.920  1.00  64.75      A    C
ATOM   1232  CD2  LEU A  270       2.170  31.034  18.771  1.00  67.97      A    C
ATOM   1233  C    LEU A  270      -1.936  29.216  18.762  1.00  60.16      A    C
ATOM   1234  O    LEU A  270      -2.085  28.137  19.317  1.00  61.13      A    O
ATOM   1235  N    LYS A  271      -2.101  29.388  17.454  1.00  59.79      A    N
ATOM   1236  CA   LYS A  271      -2.457  28.289  16.567  1.00  58.46      A    C
ATOM   1237  CB   LYS A  271      -3.904  28.357  16.097  1.00  59.31      A    C
```

Figure 2T

```
ATOM   1238  CG   LYS A 271      -4.954  28.195  17.164  1.00   59.77      A    C
ATOM   1239  CD   LYS A 271      -4.790  26.905  17.947  1.00   59.69      A    C
ATOM   1240  CE   LYS A 271      -6.085  26.568  18.646  1.00   61.18      A    C
ATOM   1241  NZ   LYS A 271      -5.924  25.504  19.648  1.00   62.99      A    N
ATOM   1242  C    LYS A 271      -1.601  28.395  15.350  1.00   58.99      A    C
ATOM   1243  O    LYS A 271      -1.895  29.206  14.455  1.00   57.96      A    O
ATOM   1244  N    ILE A 272      -0.538  27.588  15.315  1.00   61.86      A    N
ATOM   1245  CA   ILE A 272       0.370  27.566  14.168  1.00   63.81      A    C
ATOM   1246  CB   ILE A 272       1.548  26.626  14.403  1.00   62.25      A    C
ATOM   1247  CG2  ILE A 272       2.270  26.379  13.098  1.00   60.79      A    C
ATOM   1248  CG1  ILE A 272       2.456  27.210  15.478  1.00   62.05      A    C
ATOM   1249  CD1  ILE A 272       3.719  26.415  15.715  1.00   65.85      A    C
ATOM   1250  C    ILE A 272      -0.392  27.055  12.971  1.00   65.96      A    C
ATOM   1251  O    ILE A 272      -0.974  25.991  13.026  1.00   66.85      A    O
ATOM   1252  N    ALA A 273      -0.391  27.810  11.887  1.00   70.98      A    N
ATOM   1253  CA   ALA A 273      -1.112  27.382  10.697  1.00   77.37      A    C
ATOM   1254  CB   ALA A 273      -2.418  28.155  10.586  1.00   78.27      A    C
ATOM   1255  C    ALA A 273      -0.298  27.532   9.412  1.00   81.17      A    C
ATOM   1256  O    ALA A 273       0.183  28.616   9.087  1.00   84.58      A    O
ATOM   1257  N    ASP A 274      -0.143  26.437   8.678  1.00   83.86      A    N
ATOM   1258  CA   ASP A 274       0.610  26.469   7.426  1.00   83.78      A    C
ATOM   1259  CB   ASP A 274       2.111  26.677   7.696  1.00   79.07      A    C
ATOM   1260  CG   ASP A 274       2.715  25.574   8.562  1.00   77.63      A    C
ATOM   1261  OD1  ASP A 274       1.972  24.687   9.037  1.00   76.25      A    O
ATOM   1262  OD2  ASP A 274       3.945  25.595   8.777  1.00   77.42      A    O
ATOM   1263  C    ASP A 274       0.426  25.200   6.618  1.00   84.86      A    C
ATOM   1264  O    ASP A 274       1.206  24.265   6.756  1.00   85.25      A    O
ATOM   1265  N    PHE A 275      -0.616  25.144   5.795  1.00   87.85      A    N
ATOM   1266  CA   PHE A 275      -0.815  23.970   4.958  1.00   90.71      A    C
ATOM   1267  CB   PHE A 275      -2.124  23.261   5.272  1.00   94.31      A    C
ATOM   1268  CG   PHE A 275      -2.318  22.948   6.711  1.00  100.68      A    C
ATOM   1269  CD1  PHE A 275      -1.290  23.141   7.642  1.00  103.29      A    C
ATOM   1270  CD2  PHE A 275      -3.547  22.463   7.148  1.00  102.78      A    C
ATOM   1271  CE1  PHE A 275      -1.486  22.859   8.984  1.00  105.17      A    C
ATOM   1272  CE2  PHE A 275      -3.760  22.173   8.488  1.00  105.64      A    C
ATOM   1273  CZ   PHE A 275      -2.730  22.370   9.419  1.00  106.34      A    C
ATOM   1274  C    PHE A 275      -0.886  24.411   3.515  1.00   91.32      A    C
ATOM   1275  O    PHE A 275       0.131  24.575   2.828  1.00   91.62      A    O
ATOM   1276  N    GLY A 276      -2.126  24.605   3.083  1.00   92.25      A    N
ATOM   1277  CA   GLY A 276      -2.393  25.008   1.733  1.00   93.34      A    C
ATOM   1278  C    GLY A 276      -2.707  26.472   1.581  1.00   94.14      A    C
ATOM   1279  O    GLY A 276      -3.841  26.829   1.249  1.00   95.97      A    O
ATOM   1280  N    TRP A 277      -1.725  27.329   1.853  1.00   93.73      A    N
ATOM   1281  CA   TRP A 277      -1.924  28.760   1.647  1.00   92.60      A    C
ATOM   1282  CB   TRP A 277      -3.332  29.226   2.099  1.00   90.63      A    C
ATOM   1283  CG   TRP A 277      -3.685  29.027   3.534  1.00   86.21      A    C
ATOM   1284  CD2  TRP A 277      -3.579  30.004   4.587  1.00   82.11      A    C
ATOM   1285  CE2  TRP A 277      -4.076  29.404   5.764  1.00   80.84      A    C
ATOM   1286  CE3  TRP A 277      -3.113  31.325   4.645  1.00   78.55      A    C
ATOM   1287  CD1  TRP A 277      -4.222  27.902   4.104  1.00   84.13      A    C
ATOM   1288  NE1  TRP A 277      -4.462  28.124   5.446  1.00   82.59      A    N
ATOM   1289  CZ2  TRP A 277      -4.119  30.083   6.987  1.00   79.73      A    C
ATOM   1290  CZ3  TRP A 277      -3.154  32.000   5.856  1.00   74.73      A    C
ATOM   1291  CH2  TRP A 277      -3.654  31.379   7.013  1.00   76.97      A    C
ATOM   1292  C    TRP A 277      -0.865  29.733   2.164  1.00   93.14      A    C
ATOM   1293  O    TRP A 277       0.103  29.365   2.861  1.00   93.04      A    O
ATOM   1294  N    SER A 278      -1.072  30.985   1.762  1.00   92.88      A    N
ATOM   1295  CA   SER A 278      -0.195  32.108   2.064  1.00   91.95      A    C
ATOM   1296  CB   SER A 278       0.897  32.176   0.980  1.00   91.93      A    C
ATOM   1297  OG   SER A 278       1.876  33.166   1.240  1.00   89.50      A    O
ATOM   1298  C    SER A 278      -1.139  33.316   1.974  1.00   91.22      A    C
```

Figure 2U

```
ATOM   1299  O    SER A 278      -1.893  33.583   2.904  1.00  90.97      A    O
ATOM   1300  N    VAL A 279      -1.090  34.018   0.842  1.00  89.97      A    N
ATOM   1301  CA   VAL A 279      -1.952  35.175   0.550  1.00  88.55      A    C
ATOM   1302  CB   VAL A 279      -2.774  34.937  -0.743  1.00  86.75      A    C
ATOM   1305  C    VAL A 279      -2.949  35.525   1.651  1.00  87.15      A    C
ATOM   1306  O    VAL A 279      -4.098  35.049   1.506  1.00  85.02      A    O
TER    1308       VAL A 279                                                A
ATOM   1309  CB   THR A 287       8.902  46.475  -4.662  1.00 124.67      A    C
ATOM   1312  C    THR A 287       8.560  46.308  -2.217  1.00 128.38      A    C
ATOM   1313  O    THR A 287       7.713  47.203  -2.114  1.00 130.20      A    O
ATOM   1314  N    THR A 287       7.395  44.710  -3.726  1.00 126.64      A    N
ATOM   1315  CA   THR A 287       8.644  45.496  -3.501  1.00 127.54      A    C
ATOM   1316  N    THR A 288       9.433  45.989  -1.256  1.00 127.57      A    N
ATOM   1317  CA   THR A 288       9.525  46.673   0.045  1.00 125.37      A    C
ATOM   1318  CB   THR A 288       8.306  47.562   0.349  1.00 123.59      A    C
ATOM   1321  C    THR A 288       9.619  45.660   1.167  1.00 125.68      A    C
ATOM   1322  O    THR A 288      10.696  45.428   1.726  1.00 126.39      A    O
ATOM   1323  N    LEU A 289       8.475  45.068   1.503  1.00 124.65      A    N
ATOM   1324  CA   LEU A 289       8.416  44.074   2.557  1.00 123.06      A    C
ATOM   1325  CB   LEU A 289       6.983  43.547   2.709  1.00 122.14      A    C
ATOM   1329  C    LEU A 289       9.358  42.940   2.170  1.00 122.75      A    C
ATOM   1330  O    LEU A 289       9.005  42.068   1.352  1.00 123.30      A    O
ATOM   1331  N    CYS A 290      10.574  42.966   2.705  1.00 119.67      A    N
ATOM   1332  CA   CYS A 290      11.512  41.891   2.402  1.00 115.54      A    C
ATOM   1333  CB   CYS A 290      12.953  42.318   2.719  1.00 112.99      A    C
ATOM   1335  C    CYS A 290      11.051  40.785   3.348  1.00 114.21      A    C
ATOM   1336  O    CYS A 290      11.859  40.046   3.921  1.00 115.43      A    O
ATOM   1337  N    GLY A 291       9.728  40.725   3.526  1.00 111.20      A    N
ATOM   1338  CA   GLY A 291       9.104  39.740   4.395  1.00 104.53      A    C
ATOM   1339  C    GLY A 291       9.331  38.314   3.935  1.00  98.52      A    C
ATOM   1340  O    GLY A 291       8.916  37.358   4.585  1.00  97.34      A    O
ATOM   1341  N    THR A 292       9.994  38.184   2.796  1.00  92.23      A    N
ATOM   1342  CA   THR A 292      10.307  36.887   2.238  1.00  84.71      A    C
ATOM   1343  CB   THR A 292      10.598  37.013   0.723  1.00  83.69      A    C
ATOM   1344  OG1  THR A 292       9.611  37.858   0.111  1.00  81.22      A    O
ATOM   1345  CG2  THR A 292      10.542  35.656   0.059  1.00  83.67      A    C
ATOM   1346  C    THR A 292      11.541  36.363   2.989  1.00  80.47      A    C
ATOM   1347  O    THR A 292      11.489  35.303   3.610  1.00  81.07      A    O
ATOM   1348  N    LEU A 293      12.634  37.130   2.952  1.00  73.33      A    N
ATOM   1349  CA   LEU A 293      13.883  36.764   3.620  1.00  65.30      A    C
ATOM   1350  CB   LEU A 293      15.039  37.602   3.067  1.00  61.91      A    C
ATOM   1351  CG   LEU A 293      15.664  37.180   1.739  1.00  55.12      A    C
ATOM   1352  CD1  LEU A 293      16.630  38.261   1.297  1.00  49.15      A    C
ATOM   1353  CD2  LEU A 293      16.371  35.817   1.885  1.00  52.96      A    C
ATOM   1354  C    LEU A 293      13.860  36.926   5.135  1.00  60.26      A    C
ATOM   1355  O    LEU A 293      14.522  36.177   5.849  1.00  59.00      A    O
ATOM   1356  N    ASP A 294      13.092  37.914   5.596  1.00  55.84      A    N
ATOM   1357  CA   ASP A 294      12.938  38.275   7.008  1.00  51.34      A    C
ATOM   1358  CB   ASP A 294      11.655  39.083   7.205  1.00  52.57      A    C
ATOM   1359  CG   ASP A 294      11.801  40.560   6.801  1.00  53.26      A    C
ATOM   1360  OD1  ASP A 294      10.792  41.103   6.320  1.00  59.26      A    O
ATOM   1361  OD2  ASP A 294      12.891  41.181   6.975  1.00  49.59      A    O
ATOM   1362  C    ASP A 294      12.944  37.180   8.035  1.00  49.15      A    C
ATOM   1363  O    ASP A 294      13.298  37.424   9.172  1.00  49.68      A    O
ATOM   1364  N    TYR A 295      12.554  35.970   7.661  1.00  47.93      A    N
ATOM   1365  CA   TYR A 295      12.495  34.882   8.635  1.00  52.63      A    C
ATOM   1366  CB   TYR A 295      11.056  34.404   8.745  1.00  56.24      A    C
ATOM   1367  CG   TYR A 295      10.266  35.306   9.619  1.00  59.44      A    C
ATOM   1368  CD1  TYR A 295       9.640  36.451   9.116  1.00  57.70      A    C
ATOM   1369  CE1  TYR A 295       9.064  37.384   9.976  1.00  54.11      A    C
ATOM   1370  CD2  TYR A 295      10.278  35.107  10.989  1.00  57.71      A    C
```

Figure 2V

```
ATOM   1371  CE2  TYR A 295       9.714  36.023  11.842  1.00  57.14      A    C
ATOM   1372  CZ   TYR A 295       9.122  37.155  11.338  1.00  55.50      A    C
ATOM   1373  OH   TYR A 295       8.667  38.053  12.257  1.00  60.87      A    O
ATOM   1374  C    TYR A 295      13.407  33.697   8.379  1.00  53.01      A    C
ATOM   1375  O    TYR A 295      13.602  32.840   9.235  1.00  51.62      A    O
ATOM   1376  N    LEU A 296      13.954  33.647   7.181  1.00  52.76      A    N
ATOM   1377  CA   LEU A 296      14.853  32.576   6.814  1.00  48.84      A    C
ATOM   1378  CB   LEU A 296      15.127  32.653   5.299  1.00  45.66      A    C
ATOM   1379  CG   LEU A 296      13.837  32.796   4.467  1.00  41.77      A    C
ATOM   1380  CD1  LEU A 296      14.119  33.232   3.065  1.00  40.15      A    C
ATOM   1381  CD2  LEU A 296      13.103  31.499   4.454  1.00  40.24      A    C
ATOM   1382  C    LEU A 296      16.156  32.709   7.623  1.00  50.65      A    C
ATOM   1383  O    LEU A 296      16.654  33.805   7.881  1.00  51.36      A    O
ATOM   1384  N    PRO A 297      16.694  31.581   8.081  1.00  52.09      A    N
ATOM   1385  CD   PRO A 297      16.169  30.206   8.008  1.00  52.91      A    C
ATOM   1386  CA   PRO A 297      17.933  31.621   8.842  1.00  51.42      A    C
ATOM   1387  CB   PRO A 297      17.842  30.354   9.669  1.00  50.56      A    C
ATOM   1388  CG   PRO A 297      17.243  29.400   8.714  1.00  51.03      A    C
ATOM   1389  C    PRO A 297      19.085  31.579   7.827  1.00  51.79      A    C
ATOM   1390  O    PRO A 297      18.866  31.307   6.643  1.00  55.81      A    O
ATOM   1391  N    PRO A 298      20.322  31.855   8.277  1.00  49.60      A    N
ATOM   1392  CD   PRO A 298      20.638  32.489   9.575  1.00  49.41      A    C
ATOM   1393  CA   PRO A 298      21.503  31.848   7.408  1.00  45.21      A    C
ATOM   1394  CB   PRO A 298      22.627  32.179   8.376  1.00  48.70      A    C
ATOM   1395  CG   PRO A 298      21.977  33.191   9.279  1.00  49.09      A    C
ATOM   1396  C    PRO A 298      21.748  30.554   6.655  1.00  43.50      A    C
ATOM   1397  O    PRO A 298      22.004  30.563   5.448  1.00  42.56      A    O
ATOM   1398  N    GLU A 299      21.647  29.431   7.346  1.00  45.68      A    N
ATOM   1399  CA   GLU A 299      21.910  28.176   6.670  1.00  46.73      A    C
ATOM   1400  CB   GLU A 299      21.779  26.953   7.622  1.00  48.19      A    C
ATOM   1401  CG   GLU A 299      20.524  26.826   8.530  1.00  50.95      A    C
ATOM   1402  CD   GLU A 299      20.552  27.746   9.741  1.00  51.89      A    C
ATOM   1403  OE1  GLU A 299      19.995  27.375  10.822  1.00  50.56      A    O
ATOM   1404  OE2  GLU A 299      21.124  28.858   9.613  1.00  58.09      A    O
ATOM   1405  C    GLU A 299      21.033  28.020   5.443  1.00  47.16      A    C
ATOM   1406  O    GLU A 299      21.508  27.545   4.408  1.00  44.66      A    O
ATOM   1407  N    MET A 300      19.778  28.480   5.596  1.00  54.37      A    N
ATOM   1408  CA   MET A 300      18.784  28.372   4.484  1.00  58.02      A    C
ATOM   1409  CB   MET A 300      17.357  28.512   5.059  1.00  62.93      A    C
ATOM   1410  CG   MET A 300      16.270  27.601   4.428  1.00  72.31      A    C
ATOM   1411  SD   MET A 300      16.158  27.571   2.583  1.00  91.50      A    S
ATOM   1412  CE   MET A 300      14.937  28.875   2.150  1.00  85.83      A    C
ATOM   1413  C    MET A 300      18.977  29.357   3.348  1.00  55.93      A    C
ATOM   1414  O    MET A 300      18.908  28.972   2.199  1.00  57.54      A    O
ATOM   1415  N    ILE A 301      19.213  30.626   3.633  1.00  54.65      A    N
ATOM   1416  CA   ILE A 301      19.395  31.530   2.509  1.00  54.46      A    C
ATOM   1417  CB   ILE A 301      19.475  33.026   2.944  1.00  55.81      A    C
ATOM   1418  CG2  ILE A 301      18.381  33.320   3.953  1.00  53.39      A    C
ATOM   1419  CG1  ILE A 301      20.841  33.354   3.567  1.00  58.05      A    C
ATOM   1420  CD1  ILE A 301      21.027  34.860   3.983  1.00  51.64      A    C
ATOM   1421  C    ILE A 301      20.658  31.128   1.730  1.00  54.61      A    C
ATOM   1422  O    ILE A 301      20.595  30.881   0.527  1.00  52.31      A    O
ATOM   1423  N    GLU A 302      21.787  31.016   2.429  1.00  56.63      A    N
ATOM   1424  CA   GLU A 302      23.052  30.668   1.786  1.00  57.94      A    C
ATOM   1425  CB   GLU A 302      24.180  30.625   2.829  1.00  54.31      A    C
ATOM   1426  CG   GLU A 302      24.405  31.956   3.523  1.00  53.21      A    C
ATOM   1427  CD   GLU A 302      25.199  31.808   4.783  1.00  52.91      A    C
ATOM   1428  OE1  GLU A 302      25.106  30.724   5.389  1.00  55.63      A    O
ATOM   1429  OE2  GLU A 302      25.910  32.765   5.182  1.00  50.07      A    O
ATOM   1430  C    GLU A 302      23.035  29.364   0.963  1.00  60.56      A    C
ATOM   1431  O    GLU A 302      23.969  29.103   0.203  1.00  60.47      A    O
```

Figure 2W

| ATOM | 1432 | N   | GLY | A | 303 | 21.979 | 28.566 | 1.093  | 1.00 | 62.46  | A | N |
|------|------|-----|-----|---|-----|--------|--------|--------|------|--------|---|---|
| ATOM | 1433 | CA  | GLY | A | 303 | 21.891 | 27.333 | 0.329  | 1.00 | 61.40  | A | C |
| ATOM | 1434 | C   | GLY | A | 303 | 22.625 | 26.172 | 0.972  | 1.00 | 64.14  | A | C |
| ATOM | 1435 | O   | GLY | A | 303 | 23.032 | 25.222 | 0.296  | 1.00 | 62.37  | A | O |
| ATOM | 1436 | N   | ARG | A | 304 | 22.810 | 26.249 | 2.284  | 1.00 | 70.43  | A | N |
| ATOM | 1437 | CA  | ARG | A | 304 | 23.486 | 25.192 | 3.015  | 1.00 | 77.34  | A | C |
| ATOM | 1438 | CB  | ARG | A | 304 | 24.338 | 25.773 | 4.132  | 1.00 | 79.09  | A | C |
| ATOM | 1439 | CG  | ARG | A | 304 | 25.454 | 26.649 | 3.646  | 1.00 | 83.43  | A | C |
| ATOM | 1440 | CD  | ARG | A | 304 | 26.136 | 27.354 | 4.810  | 1.00 | 90.93  | A | C |
| ATOM | 1441 | NE  | ARG | A | 304 | 26.587 | 26.396 | 5.815  | 1.00 | 102.58 | A | N |
| ATOM | 1442 | CZ  | ARG | A | 304 | 27.305 | 25.301 | 5.548  | 1.00 | 109.08 | A | C |
| ATOM | 1443 | NH1 | ARG | A | 304 | 27.665 | 25.009 | 4.295  | 1.00 | 112.50 | A | N |
| ATOM | 1444 | NH2 | ARG | A | 304 | 27.669 | 24.494 | 6.539  | 1.00 | 109.83 | A | N |
| ATOM | 1445 | C   | ARG | A | 304 | 22.480 | 24.221 | 3.612  | 1.00 | 80.67  | A | C |
| ATOM | 1446 | O   | ARG | A | 304 | 21.263 | 24.393 | 3.507  | 1.00 | 80.30  | A | O |
| ATOM | 1447 | N   | MET | A | 305 | 23.013 | 23.196 | 4.254  | 1.00 | 86.43  | A | N |
| ATOM | 1448 | CA  | MET | A | 305 | 22.202 | 22.170 | 4.874  | 1.00 | 91.44  | A | C |
| ATOM | 1449 | CB  | MET | A | 305 | 23.096 | 20.999 | 5.309  | 1.00 | 95.15  | A | C |
| ATOM | 1450 | CG  | MET | A | 305 | 24.057 | 20.457 | 4.224  | 1.00 | 97.75  | A | C |
| ATOM | 1451 | SD  | MET | A | 305 | 25.346 | 21.624 | 3.627  | 1.00 | 102.71 | A | S |
| ATOM | 1452 | CE  | MET | A | 305 | 26.139 | 22.130 | 5.187  | 1.00 | 100.89 | A | C |
| ATOM | 1453 | C   | MET | A | 305 | 21.489 | 22.770 | 6.081  | 1.00 | 92.74  | A | C |
| ATOM | 1454 | O   | MET | A | 305 | 22.124 | 23.361 | 6.959  | 1.00 | 93.86  | A | O |
| ATOM | 1455 | N   | HIS | A | 306 | 20.168 | 22.626 | 6.116  | 1.00 | 93.31  | A | N |
| ATOM | 1456 | CA  | HIS | A | 306 | 19.374 | 23.147 | 7.223  | 1.00 | 95.45  | A | C |
| ATOM | 1457 | CB  | HIS | A | 306 | 18.358 | 24.155 | 6.711  | 1.00 | 95.53  | A | C |
| ATOM | 1458 | CG  | HIS | A | 306 | 17.228 | 23.519 | 5.971  | 1.00 | 96.27  | A | C |
| ATOM | 1459 | CD2 | HIS | A | 306 | 15.996 | 23.139 | 6.385  | 1.00 | 98.19  | A | C |
| ATOM | 1460 | ND1 | HIS | A | 306 | 17.343 | 23.091 | 4.668  | 1.00 | 95.71  | A | N |
| ATOM | 1461 | CE1 | HIS | A | 306 | 16.233 | 22.470 | 4.312  | 1.00 | 97.93  | A | C |
| ATOM | 1462 | NE2 | HIS | A | 306 | 15.400 | 22.484 | 5.336  | 1.00 | 98.85  | A | N |
| ATOM | 1463 | C   | HIS | A | 306 | 18.615 | 21.976 | 7.842  | 1.00 | 95.21  | A | C |
| ATOM | 1464 | O   | HIS | A | 306 | 18.352 | 20.989 | 7.151  | 1.00 | 94.72  | A | O |
| ATOM | 1465 | N   | ASP | A | 307 | 18.249 | 22.093 | 9.120  | 1.00 | 92.49  | A | N |
| ATOM | 1466 | CA  | ASP | A | 307 | 17.506 | 21.034 | 9.802  | 1.00 | 87.25  | A | C |
| ATOM | 1467 | CB  | ASP | A | 307 | 18.232 | 19.691 | 9.627  | 1.00 | 94.22  | A | C |
| ATOM | 1468 | CG  | ASP | A | 307 | 17.519 | 18.745 | 8.651  | 1.00 | 99.85  | A | C |
| ATOM | 1469 | OD1 | ASP | A | 307 | 17.353 | 19.109 | 7.461  | 1.00 | 100.61 | A | O |
| ATOM | 1470 | OD2 | ASP | A | 307 | 17.131 | 17.627 | 9.077  | 1.00 | 100.81 | A | O |
| ATOM | 1471 | C   | ASP | A | 307 | 17.248 | 21.246 | 11.299 | 1.00 | 79.95  | A | C |
| ATOM | 1472 | O   | ASP | A | 307 | 18.188 | 21.392 | 12.079 | 1.00 | 78.41  | A | O |
| ATOM | 1473 | N   | GLU | A | 308 | 15.975 | 21.248 | 11.684 | 1.00 | 73.99  | A | N |
| ATOM | 1474 | CA  | GLU | A | 308 | 15.562 | 21.361 | 13.093 | 1.00 | 71.73  | A | C |
| ATOM | 1475 | CB  | GLU | A | 308 | 16.127 | 20.183 | 13.883 | 1.00 | 73.55  | A | C |
| ATOM | 1476 | CG  | GLU | A | 308 | 16.432 | 20.492 | 15.336 | 1.00 | 75.72  | A | C |
| ATOM | 1477 | CD  | GLU | A | 308 | 17.307 | 19.418 | 15.962 | 1.00 | 79.42  | A | C |
| ATOM | 1478 | OE1 | GLU | A | 308 | 18.439 | 19.216 | 15.452 | 1.00 | 79.54  | A | O |
| ATOM | 1479 | OE2 | GLU | A | 308 | 16.859 | 18.778 | 16.950 | 1.00 | 82.63  | A | O |
| ATOM | 1480 | C   | GLU | A | 308 | 15.872 | 22.640 | 13.857 | 1.00 | 68.99  | A | C |
| ATOM | 1481 | O   | GLU | A | 308 | 14.969 | 23.249 | 14.427 | 1.00 | 69.09  | A | O |
| ATOM | 1482 | N   | LYS | A | 309 | 17.140 | 23.035 | 13.901 | 1.00 | 64.55  | A | N |
| ATOM | 1483 | CA  | LYS | A | 309 | 17.515 | 24.250 | 14.615 | 1.00 | 58.23  | A | C |
| ATOM | 1484 | CB  | LYS | A | 309 | 19.043 | 24.348 | 14.714 | 1.00 | 52.75  | A | C |
| ATOM | 1489 | C   | LYS | A | 309 | 16.909 | 25.523 | 13.970 | 1.00 | 56.91  | A | C |
| ATOM | 1490 | O   | LYS | A | 309 | 16.575 | 26.486 | 14.682 | 1.00 | 58.52  | A | O |
| ATOM | 1491 | N   | VAL | A | 310 | 16.738 | 25.525 | 12.646 | 1.00 | 53.69  | A | N |
| ATOM | 1492 | CA  | VAL | A | 310 | 16.158 | 26.685 | 11.949 | 1.00 | 48.49  | A | C |
| ATOM | 1493 | CB  | VAL | A | 310 | 15.499 | 26.343 | 10.536 | 1.00 | 46.10  | A | C |
| ATOM | 1494 | CG1 | VAL | A | 310 | 16.524 | 25.843 | 9.534  | 1.00 | 43.14  | A | C |
| ATOM | 1495 | CG2 | VAL | A | 310 | 14.411 | 25.345 | 10.698 | 1.00 | 42.09  | A | C |
| ATOM | 1496 | C   | VAL | A | 310 | 15.050 | 27.286 | 12.809 | 1.00 | 48.19  | A | C |

Figure 2X

| ATOM | 1497 | O   | VAL A 310 | 14.985 | 28.518 | 12.967 | 1.00 | 51.28 | A | O |
|------|------|-----|-----------|--------|--------|--------|------|-------|---|---|
| ATOM | 1498 | N   | ASP A 311 | 14.213 | 26.407 | 13.380 | 1.00 | 44.88 | A | N |
| ATOM | 1499 | CA  | ASP A 311 | 13.090 | 26.823 | 14.208 | 1.00 | 43.50 | A | C |
| ATOM | 1500 | CB  | ASP A 311 | 12.294 | 25.628 | 14.747 | 1.00 | 41.71 | A | C |
| ATOM | 1501 | CG  | ASP A 311 | 11.649 | 24.827 | 13.656 | 1.00 | 46.32 | A | C |
| ATOM | 1502 | OD1 | ASP A 311 | 11.171 | 25.430 | 12.680 | 1.00 | 51.41 | A | O |
| ATOM | 1503 | OD2 | ASP A 311 | 11.615 | 23.588 | 13.761 | 1.00 | 48.43 | A | O |
| ATOM | 1504 | C   | ASP A 311 | 13.477 | 27.698 | 15.356 | 1.00 | 42.81 | A | C |
| ATOM | 1505 | O   | ASP A 311 | 12.797 | 28.692 | 15.635 | 1.00 | 43.46 | A | O |
| ATOM | 1506 | N   | LEU A 312 | 14.558 | 27.362 | 16.041 | 1.00 | 42.27 | A | N |
| ATOM | 1507 | CA  | LEU A 312 | 14.957 | 28.195 | 17.175 | 1.00 | 45.36 | A | C |
| ATOM | 1508 | CB  | LEU A 312 | 16.176 | 27.582 | 17.879 | 1.00 | 45.36 | A | C |
| ATOM | 1509 | CG  | LEU A 312 | 15.953 | 26.289 | 18.689 | 1.00 | 46.26 | A | C |
| ATOM | 1510 | CD1 | LEU A 312 | 15.003 | 26.507 | 19.841 | 1.00 | 41.67 | A | C |
| ATOM | 1511 | CD2 | LEU A 312 | 15.421 | 25.208 | 17.776 | 1.00 | 49.22 | A | C |
| ATOM | 1512 | C   | LEU A 312 | 15.273 | 29.612 | 16.696 | 1.00 | 44.80 | A | C |
| ATOM | 1513 | O   | LEU A 312 | 15.150 | 30.587 | 17.439 | 1.00 | 45.76 | A | O |
| ATOM | 1514 | N   | TRP A 313 | 15.688 | 29.704 | 15.437 | 1.00 | 42.21 | A | N |
| ATOM | 1515 | CA  | TRP A 313 | 16.046 | 30.969 | 14.833 | 1.00 | 42.63 | A | C |
| ATOM | 1516 | CB  | TRP A 313 | 17.001 | 30.721 | 13.644 | 1.00 | 44.56 | A | C |
| ATOM | 1517 | CG  | TRP A 313 | 17.161 | 31.879 | 12.719 | 1.00 | 47.92 | A | C |
| ATOM | 1518 | CD2 | TRP A 313 | 18.274 | 32.768 | 12.648 | 1.00 | 47.41 | A | C |
| ATOM | 1519 | CE2 | TRP A 313 | 17.938 | 33.795 | 11.724 | 1.00 | 47.97 | A | C |
| ATOM | 1520 | CE3 | TRP A 313 | 19.525 | 32.809 | 13.277 | 1.00 | 46.27 | A | C |
| ATOM | 1521 | CD1 | TRP A 313 | 16.218 | 32.374 | 11.847 | 1.00 | 50.55 | A | C |
| ATOM | 1522 | NE1 | TRP A 313 | 16.682 | 33.527 | 11.250 | 1.00 | 51.40 | A | N |
| ATOM | 1523 | CZ2 | TRP A 313 | 18.809 | 34.844 | 11.421 | 1.00 | 45.76 | A | C |
| ATOM | 1524 | CZ3 | TRP A 313 | 20.397 | 33.864 | 12.968 | 1.00 | 44.53 | A | C |
| ATOM | 1525 | CH2 | TRP A 313 | 20.031 | 34.861 | 12.052 | 1.00 | 41.13 | A | C |
| ATOM | 1526 | C   | TRP A 313 | 14.756 | 31.661 | 14.400 | 1.00 | 43.51 | A | C |
| ATOM | 1527 | O   | TRP A 313 | 14.536 | 32.855 | 14.687 | 1.00 | 43.28 | A | O |
| ATOM | 1528 | N   | SER A 314 | 13.918 | 30.926 | 13.678 | 1.00 | 43.63 | A | N |
| ATOM | 1529 | CA  | SER A 314 | 12.653 | 31.492 | 13.266 | 1.00 | 42.23 | A | C |
| ATOM | 1530 | CB  | SER A 314 | 11.762 | 30.401 | 12.676 | 1.00 | 39.93 | A | C |
| ATOM | 1532 | C   | SER A 314 | 12.098 | 32.028 | 14.596 | 1.00 | 43.25 | A | C |
| ATOM | 1533 | O   | SER A 314 | 11.754 | 33.201 | 14.724 | 1.00 | 44.96 | A | O |
| ATOM | 1534 | N   | LEU A 315 | 12.086 | 31.164 | 15.604 | 1.00 | 43.95 | A | N |
| ATOM | 1535 | CA  | LEU A 315 | 11.622 | 31.521 | 16.941 | 1.00 | 44.48 | A | C |
| ATOM | 1536 | CB  | LEU A 315 | 11.814 | 30.338 | 17.875 | 1.00 | 45.33 | A | C |
| ATOM | 1537 | CG  | LEU A 315 | 11.311 | 30.565 | 19.281 | 1.00 | 46.97 | A | C |
| ATOM | 1538 | CD1 | LEU A 315 | 9.762  | 30.689 | 19.245 | 1.00 | 49.48 | A | C |
| ATOM | 1539 | CD2 | LEU A 315 | 11.730 | 29.407 | 20.158 | 1.00 | 46.51 | A | C |
| ATOM | 1540 | C   | LEU A 315 | 12.368 | 32.715 | 17.506 | 1.00 | 43.75 | A | C |
| ATOM | 1541 | O   | LEU A 315 | 11.860 | 33.436 | 18.365 | 1.00 | 42.92 | A | O |
| ATOM | 1542 | N   | GLY A 316 | 13.598 | 32.919 | 17.053 | 1.00 | 44.78 | A | N |
| ATOM | 1543 | CA  | GLY A 316 | 14.365 | 34.056 | 17.548 | 1.00 | 43.88 | A | C |
| ATOM | 1544 | C   | GLY A 316 | 13.841 | 35.351 | 16.948 | 1.00 | 42.75 | A | C |
| ATOM | 1545 | O   | GLY A 316 | 13.710 | 36.333 | 17.636 | 1.00 | 39.41 | A | O |
| ATOM | 1546 | N   | VAL A 317 | 13.539 | 35.333 | 15.657 | 1.00 | 43.37 | A | N |
| ATOM | 1547 | CA  | VAL A 317 | 13.029 | 36.494 | 14.955 | 1.00 | 42.78 | A | C |
| ATOM | 1548 | CB  | VAL A 317 | 12.904 | 36.199 | 13.470 | 1.00 | 43.24 | A | C |
| ATOM | 1549 | CG1 | VAL A 317 | 12.360 | 37.433 | 12.735 | 1.00 | 47.79 | A | C |
| ATOM | 1550 | CG2 | VAL A 317 | 14.286 | 35.790 | 12.927 | 1.00 | 43.06 | A | C |
| ATOM | 1551 | C   | VAL A 317 | 11.683 | 36.957 | 15.463 | 1.00 | 41.53 | A | C |
| ATOM | 1552 | O   | VAL A 317 | 11.486 | 38.127 | 15.783 | 1.00 | 41.06 | A | O |
| ATOM | 1553 | N   | LEU A 318 | 10.766 | 36.008 | 15.538 | 1.00 | 43.09 | A | N |
| ATOM | 1554 | CA  | LEU A 318 | 9.420  | 36.227 | 16.015 | 1.00 | 42.15 | A | C |
| ATOM | 1555 | CB  | LEU A 318 | 8.716  | 34.880 | 16.201 | 1.00 | 41.81 | A | C |
| ATOM | 1556 | CG  | LEU A 318 | 7.192  | 34.743 | 16.136 | 1.00 | 46.38 | A | C |
| ATOM | 1557 | CD1 | LEU A 318 | 6.631  | 35.404 | 14.897 | 1.00 | 49.07 | A | C |
| ATOM | 1558 | CD2 | LEU A 318 | 6.844  | 33.282 | 16.052 | 1.00 | 53.42 | A | C |

Figure 2Y

```
ATOM   1559  C    LEU A 318       9.490  36.915  17.347  1.00  43.57      A    C
ATOM   1560  O    LEU A 318       8.894  37.989  17.529  1.00  46.60      A    O
ATOM   1561  N    CYS A 319      10.241  36.302  18.273  1.00  45.52      A    N
ATOM   1562  CA   CYS A 319      10.320  36.837  19.624  1.00  46.48      A    C
ATOM   1563  CB   CYS A 319      11.230  36.034  20.557  1.00  52.09      A    C
ATOM   1564  SG   CYS A 319      11.390  36.845  22.199  1.00  49.92      A    S
ATOM   1565  C    CYS A 319      10.756  38.247  19.651  1.00  44.95      A    C
ATOM   1566  O    CYS A 319      10.481  38.948  20.615  1.00  46.16      A    O
ATOM   1567  N    TYR A 320      11.433  38.667  18.601  1.00  45.60      A    N
ATOM   1568  CA   TYR A 320      11.886  40.040  18.508  1.00  48.02      A    C
ATOM   1569  CB   TYR A 320      13.195  40.102  17.703  1.00  47.08      A    C
ATOM   1570  CG   TYR A 320      13.715  41.493  17.426  1.00  47.28      A    C
ATOM   1571  CD1  TYR A 320      14.818  41.982  18.109  1.00  50.06      A    C
ATOM   1572  CE1  TYR A 320      15.361  43.269  17.820  1.00  48.55      A    C
ATOM   1573  CD2  TYR A 320      13.141  42.293  16.453  1.00  49.51      A    C
ATOM   1574  CE2  TYR A 320      13.649  43.541  16.158  1.00  52.16      A    C
ATOM   1575  CZ   TYR A 320      14.766  44.031  16.847  1.00  49.70      A    C
ATOM   1576  OH   TYR A 320      15.279  45.280  16.572  1.00  47.87      A    O
ATOM   1577  C    TYR A 320      10.802  40.866  17.799  1.00  50.46      A    C
ATOM   1578  O    TYR A 320      10.639  42.063  18.088  1.00  51.59      A    O
ATOM   1579  N    GLU A 321      10.078  40.272  16.851  1.00  51.34      A    N
ATOM   1580  CA   GLU A 321       9.060  41.101  16.218  1.00  49.68      A    C
ATOM   1581  CB   GLU A 321       8.449  40.497  14.939  1.00  45.86      A    C
ATOM   1582  CG   GLU A 321       7.975  41.633  14.061  1.00  48.37      A    C
ATOM   1583  CD   GLU A 321       7.146  41.271  12.831  1.00  48.80      A    C
ATOM   1584  OE1  GLU A 321       7.310  40.171  12.273  1.00  52.55      A    O
ATOM   1585  OE2  GLU A 321       6.332  42.142  12.400  1.00  44.17      A    O
ATOM   1586  C    GLU A 321       7.966  41.401  17.235  1.00  50.20      A    C
ATOM   1587  O    GLU A 321       7.422  42.494  17.262  1.00  50.39      A    O
ATOM   1588  N    PHE A 322       7.679  40.452  18.114  1.00  49.87      A    N
ATOM   1589  CA   PHE A 322       6.640  40.697  19.098  1.00  48.27      A    C
ATOM   1590  CB   PHE A 322       6.386  39.455  19.944  1.00  47.20      A    C
ATOM   1591  CG   PHE A 322       5.825  38.290  19.185  1.00  42.45      A    C
ATOM   1592  CD1  PHE A 322       5.092  38.478  18.033  1.00  43.75      A    C
ATOM   1593  CD2  PHE A 322       5.974  36.993  19.681  1.00  41.47      A    C
ATOM   1594  CE1  PHE A 322       4.507  37.394  17.381  1.00  43.73      A    C
ATOM   1595  CE2  PHE A 322       5.400  35.929  19.041  1.00  42.73      A    C
ATOM   1596  CZ   PHE A 322       4.657  36.132  17.881  1.00  44.76      A    C
ATOM   1597  C    PHE A 322       6.948  41.874  20.022  1.00  49.87      A    C
ATOM   1598  O    PHE A 322       6.068  42.681  20.305  1.00  52.23      A    O
ATOM   1599  N    LEU A 323       8.185  41.985  20.498  1.00  52.69      A    N
ATOM   1600  CA   LEU A 323       8.516  43.088  21.395  1.00  53.90      A    C
ATOM   1601  CB   LEU A 323       9.729  42.741  22.264  1.00  54.60      A    C
ATOM   1602  CG   LEU A 323       9.630  41.472  23.105  1.00  54.07      A    C
ATOM   1603  CD1  LEU A 323      11.012  41.085  23.581  1.00  53.78      A    C
ATOM   1604  CD2  LEU A 323       8.671  41.679  24.263  1.00  53.68      A    C
ATOM   1605  C    LEU A 323       8.798  44.398  20.701  1.00  54.78      A    C
ATOM   1606  O    LEU A 323       8.643  45.465  21.295  1.00  58.12      A    O
ATOM   1607  N    VAL A 324       9.212  44.349  19.446  1.00  52.85      A    N
ATOM   1608  CA   VAL A 324       9.543  45.589  18.767  1.00  52.29      A    C
ATOM   1609  CB   VAL A 324      10.964  45.468  18.170  1.00  52.85      A    C
ATOM   1610  CG1  VAL A 324      11.359  46.753  17.441  1.00  53.29      A    C
ATOM   1611  CG2  VAL A 324      11.935  45.145  19.293  1.00  50.68      A    C
ATOM   1612  C    VAL A 324       8.547  46.067  17.711  1.00  50.93      A    C
ATOM   1613  O    VAL A 324       8.436  47.261  17.433  1.00  53.71      A    O
ATOM   1614  N    GLY A 325       7.818  45.140  17.118  1.00  48.42      A    N
ATOM   1615  CA   GLY A 325       6.848  45.553  16.130  1.00  45.98      A    C
ATOM   1616  C    GLY A 325       7.285  45.390  14.700  1.00  43.81      A    C
ATOM   1617  O    GLY A 325       6.481  45.599  13.802  1.00  42.72      A    O
ATOM   1618  N    LYS A 326       8.558  45.069  14.487  1.00  42.03      A    N
ATOM   1619  CA   LYS A 326       9.094  44.806  13.142  1.00  41.76      A    C
```

Figure 2Z

```
ATOM   1620  CB  LYS A 326       9.651  46.070  12.497  1.00  42.96      A  C
ATOM   1621  CG  LYS A 326      10.778  46.689  13.239  1.00  47.50      A  C
ATOM   1622  CD  LYS A 326      11.188  47.981  12.555  1.00  55.73      A  C
ATOM   1623  CE  LYS A 326      11.892  48.899  13.534  1.00  60.78      A  C
ATOM   1624  NZ  LYS A 326      11.073  49.010  14.787  1.00  63.79      A  N
ATOM   1625  C   LYS A 326      10.192  43.751  13.265  1.00  38.50      A  C
ATOM   1626  O   LYS A 326      10.749  43.544  14.329  1.00  32.33      A  O
ATOM   1627  N   PRO A 327      10.498  43.050  12.179  1.00  39.05      A  N
ATOM   1628  CD  PRO A 327       9.943  43.127  10.822  1.00  41.94      A  C
ATOM   1629  CA  PRO A 327      11.542  42.027  12.280  1.00  37.98      A  C
ATOM   1630  CB  PRO A 327      11.396  41.278  10.952  1.00  37.99      A  C
ATOM   1631  CG  PRO A 327      10.934  42.350  10.017  1.00  41.14      A  C
ATOM   1632  C   PRO A 327      12.929  42.639  12.538  1.00  34.88      A  C
ATOM   1633  O   PRO A 327      13.106  43.863  12.486  1.00  34.41      A  O
ATOM   1634  N   PRO A 328      13.927  41.816  12.840  1.00  34.23      A  N
ATOM   1635  CD  PRO A 328      13.878  40.507  13.502  1.00  34.09      A  C
ATOM   1636  CA  PRO A 328      15.228  42.483  13.086  1.00  38.10      A  C
ATOM   1637  CB  PRO A 328      15.828  41.670  14.233  1.00  34.71      A  C
ATOM   1638  CG  PRO A 328      15.377  40.315  13.924  1.00  31.90      A  C
ATOM   1639  C   PRO A 328      16.227  42.646  11.947  1.00  41.07      A  C
ATOM   1640  O   PRO A 328      17.333  43.118  12.170  1.00  45.00      A  O
ATOM   1641  N   PHE A 329      15.857  42.269  10.736  1.00  42.48      A  N
ATOM   1642  CA  PHE A 329      16.770  42.386   9.627  1.00  45.31      A  C
ATOM   1643  CB  PHE A 329      17.246  40.995   9.234  1.00  44.49      A  C
ATOM   1644  CG  PHE A 329      17.897  40.263  10.367  1.00  40.05      A  C
ATOM   1645  CD1 PHE A 329      19.085  40.755  10.926  1.00  40.92      A  C
ATOM   1646  CD2 PHE A 329      17.317  39.115  10.899  1.00  37.91      A  C
ATOM   1647  CE1 PHE A 329      19.696  40.128  11.983  1.00  35.39      A  C
ATOM   1648  CE2 PHE A 329      17.910  38.463  11.972  1.00  36.46      A  C
ATOM   1649  CZ  PHE A 329      19.115  38.970  12.524  1.00  34.95      A  C
ATOM   1650  C   PHE A 329      16.024  43.051   8.505  1.00  51.35      A  C
ATOM   1651  O   PHE A 329      16.442  43.051   7.332  1.00  56.54      A  O
ATOM   1652  N   GLU A 330      14.879  43.596   8.880  1.00  54.02      A  N
ATOM   1653  CA  GLU A 330      14.040  44.274   7.940  1.00  54.79      A  C
ATOM   1654  CB  GLU A 330      12.834  44.850   8.657  1.00  52.31      A  C
ATOM   1655  CG  GLU A 330      11.917  45.674   7.800  1.00  56.24      A  C
ATOM   1656  CD  GLU A 330      10.619  45.942   8.505  1.00  56.77      A  C
ATOM   1657  OE1 GLU A 330       9.731  45.079   8.466  1.00  60.81      A  O
ATOM   1658  OE2 GLU A 330      10.493  47.002   9.125  1.00  57.86      A  O
ATOM   1659  C   GLU A 330      14.882  45.365   7.289  1.00  57.36      A  C
ATOM   1660  O   GLU A 330      15.721  46.019   7.931  1.00  56.39      A  O
ATOM   1661  N   ALA A 331      14.667  45.527   5.992  1.00  59.09      A  N
ATOM   1662  CA  ALA A 331      15.403  46.509   5.261  1.00  59.33      A  C
ATOM   1663  CB  ALA A 331      16.790  46.018   5.043  1.00  54.89      A  C
ATOM   1664  C   ALA A 331      14.778  46.866   3.934  1.00  60.87      A  C
ATOM   1665  O   ALA A 331      13.780  46.306   3.502  1.00  60.55      A  O
ATOM   1666  N   ASN A 332      15.399  47.843   3.306  1.00  64.05      A  N
ATOM   1667  CA  ASN A 332      15.010  48.315   2.003  1.00  68.05      A  C
ATOM   1668  CB  ASN A 332      15.644  49.676   1.801  1.00  71.14      A  C
ATOM   1669  CG  ASN A 332      17.081  49.715   2.331  1.00  75.03      A  C
ATOM   1670  OD1 ASN A 332      17.315  49.557   3.538  1.00  77.13      A  O
ATOM   1671  ND2 ASN A 332      18.049  49.899   1.429  1.00  75.69      A  N
ATOM   1672  C   ASN A 332      15.704  47.305   1.111  1.00  69.58      A  C
ATOM   1673  O   ASN A 332      16.928  47.155   1.195  1.00  74.45      A  O
ATOM   1674  N   THR A 333      14.955  46.586   0.289  1.00  66.05      A  N
ATOM   1675  CA  THR A 333      15.586  45.629  -0.628  1.00  63.54      A  C
ATOM   1676  CB  THR A 333      16.722  46.326  -1.451  1.00  66.50      A  C
ATOM   1677  OG1 THR A 333      16.644  45.906  -2.826  1.00  71.94      A  O
ATOM   1678  CG2 THR A 333      18.139  45.978  -0.857  1.00  61.77      A  C
ATOM   1679  C   THR A 333      16.162  44.334  -0.022  1.00  58.06      A  C
ATOM   1680  O   THR A 333      16.716  44.332   1.060  1.00  58.56      A  O
```

Figure 2AA

```
ATOM  1681  N    TYR A 334      16.014  43.249  -0.768  1.00  53.45      A    N
ATOM  1682  CA   TYR A 334      16.477  41.920  -0.406  1.00  49.63      A    C
ATOM  1683  CB   TYR A 334      16.264  40.966  -1.593  1.00  52.96      A    C
ATOM  1684  CG   TYR A 334      14.836  40.528  -1.784  1.00  54.85      A    C
ATOM  1685  CD1  TYR A 334      14.140  39.950  -0.739  1.00  57.72      A    C
ATOM  1686  CE1  TYR A 334      12.819  39.600  -0.868  1.00  61.56      A    C
ATOM  1687  CD2  TYR A 334      14.171  40.743  -2.984  1.00  56.03      A    C
ATOM  1688  CE2  TYR A 334      12.845  40.396  -3.130  1.00  59.10      A    C
ATOM  1689  CZ   TYR A 334      12.169  39.822  -2.059  1.00  61.28      A    C
ATOM  1690  OH   TYR A 334      10.853  39.466  -2.152  1.00  64.44      A    O
ATOM  1691  C    TYR A 334      17.934  41.838  -0.012  1.00  49.32      A    C
ATOM  1692  O    TYR A 334      18.285  41.178   0.960  1.00  49.44      A    O
ATOM  1693  N    GLN A 335      18.778  42.485  -0.814  1.00  53.49      A    N
ATOM  1694  CA   GLN A 335      20.212  42.477  -0.615  1.00  56.61      A    C
ATOM  1695  CB   GLN A 335      20.888  43.394  -1.642  1.00  55.70      A    C
ATOM  1696  CG   GLN A 335      20.613  42.924  -3.101  1.00  59.93      A    C
ATOM  1697  CD   GLN A 335      19.150  43.151  -3.571  1.00  64.38      A    C
ATOM  1698  OE1  GLN A 335      18.664  42.485  -4.482  1.00  61.98      A    O
ATOM  1699  NE2  GLN A 335      18.469  44.111  -2.952  1.00  71.58      A    N
ATOM  1700  C    GLN A 335      20.540  42.838   0.824  1.00  58.91      A    C
ATOM  1701  O    GLN A 335      21.295  42.103   1.489  1.00  63.07      A    O
ATOM  1702  N    GLU A 336      20.009  43.963   1.304  1.00  59.80      A    N
ATOM  1703  CA   GLU A 336      20.201  44.304   2.709  1.00  60.35      A    C
ATOM  1704  CB   GLU A 336      19.948  45.781   2.969  1.00  62.45      A    C
ATOM  1705  CG   GLU A 336      20.866  46.680   2.204  1.00  66.41      A    C
ATOM  1706  CD   GLU A 336      22.055  47.122   3.026  1.00  68.37      A    C
ATOM  1707  OE1  GLU A 336      23.050  47.589   2.410  1.00  68.20      A    O
ATOM  1708  OE2  GLU A 336      21.976  47.008   4.278  1.00  66.72      A    O
ATOM  1709  C    GLU A 336      19.065  43.470   3.273  1.00  62.28      A    C
ATOM  1710  O    GLU A 336      17.970  43.480   2.745  1.00  71.79      A    O
ATOM  1711  N    THR A 337      19.337  42.743   4.328  1.00  57.60      A    N
ATOM  1712  CA   THR A 337      18.394  41.826   4.968  1.00  53.08      A    C
ATOM  1713  CB   THR A 337      17.070  41.538   4.217  1.00  53.42      A    C
ATOM  1714  OG1  THR A 337      16.310  42.732   4.037  1.00  54.38      A    O
ATOM  1715  CG2  THR A 337      16.238  40.552   5.035  1.00  49.58      A    C
ATOM  1716  C    THR A 337      19.200  40.584   4.825  1.00  52.01      A    C
ATOM  1717  O    THR A 337      19.513  39.927   5.880  1.00  51.26      A    O
ATOM  1718  N    TYR A 338      19.541  40.258   3.586  1.00  52.12      A    N
ATOM  1719  CA   TYR A 338      20.373  39.099   3.391  1.00  53.73      A    C
ATOM  1720  CB   TYR A 338      20.768  38.888   1.926  1.00  59.18      A    C
ATOM  1721  CG   TYR A 338      21.750  37.736   1.791  1.00  67.20      A    C
ATOM  1722  CD1  TYR A 338      21.356  36.502   1.276  1.00  68.39      A    C
ATOM  1723  CE1  TYR A 338      22.242  35.414   1.264  1.00  72.03      A    C
ATOM  1724  CD2  TYR A 338      23.054  37.858   2.282  1.00  71.64      A    C
ATOM  1725  CE2  TYR A 338      23.938  36.790   2.279  1.00  73.51      A    C
ATOM  1726  CZ   TYR A 338      23.533  35.573   1.775  1.00  74.22      A    C
ATOM  1727  OH   TYR A 338      24.424  34.522   1.801  1.00  77.08      A    O
ATOM  1728  C    TYR A 338      21.601  39.462   4.209  1.00  49.60      A    C
ATOM  1729  O    TYR A 338      21.908  38.820   5.211  1.00  50.06      A    O
ATOM  1730  N    LYS A 339      22.261  40.525   3.769  1.00  45.49      A    N
ATOM  1731  CA   LYS A 339      23.438  41.071   4.405  1.00  42.43      A    C
ATOM  1732  CB   LYS A 339      23.623  42.514   3.935  1.00  40.27      A    C
ATOM  1733  CG   LYS A 339      24.843  43.238   4.417  1.00  37.89      A    C
ATOM  1734  CD   LYS A 339      24.953  44.600   3.729  1.00  34.82      A    C
ATOM  1735  CE   LYS A 339      25.325  44.390   2.285  1.00  39.67      A    C
ATOM  1736  NZ   LYS A 339      25.557  45.631   1.502  1.00  45.46      A    N
ATOM  1737  C    LYS A 339      23.356  41.022   5.925  1.00  42.54      A    C
ATOM  1738  O    LYS A 339      24.273  40.494   6.594  1.00  46.81      A    O
ATOM  1739  N    ARG A 340      22.273  41.544   6.492  1.00  40.62      A    N
ATOM  1740  CA   ARG A 340      22.185  41.545   7.950  1.00  41.64      A    C
ATOM  1741  CB   ARG A 340      21.273  42.667   8.428  1.00  44.31      A    C
```

Figure 2BB

```
ATOM   1742  CG   ARG A 340      21.825  44.023   8.003  1.00  59.83      A    C
ATOM   1743  CD   ARG A 340      21.007  45.198   8.504  1.00  71.33      A    C
ATOM   1744  NE   ARG A 340      21.131  46.337   7.602  1.00  81.01      A    N
ATOM   1745  CZ   ARG A 340      20.285  47.361   7.564  1.00  82.71      A    C
ATOM   1746  NH1  ARG A 340      19.249  47.403   8.387  1.00  83.78      A    N
ATOM   1747  NH2  ARG A 340      20.457  48.324   6.665  1.00  83.76      A    N
ATOM   1748  C    ARG A 340      21.799  40.219   8.568  1.00  42.70      A    C
ATOM   1749  O    ARG A 340      22.165  39.955   9.701  1.00  47.43      A    O
ATOM   1750  N    ILE A 341      21.086  39.372   7.837  1.00  41.92      A    N
ATOM   1751  CA   ILE A 341      20.730  38.080   8.386  1.00  44.37      A    C
ATOM   1752  CB   ILE A 341      19.685  37.327   7.517  1.00  42.19      A    C
ATOM   1753  CG2  ILE A 341      19.687  35.822   7.893  1.00  44.11      A    C
ATOM   1754  CG1  ILE A 341      18.293  37.931   7.704  1.00  41.50      A    C
ATOM   1755  CD1  ILE A 341      17.288  37.477   6.660  1.00  37.46      A    C
ATOM   1756  C    ILE A 341      21.979  37.197   8.462  1.00  46.30      A    C
ATOM   1757  O    ILE A 341      22.308  36.659   9.510  1.00  47.05      A    O
ATOM   1758  N    SER A 342      22.660  37.062   7.330  1.00  47.68      A    N
ATOM   1759  CA   SER A 342      23.846  36.223   7.231  1.00  49.44      A    C
ATOM   1760  CB   SER A 342      24.315  36.104   5.780  1.00  45.11      A    C
ATOM   1761  OG   SER A 342      24.567  37.382   5.260  1.00  42.19      A    O
ATOM   1762  C    SER A 342      24.939  36.804   8.056  1.00  53.85      A    C
ATOM   1763  O    SER A 342      25.622  36.095   8.788  1.00  59.98      A    O
ATOM   1764  N    ARG A 343      25.095  38.112   7.951  1.00  55.58      A    N
ATOM   1765  CA   ARG A 343      26.127  38.789   8.719  1.00  58.12      A    C
ATOM   1766  CB   ARG A 343      26.437  40.138   8.032  1.00  64.50      A    C
ATOM   1767  CG   ARG A 343      27.536  40.999   8.622  1.00  72.73      A    C
ATOM   1768  CD   ARG A 343      27.028  41.824   9.822  1.00  79.05      A    C
ATOM   1769  NE   ARG A 343      27.247  43.257   9.634  1.00  85.87      A    N
ATOM   1770  CZ   ARG A 343      26.433  44.066   8.965  1.00  89.63      A    C
ATOM   1771  NH1  ARG A 343      25.324  43.594   8.417  1.00  95.09      A    N
ATOM   1772  NH2  ARG A 343      26.743  45.345   8.824  1.00  90.56      A    N
ATOM   1773  C    ARG A 343      25.639  38.933  10.173  1.00  54.47      A    C
ATOM   1774  O    ARG A 343      26.391  39.339  11.051  1.00  51.77      A    O
ATOM   1775  N    VAL A 344      24.387  38.549  10.415  1.00  52.67      A    N
ATOM   1776  CA   VAL A 344      23.758  38.620  11.749  1.00  51.62      A    C
ATOM   1777  CB   VAL A 344      24.395  37.612  12.721  1.00  49.15      A    C
ATOM   1778  CG1  VAL A 344      23.754  37.699  14.069  1.00  45.07      A    C
ATOM   1779  CG2  VAL A 344      24.202  36.205  12.197  1.00  48.33      A    C
ATOM   1780  C    VAL A 344      23.788  40.018  12.364  1.00  53.23      A    C
ATOM   1781  O    VAL A 344      24.050  40.286  13.543  1.00  50.74      A    O
ATOM   1782  N    GLU A 345      23.482  40.999  11.535  1.00  60.88      A    N
ATOM   1783  CA   GLU A 345      23.472  42.393  11.935  1.00  68.32      A    C
ATOM   1784  CB   GLU A 345      23.777  43.260  10.714  1.00  78.90      A    C
ATOM   1785  CG   GLU A 345      23.642  44.752  10.934  1.00  92.11      A    C
ATOM   1786  CD   GLU A 345      24.680  45.289  11.890  1.00  99.48      A    C
ATOM   1787  OE1  GLU A 345      25.890  45.068  11.645  1.00 104.34      A    O
ATOM   1788  OE2  GLU A 345      24.289  45.933  12.885  1.00 101.82      A    O
ATOM   1789  C    GLU A 345      22.130  42.797  12.520  1.00  67.83      A    C
ATOM   1790  O    GLU A 345      21.117  42.776  11.831  1.00  70.02      A    O
ATOM   1791  N    PHE A 346      22.109  43.173  13.787  1.00  66.14      A    N
ATOM   1792  CA   PHE A 346      20.849  43.578  14.386  1.00  64.32      A    C
ATOM   1793  CB   PHE A 346      19.891  42.378  14.499  1.00  59.52      A    C
ATOM   1794  CG   PHE A 346      20.120  41.563  15.705  1.00  56.13      A    C
ATOM   1795  CD1  PHE A 346      19.465  41.868  16.894  1.00  53.68      A    C
ATOM   1796  CD2  PHE A 346      21.067  40.539  15.694  1.00  57.97      A    C
ATOM   1797  CE1  PHE A 346      19.750  41.180  18.040  1.00  57.61      A    C
ATOM   1798  CE2  PHE A 346      21.365  39.833  16.860  1.00  56.32      A    C
ATOM   1799  CZ   PHE A 346      20.712  40.152  18.029  1.00  57.24      A    C
ATOM   1800  C    PHE A 346      21.032  44.201  15.754  1.00  63.96      A    C
ATOM   1801  O    PHE A 346      21.812  43.709  16.582  1.00  59.78      A    O
ATOM   1802  N    THR A 347      20.278  45.274  15.978  1.00  65.98      A    N
```

Figure 2CC

```
ATOM  1803  CA   THR A 347      20.299  46.003  17.244  1.00  64.66      A    C
ATOM  1804  CB   THR A 347      20.868  47.406  17.067  1.00  62.47      A    C
ATOM  1805  OG1  THR A 347      20.680  48.121  18.286  1.00  65.60      A    O
ATOM  1806  CG2  THR A 347      20.173  48.133  15.957  1.00  62.43      A    C
ATOM  1807  C    THR A 347      18.922  46.131  17.915  1.00  63.95      A    C
ATOM  1808  O    THR A 347      17.870  46.037  17.275  1.00  64.61      A    O
ATOM  1809  N    PHE A 348      18.939  46.352  19.216  1.00  62.36      A    N
ATOM  1810  CA   PHE A 348      17.710  46.483  19.965  1.00  64.90      A    C
ATOM  1811  CB   PHE A 348      17.887  45.863  21.338  1.00  61.18      A    C
ATOM  1812  CG   PHE A 348      18.075  44.379  21.314  1.00  56.76      A    C
ATOM  1813  CD1  PHE A 348      16.972  43.523  21.251  1.00  52.77      A    C
ATOM  1814  CD2  PHE A 348      19.359  43.831  21.375  1.00  55.34      A    C
ATOM  1815  CE1  PHE A 348      17.143  42.132  21.257  1.00  51.15      A    C
ATOM  1816  CE2  PHE A 348      19.544  42.456  21.379  1.00  53.54      A    C
ATOM  1817  CZ   PHE A 348      18.427  41.598  21.322  1.00  50.44      A    C
ATOM  1818  C    PHE A 348      17.302  47.937  20.115  1.00  68.31      A    C
ATOM  1819  O    PHE A 348      18.102  48.833  19.895  1.00  69.63      A    O
ATOM  1820  N    PRO A 349      16.030  48.190  20.453  1.00  70.74      A    N
ATOM  1821  CD   PRO A 349      14.873  47.300  20.257  1.00  72.47      A    C
ATOM  1822  CA   PRO A 349      15.585  49.571  20.620  1.00  71.83      A    C
ATOM  1823  CB   PRO A 349      14.171  49.531  20.070  1.00  73.51      A    C
ATOM  1824  CG   PRO A 349      13.705  48.213  20.529  1.00  72.22      A    C
ATOM  1825  C    PRO A 349      15.657  49.955  22.098  1.00  72.44      A    C
ATOM  1826  O    PRO A 349      15.801  49.091  22.982  1.00  69.14      A    O
ATOM  1827  N    ASP A 350      15.544  51.250  22.361  1.00  73.44      A    N
ATOM  1828  CA   ASP A 350      15.662  51.763  23.718  1.00  73.24      A    C
ATOM  1829  CB   ASP A 350      15.812  53.282  23.668  1.00  75.54      A    C
ATOM  1830  CG   ASP A 350      17.090  53.760  24.346  1.00  78.07      A    C
ATOM  1831  OD1  ASP A 350      18.190  53.328  23.938  1.00  76.23      A    O
ATOM  1832  OD2  ASP A 350      16.988  54.565  25.303  1.00  81.48      A    O
ATOM  1833  C    ASP A 350      14.556  51.392  24.691  1.00  72.27      A    C
ATOM  1834  O    ASP A 350      13.751  52.250  25.060  1.00  71.86      A    O
ATOM  1835  N    PHE A 351      14.526  50.122  25.109  1.00  71.33      A    N
ATOM  1836  CA   PHE A 351      13.519  49.642  26.061  1.00  69.65      A    C
ATOM  1837  CB   PHE A 351      12.143  50.251  25.759  1.00  66.71      A    C
ATOM  1838  CG   PHE A 351      11.472  49.659  24.562  1.00  64.49      A    C
ATOM  1839  CD1  PHE A 351      11.069  48.323  24.561  1.00  60.72      A    C
ATOM  1840  CD2  PHE A 351      11.275  50.423  23.411  1.00  64.89      A    C
ATOM  1841  CE1  PHE A 351      10.486  47.752  23.436  1.00  58.87      A    C
ATOM  1842  CE2  PHE A 351      10.693  49.862  22.280  1.00  64.08      A    C
ATOM  1843  CZ   PHE A 351      10.300  48.520  22.297  1.00  60.81      A    C
ATOM  1844  C    PHE A 351      13.344  48.124  26.176  1.00  68.28      A    C
ATOM  1845  O    PHE A 351      12.577  47.670  27.023  1.00  70.46      A    O
ATOM  1846  N    VAL A 352      14.002  47.331  25.335  1.00  68.23      A    N
ATOM  1847  CA   VAL A 352      13.830  45.882  25.446  1.00  69.78      A    C
ATOM  1848  CB   VAL A 352      14.328  45.117  24.179  1.00  71.24      A    C
ATOM  1849  CG1  VAL A 352      14.250  43.615  24.392  1.00  65.45      A    C
ATOM  1850  CG2  VAL A 352      13.478  45.494  22.984  1.00  72.78      A    C
ATOM  1851  C    VAL A 352      14.575  45.394  26.665  1.00  69.39      A    C
ATOM  1852  O    VAL A 352      15.731  45.712  26.863  1.00  68.69      A    O
ATOM  1853  N    THR A 353      13.881  44.628  27.489  1.00  70.86      A    N
ATOM  1854  CA   THR A 353      14.434  44.086  28.724  1.00  74.68      A    C
ATOM  1855  CB   THR A 353      13.355  43.284  29.475  1.00  78.59      A    C
ATOM  1856  OG1  THR A 353      13.953  42.564  30.556  1.00  86.89      A    O
ATOM  1857  CG2  THR A 353      12.699  42.282  28.543  1.00  79.25      A    C
ATOM  1858  C    THR A 353      15.656  43.189  28.518  1.00  75.55      A    C
ATOM  1859  O    THR A 353      15.677  42.327  27.636  1.00  75.77      A    O
ATOM  1860  N    GLU A 354      16.670  43.395  29.350  1.00  77.78      A    N
ATOM  1861  CA   GLU A 354      17.895  42.604  29.274  1.00  80.45      A    C
ATOM  1862  CB   GLU A 354      18.818  42.930  30.451  1.00  91.48      A    C
ATOM  1863  CG   GLU A 354      20.124  42.141  30.434  1.00 106.92      A    C
```

Figure 2DD

```
ATOM   1864  CD   GLU A 354      21.064  42.525  31.568  1.00 114.99      A    C
ATOM   1865  OE1  GLU A 354      20.639  42.450  32.748  1.00 119.30      A    O
ATOM   1866  OE2  GLU A 354      22.228  42.897  31.276  1.00 121.09      A    O
ATOM   1867  C    GLU A 354      17.612  41.112  29.262  1.00  75.57      A    C
ATOM   1868  O    GLU A 354      18.393  40.336  28.717  1.00  74.11      A    O
ATOM   1869  N    GLY A 355      16.505  40.712  29.878  1.00  71.66      A    N
ATOM   1870  CA   GLY A 355      16.149  39.306  29.894  1.00  70.66      A    C
ATOM   1871  C    GLY A 355      15.754  38.889  28.486  1.00  70.30      A    C
ATOM   1872  O    GLY A 355      15.973  37.749  28.062  1.00  68.56      A    O
ATOM   1873  N    ALA A 356      15.166  39.832  27.757  1.00  69.83      A    N
ATOM   1874  CA   ALA A 356      14.737  39.595  26.383  1.00  68.17      A    C
ATOM   1875  CB   ALA A 356      13.674  40.626  25.979  1.00  66.92      A    C
ATOM   1876  C    ALA A 356      15.958  39.704  25.472  1.00  66.14      A    C
ATOM   1877  O    ALA A 356      16.214  38.826  24.626  1.00  65.31      A    O
ATOM   1878  N    ARG A 357      16.707  40.786  25.669  1.00  63.92      A    N
ATOM   1879  CA   ARG A 357      17.916  41.031  24.901  1.00  60.47      A    C
ATOM   1880  CB   ARG A 357      18.691  42.225  25.462  1.00  56.64      A    C
ATOM   1881  CG   ARG A 357      18.229  43.572  24.905  1.00  56.72      A    C
ATOM   1882  CD   ARG A 357      18.268  44.633  25.975  1.00  58.20      A    C
ATOM   1883  NE   ARG A 357      18.121  45.992  25.457  1.00  58.90      A    N
ATOM   1884  CZ   ARG A 357      19.023  46.610  24.707  1.00  58.38      A    C
ATOM   1885  NH1  ARG A 357      20.155  45.996  24.363  1.00  54.85      A    N
ATOM   1886  NH2  ARG A 357      18.803  47.852  24.324  1.00  60.08      A    N
ATOM   1887  C    ARG A 357      18.809  39.812  24.874  1.00  60.05      A    C
ATOM   1888  O    ARG A 357      19.537  39.611  23.910  1.00  61.51      A    O
ATOM   1889  N    ASP A 358      18.744  38.970  25.896  1.00  59.94      A    N
ATOM   1890  CA   ASP A 358      19.616  37.807  25.883  1.00  59.69      A    C
ATOM   1891  CB   ASP A 358      20.252  37.591  27.272  1.00  66.38      A    C
ATOM   1892  CG   ASP A 358      19.624  36.456  28.034  1.00  70.14      A    C
ATOM   1893  OD1  ASP A 358      18.521  36.658  28.562  1.00  75.97      A    O
ATOM   1894  OD2  ASP A 358      20.228  35.368  28.097  1.00  71.29      A    O
ATOM   1895  C    ASP A 358      18.993  36.521  25.390  1.00  54.49      A    C
ATOM   1896  O    ASP A 358      19.696  35.648  24.915  1.00  55.10      A    O
ATOM   1897  N    LEU A 359      17.678  36.389  25.487  1.00  48.98      A    N
ATOM   1898  CA   LEU A 359      17.047  35.159  25.019  1.00  44.69      A    C
ATOM   1899  CB   LEU A 359      15.664  35.043  25.614  1.00  40.23      A    C
ATOM   1900  CG   LEU A 359      14.667  33.987  25.170  1.00  38.66      A    C
ATOM   1901  CD1  LEU A 359      13.946  34.472  23.932  1.00  44.87      A    C
ATOM   1902  CD2  LEU A 359      15.359  32.661  24.958  1.00  37.22      A    C
ATOM   1903  C    LEU A 359      17.010  35.126  23.493  1.00  47.42      A    C
ATOM   1904  O    LEU A 359      17.125  34.061  22.881  1.00  48.65      A    O
ATOM   1905  N    ILE A 360      16.884  36.288  22.861  1.00  50.50      A    N
ATOM   1906  CA   ILE A 360      16.884  36.295  21.406  1.00  53.67      A    C
ATOM   1907  CB   ILE A 360      16.177  37.561  20.797  1.00  54.43      A    C
ATOM   1908  CG2  ILE A 360      16.640  38.828  21.468  1.00  52.55      A    C
ATOM   1909  CG1  ILE A 360      16.445  37.605  19.294  1.00  57.63      A    C
ATOM   1910  CD1  ILE A 360      15.853  38.768  18.621  1.00  58.08      A    C
ATOM   1911  C    ILE A 360      18.326  36.169  20.899  1.00  53.44      A    C
ATOM   1912  O    ILE A 360      18.574  35.529  19.863  1.00  52.69      A    O
ATOM   1913  N    SER A 361      19.268  36.763  21.634  1.00  51.55      A    N
ATOM   1914  CA   SER A 361      20.688  36.657  21.283  1.00  50.87      A    C
ATOM   1915  CB   SER A 361      21.572  37.393  22.299  1.00  50.55      A    C
ATOM   1916  OG   SER A 361      21.607  38.799  22.099  1.00  53.11      A    O
ATOM   1917  C    SER A 361      21.063  35.175  21.318  1.00  52.18      A    C
ATOM   1918  O    SER A 361      21.862  34.705  20.519  1.00  53.10      A    O
ATOM   1919  N    ARG A 362      20.476  34.447  22.263  1.00  54.11      A    N
ATOM   1920  CA   ARG A 362      20.756  33.026  22.424  1.00  53.69      A    C
ATOM   1921  CB   ARG A 362      20.276  32.544  23.796  1.00  56.55      A    C
ATOM   1922  CG   ARG A 362      20.914  31.236  24.258  1.00  63.22      A    C
ATOM   1923  CD   ARG A 362      21.909  31.472  25.403  1.00  67.36      A    C
ATOM   1924  NE   ARG A 362      21.305  31.247  26.706  1.00  68.28      A    N
```

Figure 2EE

```
ATOM   1925  CZ   ARG A 362      20.885  30.055  27.131  1.00  73.30      A    C
ATOM   1926  NH1  ARG A 362      21.014  28.985  26.344  1.00  72.26      A    N
ATOM   1927  NH2  ARG A 362      20.327  29.928  28.336  1.00  73.66      A    N
ATOM   1928  C    ARG A 362      20.047  32.239  21.333  1.00  50.70      A    C
ATOM   1929  O    ARG A 362      20.303  31.035  21.125  1.00  47.88      A    O
ATOM   1930  N    LEU A 363      19.167  32.939  20.620  1.00  50.12      A    N
ATOM   1931  CA   LEU A 363      18.386  32.318  19.574  1.00  51.08      A    C
ATOM   1932  CB   LEU A 363      16.936  32.796  19.667  1.00  47.96      A    C
ATOM   1933  CG   LEU A 363      15.851  31.795  20.098  1.00  46.52      A    C
ATOM   1934  CD1  LEU A 363      16.434  30.476  20.607  1.00  46.57      A    C
ATOM   1935  CD2  LEU A 363      14.998  32.484  21.179  1.00  49.24      A    C
ATOM   1936  C    LEU A 363      18.926  32.591  18.192  1.00  52.62      A    C
ATOM   1937  O    LEU A 363      18.890  31.721  17.320  1.00  54.75      A    O
ATOM   1938  N    LEU A 364      19.423  33.794  17.968  1.00  54.42      A    N
ATOM   1939  CA   LEU A 364      19.925  34.086  16.640  1.00  55.77      A    C
ATOM   1940  CB   LEU A 364      19.277  35.364  16.082  1.00  60.93      A    C
ATOM   1941  CG   LEU A 364      19.712  36.773  16.483  1.00  69.73      A    C
ATOM   1942  CD1  LEU A 364      20.045  36.818  17.971  1.00  75.26      A    C
ATOM   1943  CD2  LEU A 364      20.929  37.190  15.635  1.00  74.05      A    C
ATOM   1944  C    LEU A 364      21.427  34.149  16.649  1.00  54.58      A    C
ATOM   1945  O    LEU A 364      22.049  35.110  17.096  1.00  52.94      A    O
ATOM   1946  N    LYS A 365      22.007  33.058  16.182  1.00  57.89      A    N
ATOM   1947  CA   LYS A 365      23.437  32.927  16.111  1.00  62.63      A    C
ATOM   1948  CB   LYS A 365      23.924  31.962  17.194  1.00  63.77      A    C
ATOM   1949  CG   LYS A 365      25.334  32.209  17.714  1.00  69.14      A    C
ATOM   1950  CD   LYS A 365      25.457  33.528  18.492  1.00  66.34      A    C
ATOM   1951  CE   LYS A 365      26.492  34.486  17.845  1.00  62.60      A    C
ATOM   1952  NZ   LYS A 365      26.101  34.919  16.473  1.00  56.98      A    N
ATOM   1953  C    LYS A 365      23.626  32.321  14.742  1.00  65.11      A    C
ATOM   1954  O    LYS A 365      22.800  31.510  14.304  1.00  66.58      A    O
ATOM   1955  N    HIS A 366      24.701  32.711  14.065  1.00  65.84      A    N
ATOM   1956  CA   HIS A 366      24.958  32.193  12.743  1.00  65.65      A    C
ATOM   1957  CB   HIS A 366      26.218  32.816  12.151  1.00  66.16      A    C
ATOM   1958  CG   HIS A 366      26.375  32.539  10.698  1.00  69.15      A    C
ATOM   1959  CD2  HIS A 366      26.706  31.408  10.039  1.00  74.25      A    C
ATOM   1960  ND1  HIS A 366      26.052  33.462   9.732  1.00  70.33      A    N
ATOM   1961  CE1  HIS A 366      26.174  32.911   8.536  1.00  74.91      A    C
ATOM   1962  NE2  HIS A 366      26.571  31.664   8.694  1.00  77.28      A    N
ATOM   1963  C    HIS A 366      25.110  30.684  12.761  1.00  65.51      A    C
ATOM   1964  O    HIS A 366      24.558  29.992  11.920  1.00  64.76      A    O
ATOM   1965  N    ASN A 367      25.873  30.180  13.722  1.00  66.30      A    N
ATOM   1966  CA   ASN A 367      26.096  28.744  13.840  1.00  69.53      A    C
ATOM   1967  CB   ASN A 367      27.179  28.479  14.882  1.00  75.65      A    C
ATOM   1968  CG   ASN A 367      27.971  27.225  14.589  1.00  81.83      A    C
ATOM   1969  OD1  ASN A 367      27.413  26.165  14.308  1.00  84.39      A    O
ATOM   1970  ND2  ASN A 367      29.288  27.343  14.651  1.00  85.71      A    N
ATOM   1971  C    ASN A 367      24.800  28.058  14.267  1.00  67.75      A    C
ATOM   1972  O    ASN A 367      24.232  28.370  15.322  1.00  69.67      A    O
ATOM   1973  N    PRO A 368      24.311  27.108  13.466  1.00  63.97      A    N
ATOM   1974  CD   PRO A 368      24.661  26.693  12.101  1.00  61.89      A    C
ATOM   1975  CA   PRO A 368      23.070  26.476  13.899  1.00  63.31      A    C
ATOM   1976  CB   PRO A 368      22.766  25.512  12.770  1.00  62.08      A    C
ATOM   1977  CG   PRO A 368      23.334  26.200  11.582  1.00  61.98      A    C
ATOM   1978  C    PRO A 368      23.216  25.777  15.231  1.00  65.26      A    C
ATOM   1979  O    PRO A 368      22.326  25.858  16.085  1.00  65.63      A    O
ATOM   1980  N    SER A 369      24.360  25.119  15.412  1.00  69.07      A    N
ATOM   1981  CA   SER A 369      24.642  24.364  16.628  1.00  72.93      A    C
ATOM   1982  CB   SER A 369      25.905  23.514  16.429  1.00  71.59      A    C
ATOM   1983  OG   SER A 369      27.080  24.313  16.352  1.00  69.95      A    O
ATOM   1984  C    SER A 369      24.777  25.172  17.913  1.00  75.91      A    C
ATOM   1985  O    SER A 369      24.603  24.627  18.994  1.00  76.83      A    O
```

Figure 2FF

```
ATOM   1986  N    GLN A 370      25.093  26.457  17.819  1.00   79.58      A  N
ATOM   1987  CA   GLN A 370      25.236  27.262  19.030  1.00   83.65      A  C
ATOM   1988  CB   GLN A 370      26.092  28.504  18.769  1.00   83.13      A  C
ATOM   1989  CG   GLN A 370      27.481  28.207  18.248  1.00   84.40      A  C
ATOM   1990  CD   GLN A 370      28.374  29.443  18.204  1.00   87.42      A  C
ATOM   1991  OE1  GLN A 370      29.500  29.384  17.713  1.00   88.83      A  O
ATOM   1992  NE2  GLN A 370      27.876  30.566  18.723  1.00   90.21      A  N
ATOM   1993  C    GLN A 370      23.871  27.688  19.556  1.00   86.94      A  C
ATOM   1994  O    GLN A 370      23.770  28.400  20.558  1.00   88.37      A  O
ATOM   1995  N    ARG A 371      22.816  27.245  18.881  1.00   89.17      A  N
ATOM   1996  CA   ARG A 371      21.467  27.598  19.289  1.00   90.00      A  C
ATOM   1997  CB   ARG A 371      20.567  27.766  18.057  1.00   96.17      A  C
ATOM   1998  CG   ARG A 371      21.001  28.915  17.144  1.00  104.80      A  C
ATOM   1999  CD   ARG A 371      21.284  30.211  17.937  1.00  117.05      A  C
ATOM   2000  NE   ARG A 371      22.424  30.091  18.860  1.00  126.19      A  N
ATOM   2001  CZ   ARG A 371      22.842  31.044  19.698  1.00  129.40      A  C
ATOM   2002  NH1  ARG A 371      23.887  30.826  20.491  1.00  128.85      A  N
ATOM   2003  NH2  ARG A 371      22.232  32.223  19.739  1.00  133.12      A  N
ATOM   2004  C    ARG A 371      20.893  26.580  20.250  1.00   85.05      A  C
ATOM   2005  O    ARG A 371      21.011  25.382  20.029  1.00   84.80      A  O
ATOM   2006  N    PRO A 372      20.255  27.053  21.330  1.00   80.33      A  N
ATOM   2007  CD   PRO A 372      19.881  28.462  21.520  1.00   75.06      A  C
ATOM   2008  CA   PRO A 372      19.649  26.220  22.366  1.00   79.44      A  C
ATOM   2009  CB   PRO A 372      19.058  27.245  23.319  1.00   77.16      A  C
ATOM   2010  CG   PRO A 372      18.699  28.358  22.424  1.00   73.68      A  C
ATOM   2011  C    PRO A 372      18.610  25.270  21.824  1.00   80.27      A  C
ATOM   2012  O    PRO A 372      18.210  25.385  20.678  1.00   83.31      A  O
ATOM   2013  N    MET A 373      18.182  24.310  22.635  1.00   80.21      A  N
ATOM   2014  CA   MET A 373      17.157  23.380  22.174  1.00   81.35      A  C
ATOM   2015  CB   MET A 373      17.511  21.933  22.522  1.00   78.96      A  C
ATOM   2016  CG   MET A 373      17.143  20.896  21.441  1.00   75.32      A  C
ATOM   2017  SD   MET A 373      15.388  20.761  20.867  1.00   74.22      A  S
ATOM   2018  CE   MET A 373      15.640  20.042  19.288  1.00   71.60      A  C
ATOM   2019  C    MET A 373      15.885  23.770  22.895  1.00   85.20      A  C
ATOM   2020  O    MET A 373      15.888  24.661  23.735  1.00   84.12      A  O
ATOM   2021  N    LEU A 374      14.800  23.107  22.532  1.00   91.43      A  N
ATOM   2022  CA   LEU A 374      13.487  23.304  23.130  1.00   96.00      A  C
ATOM   2023  CB   LEU A 374      12.717  21.969  23.018  1.00   97.56      A  C
ATOM   2024  CG   LEU A 374      13.518  20.663  23.254  1.00   95.49      A  C
ATOM   2025  CD1  LEU A 374      13.623  20.352  24.740  1.00   93.11      A  C
ATOM   2026  CD2  LEU A 374      12.846  19.499  22.524  1.00   91.99      A  C
ATOM   2027  C    LEU A 374      13.466  23.801  24.594  1.00   97.88      A  C
ATOM   2028  O    LEU A 374      13.000  24.906  24.889  1.00   97.21      A  O
ATOM   2029  N    ARG A 375      13.984  22.977  25.497  1.00   99.22      A  N
ATOM   2030  CA   ARG A 375      13.984  23.271  26.920  1.00  100.59      A  C
ATOM   2031  CB   ARG A 375      14.547  22.078  27.687  1.00  104.56      A  C
ATOM   2032  CG   ARG A 375      14.435  22.217  29.197  1.00  109.85      A  C
ATOM   2033  CD   ARG A 375      15.234  21.156  29.932  1.00  116.44      A  C
ATOM   2034  NE   ARG A 375      16.669  21.440  29.943  1.00  123.68      A  N
ATOM   2035  CZ   ARG A 375      17.482  21.308  28.896  1.00  128.43      A  C
ATOM   2036  NH1  ARG A 375      18.772  21.597  29.021  1.00  130.54      A  N
ATOM   2037  NH2  ARG A 375      17.017  20.881  27.728  1.00  132.85      A  N
ATOM   2038  C    ARG A 375      14.682  24.534  27.405  1.00   99.40      A  C
ATOM   2039  O    ARG A 375      14.218  25.176  28.348  1.00  100.55      A  O
ATOM   2040  N    GLU A 376      15.793  24.900  26.786  1.00   98.02      A  N
ATOM   2041  CA   GLU A 376      16.512  26.074  27.244  1.00   96.90      A  C
ATOM   2042  CB   GLU A 376      17.725  26.338  26.357  1.00  105.25      A  C
ATOM   2043  CG   GLU A 376      18.591  27.489  26.851  1.00  114.81      A  C
ATOM   2044  CD   GLU A 376      18.996  27.319  28.306  1.00  118.52      A  C
ATOM   2045  OE1  GLU A 376      19.576  26.257  28.630  1.00  121.73      A  O
ATOM   2046  OE2  GLU A 376      18.735  28.238  29.122  1.00  116.75      A  O
```

Figure 2GG

| ATOM | 2047 | C | GLU | A | 376 | 15.647 | 27.322 | 27.322 | 1.00 | 91.62 | A | C |
| --- | --- | --- | --- | --- | --- | --- | --- | --- | --- | --- | --- | --- |
| ATOM | 2048 | O | GLU | A | 376 | 15.672 | 28.028 | 28.333 | 1.00 | 88.64 | A | O |
| ATOM | 2049 | N | VAL | A | 377 | 14.886 | 27.595 | 26.261 | 1.00 | 87.66 | A | N |
| ATOM | 2050 | CA | VAL | A | 377 | 14.022 | 28.772 | 26.238 | 1.00 | 84.36 | A | C |
| ATOM | 2051 | CB | VAL | A | 377 | 13.475 | 29.065 | 24.832 | 1.00 | 84.47 | A | C |
| ATOM | 2052 | CG1 | VAL | A | 377 | 14.597 | 29.568 | 23.933 | 1.00 | 84.90 | A | C |
| ATOM | 2053 | CG2 | VAL | A | 377 | 12.823 | 27.814 | 24.254 | 1.00 | 82.93 | A | C |
| ATOM | 2054 | C | VAL | A | 377 | 12.848 | 28.582 | 27.169 | 1.00 | 81.88 | A | C |
| ATOM | 2055 | O | VAL | A | 377 | 12.446 | 29.509 | 27.873 | 1.00 | 82.61 | A | O |
| ATOM | 2056 | N | LEU | A | 378 | 12.302 | 27.372 | 27.165 | 1.00 | 76.97 | A | N |
| ATOM | 2057 | CA | LEU | A | 378 | 11.182 | 27.040 | 28.030 | 1.00 | 72.85 | A | C |
| ATOM | 2058 | CB | LEU | A | 378 | 10.752 | 25.592 | 27.767 | 1.00 | 63.89 | A | C |
| ATOM | 2059 | CG | LEU | A | 378 | 9.440 | 25.385 | 27.011 | 1.00 | 57.48 | A | C |
| ATOM | 2060 | CD1 | LEU | A | 378 | 9.049 | 26.658 | 26.300 | 1.00 | 57.13 | A | C |
| ATOM | 2061 | CD2 | LEU | A | 378 | 9.575 | 24.233 | 26.050 | 1.00 | 52.29 | A | C |
| ATOM | 2062 | C | LEU | A | 378 | 11.535 | 27.248 | 29.511 | 1.00 | 74.24 | A | C |
| ATOM | 2063 | O | LEU | A | 378 | 10.659 | 27.509 | 30.327 | 1.00 | 74.43 | A | O |
| ATOM | 2064 | N | GLU | A | 379 | 12.818 | 27.143 | 29.847 | 1.00 | 74.45 | A | N |
| ATOM | 2065 | CA | GLU | A | 379 | 13.284 | 27.328 | 31.224 | 1.00 | 75.07 | A | C |
| ATOM | 2066 | CB | GLU | A | 379 | 14.192 | 26.158 | 31.629 | 1.00 | 81.37 | A | C |
| ATOM | 2067 | CG | GLU | A | 379 | 14.548 | 26.085 | 33.124 | 1.00 | 94.68 | A | C |
| ATOM | 2068 | CD | GLU | A | 379 | 15.900 | 26.731 | 33.504 | 1.00 | 99.79 | A | C |
| ATOM | 2069 | OE1 | GLU | A | 379 | 16.238 | 26.727 | 34.712 | 1.00 | 103.20 | A | O |
| ATOM | 2070 | OE2 | GLU | A | 379 | 16.622 | 27.233 | 32.614 | 1.00 | 101.24 | A | O |
| ATOM | 2071 | C | GLU | A | 379 | 14.051 | 28.644 | 31.352 | 1.00 | 72.61 | A | C |
| ATOM | 2072 | O | GLU | A | 379 | 14.693 | 28.919 | 32.363 | 1.00 | 74.67 | A | O |
| ATOM | 2073 | N | HIS | A | 380 | 13.989 | 29.471 | 30.323 | 1.00 | 69.17 | A | N |
| ATOM | 2074 | CA | HIS | A | 380 | 14.711 | 30.713 | 30.374 | 1.00 | 67.78 | A | C |
| ATOM | 2075 | CB | HIS | A | 380 | 14.722 | 31.379 | 29.008 | 1.00 | 65.12 | A | C |
| ATOM | 2076 | CG | HIS | A | 380 | 15.578 | 32.602 | 28.937 | 1.00 | 64.64 | A | C |
| ATOM | 2077 | CD2 | HIS | A | 380 | 16.680 | 32.882 | 28.200 | 1.00 | 64.84 | A | C |
| ATOM | 2078 | ND1 | HIS | A | 380 | 15.342 | 33.714 | 29.715 | 1.00 | 62.16 | A | N |
| ATOM | 2079 | CE1 | HIS | A | 380 | 16.261 | 34.629 | 29.459 | 1.00 | 64.59 | A | C |
| ATOM | 2080 | NE2 | HIS | A | 380 | 17.084 | 34.149 | 28.543 | 1.00 | 65.94 | A | N |
| ATOM | 2081 | C | HIS | A | 380 | 14.145 | 31.676 | 31.405 | 1.00 | 67.54 | A | C |
| ATOM | 2082 | O | HIS | A | 380 | 12.937 | 31.857 | 31.506 | 1.00 | 65.56 | A | O |
| ATOM | 2083 | N | PRO | A | 381 | 15.032 | 32.319 | 32.179 | 1.00 | 70.03 | A | N |
| ATOM | 2084 | CD | PRO | A | 381 | 16.502 | 32.201 | 32.078 | 1.00 | 73.09 | A | C |
| ATOM | 2085 | CA | PRO | A | 381 | 14.673 | 33.281 | 33.216 | 1.00 | 72.41 | A | C |
| ATOM | 2086 | CB | PRO | A | 381 | 16.015 | 33.936 | 33.548 | 1.00 | 74.53 | A | C |
| ATOM | 2087 | CG | PRO | A | 381 | 16.980 | 32.810 | 33.384 | 1.00 | 73.59 | A | C |
| ATOM | 2088 | C | PRO | A | 381 | 13.657 | 34.300 | 32.726 | 1.00 | 72.56 | A | C |
| ATOM | 2089 | O | PRO | A | 381 | 13.031 | 35.001 | 33.525 | 1.00 | 76.18 | A | O |
| ATOM | 2090 | N | TRP | A | 382 | 13.490 | 34.394 | 31.415 | 1.00 | 68.97 | A | N |
| ATOM | 2091 | CA | TRP | A | 382 | 12.552 | 35.365 | 30.889 | 1.00 | 66.42 | A | C |
| ATOM | 2092 | CB | TRP | A | 382 | 13.142 | 36.048 | 29.667 | 1.00 | 67.04 | A | C |
| ATOM | 2093 | CG | TRP | A | 382 | 12.521 | 37.359 | 29.372 | 1.00 | 68.56 | A | C |
| ATOM | 2094 | CD2 | TRP | A | 382 | 11.639 | 37.662 | 28.285 | 1.00 | 68.32 | A | C |
| ATOM | 2095 | CE2 | TRP | A | 382 | 11.306 | 39.029 | 28.387 | 1.00 | 70.67 | A | C |
| ATOM | 2096 | CE3 | TRP | A | 382 | 11.100 | 36.910 | 27.235 | 1.00 | 65.32 | A | C |
| ATOM | 2097 | CD1 | TRP | A | 382 | 12.680 | 38.512 | 30.073 | 1.00 | 70.66 | A | C |
| ATOM | 2098 | NE1 | TRP | A | 382 | 11.953 | 39.528 | 29.486 | 1.00 | 70.62 | A | N |
| ATOM | 2099 | CZ2 | TRP | A | 382 | 10.457 | 39.661 | 27.477 | 1.00 | 71.40 | A | C |
| ATOM | 2100 | CZ3 | TRP | A | 382 | 10.262 | 37.536 | 26.335 | 1.00 | 65.56 | A | C |
| ATOM | 2101 | CH2 | TRP | A | 382 | 9.948 | 38.899 | 26.460 | 1.00 | 69.28 | A | C |
| ATOM | 2102 | C | TRP | A | 382 | 11.204 | 34.744 | 30.539 | 1.00 | 65.66 | A | C |
| ATOM | 2103 | O | TRP | A | 382 | 10.167 | 35.335 | 30.796 | 1.00 | 64.09 | A | O |
| ATOM | 2104 | N | ILE | A | 383 | 11.210 | 33.558 | 29.946 | 1.00 | 65.21 | A | N |
| ATOM | 2105 | CA | ILE | A | 383 | 9.951 | 32.923 | 29.615 | 1.00 | 64.53 | A | C |
| ATOM | 2106 | CB | ILE | A | 383 | 10.157 | 31.575 | 28.918 | 1.00 | 62.96 | A | C |
| ATOM | 2107 | CG2 | ILE | A | 383 | 8.874 | 30.765 | 28.959 | 1.00 | 66.81 | A | C |

Figure 2HH

| | | | | | | | | | | | |
|---|---|---|---|---|---|---|---|---|---|---|---|
| ATOM | 2108 | CG1 | ILE | A | 383 | 10.571 | 31.806 | 27.466 | 1.00 | 62.65 | A | C |
| ATOM | 2109 | CD1 | ILE | A | 383 | 11.983 | 32.338 | 27.293 | 1.00 | 58.44 | A | C |
| ATOM | 2110 | C | ILE | A | 383 | 9.232 | 32.724 | 30.934 | 1.00 | 65.61 | A | C |
| ATOM | 2111 | O | ILE | A | 383 | 8.033 | 32.952 | 31.044 | 1.00 | 67.02 | A | O |
| ATOM | 2112 | N | THR | A | 384 | 9.991 | 32.313 | 31.941 | 1.00 | 68.02 | A | N |
| ATOM | 2113 | CA | THR | A | 384 | 9.447 | 32.106 | 33.281 | 1.00 | 71.46 | A | C |
| ATOM | 2114 | CB | THR | A | 384 | 10.246 | 31.031 | 34.022 | 1.00 | 73.46 | A | C |
| ATOM | 2115 | OG1 | THR | A | 384 | 11.582 | 31.499 | 34.253 | 1.00 | 78.58 | A | O |
| ATOM | 2116 | CG2 | THR | A | 384 | 10.307 | 29.766 | 33.186 | 1.00 | 70.85 | A | C |
| ATOM | 2117 | C | THR | A | 384 | 9.533 | 33.424 | 34.056 | 1.00 | 72.04 | A | C |
| ATOM | 2118 | O | THR | A | 384 | 10.630 | 33.889 | 34.369 | 1.00 | 74.73 | A | O |
| ATOM | 2119 | N | ALA | A | 385 | 8.372 | 34.012 | 34.338 | 1.00 | 71.40 | A | N |
| ATOM | 2120 | CA | ALA | A | 385 | 8.234 | 35.290 | 35.061 | 1.00 | 75.23 | A | C |
| ATOM | 2121 | CB | ALA | A | 385 | 9.553 | 36.065 | 35.094 | 1.00 | 75.05 | A | C |
| ATOM | 2122 | C | ALA | A | 385 | 7.183 | 36.106 | 34.323 | 1.00 | 76.36 | A | C |
| ATOM | 2123 | O | ALA | A | 385 | 5.980 | 35.988 | 34.578 | 1.00 | 77.74 | A | O |
| ATOM | 2124 | N | ASN | A | 386 | 7.647 | 36.961 | 33.422 | 1.00 | 75.64 | A | N |
| ATOM | 2125 | CA | ASN | A | 386 | 6.735 | 37.734 | 32.605 | 1.00 | 72.43 | A | C |
| ATOM | 2126 | CB | ASN | A | 386 | 7.493 | 38.806 | 31.843 | 1.00 | 69.05 | A | C |
| ATOM | 2127 | CG | ASN | A | 386 | 8.911 | 38.429 | 31.631 | 1.00 | 69.63 | A | C |
| ATOM | 2128 | OD1 | ASN | A | 386 | 9.189 | 37.395 | 31.048 | 1.00 | 71.83 | A | O |
| ATOM | 2129 | ND2 | ASN | A | 386 | 9.831 | 39.248 | 32.125 | 1.00 | 70.84 | A | N |
| ATOM | 2130 | C | ASN | A | 386 | 6.341 | 36.607 | 31.694 | 1.00 | 71.63 | A | C |
| ATOM | 2131 | O | ASN | A | 386 | 7.178 | 36.079 | 30.992 | 1.00 | 69.35 | A | O |
| ATOM | 2132 | N | SER | A | 387 | 5.082 | 36.206 | 31.769 | 1.00 | 74.69 | A | N |
| ATOM | 2133 | CA | SER | A | 387 | 4.556 | 35.104 | 30.986 | 1.00 | 79.07 | A | C |
| ATOM | 2134 | CB | SER | A | 387 | 5.466 | 33.886 | 31.104 | 1.00 | 74.02 | A | C |
| ATOM | 2135 | OG | SER | A | 387 | 5.008 | 32.832 | 30.277 | 1.00 | 69.72 | A | O |
| ATOM | 2136 | C | SER | A | 387 | 3.187 | 34.765 | 31.566 | 1.00 | 85.99 | A | C |
| ATOM | 2137 | O | SER | A | 387 | 2.884 | 35.145 | 32.698 | 1.00 | 89.72 | A | O |
| ATOM | 2138 | N | SER | A | 388 | 2.371 | 34.050 | 30.794 | 1.00 | 90.29 | A | N |
| ATOM | 2139 | CA | SER | A | 388 | 1.022 | 33.671 | 31.224 | 1.00 | 90.60 | A | C |
| ATOM | 2140 | CB | SER | A | 388 | 1.092 | 32.519 | 32.240 | 1.00 | 89.06 | A | C |
| ATOM | 2141 | OG | SER | A | 388 | 1.645 | 31.345 | 31.669 | 1.00 | 81.60 | A | O |
| ATOM | 2142 | C | SER | A | 388 | 0.256 | 34.858 | 31.838 | 1.00 | 92.18 | A | C |
| ATOM | 2143 | O | SER | A | 388 | 0.179 | 35.934 | 31.189 | 1.00 | 90.40 | A | O |
| TER | 2145 | | SER | A | 388 | | | | | | A | |
| ATOM | 2146 | C1 | 071 | B | 1 | -6.880 | 35.378 | 7.060 | 1.00 | 61.02 | B | C |
| ATOM | 2147 | C2 | 071 | B | 1 | -7.767 | 34.356 | 7.351 | 1.00 | 62.09 | B | C |
| ATOM | 2148 | C3 | 071 | B | 1 | -7.918 | 33.307 | 6.448 | 1.00 | 59.96 | B | C |
| ATOM | 2149 | C4 | 071 | B | 1 | -7.161 | 33.271 | 5.241 | 1.00 | 57.29 | B | C |
| ATOM | 2150 | C55 | 071 | B | 1 | -6.268 | 34.293 | 4.960 | 1.00 | 58.62 | B | C |
| ATOM | 2151 | C6 | 071 | B | 1 | -6.126 | 35.353 | 5.872 | 1.00 | 59.65 | B | C |
| ATOM | 2152 | C7 | 071 | B | 1 | -10.003 | 34.352 | 10.885 | 1.00 | 64.92 | B | C |
| ATOM | 2153 | C9 | 071 | B | 1 | -9.793 | 35.555 | 10.174 | 1.00 | 67.16 | B | C |
| ATOM | 2154 | N | 071 | B | 1 | -9.061 | 35.542 | 9.004 | 1.00 | 66.96 | B | N |
| ATOM | 2155 | C14 | 071 | B | 1 | -8.492 | 34.368 | 8.544 | 1.00 | 64.43 | B | C |
| ATOM | 2156 | N2 | 071 | B | 1 | -8.670 | 33.200 | 9.262 | 1.00 | 64.57 | B | N |
| ATOM | 2157 | C17 | 071 | B | 1 | -9.422 | 33.180 | 10.418 | 1.00 | 63.54 | B | C |
| ATOM | 2158 | C8 | 071 | B | 1 | -8.630 | 28.910 | 9.243 | 1.00 | 57.82 | B | C |
| ATOM | 2159 | S1 | 071 | B | 1 | -8.634 | 30.449 | 9.248 | 1.00 | 57.42 | B | S |
| ATOM | 2160 | C12 | 071 | B | 1 | -9.315 | 30.765 | 10.618 | 1.00 | 58.31 | B | C |
| ATOM | 2161 | N4 | 071 | B | 1 | -9.625 | 29.584 | 11.252 | 1.00 | 56.40 | B | N |
| ATOM | 2162 | C18 | 071 | B | 1 | -9.223 | 28.493 | 10.450 | 1.00 | 55.53 | B | C |
| ATOM | 2163 | C15 | 071 | B | 1 | -8.151 | 28.099 | 8.245 | 1.00 | 61.33 | B | C |
| ATOM | 2164 | C11 | 071 | B | 1 | -10.716 | 34.365 | 12.100 | 1.00 | 61.72 | B | C |
| ATOM | 2165 | C13 | 071 | B | 1 | -11.201 | 35.572 | 12.616 | 1.00 | 60.76 | B | C |
| ATOM | 2166 | C16 | 071 | B | 1 | -10.985 | 36.771 | 11.917 | 1.00 | 61.57 | B | C |
| ATOM | 2167 | C5 | 071 | B | 1 | -10.282 | 36.763 | 10.692 | 1.00 | 65.67 | B | C |
| ATOM | 2168 | N6 | 071 | B | 1 | -9.582 | 32.016 | 11.141 | 1.00 | 61.24 | B | N |
| TER | 2169 | | 071 | B | 1 | | | | | | B | END |

Figure 3A

| | Atom | Type | Resid | # | X | Y | Z | Occ | B | Mol | |
|---|---|---|---|---|---|---|---|---|---|---|---|
| ATOM | 1 | CB | TRP A | 128 | -15.553 | 14.572 | 4.229 | 1.00 | 77.31 | A | C |
| ATOM | 2 | CG | TRP A | 128 | -15.362 | 14.455 | 5.718 | 1.00 | 85.23 | A | C |
| ATOM | 3 | CD2 | TRP A | 128 | -16.385 | 14.507 | 6.723 | 1.00 | 86.59 | A | C |
| ATOM | 4 | CE2 | TRP A | 128 | -15.760 | 14.275 | 7.970 | 1.00 | 87.74 | A | C |
| ATOM | 5 | CE3 | TRP A | 128 | -17.769 | 14.722 | 6.691 | 1.00 | 86.90 | A | C |
| ATOM | 6 | CD1 | TRP A | 128 | -14.192 | 14.211 | 6.382 | 1.00 | 90.48 | A | C |
| ATOM | 7 | NE1 | TRP A | 128 | -14.424 | 14.097 | 7.734 | 1.00 | 89.69 | A | N |
| ATOM | 8 | CZ2 | TRP A | 128 | -16.474 | 14.251 | 9.172 | 1.00 | 88.40 | A | C |
| ATOM | 9 | CZ3 | TRP A | 128 | -18.478 | 14.698 | 7.890 | 1.00 | 89.69 | A | C |
| ATOM | 10 | CH2 | TRP A | 128 | -17.828 | 14.464 | 9.111 | 1.00 | 89.34 | A | C |
| ATOM | 11 | C | TRP A | 128 | -17.013 | 14.056 | 2.258 | 1.00 | 83.98 | A | C |
| ATOM | 12 | O | TRP A | 128 | -16.503 | 13.454 | 1.297 | 1.00 | 83.56 | A | O |
| ATOM | 13 | N | TRP A | 128 | -16.342 | 12.243 | 3.830 | 1.00 | 76.50 | A | N |
| ATOM | 14 | CA | TRP A | 128 | -16.696 | 13.688 | 3.702 | 1.00 | 79.54 | A | C |
| ATOM | 15 | N | ALA A | 129 | -17.890 | 15.040 | 2.123 | 1.00 | 88.41 | A | N |
| ATOM | 16 | CA | ALA A | 129 | -18.304 | 15.541 | 0.825 | 1.00 | 92.73 | A | C |
| ATOM | 17 | CB | ALA A | 129 | -19.405 | 14.659 | 0.238 | 1.00 | 93.48 | A | C |
| ATOM | 18 | C | ALA A | 129 | -18.814 | 16.960 | 1.078 | 1.00 | 95.42 | A | C |
| ATOM | 19 | O | ALA A | 129 | -19.115 | 17.318 | 2.226 | 1.00 | 95.13 | A | O |
| ATOM | 20 | N | LEU A | 130 | -18.907 | 17.764 | 0.021 | 1.00 | 96.54 | A | N |
| ATOM | 21 | CA | LEU A | 130 | -19.351 | 19.145 | 0.154 | 1.00 | 94.67 | A | C |
| ATOM | 22 | CB | LEU A | 130 | -19.346 | 19.821 | -1.206 | 1.00 | 91.24 | A | C |
| ATOM | 23 | CG | LEU A | 130 | -19.491 | 21.323 | -1.047 | 1.00 | 91.28 | A | C |
| ATOM | 24 | CD1 | LEU A | 130 | -18.266 | 21.860 | -0.324 | 1.00 | 87.66 | A | C |
| ATOM | 25 | CD2 | LEU A | 130 | -19.649 | 21.967 | -2.402 | 1.00 | 97.34 | A | C |
| ATOM | 26 | C | LEU A | 130 | -20.733 | 19.299 | 0.786 | 1.00 | 94.87 | A | C |
| ATOM | 27 | O | LEU A | 130 | -20.943 | 20.168 | 1.632 | 1.00 | 95.15 | A | O |
| ATOM | 28 | N | GLU A | 131 | -21.666 | 18.450 | 0.366 | 1.00 | 94.46 | A | N |
| ATOM | 29 | CA | GLU A | 131 | -23.043 | 18.462 | 0.865 | 1.00 | 96.62 | A | C |
| ATOM | 30 | CB | GLU A | 131 | -23.795 | 17.239 | 0.323 | 1.00 | 102.53 | A | C |
| ATOM | 31 | CG | GLU A | 131 | -25.288 | 17.184 | 0.689 | 1.00 | 112.45 | A | C |
| ATOM | 32 | CD | GLU A | 131 | -25.929 | 15.787 | 0.495 | 1.00 | 116.42 | A | C |
| ATOM | 33 | OE1 | GLU A | 131 | -25.774 | 15.179 | -0.597 | 1.00 | 113.92 | A | O |
| ATOM | 34 | OE2 | GLU A | 131 | -26.602 | 15.304 | 1.445 | 1.00 | 120.54 | A | O |
| ATOM | 35 | C | GLU A | 131 | -23.153 | 18.478 | 2.393 | 1.00 | 94.79 | A | C |
| ATOM | 36 | O | GLU A | 131 | -24.053 | 19.108 | 2.948 | 1.00 | 97.60 | A | O |
| ATOM | 37 | N | ASP A | 132 | -22.238 | 17.777 | 3.059 | 1.00 | 90.89 | A | N |
| ATOM | 38 | CA | ASP A | 132 | -22.232 | 17.679 | 4.520 | 1.00 | 87.25 | A | C |
| ATOM | 39 | CB | ASP A | 132 | -21.206 | 16.630 | 4.997 | 1.00 | 87.32 | A | C |
| ATOM | 40 | CG | ASP A | 132 | -21.388 | 15.264 | 4.350 | 1.00 | 85.90 | A | C |
| ATOM | 41 | OD1 | ASP A | 132 | -20.601 | 14.921 | 3.450 | 1.00 | 85.52 | A | O |
| ATOM | 42 | OD2 | ASP A | 132 | -22.307 | 14.527 | 4.744 | 1.00 | 84.66 | A | O |
| ATOM | 43 | C | ASP A | 132 | -21.931 | 19.001 | 5.245 | 1.00 | 86.25 | A | C |
| ATOM | 44 | O | ASP A | 132 | -21.973 | 19.055 | 6.481 | 1.00 | 80.94 | A | O |
| ATOM | 45 | N | PHE A | 133 | -21.627 | 20.063 | 4.498 | 1.00 | 86.93 | A | N |
| ATOM | 46 | CA | PHE A | 133 | -21.306 | 21.339 | 5.137 | 1.00 | 86.09 | A | C |
| ATOM | 47 | CB | PHE A | 133 | -19.805 | 21.626 | 5.025 | 1.00 | 80.07 | A | C |
| ATOM | 48 | CG | PHE A | 133 | -18.928 | 20.483 | 5.436 | 1.00 | 78.44 | A | C |
| ATOM | 49 | CD1 | PHE A | 133 | -18.638 | 19.459 | 4.549 | 1.00 | 82.03 | A | C |
| ATOM | 50 | CD2 | PHE A | 133 | -18.382 | 20.433 | 6.711 | 1.00 | 77.09 | A | C |
| ATOM | 51 | CE1 | PHE A | 133 | -17.815 | 18.403 | 4.926 | 1.00 | 84.91 | A | C |
| ATOM | 52 | CE2 | PHE A | 133 | -17.555 | 19.379 | 7.098 | 1.00 | 79.24 | A | C |
| ATOM | 53 | CZ | PHE A | 133 | -17.272 | 18.363 | 6.203 | 1.00 | 83.43 | A | C |
| ATOM | 54 | C | PHE A | 133 | -22.057 | 22.559 | 4.609 | 1.00 | 89.60 | A | C |
| ATOM | 55 | O | PHE A | 133 | -22.246 | 22.717 | 3.399 | 1.00 | 95.80 | A | O |
| ATOM | 56 | N | GLU A | 134 | -22.482 | 23.420 | 5.533 | 1.00 | 87.87 | A | N |
| ATOM | 57 | CA | GLU A | 134 | -23.159 | 24.677 | 5.193 | 1.00 | 85.28 | A | C |
| ATOM | 58 | CB | GLU A | 134 | -24.174 | 25.050 | 6.281 | 1.00 | 79.70 | A | C |

Figure 3B

| ATOM | 63 | C | GLU | A | 134 | -21.995 | 25.677 | 5.184 | 1.00 | 87.50 | A | C |
|---|---|---|---|---|---|---|---|---|---|---|---|---|
| ATOM | 64 | O | GLU | A | 134 | -21.261 | 25.787 | 6.180 | 1.00 | 86.82 | A | O |
| ATOM | 65 | N | ILE | A | 135 | -21.796 | 26.396 | 4.085 | 1.00 | 90.97 | A | N |
| ATOM | 66 | CA | ILE | A | 135 | -20.655 | 27.302 | 4.056 | 1.00 | 96.38 | A | C |
| ATOM | 67 | CB | ILE | A | 135 | -19.878 | 27.109 | 2.757 | 1.00 | 95.44 | A | C |
| ATOM | 68 | CG2 | ILE | A | 135 | -19.649 | 25.639 | 2.516 | 1.00 | 92.77 | A | C |
| ATOM | 69 | CG1 | ILE | A | 135 | -20.682 | 27.643 | 1.582 | 1.00 | 95.02 | A | C |
| ATOM | 70 | CD1 | ILE | A | 135 | -19.855 | 27.735 | 0.306 | 1.00 | 93.84 | A | C |
| ATOM | 71 | C | ILE | A | 135 | -20.973 | 28.791 | 4.266 | 1.00 | 99.65 | A | C |
| ATOM | 72 | O | ILE | A | 135 | -21.885 | 29.334 | 3.627 | 1.00 | 102.52 | A | O |
| ATOM | 73 | N | GLY | A | 136 | -20.201 | 29.448 | 5.144 | 1.00 | 100.02 | A | N |
| ATOM | 74 | CA | GLY | A | 136 | -20.429 | 30.857 | 5.454 | 1.00 | 99.30 | A | C |
| ATOM | 75 | C | GLY | A | 136 | -19.492 | 31.933 | 4.915 | 1.00 | 97.66 | A | C |
| ATOM | 76 | O | GLY | A | 136 | -19.006 | 31.864 | 3.784 | 1.00 | 98.59 | A | O |
| ATOM | 77 | N | ARG | A | 137 | -19.267 | 32.957 | 5.733 | 1.00 | 95.67 | A | N |
| ATOM | 78 | CA | ARG | A | 137 | -18.395 | 34.085 | 5.383 | 1.00 | 93.46 | A | C |
| ATOM | 79 | CB | ARG | A | 137 | -18.061 | 34.869 | 6.670 | 1.00 | 94.85 | A | C |
| ATOM | 80 | CG | ARG | A | 137 | -17.295 | 36.188 | 6.516 | 1.00 | 90.17 | A | C |
| ATOM | 81 | CD | ARG | A | 137 | -17.134 | 36.844 | 7.872 | 1.00 | 92.55 | A | C |
| ATOM | 82 | NE | ARG | A | 137 | -16.090 | 36.208 | 8.670 | 1.00 | 97.19 | A | N |
| ATOM | 83 | CZ | ARG | A | 137 | -15.990 | 36.314 | 9.991 | 1.00 | 97.06 | A | C |
| ATOM | 84 | NH1 | ARG | A | 137 | -15.005 | 35.718 | 10.645 | 1.00 | 94.41 | A | N |
| ATOM | 85 | NH2 | ARG | A | 137 | -16.895 | 37.004 | 10.662 | 1.00 | 100.09 | A | N |
| ATOM | 86 | C | ARG | A | 137 | -17.112 | 33.590 | 4.705 | 1.00 | 91.91 | A | C |
| ATOM | 87 | O | ARG | A | 137 | -16.668 | 32.476 | 4.950 | 1.00 | 88.62 | A | O |
| ATOM | 88 | N | PRO | A | 138 | -16.512 | 34.405 | 3.832 | 1.00 | 93.60 | A | N |
| ATOM | 89 | CD | PRO | A | 138 | -17.074 | 35.619 | 3.227 | 1.00 | 96.09 | A | C |
| ATOM | 90 | CA | PRO | A | 138 | -15.281 | 34.023 | 3.140 | 1.00 | 97.65 | A | C |
| ATOM | 91 | CB | PRO | A | 138 | -15.388 | 34.774 | 1.832 | 1.00 | 99.93 | A | C |
| ATOM | 92 | CG | PRO | A | 138 | -15.942 | 36.068 | 2.297 | 1.00 | 100.66 | A | C |
| ATOM | 93 | C | PRO | A | 138 | -14.035 | 34.438 | 3.914 | 1.00 | 99.90 | A | C |
| ATOM | 94 | O | PRO | A | 138 | -13.309 | 35.332 | 3.481 | 1.00 | 104.10 | A | O |
| ATOM | 95 | N | LEU | A | 139 | -13.802 | 33.778 | 5.048 | 1.00 | 101.15 | A | N |
| ATOM | 96 | CA | LEU | A | 139 | -12.655 | 34.038 | 5.913 | 1.00 | 105.20 | A | C |
| ATOM | 97 | CB | LEU | A | 139 | -12.274 | 32.755 | 6.640 | 1.00 | 90.42 | A | C |
| ATOM | 98 | CG | LEU | A | 139 | -13.329 | 32.241 | 7.607 | 1.00 | 77.92 | A | C |
| ATOM | 99 | CD1 | LEU | A | 139 | -12.993 | 30.849 | 8.042 | 1.00 | 78.13 | A | C |
| ATOM | 100 | CD2 | LEU | A | 139 | -13.391 | 33.148 | 8.800 | 1.00 | 77.06 | A | C |
| ATOM | 101 | C | LEU | A | 139 | -11.427 | 34.610 | 5.192 | 1.00 | 117.43 | A | C |
| ATOM | 102 | O | LEU | A | 139 | -10.771 | 33.943 | 4.380 | 1.00 | 119.91 | A | O |
| ATOM | 103 | N | GLY | A | 140 | -11.062 | 35.868 | 5.389 | 1.00 | 128.58 | A | N |
| ATOM | 104 | CA | GLY | A | 140 | -9.894 | 36.337 | 4.633 | 1.00 | 138.05 | A | C |
| ATOM | 105 | C | GLY | A | 140 | -9.817 | 35.762 | 3.200 | 1.00 | 142.86 | A | C |
| ATOM | 106 | O | GLY | A | 140 | -10.852 | 35.654 | 2.533 | 1.00 | 145.31 | A | O |
| ATOM | 107 | N | LYS | A | 141 | -8.629 | 35.369 | 2.721 | 1.00 | 144.54 | A | N |
| ATOM | 108 | CA | LYS | A | 141 | -8.513 | 34.822 | 1.354 | 1.00 | 143.46 | A | C |
| ATOM | 109 | CB | LYS | A | 141 | -8.718 | 35.945 | 0.326 | 1.00 | 144.47 | A | C |
| ATOM | 114 | C | LYS | A | 141 | -7.226 | 34.054 | 0.994 | 1.00 | 141.14 | A | C |
| ATOM | 115 | O | LYS | A | 141 | -6.356 | 33.838 | 1.838 | 1.00 | 140.51 | A | O |
| ATOM | 116 | N | GLY | A | 142 | -7.120 | 33.651 | -0.275 | 1.00 | 137.64 | A | N |
| ATOM | 117 | CA | GLY | A | 142 | -5.952 | 32.911 | -0.725 | 1.00 | 134.77 | A | C |
| ATOM | 118 | C | GLY | A | 142 | -5.729 | 32.865 | -2.233 | 1.00 | 134.01 | A | C |
| ATOM | 119 | O | GLY | A | 142 | -6.670 | 33.036 | -3.025 | 1.00 | 131.68 | A | O |
| ATOM | 120 | N | LYS | A | 143 | -4.468 | 32.611 | -2.610 | 1.00 | 133.98 | A | N |
| ATOM | 121 | CA | LYS | A | 143 | -3.993 | 32.538 | -4.004 | 1.00 | 130.27 | A | C |
| ATOM | 122 | CB | LYS | A | 143 | -2.463 | 32.412 | -4.017 | 1.00 | 130.74 | A | C |
| ATOM | 127 | C | LYS | A | 143 | -4.587 | 31.391 | -4.816 | 1.00 | 127.42 | A | C |
| ATOM | 128 | O | LYS | A | 143 | -5.442 | 31.603 | -5.685 | 1.00 | 125.93 | A | O |
| ATOM | 129 | N | PHE | A | 144 | -4.097 | 30.182 | -4.545 | 1.00 | 126.26 | A | N |
| ATOM | 130 | CA | PHE | A | 144 | -4.584 | 28.975 | -5.222 | 1.00 | 123.04 | A | C |
| ATOM | 131 | CB | PHE | A | 144 | -3.415 | 27.997 | -5.491 | 1.00 | 127.84 | A | C |

Figure 3C

| ATOM | 132 | CG | PHE A 144 | -2.572 | 27.697 | -4.273 | 1.00 | 134.57 | A | C |
| ATOM | 133 | CD1 | PHE A 144 | -1.190 | 27.485 | -4.400 | 1.00 | 135.67 | A | C |
| ATOM | 134 | CD2 | PHE A 144 | -3.156 | 27.605 | -2.996 | 1.00 | 139.76 | A | C |
| ATOM | 135 | CE1 | PHE A 144 | -0.396 | 27.182 | -3.264 | 1.00 | 135.40 | A | C |
| ATOM | 136 | CE2 | PHE A 144 | -2.379 | 27.304 | -1.860 | 1.00 | 141.38 | A | C |
| ATOM | 137 | CZ | PHE A 144 | -0.996 | 27.090 | -1.993 | 1.00 | 138.23 | A | C |
| ATOM | 138 | C | PHE A 144 | -5.684 | 28.294 | -4.385 | 1.00 | 117.70 | A | C |
| ATOM | 139 | O | PHE A 144 | -5.995 | 27.115 | -4.599 | 1.00 | 115.14 | A | O |
| ATOM | 140 | N | GLY A 145 | -6.255 | 29.059 | -3.444 | 1.00 | 112.93 | A | N |
| ATOM | 141 | CA | GLY A 145 | -7.316 | 28.567 | -2.572 | 1.00 | 107.72 | A | C |
| ATOM | 142 | C | GLY A 145 | -7.953 | 29.592 | -1.629 | 1.00 | 101.63 | A | C |
| ATOM | 143 | O | GLY A 145 | -7.306 | 30.555 | -1.224 | 1.00 | 100.71 | A | O |
| ATOM | 144 | N | ASN A 146 | -9.226 | 29.374 | -1.280 | 1.00 | 94.19 | A | N |
| ATOM | 145 | CA | ASN A 146 | -10.003 | 30.245 | -0.375 | 1.00 | 82.32 | A | C |
| ATOM | 146 | CB | ASN A 146 | -11.299 | 30.687 | -1.069 | 1.00 | 86.43 | A | C |
| ATOM | 147 | CG | ASN A 146 | -11.220 | 32.083 | -1.645 | 1.00 | 91.63 | A | C |
| ATOM | 148 | OD1 | ASN A 146 | -10.125 | 32.626 | -1.863 | 1.00 | 93.69 | A | O |
| ATOM | 149 | ND2 | ASN A 146 | -12.386 | 32.676 | -1.914 | 1.00 | 96.13 | A | N |
| ATOM | 150 | C | ASN A 146 | -10.382 | 29.469 | 0.894 | 1.00 | 72.23 | A | C |
| ATOM | 151 | O | ASN A 146 | -10.322 | 28.236 | 0.906 | 1.00 | 65.89 | A | O |
| ATOM | 152 | N | VAL A 147 | -10.753 | 30.160 | 1.968 | 1.00 | 62.79 | A | N |
| ATOM | 153 | CA | VAL A 147 | -11.184 | 29.414 | 3.143 | 1.00 | 54.74 | A | C |
| ATOM | 154 | CB | VAL A 147 | -10.122 | 29.358 | 4.229 | 1.00 | 48.60 | A | C |
| ATOM | 155 | CG1 | VAL A 147 | -10.666 | 28.666 | 5.444 | 1.00 | 48.86 | A | C |
| ATOM | 156 | CG2 | VAL A 147 | -8.973 | 28.590 | 3.755 | 1.00 | 50.37 | A | C |
| ATOM | 157 | C | VAL A 147 | -12.456 | 30.000 | 3.735 | 1.00 | 53.07 | A | C |
| ATOM | 158 | O | VAL A 147 | -12.420 | 31.047 | 4.389 | 1.00 | 52.63 | A | O |
| ATOM | 159 | N | TYR A 148 | -13.580 | 29.323 | 3.490 | 1.00 | 50.14 | A | N |
| ATOM | 160 | CA | TYR A 148 | -14.876 | 29.758 | 3.994 | 1.00 | 45.39 | A | C |
| ATOM | 161 | CB | TYR A 148 | -15.956 | 29.274 | 3.013 | 1.00 | 51.26 | A | C |
| ATOM | 162 | CG | TYR A 148 | -15.534 | 29.573 | 1.586 | 1.00 | 56.30 | A | C |
| ATOM | 163 | CD1 | TYR A 148 | -14.369 | 29.035 | 1.087 | 1.00 | 58.16 | A | C |
| ATOM | 164 | CE1 | TYR A 148 | -13.854 | 29.423 | -0.127 | 1.00 | 60.14 | A | C |
| ATOM | 165 | CD2 | TYR A 148 | -16.205 | 30.515 | 0.794 | 1.00 | 56.63 | A | C |
| ATOM | 166 | CE2 | TYR A 148 | -15.681 | 30.916 | -0.477 | 1.00 | 54.78 | A | C |
| ATOM | 167 | CZ | TYR A 148 | -14.492 | 30.354 | -0.898 | 1.00 | 57.89 | A | C |
| ATOM | 168 | OH | TYR A 148 | -13.863 | 30.729 | -2.040 | 1.00 | 58.06 | A | O |
| ATOM | 169 | C | TYR A 148 | -15.087 | 29.231 | 5.407 | 1.00 | 41.28 | A | C |
| ATOM | 170 | O | TYR A 148 | -14.439 | 28.268 | 5.803 | 1.00 | 38.71 | A | O |
| ATOM | 171 | N | LEU A 149 | -15.893 | 29.938 | 6.195 | 1.00 | 36.58 | A | N |
| ATOM | 172 | CA | LEU A 149 | -16.256 | 29.515 | 7.528 | 1.00 | 39.96 | A | C |
| ATOM | 173 | CB | LEU A 149 | -16.644 | 30.738 | 8.324 | 1.00 | 42.23 | A | C |
| ATOM | 174 | CG | LEU A 149 | -17.285 | 30.533 | 9.681 | 1.00 | 45.82 | A | C |
| ATOM | 175 | CD1 | LEU A 149 | -16.286 | 30.075 | 10.747 | 1.00 | 39.65 | A | C |
| ATOM | 176 | CD2 | LEU A 149 | -17.898 | 31.875 | 10.031 | 1.00 | 45.90 | A | C |
| ATOM | 177 | C | LEU A 149 | -17.463 | 28.606 | 7.286 | 1.00 | 40.87 | A | C |
| ATOM | 178 | O | LEU A 149 | -18.378 | 28.990 | 6.552 | 1.00 | 38.84 | A | O |
| ATOM | 179 | N | ALA A 150 | -17.469 | 27.408 | 7.875 | 1.00 | 44.73 | A | N |
| ATOM | 180 | CA | ALA A 150 | -18.574 | 26.476 | 7.642 | 1.00 | 48.40 | A | C |
| ATOM | 181 | CB | ALA A 150 | -18.204 | 25.507 | 6.541 | 1.00 | 42.43 | A | C |
| ATOM | 182 | C | ALA A 150 | -19.051 | 25.703 | 8.857 | 1.00 | 53.67 | A | C |
| ATOM | 183 | O | ALA A 150 | -18.529 | 25.872 | 9.954 | 1.00 | 52.06 | A | O |
| ATOM | 184 | N | ARG A 151 | -20.041 | 24.838 | 8.628 | 1.00 | 61.27 | A | N |
| ATOM | 185 | CA | ARG A 151 | -20.666 | 24.026 | 9.680 | 1.00 | 69.32 | A | C |
| ATOM | 186 | CB | ARG A 151 | -21.959 | 24.699 | 10.147 | 1.00 | 71.06 | A | C |
| ATOM | 187 | CG | ARG A 151 | -22.129 | 24.876 | 11.654 | 1.00 | 70.20 | A | C |
| ATOM | 188 | CD | ARG A 151 | -23.262 | 25.869 | 11.928 | 1.00 | 66.99 | A | C |
| ATOM | 189 | NE | ARG A 151 | -23.290 | 26.411 | 13.282 | 1.00 | 61.89 | A | N |
| ATOM | 190 | CZ | ARG A 151 | -23.707 | 27.640 | 13.563 | 1.00 | 58.11 | A | C |
| ATOM | 191 | NH1 | ARG A 151 | -24.123 | 28.439 | 12.583 | 1.00 | 51.52 | A | N |
| ATOM | 192 | NH2 | ARG A 151 | -23.707 | 28.071 | 14.817 | 1.00 | 54.97 | A | N |

Figure 3D

```
ATOM    193  C   ARG A 151     -21.030  22.657   9.147  1.00  71.14      A   C
ATOM    194  O   ARG A 151     -21.553  22.553   8.047  1.00  64.70      A   O
ATOM    195  N   GLU A 152     -20.752  21.607   9.907  1.00  77.25      A   N
ATOM    196  CA  GLU A 152     -21.140  20.284   9.457  1.00  87.55      A   C
ATOM    197  CB  GLU A 152     -20.449  19.190  10.249  1.00  90.69      A   C
ATOM    198  CG  GLU A 152     -21.090  17.841   9.964  1.00  99.83      A   C
ATOM    199  CD  GLU A 152     -20.453  16.699  10.716  1.00 106.11      A   C
ATOM    200  OE1 GLU A 152     -20.148  16.882  11.915  1.00 111.30      A   O
ATOM    201  OE2 GLU A 152     -20.273  15.619  10.110  1.00 106.43      A   O
ATOM    202  C   GLU A 152     -22.625  20.221   9.749  1.00  92.09      A   C
ATOM    203  O   GLU A 152     -23.037  20.574  10.848  1.00  96.88      A   O
ATOM    204  N   ALA A 153     -23.430  19.765   8.792  1.00  93.64      A   N
ATOM    205  CA  ALA A 153     -24.885  19.710   8.985  1.00  92.55      A   C
ATOM    206  CB  ALA A 153     -25.576  19.383   7.653  1.00  92.47      A   C
ATOM    207  C   ALA A 153     -25.382  18.762  10.092  1.00  91.12      A   C
ATOM    208  O   ALA A 153     -26.504  18.906  10.587  1.00  88.22      A   O
ATOM    209  N   ALA A 154     -24.555  17.799  10.481  1.00  91.50      A   N
ATOM    210  CA  ALA A 154     -24.943  16.869  11.531  1.00  90.00      A   C
ATOM    211  CB  ALA A 154     -24.027  15.644  11.521  1.00  87.30      A   C
ATOM    212  C   ALA A 154     -24.869  17.569  12.881  1.00  88.61      A   C
ATOM    213  O   ALA A 154     -25.869  18.109  13.362  1.00  90.52      A   O
ATOM    214  N   SER A 155     -23.668  17.577  13.463  1.00  85.98      A   N
ATOM    215  CA  SER A 155     -23.387  18.173  14.778  1.00  84.79      A   C
ATOM    216  CB  SER A 155     -22.013  17.665  15.282  1.00  83.43      A   C
ATOM    217  OG  SER A 155     -20.963  17.879  14.340  1.00  83.48      A   O
ATOM    218  C   SER A 155     -23.458  19.707  14.929  1.00  83.11      A   C
ATOM    219  O   SER A 155     -23.015  20.254  15.937  1.00  81.27      A   O
ATOM    220  N   ALA A 156     -24.026  20.396  13.947  1.00  80.52      A   N
ATOM    221  CA  ALA A 156     -24.138  21.854  14.002  1.00  78.57      A   C
ATOM    222  CB  ALA A 156     -25.276  22.257  14.909  1.00  75.82      A   C
ATOM    223  C   ALA A 156     -22.835  22.466  14.490  1.00  79.48      A   C
ATOM    224  O   ALA A 156     -22.786  23.622  14.913  1.00  80.86      A   O
ATOM    225  N   PHE A 157     -21.784  21.656  14.413  1.00  78.71      A   N
ATOM    226  CA  PHE A 157     -20.433  22.034  14.805  1.00  75.49      A   C
ATOM    227  CB  PHE A 157     -19.525  20.804  14.770  1.00  73.43      A   C
ATOM    228  CG  PHE A 157     -18.165  21.050  15.320  1.00  69.44      A   C
ATOM    229  CD1 PHE A 157     -18.017  21.685  16.544  1.00  71.28      A   C
ATOM    230  CD2 PHE A 157     -17.033  20.626  14.636  1.00  67.24      A   C
ATOM    231  CE1 PHE A 157     -16.771  21.895  17.082  1.00  73.58      A   C
ATOM    232  CE2 PHE A 157     -15.779  20.831  15.167  1.00  69.72      A   C
ATOM    233  CZ  PHE A 157     -15.646  21.469  16.395  1.00  73.86      A   C
ATOM    234  C   PHE A 157     -19.894  23.092  13.844  1.00  72.57      A   C
ATOM    235  O   PHE A 157     -20.233  23.100  12.662  1.00  70.95      A   O
ATOM    236  N   ILE A 158     -19.044  23.976  14.343  1.00  67.81      A   N
ATOM    237  CA  ILE A 158     -18.512  25.017  13.496  1.00  64.30      A   C
ATOM    238  CB  ILE A 158     -18.729  26.390  14.159  1.00  63.36      A   C
ATOM    239  CG2 ILE A 158     -18.436  26.294  15.642  1.00  68.60      A   C
ATOM    240  CG1 ILE A 158     -17.877  27.452  13.472  1.00  67.69      A   C
ATOM    241  CD1 ILE A 158     -18.128  27.587  11.992  1.00  67.96      A   C
ATOM    242  C   ILE A 158     -17.044  24.750  13.198  1.00  64.51      A   C
ATOM    243  O   ILE A 158     -16.295  24.321  14.078  1.00  61.45      A   O
ATOM    244  N   LEU A 159     -16.657  24.995  11.943  1.00  65.49      A   N
ATOM    245  CA  LEU A 159     -15.298  24.767  11.461  1.00  65.08      A   C
ATOM    246  CB  LEU A 159     -15.196  23.392  10.826  1.00  66.01      A   C
ATOM    247  CG  LEU A 159     -15.364  22.251  11.802  1.00  65.69      A   C
ATOM    248  CD1 LEU A 159     -15.351  20.936  11.040  1.00  65.16      A   C
ATOM    249  CD2 LEU A 159     -14.242  22.339  12.842  1.00  67.69      A   C
ATOM    250  C   LEU A 159     -14.799  25.748  10.430  1.00  63.07      A   C
ATOM    251  O   LEU A 159     -15.473  26.715  10.078  1.00  60.37      A   O
ATOM    252  N   ALA A 160     -13.603  25.436   9.938  1.00  63.97      A   N
ATOM    253  CA  ALA A 160     -12.902  26.198   8.912  1.00  63.42      A   C
```

Figure 3E

| ATOM | 254 | CB | ALA | A | 160 | -11.591 | 26.758 | 9.464 | 1.00 | 62.98 | A | C |
|---|---|---|---|---|---|---|---|---|---|---|---|---|
| ATOM | 255 | C | ALA | A | 160 | -12.624 | 25.183 | 7.812 | 1.00 | 63.12 | A | C |
| ATOM | 256 | O | ALA | A | 160 | -11.940 | 24.194 | 8.041 | 1.00 | 59.21 | A | O |
| ATOM | 257 | N | LEU | A | 161 | -13.164 | 25.430 | 6.627 | 1.00 | 64.59 | A | N |
| ATOM | 258 | CA | LEU | A | 161 | -13.008 | 24.528 | 5.502 | 1.00 | 69.26 | A | C |
| ATOM | 259 | CB | LEU | A | 161 | -14.414 | 24.146 | 5.032 | 1.00 | 72.36 | A | C |
| ATOM | 260 | CG | LEU | A | 161 | -14.776 | 23.257 | 3.853 | 1.00 | 77.16 | A | C |
| ATOM | 261 | CD1 | LEU | A | 161 | -16.180 | 22.727 | 4.025 | 1.00 | 78.53 | A | C |
| ATOM | 262 | CD2 | LEU | A | 161 | -14.679 | 24.055 | 2.579 | 1.00 | 77.95 | A | C |
| ATOM | 263 | C | LEU | A | 161 | -12.192 | 25.255 | 4.427 | 1.00 | 71.39 | A | C |
| ATOM | 264 | O | LEU | A | 161 | -12.598 | 26.314 | 3.941 | 1.00 | 70.83 | A | O |
| ATOM | 265 | N | LYS | A | 162 | -11.033 | 24.661 | 4.116 | 1.00 | 73.87 | A | N |
| ATOM | 266 | CA | LYS | A | 162 | -10.090 | 25.201 | 3.145 | 1.00 | 78.58 | A | C |
| ATOM | 267 | CB | LYS | A | 162 | -8.659 | 24.991 | 3.596 | 1.00 | 80.39 | A | C |
| ATOM | 268 | CG | LYS | A | 162 | -7.669 | 25.678 | 2.688 | 1.00 | 84.40 | A | C |
| ATOM | 269 | CD | LYS | A | 162 | -6.211 | 25.555 | 3.169 | 1.00 | 90.20 | A | C |
| ATOM | 270 | CE | LYS | A | 162 | -5.834 | 26.419 | 4.390 | 1.00 | 95.76 | A | C |
| ATOM | 271 | NZ | LYS | A | 162 | -4.372 | 26.291 | 4.740 | 1.00 | 97.90 | A | N |
| ATOM | 272 | C | LYS | A | 162 | -10.249 | 24.543 | 1.821 | 1.00 | 81.19 | A | C |
| ATOM | 273 | O | LYS | A | 162 | -10.113 | 23.334 | 1.727 | 1.00 | 78.25 | A | O |
| ATOM | 274 | N | VAL | A | 163 | -10.516 | 25.363 | 0.806 | 1.00 | 87.52 | A | N |
| ATOM | 275 | CA | VAL | A | 163 | -10.730 | 24.940 | -0.579 | 1.00 | 93.77 | A | C |
| ATOM | 276 | CB | VAL | A | 163 | -11.807 | 25.806 | -1.248 | 1.00 | 91.82 | A | C |
| ATOM | 277 | CG1 | VAL | A | 163 | -11.176 | 26.736 | -2.246 | 1.00 | 92.36 | A | C |
| ATOM | 278 | CG2 | VAL | A | 163 | -12.849 | 24.956 | -1.896 | 1.00 | 90.93 | A | C |
| ATOM | 279 | C | VAL | A | 163 | -9.446 | 25.129 | -1.371 | 1.00 | 101.54 | A | C |
| ATOM | 280 | O | VAL | A | 163 | -8.678 | 26.057 | -1.104 | 1.00 | 104.47 | A | O |
| ATOM | 281 | N | LEU | A | 164 | -9.214 | 24.244 | -2.337 | 1.00 | 109.10 | A | N |
| ATOM | 282 | CA | LEU | A | 164 | -8.037 | 24.317 | -3.203 | 1.00 | 112.72 | A | C |
| ATOM | 283 | CB | LEU | A | 164 | -6.902 | 23.446 | -2.677 | 1.00 | 113.10 | A | C |
| ATOM | 284 | CG | LEU | A | 164 | -5.964 | 24.163 | -1.731 | 1.00 | 112.48 | A | C |
| ATOM | 285 | CD1 | LEU | A | 164 | -5.660 | 25.539 | -2.272 | 1.00 | 113.22 | A | C |
| ATOM | 286 | CD2 | LEU | A | 164 | -6.601 | 24.272 | -0.394 | 1.00 | 111.32 | A | C |
| ATOM | 287 | C | LEU | A | 164 | -8.356 | 23.923 | -4.644 | 1.00 | 114.09 | A | C |
| ATOM | 288 | O | LEU | A | 164 | -8.312 | 22.735 | -4.997 | 1.00 | 111.80 | A | O |
| ATOM | 289 | N | PHE | A | 165 | -8.689 | 24.936 | -5.457 | 1.00 | 116.34 | A | N |
| ATOM | 290 | CA | PHE | A | 165 | -9.018 | 24.744 | -6.868 | 1.00 | 117.46 | A | C |
| ATOM | 291 | CB | PHE | A | 165 | -9.114 | 26.102 | -7.607 | 1.00 | 118.05 | A | C |
| ATOM | 292 | CG | PHE | A | 165 | -10.289 | 26.985 | -7.160 | 1.00 | 123.74 | A | C |
| ATOM | 293 | CD1 | PHE | A | 165 | -10.154 | 27.887 | -6.094 | 1.00 | 126.01 | A | C |
| ATOM | 294 | CD2 | PHE | A | 165 | -11.531 | 26.923 | -7.817 | 1.00 | 126.36 | A | C |
| ATOM | 295 | CE1 | PHE | A | 165 | -11.236 | 28.716 | -5.688 | 1.00 | 126.54 | A | C |
| ATOM | 296 | CE2 | PHE | A | 165 | -12.624 | 27.749 | -7.421 | 1.00 | 126.31 | A | C |
| ATOM | 297 | CZ | PHE | A | 165 | -12.467 | 28.644 | -6.353 | 1.00 | 125.83 | A | C |
| ATOM | 298 | C | PHE | A | 165 | -7.843 | 23.915 | -7.351 | 1.00 | 118.07 | A | C |
| ATOM | 299 | O | PHE | A | 165 | -6.698 | 24.251 | -7.089 | 1.00 | 112.70 | A | O |
| ATOM | 300 | N | LYS | A | 166 | -8.123 | 22.798 | -8.000 | 1.00 | 124.06 | A | N |
| ATOM | 301 | CA | LYS | A | 166 | -7.047 | 21.937 | -8.455 | 1.00 | 132.23 | A | C |
| ATOM | 302 | CB | LYS | A | 166 | -7.591 | 20.559 | -8.854 | 1.00 | 134.10 | A | C |
| ATOM | 307 | C | LYS | A | 166 | -6.330 | 22.590 | -9.617 | 1.00 | 138.16 | A | C |
| ATOM | 308 | O | LYS | A | 166 | -5.134 | 22.367 | -9.817 | 1.00 | 138.17 | A | O |
| ATOM | 309 | N | ALA | A | 167 | -7.072 | 23.393 | -10.381 | 1.00 | 144.68 | A | N |
| ATOM | 310 | CA | ALA | A | 167 | -6.494 | 24.116 | -11.515 | 1.00 | 148.10 | A | C |
| ATOM | 311 | CB | ALA | A | 167 | -7.546 | 25.077 | -12.140 | 1.00 | 148.09 | A | C |
| ATOM | 312 | C | ALA | A | 167 | -5.268 | 24.896 | -10.989 | 1.00 | 148.80 | A | C |
| ATOM | 313 | O | ALA | A | 167 | -4.144 | 24.418 | -11.115 | 1.00 | 151.89 | A | O |
| ATOM | 314 | N | GLN | A | 168 | -5.529 | 26.551 | -10.435 | 1.00 | 149.06 | A | N |
| ATOM | 315 | CA | GLN | A | 168 | -4.377 | 27.128 | -9.778 | 1.00 | 146.35 | A | C |
| ATOM | 316 | CB | GLN | A | 168 | -4.832 | 27.918 | -8.559 | 1.00 | 147.48 | A | C |
| ATOM | 317 | CG | GLN | A | 168 | -5.811 | 29.044 | -8.878 | 1.00 | 153.35 | A | C |
| ATOM | 318 | CD | GLN | A | 168 | -5.212 | 30.126 | -9.754 | 1.00 | 158.45 | A | C |

Figure 3F

```
ATOM    319  OE1 GLN A 168      -4.099  30.594  -9.513  1.00 163.83      A  O
ATOM    320  NE2 GLN A 168      -5.951  30.526 -10.784  1.00 158.04      A  N
ATOM    321  C   GLN A 168      -3.434  26.006  -9.361  1.00 144.67      A  C
ATOM    322  O   GLN A 168      -2.270  25.976  -9.761  1.00 144.23      A  O
ATOM    323  N   LEU A 169      -3.953  24.703  -8.703  1.00 140.59      A  N
ATOM    324  CA  LEU A 169      -3.195  23.639  -8.058  1.00 140.61      A  C
ATOM    325  CB  LEU A 169      -4.076  22.810  -7.119  1.00 138.01      A  C
ATOM    329  C   LEU A 169      -2.795  22.784  -9.229  1.00 142.44      A  C
ATOM    330  O   LEU A 169      -3.020  21.574  -9.223  1.00 142.01      A  O
ATOM    331  N   GLU A 170      -2.242  23.445 -10.249  1.00 146.41      A  N
ATOM    332  CA  GLU A 170      -1.791  22.805 -11.507  1.00 148.77      A  C
ATOM    333  CB  GLU A 170      -2.991  22.156 -12.222  1.00 152.02      A  C
ATOM    338  C   GLU A 170      -1.043  23.760 -12.491  1.00 147.17      A  C
ATOM    339  O   GLU A 170      -0.359  23.297 -13.428  1.00 144.27      A  O
ATOM    340  N   LYS A 171      -1.207  25.074 -12.283  1.00 145.29      A  N
ATOM    341  CA  LYS A 171      -0.536  26.118 -13.067  1.00 139.63      A  C
ATOM    342  CB  LYS A 171      -1.378  27.404 -13.073  1.00 134.52      A  C
ATOM    347  C   LYS A 171       0.818  26.336 -12.341  1.00 137.12      A  C
ATOM    348  O   LYS A 171       1.598  27.254 -12.655  1.00 136.48      A  O
ATOM    349  N   ALA A 172       1.048  25.457 -11.358  1.00 133.18      A  N
ATOM    350  CA  ALA A 172       2.249  25.373 -10.521  1.00 126.97      A  C
ATOM    351  CB  ALA A 172       2.014  26.019  -9.160  1.00 123.45      A  C
ATOM    352  C   ALA A 172       2.475  23.860 -10.357  1.00 123.95      A  C
ATOM    353  O   ALA A 172       2.155  23.081 -11.271  1.00 127.57      A  O
ATOM    354  N   GLY A 173       2.993  23.425  -9.208  1.00 117.34      A  N
ATOM    355  CA  GLY A 173       3.227  21.999  -9.052  1.00 111.94      A  C
ATOM    356  C   GLY A 173       3.560  21.494  -7.664  1.00 110.26      A  C
ATOM    357  O   GLY A 173       4.728  21.545  -7.251  1.00 110.13      A  O
ATOM    358  N   VAL A 174       2.524  21.003  -6.964  1.00 107.18      A  N
ATOM    359  CA  VAL A 174       2.616  20.427  -5.608  1.00 100.57      A  C
ATOM    360  CB  VAL A 174       2.339  21.487  -4.512  1.00  98.60      A  C
ATOM    363  C   VAL A 174       1.575  19.312  -5.498  1.00  96.48      A  C
ATOM    364  O   VAL A 174       0.580  19.306  -6.216  1.00  94.14      A  O
ATOM    365  N   GLU A 175       1.811  18.355  -4.620  1.00  94.91      A  N
ATOM    366  CA  GLU A 175       0.872  17.253  -4.461  1.00  96.03      A  C
ATOM    367  CB  GLU A 175       0.801  16.388  -5.743  1.00  93.20      A  C
ATOM    368  CG  GLU A 175       0.852  14.844  -5.524  1.00  85.82      A  C
ATOM    369  CD  GLU A 175       2.214  14.182  -5.862  1.00  83.39      A  C
ATOM    370  OE1 GLU A 175       2.386  13.712  -7.012  1.00  81.36      A  O
ATOM    371  OE2 GLU A 175       3.108  14.128  -4.979  1.00  78.96      A  O
ATOM    372  C   GLU A 175       1.303  16.405  -3.279  1.00  99.54      A  C
ATOM    373  O   GLU A 175       2.322  16.677  -2.654  1.00  99.67      A  O
ATOM    374  N   HIS A 176       3.605  17.574  -5.870  1.00 103.10      A  N
ATOM    375  CA  HIS A 176       4.828  17.421  -5.105  1.00 105.22      A  C
ATOM    376  CB  HIS A 176       5.880  18.435  -5.617  1.00 107.53      A  C
ATOM    377  CG  HIS A 176       7.058  18.655  -4.702  1.00 110.66      A  C
ATOM    378  CD2 HIS A 176       8.246  18.008  -4.603  1.00 110.65      A  C
ATOM    379  ND1 HIS A 176       7.137  19.724  -3.830  1.00 111.34      A  N
ATOM    380  CE1 HIS A 176       8.322  19.732  -3.244  1.00 112.37      A  C
ATOM    381  NE2 HIS A 176       9.014  18.702  -3.697  1.00 110.61      A  N
ATOM    382  C   HIS A 176       4.570  17.591  -3.612  1.00 105.67      A  C
ATOM    383  O   HIS A 176       4.687  16.617  -2.846  1.00 105.54      A  O
ATOM    384  N   GLN A 177       4.170  18.810  -3.226  1.00 103.45      A  N
ATOM    385  CA  GLN A 177       3.965  19.201  -1.817  1.00  98.22      A  C
ATOM    386  CB  GLN A 177       4.079  20.727  -1.718  1.00  90.87      A  C
ATOM    387  CG  GLN A 177       5.315  21.208  -0.987  1.00  85.76      A  C
ATOM    388  CD  GLN A 177       5.450  22.737  -1.009  1.00  84.63      A  C
ATOM    389  OE1 GLN A 177       6.001  23.317  -1.959  1.00  83.32      A  O
ATOM    390  NE2 GLN A 177       4.933  23.397   0.039  1.00  81.24      A  N
ATOM    391  C   GLN A 177       2.738  18.744  -1.007  1.00  99.24      A  C
ATOM    392  O   GLN A 177       2.879  18.222   0.117  1.00 100.33      A  O
```

Figure 3G

| ATOM | 393 | N   | LEU | A | 178 | 1.550  | 18.962 | -1.576 | 1.00 | 100.36 | A | N |
|------|-----|-----|-----|---|-----|--------|--------|--------|------|--------|---|---|
| ATOM | 394 | CA  | LEU | A | 178 | 0.288  | 18.621 | -0.929 | 1.00 | 101.59 | A | C |
| ATOM | 395 | CB  | LEU | A | 178 | -0.794 | 18.333 | -1.972 | 1.00 | 95.71  | A | C |
| ATOM | 399 | C   | LEU | A | 178 | 0.454  | 17.435 | 0.002  | 1.00 | 105.74 | A | C |
| ATOM | 400 | O   | LEU | A | 178 | 1.006  | 17.601 | 1.095  | 1.00 | 110.45 | A | O |
| ATOM | 401 | N   | ARG | A | 179 | -0.010 | 16.260 | -0.452 | 1.00 | 108.52 | A | N |
| ATOM | 402 | CA  | ARG | A | 179 | 0.014  | 14.980 | 0.270  | 1.00 | 109.52 | A | C |
| ATOM | 403 | CB  | ARG | A | 179 | 0.315  | 13.821 | -0.693 | 1.00 | 109.92 | A | C |
| ATOM | 410 | C   | ARG | A | 179 | 1.005  | 14.971 | 1.434  | 1.00 | 109.11 | A | C |
| ATOM | 411 | O   | ARG | A | 179 | 0.763  | 14.311 | 2.451  | 1.00 | 108.59 | A | O |
| ATOM | 412 | N   | ARG | A | 180 | 2.101  | 15.720 | 1.287  | 1.00 | 107.22 | A | N |
| ATOM | 413 | CA  | ARG | A | 180 | 3.126  | 15.819 | 2.326  | 1.00 | 103.65 | A | C |
| ATOM | 414 | CB  | ARG | A | 180 | 4.364  | 16.525 | 1.766  | 1.00 | 103.61 | A | C |
| ATOM | 421 | C   | ARG | A | 180 | 2.646  | 16.535 | 3.608  | 1.00 | 101.41 | A | C |
| ATOM | 422 | O   | ARG | A | 180 | 2.510  | 15.892 | 4.662  | 1.00 | 99.47  | A | O |
| ATOM | 423 | N   | GLU | A | 181 | 2.401  | 17.851 | 3.523  | 1.00 | 98.19  | A | N |
| ATOM | 424 | CA  | GLU | A | 181 | 1.923  | 18.628 | 4.682  | 1.00 | 92.21  | A | C |
| ATOM | 425 | CB  | GLU | A | 181 | 1.782  | 20.124 | 4.318  | 1.00 | 94.86  | A | C |
| ATOM | 426 | CG  | GLU | A | 181 | 3.110  | 20.893 | 4.187  | 1.00 | 95.88  | A | C |
| ATOM | 427 | CD  | GLU | A | 181 | 2.942  | 22.375 | 3.812  | 1.00 | 94.20  | A | C |
| ATOM | 428 | OE1 | GLU | A | 181 | 2.215  | 22.663 | 2.838  | 1.00 | 100.44 | A | O |
| ATOM | 429 | OE2 | GLU | A | 181 | 3.555  | 23.245 | 4.481  | 1.00 | 88.32  | A | O |
| ATOM | 430 | C   | GLU | A | 181 | 0.568  | 18.087 | 5.190  | 1.00 | 88.24  | A | C |
| ATOM | 431 | O   | GLU | A | 181 | 0.229  | 18.208 | 6.372  | 1.00 | 83.36  | A | O |
| ATOM | 432 | N   | VAL | A | 182 | -0.190 | 17.483 | 4.276  | 1.00 | 85.49  | A | N |
| ATOM | 433 | CA  | VAL | A | 182 | -1.497 | 16.912 | 4.564  | 1.00 | 82.64  | A | C |
| ATOM | 434 | CB  | VAL | A | 182 | -2.231 | 16.613 | 3.256  | 1.00 | 74.74  | A | C |
| ATOM | 435 | CG1 | VAL | A | 182 | -3.502 | 15.859 | 3.541  | 1.00 | 71.90  | A | C |
| ATOM | 436 | CG2 | VAL | A | 182 | -2.534 | 17.918 | 2.535  | 1.00 | 71.31  | A | C |
| ATOM | 437 | C   | VAL | A | 182 | -1.433 | 15.638 | 5.407  | 1.00 | 87.09  | A | C |
| ATOM | 438 | O   | VAL | A | 182 | -2.295 | 15.396 | 6.251  | 1.00 | 86.81  | A | O |
| ATOM | 439 | N   | GLU | A | 183 | -0.415 | 14.819 | 5.184  | 1.00 | 93.45  | A | N |
| ATOM | 440 | CA  | GLU | A | 183 | -0.285 | 13.587 | 5.952  | 1.00 | 102.25 | A | C |
| ATOM | 441 | CB  | GLU | A | 183 | 0.435  | 12.513 | 5.120  | 1.00 | 108.73 | A | C |
| ATOM | 442 | CG  | GLU | A | 183 | 0.415  | 11.138 | 5.762  | 1.00 | 120.23 | A | C |
| ATOM | 443 | CD  | GLU | A | 183 | -0.957 | 10.785 | 6.314  | 1.00 | 126.97 | A | C |
| ATOM | 444 | OE1 | GLU | A | 183 | -1.866 | 10.456 | 5.519  | 1.00 | 127.18 | A | O |
| ATOM | 445 | OE2 | GLU | A | 183 | -1.130 | 10.856 | 7.551  | 1.00 | 133.27 | A | O |
| ATOM | 446 | C   | GLU | A | 183 | 0.453  | 13.834 | 7.268  | 1.00 | 104.36 | A | C |
| ATOM | 447 | O   | GLU | A | 183 | 0.495  | 12.967 | 8.142  | 1.00 | 102.11 | A | O |
| ATOM | 448 | N   | ILE | A | 184 | 1.029  | 15.024 | 7.403  | 1.00 | 109.43 | A | N |
| ATOM | 449 | CA  | ILE | A | 184 | 1.751  | 15.391 | 8.619  | 1.00 | 116.61 | A | C |
| ATOM | 450 | CB  | ILE | A | 184 | 2.991  | 16.227 | 8.308  | 1.00 | 118.69 | A | C |
| ATOM | 451 | CG2 | ILE | A | 184 | 3.907  | 16.264 | 9.528  | 1.00 | 121.87 | A | C |
| ATOM | 452 | CG1 | ILE | A | 184 | 3.736  | 15.614 | 7.130  | 1.00 | 117.81 | A | C |
| ATOM | 453 | CD1 | ILE | A | 184 | 4.783  | 16.522 | 6.549  | 1.00 | 118.04 | A | C |
| ATOM | 454 | C   | ILE | A | 184 | 0.860  | 16.193 | 9.582  | 1.00 | 119.29 | A | C |
| ATOM | 455 | O   | ILE | A | 184 | 1.062  | 16.152 | 10.800 | 1.00 | 122.94 | A | O |
| ATOM | 456 | N   | GLN | A | 185 | -0.100 | 16.948 | 9.040  | 1.00 | 119.04 | A | N |
| ATOM | 457 | CA  | GLN | A | 185 | -1.030 | 17.701 | 9.886  | 1.00 | 118.41 | A | C |
| ATOM | 458 | CB  | GLN | A | 185 | -1.702 | 18.856 | 9.116  | 1.00 | 120.00 | A | C |
| ATOM | 459 | CG  | GLN | A | 185 | -0.816 | 20.098 | 8.887  | 1.00 | 120.95 | A | C |
| ATOM | 460 | CD  | GLN | A | 185 | -0.143 | 20.632 | 10.165 | 1.00 | 120.15 | A | C |
| ATOM | 461 | OE1 | GLN | A | 185 | 1.007  | 20.289 | 10.469 | 1.00 | 118.86 | A | O |
| ATOM | 462 | NE2 | GLN | A | 185 | -0.863 | 21.466 | 10.914 | 1.00 | 115.74 | A | N |
| ATOM | 463 | C   | GLN | A | 185 | -2.058 | 16.654 | 10.286 | 1.00 | 116.11 | A | C |
| ATOM | 464 | O   | GLN | A | 185 | -2.359 | 16.486 | 11.468 | 1.00 | 114.96 | A | O |
| ATOM | 465 | N   | SER | A | 186 | -2.563 | 15.933 | 9.286  | 1.00 | 113.50 | A | N |
| ATOM | 466 | CA  | SER | A | 186 | -3.532 | 14.873 | 9.523  | 1.00 | 110.46 | A | C |
| ATOM | 467 | CB  | SER | A | 186 | -3.906 | 14.172 | 8.213  | 1.00 | 111.00 | A | C |
| ATOM | 468 | OG  | SER | A | 186 | -4.950 | 13.238 | 8.426  | 1.00 | 110.96 | A | O |

Figure 3H

```
ATOM    469  C    SER A 186      -2.844   13.891   10.453  1.00  106.61      A    C
ATOM    470  O    SER A 186      -2.120   13.007    9.995  1.00  107.58      A    O
ATOM    471  N    HIS A 187      -3.069   14.078   11.752  1.00  101.61      A    N
ATOM    472  CA   HIS A 187      -2.492   13.255   12.805  1.00   98.17      A    C
ATOM    473  CB   HIS A 187      -1.271   12.486   12.303  1.00  103.48      A    C
ATOM    474  CG   HIS A 187      -1.247   11.048   12.722  1.00  108.31      A    C
ATOM    475  CD2  HIS A 187      -0.297   10.319   13.354  1.00  109.64      A    C
ATOM    476  ND1  HIS A 187      -2.289   10.182   12.466  1.00  107.48      A    N
ATOM    477  CE1  HIS A 187      -1.981    8.981   12.921  1.00  108.29      A    C
ATOM    478  NE2  HIS A 187      -0.779    9.037   13.464  1.00  109.59      A    N
ATOM    479  C    HIS A 187      -2.047   14.194   13.907  1.00   92.88      A    C
ATOM    480  O    HIS A 187      -2.533   14.126   15.029  1.00   91.44      A    O
ATOM    481  N    LEU A 188      -1.116   15.075   13.564  1.00   87.30      A    N
ATOM    482  CA   LEU A 188      -0.567   16.053   14.498  1.00   84.14      A    C
ATOM    483  CB   LEU A 188       0.083   17.188   13.693  1.00   81.14      A    C
ATOM    484  CG   LEU A 188       1.507   17.631   14.055  1.00   75.81      A    C
ATOM    485  CD1  LEU A 188       2.199   16.528   14.810  1.00   70.84      A    C
ATOM    486  CD2  LEU A 188       2.279   18.022   12.779  1.00   69.30      A    C
ATOM    487  C    LEU A 188      -1.620   16.601   15.477  1.00   82.49      A    C
ATOM    488  O    LEU A 188      -2.338   17.567   15.181  1.00   83.36      A    O
ATOM    489  N    ARG A 189      -1.695   15.973   16.648  1.00   77.92      A    N
ATOM    490  CA   ARG A 189      -2.654   16.349   17.689  1.00   72.19      A    C
ATOM    491  CB   ARG A 189      -3.210   15.068   18.347  1.00   74.40      A    C
ATOM    492  CG   ARG A 189      -4.556   15.170   19.105  1.00   80.93      A    C
ATOM    493  CD   ARG A 189      -5.455   13.963   18.715  1.00   88.55      A    C
ATOM    494  NE   ARG A 189      -6.619   13.737   19.585  1.00   95.81      A    N
ATOM    495  CZ   ARG A 189      -7.545   12.794   19.382  1.00   92.81      A    C
ATOM    496  NH1  ARG A 189      -7.449   11.989   18.331  1.00   93.22      A    N
ATOM    497  NH2  ARG A 189      -8.557   12.642   20.236  1.00   84.15      A    N
ATOM    498  C    ARG A 189      -1.955   17.215   18.733  1.00   64.94      A    C
ATOM    499  O    ARG A 189      -1.105   16.732   19.472  1.00   65.95      A    O
ATOM    500  N    HIS A 190      -2.303   18.493   18.798  1.00   56.75      A    N
ATOM    501  CA   HIS A 190      -1.669   19.363   19.776  1.00   51.00      A    C
ATOM    502  CB   HIS A 190      -0.226   19.675   19.377  1.00   47.39      A    C
ATOM    503  CG   HIS A 190       0.529   20.451   20.410  1.00   47.75      A    C
ATOM    504  CD2  HIS A 190       0.895   21.753   20.458  1.00   47.13      A    C
ATOM    505  ND1  HIS A 190       0.959   19.892   21.591  1.00   49.87      A    N
ATOM    506  CE1  HIS A 190       1.556   20.815   22.325  1.00   44.35      A    C
ATOM    507  NE2  HIS A 190       1.531   21.955   21.661  1.00   45.59      A    N
ATOM    508  C    HIS A 190      -2.407   20.673   19.937  1.00   48.28      A    C
ATOM    509  O    HIS A 190      -2.917   21.246   18.955  1.00   39.14      A    O
ATOM    510  N    PRO A 191      -2.479   21.167   21.193  1.00   50.04      A    N
ATOM    511  CD   PRO A 191      -2.036   20.502   22.430  1.00   47.47      A    C
ATOM    512  CA   PRO A 191      -3.153   22.430   21.511  1.00   51.00      A    C
ATOM    513  CB   PRO A 191      -2.829   22.643   23.003  1.00   46.77      A    C
ATOM    514  CG   PRO A 191      -1.719   21.679   23.298  1.00   44.44      A    C
ATOM    515  C    PRO A 191      -2.725   23.609   20.627  1.00   52.63      A    C
ATOM    516  O    PRO A 191      -3.565   24.260   20.006  1.00   55.11      A    O
ATOM    517  N    ASN A 192      -1.427   23.866   20.544  1.00   54.13      A    N
ATOM    518  CA   ASN A 192      -0.950   24.974   19.744  1.00   49.74      A    C
ATOM    519  CB   ASN A 192       0.274   25.581   20.421  1.00   51.26      A    C
ATOM    520  CG   ASN A 192       0.054   25.825   21.912  1.00   54.13      A    C
ATOM    521  OD1  ASN A 192       0.530   25.068   22.753  1.00   58.83      A    O
ATOM    522  ND2  ASN A 192      -0.671   26.879   22.239  1.00   54.81      A    N
ATOM    523  C    ASN A 192      -0.684   24.687   18.256  1.00   49.04      A    C
ATOM    524  O    ASN A 192      -0.033   25.486   17.573  1.00   46.63      A    O
ATOM    525  N    ILE A 193      -1.189   23.550   17.764  1.00   48.31      A    N
ATOM    526  CA   ILE A 193      -1.083   23.186   16.333  1.00   47.23      A    C
ATOM    527  CB   ILE A 193      -0.493   21.771   16.044  1.00   49.41      A    C
ATOM    528  CG2  ILE A 193      -0.437   21.568   14.533  1.00   47.50      A    C
ATOM    529  CG1  ILE A 193       0.887   21.588   16.673  1.00   53.44      A    C
```

Figure 3I

| ATOM | 530 | CD1 | ILE | A | 193 | 2.006 | 22.283 | 15.958 | 1.00 | 57.72 | A | C |
|---|---|---|---|---|---|---|---|---|---|---|---|---|
| ATOM | 531 | C | ILE | A | 193 | -2.521 | 23.117 | 15.809 | 1.00 | 46.37 | A | C |
| ATOM | 532 | O | ILE | A | 193 | -3.357 | 22.365 | 16.352 | 1.00 | 42.34 | A | O |
| ATOM | 533 | N | LEU | A | 194 | -2.810 | 23.888 | 14.763 | 1.00 | 49.54 | A | N |
| ATOM | 534 | CA | LEU | A | 194 | -4.151 | 23.889 | 14.194 | 1.00 | 58.82 | A | C |
| ATOM | 535 | CB | LEU | A | 194 | -4.191 | 24.777 | 12.953 | 1.00 | 56.73 | A | C |
| ATOM | 536 | CG | LEU | A | 194 | -5.567 | 25.074 | 12.369 | 1.00 | 55.12 | A | C |
| ATOM | 537 | CD1 | LEU | A | 194 | -6.392 | 25.823 | 13.380 | 1.00 | 57.56 | A | C |
| ATOM | 538 | CD2 | LEU | A | 194 | -5.417 | 25.879 | 11.098 | 1.00 | 58.91 | A | C |
| ATOM | 539 | C | LEU | A | 194 | -4.406 | 22.439 | 13.821 | 1.00 | 66.41 | A | C |
| ATOM | 540 | O | LEU | A | 194 | -3.541 | 21.815 | 13.221 | 1.00 | 76.54 | A | O |
| ATOM | 541 | N | ARG | A | 195 | -5.557 | 21.884 | 14.185 | 1.00 | 68.19 | A | N |
| ATOM | 542 | CA | ARG | A | 195 | -5.809 | 20.492 | 13.860 | 1.00 | 72.63 | A | C |
| ATOM | 543 | CB | ARG | A | 195 | -6.848 | 19.912 | 14.807 | 1.00 | 81.50 | A | C |
| ATOM | 544 | CG | ARG | A | 195 | -6.952 | 18.417 | 14.648 | 1.00 | 96.26 | A | C |
| ATOM | 545 | CD | ARG | A | 195 | -7.761 | 17.718 | 15.712 | 1.00 | 108.70 | A | C |
| ATOM | 546 | NE | ARG | A | 195 | -7.847 | 16.298 | 15.371 | 1.00 | 121.99 | A | N |
| ATOM | 547 | CZ | ARG | A | 195 | -8.425 | 15.366 | 16.124 | 1.00 | 128.81 | A | C |
| ATOM | 548 | NH1 | ARG | A | 195 | -8.444 | 14.092 | 15.713 | 1.00 | 132.70 | A | N |
| ATOM | 549 | NH2 | ARG | A | 195 | -8.984 | 15.707 | 17.286 | 1.00 | 130.96 | A | N |
| ATOM | 550 | C | ARG | A | 195 | -6.245 | 20.312 | 12.412 | 1.00 | 70.38 | A | C |
| ATOM | 551 | O | ARG | A | 195 | -6.578 | 21.291 | 11.760 | 1.00 | 64.84 | A | O |
| ATOM | 552 | N | LEU | A | 196 | -6.241 | 19.074 | 11.904 | 1.00 | 71.48 | A | N |
| ATOM | 553 | CA | LEU | A | 196 | -6.629 | 18.826 | 10.507 | 1.00 | 71.75 | A | C |
| ATOM | 554 | CB | LEU | A | 196 | -5.409 | 18.386 | 9.702 | 1.00 | 75.54 | A | C |
| ATOM | 555 | CG | LEU | A | 196 | -5.634 | 18.158 | 8.208 | 1.00 | 75.85 | A | C |
| ATOM | 556 | CD1 | LEU | A | 196 | -6.218 | 19.402 | 7.563 | 1.00 | 76.37 | A | C |
| ATOM | 557 | CD2 | LEU | A | 196 | -4.318 | 17.769 | 7.578 | 1.00 | 78.11 | A | C |
| ATOM | 558 | C | LEU | A | 196 | -7.791 | 17.859 | 10.221 | 1.00 | 71.19 | A | C |
| ATOM | 559 | O | LEU | A | 196 | -7.793 | 17.143 | 9.224 | 1.00 | 69.85 | A | O |
| ATOM | 560 | N | TYR | A | 197 | -8.784 | 17.871 | 11.098 | 1.00 | 71.20 | A | N |
| ATOM | 561 | CA | TYR | A | 197 | -9.997 | 17.061 | 11.005 | 1.00 | 69.07 | A | C |
| ATOM | 562 | CB | TYR | A | 197 | -11.197 | 18.007 | 11.082 | 1.00 | 69.72 | A | C |
| ATOM | 563 | CG | TYR | A | 197 | -11.300 | 18.786 | 12.375 | 1.00 | 67.85 | A | C |
| ATOM | 564 | CD1 | TYR | A | 197 | -11.219 | 20.175 | 12.383 | 1.00 | 66.00 | A | C |
| ATOM | 565 | CE1 | TYR | A | 197 | -11.330 | 20.891 | 13.559 | 1.00 | 74.03 | A | C |
| ATOM | 566 | CD2 | TYR | A | 197 | -11.491 | 18.131 | 13.580 | 1.00 | 71.26 | A | C |
| ATOM | 567 | CE2 | TYR | A | 197 | -11.602 | 18.834 | 14.765 | 1.00 | 80.65 | A | C |
| ATOM | 568 | CZ | TYR | A | 197 | -11.520 | 20.217 | 14.760 | 1.00 | 81.54 | A | C |
| ATOM | 569 | OH | TYR | A | 197 | -11.610 | 20.912 | 15.964 | 1.00 | 90.21 | A | O |
| ATOM | 570 | C | TYR | A | 197 | -10.226 | 16.050 | 9.853 | 1.00 | 68.26 | A | C |
| ATOM | 571 | O | TYR | A | 197 | -10.343 | 14.848 | 10.101 | 1.00 | 67.94 | A | O |
| ATOM | 572 | N | GLY | A | 198 | -10.324 | 16.510 | 8.608 | 1.00 | 67.62 | A | N |
| ATOM | 573 | CA | GLY | A | 198 | -10.572 | 15.569 | 7.527 | 1.00 | 66.61 | A | C |
| ATOM | 574 | C | GLY | A | 198 | -10.196 | 16.095 | 6.163 | 1.00 | 66.51 | A | C |
| ATOM | 575 | O | GLY | A | 198 | -10.111 | 17.302 | 5.960 | 1.00 | 64.63 | A | O |
| ATOM | 576 | N | TYR | A | 199 | -10.007 | 15.175 | 5.220 | 1.00 | 68.42 | A | N |
| ATOM | 577 | CA | TYR | A | 199 | -9.586 | 15.486 | 3.847 | 1.00 | 70.71 | A | C |
| ATOM | 578 | CB | TYR | A | 199 | -8.153 | 14.942 | 3.650 | 1.00 | 75.76 | A | C |
| ATOM | 579 | CG | TYR | A | 199 | -7.744 | 14.594 | 2.227 | 1.00 | 83.90 | A | C |
| ATOM | 580 | CD1 | TYR | A | 199 | -6.839 | 13.549 | 1.975 | 1.00 | 86.31 | A | C |
| ATOM | 581 | CE1 | TYR | A | 199 | -6.422 | 13.248 | 0.648 | 1.00 | 83.56 | A | C |
| ATOM | 582 | CD2 | TYR | A | 199 | -8.227 | 15.329 | 1.127 | 1.00 | 85.70 | A | C |
| ATOM | 583 | CE2 | TYR | A | 199 | -7.818 | 15.038 | -0.196 | 1.00 | 84.50 | A | C |
| ATOM | 584 | CZ | TYR | A | 199 | -6.919 | 14.004 | -0.426 | 1.00 | 82.85 | A | C |
| ATOM | 585 | OH | TYR | A | 199 | -6.513 | 13.762 | -1.718 | 1.00 | 80.99 | A | O |
| ATOM | 586 | C | TYR | A | 199 | -10.511 | 14.880 | 2.791 | 1.00 | 68.57 | A | C |
| ATOM | 587 | O | TYR | A | 199 | -10.775 | 13.678 | 2.819 | 1.00 | 68.21 | A | O |
| ATOM | 588 | N | PHE | A | 200 | -10.997 | 15.702 | 1.861 | 1.00 | 64.46 | A | N |
| ATOM | 589 | CA | PHE | A | 200 | -11.849 | 15.190 | 0.774 | 1.00 | 61.99 | A | C |
| ATOM | 590 | CB | PHE | A | 200 | -13.325 | 15.086 | 1.212 | 1.00 | 63.35 | A | C |

Figure 3J

| ATOM | 591 | CG | PHE | A | 200 | -13.998 | 16.409 | 1.500 | 1.00 | 58.91 | A | C |
|---|---|---|---|---|---|---|---|---|---|---|---|---|
| ATOM | 592 | CD1 | PHE | A | 200 | -13.882 | 17.000 | 2.743 | 1.00 | 53.59 | A | C |
| ATOM | 593 | CD2 | PHE | A | 200 | -14.792 | 17.022 | 0.537 | 1.00 | 55.17 | A | C |
| ATOM | 594 | CE1 | PHE | A | 200 | -14.551 | 18.173 | 3.022 | 1.00 | 53.96 | A | C |
| ATOM | 595 | CE2 | PHE | A | 200 | -15.459 | 18.187 | 0.811 | 1.00 | 51.28 | A | C |
| ATOM | 596 | CZ | PHE | A | 200 | -15.341 | 18.766 | 2.053 | 1.00 | 48.79 | A | C |
| ATOM | 597 | C | PHE | A | 200 | -11.723 | 16.049 | -0.480 | 1.00 | 57.46 | A | C |
| ATOM | 598 | O | PHE | A | 200 | -11.415 | 17.228 | -0.381 | 1.00 | 51.28 | A | O |
| ATOM | 599 | N | HIS | A | 201 | -11.971 | 15.477 | -1.652 | 1.00 | 59.81 | A | N |
| ATOM | 600 | CA | HIS | A | 201 | -11.818 | 16.242 | -2.883 | 1.00 | 67.84 | A | C |
| ATOM | 601 | CB | HIS | A | 201 | -10.482 | 15.898 | -3.521 | 1.00 | 80.86 | A | C |
| ATOM | 602 | CG | HIS | A | 201 | -10.218 | 14.421 | -3.590 | 1.00 | 95.43 | A | C |
| ATOM | 603 | CD2 | HIS | A | 201 | -9.457 | 13.614 | -2.805 | 1.00 | 100.35 | A | C |
| ATOM | 604 | ND1 | HIS | A | 201 | -10.819 | 13.594 | -4.519 | 1.00 | 101.77 | A | N |
| ATOM | 605 | CE1 | HIS | A | 201 | -10.442 | 12.344 | -4.304 | 1.00 | 105.34 | A | C |
| ATOM | 606 | NE2 | HIS | A | 201 | -9.616 | 12.328 | -3.269 | 1.00 | 104.92 | A | N |
| ATOM | 607 | C | HIS | A | 201 | -12.890 | 15.978 | -3.892 | 1.00 | 65.62 | A | C |
| ATOM | 608 | O | HIS | A | 201 | -13.284 | 14.842 | -4.080 | 1.00 | 64.82 | A | O |
| ATOM | 609 | N | ASP | A | 202 | -13.356 | 17.023 | -4.562 | 1.00 | 67.53 | A | N |
| ATOM | 610 | CA | ASP | A | 202 | -14.373 | 16.836 | -5.591 | 1.00 | 69.70 | A | C |
| ATOM | 611 | CB | ASP | A | 202 | -15.385 | 18.021 | -5.649 | 1.00 | 74.35 | A | C |
| ATOM | 612 | CG | ASP | A | 202 | -14.779 | 19.341 | -6.152 | 1.00 | 74.67 | A | C |
| ATOM | 613 | OD1 | ASP | A | 202 | -14.185 | 19.345 | -7.241 | 1.00 | 71.87 | A | O |
| ATOM | 614 | OD2 | ASP | A | 202 | -14.923 | 20.385 | -5.473 | 1.00 | 74.10 | A | O |
| ATOM | 615 | C | ASP | A | 202 | -13.624 | 16.670 | -6.898 | 1.00 | 70.98 | A | C |
| ATOM | 616 | O | ASP | A | 202 | -12.529 | 16.114 | -6.910 | 1.00 | 70.70 | A | O |
| ATOM | 617 | N | ALA | A | 203 | -14.199 | 17.132 | -7.996 | 1.00 | 70.67 | A | N |
| ATOM | 618 | CA | ALA | A | 203 | -13.534 | 17.024 | -9.285 | 1.00 | 74.56 | A | C |
| ATOM | 619 | CB | ALA | A | 203 | -14.577 | 17.043 | -10.392 | 1.00 | 78.53 | A | C |
| ATOM | 620 | C | ALA | A | 203 | -12.554 | 18.186 | -9.471 | 1.00 | 76.27 | A | C |
| ATOM | 621 | O | ALA | A | 203 | -11.330 | 18.020 | -9.449 | 1.00 | 71.67 | A | O |
| ATOM | 622 | N | THR | A | 204 | -13.135 | 19.365 | -9.648 | 1.00 | 81.65 | A | N |
| ATOM | 623 | CA | THR | A | 204 | -12.421 | 20.623 | -9.849 | 1.00 | 89.51 | A | C |
| ATOM | 624 | CB | THR | A | 204 | -13.469 | 21.760 | -10.179 | 1.00 | 92.73 | A | C |
| ATOM | 625 | OG1 | THR | A | 204 | -13.139 | 22.965 | -9.473 | 1.00 | 98.44 | A | O |
| ATOM | 626 | CG2 | THR | A | 204 | -14.885 | 21.323 | -9.788 | 1.00 | 93.07 | A | C |
| ATOM | 627 | C | THR | A | 204 | -11.486 | 21.090 | -8.702 | 1.00 | 90.46 | A | C |
| ATOM | 628 | O | THR | A | 204 | -10.288 | 21.344 | -8.926 | 1.00 | 92.45 | A | O |
| ATOM | 629 | N | ARG | A | 205 | -12.047 | 21.182 | -7.490 | 1.00 | 89.13 | A | N |
| ATOM | 630 | CA | ARG | A | 205 | -11.359 | 21.660 | -6.286 | 1.00 | 85.22 | A | C |
| ATOM | 631 | CB | ARG | A | 205 | -12.221 | 22.763 | -5.672 | 1.00 | 93.07 | A | C |
| ATOM | 632 | CG | ARG | A | 205 | -13.662 | 22.770 | -6.219 | 1.00 | 104.05 | A | C |
| ATOM | 633 | CD | ARG | A | 205 | -14.509 | 23.907 | -5.644 | 1.00 | 114.67 | A | C |
| ATOM | 634 | NE | ARG | A | 205 | -15.771 | 24.116 | -6.366 | 1.00 | 120.94 | A | N |
| ATOM | 635 | CZ | ARG | A | 205 | -16.715 | 24.996 | -6.013 | 1.00 | 125.05 | A | C |
| ATOM | 636 | NH1 | ARG | A | 205 | -16.552 | 25.763 | -4.934 | 1.00 | 129.67 | A | N |
| ATOM | 637 | NH2 | ARG | A | 205 | -17.823 | 25.121 | -6.745 | 1.00 | 122.18 | A | N |
| ATOM | 638 | C | ARG | A | 205 | -11.071 | 20.593 | -5.229 | 1.00 | 79.83 | A | C |
| ATOM | 639 | O | ARG | A | 205 | -11.513 | 19.456 | -5.357 | 1.00 | 70.49 | A | O |
| ATOM | 640 | N | VAL | A | 206 | -10.308 | 20.955 | -4.198 | 1.00 | 82.29 | A | N |
| ATOM | 641 | CA | VAL | A | 206 | -10.025 | 20.019 | -3.104 | 1.00 | 88.98 | A | C |
| ATOM | 642 | CB | VAL | A | 206 | -8.509 | 19.649 | -2.982 | 1.00 | 93.12 | A | C |
| ATOM | 643 | CG1 | VAL | A | 206 | -7.866 | 19.645 | -4.353 | 1.00 | 98.17 | A | C |
| ATOM | 644 | CG2 | VAL | A | 206 | -7.805 | 20.566 | -2.022 | 1.00 | 94.89 | A | C |
| ATOM | 645 | C | VAL | A | 206 | -10.540 | 20.619 | -1.781 | 1.00 | 87.37 | A | C |
| ATOM | 646 | O | VAL | A | 206 | -10.858 | 21.809 | -1.711 | 1.00 | 87.88 | A | O |
| ATOM | 647 | N | TYR | A | 207 | -10.627 | 19.804 | -0.736 | 1.00 | 85.04 | A | N |
| ATOM | 648 | CA | TYR | A | 207 | -11.160 | 20.287 | 0.523 | 1.00 | 81.96 | A | C |
| ATOM | 649 | CB | TYR | A | 207 | -12.623 | 19.899 | 0.603 | 1.00 | 77.56 | A | C |
| ATOM | 650 | CG | TYR | A | 207 | -13.419 | 20.439 | -0.544 | 1.00 | 74.00 | A | C |
| ATOM | 651 | CD1 | TYR | A | 207 | -14.086 | 19.590 | -1.416 | 1.00 | 71.96 | A | C |

Figure 3K

```
ATOM    652  CE1 TYR A 207     -14.806  20.085  -2.488  1.00  77.80      A  C
ATOM    653  CD2 TYR A 207     -13.492  21.805  -0.771  1.00  76.62      A  C
ATOM    654  CE2 TYR A 207     -14.209  22.315  -1.842  1.00  83.65      A  C
ATOM    655  CZ  TYR A 207     -14.861  21.452  -2.699  1.00  84.30      A  C
ATOM    656  OH  TYR A 207     -15.545  21.960  -3.780  1.00  94.32      A  O
ATOM    657  C   TYR A 207     -10.445  19.843   1.789  1.00  84.31      A  C
ATOM    658  O   TYR A 207     -10.427  18.654   2.148  1.00  84.87      A  O
ATOM    659  N   LEU A 208      -9.866  20.827   2.467  1.00  85.26      A  N
ATOM    660  CA  LEU A 208      -9.154  20.605   3.711  1.00  88.23      A  C
ATOM    661  CB  LEU A 208      -7.856  21.419   3.728  1.00  91.53      A  C
ATOM    662  CG  LEU A 208      -6.614  20.869   3.023  1.00  91.59      A  C
ATOM    663  CD1 LEU A 208      -5.543  21.939   2.902  1.00  93.02      A  C
ATOM    664  CD2 LEU A 208      -6.081  19.710   3.800  1.00  95.04      A  C
ATOM    665  C   LEU A 208     -10.047  21.035   4.877  1.00  86.49      A  C
ATOM    666  O   LEU A 208     -10.451  22.200   4.952  1.00  88.88      A  O
ATOM    667  N   ILE A 209     -10.367  20.092   5.765  1.00  79.00      A  N
ATOM    668  CA  ILE A 209     -11.189  20.375   6.934  1.00  67.40      A  C
ATOM    669  CB  ILE A 209     -12.081  19.162   7.322  1.00  65.42      A  C
ATOM    670  CG2 ILE A 209     -12.945  19.503   8.521  1.00  68.14      A  C
ATOM    671  CG1 ILE A 209     -13.012  18.784   6.181  1.00  66.25      A  C
ATOM    672  CD1 ILE A 209     -14.057  17.742   6.577  1.00  58.82      A  C
ATOM    673  C   ILE A 209     -10.233  20.633   8.090  1.00  61.72      A  C
ATOM    674  O   ILE A 209      -9.473  19.750   8.443  1.00  63.43      A  O
ATOM    675  N   LEU A 210     -10.254  21.821   8.686  1.00  53.29      A  N
ATOM    676  CA  LEU A 210      -9.357  22.083   9.807  1.00  43.66      A  C
ATOM    677  CB  LEU A 210      -8.173  22.942   9.380  1.00  51.28      A  C
ATOM    678  CG  LEU A 210      -7.483  22.794   8.036  1.00  53.50      A  C
ATOM    679  CD1 LEU A 210      -8.439  23.312   6.985  1.00  54.60      A  C
ATOM    680  CD2 LEU A 210      -6.166  23.592   8.016  1.00  53.47      A  C
ATOM    681  C   LEU A 210     -10.012  22.797  10.968  1.00  39.82      A  C
ATOM    682  O   LEU A 210     -11.121  23.297  10.861  1.00  40.71      A  O
ATOM    683  N   GLU A 211      -9.286  22.852  12.077  1.00  38.14      A  N
ATOM    684  CA  GLU A 211      -9.716  23.551  13.277  1.00  35.96      A  C
ATOM    685  CB  GLU A 211      -8.543  23.628  14.274  1.00  32.26      A  C
ATOM    686  CG  GLU A 211      -8.902  23.950  15.735  1.00  33.26      A  C
ATOM    687  CD  GLU A 211      -7.725  23.765  16.715  1.00  33.19      A  C
ATOM    688  OE1 GLU A 211      -6.927  22.822  16.527  1.00  33.06      A  O
ATOM    689  OE2 GLU A 211      -7.601  24.545  17.688  1.00  36.20      A  O
ATOM    690  C   GLU A 211     -10.072  24.947  12.771  1.00  35.87      A  C
ATOM    691  O   GLU A 211      -9.721  25.315  11.648  1.00  30.07      A  O
ATOM    692  N   TYR A 212     -10.792  25.714  13.578  1.00  37.47      A  N
ATOM    693  CA  TYR A 212     -11.163  27.077  13.211  1.00  38.73      A  C
ATOM    694  CB  TYR A 212     -12.691  27.185  12.995  1.00  42.94      A  C
ATOM    695  CG  TYR A 212     -13.252  28.595  13.146  1.00  45.80      A  C
ATOM    696  CD1 TYR A 212     -12.874  29.628  12.282  1.00  47.17      A  C
ATOM    697  CE1 TYR A 212     -13.312  30.937  12.495  1.00  46.25      A  C
ATOM    698  CD2 TYR A 212     -14.092  28.908  14.216  1.00  45.65      A  C
ATOM    699  CE2 TYR A 212     -14.530  30.204  14.439  1.00  46.16      A  C
ATOM    700  CZ  TYR A 212     -14.137  31.220  13.587  1.00  45.98      A  C
ATOM    701  OH  TYR A 212     -14.529  32.516  13.887  1.00  43.32      A  O
ATOM    702  C   TYR A 212     -10.708  27.955  14.369  1.00  35.32      A  C
ATOM    703  O   TYR A 212     -10.797  27.559  15.525  1.00  28.60      A  O
ATOM    704  N   ALA A 213     -10.197  29.133  14.059  1.00  36.72      A  N
ATOM    705  CA  ALA A 213      -9.743  30.031  15.106  1.00  37.52      A  C
ATOM    706  CB  ALA A 213      -8.250  30.212  15.022  1.00  42.50      A  C
ATOM    707  C   ALA A 213     -10.440  31.368  14.984  1.00  39.83      A  C
ATOM    708  O   ALA A 213     -10.195  32.134  14.057  1.00  34.00      A  O
ATOM    709  N   PRO A 214     -11.309  31.677  15.945  1.00  46.72      A  N
ATOM    710  CD  PRO A 214     -11.495  30.880  17.169  1.00  50.90      A  C
ATOM    711  CA  PRO A 214     -12.097  32.912  16.012  1.00  46.86      A  C
ATOM    712  CB  PRO A 214     -13.024  32.647  17.185  1.00  50.42      A  C
```

Figure 3L

| ATOM | 713 | CG | PRO | A | 214 | -12.114 | 31.885 | 18.110 | 1.00 | 51.64 | A | C |
|---|---|---|---|---|---|---|---|---|---|---|---|---|
| ATOM | 714 | C | PRO | A | 214 | -11.338 | 34.225 | 16.196 | 1.00 | 43.43 | A | C |
| ATOM | 715 | O | PRO | A | 214 | -11.694 | 35.250 | 15.607 | 1.00 | 40.84 | A | O |
| ATOM | 716 | N | LEU | A | 215 | -10.295 | 34.207 | 17.009 | 1.00 | 38.39 | A | N |
| ATOM | 717 | CA | LEU | A | 215 | -9.584 | 35.433 | 17.265 | 1.00 | 37.94 | A | C |
| ATOM | 718 | CB | LEU | A | 215 | -8.760 | 35.261 | 18.520 | 1.00 | 44.50 | A | C |
| ATOM | 719 | CG | LEU | A | 215 | -9.598 | 35.763 | 19.680 | 1.00 | 48.05 | A | C |
| ATOM | 720 | CD1 | LEU | A | 215 | -8.962 | 35.366 | 20.993 | 1.00 | 56.16 | A | C |
| ATOM | 721 | CD2 | LEU | A | 215 | -9.736 | 37.287 | 19.544 | 1.00 | 47.41 | A | C |
| ATOM | 722 | C | LEU | A | 215 | -8.749 | 36.047 | 16.161 | 1.00 | 38.31 | A | C |
| ATOM | 723 | O | LEU | A | 215 | -8.123 | 37.084 | 16.363 | 1.00 | 43.75 | A | O |
| ATOM | 724 | N | GLY | A | 216 | -8.748 | 35.436 | 14.990 | 1.00 | 38.55 | A | N |
| ATOM | 725 | CA | GLY | A | 216 | -7.960 | 35.994 | 13.902 | 1.00 | 48.83 | A | C |
| ATOM | 726 | C | GLY | A | 216 | -6.483 | 35.611 | 13.916 | 1.00 | 51.10 | A | C |
| ATOM | 727 | O | GLY | A | 216 | -6.014 | 34.856 | 14.784 | 1.00 | 48.91 | A | O |
| ATOM | 728 | N | THR | A | 217 | -5.731 | 36.142 | 12.959 | 1.00 | 49.53 | A | N |
| ATOM | 729 | CA | THR | A | 217 | -4.320 | 35.812 | 12.883 | 1.00 | 44.63 | A | C |
| ATOM | 730 | CB | THR | A | 217 | -3.917 | 35.773 | 11.417 | 1.00 | 38.70 | A | C |
| ATOM | 731 | OG1 | THR | A | 217 | -2.575 | 35.315 | 11.301 | 1.00 | 44.10 | A | O |
| ATOM | 732 | CG2 | THR | A | 217 | -4.048 | 37.126 | 10.807 | 1.00 | 38.24 | A | C |
| ATOM | 733 | C | THR | A | 217 | -3.397 | 36.753 | 13.700 | 1.00 | 44.78 | A | C |
| ATOM | 734 | O | THR | A | 217 | -3.627 | 37.961 | 13.768 | 1.00 | 42.48 | A | O |
| ATOM | 735 | N | VAL | A | 218 | -2.367 | 36.186 | 14.333 | 1.00 | 46.56 | A | N |
| ATOM | 736 | CA | VAL | A | 218 | -1.401 | 36.946 | 15.146 | 1.00 | 46.39 | A | C |
| ATOM | 737 | CB | VAL | A | 218 | -0.164 | 36.066 | 15.514 | 1.00 | 44.78 | A | C |
| ATOM | 738 | CG1 | VAL | A | 218 | 1.071 | 36.935 | 15.664 | 1.00 | 44.70 | A | C |
| ATOM | 739 | CG2 | VAL | A | 218 | -0.417 | 35.318 | 16.818 | 1.00 | 44.46 | A | C |
| ATOM | 740 | C | VAL | A | 218 | -0.906 | 38.220 | 14.453 | 1.00 | 44.26 | A | C |
| ATOM | 741 | O | VAL | A | 218 | -0.460 | 39.177 | 15.100 | 1.00 | 39.89 | A | O |
| ATOM | 742 | N | TYR | A | 219 | -0.983 | 38.206 | 13.130 | 1.00 | 44.17 | A | N |
| ATOM | 743 | CA | TYR | A | 219 | -0.558 | 39.329 | 12.327 | 1.00 | 48.66 | A | C |
| ATOM | 744 | CB | TYR | A | 219 | -0.650 | 38.959 | 10.846 | 1.00 | 51.43 | A | C |
| ATOM | 745 | CG | TYR | A | 219 | -0.229 | 40.036 | 9.865 | 1.00 | 58.02 | A | C |
| ATOM | 746 | CD1 | TYR | A | 219 | 1.071 | 40.553 | 9.861 | 1.00 | 63.18 | A | C |
| ATOM | 747 | CE1 | TYR | A | 219 | 1.476 | 41.499 | 8.895 | 1.00 | 65.99 | A | C |
| ATOM | 748 | CD2 | TYR | A | 219 | -1.117 | 40.492 | 8.892 | 1.00 | 61.04 | A | C |
| ATOM | 749 | CE2 | TYR | A | 219 | -0.728 | 41.432 | 7.929 | 1.00 | 67.96 | A | C |
| ATOM | 750 | CZ | TYR | A | 219 | 0.565 | 41.931 | 7.931 | 1.00 | 67.88 | A | C |
| ATOM | 751 | OH | TYR | A | 219 | 0.919 | 42.846 | 6.959 | 1.00 | 62.74 | A | O |
| ATOM | 752 | C | TYR | A | 219 | -1.488 | 40.475 | 12.652 | 1.00 | 51.83 | A | C |
| ATOM | 753 | O | TYR | A | 219 | -1.091 | 41.438 | 13.297 | 1.00 | 50.71 | A | O |
| ATOM | 754 | N | ARG | A | 220 | -2.739 | 40.352 | 12.222 | 1.00 | 59.10 | A | N |
| ATOM | 755 | CA | ARG | A | 220 | -3.742 | 41.396 | 12.451 | 1.00 | 63.20 | A | C |
| ATOM | 756 | CB | ARG | A | 220 | -5.161 | 40.893 | 12.078 | 1.00 | 66.35 | A | C |
| ATOM | 757 | CG | ARG | A | 220 | -5.298 | 40.216 | 10.682 | 1.00 | 66.02 | A | C |
| ATOM | 758 | CD | ARG | A | 220 | -6.625 | 39.399 | 10.587 | 1.00 | 64.68 | A | C |
| ATOM | 759 | NE | ARG | A | 220 | -6.675 | 38.338 | 9.554 | 1.00 | 56.48 | A | N |
| ATOM | 760 | CZ | ARG | A | 220 | -6.460 | 38.513 | 8.243 | 1.00 | 52.81 | A | C |
| ATOM | 761 | NH1 | ARG | A | 220 | -6.542 | 37.488 | 7.393 | 1.00 | 38.03 | A | N |
| ATOM | 762 | NH2 | ARG | A | 220 | -6.138 | 39.714 | 7.780 | 1.00 | 53.07 | A | N |
| ATOM | 763 | C | ARG | A | 220 | -3.709 | 41.848 | 13.915 | 1.00 | 61.93 | A | C |
| ATOM | 764 | O | ARG | A | 220 | -4.010 | 43.001 | 14.219 | 1.00 | 59.82 | A | O |
| ATOM | 765 | N | GLU | A | 221 | -3.327 | 40.947 | 14.816 | 1.00 | 61.29 | A | N |
| ATOM | 766 | CA | GLU | A | 221 | -3.280 | 41.295 | 16.227 | 1.00 | 62.35 | A | C |
| ATOM | 767 | CB | GLU | A | 221 | -3.250 | 40.042 | 17.108 | 1.00 | 68.29 | A | C |
| ATOM | 768 | CG | GLU | A | 221 | -3.221 | 40.361 | 18.597 | 1.00 | 78.85 | A | C |
| ATOM | 769 | CD | GLU | A | 221 | -4.473 | 41.087 | 19.054 | 1.00 | 84.92 | A | C |
| ATOM | 770 | OE1 | GLU | A | 221 | -5.038 | 41.842 | 18.240 | 1.00 | 92.38 | A | O |
| ATOM | 771 | OE2 | GLU | A | 221 | -4.895 | 40.915 | 20.219 | 1.00 | 84.44 | A | O |
| ATOM | 772 | C | GLU | A | 221 | -2.066 | 42.146 | 16.536 | 1.00 | 59.60 | A | C |
| ATOM | 773 | O | GLU | A | 221 | -2.089 | 42.962 | 17.456 | 1.00 | 56.87 | A | O |

Figure 3M

| ATOM | 774 | N | LEU | A | 222 | -1.010 | 41.956 | 15.756 | 1.00 | 57.41 | A | N |
| --- | --- | --- | --- | --- | --- | --- | --- | --- | --- | --- | --- | --- |
| ATOM | 775 | CA | LEU | A | 222 | 0.238 | 42.683 | 15.954 | 1.00 | 55.11 | A | C |
| ATOM | 776 | CB | LEU | A | 222 | 1.406 | 41.857 | 15.413 | 1.00 | 57.36 | A | C |
| ATOM | 777 | CG | LEU | A | 222 | 2.816 | 42.453 | 15.339 | 1.00 | 58.26 | A | C |
| ATOM | 778 | CD1 | LEU | A | 222 | 3.193 | 43.149 | 16.621 | 1.00 | 58.09 | A | C |
| ATOM | 779 | CD2 | LEU | A | 222 | 3.793 | 41.320 | 15.035 | 1.00 | 60.99 | A | C |
| ATOM | 780 | C | LEU | A | 222 | 0.274 | 44.078 | 15.358 | 1.00 | 52.81 | A | C |
| ATOM | 781 | O | LEU | A | 222 | 1.032 | 44.927 | 15.807 | 1.00 | 54.33 | A | O |
| ATOM | 782 | N | GLN | A | 223 | -0.522 | 44.329 | 14.336 | 1.00 | 53.36 | A | N |
| ATOM | 783 | CA | GLN | A | 223 | -0.521 | 45.667 | 13.778 | 1.00 | 56.35 | A | C |
| ATOM | 784 | CB | GLN | A | 223 | -0.848 | 45.633 | 12.293 | 1.00 | 60.52 | A | C |
| ATOM | 785 | CG | GLN | A | 223 | -2.030 | 44.818 | 11.973 | 1.00 | 62.89 | A | C |
| ATOM | 786 | CD | GLN | A | 223 | -1.956 | 44.324 | 10.575 | 1.00 | 69.02 | A | C |
| ATOM | 787 | OE1 | GLN | A | 223 | -2.749 | 43.471 | 10.162 | 1.00 | 76.87 | A | O |
| ATOM | 788 | NE2 | GLN | A | 223 | -0.996 | 44.854 | 9.813 | 1.00 | 68.83 | A | N |
| ATOM | 789 | C | GLN | A | 223 | -1.513 | 46.554 | 14.524 | 1.00 | 53.22 | A | C |
| ATOM | 790 | O | GLN | A | 223 | -1.449 | 47.780 | 14.435 | 1.00 | 51.68 | A | O |
| ATOM | 791 | N | LYS | A | 224 | -2.431 | 45.949 | 15.269 | 1.00 | 52.10 | A | N |
| ATOM | 792 | CA | LYS | A | 224 | -3.372 | 46.765 | 16.002 | 1.00 | 54.36 | A | C |
| ATOM | 793 | CB | LYS | A | 224 | -4.656 | 45.990 | 16.309 | 1.00 | 57.97 | A | C |
| ATOM | 794 | CG | LYS | A | 224 | -5.782 | 46.375 | 15.337 | 1.00 | 64.10 | A | C |
| ATOM | 795 | CD | LYS | A | 224 | -6.925 | 45.346 | 15.242 | 1.00 | 69.79 | A | C |
| ATOM | 796 | CE | LYS | A | 224 | -7.985 | 45.478 | 16.341 | 1.00 | 76.21 | A | C |
| ATOM | 797 | NZ | LYS | A | 224 | -9.076 | 44.471 | 16.158 | 1.00 | 70.29 | A | N |
| ATOM | 798 | C | LYS | A | 224 | -2.713 | 47.308 | 17.258 | 1.00 | 51.88 | A | C |
| ATOM | 799 | O | LYS | A | 224 | -2.807 | 48.513 | 17.529 | 1.00 | 53.76 | A | O |
| ATOM | 800 | N | LEU | A | 225 | -2.009 | 46.461 | 18.006 | 1.00 | 43.94 | A | N |
| ATOM | 801 | CA | LEU | A | 225 | -1.350 | 46.945 | 19.219 | 1.00 | 42.30 | A | C |
| ATOM | 802 | CB | LEU | A | 225 | -1.356 | 45.869 | 20.289 | 1.00 | 45.89 | A | C |
| ATOM | 803 | CG | LEU | A | 225 | -2.669 | 45.751 | 21.040 | 1.00 | 53.53 | A | C |
| ATOM | 804 | CD1 | LEU | A | 225 | -3.776 | 45.497 | 20.043 | 1.00 | 54.36 | A | C |
| ATOM | 805 | CD2 | LEU | A | 225 | -2.593 | 44.629 | 22.063 | 1.00 | 62.84 | A | C |
| ATOM | 806 | C | LEU | A | 225 | 0.079 | 47.462 | 19.038 | 1.00 | 42.71 | A | C |
| ATOM | 807 | O | LEU | A | 225 | 0.768 | 47.715 | 20.020 | 1.00 | 41.91 | A | O |
| ATOM | 808 | N | SER | A | 226 | 0.515 | 47.630 | 17.791 | 1.00 | 41.46 | A | N |
| ATOM | 809 | CA | SER | A | 226 | 1.864 | 48.108 | 17.480 | 1.00 | 40.21 | A | C |
| ATOM | 810 | CB | SER | A | 226 | 2.152 | 49.435 | 18.192 | 1.00 | 43.40 | A | C |
| ATOM | 811 | OG | SER | A | 226 | 3.073 | 50.238 | 17.456 | 1.00 | 41.30 | A | O |
| ATOM | 812 | C | SER | A | 226 | 2.911 | 47.068 | 17.869 | 1.00 | 41.79 | A | C |
| ATOM | 813 | O | SER | A | 226 | 3.605 | 46.532 | 17.002 | 1.00 | 45.18 | A | O |
| ATOM | 814 | N | LYS | A | 227 | 3.038 | 46.789 | 19.162 | 1.00 | 42.45 | A | N |
| ATOM | 815 | CA | LYS | A | 227 | 3.988 | 45.782 | 19.622 | 1.00 | 46.59 | A | C |
| ATOM | 816 | CB | LYS | A | 227 | 5.371 | 46.404 | 19.887 | 1.00 | 50.09 | A | C |
| ATOM | 817 | CG | LYS | A | 227 | 5.591 | 46.911 | 21.306 | 1.00 | 59.10 | A | C |
| ATOM | 818 | CD | LYS | A | 227 | 6.713 | 46.143 | 22.027 | 1.00 | 59.92 | A | C |
| ATOM | 819 | CE | LYS | A | 227 | 6.881 | 46.550 | 23.500 | 1.00 | 65.32 | A | C |
| ATOM | 820 | NZ | LYS | A | 227 | 7.978 | 45.831 | 24.203 | 1.00 | 65.66 | A | N |
| ATOM | 821 | C | LYS | A | 227 | 3.441 | 45.120 | 20.884 | 1.00 | 47.16 | A | C |
| ATOM | 822 | O | LYS | A | 227 | 2.670 | 45.722 | 21.613 | 1.00 | 44.36 | A | O |
| ATOM | 823 | N | PHE | A | 228 | 3.834 | 43.881 | 21.146 | 1.00 | 52.52 | A | N |
| ATOM | 824 | CA | PHE | A | 228 | 3.340 | 43.174 | 22.325 | 1.00 | 54.36 | A | C |
| ATOM | 825 | CB | PHE | A | 228 | 3.300 | 41.663 | 22.104 | 1.00 | 51.99 | A | C |
| ATOM | 826 | CG | PHE | A | 228 | 2.668 | 41.247 | 20.828 | 1.00 | 50.48 | A | C |
| ATOM | 827 | CD1 | PHE | A | 228 | 2.041 | 42.157 | 20.016 | 1.00 | 48.97 | A | C |
| ATOM | 828 | CD2 | PHE | A | 228 | 2.722 | 39.926 | 20.434 | 1.00 | 51.71 | A | C |
| ATOM | 829 | CE1 | PHE | A | 228 | 1.488 | 41.756 | 18.836 | 1.00 | 54.43 | A | C |
| ATOM | 830 | CE2 | PHE | A | 228 | 2.169 | 39.520 | 19.252 | 1.00 | 51.46 | A | C |
| ATOM | 831 | CZ | PHE | A | 228 | 1.550 | 40.434 | 18.448 | 1.00 | 53.61 | A | C |
| ATOM | 832 | C | PHE | A | 228 | 4.146 | 43.396 | 23.588 | 1.00 | 54.18 | A | C |
| ATOM | 833 | O | PHE | A | 228 | 5.382 | 43.406 | 23.568 | 1.00 | 53.36 | A | O |
| ATOM | 834 | N | ASP | A | 229 | 3.422 | 43.544 | 24.695 | 1.00 | 56.23 | A | N |

Figure 3N

| ATOM | 835 | CA | ASP | A | 229 | 4.047 | 43.713 | 25.995 | 1.00 | 58.19 | A | C |
|---|---|---|---|---|---|---|---|---|---|---|---|---|
| ATOM | 836 | CB | ASP | A | 229 | 3.026 | 44.162 | 27.064 | 1.00 | 62.05 | A | C |
| ATOM | 837 | CG | ASP | A | 229 | 1.848 | 43.211 | 27.197 | 1.00 | 62.68 | A | C |
| ATOM | 838 | OD1 | ASP | A | 229 | 0.846 | 43.413 | 26.469 | 1.00 | 58.88 | A | O |
| ATOM | 839 | OD2 | ASP | A | 229 | 1.928 | 42.264 | 28.020 | 1.00 | 58.91 | A | O |
| ATOM | 840 | C | ASP | A | 229 | 4.690 | 42.382 | 26.388 | 1.00 | 53.12 | A | C |
| ATOM | 841 | O | ASP | A | 229 | 4.406 | 41.332 | 25.810 | 1.00 | 48.18 | A | O |
| ATOM | 842 | N | GLU | A | 230 | 5.557 | 42.440 | 27.380 | 1.00 | 50.98 | A | N |
| ATOM | 843 | CA | GLU | A | 230 | 6.273 | 41.275 | 27.808 | 1.00 | 60.44 | A | C |
| ATOM | 844 | CB | GLU | A | 230 | 7.321 | 41.708 | 28.818 | 1.00 | 67.90 | A | C |
| ATOM | 845 | CG | GLU | A | 230 | 8.243 | 42.757 | 28.224 | 1.00 | 79.97 | A | C |
| ATOM | 846 | CD | GLU | A | 230 | 9.421 | 43.059 | 29.103 | 1.00 | 84.27 | A | C |
| ATOM | 847 | OE1 | GLU | A | 230 | 10.178 | 42.114 | 29.415 | 1.00 | 86.02 | A | O |
| ATOM | 848 | OE2 | GLU | A | 230 | 9.582 | 44.244 | 29.475 | 1.00 | 88.59 | A | O |
| ATOM | 849 | C | GLU | A | 230 | 5.386 | 40.164 | 28.326 | 1.00 | 66.70 | A | C |
| ATOM | 850 | O | GLU | A | 230 | 5.821 | 39.017 | 28.467 | 1.00 | 70.84 | A | O |
| ATOM | 851 | N | GLN | A | 231 | 4.131 | 40.489 | 28.605 | 1.00 | 71.78 | A | N |
| ATOM | 852 | CA | GLN | A | 231 | 3.213 | 39.453 | 29.060 | 1.00 | 74.62 | A | C |
| ATOM | 853 | CB | GLN | A | 231 | 1.868 | 40.053 | 29.503 | 1.00 | 79.18 | A | C |
| ATOM | 854 | CG | GLN | A | 231 | 1.872 | 40.766 | 30.848 | 1.00 | 87.57 | A | C |
| ATOM | 855 | CD | GLN | A | 231 | 3.040 | 41.713 | 31.007 | 1.00 | 94.32 | A | C |
| ATOM | 856 | OE1 | GLN | A | 231 | 4.181 | 41.286 | 31.224 | 1.00 | 99.33 | A | O |
| ATOM | 857 | NE2 | GLN | A | 231 | 2.768 | 43.009 | 30.892 | 1.00 | 92.95 | A | N |
| ATOM | 858 | C | GLN | A | 231 | 3.002 | 38.609 | 27.810 | 1.00 | 71.80 | A | C |
| ATOM | 859 | O | GLN | A | 231 | 3.678 | 37.599 | 27.584 | 1.00 | 68.85 | A | O |
| ATOM | 860 | N | ARG | A | 232 | 2.074 | 39.073 | 26.985 | 1.00 | 69.31 | A | N |
| ATOM | 861 | CA | ARG | A | 232 | 1.721 | 38.420 | 25.741 | 1.00 | 69.56 | A | C |
| ATOM | 862 | CB | ARG | A | 232 | 1.056 | 39.454 | 24.845 | 1.00 | 76.48 | A | C |
| ATOM | 863 | CG | ARG | A | 232 | 0.233 | 38.921 | 23.715 | 1.00 | 91.88 | A | C |
| ATOM | 864 | CD | ARG | A | 232 | 0.172 | 39.986 | 22.631 | 1.00 | 101.76 | A | C |
| ATOM | 865 | NE | ARG | A | 232 | -1.157 | 40.160 | 22.044 | 1.00 | 107.10 | A | N |
| ATOM | 866 | CZ | ARG | A | 232 | -2.141 | 40.901 | 22.567 | 1.00 | 107.88 | A | C |
| ATOM | 867 | NH1 | ARG | A | 232 | -1.972 | 41.563 | 23.713 | 1.00 | 106.99 | A | N |
| ATOM | 868 | NH2 | ARG | A | 232 | -3.304 | 40.991 | 21.928 | 1.00 | 105.36 | A | N |
| ATOM | 869 | C | ARG | A | 232 | 2.937 | 37.789 | 25.024 | 1.00 | 66.57 | A | C |
| ATOM | 870 | O | ARG | A | 232 | 3.040 | 36.553 | 24.910 | 1.00 | 63.64 | A | O |
| ATOM | 871 | N | THR | A | 233 | 3.866 | 38.632 | 24.566 | 1.00 | 63.52 | A | N |
| ATOM | 872 | CA | THR | A | 233 | 5.045 | 38.156 | 23.833 | 1.00 | 61.82 | A | C |
| ATOM | 873 | CB | THR | A | 233 | 6.067 | 39.303 | 23.614 | 1.00 | 61.91 | A | C |
| ATOM | 874 | OG1 | THR | A | 233 | 7.241 | 38.802 | 22.959 | 1.00 | 59.56 | A | O |
| ATOM | 875 | CG2 | THR | A | 233 | 6.447 | 39.902 | 24.912 | 1.00 | 62.29 | A | C |
| ATOM | 876 | C | THR | A | 233 | 5.788 | 36.938 | 24.396 | 1.00 | 59.02 | A | C |
| ATOM | 877 | O | THR | A | 233 | 6.216 | 36.063 | 23.636 | 1.00 | 55.98 | A | O |
| ATOM | 878 | N | ALA | A | 234 | 5.919 | 36.853 | 25.714 | 1.00 | 56.46 | A | N |
| ATOM | 879 | CA | ALA | A | 234 | 6.665 | 35.751 | 26.299 | 1.00 | 50.51 | A | C |
| ATOM | 880 | CB | ALA | A | 234 | 7.219 | 36.171 | 27.625 | 1.00 | 47.88 | A | C |
| ATOM | 881 | C | ALA | A | 234 | 5.934 | 34.433 | 26.439 | 1.00 | 44.56 | A | C |
| ATOM | 882 | O | ALA | A | 234 | 6.534 | 33.373 | 26.295 | 1.00 | 43.41 | A | O |
| ATOM | 883 | N | THR | A | 235 | 4.643 | 34.476 | 26.715 | 1.00 | 36.78 | A | N |
| ATOM | 884 | CA | THR | A | 235 | 3.925 | 33.232 | 26.862 | 1.00 | 38.11 | A | C |
| ATOM | 885 | CB | THR | A | 235 | 2.643 | 33.416 | 27.581 | 1.00 | 41.37 | A | C |
| ATOM | 886 | OG1 | THR | A | 235 | 1.852 | 32.249 | 27.370 | 1.00 | 49.66 | A | O |
| ATOM | 887 | CG2 | THR | A | 235 | 1.911 | 34.627 | 27.053 | 1.00 | 41.45 | A | C |
| ATOM | 888 | C | THR | A | 235 | 3.617 | 32.592 | 25.522 | 1.00 | 38.38 | A | C |
| ATOM | 889 | O | THR | A | 235 | 3.267 | 31.415 | 25.450 | 1.00 | 41.95 | A | O |
| ATOM | 890 | N | TYR | A | 236 | 3.727 | 33.383 | 24.459 | 1.00 | 40.40 | A | N |
| ATOM | 891 | CA | TYR | A | 236 | 3.499 | 32.880 | 23.102 | 1.00 | 45.47 | A | C |
| ATOM | 892 | CB | TYR | A | 236 | 3.483 | 34.037 | 22.085 | 1.00 | 55.45 | A | C |
| ATOM | 893 | CG | TYR | A | 236 | 2.148 | 34.722 | 21.894 | 1.00 | 66.59 | A | C |
| ATOM | 894 | CD1 | TYR | A | 236 | 1.115 | 34.559 | 22.818 | 1.00 | 70.13 | A | C |
| ATOM | 895 | CE1 | TYR | A | 236 | -0.062 | 35.270 | 22.700 | 1.00 | 74.91 | A | C |

Figure 30

```
ATOM    896  CD2 TYR A 236       1.959  35.609  20.838  1.00  71.57      A  C
ATOM    897  CE2 TYR A 236       0.792  36.328  20.708  1.00  75.91      A  C
ATOM    898  CZ  TYR A 236      -0.220  36.166  21.642  1.00  77.30      A  C
ATOM    899  OH  TYR A 236      -1.367  36.937  21.540  1.00  81.01      A  O
ATOM    900  C   TYR A 236       4.632  31.911  22.735  1.00  38.50      A  C
ATOM    901  O   TYR A 236       4.406  30.849  22.156  1.00  33.41      A  O
ATOM    902  N   ILE A 237       5.853  32.301  23.078  1.00  35.01      A  N
ATOM    903  CA  ILE A 237       7.016  31.491  22.793  1.00  31.23      A  C
ATOM    904  CB  ILE A 237       8.271  32.259  23.155  1.00  19.44      A  C
ATOM    905  CG2 ILE A 237       9.479  31.479  22.761  1.00  23.51      A  C
ATOM    906  CG1 ILE A 237       8.289  33.554  22.369  1.00  14.01      A  C
ATOM    907  CD1 ILE A 237       8.265  33.312  20.885  1.00  12.88      A  C
ATOM    908  C   ILE A 237       6.945  30.151  23.525  1.00  32.97      A  C
ATOM    909  O   ILE A 237       7.252  29.103  22.943  1.00  31.27      A  O
ATOM    910  N   THR A 238       6.524  30.181  24.789  1.00  34.53      A  N
ATOM    911  CA  THR A 238       6.373  28.939  25.552  1.00  44.20      A  C
ATOM    912  CB  THR A 238       5.929  29.221  27.009  1.00  49.15      A  C
ATOM    913  OG1 THR A 238       4.833  28.369  27.357  1.00  49.73      A  O
ATOM    914  CG2 THR A 238       5.510  30.653  27.155  1.00  53.69      A  C
ATOM    915  C   THR A 238       5.334  28.039  24.860  1.00  47.12      A  C
ATOM    916  O   THR A 238       5.526  26.838  24.738  1.00  44.22      A  O
ATOM    917  N   GLU A 239       4.229  28.624  24.416  1.00  52.02      A  N
ATOM    918  CA  GLU A 239       3.209  27.851  23.715  1.00  58.67      A  C
ATOM    919  CB  GLU A 239       1.980  28.714  23.394  1.00  66.04      A  C
ATOM    920  CG  GLU A 239       1.135  29.121  24.594  1.00  73.68      A  C
ATOM    921  CD  GLU A 239      -0.111  29.911  24.211  1.00  75.31      A  C
ATOM    922  OE1 GLU A 239      -0.912  30.218  25.122  1.00  72.95      A  O
ATOM    923  OE2 GLU A 239      -0.287  30.225  23.012  1.00  73.83      A  O
ATOM    924  C   GLU A 239       3.830  27.400  22.405  1.00  57.67      A  C
ATOM    925  O   GLU A 239       3.566  26.304  21.910  1.00  54.44      A  O
ATOM    926  N   LEU A 240       4.661  28.280  21.854  1.00  57.74      A  N
ATOM    927  CA  LEU A 240       5.349  28.053  20.582  1.00  56.95      A  C
ATOM    928  CB  LEU A 240       6.003  29.359  20.121  1.00  51.97      A  C
ATOM    929  CG  LEU A 240       5.994  29.675  18.636  1.00  51.90      A  C
ATOM    930  CD1 LEU A 240       4.905  28.941  17.871  1.00  57.33      A  C
ATOM    931  CD2 LEU A 240       5.789  31.147  18.551  1.00  50.91      A  C
ATOM    932  C   LEU A 240       6.402  26.958  20.720  1.00  57.51      A  C
ATOM    933  O   LEU A 240       6.397  25.961  19.989  1.00  55.95      A  O
ATOM    934  N   ALA A 241       7.309  27.158  21.663  1.00  59.16      A  N
ATOM    935  CA  ALA A 241       8.354  26.186  21.924  1.00  59.19      A  C
ATOM    936  CB  ALA A 241       9.018  26.495  23.252  1.00  62.26      A  C
ATOM    937  C   ALA A 241       7.753  24.788  21.953  1.00  55.24      A  C
ATOM    938  O   ALA A 241       8.209  23.904  21.262  1.00  50.97      A  O
ATOM    939  N   ASN A 242       6.722  24.598  22.761  1.00  54.53      A  N
ATOM    940  CA  ASN A 242       6.050  23.304  22.873  1.00  54.17      A  C
ATOM    941  CB  ASN A 242       4.878  23.405  23.852  1.00  57.22      A  C
ATOM    942  CG  ASN A 242       5.253  24.087  25.132  1.00  56.71      A  C
ATOM    943  OD1 ASN A 242       4.387  24.637  25.820  1.00  54.75      A  O
ATOM    944  ND2 ASN A 242       6.548  24.055  25.472  1.00  57.66      A  N
ATOM    945  C   ASN A 242       5.504  22.823  21.529  1.00  52.08      A  C
ATOM    946  O   ASN A 242       5.962  21.824  20.977  1.00  48.09      A  O
ATOM    947  N   ALA A 243       4.500  23.527  21.023  1.00  53.90      A  N
ATOM    948  CA  ALA A 243       3.895  23.160  19.759  1.00  59.18      A  C
ATOM    949  CB  ALA A 243       3.119  24.324  19.206  1.00  62.18      A  C
ATOM    950  C   ALA A 243       5.011  22.788  18.813  1.00  60.69      A  C
ATOM    951  O   ALA A 243       4.806  22.104  17.811  1.00  62.87      A  O
ATOM    952  N   LEU A 244       6.201  23.253  19.166  1.00  62.13      A  N
ATOM    953  CA  LEU A 244       7.414  23.031  18.393  1.00  66.20      A  C
ATOM    954  CB  LEU A 244       8.313  24.266  18.569  1.00  63.08      A  C
ATOM    955  CG  LEU A 244       9.123  24.867  17.429  1.00  62.33      A  C
ATOM    956  CD1 LEU A 244       8.524  24.562  16.048  1.00  62.03      A  C
```

Figure 3P

```
ATOM    957  CD2 LEU A 244       9.176  26.345  17.711  1.00   58.66      A C
ATOM    958  C   LEU A 244       8.155  21.732  18.809  1.00   69.75      A C
ATOM    959  O   LEU A 244       8.449  20.870  17.966  1.00   70.85      A O
ATOM    960  N   SER A 245       8.456  21.600  20.099  1.00   73.70      A N
ATOM    961  CA  SER A 245       9.147  20.424  20.611  1.00   78.27      A C
ATOM    962  CB  SER A 245       9.317  20.517  22.127  1.00   84.64      A C
ATOM    963  OG  SER A 245       9.342  19.224  22.711  1.00   94.91      A O
ATOM    964  C   SER A 245       8.368  19.176  20.271  1.00   80.42      A C
ATOM    965  O   SER A 245       8.937  18.212  19.789  1.00   78.52      A O
ATOM    966  N   TYR A 246       7.066  19.188  20.530  1.00   86.84      A N
ATOM    967  CA  TYR A 246       6.244  18.030  20.218  1.00   96.04      A C
ATOM    968  CB  TYR A 246       4.767  18.314  20.504  1.00   98.89      A C
ATOM    969  CG  TYR A 246       3.818  17.390  19.763  1.00  105.13      A C
ATOM    970  CD1 TYR A 246       3.458  16.145  20.281  1.00  107.12      A C
ATOM    971  CE1 TYR A 246       2.608  15.281  19.557  1.00  110.61      A C
ATOM    972  CD2 TYR A 246       3.312  17.751  18.511  1.00  108.23      A C
ATOM    973  CE2 TYR A 246       2.475  16.905  17.786  1.00  109.34      A C
ATOM    974  CZ  TYR A 246       2.122  15.672  18.305  1.00  110.30      A C
ATOM    975  OH  TYR A 246       1.288  14.846  17.570  1.00  106.48      A O
ATOM    976  C   TYR A 246       6.426  17.668  18.741  1.00  102.38      A C
ATOM    977  O   TYR A 246       6.118  16.547  18.333  1.00  106.46      A O
ATOM    978  N   CYS A 247       6.907  18.613  17.934  1.00  105.78      A N
ATOM    979  CA  CYS A 247       7.146  18.333  16.518  1.00  106.40      A C
ATOM    980  CB  CYS A 247       6.990  19.592  15.667  1.00  110.42      A C
ATOM    981  SG  CYS A 247       5.359  19.737  14.910  1.00  117.71      A S
ATOM    982  C   CYS A 247       8.554  17.784  16.384  1.00  103.70      A C
ATOM    983  O   CYS A 247       8.773  16.760  15.748  1.00  104.03      A O
ATOM    984  N   HIS A 248       9.506  18.466  17.006  1.00  100.96      A N
ATOM    985  CA  HIS A 248      10.896  18.034  16.984  1.00   99.23      A C
ATOM    986  CB  HIS A 248      11.753  18.969  17.851  1.00   99.09      A C
ATOM    987  CG  HIS A 248      12.319  20.144  17.114  1.00   96.77      A C
ATOM    988  CD2 HIS A 248      13.578  20.640  17.064  1.00   94.31      A C
ATOM    989  ND1 HIS A 248      11.550  20.972  16.327  1.00   96.50      A N
ATOM    990  CE1 HIS A 248      12.311  21.927  15.825  1.00   92.48      A C
ATOM    991  NE2 HIS A 248      13.545  21.749  16.255  1.00   90.90      A N
ATOM    992  C   HIS A 248      11.043  16.592  17.489  1.00   96.19      A C
ATOM    993  O   HIS A 248      12.014  15.920  17.164  1.00   99.92      A O
ATOM    994  N   SER A 249      10.104  16.115  18.298  1.00   90.24      A N
ATOM    995  CA  SER A 249      10.208  14.747  18.779  1.00   85.03      A C
ATOM    996  CB  SER A 249       9.295  14.492  19.979  1.00   81.64      A C
ATOM    997  OG  SER A 249       8.020  14.022  19.582  1.00   72.88      A O
ATOM    998  C   SER A 249       9.757  13.888  17.629  1.00   85.40      A C
ATOM    999  O   SER A 249      10.546  13.170  17.033  1.00   88.47      A O
ATOM   1000  N   LYS A 250       8.477  13.995  17.307  1.00   83.68      A N
ATOM   1001  CA  LYS A 250       7.860  13.240  16.231  1.00   83.38      A C
ATOM   1002  CB  LYS A 250       6.406  13.692  16.128  1.00   87.13      A C
ATOM   1003  CG  LYS A 250       5.656  13.260  14.913  1.00  100.15      A C
ATOM   1004  CD  LYS A 250       4.607  14.302  14.615  1.00  113.49      A C
ATOM   1005  CE  LYS A 250       5.196  15.727  14.655  1.00  119.58      A C
ATOM   1006  NZ  LYS A 250       5.281  16.284  16.034  1.00  118.84      A N
ATOM   1007  C   LYS A 250       8.597  13.361  14.883  1.00   82.38      A C
ATOM   1008  O   LYS A 250       8.140  12.858  13.857  1.00   81.73      A O
ATOM   1009  N   ARG A 251       9.749  14.018  14.893  1.00   83.73      A N
ATOM   1010  CA  ARG A 251      10.552  14.182  13.690  1.00   89.24      A C
ATOM   1011  CB  ARG A 251      11.148  12.837  13.274  1.00   99.32      A C
ATOM   1012  CG  ARG A 251      12.354  12.457  14.129  1.00  112.74      A C
ATOM   1013  CD  ARG A 251      13.181  11.326  13.532  1.00  122.34      A C
ATOM   1014  NE  ARG A 251      14.512  11.274  14.141  1.00  133.01      A N
ATOM   1015  CZ  ARG A 251      15.436  10.355  13.868  1.00  137.24      A C
ATOM   1016  NH1 ARG A 251      15.186   9.389  12.987  1.00  140.46      A N
ATOM   1017  NH2 ARG A 251      16.615  10.401  14.478  1.00  137.41      A N
```

Figure 3Q

```
ATOM   1018  C    ARG A 251       9.871   14.846   12.503  1.00   88.64      A    C
ATOM   1019  O    ARG A 251       9.440   14.195   11.549  1.00   89.26      A    O
ATOM   1020  N    VAL A 252       9.813   16.171   12.595  1.00   87.34      A    N
ATOM   1021  CA   VAL A 252       9.234   17.054   11.597  1.00   90.39      A    C
ATOM   1022  CB   VAL A 252       7.684   17.004   11.624  1.00   89.80      A    C
ATOM   1023  CG1  VAL A 252       7.120   18.086   10.740  1.00   92.45      A    C
ATOM   1024  CG2  VAL A 252       7.187   15.657   11.131  1.00   88.51      A    C
ATOM   1025  C    VAL A 252       9.718   18.465   11.962  1.00   92.45      A    C
ATOM   1026  O    VAL A 252       9.587   18.896   13.108  1.00   91.52      A    O
ATOM   1027  N    ILE A 253      10.300   19.159   10.984  1.00   97.53      A    N
ATOM   1028  CA   ILE A 253      10.828   20.521   11.152  1.00  100.27      A    C
ATOM   1029  CB   ILE A 253      12.331   20.580   10.828  1.00  105.49      A    C
ATOM   1030  CG2  ILE A 253      12.770   22.012   10.764  1.00  108.25      A    C
ATOM   1031  CG1  ILE A 253      13.144   19.828   11.882  1.00  107.85      A    C
ATOM   1032  CD1  ILE A 253      12.925   18.346   11.889  1.00  108.10      A    C
ATOM   1033  C    ILE A 253      10.111   21.541   10.252  1.00   98.71      A    C
ATOM   1034  O    ILE A 253      10.229   21.513    9.027  1.00   97.73      A    O
ATOM   1035  N    HIS A 254       9.385   22.457   10.876  1.00   98.30      A    N
ATOM   1036  CA   HIS A 254       8.623   23.459   10.150  1.00  101.26      A    C
ATOM   1037  CB   HIS A 254       7.559   24.074   11.067  1.00  102.81      A    C
ATOM   1038  CG   HIS A 254       6.214   23.438   10.939  1.00  108.06      A    C
ATOM   1039  CD2  HIS A 254       5.352   22.973   11.871  1.00  108.21      A    C
ATOM   1040  ND1  HIS A 254       5.604   23.243    9.719  1.00  112.19      A    N
ATOM   1041  CE1  HIS A 254       4.422   22.684    9.904  1.00  111.89      A    C
ATOM   1042  NE2  HIS A 254       4.245   22.511   11.200  1.00  110.82      A    N
ATOM   1043  C    HIS A 254       9.457   24.569    9.555  1.00  102.47      A    C
ATOM   1044  O    HIS A 254      10.219   24.361    8.614  1.00  101.81      A    O
ATOM   1045  N    ARG A 255       9.275   25.748   10.147  1.00  106.28      A    N
ATOM   1046  CA   ARG A 255       9.904   27.020    9.783  1.00  107.89      A    C
ATOM   1047  CB   ARG A 255      11.104   26.811    8.858  1.00  109.62      A    C
ATOM   1054  C    ARG A 255       8.819   27.849    9.074  1.00  107.89      A    C
ATOM   1055  O    ARG A 255       7.612   27.559    9.222  1.00  110.05      A    O
ATOM   1056  N    ASP A 256       9.238   28.866    8.313  1.00  101.96      A    N
ATOM   1057  CA   ASP A 256       8.306   29.725    7.577  1.00   91.62      A    C
ATOM   1058  CB   ASP A 256       7.997   29.112    6.204  1.00   82.66      A    C
ATOM   1062  C    ASP A 256       7.005   29.930    8.365  1.00   87.64      A    C
ATOM   1063  O    ASP A 256       5.895   29.929    7.800  1.00   87.53      A    O
ATOM   1064  N    ILE A 257       7.153   30.049    9.682  1.00   82.63      A    N
ATOM   1065  CA   ILE A 257       6.027   30.299   10.563  1.00   69.93      A    C
ATOM   1066  CB   ILE A 257       6.165   29.535   11.874  1.00   63.21      A    C
ATOM   1067  CG2  ILE A 257       6.295   28.063   11.577  1.00   56.79      A    C
ATOM   1068  CG1  ILE A 257       7.369   30.057   12.656  1.00   55.36      A    C
ATOM   1069  CD1  ILE A 257       7.543   29.435   13.985  1.00   49.65      A    C
ATOM   1070  C    ILE A 257       6.258   31.784   10.799  1.00   67.29      A    C
ATOM   1071  O    ILE A 257       7.376   32.263   10.568  1.00   70.67      A    O
ATOM   1072  N    LYS A 258       5.223   32.510   11.209  1.00   59.09      A    N
ATOM   1073  CA   LYS A 258       5.341   33.938   11.461  1.00   56.36      A    C
ATOM   1074  CB   LYS A 258       6.088   34.635   10.321  1.00   53.62      A    C
ATOM   1075  CG   LYS A 258       5.680   34.194    8.939  1.00   53.49      A    C
ATOM   1076  CD   LYS A 258       6.664   34.694    7.895  1.00   60.51      A    C
ATOM   1077  CE   LYS A 258       6.348   34.115    6.535  1.00   64.60      A    C
ATOM   1078  NZ   LYS A 258       7.444   34.353    5.567  1.00   68.38      A    N
ATOM   1079  C    LYS A 258       3.947   34.489   11.595  1.00   53.82      A    C
ATOM   1080  O    LYS A 258       2.984   33.782   11.345  1.00   51.46      A    O
ATOM   1081  N    PRO A 259       3.822   35.754   12.010  1.00   54.35      A    N
ATOM   1082  CD   PRO A 259       4.921   36.722   12.172  1.00   58.90      A    C
ATOM   1083  CA   PRO A 259       2.536   36.417   12.190  1.00   49.47      A    C
ATOM   1084  CB   PRO A 259       2.894   37.873   11.958  1.00   56.38      A    C
ATOM   1085  CG   PRO A 259       4.206   37.974   12.653  1.00   60.81      A    C
ATOM   1086  C    PRO A 259       1.466   35.921   11.240  1.00   42.86      A    C
ATOM   1087  O    PRO A 259       0.459   35.373   11.650  1.00   37.18      A    O
```

Figure 3R

```
ATOM   1088  N    GLU A 260       1.716  36.115   9.961  1.00  43.06      A    N
ATOM   1089  CA   GLU A 260       0.811  35.712   8.901  1.00  46.11      A    C
ATOM   1090  CB   GLU A 260       1.559  35.828   7.548  1.00  53.53      A    C
ATOM   1091  CG   GLU A 260       2.165  37.243   7.176  1.00  59.82      A    C
ATOM   1092  CD   GLU A 260       3.312  37.752   8.101  1.00  63.40      A    C
ATOM   1093  OE1  GLU A 260       3.721  38.936   7.949  1.00  62.02      A    O
ATOM   1094  OE2  GLU A 260       3.804  36.986   8.972  1.00  59.24      A    O
ATOM   1095  C    GLU A 260       0.229  34.283   9.088  1.00  46.29      A    C
ATOM   1096  O    GLU A 260      -0.933  34.027   8.758  1.00  44.46      A    O
ATOM   1097  N    ASN A 261       1.035  33.360   9.616  1.00  49.66      A    N
ATOM   1098  CA   ASN A 261       0.615  31.964   9.828  1.00  53.24      A    C
ATOM   1099  CB   ASN A 261       1.663  30.963   9.340  1.00  55.31      A    C
ATOM   1100  CG   ASN A 261       1.799  30.939   7.866  1.00  65.18      A    C
ATOM   1101  OD1  ASN A 261       0.809  30.951   7.144  1.00  76.46      A    O
ATOM   1102  ND2  ASN A 261       3.038  30.881   7.391  1.00  68.38      A    N
ATOM   1103  C    ASN A 261       0.334  31.561  11.263  1.00  52.11      A    C
ATOM   1104  O    ASN A 261       0.402  30.374  11.569  1.00  50.99      A    O
ATOM   1105  N    LEU A 262       0.049  32.499  12.155  1.00  47.05      A    N
ATOM   1106  CA   LEU A 262      -0.237  32.093  13.520  1.00  42.96      A    C
ATOM   1107  CB   LEU A 262       0.872  32.576  14.447  1.00  40.51      A    C
ATOM   1108  CG   LEU A 262       2.151  31.839  14.092  1.00  27.59      A    C
ATOM   1109  CD1  LEU A 262       3.266  32.178  15.017  1.00  28.42      A    C
ATOM   1110  CD2  LEU A 262       1.872  30.401  14.205  1.00  18.90      A    C
ATOM   1111  C    LEU A 262      -1.600  32.599  13.974  1.00  41.66      A    C
ATOM   1112  O    LEU A 262      -1.798  33.803  14.131  1.00  43.92      A    O
ATOM   1113  N    LEU A 263      -2.552  31.686  14.154  1.00  38.96      A    N
ATOM   1114  CA   LEU A 263      -3.890  32.063  14.596  1.00  39.47      A    C
ATOM   1115  CB   LEU A 263      -4.899  31.068  14.065  1.00  27.55      A    C
ATOM   1116  CG   LEU A 263      -4.782  31.047  12.577  1.00  18.30      A    C
ATOM   1117  CD1  LEU A 263      -5.591  29.971  11.974  1.00  15.98      A    C
ATOM   1118  CD2  LEU A 263      -5.234  32.385  12.141  1.00   9.45      A    C
ATOM   1119  C    LEU A 263      -3.967  32.084  16.120  1.00  48.24      A    C
ATOM   1120  O    LEU A 263      -3.011  31.746  16.832  1.00  47.09      A    O
ATOM   1121  N    LEU A 264      -5.122  32.466  16.631  1.00  55.21      A    N
ATOM   1122  CA   LEU A 264      -5.299  32.513  18.062  1.00  58.52      A    C
ATOM   1123  CB   LEU A 264      -5.291  33.965  18.508  1.00  55.51      A    C
ATOM   1124  CG   LEU A 264      -4.082  34.643  17.900  1.00  54.53      A    C
ATOM   1125  CD1  LEU A 264      -4.480  35.911  17.209  1.00  50.27      A    C
ATOM   1126  CD2  LEU A 264      -3.078  34.867  18.972  1.00  60.70      A    C
ATOM   1127  C    LEU A 264      -6.637  31.863  18.335  1.00  61.35      A    C
ATOM   1128  O    LEU A 264      -7.548  31.953  17.516  1.00  64.20      A    O
ATOM   1129  N    GLY A 265      -6.759  31.204  19.477  1.00  63.50      A    N
ATOM   1130  CA   GLY A 265      -8.012  30.550  19.802  1.00  64.53      A    C
ATOM   1131  C    GLY A 265      -8.998  31.420  20.557  1.00  68.14      A    C
ATOM   1132  O    GLY A 265      -8.890  32.650  20.562  1.00  65.96      A    O
ATOM   1133  N    SER A 266      -9.979  30.764  21.175  1.00  73.20      A    N
ATOM   1134  CA   SER A 266     -10.994  31.446  21.964  1.00  78.83      A    C
ATOM   1135  CB   SER A 266     -11.977  30.433  22.576  1.00  82.41      A    C
ATOM   1136  OG   SER A 266     -13.120  30.180  21.760  1.00  84.79      A    O
ATOM   1137  C    SER A 266     -10.248  32.143  23.082  1.00  78.54      A    C
ATOM   1138  O    SER A 266     -10.300  33.363  23.228  1.00  76.66      A    O
ATOM   1139  N    ALA A 267      -9.542  31.335  23.861  1.00  79.99      A    N
ATOM   1140  CA   ALA A 267      -8.769  31.812  24.990  1.00  82.59      A    C
ATOM   1141  CB   ALA A 267      -8.210  30.624  25.757  1.00  84.33      A    C
ATOM   1142  C    ALA A 267      -7.641  32.725  24.532  1.00  81.88      A    C
ATOM   1143  O    ALA A 267      -6.983  33.375  25.349  1.00  80.27      A    O
ATOM   1144  N    GLY A 268      -7.427  32.777  23.222  1.00  80.66      A    N
ATOM   1145  CA   GLY A 268      -6.364  33.606  22.683  1.00  77.38      A    C
ATOM   1146  C    GLY A 268      -5.047  32.855  22.545  1.00  77.08      A    C
ATOM   1147  O    GLY A 268      -3.991  33.474  22.420  1.00  73.27      A    O
ATOM   1148  N    GLU A 269      -5.114  31.521  22.569  1.00  78.84      A    N
```

Figure 3S

```
ATOM  1149  CA   GLU A 269      -3.936   30.662   22.436  1.00   79.80      A    C
ATOM  1150  CB   GLU A 269      -4.234   29.253   22.983  1.00   83.52      A    C
ATOM  1151  CG   GLU A 269      -5.679   29.002   23.446  1.00   89.77      A    C
ATOM  1152  CD   GLU A 269      -6.383   27.856   22.703  1.00   90.98      A    C
ATOM  1153  OE1  GLU A 269      -5.813   26.747   22.585  1.00   97.21      A    O
ATOM  1154  OE2  GLU A 269      -7.526   28.066   22.246  1.00   83.35      A    O
ATOM  1155  C    GLU A 269      -3.455   30.555   20.976  1.00   78.35      A    C
ATOM  1156  O    GLU A 269      -4.253   30.594   20.032  1.00   79.24      A    O
ATOM  1157  N    LEU A 270      -2.143   30.418   20.797  1.00   75.50      A    N
ATOM  1158  CA   LEU A 270      -1.550   30.300   19.466  1.00   71.01      A    C
ATOM  1159  CB   LEU A 270      -0.029   30.292   19.581  1.00   72.84      A    C
ATOM  1160  CG   LEU A 270       0.564   31.642   19.201  1.00   75.37      A    C
ATOM  1161  CD1  LEU A 270       1.934   31.817   19.810  1.00   75.57      A    C
ATOM  1162  CD2  LEU A 270       0.604   31.738   17.682  1.00   79.94      A    C
ATOM  1163  C    LEU A 270      -2.026   29.049   18.748  1.00   64.19      A    C
ATOM  1164  O    LEU A 270      -2.729   28.239   19.327  1.00   64.26      A    O
ATOM  1165  N    LYS A 271      -1.647   28.895   17.487  1.00   58.39      A    N
ATOM  1166  CA   LYS A 271      -2.045   27.732   16.699  1.00   56.02      A    C
ATOM  1167  CB   LYS A 271      -3.547   27.755   16.375  1.00   55.68      A    C
ATOM  1168  CG   LYS A 271      -4.519   27.800   17.541  1.00   61.54      A    C
ATOM  1169  CD   LYS A 271      -4.765   26.444   18.181  1.00   64.50      A    C
ATOM  1170  CE   LYS A 271      -5.611   26.596   19.436  1.00   70.91      A    C
ATOM  1171  NZ   LYS A 271      -5.876   25.314   20.130  1.00   72.98      A    N
ATOM  1172  C    LYS A 271      -1.288   27.818   15.382  1.00   54.45      A    C
ATOM  1173  O    LYS A 271      -1.839   28.316   14.390  1.00   48.43      A    O
ATOM  1174  N    ILE A 272      -0.046   27.338   15.341  1.00   57.56      A    N
ATOM  1175  CA   ILE A 272       0.698   27.440   14.093  1.00   64.74      A    C
ATOM  1176  CB   ILE A 272       2.897   26.823   14.160  1.00   71.56      A    C
ATOM  1177  CG2  ILE A 272       2.897   27.459   15.274  1.00   74.70      A    C
ATOM  1178  CG1  ILE A 272       2.005   25.330   14.373  1.00   76.49      A    C
ATOM  1179  CD1  ILE A 272       3.344   24.679   14.255  1.00   81.85      A    C
ATOM  1180  C    ILE A 272      -0.064   26.787   12.975  1.00   62.89      A    C
ATOM  1181  O    ILE A 272      -0.654   25.731   13.144  1.00   56.99      A    O
ATOM  1182  N    ALA A 273      -0.046   27.443   11.829  1.00   68.21      A    N
ATOM  1183  CA   ALA A 273      -0.759   26.965   10.671  1.00   72.24      A    C
ATOM  1184  CB   ALA A 273      -2.053   27.749   10.527  1.00   70.73      A    C
ATOM  1185  C    ALA A 273       0.067   27.077    9.396  1.00   77.78      A    C
ATOM  1186  O    ALA A 273       0.658   28.126    9.119  1.00   79.02      A    O
ATOM  1187  N    ASP A 274       0.035   26.007    8.595  1.00   82.60      A    N
ATOM  1188  CA   ASP A 274       0.738   25.932    7.302  1.00   85.59      A    C
ATOM  1189  CB   ASP A 274       1.937   24.984    7.422  1.00   78.15      A    C
ATOM  1190  CG   ASP A 274       2.878   25.385    8.543  1.00   77.45      A    C
ATOM  1191  OD1  ASP A 274       3.659   26.349    8.361  1.00   68.37      A    O
ATOM  1192  OD2  ASP A 274       2.818   24.744    9.615  1.00   80.34      A    O
ATOM  1193  C    ASP A 274      -0.232   25.462    6.182  1.00   91.38      A    C
ATOM  1194  O    ASP A 274      -1.398   25.889    6.158  1.00   91.55      A    O
ATOM  1195  N    PHE A 275       0.249   24.619    5.260  1.00   99.72      A    N
ATOM  1196  CA   PHE A 275      -0.574   24.081    4.152  1.00  113.09      A    C
ATOM  1197  CB   PHE A 275      -2.064   24.106    4.494  1.00  115.47      A    C
ATOM  1198  CG   PHE A 275      -2.445   23.138    5.521  1.00  125.01      A    C
ATOM  1199  CD1  PHE A 275      -2.657   23.551    6.841  1.00  128.90      A    C
ATOM  1200  CD2  PHE A 275      -2.563   21.791    5.192  1.00  130.01      A    C
ATOM  1201  CE1  PHE A 275      -2.990   22.623    7.841  1.00  133.49      A    C
ATOM  1202  CE2  PHE A 275      -2.892   20.848    6.170  1.00  135.51      A    C
ATOM  1203  CZ   PHE A 275      -3.109   21.265    7.504  1.00  136.40      A    C
ATOM  1204  C    PHE A 275      -0.478   24.716    2.767  1.00  119.03      A    C
ATOM  1205  O    PHE A 275       0.508   24.561    2.026  1.00  123.97      A    O
ATOM  1206  N    GLY A 276      -1.570   25.372    2.416  1.00  121.77      A    N
ATOM  1207  CA   GLY A 276      -1.722   26.069    1.154  1.00  124.74      A    C
ATOM  1208  C    GLY A 276      -2.484   27.306    1.590  1.00  126.82      A    C
ATOM  1209  O    GLY A 276      -2.834   27.411    2.777  1.00  129.75      A    O
```

Figure 3T

```
ATOM   1210  N    TRP A 277      -2.738  28.245   0.679  1.00  126.79      A  N
ATOM   1211  CA   TRP A 277      -3.431  29.493   1.048  1.00  126.04      A  C
ATOM   1212  CB   TRP A 277      -2.410  30.492   1.663  1.00  121.80      A  C
ATOM   1213  CG   TRP A 277      -1.275  29.799   2.419  1.00  117.48      A  C
ATOM   1214  CD2  TRP A 277      -0.278  28.934   1.841  1.00  116.82      A  C
ATOM   1215  CE2  TRP A 277       0.414  28.313   2.912  1.00  117.21      A  C
ATOM   1216  CE3  TRP A 277       0.086  28.609   0.514  1.00  115.18      A  C
ATOM   1217  CD1  TRP A 277      -1.131  29.688   3.783  1.00  113.36      A  C
ATOM   1218  NE1  TRP A 277      -0.125  28.790   4.083  1.00  112.49      A  N
ATOM   1219  CZ2  TRP A 277       1.456  27.380   2.695  1.00  119.15      A  C
ATOM   1220  CZ3  TRP A 277       1.121  27.677   0.295  1.00  112.92      A  C
ATOM   1221  CH2  TRP A 277       1.791  27.078   1.381  1.00  116.41      A  C
ATOM   1222  C    TRP A 277      -4.122  30.122  -0.172  1.00  126.26      A  C
ATOM   1223  O    TRP A 277      -3.648  29.892  -1.311  1.00  127.14      A  O
TER    1225       TRP A 277                                                A
ATOM   1226  C    GLY A 291       9.725  38.836   3.931  1.00   96.32      A  C
ATOM   1227  O    GLY A 291       9.036  38.133   4.681  1.00   96.44      A  O
ATOM   1228  N    GLY A 291      11.317  40.806   3.965  1.00   92.80      A  N
ATOM   1229  CA   GLY A 291       9.904  40.330   4.180  1.00   96.64      A  C
ATOM   1230  N    THR A 292      10.340  38.352   2.856  1.00   94.78      A  N
ATOM   1231  CA   THR A 292      10.282  36.936   2.496  1.00   89.04      A  C
ATOM   1232  CB   THR A 292      10.385  36.722   0.969  1.00   91.48      A  C
ATOM   1233  OG1  THR A 292       9.554  37.669   0.273  1.00   84.85      A  O
ATOM   1234  CG2  THR A 292       9.950  35.300   0.631  1.00   92.75      A  C
ATOM   1235  C    THR A 292      11.485  36.251   3.154  1.00   83.29      A  C
ATOM   1236  O    THR A 292      11.423  35.059   3.485  1.00   82.70      A  O
ATOM   1237  N    LEU A 293      12.567  37.030   3.310  1.00   75.14      A  N
ATOM   1238  CA   LEU A 293      13.825  36.622   3.944  1.00   64.63      A  C
ATOM   1239  CB   LEU A 293      14.973  37.527   3.494  1.00   65.46      A  C
ATOM   1240  CG   LEU A 293      15.444  37.388   2.060  1.00   65.92      A  C
ATOM   1241  CD1  LEU A 293      16.228  38.585   1.603  1.00   63.00      A  C
ATOM   1242  CD2  LEU A 293      16.277  36.146   1.994  1.00   67.74      A  C
ATOM   1243  C    LEU A 293      13.686  36.776   5.453  1.00   55.24      A  C
ATOM   1244  O    LEU A 293      13.953  35.849   6.203  1.00   53.79      A  O
ATOM   1245  N    ASP A 294      13.260  37.970   5.869  1.00   46.46      A  N
ATOM   1246  CA   ASP A 294      13.088  38.350   7.274  1.00   39.11      A  C
ATOM   1247  CB   ASP A 294      11.857  39.245   7.485  1.00   37.16      A  C
ATOM   1248  CG   ASP A 294      12.019  40.664   6.920  1.00   40.47      A  C
ATOM   1249  OD1  ASP A 294      10.994  41.398   6.895  1.00   44.84      A  O
ATOM   1250  OD2  ASP A 294      13.141  41.053   6.519  1.00   38.47      A  O
ATOM   1251  C    ASP A 294      12.971  37.184   8.209  1.00   37.03      A  C
ATOM   1252  O    ASP A 294      13.207  37.364   9.380  1.00   35.97      A  O
ATOM   1253  N    TYR A 295      12.613  35.999   7.722  1.00   35.64      A  N
ATOM   1254  CA   TYR A 295      12.488  34.852   8.617  1.00   40.90      A  C
ATOM   1255  CB   TYR A 295      11.052  34.345   8.596  1.00   42.06      A  C
ATOM   1256  CG   TYR A 295      10.140  35.320   9.264  1.00   48.52      A  C
ATOM   1257  CD1  TYR A 295       9.385  36.233   8.510  1.00   46.39      A  C
ATOM   1258  CE1  TYR A 295       8.691  37.236   9.129  1.00   47.97      A  C
ATOM   1259  CD2  TYR A 295      10.150  35.440  10.660  1.00   49.00      A  C
ATOM   1260  CE2  TYR A 295       9.463  36.439  11.288  1.00   48.15      A  C
ATOM   1261  CZ   TYR A 295       8.749  37.338  10.523  1.00   52.16      A  C
ATOM   1262  OH   TYR A 295       8.174  38.399  11.156  1.00   52.12      A  O
ATOM   1263  C    TYR A 295      13.421  33.658   8.468  1.00   42.76      A  C
ATOM   1264  O    TYR A 295      13.786  33.001   9.444  1.00   41.69      A  O
ATOM   1265  N    LEU A 296      13.793  33.344   7.248  1.00   43.93      A  N
ATOM   1266  CA   LEU A 296      14.650  32.195   7.059  1.00   40.96      A  C
ATOM   1267  CB   LEU A 296      14.939  32.017   5.563  1.00   47.98      A  C
ATOM   1268  CG   LEU A 296      13.740  32.233   4.618  1.00   52.97      A  C
ATOM   1269  CD1  LEU A 296      14.214  32.475   3.198  1.00   58.28      A  C
ATOM   1270  CD2  LEU A 296      12.805  31.049   4.674  1.00   58.38      A  C
ATOM   1271  C    LEU A 296      15.926  32.529   7.834  1.00   38.62      A  C
```

Figure 3U

| ATOM | 1272 | O | LEU | A | 296 | 16.195 | 33.698 | 8.136 | 1.00 | 38.87 | A | O |
|---|---|---|---|---|---|---|---|---|---|---|---|---|
| ATOM | 1273 | N | PRO | A | 297 | 16.708 | 31.508 | 8.199 | 1.00 | 37.70 | A | N |
| ATOM | 1274 | CD | PRO | A | 297 | 16.323 | 30.095 | 8.111 | 1.00 | 40.76 | A | C |
| ATOM | 1275 | CA | PRO | A | 297 | 17.966 | 31.643 | 8.935 | 1.00 | 41.77 | A | C |
| ATOM | 1276 | CB | PRO | A | 297 | 17.951 | 30.421 | 9.808 | 1.00 | 40.27 | A | C |
| ATOM | 1277 | CG | PRO | A | 297 | 17.478 | 29.404 | 8.824 | 1.00 | 41.45 | A | C |
| ATOM | 1278 | C | PRO | A | 297 | 19.094 | 31.594 | 7.883 | 1.00 | 42.30 | A | C |
| ATOM | 1279 | O | PRO | A | 297 | 18.831 | 31.258 | 6.717 | 1.00 | 42.54 | A | O |
| ATOM | 1280 | N | PRO | A | 298 | 20.356 | 31.910 | 8.268 | 1.00 | 42.84 | A | N |
| ATOM | 1281 | CD | PRO | A | 298 | 20.833 | 32.537 | 9.513 | 1.00 | 47.33 | A | C |
| ATOM | 1282 | CA | PRO | A | 298 | 21.441 | 31.880 | 7.285 | 1.00 | 40.17 | A | C |
| ATOM | 1283 | CB | PRO | A | 298 | 22.641 | 32.334 | 8.096 | 1.00 | 42.71 | A | C |
| ATOM | 1284 | CG | PRO | A | 298 | 22.033 | 33.320 | 9.029 | 1.00 | 41.22 | A | C |
| ATOM | 1285 | C | PRO | A | 298 | 21.673 | 30.570 | 6.567 | 1.00 | 39.59 | A | C |
| ATOM | 1286 | O | PRO | A | 298 | 21.985 | 30.568 | 5.380 | 1.00 | 35.71 | A | O |
| ATOM | 1287 | N | GLU | A | 299 | 21.513 | 29.455 | 7.262 | 1.00 | 39.73 | A | N |
| ATOM | 1288 | CA | GLU | A | 299 | 21.727 | 28.194 | 6.581 | 1.00 | 48.18 | A | C |
| ATOM | 1289 | CB | GLU | A | 299 | 21.401 | 27.005 | 7.484 | 1.00 | 52.94 | A | C |
| ATOM | 1290 | CG | GLU | A | 299 | 20.298 | 27.252 | 8.467 | 1.00 | 59.22 | A | C |
| ATOM | 1291 | CD | GLU | A | 299 | 20.832 | 27.543 | 9.845 | 1.00 | 60.28 | A | C |
| ATOM | 1292 | OE1 | GLU | A | 299 | 20.745 | 26.641 | 10.706 | 1.00 | 58.87 | A | O |
| ATOM | 1293 | OE2 | GLU | A | 299 | 21.346 | 28.664 | 10.059 | 1.00 | 60.59 | A | O |
| ATOM | 1294 | C | GLU | A | 299 | 20.936 | 28.074 | 5.286 | 1.00 | 53.50 | A | C |
| ATOM | 1295 | O | GLU | A | 299 | 21.482 | 27.645 | 4.267 | 1.00 | 54.44 | A | O |
| ATOM | 1296 | N | MET | A | 300 | 19.661 | 28.463 | 5.305 | 1.00 | 60.34 | A | N |
| ATOM | 1297 | CA | MET | A | 300 | 18.847 | 28.337 | 4.101 | 1.00 | 67.53 | A | C |
| ATOM | 1298 | CB | MET | A | 300 | 17.390 | 28.030 | 4.464 | 1.00 | 74.61 | A | C |
| ATOM | 1299 | CG | MET | A | 300 | 16.634 | 27.340 | 3.324 | 1.00 | 92.03 | A | C |
| ATOM | 1300 | SD | MET | A | 300 | 14.890 | 27.852 | 3.118 | 1.00 | 108.94 | A | S |
| ATOM | 1301 | CE | MET | A | 300 | 14.843 | 28.434 | 1.366 | 1.00 | 102.65 | A | C |
| ATOM | 1302 | C | MET | A | 300 | 18.908 | 29.531 | 3.137 | 1.00 | 68.22 | A | C |
| ATOM | 1303 | O | MET | A | 300 | 18.480 | 29.429 | 1.982 | 1.00 | 72.31 | A | O |
| ATOM | 1304 | N | ILE | A | 301 | 19.415 | 30.671 | 3.580 | 1.00 | 65.22 | A | N |
| ATOM | 1305 | CA | ILE | A | 301 | 19.499 | 31.750 | 2.629 | 1.00 | 65.47 | A | C |
| ATOM | 1306 | CB | ILE | A | 301 | 19.494 | 33.124 | 3.309 | 1.00 | 67.97 | A | C |
| ATOM | 1307 | CG2 | ILE | A | 301 | 18.537 | 33.090 | 4.473 | 1.00 | 67.42 | A | C |
| ATOM | 1308 | CG1 | ILE | A | 301 | 20.891 | 33.509 | 3.792 | 1.00 | 74.32 | A | C |
| ATOM | 1309 | CD1 | ILE | A | 301 | 20.989 | 34.937 | 4.307 | 1.00 | 75.01 | A | C |
| ATOM | 1310 | C | ILE | A | 301 | 20.812 | 31.499 | 1.906 | 1.00 | 65.29 | A | C |
| ATOM | 1311 | O | ILE | A | 301 | 20.937 | 31.753 | 0.713 | 1.00 | 60.84 | A | O |
| ATOM | 1312 | N | GLU | A | 302 | 21.783 | 30.960 | 2.643 | 1.00 | 66.82 | A | N |
| ATOM | 1313 | CA | GLU | A | 302 | 23.101 | 30.644 | 2.087 | 1.00 | 67.89 | A | C |
| ATOM | 1314 | CB | GLU | A | 302 | 24.174 | 30.609 | 3.202 | 1.00 | 68.22 | A | C |
| ATOM | 1315 | CG | GLU | A | 302 | 24.479 | 31.983 | 3.835 | 1.00 | 70.47 | A | C |
| ATOM | 1316 | CD | GLU | A | 302 | 25.273 | 31.920 | 5.150 | 1.00 | 68.65 | A | C |
| ATOM | 1317 | OE1 | GLU | A | 302 | 24.969 | 31.050 | 5.996 | 1.00 | 65.41 | A | O |
| ATOM | 1318 | OE2 | GLU | A | 302 | 26.184 | 32.760 | 5.353 | 1.00 | 71.35 | A | O |
| ATOM | 1319 | C | GLU | A | 302 | 23.049 | 29.301 | 1.347 | 1.00 | 68.13 | A | C |
| ATOM | 1320 | O | GLU | A | 302 | 24.036 | 28.875 | 0.749 | 1.00 | 64.17 | A | O |
| ATOM | 1321 | N | GLY | A | 303 | 21.891 | 28.641 | 1.393 | 1.00 | 70.39 | A | N |
| ATOM | 1322 | CA | GLY | A | 303 | 21.710 | 27.372 | 0.705 | 1.00 | 73.08 | A | C |
| ATOM | 1323 | C | GLY | A | 303 | 22.464 | 26.178 | 1.255 | 1.00 | 75.93 | A | C |
| ATOM | 1324 | O | GLY | A | 303 | 22.531 | 25.128 | 0.612 | 1.00 | 71.91 | A | O |
| ATOM | 1325 | N | ARG | A | 304 | 23.053 | 26.338 | 2.431 | 1.00 | 81.09 | A | N |
| ATOM | 1326 | CA | ARG | A | 304 | 23.775 | 25.251 | 3.064 | 1.00 | 87.87 | A | C |
| ATOM | 1327 | CB | ARG | A | 304 | 24.483 | 25.759 | 4.309 | 1.00 | 88.53 | A | C |
| ATOM | 1328 | CG | ARG | A | 304 | 25.470 | 26.878 | 4.043 | 1.00 | 94.07 | A | C |
| ATOM | 1329 | CD | ARG | A | 304 | 25.980 | 27.482 | 5.347 | 1.00 | 101.65 | A | C |
| ATOM | 1330 | NE | ARG | A | 304 | 26.288 | 26.452 | 6.332 | 1.00 | 108.61 | A | N |
| ATOM | 1331 | CZ | ARG | A | 304 | 27.083 | 25.410 | 6.100 | 1.00 | 111.93 | A | C |
| ATOM | 1332 | NH1 | ARG | A | 304 | 27.658 | 25.248 | 4.909 | 1.00 | 112.63 | A | N |

Figure 3V

```
ATOM   1333  NH2 ARG A 304      27.305  24.523   7.060  1.00 113.14      A    N
ATOM   1334  C   ARG A 304      22.706  24.246   3.458  1.00  93.23      A    C
ATOM   1335  O   ARG A 304      21.526  24.464   3.188  1.00  93.41      A    O
ATOM   1336  N   MET A 305      23.092  23.144   4.092  1.00 100.97      A    N
ATOM   1337  CA  MET A 305      22.081  22.172   4.499  1.00 107.01      A    C
ATOM   1338  CB  MET A 305      22.594  20.709   4.403  1.00 115.87      A    C
ATOM   1339  CG  MET A 305      23.798  20.321   5.263  1.00 126.37      A    C
ATOM   1340  SD  MET A 305      25.396  20.345   4.397  1.00 135.35      A    S
ATOM   1341  CE  MET A 305      26.108  21.926   5.032  1.00 138.87      A    C
ATOM   1342  C   MET A 305      21.579  22.503   5.905  1.00 104.19      A    C
ATOM   1343  O   MET A 305      22.271  22.314   6.919  1.00 101.63      A    O
ATOM   1344  N   HIS A 306      20.368  23.047   5.933  1.00 103.03      A    N
ATOM   1345  CA  HIS A 306      19.703  23.430   7.169  1.00 102.83      A    C
ATOM   1346  CB  HIS A 306      18.627  24.460   6.864  1.00 112.22      A    C
ATOM   1347  CG  HIS A 306      17.630  23.980   5.860  1.00 118.55      A    C
ATOM   1348  CD2 HIS A 306      16.413  23.408   6.020  1.00 120.69      A    C
ATOM   1349  ND1 HIS A 306      17.896  23.950   4.509  1.00 121.52      A    N
ATOM   1350  CE1 HIS A 306      16.887  23.376   3.880  1.00 123.44      A    C
ATOM   1351  NE2 HIS A 306      15.975  23.037   4.774  1.00 125.05      A    N
ATOM   1352  C   HIS A 306      19.039  22.174   7.690  1.00  97.06      A    C
ATOM   1353  O   HIS A 306      18.811  21.247   6.916  1.00  97.46      A    O
ATOM   1354  N   ASP A 307      18.711  22.143   8.978  1.00  89.60      A    N
ATOM   1355  CA  ASP A 307      18.064  20.973   9.538  1.00  83.24      A    C
ATOM   1356  CB  ASP A 307      18.902  19.701   9.264  1.00  85.61      A    C
ATOM   1357  CG  ASP A 307      18.217  18.712   8.277  1.00  88.63      A    C
ATOM   1358  OD1 ASP A 307      18.137  19.010   7.057  1.00  91.87      A    O
ATOM   1359  OD2 ASP A 307      17.759  17.626   8.723  1.00  86.12      A    O
ATOM   1360  C   ASP A 307      17.806  21.060  11.026  1.00  77.32      A    C
ATOM   1361  O   ASP A 307      18.729  20.909  11.820  1.00  70.83      A    O
ATOM   1362  N   GLU A 308      16.555  21.318  11.396  1.00  75.53      A    N
ATOM   1363  CA  GLU A 308      16.137  21.334  12.803  1.00  74.45      A    C
ATOM   1364  CB  GLU A 308      16.527  20.012  13.457  1.00  80.50      A    C
ATOM   1365  CG  GLU A 308      17.895  20.185  14.847  1.00  82.30      A    C
ATOM   1366  CD  GLU A 308      17.628  18.894  15.416  1.00  85.17      A    C
ATOM   1367  OE1 GLU A 308      18.431  18.218  14.724  1.00  86.56      A    O
ATOM   1368  OE2 GLU A 308      17.243  18.565  16.561  1.00  89.63      A    O
ATOM   1369  C   GLU A 308      16.504  22.450  13.775  1.00  66.36      A    C
ATOM   1370  O   GLU A 308      15.805  22.633  14.774  1.00  63.84      A    O
ATOM   1371  N   LYS A 309      17.607  23.151  13.544  1.00  54.88      A    N
ATOM   1372  CA  LYS A 309      17.972  24.253  14.434  1.00  45.13      A    C
ATOM   1373  CB  LYS A 309      19.483  24.538  14.371  1.00  30.83      A    C
ATOM   1378  C   LYS A 309      17.175  25.498  13.998  1.00  41.19      A    C
ATOM   1379  O   LYS A 309      16.820  26.347  14.833  1.00  33.26      A    O
ATOM   1380  N   VAL A 310      16.850  25.572  12.702  1.00  40.89      A    N
ATOM   1381  CA  VAL A 310      16.136  26.724  12.185  1.00  43.85      A    C
ATOM   1382  CB  VAL A 310      15.514  26.525  10.755  1.00  49.26      A    C
ATOM   1383  CG1 VAL A 310      16.500  25.886   9.828  1.00  51.33      A    C
ATOM   1384  CG2 VAL A 310      14.267  25.733  10.822  1.00  48.70      A    C
ATOM   1385  C   VAL A 310      15.047  27.067  13.161  1.00  43.38      A    C
ATOM   1386  O   VAL A 310      15.006  28.189  13.645  1.00  49.35      A    O
ATOM   1387  N   ASP A 311      14.201  26.104  13.507  1.00  41.66      A    N
ATOM   1388  CA  ASP A 311      13.100  26.396  14.415  1.00  42.10      A    C
ATOM   1389  CB  ASP A 311      12.473  25.118  14.941  1.00  45.22      A    C
ATOM   1390  CG  ASP A 311      11.630  24.456  13.916  1.00  42.00      A    C
ATOM   1391  OD1 ASP A 311      10.958  25.198  13.181  1.00  38.71      A    O
ATOM   1392  OD2 ASP A 311      11.633  23.217  13.833  1.00  38.86      A    O
ATOM   1393  C   ASP A 311      13.460  27.297  15.572  1.00  39.54      A    C
ATOM   1394  O   ASP A 311      12.593  27.985  16.116  1.00  32.58      A    O
ATOM   1395  N   LEU A 312      14.735  27.305  15.940  1.00  39.95      A    N
ATOM   1396  CA  LEU A 312      15.189  28.147  17.030  1.00  43.57      A    C
ATOM   1397  CB  LEU A 312      16.472  27.561  17.616  1.00  47.41      A    C
```

Figure 3W

```
ATOM   1398  CG   LEU A 312      16.319  26.628  18.811  1.00  50.01      A    C
ATOM   1399  CD1  LEU A 312      15.921  27.432  20.015  1.00  56.88      A    C
ATOM   1400  CD2  LEU A 312      15.296  25.571  18.526  1.00  54.49      A    C
ATOM   1401  C    LEU A 312      15.415  29.588  16.554  1.00  41.41      A    C
ATOM   1402  O    LEU A 312      15.236  30.539  17.315  1.00  38.14      A    O
ATOM   1403  N    TRP A 313      15.812  29.726  15.291  1.00  42.35      A    N
ATOM   1404  CA   TRP A 313      16.070  31.016  14.667  1.00  47.76      A    C
ATOM   1405  CB   TRP A 313      17.037  30.830  13.491  1.00  57.23      A    C
ATOM   1406  CG   TRP A 313      17.273  32.039  12.647  1.00  62.84      A    C
ATOM   1407  CD2  TRP A 313      18.469  32.828  12.569  1.00  63.97      A    C
ATOM   1408  CE2  TRP A 313      18.228  33.858  11.650  1.00  61.27      A    C
ATOM   1409  CE3  TRP A 313      19.716  32.765  13.188  1.00  70.04      A    C
ATOM   1410  CD1  TRP A 313      16.394  32.604  11.796  1.00  66.64      A    C
ATOM   1411  NE1  TRP A 313      16.954  33.698  11.187  1.00  64.38      A    N
ATOM   1412  CZ2  TRP A 313      19.188  34.820  11.329  1.00  60.63      A    C
ATOM   1413  CZ3  TRP A 313      20.675  33.729  12.863  1.00  70.23      A    C
ATOM   1414  CH2  TRP A 313      20.400  34.739  11.946  1.00  62.67      A    C
ATOM   1415  C    TRP A 313      14.739  31.578  14.211  1.00  46.05      A    C
ATOM   1416  O    TRP A 313      14.490  32.773  14.319  1.00  46.23      A    O
ATOM   1417  N    SER A 314      13.880  30.716  13.691  1.00  44.50      A    N
ATOM   1418  CA   SER A 314      12.562  31.160  13.292  1.00  40.25      A    C
ATOM   1419  CB   SER A 314      11.718  29.976  12.825  1.00  40.94      A    C
ATOM   1421  C    SER A 314      12.014  31.719  14.596  1.00  37.13      A    C
ATOM   1422  O    SER A 314      11.549  32.849  14.663  1.00  37.32      A    O
ATOM   1423  N    LEU A 315      12.132  30.917  15.646  1.00  32.06      A    N
ATOM   1424  CA   LEU A 315      11.692  31.258  17.009  1.00  33.25      A    C
ATOM   1425  CB   LEU A 315      11.880  30.045  17.909  1.00  36.08      A    C
ATOM   1426  CG   LEU A 315      10.984  30.133  19.126  1.00  37.55      A    C
ATOM   1427  CD1  LEU A 315       9.700  29.399  18.757  1.00  37.40      A    C
ATOM   1428  CD2  LEU A 315      11.636  29.536  20.360  1.00  38.11      A    C
ATOM   1429  C    LEU A 315      12.402  32.462  17.696  1.00  32.34      A    C
ATOM   1430  O    LEU A 315      11.916  33.038  18.678  1.00  29.15      A    O
ATOM   1431  N    GLY A 316      13.586  32.804  17.220  1.00  31.11      A    N
ATOM   1432  CA   GLY A 316      14.271  33.922  17.812  1.00  25.39      A    C
ATOM   1433  C    GLY A 316      13.645  35.116  17.161  1.00  22.09      A    C
ATOM   1434  O    GLY A 316      12.932  35.867  17.796  1.00  20.03      A    O
ATOM   1435  N    VAL A 317      13.883  35.256  15.869  1.00  22.56      A    N
ATOM   1436  CA   VAL A 317      13.360  36.384  15.165  1.00  28.75      A    C
ATOM   1437  CB   VAL A 317      13.150  36.087  13.686  1.00  32.79      A    C
ATOM   1438  CG1  VAL A 317      12.434  37.269  13.041  1.00  33.42      A    C
ATOM   1439  CG2  VAL A 317      14.478  35.864  12.993  1.00  37.69      A    C
ATOM   1440  C    VAL A 317      12.040  36.817  15.771  1.00  30.61      A    C
ATOM   1441  O    VAL A 317      11.937  37.932  16.316  1.00  30.27      A    O
ATOM   1442  N    LEU A 318      11.047  35.925  15.698  1.00  29.05      A    N
ATOM   1443  CA   LEU A 318       9.693  36.184  16.211  1.00  24.26      A    C
ATOM   1444  CB   LEU A 318       8.967  34.841  16.474  1.00  30.26      A    C
ATOM   1445  CG   LEU A 318       7.591  34.451  15.889  1.00  39.57      A    C
ATOM   1446  CD1  LEU A 318       6.988  35.636  15.191  1.00  43.99      A    C
ATOM   1447  CD2  LEU A 318       7.716  33.278  14.917  1.00  38.41      A    C
ATOM   1448  C    LEU A 318       9.736  37.037  17.492  1.00  20.55      A    C
ATOM   1449  O    LEU A 318       9.384  38.216  17.483  1.00  10.54      A    O
ATOM   1450  N    CYS A 319      10.188  36.433  18.583  1.00  25.03      A    N
ATOM   1451  CA   CYS A 319      10.288  37.108  19.868  1.00  29.70      A    C
ATOM   1452  CB   CYS A 319      11.318  36.369  20.751  1.00  38.57      A    C
ATOM   1453  SG   CYS A 319      11.544  36.901  22.509  1.00  46.56      A    S
ATOM   1454  C    CYS A 319      10.684  38.572  19.656  1.00  25.40      A    C
ATOM   1455  O    CYS A 319      10.046  39.472  20.197  1.00  23.93      A    O
ATOM   1456  N    TYR A 320      11.719  38.822  18.862  1.00  21.10      A    N
ATOM   1457  CA   TYR A 320      12.131  40.202  18.627  1.00  24.44      A    C
ATOM   1458  CB   TYR A 320      13.287  40.251  17.625  1.00  31.60      A    C
ATOM   1459  CG   TYR A 320      13.866  41.638  17.371  1.00  38.15      A    C
```

Figure 3X

| ATOM | 1460 | CD1 | TYR | A | 320 | 14.560 | 42.334 | 18.365 | 1.00 | 38.02 | A | C |
| --- | --- | --- | --- | --- | --- | --- | --- | --- | --- | --- | --- | --- |
| ATOM | 1461 | CE1 | TYR | A | 320 | 15.154 | 43.584 | 18.098 | 1.00 | 38.53 | A | C |
| ATOM | 1462 | CD2 | TYR | A | 320 | 13.772 | 42.226 | 16.111 | 1.00 | 42.15 | A | C |
| ATOM | 1463 | CE2 | TYR | A | 320 | 14.361 | 43.472 | 15.837 | 1.00 | 43.63 | A | C |
| ATOM | 1464 | CZ | TYR | A | 320 | 15.052 | 44.145 | 16.829 | 1.00 | 40.37 | A | C |
| ATOM | 1465 | OH | TYR | A | 320 | 15.639 | 45.357 | 16.522 | 1.00 | 32.05 | A | O |
| ATOM | 1466 | C | TYR | A | 320 | 10.973 | 41.056 | 18.091 | 1.00 | 24.68 | A | C |
| ATOM | 1467 | O | TYR | A | 320 | 10.692 | 42.154 | 18.608 | 1.00 | 18.16 | A | O |
| ATOM | 1468 | N | GLU | A | 321 | 10.298 | 40.541 | 17.060 | 1.00 | 27.62 | A | N |
| ATOM | 1469 | CA | GLU | A | 321 | 9.214 | 41.288 | 16.435 | 1.00 | 33.94 | A | C |
| ATOM | 1470 | CB | GLU | A | 321 | 8.771 | 40.691 | 15.111 | 1.00 | 42.38 | A | C |
| ATOM | 1471 | CG | GLU | A | 321 | 7.834 | 41.622 | 14.373 | 1.00 | 55.72 | A | C |
| ATOM | 1472 | CD | GLU | A | 321 | 7.233 | 40.995 | 13.137 | 1.00 | 62.86 | A | C |
| ATOM | 1473 | OE1 | GLU | A | 321 | 7.978 | 40.301 | 12.419 | 1.00 | 66.45 | A | O |
| ATOM | 1474 | OE2 | GLU | A | 321 | 6.030 | 41.204 | 12.871 | 1.00 | 69.35 | A | O |
| ATOM | 1475 | C | GLU | A | 321 | 8.009 | 41.416 | 17.295 | 1.00 | 32.32 | A | C |
| ATOM | 1476 | O | GLU | A | 321 | 7.174 | 42.260 | 17.022 | 1.00 | 32.55 | A | O |
| ATOM | 1477 | N | PHE | A | 322 | 7.890 | 40.571 | 18.310 | 1.00 | 32.13 | A | N |
| ATOM | 1478 | CA | PHE | A | 322 | 6.756 | 40.686 | 19.210 | 1.00 | 31.66 | A | C |
| ATOM | 1479 | CB | PHE | A | 322 | 6.621 | 39.470 | 20.109 | 1.00 | 27.27 | A | C |
| ATOM | 1480 | CG | PHE | A | 322 | 6.153 | 38.255 | 19.401 | 1.00 | 27.63 | A | C |
| ATOM | 1481 | CD1 | PHE | A | 322 | 5.389 | 38.367 | 18.239 | 1.00 | 23.79 | A | C |
| ATOM | 1482 | CD2 | PHE | A | 322 | 6.450 | 36.990 | 19.901 | 1.00 | 31.93 | A | C |
| ATOM | 1483 | CE1 | PHE | A | 322 | 4.927 | 37.258 | 17.583 | 1.00 | 21.66 | A | C |
| ATOM | 1484 | CE2 | PHE | A | 322 | 5.989 | 35.856 | 19.254 | 1.00 | 34.07 | A | C |
| ATOM | 1485 | CZ | PHE | A | 322 | 5.224 | 35.988 | 18.089 | 1.00 | 30.95 | A | C |
| ATOM | 1486 | C | PHE | A | 322 | 7.043 | 41.880 | 20.082 | 1.00 | 36.50 | A | C |
| ATOM | 1487 | O | PHE | A | 322 | 6.160 | 42.696 | 20.344 | 1.00 | 36.31 | A | O |
| ATOM | 1488 | N | LEU | A | 323 | 8.303 | 41.980 | 20.509 | 1.00 | 44.09 | A | N |
| ATOM | 1489 | CA | LEU | A | 323 | 8.772 | 43.051 | 21.383 | 1.00 | 49.16 | A | C |
| ATOM | 1490 | CB | LEU | A | 323 | 10.048 | 42.613 | 22.105 | 1.00 | 52.42 | A | C |
| ATOM | 1491 | CG | LEU | A | 323 | 9.935 | 41.515 | 23.155 | 1.00 | 52.95 | A | C |
| ATOM | 1492 | CD1 | LEU | A | 323 | 11.219 | 41.424 | 23.956 | 1.00 | 54.05 | A | C |
| ATOM | 1493 | CD2 | LEU | A | 323 | 8.773 | 41.850 | 24.065 | 1.00 | 55.22 | A | C |
| ATOM | 1494 | C | LEU | A | 323 | 9.042 | 44.386 | 20.712 | 1.00 | 50.67 | A | C |
| ATOM | 1495 | O | LEU | A | 323 | 9.130 | 45.405 | 21.398 | 1.00 | 49.63 | A | O |
| ATOM | 1496 | N | VAL | A | 324 | 9.187 | 44.393 | 19.387 | 1.00 | 50.72 | A | N |
| ATOM | 1497 | CA | VAL | A | 324 | 9.482 | 45.640 | 18.689 | 1.00 | 51.71 | A | C |
| ATOM | 1498 | CB | VAL | A | 324 | 10.920 | 45.663 | 18.164 | 1.00 | 48.45 | A | C |
| ATOM | 1499 | CG1 | VAL | A | 324 | 11.397 | 47.103 | 18.059 | 1.00 | 46.20 | A | C |
| ATOM | 1500 | CG2 | VAL | A | 324 | 11.817 | 44.853 | 19.050 | 1.00 | 51.44 | A | C |
| ATOM | 1501 | C | VAL | A | 324 | 8.596 | 45.963 | 17.502 | 1.00 | 51.30 | A | C |
| ATOM | 1502 | O | VAL | A | 324 | 8.847 | 46.922 | 16.772 | 1.00 | 55.61 | A | O |
| ATOM | 1503 | N | GLY | A | 325 | 7.573 | 45.173 | 17.272 | 1.00 | 44.65 | A | N |
| ATOM | 1504 | CA | GLY | A | 325 | 6.743 | 45.502 | 16.146 | 1.00 | 42.97 | A | C |
| ATOM | 1505 | C | GLY | A | 325 | 7.394 | 45.291 | 14.789 | 1.00 | 43.64 | A | C |
| ATOM | 1506 | O | GLY | A | 325 | 6.720 | 45.497 | 13.785 | 1.00 | 43.99 | A | O |
| ATOM | 1507 | N | LYS | A | 326 | 8.674 | 44.925 | 14.714 | 1.00 | 44.17 | A | N |
| ATOM | 1508 | CA | LYS | A | 326 | 9.277 | 44.649 | 13.396 | 1.00 | 44.93 | A | C |
| ATOM | 1509 | CB | LYS | A | 326 | 9.713 | 45.919 | 12.664 | 1.00 | 50.16 | A | C |
| ATOM | 1510 | CG | LYS | A | 326 | 10.860 | 46.622 | 13.296 | 1.00 | 58.50 | A | C |
| ATOM | 1511 | CD | LYS | A | 326 | 11.300 | 47.773 | 12.424 | 1.00 | 69.92 | A | C |
| ATOM | 1512 | CE | LYS | A | 326 | 12.146 | 48.769 | 13.210 | 1.00 | 76.56 | A | C |
| ATOM | 1513 | NZ | LYS | A | 326 | 11.357 | 49.501 | 14.249 | 1.00 | 81.05 | A | N |
| ATOM | 1514 | C | LYS | A | 326 | 10.448 | 43.678 | 13.461 | 1.00 | 40.86 | A | C |
| ATOM | 1515 | O | LYS | A | 326 | 11.016 | 43.441 | 14.522 | 1.00 | 32.62 | A | O |
| ATOM | 1516 | N | PRO | A | 327 | 10.805 | 43.078 | 12.318 | 1.00 | 42.70 | A | N |
| ATOM | 1517 | CD | PRO | A | 327 | 10.062 | 42.972 | 11.050 | 1.00 | 47.67 | A | C |
| ATOM | 1518 | CA | PRO | A | 327 | 11.915 | 42.137 | 12.324 | 1.00 | 44.41 | A | C |
| ATOM | 1519 | CB | PRO | A | 327 | 11.818 | 41.474 | 10.945 | 1.00 | 50.93 | A | C |
| ATOM | 1520 | CG | PRO | A | 327 | 10.353 | 41.537 | 10.632 | 1.00 | 50.00 | A | C |

Figure 3Y

```
ATOM   1521  C    PRO A 327      13.263  42.795  12.570  1.00  40.13      A  C
ATOM   1522  O    PRO A 327      13.417  43.999  12.449  1.00  28.48      A  O
ATOM   1523  N    PRO A 328      14.258  41.983  12.921  1.00  40.30      A  N
ATOM   1524  CD   PRO A 328      14.062  40.530  13.104  1.00  40.51      A  C
ATOM   1525  CA   PRO A 328      15.630  42.359  13.216  1.00  43.78      A  C
ATOM   1526  CB   PRO A 328      16.094  41.192  14.053  1.00  42.57      A  C
ATOM   1527  CG   PRO A 328      15.437  40.035  13.349  1.00  42.85      A  C
ATOM   1528  C    PRO A 328      16.483  42.554  11.968  1.00  49.81      A  C
ATOM   1529  O    PRO A 328      17.504  43.243  11.992  1.00  47.07      A  O
ATOM   1530  N    PHE A 329      16.076  41.947  10.867  1.00  55.71      A  N
ATOM   1531  CA   PHE A 329      16.855  42.107   9.663  1.00  59.76      A  C
ATOM   1532  CB   PHE A 329      17.376  40.741   9.242  1.00  60.96      A  C
ATOM   1533  CG   PHE A 329      18.054  40.007  10.346  1.00  61.29      A  C
ATOM   1534  CD1  PHE A 329      19.341  40.322  10.716  1.00  61.25      A  C
ATOM   1535  CD2  PHE A 329      17.371  39.046  11.071  1.00  67.49      A  C
ATOM   1536  CE1  PHE A 329      19.938  39.693  11.798  1.00  62.91      A  C
ATOM   1537  CE2  PHE A 329      17.962  38.410  12.159  1.00  68.85      A  C
ATOM   1538  CZ   PHE A 329      19.245  38.737  12.520  1.00  66.33      A  C
ATOM   1539  C    PHE A 329      16.041  42.795   8.558  1.00  61.32      A  C
ATOM   1540  O    PHE A 329      16.449  42.857   7.397  1.00  63.12      A  O
ATOM   1541  N    GLU A 330      14.880  43.321   8.928  1.00  62.98      A  N
ATOM   1542  CA   GLU A 330      14.038  44.037   7.982  1.00  64.41      A  C
ATOM   1543  CB   GLU A 330      12.821  44.623   8.710  1.00  68.90      A  C
ATOM   1544  CG   GLU A 330      11.975  45.598   7.891  1.00  70.67      A  C
ATOM   1545  CD   GLU A 330      10.776  46.124   8.666  1.00  73.43      A  C
ATOM   1546  OE1  GLU A 330       9.879  45.317   8.993  1.00  74.41      A  O
ATOM   1547  OE2  GLU A 330      10.735  47.340   8.953  1.00  73.94      A  O
ATOM   1548  C    GLU A 330      14.901  45.152   7.389  1.00  62.88      A  C
ATOM   1549  O    GLU A 330      15.841  45.632   8.040  1.00  64.68      A  O
ATOM   1550  N    ALA A 331      14.591  45.552   6.158  1.00  58.49      A  N
ATOM   1551  CA   ALA A 331      15.366  46.593   5.509  1.00  55.73      A  C
ATOM   1552  CB   ALA A 331      16.832  46.196   5.506  1.00  52.91      A  C
ATOM   1553  C    ALA A 331      14.935  46.956   4.095  1.00  57.63      A  C
ATOM   1554  O    ALA A 331      14.187  46.238   3.445  1.00  53.53      A  O
ATOM   1555  N    ASN A 332      15.463  48.084   3.638  1.00  67.25      A  N
ATOM   1556  CA   ASN A 332      15.217  48.677   2.319  1.00  76.89      A  C
ATOM   1557  CB   ASN A 332      16.027  49.977   2.217  1.00  79.62      A  C
ATOM   1558  CG   ASN A 332      17.529  49.763   2.525  1.00  81.85      A  C
ATOM   1559  OD1  ASN A 332      17.926  49.577   3.683  1.00  82.59      A  O
ATOM   1560  ND2  ASN A 332      18.357  49.777   1.482  1.00  80.21      A  N
ATOM   1561  C    ASN A 332      15.525  47.839   1.070  1.00  79.53      A  C
ATOM   1562  O    ASN A 332      16.005  48.399   0.083  1.00  82.00      A  O
ATOM   1563  N    THR A 333      15.252  46.533   1.095  1.00  79.64      A  N
ATOM   1564  CA   THR A 333      15.540  45.650  -0.051  1.00  80.36      A  C
ATOM   1565  CB   THR A 333      16.558  46.301  -1.046  1.00  83.37      A  C
ATOM   1566  OG1  THR A 333      16.549  45.584  -2.285  1.00  91.78      A  O
ATOM   1567  CG2  THR A 333      17.973  46.284  -0.474  1.00  76.50      A  C
ATOM   1568  C    THR A 333      16.116  44.294   0.398  1.00  74.55      A  C
ATOM   1569  O    THR A 333      16.563  44.139   1.533  1.00  74.67      A  O
ATOM   1570  N    TYR A 334      16.117  43.314  -0.495  1.00  64.53      A  N
ATOM   1571  CA   TYR A 334      16.636  42.015  -0.139  1.00  56.54      A  C
ATOM   1572  CB   TYR A 334      16.362  40.997  -1.244  1.00  57.90      A  C
ATOM   1573  CG   TYR A 334      14.911  40.659  -1.463  1.00  61.02      A  C
ATOM   1574  CD1  TYR A 334      13.963  40.858  -0.461  1.00  65.37      A  C
ATOM   1575  CE1  TYR A 334      12.614  40.552  -0.671  1.00  69.31      A  C
ATOM   1576  CD2  TYR A 334      14.481  40.140  -2.678  1.00  64.19      A  C
ATOM   1577  CE2  TYR A 334      13.138  39.832  -2.901  1.00  67.31      A  C
ATOM   1578  CZ   TYR A 334      12.210  40.041  -1.897  1.00  69.75      A  C
ATOM   1579  OH   TYR A 334      10.884  39.755  -2.132  1.00  71.23      A  O
ATOM   1580  C    TYR A 334      18.130  42.024   0.164  1.00  54.62      A  C
ATOM   1581  O    TYR A 334      18.588  41.231   0.974  1.00  54.28      A  O
```

Figure 3Z

```
ATOM   1582  N   GLN A 335      18.905  42.898  -0.471  1.00  52.79      A    N
ATOM   1583  CA  GLN A 335      20.337  42.916  -0.200  1.00  51.08      A    C
ATOM   1584  CB  GLN A 335      21.039  43.971  -1.040  1.00  56.98      A    C
ATOM   1585  CG  GLN A 335      21.167  43.616  -2.517  1.00  72.09      A    C
ATOM   1586  CD  GLN A 335      19.826  43.541  -3.246  1.00  80.01      A    C
ATOM   1587  OE1 GLN A 335      19.051  42.619  -3.020  1.00  86.56      A    O
ATOM   1588  NE2 GLN A 335      19.551  44.517  -4.122  1.00  85.47      A    N
ATOM   1589  C   GLN A 335      20.651  43.140   1.276  1.00  51.33      A    C
ATOM   1590  O   GLN A 335      21.150  42.237   1.936  1.00  49.14      A    O
ATOM   1591  N   GLU A 336      20.359  44.325   1.808  1.00  54.30      A    N
ATOM   1592  CA  GLU A 336      20.637  44.612   3.228  1.00  60.67      A    C
ATOM   1593  CB  GLU A 336      19.919  45.891   3.679  1.00  72.90      A    C
ATOM   1594  CG  GLU A 336      20.300  47.180   2.964  1.00  86.38      A    C
ATOM   1595  CD  GLU A 336      21.552  47.810   3.526  1.00  92.32      A    C
ATOM   1596  OE1 GLU A 336      22.652  47.482   3.030  1.00  91.22      A    O
ATOM   1597  OE2 GLU A 336      21.428  48.628   4.470  1.00  96.44      A    O
ATOM   1598  C   GLU A 336      20.203  43.480   4.172  1.00  56.11      A    C
ATOM   1599  O   GLU A 336      21.009  42.913   4.904  1.00  51.57      A    O
ATOM   1600  N   THR A 337      18.905  43.197   4.172  1.00  53.26      A    N
ATOM   1601  CA  THR A 337      18.324  42.148   4.994  1.00  49.20      A    C
ATOM   1602  CB  THR A 337      16.943  41.738   4.444  1.00  51.40      A    C
ATOM   1603  OG1 THR A 337      15.973  42.736   4.792  1.00  51.20      A    O
ATOM   1604  CG2 THR A 337      16.520  40.393   4.990  1.00  53.69      A    C
ATOM   1605  C   THR A 337      19.248  40.948   5.010  1.00  43.93      A    C
ATOM   1606  O   THR A 337      19.661  40.508   6.074  1.00  37.72      A    O
ATOM   1607  N   TYR A 338      19.564  40.426   3.821  1.00  46.03      A    N
ATOM   1608  CA  TYR A 338      20.473  39.279   3.669  1.00  49.15      A    C
ATOM   1609  CB  TYR A 338      20.785  39.003   2.177  1.00  57.12      A    C
ATOM   1610  CG  TYR A 338      21.740  37.845   1.946  1.00  71.41      A    C
ATOM   1611  CD1 TYR A 338      21.335  36.706   1.281  1.00  78.70      A    C
ATOM   1612  CE1 TYR A 338      22.178  35.616   1.146  1.00  87.18      A    C
ATOM   1613  CD2 TYR A 338      23.026  37.868   2.464  1.00  80.24      A    C
ATOM   1614  CE2 TYR A 338      23.879  36.790   2.335  1.00  87.60      A    C
ATOM   1615  CZ  TYR A 338      23.452  35.664   1.676  1.00  89.52      A    C
ATOM   1616  OH  TYR A 338      24.301  34.580   1.548  1.00  92.35      A    O
ATOM   1617  C   TYR A 338      21.754  39.679   4.378  1.00  47.29      A    C
ATOM   1618  O   TYR A 338      22.162  39.051   5.360  1.00  44.58      A    O
ATOM   1619  N   LYS A 339      22.374  40.727   3.835  1.00  47.80      A    N
ATOM   1620  CA  LYS A 339      23.588  41.316   4.352  1.00  45.74      A    C
ATOM   1621  CB  LYS A 339      23.667  42.735   3.790  1.00  45.18      A    C
ATOM   1622  CG  LYS A 339      24.515  43.747   4.524  1.00  44.41      A    C
ATOM   1623  CD  LYS A 339      24.676  45.039   3.695  1.00  47.17      A    C
ATOM   1624  CE  LYS A 339      25.566  44.807   2.460  1.00  58.17      A    C
ATOM   1625  NZ  LYS A 339      25.803  46.020   1.610  1.00  66.40      A    N
ATOM   1626  C   LYS A 339      23.505  41.265   5.883  1.00  46.23      A    C
ATOM   1627  O   LYS A 339      24.324  40.615   6.520  1.00  44.50      A    O
ATOM   1628  N   ARG A 340      22.495  41.892   6.475  1.00  45.42      A    N
ATOM   1629  CA  ARG A 340      22.354  41.851   7.922  1.00  50.17      A    C
ATOM   1630  CB  ARG A 340      21.344  42.883   8.385  1.00  62.49      A    C
ATOM   1631  CG  ARG A 340      21.797  44.314   8.194  1.00  81.35      A    C
ATOM   1632  CD  ARG A 340      20.668  45.295   8.471  1.00  93.90      A    C
ATOM   1633  NE  ARG A 340      20.678  46.395   7.509  1.00 101.42      A    N
ATOM   1634  CZ  ARG A 340      19.683  47.257   7.355  1.00 102.33      A    C
ATOM   1635  NH1 ARG A 340      18.592  47.141   8.108  1.00 103.01      A    N
ATOM   1636  NH2 ARG A 340      19.783  48.230   6.454  1.00 101.86      A    N
ATOM   1637  C   ARG A 340      21.955  40.490   8.493  1.00  48.56      A    C
ATOM   1638  O   ARG A 340      22.301  40.178   9.624  1.00  47.39      A    O
ATOM   1639  N   ILE A 341      21.217  39.674   7.740  1.00  47.03      A    N
ATOM   1640  CA  ILE A 341      20.813  38.349   8.246  1.00  41.13      A    C
ATOM   1641  CB  ILE A 341      19.807  37.647   7.280  1.00  36.36      A    C
ATOM   1642  CG2 ILE A 341      19.713  36.161   7.584  1.00  37.23      A    C
```

Figure 3AA

```
ATOM   1643  CG1 ILE A 341      18.423  38.264   7.433  1.00  31.72      A    C
ATOM   1644  CD1 ILE A 341      17.437  37.729   6.451  1.00  34.26      A    C
ATOM   1645  C   ILE A 341      22.037  37.452   8.460  1.00  38.07      A    C
ATOM   1646  O   ILE A 341      22.259  36.941   9.564  1.00  34.92      A    O
ATOM   1647  N   SER A 342      22.835  37.280   7.409  1.00  35.66      A    N
ATOM   1648  CA  SER A 342      24.018  36.447   7.521  1.00  36.42      A    C
ATOM   1649  CB  SER A 342      24.490  35.923   6.160  1.00  32.59      A    C
ATOM   1650  OG  SER A 342      25.100  36.931   5.395  1.00  37.12      A    O
ATOM   1651  C   SER A 342      25.123  37.220   8.196  1.00  34.08      A    C
ATOM   1652  O   SER A 342      25.889  36.648   8.949  1.00  35.28      A    O
ATOM   1653  N   ARG A 343      25.238  38.512   7.949  1.00  33.99      A    N
ATOM   1654  CA  ARG A 343      26.282  39.242   8.652  1.00  41.52      A    C
ATOM   1655  CB  ARG A 343      26.559  40.583   7.912  1.00  52.78      A    C
ATOM   1656  CG  ARG A 343      27.421  41.703   8.600  1.00  68.09      A    C
ATOM   1657  CD  ARG A 343      26.617  42.590   9.635  1.00  79.81      A    C
ATOM   1658  NE  ARG A 343      26.460  44.024   9.296  1.00  91.78      A    N
ATOM   1659  CZ  ARG A 343      25.441  44.563   8.608  1.00  93.76      A    C
ATOM   1660  NH1 ARG A 343      24.464  43.798   8.155  1.00  97.36      A    N
ATOM   1661  NH2 ARG A 343      25.360  45.879   8.409  1.00  88.77      A    N
ATOM   1662  C   ARG A 343      25.722  39.408  10.091  1.00  39.37      A    C
ATOM   1663  O   ARG A 343      26.370  39.994  10.974  1.00  36.75      A    O
ATOM   1664  N   VAL A 344      24.532  38.826  10.311  1.00  43.31      A    N
ATOM   1665  CA  VAL A 344      23.802  38.901  11.586  1.00  51.93      A    C
ATOM   1666  CB  VAL A 344      24.245  37.825  12.560  1.00  52.96      A    C
ATOM   1667  CG1 VAL A 344      23.684  38.107  13.949  1.00  49.07      A    C
ATOM   1668  CG2 VAL A 344      23.757  36.479  12.062  1.00  54.22      A    C
ATOM   1669  C   VAL A 344      23.984  40.264  12.223  1.00  57.93      A    C
ATOM   1670  O   VAL A 344      24.711  40.427  13.190  1.00  54.91      A    O
ATOM   1671  N   GLU A 345      23.288  41.236  11.654  1.00  70.29      A    N
ATOM   1672  CA  GLU A 345      23.345  42.632  12.059  1.00  84.01      A    C
ATOM   1673  CB  GLU A 345      23.677  43.466  10.822  1.00  95.43      A    C
ATOM   1674  CG  GLU A 345      23.425  44.955  10.921  1.00 109.36      A    C
ATOM   1675  CD  GLU A 345      24.578  45.698  11.538  1.00 117.01      A    C
ATOM   1676  OE1 GLU A 345      25.686  45.671  10.969  1.00 125.79      A    O
ATOM   1677  OE2 GLU A 345      24.379  46.313  12.598  1.00 121.00      A    O
ATOM   1678  C   GLU A 345      22.048  43.133  12.676  1.00  87.52      A    C
ATOM   1679  O   GLU A 345      21.151  43.580  11.967  1.00  88.71      A    O
ATOM   1680  N   PHE A 346      21.946  43.065  13.996  1.00  91.51      A    N
ATOM   1681  CA  PHE A 346      20.748  43.546  14.660  1.00  94.48      A    C
ATOM   1682  CB  PHE A 346      19.794  42.385  14.937  1.00  95.21      A    C
ATOM   1683  CG  PHE A 346      20.224  41.499  16.045  1.00  96.87      A    C
ATOM   1684  CD1 PHE A 346      19.560  41.525  17.257  1.00  98.35      A    C
ATOM   1685  CD2 PHE A 346      21.287  40.632  15.884  1.00  97.67      A    C
ATOM   1686  CE1 PHE A 346      19.949  40.698  18.296  1.00 101.86      A    C
ATOM   1687  CE2 PHE A 346      21.688  39.798  16.922  1.00  99.76      A    C
ATOM   1688  CZ  PHE A 346      21.017  39.832  18.129  1.00 101.79      A    C
ATOM   1689  C   PHE A 346      21.082  44.315  15.940  1.00  95.80      A    C
ATOM   1690  O   PHE A 346      21.971  43.926  16.698  1.00  96.22      A    O
ATOM   1691  N   THR A 347      20.355  45.414  16.152  1.00  96.60      A    N
ATOM   1692  CA  THR A 347      20.546  46.316  17.285  1.00  94.61      A    C
ATOM   1693  CB  THR A 347      21.047  47.644  16.760  1.00  96.49      A    C
ATOM   1694  OG1 THR A 347      21.375  48.494  17.853  1.00  96.97      A    O
ATOM   1695  CG2 THR A 347      19.983  48.306  15.932  1.00 100.44      A    C
ATOM   1696  C   THR A 347      19.234  46.555  18.048  1.00  91.67      A    C
ATOM   1697  O   THR A 347      18.203  46.793  17.424  1.00  88.78      A    O
ATOM   1698  N   PHE A 348      19.279  46.532  19.383  1.00  89.08      A    N
ATOM   1699  CA  PHE A 348      18.078  46.709  20.224  1.00  88.94      A    C
ATOM   1700  CB  PHE A 348      18.284  45.958  21.536  1.00  82.58      A    C
ATOM   1701  CG  PHE A 348      18.292  44.479  21.377  1.00  79.27      A    C
ATOM   1702  CD1 PHE A 348      17.134  43.796  21.041  1.00  76.61      A    C
ATOM   1703  CD2 PHE A 348      19.455  43.762  21.531  1.00  78.96      A    C
```

Figure 3BB

| ATOM | 1704 | CE1 | PHE | A | 348 | 17.138 | 42.416 | 20.858 | 1.00 | 70.66 | A | C |
|------|------|-----|-----|---|-----|--------|--------|--------|------|-------|---|---|
| ATOM | 1705 | CE2 | PHE | A | 348 | 19.466 | 42.384 | 21.350 | 1.00 | 74.38 | A | C |
| ATOM | 1706 | CZ  | PHE | A | 348 | 18.305 | 41.716 | 21.013 | 1.00 | 68.33 | A | C |
| ATOM | 1707 | C   | PHE | A | 348 | 17.549 | 48.128 | 20.547 | 1.00 | 91.65 | A | C |
| ATOM | 1708 | O   | PHE | A | 348 | 18.334 | 49.044 | 20.813 | 1.00 | 91.98 | A | O |
| ATOM | 1709 | N   | PRO | A | 349 | 16.200 | 48.310 | 20.564 | 1.00 | 93.26 | A | N |
| ATOM | 1710 | CD  | PRO | A | 349 | 15.161 | 47.271 | 20.463 | 1.00 | 94.54 | A | C |
| ATOM | 1711 | CA  | PRO | A | 349 | 15.563 | 49.597 | 20.854 | 1.00 | 92.51 | A | C |
| ATOM | 1712 | CB  | PRO | A | 349 | 14.113 | 49.340 | 20.506 | 1.00 | 92.56 | A | C |
| ATOM | 1713 | CG  | PRO | A | 349 | 13.936 | 47.984 | 21.010 | 1.00 | 92.05 | A | C |
| ATOM | 1714 | C   | PRO | A | 349 | 15.726 | 49.914 | 22.321 | 1.00 | 91.43 | A | C |
| ATOM | 1715 | O   | PRO | A | 349 | 15.877 | 49.015 | 23.142 | 1.00 | 89.95 | A | O |
| ATOM | 1716 | N   | ASP | A | 350 | 15.683 | 51.190 | 22.666 | 1.00 | 89.09 | A | N |
| ATOM | 1717 | CA  | ASP | A | 350 | 15.853 | 51.542 | 24.056 | 1.00 | 83.53 | A | C |
| ATOM | 1718 | CB  | ASP | A | 350 | 16.356 | 52.972 | 24.174 | 1.00 | 87.10 | A | C |
| ATOM | 1719 | CG  | ASP | A | 350 | 17.776 | 53.034 | 24.710 | 1.00 | 89.42 | A | C |
| ATOM | 1720 | OD1 | ASP | A | 350 | 18.661 | 52.370 | 24.121 | 1.00 | 86.26 | A | O |
| ATOM | 1721 | OD2 | ASP | A | 350 | 18.006 | 53.739 | 25.722 | 1.00 | 91.36 | A | O |
| ATOM | 1722 | C   | ASP | A | 350 | 14.593 | 51.339 | 24.884 | 1.00 | 78.87 | A | C |
| ATOM | 1723 | O   | ASP | A | 350 | 13.732 | 52.230 | 24.976 | 1.00 | 75.15 | A | O |
| ATOM | 1724 | N   | PHE | A | 351 | 14.504 | 50.141 | 25.469 | 1.00 | 71.54 | A | N |
| ATOM | 1725 | CA  | PHE | A | 351 | 13.394 | 49.724 | 26.326 | 1.00 | 65.36 | A | C |
| ATOM | 1726 | CB  | PHE | A | 351 | 12.036 | 50.238 | 25.804 | 1.00 | 61.38 | A | C |
| ATOM | 1727 | CG  | PHE | A | 351 | 11.420 | 49.385 | 24.715 | 1.00 | 55.02 | A | C |
| ATOM | 1728 | CD1 | PHE | A | 351 | 10.842 | 48.147 | 25.009 | 1.00 | 45.80 | A | C |
| ATOM | 1729 | CD2 | PHE | A | 351 | 11.408 | 49.830 | 23.391 | 1.00 | 52.37 | A | C |
| ATOM | 1730 | CE1 | PHE | A | 351 | 10.268 | 47.371 | 24.010 | 1.00 | 43.60 | A | C |
| ATOM | 1731 | CE2 | PHE | A | 351 | 10.834 | 49.056 | 22.380 | 1.00 | 48.80 | A | C |
| ATOM | 1732 | CZ  | PHE | A | 351 | 10.262 | 47.822 | 22.696 | 1.00 | 46.46 | A | C |
| ATOM | 1733 | C   | PHE | A | 351 | 13.346 | 48.206 | 26.455 | 1.00 | 62.55 | A | C |
| ATOM | 1734 | O   | PHE | A | 351 | 12.797 | 47.690 | 27.426 | 1.00 | 58.07 | A | O |
| ATOM | 1735 | N   | VAL | A | 352 | 13.898 | 47.479 | 25.485 | 1.00 | 63.79 | A | N |
| ATOM | 1736 | CA  | VAL | A | 352 | 13.865 | 46.017 | 25.597 | 1.00 | 65.68 | A | C |
| ATOM | 1737 | CB  | VAL | A | 352 | 14.364 | 45.245 | 24.290 | 1.00 | 65.27 | A | C |
| ATOM | 1738 | CG1 | VAL | A | 352 | 14.455 | 43.744 | 24.559 | 1.00 | 57.23 | A | C |
| ATOM | 1739 | CG2 | VAL | A | 352 | 13.385 | 45.451 | 23.131 | 1.00 | 63.19 | A | C |
| ATOM | 1740 | C   | VAL | A | 352 | 14.697 | 45.596 | 26.805 | 1.00 | 64.30 | A | C |
| ATOM | 1741 | O   | VAL | A | 352 | 15.901 | 45.860 | 26.911 | 1.00 | 65.67 | A | O |
| ATOM | 1742 | N   | THR | A | 353 | 13.999 | 44.970 | 27.735 | 1.00 | 59.80 | A | N |
| ATOM | 1743 | CA  | THR | A | 353 | 14.584 | 44.474 | 28.949 | 1.00 | 63.12 | A | C |
| ATOM | 1744 | CB  | THR | A | 353 | 13.608 | 43.616 | 29.659 | 1.00 | 63.77 | A | C |
| ATOM | 1745 | OG1 | THR | A | 353 | 14.318 | 42.784 | 30.579 | 1.00 | 70.40 | A | O |
| ATOM | 1746 | CG2 | THR | A | 353 | 12.870 | 42.746 | 28.653 | 1.00 | 61.53 | A | C |
| ATOM | 1747 | C   | THR | A | 353 | 15.791 | 43.602 | 28.685 | 1.00 | 66.61 | A | C |
| ATOM | 1748 | O   | THR | A | 353 | 15.783 | 42.787 | 27.763 | 1.00 | 66.09 | A | O |
| ATOM | 1749 | N   | GLU | A | 354 | 16.808 | 43.758 | 29.528 | 1.00 | 72.19 | A | N |
| ATOM | 1750 | CA  | GLU | A | 354 | 18.045 | 42.981 | 29.441 | 1.00 | 76.06 | A | C |
| ATOM | 1751 | CB  | GLU | A | 354 | 18.922 | 43.244 | 30.667 | 1.00 | 85.78 | A | C |
| ATOM | 1752 | CG  | GLU | A | 354 | 20.031 | 42.217 | 30.868 | 1.00 | 100.57 | A | C |
| ATOM | 1753 | CD  | GLU | A | 354 | 20.596 | 42.220 | 32.288 | 1.00 | 106.47 | A | C |
| ATOM | 1754 | OE1 | GLU | A | 354 | 19.817 | 41.976 | 33.245 | 1.00 | 103.80 | A | O |
| ATOM | 1755 | OE2 | GLU | A | 354 | 21.819 | 42.462 | 32.440 | 1.00 | 110.46 | A | O |
| ATOM | 1756 | C   | GLU | A | 354 | 17.745 | 41.492 | 29.363 | 1.00 | 74.65 | A | C |
| ATOM | 1757 | O   | GLU | A | 354 | 18.339 | 40.765 | 28.565 | 1.00 | 75.75 | A | O |
| ATOM | 1758 | N   | GLY | A | 355 | 16.832 | 41.041 | 30.211 | 1.00 | 73.65 | A | N |
| ATOM | 1759 | CA  | GLY | A | 355 | 16.472 | 39.640 | 30.205 | 1.00 | 73.31 | A | C |
| ATOM | 1760 | C   | GLY | A | 355 | 16.115 | 39.221 | 28.798 | 1.00 | 71.62 | A | C |
| ATOM | 1761 | O   | GLY | A | 355 | 16.403 | 38.102 | 28.367 | 1.00 | 67.84 | A | O |
| ATOM | 1762 | N   | ALA | A | 356 | 15.482 | 40.136 | 28.077 | 1.00 | 70.44 | A | N |
| ATOM | 1763 | CA  | ALA | A | 356 | 15.086 | 39.874 | 26.708 | 1.00 | 68.66 | A | C |
| ATOM | 1764 | CB  | ALA | A | 356 | 14.249 | 41.029 | 26.179 | 1.00 | 68.10 | A | C |

Figure 3CC

```
ATOM   1765  C    ALA A 356      16.338  39.717  25.867  1.00  67.16      A  C
ATOM   1766  O    ALA A 356      16.564  38.678  25.236  1.00  65.22      A  O
ATOM   1767  N    ARG A 357      17.153  40.766  25.884  1.00  63.55      A  N
ATOM   1768  CA   ARG A 357      18.382  40.804  25.117  1.00  59.76      A  C
ATOM   1769  CB   ARG A 357      19.318  41.871  25.681  1.00  53.94      A  C
ATOM   1770  CG   ARG A 357      18.991  43.279  25.172  1.00  57.49      A  C
ATOM   1771  CD   ARG A 357      19.006  44.325  26.293  1.00  63.69      A  C
ATOM   1772  NE   ARG A 357      18.824  45.691  25.810  1.00  66.73      A  N
ATOM   1773  CZ   ARG A 357      19.760  46.391  25.177  1.00  71.81      A  C
ATOM   1774  NH1  ARG A 357      20.959  45.864  24.938  1.00  75.34      A  N
ATOM   1775  NH2  ARG A 357      19.498  47.634  24.798  1.00  75.86      A  N
ATOM   1776  C    ARG A 357      19.087  39.467  25.019  1.00  59.86      A  C
ATOM   1777  O    ARG A 357      19.530  39.081  23.937  1.00  63.20      A  O
ATOM   1778  N    ASP A 358      19.180  38.729  26.114  1.00  59.07      A  N
ATOM   1779  CA   ASP A 358      19.876  37.464  25.989  1.00  54.78      A  C
ATOM   1780  CB   ASP A 358      20.837  37.227  27.166  1.00  63.30      A  C
ATOM   1781  CG   ASP A 358      20.185  37.401  28.503  1.00  70.77      A  C
ATOM   1782  OD1  ASP A 358      19.830  38.550  28.847  1.00  73.52      A  O
ATOM   1783  OD2  ASP A 358      20.040  36.380  29.206  1.00  77.06      A  O
ATOM   1784  C    ASP A 358      19.038  36.227  25.735  1.00  47.71      A  C
ATOM   1785  O    ASP A 358      19.584  35.129  25.668  1.00  42.20      A  O
ATOM   1786  N    LEU A 359      17.724  36.364  25.597  1.00  44.23      A  N
ATOM   1787  CA   LEU A 359      16.954  35.169  25.279  1.00  51.82      A  C
ATOM   1788  CB   LEU A 359      15.519  35.203  25.801  1.00  50.69      A  C
ATOM   1789  CG   LEU A 359      14.598  34.034  25.366  1.00  50.60      A  C
ATOM   1790  CD1  LEU A 359      14.033  34.280  23.969  1.00  45.72      A  C
ATOM   1791  CD2  LEU A 359      15.347  32.719  25.427  1.00  54.34      A  C
ATOM   1792  C    LEU A 359      16.922  35.122  23.779  1.00  57.56      A  C
ATOM   1793  O    LEU A 359      16.661  34.077  23.183  1.00  62.18      A  O
ATOM   1794  N    ILE A 360      17.163  36.268  23.158  1.00  64.80      A  N
ATOM   1795  CA   ILE A 360      17.183  36.285  21.715  1.00  74.60      A  C
ATOM   1796  CB   ILE A 360      16.428  37.516  21.145  1.00  81.71      A  C
ATOM   1797  CG2  ILE A 360      17.003  38.793  21.701  1.00  83.67      A  C
ATOM   1798  CG1  ILE A 360      16.448  37.457  19.615  1.00  85.27      A  C
ATOM   1799  CD1  ILE A 360      15.309  38.191  18.960  1.00  82.85      A  C
ATOM   1800  C    ILE A 360      18.642  36.222  21.269  1.00  72.26      A  C
ATOM   1801  O    ILE A 360      18.997  35.401  20.426  1.00  71.73      A  O
ATOM   1802  N    SER A 361      19.503  37.043  21.858  1.00  69.17      A  N
ATOM   1803  CA   SER A 361      20.907  36.994  21.478  1.00  68.51      A  C
ATOM   1804  CB   SER A 361      21.754  37.827  22.426  1.00  68.11      A  C
ATOM   1805  OG   SER A 361      21.464  39.193  22.271  1.00  66.69      A  O
ATOM   1806  C    SER A 361      21.372  35.553  21.548  1.00  66.75      A  C
ATOM   1807  O    SER A 361      22.328  35.158  20.890  1.00  65.50      A  O
ATOM   1808  N    ARG A 362      20.670  34.768  22.348  1.00  64.87      A  N
ATOM   1809  CA   ARG A 362      21.019  33.382  22.548  1.00  67.02      A  C
ATOM   1810  CB   ARG A 362      20.608  32.952  23.942  1.00  69.78      A  C
ATOM   1811  CG   ARG A 362      21.234  31.680  24.378  1.00  80.64      A  C
ATOM   1812  CD   ARG A 362      22.181  31.961  25.512  1.00  92.81      A  C
ATOM   1813  NE   ARG A 362      21.630  31.480  26.766  1.00 101.50      A  N
ATOM   1814  CZ   ARG A 362      21.330  30.205  27.002  1.00 104.13      A  C
ATOM   1815  NH1  ARG A 362      21.528  29.273  26.068  1.00  99.14      A  N
ATOM   1816  NH2  ARG A 362      20.832  29.862  28.181  1.00 106.78      A  N
ATOM   1817  C    ARG A 362      20.342  32.479  21.558  1.00  69.90      A  C
ATOM   1818  O    ARG A 362      20.682  31.307  21.481  1.00  70.10      A  O
ATOM   1819  N    LEU A 363      19.383  33.023  20.807  1.00  72.86      A  N
ATOM   1820  CA   LEU A 363      18.609  32.251  19.823  1.00  75.57      A  C
ATOM   1821  CB   LEU A 363      17.129  32.554  19.979  1.00  68.14      A  C
ATOM   1822  CG   LEU A 363      16.275  31.328  20.227  1.00  61.69      A  C
ATOM   1823  CD1  LEU A 363      16.990  30.310  21.085  1.00  55.05      A  C
ATOM   1824  CD2  LEU A 363      15.037  31.800  20.901  1.00  68.72      A  C
ATOM   1825  C    LEU A 363      19.001  32.501  18.384  1.00  80.34      A  C
```

Figure 3DD

| | | | | | | | | | | |
|---|---|---|---|---|---|---|---|---|---|---|
| ATOM | 1826 | O   | LEU | A | 363 | 18.773 | 31.665 | 17.503 | 1.00 | 79.68 | A | O |
| ATOM | 1827 | N   | LEU | A | 364 | 19.571 | 33.675 | 18.150 | 1.00 | 86.45 | A | N |
| ATOM | 1828 | CA  | LEU | A | 364 | 20.013 | 34.037 | 16.824 | 1.00 | 90.95 | A | C |
| ATOM | 1829 | CB  | LEU | A | 364 | 19.567 | 35.478 | 16.496 | 1.00 | 94.41 | A | C |
| ATOM | 1830 | CG  | LEU | A | 364 | 20.403 | 36.708 | 16.874 | 1.00 | 99.69 | A | C |
| ATOM | 1831 | CD1 | LEU | A | 364 | 20.929 | 36.598 | 18.310 | 1.00 | 101.56 | A | C |
| ATOM | 1832 | CD2 | LEU | A | 364 | 21.566 | 36.837 | 15.895 | 1.00 | 103.54 | A | C |
| ATOM | 1833 | C   | LEU | A | 364 | 21.538 | 33.870 | 16.784 | 1.00 | 91.64 | A | C |
| ATOM | 1834 | O   | LEU | A | 364 | 22.293 | 34.712 | 17.251 | 1.00 | 89.95 | A | O |
| ATOM | 1835 | N   | LYS | A | 365 | 21.985 | 32.733 | 16.274 | 1.00 | 93.08 | A | N |
| ATOM | 1836 | CA  | LYS | A | 365 | 23.405 | 32.485 | 16.165 | 1.00 | 91.91 | A | C |
| ATOM | 1837 | CB  | LYS | A | 365 | 23.875 | 31.487 | 17.204 | 1.00 | 97.36 | A | C |
| ATOM | 1838 | CG  | LYS | A | 365 | 25.372 | 31.475 | 17.421 | 1.00 | 104.52 | A | C |
| ATOM | 1839 | CD  | LYS | A | 365 | 25.864 | 32.755 | 18.114 | 1.00 | 107.60 | A | C |
| ATOM | 1840 | CE  | LYS | A | 365 | 26.619 | 33.719 | 17.168 | 1.00 | 105.34 | A | C |
| ATOM | 1841 | NZ  | LYS | A | 365 | 25.762 | 34.449 | 16.171 | 1.00 | 105.53 | A | N |
| ATOM | 1842 | C   | LYS | A | 365 | 23.620 | 31.918 | 14.793 | 1.00 | 88.85 | A | C |
| ATOM | 1843 | O   | LYS | A | 365 | 22.881 | 31.036 | 14.347 | 1.00 | 86.15 | A | O |
| ATOM | 1844 | N   | HIS | A | 366 | 24.637 | 32.441 | 14.124 | 1.00 | 86.85 | A | N |
| ATOM | 1845 | CA  | HIS | A | 366 | 24.971 | 32.022 | 12.783 | 1.00 | 84.66 | A | C |
| ATOM | 1846 | CB  | HIS | A | 366 | 26.190 | 32.786 | 12.312 | 1.00 | 89.33 | A | C |
| ATOM | 1847 | CG  | HIS | A | 366 | 26.442 | 32.639 | 10.855 | 1.00 | 96.75 | A | C |
| ATOM | 1848 | CD2 | HIS | A | 366 | 27.074 | 31.671 | 10.155 | 1.00 | 100.67 | A | C |
| ATOM | 1849 | ND1 | HIS | A | 366 | 25.924 | 33.510 | 9.925 | 1.00 | 98.80 | A | N |
| ATOM | 1850 | CE1 | HIS | A | 366 | 26.223 | 33.083 | 8.711 | 1.00 | 101.84 | A | C |
| ATOM | 1851 | NE2 | HIS | A | 366 | 26.920 | 31.968 | 8.823 | 1.00 | 101.49 | A | N |
| ATOM | 1852 | C   | HIS | A | 366 | 25.233 | 30.519 | 12.647 | 1.00 | 81.57 | A | C |
| ATOM | 1853 | O   | HIS | A | 366 | 24.923 | 29.915 | 11.609 | 1.00 | 71.88 | A | O |
| ATOM | 1854 | N   | ASN | A | 367 | 25.798 | 29.921 | 13.697 | 1.00 | 82.68 | A | N |
| ATOM | 1855 | CA  | ASN | A | 367 | 26.132 | 28.493 | 13.705 | 1.00 | 84.38 | A | C |
| ATOM | 1856 | CB  | ASN | A | 367 | 27.448 | 28.268 | 14.452 | 1.00 | 87.91 | A | C |
| ATOM | 1857 | CG  | ASN | A | 367 | 28.091 | 26.934 | 14.105 | 1.00 | 89.90 | A | C |
| ATOM | 1858 | OD1 | ASN | A | 367 | 27.486 | 25.865 | 14.278 | 1.00 | 86.54 | A | O |
| ATOM | 1859 | ND2 | ASN | A | 367 | 29.325 | 26.990 | 13.600 | 1.00 | 92.69 | A | N |
| ATOM | 1860 | C   | ASN | A | 367 | 25.063 | 27.594 | 14.321 | 1.00 | 81.67 | A | C |
| ATOM | 1861 | O   | ASN | A | 367 | 24.855 | 27.601 | 15.532 | 1.00 | 80.79 | A | O |
| ATOM | 1862 | N   | PRO | A | 368 | 24.396 | 26.779 | 13.496 | 1.00 | 78.80 | A | N |
| ATOM | 1863 | CD  | PRO | A | 368 | 24.615 | 26.547 | 12.057 | 1.00 | 77.22 | A | C |
| ATOM | 1864 | CA  | PRO | A | 368 | 23.355 | 25.892 | 14.025 | 1.00 | 76.67 | A | C |
| ATOM | 1865 | CB  | PRO | A | 368 | 23.164 | 24.890 | 12.899 | 1.00 | 78.68 | A | C |
| ATOM | 1866 | CG  | PRO | A | 368 | 23.396 | 25.747 | 11.671 | 1.00 | 79.08 | A | C |
| ATOM | 1867 | C   | PRO | A | 368 | 23.781 | 25.238 | 15.328 | 1.00 | 72.81 | A | C |
| ATOM | 1868 | O   | PRO | A | 368 | 23.044 | 25.207 | 16.301 | 1.00 | 67.46 | A | O |
| ATOM | 1869 | N   | SER | A | 369 | 25.000 | 24.738 | 15.330 | 1.00 | 73.58 | A | N |
| ATOM | 1870 | CA  | SER | A | 369 | 25.573 | 24.079 | 16.485 | 1.00 | 75.54 | A | C |
| ATOM | 1871 | CB  | SER | A | 369 | 27.063 | 23.840 | 16.230 | 1.00 | 79.27 | A | C |
| ATOM | 1872 | OG  | SER | A | 369 | 27.817 | 23.866 | 17.438 | 1.00 | 85.06 | A | O |
| ATOM | 1873 | C   | SER | A | 369 | 25.423 | 24.812 | 17.808 | 1.00 | 76.40 | A | C |
| ATOM | 1874 | O   | SER | A | 369 | 25.452 | 24.184 | 18.872 | 1.00 | 74.15 | A | O |
| ATOM | 1875 | N   | GLN | A | 370 | 25.265 | 26.129 | 17.757 | 1.00 | 78.67 | A | N |
| ATOM | 1876 | CA  | GLN | A | 370 | 25.191 | 26.905 | 18.990 | 1.00 | 81.51 | A | C |
| ATOM | 1877 | CB  | GLN | A | 370 | 25.997 | 28.194 | 18.854 | 1.00 | 82.32 | A | C |
| ATOM | 1878 | CG  | GLN | A | 370 | 27.274 | 28.043 | 18.074 | 1.00 | 80.54 | A | C |
| ATOM | 1879 | CD  | GLN | A | 370 | 28.262 | 29.134 | 18.383 | 1.00 | 84.05 | A | C |
| ATOM | 1880 | OE1 | GLN | A | 370 | 29.203 | 29.347 | 17.629 | 1.00 | 87.57 | A | O |
| ATOM | 1881 | NE2 | GLN | A | 370 | 28.066 | 29.825 | 19.506 | 1.00 | 85.89 | A | N |
| ATOM | 1882 | C   | GLN | A | 370 | 23.815 | 27.272 | 19.474 | 1.00 | 82.51 | A | C |
| ATOM | 1883 | O   | GLN | A | 370 | 23.665 | 27.737 | 20.601 | 1.00 | 81.63 | A | O |
| ATOM | 1884 | N   | ARG | A | 371 | 22.806 | 27.082 | 18.636 | 1.00 | 83.02 | A | N |
| ATOM | 1885 | CA  | ARG | A | 371 | 21.471 | 27.452 | 19.055 | 1.00 | 83.67 | A | C |
| ATOM | 1886 | CB  | ARG | A | 371 | 20.553 | 27.653 | 17.843 | 1.00 | 92.66 | A | C |

Figure 3EE

```
ATOM 1887  CG   ARG A 371     20.868  28.945  17.070  1.00  104.82      A  C
ATOM 1888  CD   ARG A 371     21.173  30.141  18.024  1.00  119.98      A  C
ATOM 1889  NE   ARG A 371     22.255  29.858  18.987  1.00  129.96      A  N
ATOM 1890  CZ   ARG A 371     22.812  30.739  19.825  1.00  132.05      A  C
ATOM 1891  NH1  ARG A 371     23.781  30.348  20.650  1.00  132.25      A  N
ATOM 1892  NH2  ARG A 371     22.425  32.011  19.829  1.00  134.27      A  N
ATOM 1893  C    ARG A 371     20.881  26.504  20.063  1.00   76.57      A  C
ATOM 1894  O    ARG A 371     20.844  25.293  19.853  1.00   75.92      A  O
ATOM 1895  N    PRO A 372     20.417  27.062  21.189  1.00   69.45      A  N
ATOM 1896  CD   PRO A 372     20.166  28.504  21.279  1.00   65.18      A  C
ATOM 1897  CA   PRO A 372     19.807  26.383  22.327  1.00   66.81      A  C
ATOM 1898  CB   PRO A 372     19.134  27.523  23.071  1.00   62.53      A  C
ATOM 1899  CG   PRO A 372     19.971  28.678  22.731  1.00   61.51      A  C
ATOM 1900  C    PRO A 372     18.806  25.353  21.848  1.00   70.16      A  C
ATOM 1901  O    PRO A 372     18.181  25.549  20.813  1.00   76.53      A  O
ATOM 1902  N    MET A 373     18.648  24.251  22.572  1.00   70.74      A  N
ATOM 1903  CA   MET A 373     17.674  23.271  22.134  1.00   71.42      A  C
ATOM 1904  CB   MET A 373     18.095  21.850  22.538  1.00   71.25      A  C
ATOM 1905  CG   MET A 373     17.671  20.759  21.541  1.00   71.53      A  C
ATOM 1906  SD   MET A 373     15.962  20.936  20.935  1.00   77.93      A  S
ATOM 1907  CE   MET A 373     15.574  19.302  20.223  1.00   76.18      A  C
ATOM 1908  C    MET A 373     16.350  23.629  22.796  1.00   72.26      A  C
ATOM 1909  O    MET A 373     16.249  24.595  23.552  1.00   69.03      A  O
ATOM 1910  N    LEU A 374     15.337  22.842  22.479  1.00   76.21      A  N
ATOM 1911  CA   LEU A 374     13.995  22.971  23.018  1.00   83.32      A  C
ATOM 1912  CB   LEU A 374     13.292  21.593  22.874  1.00   80.59      A  C
ATOM 1913  CG   LEU A 374     14.017  20.247  23.187  1.00   73.28      A  C
ATOM 1914  CD1  LEU A 374     14.056  19.950  24.696  1.00   66.69      A  C
ATOM 1915  CD2  LEU A 374     13.300  19.098  22.458  1.00   63.53      A  C
ATOM 1916  C    LEU A 374     13.916  23.459  24.486  1.00   88.94      A  C
ATOM 1917  O    LEU A 374     13.669  24.644  24.768  1.00   86.25      A  O
ATOM 1918  N    ARG A 375     14.135  22.509  25.395  1.00   96.78      A  N
ATOM 1919  CA   ARG A 375     14.067  22.686  26.835  1.00  103.22      A  C
ATOM 1920  CB   ARG A 375     14.581  21.416  27.492  1.00  113.71      A  C
ATOM 1921  CG   ARG A 375     14.508  21.393  28.997  1.00  125.70      A  C
ATOM 1922  CD   ARG A 375     15.266  20.183  29.526  1.00  138.28      A  C
ATOM 1923  NE   ARG A 375     16.719  20.387  29.626  1.00  150.11      A  N
ATOM 1924  CZ   ARG A 375     17.550  20.632  28.608  1.00  154.89      A  C
ATOM 1925  NH1  ARG A 375     18.852  20.796  28.839  1.00  153.17      A  N
ATOM 1926  NH2  ARG A 375     17.096  20.718  27.362  1.00  161.43      A  N
ATOM 1927  C    ARG A 375     14.761  23.896  27.439  1.00  100.28      A  C
ATOM 1928  O    ARG A 375     14.596  24.163  28.632  1.00   99.03      A  O
ATOM 1929  N    GLU A 376     15.521  24.629  26.630  1.00   97.34      A  N
ATOM 1930  CA   GLU A 376     16.238  25.805  27.120  1.00   95.37      A  C
ATOM 1931  CB   GLU A 376     17.425  26.135  26.214  1.00  106.76      A  C
ATOM 1932  CG   GLU A 376     18.260  27.312  26.707  1.00  124.32      A  C
ATOM 1933  CD   GLU A 376     18.842  27.078  28.096  1.00  135.59      A  C
ATOM 1934  OE1  GLU A 376     19.604  26.093  28.259  1.00  142.83      A  O
ATOM 1935  OE2  GLU A 376     18.535  27.876  29.019  1.00  140.57      A  O
ATOM 1936  C    GLU A 376     15.349  27.028  27.242  1.00   87.29      A  C
ATOM 1937  O    GLU A 376     15.235  27.617  28.313  1.00   79.74      A  O
ATOM 1938  N    VAL A 377     14.729  27.424  26.139  1.00   83.15      A  N
ATOM 1939  CA   VAL A 377     13.855  28.578  26.186  1.00   81.49      A  C
ATOM 1940  CB   VAL A 377     13.145  28.834  24.839  1.00   79.47      A  C
ATOM 1941  CG1  VAL A 377     14.131  29.337  23.827  1.00   79.27      A  C
ATOM 1942  CG2  VAL A 377     12.484  27.571  24.348  1.00   79.59      A  C
ATOM 1943  C    VAL A 377     12.804  28.328  27.252  1.00   81.85      A  C
ATOM 1944  O    VAL A 377     12.616  29.142  28.154  1.00   86.53      A  O
ATOM 1945  N    LEU A 378     12.132  27.188  27.152  1.00   79.82      A  N
ATOM 1946  CA   LEU A 378     11.092  26.838  28.101  1.00   80.69      A  C
ATOM 1947  CB   LEU A 378     10.663  25.379  27.887  1.00   73.33      A  C
```

Figure 3PF

```
ATOM   1948  CG   LEU A 378       9.344  25.072  27.160  1.00  65.91      A  C
ATOM   1949  CD1  LEU A 378       8.761  26.319  26.549  1.00  60.22      A  C
ATOM   1950  CD2  LEU A 378       9.584  24.023  26.098  1.00  63.01      A  C
ATOM   1951  C    LEU A 378      11.507  27.080  29.554  1.00  84.79      A  C
ATOM   1952  O    LEU A 378      10.662  27.389  30.387  1.00  87.16      A  O
ATOM   1953  N    GLU A 379      12.799  26.969  29.857  1.00  85.21      A  N
ATOM   1954  CA   GLU A 379      13.270  27.181  31.226  1.00  84.39      A  C
ATOM   1955  CB   GLU A 379      14.168  26.016  31.671  1.00  88.12      A  C
ATOM   1956  CG   GLU A 379      14.579  26.043  33.158  1.00  94.28      A  C
ATOM   1957  CD   GLU A 379      15.792  26.944  33.479  1.00  98.07      A  C
ATOM   1958  OE1  GLU A 379      16.097  27.107  34.683  1.00  99.07      A  O
ATOM   1959  OE2  GLU A 379      16.446  27.480  32.551  1.00  97.87      A  O
ATOM   1960  C    GLU A 379      14.023  28.502  31.395  1.00  82.14      A  C
ATOM   1961  O    GLU A 379      14.283  28.941  32.523  1.00  83.12      A  O
ATOM   1962  N    HIS A 380      14.375  29.146  30.286  1.00  77.12      A  N
ATOM   1963  CA   HIS A 380      15.098  30.404  30.393  1.00  73.06      A  C
ATOM   1964  CB   HIS A 380      15.177  31.144  29.051  1.00  76.12      A  C
ATOM   1965  CG   HIS A 380      15.975  32.418  29.105  1.00  77.81      A  C
ATOM   1966  CD2  HIS A 380      17.204  32.720  28.624  1.00  75.81      A  C
ATOM   1967  ND1  HIS A 380      15.510  33.569  29.707  1.00  76.82      A  N
ATOM   1968  CE1  HIS A 380      16.415  34.523  29.590  1.00  73.10      A  C
ATOM   1969  NE2  HIS A 380      17.452  34.034  28.938  1.00  71.49      A  N
ATOM   1970  C    HIS A 380      14.443  31.296  31.428  1.00  69.83      A  C
ATOM   1971  O    HIS A 380      13.228  31.441  31.495  1.00  61.10      A  O
ATOM   1972  N    PRO A 381      15.260  31.900  32.265  1.00  71.01      A  N
ATOM   1973  CD   PRO A 381      16.730  31.835  32.294  1.00  72.91      A  C
ATOM   1974  CA   PRO A 381      14.742  32.778  33.300  1.00  72.72      A  C
ATOM   1975  CB   PRO A 381      16.019  33.295  33.978  1.00  77.20      A  C
ATOM   1976  CG   PRO A 381      17.087  33.154  32.895  1.00  72.88      A  C
ATOM   1977  C    PRO A 381      13.819  33.894  32.805  1.00  73.49      A  C
ATOM   1978  O    PRO A 381      13.130  34.514  33.610  1.00  73.11      A  O
ATOM   1979  N    TRP A 382      13.792  34.163  31.504  1.00  76.65      A  N
ATOM   1980  CA   TRP A 382      12.917  35.226  31.018  1.00  78.77      A  C
ATOM   1981  CB   TRP A 382      13.529  35.962  29.834  1.00  92.91      A  C
ATOM   1982  CG   TRP A 382      12.896  37.301  29.605  1.00 105.61      A  C
ATOM   1983  CD2  TRP A 382      11.926  37.653  28.595  1.00 109.44      A  C
ATOM   1984  CE2  TRP A 382      11.630  39.022  28.763  1.00 112.17      A  C
ATOM   1985  CE3  TRP A 382      11.284  36.946  27.570  1.00 107.97      A  C
ATOM   1986  CD1  TRP A 382      13.130  38.434  30.318  1.00 109.46      A  C
ATOM   1987  NE1  TRP A 382      12.377  39.473  29.819  1.00 114.96      A  N
ATOM   1988  CZ2  TRP A 382      10.722  39.700  27.947  1.00 109.26      A  C
ATOM   1989  CZ3  TRP A 382      10.386  37.620  26.761  1.00 106.63      A  C
ATOM   1990  CH2  TRP A 382      10.114  38.985  26.956  1.00 107.12      A  C
ATOM   1991  C    TRP A 382      11.560  34.684  30.610  1.00  74.34      A  C
ATOM   1992  O    TRP A 382      10.562  35.384  30.729  1.00  75.02      A  O
ATOM   1993  N    ILE A 383      11.522  33.452  30.108  1.00  70.82      A  N
ATOM   1994  CA   ILE A 383      10.257  32.852  29.730  1.00  70.10      A  C
ATOM   1995  CB   ILE A 383      10.423  31.458  29.149  1.00  71.61      A  C
ATOM   1996  CG2  ILE A 383      11.181  30.587  30.117  1.00  65.61      A  C
ATOM   1997  CG1  ILE A 383       9.034  30.868  28.874  1.00  80.47      A  C
ATOM   1998  CD1  ILE A 383       8.942  29.339  28.841  1.00  83.18      A  C
ATOM   1999  C    ILE A 383       9.513  32.708  31.049  1.00  68.89      A  C
ATOM   2000  O    ILE A 383       8.315  32.977  31.143  1.00  66.86      A  O
ATOM   2001  N    THR A 384      10.242  32.276  32.072  1.00  66.22      A  N
ATOM   2002  CA   THR A 384       9.666  32.114  33.398  1.00  66.21      A  C
ATOM   2003  CB   THR A 384      10.519  31.172  34.266  1.00  64.92      A  C
ATOM   2004  OG1  THR A 384      11.608  31.912  34.833  1.00  75.34      A  O
ATOM   2005  CG2  THR A 384      11.077  30.025  33.426  1.00  50.61      A  C
ATOM   2006  C    THR A 384       9.637  33.493  34.064  1.00  69.82      A  C
ATOM   2007  O    THR A 384      10.675  34.124  34.228  1.00  68.66      A  O
ATOM   2008  N    ALA A 385       8.444  33.944  34.440  1.00  76.43      A  N
```

Figure 3GG

```
ATOM  2009  CA   ALA A 385      8.217  35.243  35.084  1.00   81.12      A  C
ATOM  2010  CB   ALA A 385      9.530  35.848  35.613  1.00   80.53      A  C
ATOM  2011  C    ALA A 385      7.546  36.199  34.097  1.00   82.87      A  C
ATOM  2012  O    ALA A 385      6.316  36.291  34.066  1.00   85.34      A  O
ATOM  2013  N    ASN A 386      8.334  36.918  33.302  1.00   83.36      A  N
ATOM  2014  CA   ASN A 386      7.745  37.825  32.331  1.00   82.74      A  C
ATOM  2015  CB   ASN A 386      8.789  38.344  31.356  1.00   83.56      A  C
ATOM  2016  CG   ASN A 386      9.639  39.461  31.942  1.00   86.73      A  C
ATOM  2017  OD1  ASN A 386      9.187  40.605  32.066  1.00   84.34      A  O
ATOM  2018  ND2  ASN A 386     10.884  39.135  32.309  1.00   88.09      A  N
ATOM  2019  C    ASN A 386      6.813  36.926  31.596  1.00   82.97      A  C
ATOM  2020  O    ASN A 386      7.261  35.992  30.958  1.00   83.21      A  O
ATOM  2021  N    SER A 387      5.516  37.167  31.732  1.00   84.29      A  N
ATOM  2022  CA   SER A 387      4.522  36.347  31.047  1.00   86.33      A  C
ATOM  2023  CB   SER A 387      4.810  36.353  29.544  1.00   93.76      A  C
ATOM  2024  OG   SER A 387      4.204  35.245  28.889  1.00  103.67      A  O
ATOM  2025  C    SER A 387      4.399  34.892  31.517  1.00   82.84      A  C
ATOM  2026  O    SER A 387      5.387  34.244  31.869  1.00   79.51      A  O
ATOM  2027  N    SER A 388      3.168  34.387  31.478  1.00   79.11      A  N
ATOM  2028  CA   SER A 388      2.874  33.019  31.873  1.00   73.64      A  C
ATOM  2029  CB   SER A 388      1.376  32.750  31.755  1.00   69.41      A  C
ATOM  2030  OG   SER A 388      1.100  31.420  32.131  1.00   67.33      A  O
ATOM  2031  C    SER A 388      3.642  32.016  31.013  1.00   72.12      A  C
ATOM  2032  O    SER A 388      4.646  32.430  30.392  1.00   69.89      A  O
TER   2034       SER A 388                                                A
ATOM  2035  C1   212 B   1     -4.302  30.253   8.464  1.00   68.60      B  C
ATOM  2036  C2   212 B   1     -4.851  31.084   9.411  1.00   68.12      B  C
ATOM  2037  C3   212 B   1     -5.317  32.331   9.022  1.00   70.88      B  C
ATOM  2038  C4   212 B   1     -5.251  32.762   7.698  1.00   69.06      B  C
ATOM  2039  C55  212 B   1     -4.687  31.914   6.771  1.00   73.11      B  C
ATOM  2040  C7   212 B   1     -9.623  34.126  10.749  1.00   62.88      B  C
ATOM  2041  C9   212 B   1     -9.260  35.315  10.076  1.00   66.59      B  C
ATOM  2042  N    212 B   1     -8.544  35.273   8.892  1.00   64.04      B  N
ATOM  2043  C14  212 B   1     -8.181  34.044   8.363  1.00   58.85      B  C
ATOM  2044  N2   212 B   1     -8.569  32.905   9.061  1.00   56.27      B  N
ATOM  2045  C17  212 B   1     -9.268  32.945  10.249  1.00   57.06      B  C
ATOM  2046  C8   212 B   1     -8.861  28.850   9.398  1.00   45.58      B  C
ATOM  2047  C10  212 B   1     -8.822  30.233   9.511  1.00   44.13      B  C
ATOM  2048  C12  212 B   1     -9.224  30.505  10.802  1.00   44.58      B  C
ATOM  2049  N3   212 B   1     -9.185  28.311  10.732  1.00   39.51      B  N
ATOM  2050  N4   212 B   1     -9.375  29.358  11.605  1.00   39.86      B  N
ATOM  2051  C18  212 B   1     -5.876  34.076   7.274  1.00   63.34      B  C
ATOM  2052  C15  212 B   1     -8.677  28.167   8.191  1.00   48.92      B  C
ATOM  2053  C11  212 B   1    -10.373  34.156  11.968  1.00   64.95      B  C
ATOM  2054  C13  212 B   1    -10.752  35.364  12.523  1.00   72.34      B  C
ATOM  2055  C16  212 B   1    -10.386  36.566  11.876  1.00   75.43      B  C
ATOM  2056  C5   212 B   1     -9.633  36.546  10.648  1.00   72.28      B  C
ATOM  2057  N6   212 B   1     -9.501  31.845  11.052  1.00   51.85      B  N
ATOM  2058  N9   212 B   1     -7.358  33.964   7.215  1.00   56.80      B  N
ATOM  2059  N8   212 B   1     -4.216  30.663   7.155  1.00   73.15      B  N
TER   2060       212 B   1                                                B
END
```

Figure 4A

| Atom | Type | Resid | # | X | Y | Z | Occ | B | Mol | |
|------|------|-------|---|---|---|---|-----|---|-----|---|
| ATOM | 1 | CB | TRP A 128 | 27.817 | 61.000 | 21.182 | 1.00 | 98.41 | A | C |
| ATOM | 2 | CG | TRP A 128 | 28.380 | 61.241 | 19.859 | 1.00 | 107.87 | A | C |
| ATOM | 3 | CD2 | TRP A 128 | 27.665 | 61.221 | 18.610 | 1.00 | 111.93 | A | C |
| ATOM | 4 | CE2 | TRP A 128 | 28.595 | 61.542 | 17.590 | 1.00 | 114.01 | A | C |
| ATOM | 5 | CE3 | TRP A 128 | 26.328 | 60.967 | 18.253 | 1.00 | 112.66 | A | C |
| ATOM | 6 | CD1 | TRP A 128 | 29.678 | 61.561 | 19.563 | 1.00 | 111.45 | A | C |
| ATOM | 7 | NE1 | TRP A 128 | 29.813 | 61.742 | 18.198 | 1.00 | 115.64 | A | N |
| ATOM | 8 | CZ2 | TRP A 128 | 28.225 | 61.615 | 16.219 | 1.00 | 114.76 | A | C |
| ATOM | 9 | CZ3 | TRP A 128 | 25.961 | 61.040 | 16.893 | 1.00 | 112.93 | A | C |
| ATOM | 10 | CH2 | TRP A 128 | 26.909 | 61.362 | 15.898 | 1.00 | 113.35 | A | C |
| ATOM | 11 | C | TRP A 128 | 26.497 | 61.762 | 23.050 | 1.00 | 95.74 | A | C |
| ATOM | 12 | O | TRP A 128 | 26.902 | 62.356 | 24.039 | 1.00 | 95.36 | A | O |
| ATOM | 13 | N | TRP A 128 | 27.731 | 63.429 | 21.703 | 1.00 | 91.77 | A | N |
| ATOM | 14 | CA | TRP A 128 | 26.958 | 62.149 | 21.678 | 1.00 | 94.64 | A | C |
| ATOM | 15 | N | ALA A 129 | 25.659 | 60.735 | 23.100 | 1.00 | 97.32 | A | N |
| ATOM | 16 | CA | ALA A 129 | 25.156 | 60.205 | 24.363 | 1.00 | 98.31 | A | C |
| ATOM | 17 | CB | ALA A 129 | 23.911 | 60.985 | 24.843 | 1.00 | 96.54 | A | C |
| ATOM | 18 | C | ALA A 129 | 24.821 | 58.737 | 24.127 | 1.00 | 98.04 | A | C |
| ATOM | 19 | O | ALA A 129 | 24.471 | 58.341 | 23.009 | 1.00 | 94.27 | A | O |
| ATOM | 20 | N | LEU A 130 | 24.959 | 57.930 | 25.177 | 1.00 | 108.85 | A | N |
| ATOM | 21 | CA | LEU A 130 | 24.681 | 56.495 | 25.086 | 1.00 | 103.78 | A | C |
| ATOM | 22 | CB | LEU A 130 | 24.893 | 55.813 | 26.447 | 1.00 | 102.54 | A | C |
| ATOM | 23 | CG | LEU A 130 | 24.512 | 54.324 | 26.544 | 1.00 | 100.22 | A | C |
| ATOM | 24 | CD1 | LEU A 130 | 25.310 | 53.540 | 25.509 | 1.00 | 97.26 | A | C |
| ATOM | 25 | CD2 | LEU A 130 | 24.757 | 53.788 | 27.981 | 1.00 | 99.07 | A | C |
| ATOM | 26 | C | LEU A 130 | 23.247 | 56.283 | 24.639 | 1.00 | 105.99 | A | C |
| ATOM | 27 | O | LEU A 130 | 22.857 | 55.200 | 24.186 | 1.00 | 105.36 | A | O |
| ATOM | 28 | N | GLU A 131 | 22.462 | 57.339 | 24.778 | 1.00 | 107.82 | A | N |
| ATOM | 29 | CA | GLU A 131 | 21.078 | 57.277 | 24.410 | 1.00 | 109.20 | A | C |
| ATOM | 30 | CB | GLU A 131 | 20.341 | 58.416 | 25.035 | 1.00 | 113.38 | A | C |
| ATOM | 31 | CG | GLU A 131 | 18.893 | 58.320 | 24.735 | 1.00 | 121.43 | A | C |
| ATOM | 32 | CD | GLU A 131 | 18.300 | 59.669 | 24.441 | 1.00 | 126.00 | A | C |
| ATOM | 33 | OE1 | GLU A 131 | 18.660 | 60.636 | 25.155 | 1.00 | 130.23 | A | O |
| ATOM | 34 | OE2 | GLU A 131 | 17.473 | 59.759 | 23.503 | 1.00 | 129.08 | A | O |
| ATOM | 35 | C | GLU A 131 | 20.890 | 57.366 | 22.916 | 1.00 | 108.63 | A | C |
| ATOM | 36 | O | GLU A 131 | 19.880 | 56.900 | 22.396 | 1.00 | 108.44 | A | O |
| ATOM | 37 | N | ASP A 132 | 21.865 | 57.974 | 22.240 | 1.00 | 107.80 | A | N |
| ATOM | 38 | CA | ASP A 132 | 21.848 | 58.186 | 20.785 | 1.00 | 105.97 | A | C |
| ATOM | 39 | CB | ASP A 132 | 22.988 | 59.125 | 20.403 | 1.00 | 109.93 | A | C |
| ATOM | 40 | CG | ASP A 132 | 22.946 | 60.433 | 21.169 | 1.00 | 112.63 | A | C |
| ATOM | 41 | OD1 | ASP A 132 | 22.899 | 60.396 | 22.416 | 1.00 | 115.57 | A | O |
| ATOM | 42 | OD2 | ASP A 132 | 22.964 | 61.499 | 20.527 | 1.00 | 111.61 | A | O |
| ATOM | 43 | C | ASP A 132 | 21.943 | 56.944 | 19.913 | 1.00 | 102.68 | A | C |
| ATOM | 44 | O | ASP A 132 | 21.824 | 57.020 | 18.691 | 1.00 | 99.16 | A | O |
| ATOM | 45 | N | PHE A 133 | 22.161 | 55.801 | 20.546 | 1.00 | 102.67 | A | N |
| ATOM | 46 | CA | PHE A 133 | 22.298 | 54.550 | 19.812 | 1.00 | 103.51 | A | C |
| ATOM | 47 | CB | PHE A 133 | 23.751 | 54.136 | 19.764 | 1.00 | 102.19 | A | C |
| ATOM | 48 | CG | PHE A 133 | 24.683 | 55.252 | 19.525 | 1.00 | 100.58 | A | C |
| ATOM | 49 | CD1 | PHE A 133 | 24.942 | 56.204 | 20.519 | 1.00 | 101.82 | A | C |
| ATOM | 50 | CD2 | PHE A 133 | 25.347 | 55.329 | 18.324 | 1.00 | 101.04 | A | C |
| ATOM | 51 | CE1 | PHE A 133 | 25.866 | 57.218 | 20.310 | 1.00 | 102.23 | A | C |
| ATOM | 52 | CE2 | PHE A 133 | 26.268 | 56.329 | 18.097 | 1.00 | 101.45 | A | C |
| ATOM | 53 | CZ | PHE A 133 | 26.534 | 57.279 | 19.092 | 1.00 | 101.79 | A | C |
| ATOM | 54 | C | PHE A 133 | 21.526 | 53.357 | 20.364 | 1.00 | 104.23 | A | C |
| ATOM | 55 | O | PHE A 133 | 21.140 | 53.326 | 21.543 | 1.00 | 106.87 | A | O |
| ATOM | 56 | N | GLU A 134 | 21.346 | 52.362 | 19.493 | 1.00 | 103.16 | A | N |
| ATOM | 57 | CA | GLU A 134 | 20.662 | 51.110 | 19.828 | 1.00 | 100.36 | A | C |
| ATOM | 58 | CB | GLU A 134 | 19.634 | 50.757 | 18.741 | 1.00 | 101.25 | A | C |

Figure 4B

| ATOM | 63 | C | GLU | A | 134 | 21.758 | 50.050 | 19.899 | 1.00 | 97.35 | A | C |
|------|----|----|----|----|----|--------|--------|--------|------|-------|---|---|
| ATOM | 64 | O | GLU | A | 134 | 22.500 | 49.835 | 18.932 | 1.00 | 96.32 | A | O |
| ATOM | 65 | N | ILE | A | 135 | 21.876 | 49.391 | 21.041 | 1.00 | 93.66 | A | N |
| ATOM | 66 | CA | ILE | A | 135 | 22.933 | 48.417 | 21.159 | 1.00 | 92.68 | A | C |
| ATOM | 67 | CB | ILE | A | 135 | 23.393 | 48.248 | 22.625 | 1.00 | 91.30 | A | C |
| ATOM | 68 | CG2 | ILE | A | 135 | 23.993 | 49.540 | 23.132 | 1.00 | 89.41 | A | C |
| ATOM | 69 | CG1 | ILE | A | 135 | 22.217 | 47.852 | 23.513 | 1.00 | 94.10 | A | C |
| ATOM | 70 | CD1 | ILE | A | 135 | 22.639 | 47.482 | 24.939 | 1.00 | 97.81 | A | C |
| ATOM | 71 | C | ILE | A | 135 | 22.532 | 47.080 | 20.598 | 1.00 | 94.15 | A | C |
| ATOM | 72 | O | ILE | A | 135 | 21.384 | 46.663 | 20.730 | 1.00 | 95.53 | A | O |
| ATOM | 73 | N | GLY | A | 136 | 23.500 | 46.427 | 19.959 | 1.00 | 94.95 | A | N |
| ATOM | 74 | CA | GLY | A | 136 | 23.295 | 45.115 | 19.373 | 1.00 | 95.53 | A | C |
| ATOM | 75 | C | GLY | A | 136 | 24.037 | 44.042 | 20.157 | 1.00 | 94.17 | A | C |
| ATOM | 76 | O | GLY | A | 136 | 24.522 | 44.289 | 21.263 | 1.00 | 93.61 | A | O |
| ATOM | 77 | N | ARG | A | 137 | 24.146 | 42.850 | 19.583 | 1.00 | 93.77 | A | N |
| ATOM | 78 | CA | ARG | A | 137 | 24.808 | 41.752 | 20.270 | 1.00 | 95.52 | A | C |
| ATOM | 79 | CB | ARG | A | 137 | 24.786 | 40.490 | 19.406 | 1.00 | 94.16 | A | C |
| ATOM | 80 | CG | ARG | A | 137 | 26.050 | 40.280 | 18.626 | 1.00 | 90.11 | A | C |
| ATOM | 81 | CD | ARG | A | 137 | 25.799 | 39.408 | 17.442 | 1.00 | 86.38 | A | C |
| ATOM | 82 | NE | ARG | A | 137 | 27.036 | 39.145 | 16.718 | 1.00 | 84.37 | A | N |
| ATOM | 83 | CZ | ARG | A | 137 | 27.175 | 39.262 | 15.399 | 1.00 | 83.10 | A | C |
| ATOM | 84 | NH1 | ARG | A | 137 | 28.346 | 38.992 | 14.828 | 1.00 | 84.17 | A | N |
| ATOM | 85 | NH2 | ARG | A | 137 | 26.149 | 39.659 | 14.653 | 1.00 | 80.96 | A | N |
| ATOM | 86 | C | ARG | A | 137 | 26.245 | 42.093 | 20.609 | 1.00 | 98.31 | A | C |
| ATOM | 87 | O | ARG | A | 137 | 26.791 | 43.097 | 20.134 | 1.00 | 97.34 | A | O |
| ATOM | 88 | N | PRO | A | 138 | 26.868 | 41.263 | 21.459 | 1.00 | 101.62 | A | N |
| ATOM | 89 | CD | PRO | A | 138 | 26.198 | 40.252 | 22.303 | 1.00 | 102.67 | A | C |
| ATOM | 90 | CA | PRO | A | 138 | 28.261 | 41.453 | 21.872 | 1.00 | 104.24 | A | C |
| ATOM | 91 | CB | PRO | A | 138 | 28.331 | 40.699 | 23.196 | 1.00 | 104.85 | A | C |
| ATOM | 92 | CG | PRO | A | 138 | 27.358 | 39.560 | 22.978 | 1.00 | 103.75 | A | C |
| ATOM | 93 | C | PRO | A | 138 | 29.179 | 40.859 | 20.806 | 1.00 | 106.04 | A | C |
| ATOM | 94 | O | PRO | A | 138 | 29.285 | 39.643 | 20.662 | 1.00 | 105.49 | A | O |
| ATOM | 95 | N | LEU | A | 139 | 29.827 | 41.732 | 20.049 | 1.00 | 108.54 | A | N |
| ATOM | 96 | CA | LEU | A | 139 | 30.718 | 41.315 | 18.975 | 1.00 | 111.07 | A | C |
| ATOM | 97 | CB | LEU | A | 139 | 31.247 | 42.533 | 18.243 | 1.00 | 110.35 | A | C |
| ATOM | 98 | CG | LEU | A | 139 | 30.100 | 43.437 | 17.834 | 1.00 | 111.80 | A | C |
| ATOM | 99 | CD1 | LEU | A | 139 | 30.658 | 44.617 | 17.076 | 1.00 | 113.69 | A | C |
| ATOM | 100 | CD2 | LEU | A | 139 | 29.105 | 42.643 | 16.994 | 1.00 | 115.59 | A | C |
| ATOM | 101 | C | LEU | A | 139 | 31.887 | 40.502 | 19.462 | 1.00 | 112.97 | A | C |
| ATOM | 102 | O | LEU | A | 139 | 32.431 | 39.679 | 18.730 | 1.00 | 113.42 | A | O |
| ATOM | 103 | N | GLY | A | 140 | 32.272 | 40.759 | 20.705 | 1.00 | 115.33 | A | N |
| ATOM | 104 | CA | GLY | A | 140 | 33.381 | 40.050 | 21.307 | 1.00 | 120.54 | A | C |
| ATOM | 105 | C | GLY | A | 140 | 33.463 | 40.286 | 22.805 | 1.00 | 124.00 | A | C |
| ATOM | 106 | O | GLY | A | 140 | 32.521 | 40.790 | 23.426 | 1.00 | 123.79 | A | O |
| ATOM | 107 | N | LYS | A | 141 | 34.604 | 39.924 | 23.384 | 1.00 | 127.61 | A | N |
| ATOM | 108 | CA | LYS | A | 141 | 34.821 | 40.087 | 24.814 | 1.00 | 129.26 | A | C |
| ATOM | 109 | CB | LYS | A | 141 | 35.178 | 38.738 | 25.448 | 1.00 | 129.77 | A | C |
| ATOM | 114 | C | LYS | A | 141 | 35.919 | 41.099 | 25.125 | 1.00 | 130.38 | A | C |
| ATOM | 115 | O | LYS | A | 141 | 36.667 | 41.535 | 24.241 | 1.00 | 130.89 | A | O |
| ATOM | 116 | N | GLY | A | 142 | 36.007 | 41.457 | 26.402 | 1.00 | 130.44 | A | N |
| ATOM | 117 | CA | GLY | A | 142 | 37.007 | 42.406 | 26.846 | 1.00 | 128.74 | A | C |
| ATOM | 118 | C | GLY | A | 142 | 37.096 | 42.475 | 28.357 | 1.00 | 126.17 | A | C |
| ATOM | 119 | O | GLY | A | 142 | 36.104 | 42.752 | 29.045 | 1.00 | 125.25 | A | O |
| ATOM | 120 | N | LYS | A | 143 | 38.282 | 42.203 | 28.884 | 1.00 | 123.43 | A | N |
| ATOM | 121 | CA | LYS | A | 143 | 38.469 | 42.280 | 30.313 | 1.00 | 120.07 | A | C |
| ATOM | 122 | CB | LYS | A | 143 | 39.916 | 41.932 | 30.664 | 1.00 | 119.32 | A | C |
| ATOM | 127 | C | LYS | A | 143 | 38.120 | 43.718 | 30.730 | 1.00 | 119.74 | A | C |
| ATOM | 128 | O | LYS | A | 143 | 37.310 | 43.930 | 31.641 | 1.00 | 116.79 | A | O |
| ATOM | 129 | N | PHE | A | 144 | 38.721 | 44.701 | 30.052 | 1.00 | 119.93 | A | N |
| ATOM | 130 | CA | PHE | A | 144 | 38.444 | 46.118 | 30.344 | 1.00 | 118.94 | A | C |
| ATOM | 131 | CB | PHE | A | 144 | 39.218 | 47.082 | 29.420 | 1.00 | 80.18 | A | C |

Figure 4C

```
ATOM    132  CG   PHE A 144      40.737  47.025  29.540  1.00  80.18      A    C
ATOM    133  CD1  PHE A 144      41.378  46.117  30.396  1.00  80.18      A    C
ATOM    134  CD2  PHE A 144      41.532  47.899  28.762  1.00  80.18      A    C
ATOM    135  CE1  PHE A 144      42.793  46.076  30.478  1.00  80.18      A    C
ATOM    136  CE2  PHE A 144      42.945  47.875  28.828  1.00  80.18      A    C
ATOM    137  CZ   PHE A 144      43.579  46.961  29.687  1.00  80.18      A    C
ATOM    138  C    PHE A 144      36.962  46.347  30.068  1.00  118.20     A    C
ATOM    139  O    PHE A 144      36.123  46.212  30.957  1.00  116.18     A    O
ATOM    140  N    GLY A 145      36.660  46.680  28.812  1.00  118.56     A    N
ATOM    141  CA   GLY A 145      35.291  46.926  28.399  1.00  117.56     A    C
ATOM    142  C    GLY A 145      34.826  46.088  27.215  1.00  117.62     A    C
ATOM    143  O    GLY A 145      35.627  45.432  26.550  1.00  116.93     A    O
ATOM    144  N    ASN A 146      33.518  46.126  26.956  1.00  118.53     A    N
ATOM    145  CA   ASN A 146      32.872  45.373  25.871  1.00  119.35     A    C
ATOM    146  CB   ASN A 146      31.413  45.050  26.254  1.00  122.17     A    C
ATOM    147  CG   ASN A 146      31.302  44.040  27.389  1.00  123.33     A    C
ATOM    148  OD1  ASN A 146      30.271  43.971  28.063  1.00  122.65     A    O
ATOM    149  ND2  ASN A 146      32.353  43.238  27.590  1.00  120.18     A    N
ATOM    150  C    ASN A 146      32.871  46.096  24.514  1.00  116.63     A    C
ATOM    151  O    ASN A 146      33.809  46.826  24.170  1.00  114.94     A    O
ATOM    152  N    VAL A 147      31.792  45.880  23.763  1.00  115.02     A    N
ATOM    153  CA   VAL A 147      31.601  46.468  22.439  1.00  113.48     A    C
ATOM    154  CB   VAL A 147      32.899  46.361  21.596  1.00  113.14     A    C
ATOM    155  CG1  VAL A 147      33.378  44.919  21.566  1.00  111.53     A    C
ATOM    156  CG2  VAL A 147      32.663  46.890  20.183  1.00  113.50     A    C
ATOM    157  C    VAL A 147      30.453  45.741  21.726  1.00  111.73     A    C
ATOM    158  O    VAL A 147      30.648  44.712  21.072  1.00  113.71     A    O
ATOM    159  N    TYR A 148      29.250  46.285  21.850  1.00  106.83     A    N
ATOM    160  CA   TYR A 148      28.090  45.659  21.244  1.00  100.85     A    C
ATOM    161  CB   TYR A 148      26.869  45.825  22.167  1.00  104.88     A    C
ATOM    162  CG   TYR A 148      27.139  45.923  23.686  1.00  109.95     A    C
ATOM    163  CD1  TYR A 148      28.061  45.087  24.332  1.00  111.84     A    C
ATOM    164  CE1  TYR A 148      28.240  45.146  25.728  1.00  112.26     A    C
ATOM    165  CD2  TYR A 148      26.409  46.820  24.486  1.00  112.30     A    C
ATOM    166  CE2  TYR A 148      26.582  46.876  25.879  1.00  112.24     A    C
ATOM    167  CZ   TYR A 148      27.497  46.042  26.485  1.00  112.79     A    C
ATOM    168  OH   TYR A 148      27.663  46.114  27.848  1.00  116.36     A    O
ATOM    169  C    TYR A 148      27.785  46.272  19.877  1.00  94.59      A    C
ATOM    170  O    TYR A 148      28.151  47.417  19.614  1.00  93.90      A    O
ATOM    171  N    LEU A 149      27.158  45.495  18.996  1.00  87.77      A    N
ATOM    172  CA   LEU A 149      26.748  45.994  17.713  1.00  83.47      A    C
ATOM    173  CB   LEU A 149      25.826  44.997  17.038  1.00  83.90      A    C
ATOM    174  CG   LEU A 149      26.439  44.182  15.905  1.00  83.82      A    C
ATOM    175  CD1  LEU A 149      25.373  43.254  15.306  1.00  84.05      A    C
ATOM    176  CD2  LEU A 149      27.011  45.135  14.847  1.00  82.25      A    C
ATOM    177  C    LEU A 149      25.984  47.244  18.124  1.00  81.35      A    C
ATOM    178  O    LEU A 149      25.421  47.284  19.211  1.00  78.76      A    O
ATOM    179  N    ALA A 150      25.979  48.272  17.287  1.00  81.47      A    N
ATOM    180  CA   ALA A 150      25.272  49.496  17.641  1.00  80.57      A    C
ATOM    181  CB   ALA A 150      26.195  50.435  18.388  1.00  75.69      A    C
ATOM    182  C    ALA A 150      24.710  50.189  16.423  1.00  81.24      A    C
ATOM    183  O    ALA A 150      25.145  49.947  15.301  1.00  81.10      A    O
ATOM    184  N    ARG A 151      23.747  51.069  16.661  1.00  83.00      A    N
ATOM    185  CA   ARG A 151      23.092  51.796  15.584  1.00  84.33      A    C
ATOM    186  CB   ARG A 151      21.828  51.034  15.153  1.00  87.82      A    C
ATOM    187  CG   ARG A 151      21.621  50.814  13.634  1.00  90.24      A    C
ATOM    188  CD   ARG A 151      20.396  49.904  13.422  1.00  91.47      A    C
ATOM    189  NE   ARG A 151      20.352  49.232  12.126  1.00  91.82      A    N
ATOM    190  CZ   ARG A 151      19.789  48.041  11.931  1.00  92.21      A    C
ATOM    191  NH1  ARG A 151      19.225  47.396  12.947  1.00  92.38      A    N
ATOM    192  NH2  ARG A 151      19.796  47.491  10.724  1.00  90.11      A    N
```

Figure 4D

```
ATOM    193  C   ARG A 151      22.700  53.189  16.049  1.00  81.62      A    C
ATOM    194  O   ARG A 151      22.084  53.349  17.094  1.00  79.22      A    O
ATOM    195  N   GLU A 152      23.066  54.205  15.287  1.00  81.47      A    N
ATOM    196  CA  GLU A 152      22.667  55.536  15.673  1.00  85.29      A    C
ATOM    197  CB  GLU A 152      23.409  56.601  14.904  1.00  84.17      A    C
ATOM    198  CG  GLU A 152      22.686  57.927  14.979  1.00  85.29      A    C
ATOM    199  CD  GLU A 152      23.529  59.056  14.491  1.00  88.90      A    C
ATOM    200  OE1 GLU A 152      23.912  59.046  13.301  1.00  89.54      A    O
ATOM    201  OE2 GLU A 152      23.814  59.953  15.311  1.00  91.63      A    O
ATOM    202  C   GLU A 152      21.222  55.663  15.306  1.00  90.26      A    C
ATOM    203  O   GLU A 152      20.872  55.552  14.132  1.00  90.70      A    O
ATOM    204  N   ALA A 153      20.388  55.925  16.304  1.00  95.96      A    N
ATOM    205  CA  ALA A 153      18.943  56.072  16.095  1.00  99.27      A    C
ATOM    206  CB  ALA A 153      18.275  56.507  17.414  1.00 102.05      A    C
ATOM    207  C   ALA A 153      18.568  57.049  14.956  1.00  99.25      A    C
ATOM    208  O   ALA A 153      17.580  56.835  14.235  1.00  97.61      A    O
ATOM    209  N   ALA A 154      19.357  58.115  14.807  1.00  99.31      A    N
ATOM    210  CA  ALA A 154      19.114  59.107  13.769  1.00  99.12      A    C
ATOM    211  CB  ALA A 154      20.048  60.312  13.955  1.00  97.38      A    C
ATOM    212  C   ALA A 154      19.320  58.484  12.388  1.00  99.26      A    C
ATOM    213  O   ALA A 154      18.349  58.190  11.686  1.00  99.46      A    O
ATOM    214  N   SER A 155      20.580  58.255  12.021  1.00  98.40      A    N
ATOM    215  CA  SER A 155      20.937  57.692  10.713  1.00  95.21      A    C
ATOM    216  CB  SER A 155      22.409  57.983  10.434  1.00  93.37      A    C
ATOM    217  OG  SER A 155      23.209  57.532  11.513  1.00  87.72      A    O
ATOM    218  C   SER A 155      20.679  56.197  10.502  1.00  92.98      A    C
ATOM    219  O   SER A 155      20.938  55.659   9.414  1.00  88.45      A    O
ATOM    220  N   ALA A 156      20.170  55.534  11.534  1.00  93.37      A    N
ATOM    221  CA  ALA A 156      19.894  54.101  11.471  1.00  97.04      A    C
ATOM    222  CB  ALA A 156      18.713  53.822  10.558  1.00  95.44      A    C
ATOM    223  C   ALA A 156      21.131  53.393  10.952  1.00 100.00      A    C
ATOM    224  O   ALA A 156      21.075  52.243  10.516  1.00 100.16      A    O
ATOM    225  N   PHE A 157      22.249  54.109  11.016  1.00 103.68      A    N
ATOM    226  CA  PHE A 157      23.540  53.616  10.553  1.00 103.38      A    C
ATOM    227  CB  PHE A 157      24.495  54.789  10.314  1.00 106.33      A    C
ATOM    228  CG  PHE A 157      25.784  54.390   9.667  1.00 107.04      A    C
ATOM    229  CD1 PHE A 157      25.786  53.849   8.387  1.00 109.27      A    C
ATOM    230  CD2 PHE A 157      26.993  54.556  10.329  1.00 107.31      A    C
ATOM    231  CE1 PHE A 157      26.976  53.479   7.774  1.00 111.22      A    C
ATOM    232  CE2 PHE A 157      28.182  54.188   9.723  1.00 108.18      A    C
ATOM    233  CZ  PHE A 157      28.173  53.647   8.440  1.00 109.95      A    C
ATOM    234  C   PHE A 157      24.199  52.627  11.511  1.00 100.93      A    C
ATOM    235  O   PHE A 157      24.549  52.956  12.655  1.00 100.02      A    O
ATOM    236  N   ILE A 158      24.481  51.426  11.031  1.00  98.13      A    N
ATOM    237  CA  ILE A 158      25.143  50.440  11.885  1.00  95.61      A    C
ATOM    238  CB  ILE A 158      25.374  49.117  11.147  1.00  96.93      A    C
ATOM    239  CG2 ILE A 158      24.063  48.590  10.622  1.00  97.24      A    C
ATOM    240  CG1 ILE A 158      26.328  49.333   9.975  1.00  99.95      A    C
ATOM    241  CD1 ILE A 158      25.756  50.222   8.847  1.00 104.38      A    C
ATOM    242  C   ILE A 158      26.500  50.960  12.368  1.00  93.56      A    C
ATOM    243  O   ILE A 158      27.180  51.712  11.664  1.00  92.38      A    O
ATOM    244  N   LEU A 159      26.882  50.544  13.573  1.00  91.06      A    N
ATOM    245  CA  LEU A 159      28.144  50.952  14.179  1.00  89.77      A    C
ATOM    246  CB  LEU A 159      27.951  52.166  15.085  1.00  87.15      A    C
ATOM    247  CG  LEU A 159      28.254  53.516  14.464  1.00  88.71      A    C
ATOM    248  CD1 LEU A 159      29.608  53.461  13.799  1.00  87.78      A    C
ATOM    249  CD2 LEU A 159      27.183  53.858  13.451  1.00  91.23      A    C
ATOM    250  C   LEU A 159      28.764  49.860  15.018  1.00  88.92      A    C
ATOM    251  O   LEU A 159      28.498  48.674  14.833  1.00  88.85      A    O
ATOM    252  N   ALA A 160      29.592  50.298  15.956  1.00  87.59      A    N
ATOM    253  CA  ALA A 160      30.284  49.420  16.872  1.00  86.36      A    C
```

Figure 4E

| ATOM | 254 | CB  | ALA A 160 | 31.523 | 48.849 | 16.205 | 1.00 | 89.32  | A | C |
|------|-----|-----|-----------|--------|--------|--------|------|--------|---|---|
| ATOM | 255 | C   | ALA A 160 | 30.673 | 50.296 | 18.038 | 1.00 | 84.04  | A | C |
| ATOM | 256 | O   | ALA A 160 | 31.198 | 51.388 | 17.843 | 1.00 | 84.38  | A | O |
| ATOM | 257 | N   | LEU A 161 | 30.441 | 49.825 | 19.251 | 1.00 | 80.78  | A | N |
| ATOM | 258 | CA  | LEU A 161 | 30.774 | 50.645 | 20.389 | 1.00 | 78.78  | A | C |
| ATOM | 259 | CB  | LEU A 161 | 29.504 | 51.034 | 21.104 | 1.00 | 75.84  | A | C |
| ATOM | 260 | CG  | LEU A 161 | 29.836 | 52.021 | 22.211 | 1.00 | 76.35  | A | C |
| ATOM | 261 | CD1 | LEU A 161 | 30.227 | 53.349 | 21.573 | 1.00 | 80.80  | A | C |
| ATOM | 262 | CD2 | LEU A 161 | 28.655 | 52.188 | 23.136 | 1.00 | 77.68  | A | C |
| ATOM | 263 | C   | LEU A 161 | 31.736 | 50.056 | 21.409 | 1.00 | 80.92  | A | C |
| ATOM | 264 | O   | LEU A 161 | 31.300 | 49.419 | 22.368 | 1.00 | 83.48  | A | O |
| ATOM | 265 | N   | LYS A 162 | 33.034 | 50.294 | 21.231 | 1.00 | 82.11  | A | N |
| ATOM | 266 | CA  | LYS A 162 | 34.035 | 49.779 | 22.168 | 1.00 | 84.66  | A | C |
| ATOM | 267 | CB  | LYS A 162 | 35.444 | 49.853 | 21.580 | 1.00 | 80.18  | A | C |
| ATOM | 268 | CG  | LYS A 162 | 36.544 | 49.324 | 22.518 | 1.00 | 80.18  | A | C |
| ATOM | 269 | CD  | LYS A 162 | 37.908 | 49.217 | 21.802 | 1.00 | 80.18  | A | C |
| ATOM | 270 | CE  | LYS A 162 | 37.965 | 48.049 | 20.809 | 1.00 | 80.18  | A | C |
| ATOM | 271 | NZ  | LYS A 162 | 38.810 | 48.330 | 19.599 | 1.00 | 80.18  | A | N |
| ATOM | 272 | C   | LYS A 162 | 34.017 | 50.550 | 23.467 | 1.00 | 88.43  | A | C |
| ATOM | 273 | O   | LYS A 162 | 34.709 | 51.554 | 23.621 | 1.00 | 87.47  | A | O |
| ATOM | 274 | N   | VAL A 163 | 33.208 | 50.065 | 24.397 | 1.00 | 94.72  | A | N |
| ATOM | 275 | CA  | VAL A 163 | 33.068 | 50.665 | 25.721 | 1.00 | 100.48 | A | C |
| ATOM | 276 | CB  | VAL A 163 | 31.637 | 50.371 | 26.310 | 1.00 | 101.33 | A | C |
| ATOM | 277 | CG1 | VAL A 163 | 31.099 | 49.035 | 25.801 | 1.00 | 101.67 | A | C |
| ATOM | 278 | CG2 | VAL A 163 | 31.687 | 50.348 | 27.816 | 1.00 | 99.58  | A | C |
| ATOM | 279 | C   | VAL A 163 | 34.169 | 50.111 | 26.646 | 1.00 | 104.18 | A | C |
| ATOM | 280 | O   | VAL A 163 | 34.465 | 48.917 | 26.610 | 1.00 | 107.88 | A | O |
| ATOM | 281 | N   | LEU A 164 | 34.779 | 50.977 | 27.457 | 1.00 | 105.67 | A | N |
| ATOM | 282 | CA  | LEU A 164 | 35.847 | 50.557 | 28.368 | 1.00 | 106.96 | A | C |
| ATOM | 283 | CB  | LEU A 164 | 37.190 | 51.094 | 27.893 | 1.00 | 102.71 | A | C |
| ATOM | 284 | CG  | LEU A 164 | 37.398 | 51.063 | 26.383 | 1.00 | 101.07 | A | C |
| ATOM | 285 | CD1 | LEU A 164 | 36.657 | 52.223 | 25.726 | 1.00 | 98.23  | A | C |
| ATOM | 286 | CD2 | LEU A 164 | 38.873 | 51.151 | 26.090 | 1.00 | 101.16 | A | C |
| ATOM | 287 | C   | LEU A 164 | 35.596 | 51.076 | 29.771 | 1.00 | 110.46 | A | C |
| ATOM | 288 | O   | LEU A 164 | 35.322 | 52.257 | 29.947 | 1.00 | 112.35 | A | O |
| ATOM | 289 | N   | PHE A 165 | 35.718 | 50.202 | 30.767 | 1.00 | 114.28 | A | N |
| ATOM | 290 | CA  | PHE A 165 | 35.484 | 50.580 | 32.165 | 1.00 | 116.40 | A | C |
| ATOM | 291 | CB  | PHE A 165 | 35.505 | 49.333 | 33.053 | 1.00 | 117.19 | A | C |
| ATOM | 292 | CG  | PHE A 165 | 34.315 | 48.428 | 32.881 | 1.00 | 117.42 | A | C |
| ATOM | 293 | CD1 | PHE A 165 | 33.984 | 47.908 | 31.633 | 1.00 | 115.85 | A | C |
| ATOM | 294 | CD2 | PHE A 165 | 33.541 | 48.063 | 33.989 | 1.00 | 120.17 | A | C |
| ATOM | 295 | CE1 | PHE A 165 | 32.900 | 47.033 | 31.488 | 1.00 | 117.35 | A | C |
| ATOM | 296 | CE2 | PHE A 165 | 32.452 | 47.188 | 33.857 | 1.00 | 119.43 | A | C |
| ATOM | 297 | CZ  | PHE A 165 | 32.131 | 46.671 | 32.603 | 1.00 | 118.98 | A | C |
| ATOM | 298 | C   | PHE A 165 | 36.466 | 51.608 | 32.755 | 1.00 | 117.76 | A | C |
| ATOM | 299 | O   | PHE A 165 | 37.660 | 51.618 | 32.421 | 1.00 | 117.93 | A | O |
| ATOM | 300 | N   | LYS A 166 | 35.956 | 52.469 | 33.638 | 1.00 | 118.50 | A | N |
| ATOM | 301 | CA  | LYS A 166 | 36.799 | 53.459 | 34.289 | 1.00 | 120.27 | A | C |
| ATOM | 302 | CB  | LYS A 166 | 35.956 | 54.468 | 35.076 | 1.00 | 116.78 | A | C |
| ATOM | 307 | C   | LYS A 166 | 37.697 | 52.662 | 35.231 | 1.00 | 123.34 | A | C |
| ATOM | 308 | O   | LYS A 166 | 38.917 | 52.816 | 35.201 | 1.00 | 122.78 | A | O |
| ATOM | 309 | N   | ALA A 167 | 37.085 | 51.784 | 36.034 | 1.00 | 128.28 | A | N |
| ATOM | 310 | CA  | ALA A 167 | 37.807 | 50.928 | 36.985 | 1.00 | 132.90 | A | C |
| ATOM | 311 | CB  | ALA A 167 | 36.858 | 49.849 | 37.546 | 1.00 | 135.29 | A | C |
| ATOM | 312 | C   | ALA A 167 | 39.031 | 50.251 | 36.366 | 1.00 | 134.37 | A | C |
| ATOM | 313 | O   | ALA A 167 | 40.137 | 50.341 | 36.902 | 1.00 | 135.65 | A | O |
| ATOM | 314 | N   | GLN A 168 | 38.811 | 49.552 | 35.251 | 1.00 | 135.71 | A | N |
| ATOM | 315 | CA  | GLN A 168 | 39.885 | 48.850 | 34.542 | 1.00 | 135.07 | A | C |
| ATOM | 316 | CB  | GLN A 168 | 39.331 | 48.070 | 33.314 | 1.00 | 135.10 | A | C |
| ATOM | 317 | CG  | GLN A 168 | 38.092 | 47.160 | 33.578 | 1.00 | 132.38 | A | C |
| ATOM | 318 | CD  | GLN A 168 | 38.294 | 46.133 | 34.694 | 1.00 | 129.59 | A | C |

Figure 4F

```
ATOM    319  OE1 GLN A 168      38.373  46.480  35.881  1.00  127.94      A    O
ATOM    320  NE2 GLN A 168      38.380  44.859  34.313  1.00  128.23      A    N
ATOM    321  C   GLN A 168      40.907  49.904  34.090  1.00  134.22      A    C
ATOM    322  O   GLN A 168      42.105  49.785  34.375  1.00  134.47      A    O
ATOM    323  N   LEU A 169      40.423  50.941  33.409  1.00  133.42      A    N
ATOM    324  CA  LEU A 169      41.289  52.014  32.931  1.00  133.66      A    C
ATOM    325  CB  LEU A 169      40.458  53.063  32.196  1.00  134.97      A    C
ATOM    329  C   LEU A 169      42.059  52.672  34.080  1.00  134.00      A    C
ATOM    330  O   LEU A 169      43.120  53.258  33.864  1.00  134.55      A    O
ATOM    331  N   GLU A 170      41.517  52.574  35.293  1.00  133.96      A    N
ATOM    332  CA  GLU A 170      42.153  53.139  36.484  1.00  133.46      A    C
ATOM    333  CB  GLU A 170      41.087  53.475  37.537  1.00  132.60      A    C
ATOM    338  C   GLU A 170      43.186  52.169  37.086  1.00  132.63      A    C
ATOM    339  O   GLU A 170      44.321  52.561  37.397  1.00  130.27      A    O
ATOM    340  N   LYS A 171      42.768  50.906  37.233  1.00  132.48      A    N
ATOM    341  CA  LYS A 171      43.588  49.821  37.792  1.00  130.46      A    C
ATOM    342  CB  LYS A 171      42.729  48.553  38.018  1.00  127.22      A    C
ATOM    347  C   LYS A 171      44.777  49.481  36.888  1.00  129.86      A    C
ATOM    348  O   LYS A 171      45.270  48.340  36.897  1.00  129.89      A    O
ATOM    349  N   ALA A 172      45.238  50.475  36.123  1.00  129.81      A    N
ATOM    350  CA  ALA A 172      46.361  50.293  35.200  1.00  129.08      A    C
ATOM    351  CB  ALA A 172      46.042  49.169  34.206  1.00  129.86      A    C
ATOM    352  C   ALA A 172      46.704  51.564  34.423  1.00  127.52      A    C
ATOM    353  O   ALA A 172      46.477  51.614  33.209  1.00  127.99      A    O
ATOM    354  N   GLY A 173      47.255  52.567  35.112  1.00  123.87      A    N
ATOM    355  CA  GLY A 173      47.621  53.816  34.463  1.00  119.72      A    C
ATOM    356  C   GLY A 173      47.655  53.709  32.947  1.00  117.31      A    C
ATOM    357  O   GLY A 173      48.707  53.464  32.355  1.00  115.16      A    O
ATOM    358  N   VAL A 174      46.486  53.867  32.328  1.00  136.72      A    N
ATOM    359  CA  VAL A 174      46.335  53.795  30.877  1.00  116.63      A    C
ATOM    360  CB  VAL A 174      45.542  52.547  30.429  1.00  115.44      A    C
ATOM    363  C   VAL A 174      45.577  55.010  30.386  1.00  117.69      A    C
ATOM    364  O   VAL A 174      45.575  55.281  29.195  1.00  118.15      A    O
ATOM    365  N   GLU A 175      44.920  55.725  31.303  1.00  118.79      A    N
ATOM    366  CA  GLU A 175      44.173  56.937  30.947  1.00  118.78      A    C
ATOM    367  CB  GLU A 175      43.721  57.688  32.211  1.00  117.30      A    C
ATOM    372  C   GLU A 175      45.125  57.818  30.128  1.00  119.42      A    C
ATOM    373  O   GLU A 175      44.703  58.596  29.251  1.00  117.06      A    O
ATOM    374  N   HIS A 176      46.416  57.669  30.430  1.00  120.72      A    N
ATOM    375  CA  HIS A 176      47.477  58.395  29.746  1.00  122.24      A    C
ATOM    376  CB  HIS A 176      48.782  58.289  30.528  1.00  119.76      A    C
ATOM    382  C   HIS A 176      47.653  57.746  28.394  1.00  123.74      A    C
ATOM    383  O   HIS A 176      47.657  58.429  27.371  1.00  124.46      A    O
ATOM    384  N   GLN A 177      47.798  56.421  28.410  1.00  126.26      A    N
ATOM    385  CA  GLN A 177      47.963  55.618  27.188  1.00  129.43      A    C
ATOM    386  CB  GLN A 177      47.999  54.122  27.543  1.00  129.56      A    C
ATOM    391  C   GLN A 177      46.813  55.889  26.200  1.00  130.09      A    C
ATOM    392  O   GLN A 177      46.995  55.949  24.970  1.00  129.63      A    O
ATOM    393  N   LEU A 178      45.623  56.044  26.768  1.00  131.63      A    N
ATOM    394  CA  LEU A 178      44.422  56.340  26.002  1.00  131.75      A    C
ATOM    395  CB  LEU A 178      43.193  56.222  26.924  1.00  135.82      A    C
ATOM    396  CG  LEU A 178      42.166  55.135  26.544  1.00  137.70      A    C
ATOM    397  CD1 LEU A 178      41.586  54.461  27.803  1.00  137.55      A    C
ATOM    398  CD2 LEU A 178      41.070  55.771  25.662  1.00  138.30      A    C
ATOM    399  C   LEU A 178      44.595  57.765  25.476  1.00  129.35      A    C
ATOM    400  O   LEU A 178      45.720  58.251  25.409  1.00  128.48      A    O
ATOM    401  N   ARG A 179      43.505  58.437  25.121  1.00  127.11      A    N
ATOM    402  CA  ARG A 179      43.596  59.798  24.603  1.00  125.92      A    C
ATOM    403  CB  ARG A 179      44.037  60.781  25.697  1.00  128.19      A    C
ATOM    404  CG  ARG A 179      43.034  61.029  26.812  1.00  134.75      A    C
ATOM    405  CD  ARG A 179      43.478  62.247  27.647  1.00  142.21      A    C
```

Figure 4G

```
ATOM    406  NE   ARG A 179      42.556  62.632  28.744  1.00  148.31      A    N
ATOM    407  CZ   ARG A 179      42.526  62.088  29.974  1.00  149.47      A    C
ATOM    408  NH1  ARG A 179      41.646  62.525  30.885  1.00  148.53      A    N
ATOM    409  NH2  ARG A 179      43.374  61.109  30.307  1.00  149.92      A    N
ATOM    410  C    ARG A 179      44.616  59.832  23.472  1.00  123.64      A    C
ATOM    411  O    ARG A 179      44.288  60.156  22.336  1.00  123.65      A    O
ATOM    412  N    ARG A 180      45.863  59.512  23.804  1.00  121.97      A    N
ATOM    413  CA   ARG A 180      46.943  59.494  22.840  1.00  122.56      A    C
ATOM    414  CB   ARG A 180      48.125  58.676  23.369  1.00  118.93      A    C
ATOM    421  C    ARG A 180      46.417  58.892  21.557  1.00  124.12      A    C
ATOM    422  O    ARG A 180      46.169  59.628  20.598  1.00  123.29      A    O
ATOM    423  N    GLU A 181      46.216  57.567  21.560  1.00  127.74      A    N
ATOM    424  CA   GLU A 181      45.714  56.824  20.381  1.00  130.08      A    C
ATOM    425  CB   GLU A 181      45.473  55.337  20.671  1.00  135.75      A    C
ATOM    426  CG   GLU A 181      46.404  54.674  21.699  1.00  144.19      A    C
ATOM    427  CD   GLU A 181      46.170  53.136  21.838  1.00  148.29      A    C
ATOM    428  OE1  GLU A 181      44.987  52.668  21.858  1.00  150.00      A    O
ATOM    429  OE2  GLU A 181      47.184  52.394  21.943  1.00  150.00      A    O
ATOM    430  C    GLU A 181      44.388  57.399  19.961  1.00  128.41      A    C
ATOM    431  O    GLU A 181      44.095  57.518  18.775  1.00  127.16      A    O
ATOM    432  N    VAL A 182      43.572  57.706  20.959  1.00  126.62      A    N
ATOM    433  CA   VAL A 182      42.279  58.311  20.715  1.00  125.12      A    C
ATOM    434  CB   VAL A 182      41.703  58.867  22.022  1.00  123.73      A    C
ATOM    435  CG1  VAL A 182      40.523  59.809  21.729  1.00  123.65      A    C
ATOM    436  CG2  VAL A 182      41.301  57.714  22.915  1.00  121.61      A    C
ATOM    437  C    VAL A 182      42.438  59.463  19.719  1.00  125.84      A    C
ATOM    438  O    VAL A 182      42.071  59.355  18.544  1.00  125.00      A    O
ATOM    439  N    GLU A 183      42.994  60.566  20.204  1.00  126.31      A    N
ATOM    440  CA   GLU A 183      43.210  61.726  19.372  1.00  126.61      A    C
ATOM    441  CB   GLU A 183      44.121  62.722  20.097  1.00  130.31      A    C
ATOM    442  CG   GLU A 183      44.386  63.969  19.253  1.00  138.64      A    C
ATOM    443  CD   GLU A 183      43.101  64.527  18.600  1.00  143.22      A    C
ATOM    444  OE1  GLU A 183      42.247  65.035  19.353  1.00  145.29      A    O
ATOM    445  OE2  GLU A 183      42.933  64.463  17.348  1.00  146.15      A    O
ATOM    446  C    GLU A 183      43.834  61.326  18.031  1.00  124.80      A    C
ATOM    447  O    GLU A 183      43.556  61.913  16.974  1.00  123.96      A    O
ATOM    448  N    ILE A 184      44.676  60.311  18.076  1.00  123.34      A    N
ATOM    449  CA   ILE A 184      45.342  59.856  16.874  1.00  123.24      A    C
ATOM    450  CB   ILE A 184      46.478  58.902  17.264  1.00  126.50      A    C
ATOM    451  CG2  ILE A 184      47.222  58.449  16.011  1.00  129.77      A    C
ATOM    452  CG1  ILE A 184      47.427  59.614  18.246  1.00  128.57      A    C
ATOM    453  CD1  ILE A 184      48.521  58.723  18.853  1.00  132.81      A    C
ATOM    454  C    ILE A 184      44.398  59.197  15.848  1.00  120.31      A    C
ATOM    455  O    ILE A 184      44.314  59.632  14.683  1.00  118.97      A    O
ATOM    456  N    GLN A 185      43.696  58.152  16.282  1.00  118.12      A    N
ATOM    457  CA   GLN A 185      42.758  57.438  15.419  1.00  115.72      A    C
ATOM    458  CB   GLN A 185      42.120  56.271  16.195  1.00  116.69      A    C
ATOM    459  CG   GLN A 185      43.135  55.206  16.702  1.00  118.90      A    C
ATOM    460  CD   GLN A 185      43.704  54.302  15.580  1.00  119.38      A    C
ATOM    461  OE1  GLN A 185      44.760  53.653  15.741  1.00  119.38      A    O
ATOM    462  NE2  GLN A 185      42.994  54.249  14.448  1.00  118.09      A    N
ATOM    463  C    GLN A 185      41.706  58.453  15.004  1.00  113.84      A    C
ATOM    464  O    GLN A 185      41.213  58.450  13.872  1.00  111.42      A    O
ATOM    465  N    SER A 186      41.394  59.327  15.959  1.00  113.54      A    N
ATOM    466  CA   SER A 186      40.432  60.421  15.809  1.00  112.30      A    C
ATOM    467  CB   SER A 186      40.239  61.181  17.184  1.00  113.52      A    C
ATOM    468  OG   SER A 186      39.541  62.334  17.086  1.00  117.00      A    O
ATOM    469  C    SER A 186      40.994  61.410  14.772  1.00  108.59      A    C
ATOM    470  O    SER A 186      41.341  62.556  15.086  1.00  108.18      A    O
ATOM    471  N    HIS A 187      41.065  60.961  13.530  1.00  103.89      A    N
ATOM    472  CA   HIS A 187      41.633  61.786  12.507  1.00  100.30      A    C
```

Figure 4H

| ATOM | 473 | CB | HIS | A | 187 | 42.923 | 62.376 | 13.017 | 1.00 | 104.02 | A | C |
|---|---|---|---|---|---|---|---|---|---|---|---|---|
| ATOM | 474 | CG | HIS | A | 187 | 43.054 | 63.814 | 12.697 | 1.00 | 111.28 | A | C |
| ATOM | 475 | CD2 | HIS | A | 187 | 44.022 | 64.505 | 12.052 | 1.00 | 114.31 | A | C |
| ATOM | 476 | ND1 | HIS | A | 187 | 42.051 | 64.718 | 12.979 | 1.00 | 114.80 | A | N |
| ATOM | 477 | CE1 | HIS | A | 187 | 42.394 | 65.908 | 12.516 | 1.00 | 115.35 | A | C |
| ATOM | 478 | NE2 | HIS | A | 187 | 43.585 | 65.806 | 11.948 | 1.00 | 117.17 | A | N |
| ATOM | 479 | C | HIS | A | 187 | 41.965 | 60.852 | 11.410 | 1.00 | 97.15 | A | C |
| ATOM | 480 | O | HIS | A | 187 | 41.446 | 60.940 | 10.312 | 1.00 | 93.66 | A | O |
| ATOM | 481 | N | LEU | A | 188 | 42.874 | 59.956 | 11.756 | 1.00 | 97.25 | A | N |
| ATOM | 482 | CA | LEU | A | 188 | 43.365 | 58.904 | 10.891 | 1.00 | 97.55 | A | C |
| ATOM | 483 | CB | LEU | A | 188 | 43.815 | 57.739 | 11.755 | 1.00 | 101.27 | A | C |
| ATOM | 484 | CG | LEU | A | 188 | 45.220 | 57.250 | 11.437 | 1.00 | 105.84 | A | C |
| ATOM | 485 | CD1 | LEU | A | 188 | 46.142 | 58.435 | 11.387 | 1.00 | 109.11 | A | C |
| ATOM | 486 | CD2 | LEU | A | 188 | 45.688 | 56.266 | 12.496 | 1.00 | 111.20 | A | C |
| ATOM | 487 | C | LEU | A | 188 | 42.319 | 58.411 | 9.915 | 1.00 | 96.45 | A | C |
| ATOM | 488 | O | LEU | A | 188 | 41.561 | 57.474 | 10.223 | 1.00 | 93.73 | A | O |
| ATOM | 489 | N | ARG | A | 189 | 42.307 | 59.024 | 8.733 | 1.00 | 95.72 | A | N |
| ATOM | 490 | CA | ARG | A | 189 | 41.347 | 58.696 | 7.681 | 1.00 | 95.01 | A | C |
| ATOM | 491 | CB | ARG | A | 189 | 40.768 | 59.995 | 7.107 | 1.00 | 99.98 | A | C |
| ATOM | 492 | CG | ARG | A | 189 | 39.330 | 59.921 | 6.538 | 1.00 | 106.69 | A | C |
| ATOM | 493 | CD | ARG | A | 189 | 38.552 | 61.241 | 6.855 | 1.00 | 111.79 | A | C |
| ATOM | 494 | NE | ARG | A | 189 | 37.199 | 61.343 | 6.279 | 1.00 | 113.35 | A | N |
| ATOM | 495 | CZ | ARG | A | 189 | 36.336 | 62.332 | 6.552 | 1.00 | 115.46 | A | C |
| ATOM | 496 | NH1 | ARG | A | 189 | 36.679 | 63.310 | 7.396 | 1.00 | 115.47 | A | N |
| ATOM | 497 | NH2 | ARG | A | 189 | 35.126 | 62.350 | 5.987 | 1.00 | 113.81 | A | N |
| ATOM | 498 | C | ARG | A | 189 | 41.943 | 57.842 | 6.563 | 1.00 | 91.35 | A | C |
| ATOM | 499 | O | ARG | A | 189 | 42.630 | 58.332 | 5.663 | 1.00 | 88.64 | A | O |
| ATOM | 500 | N | HIS | A | 190 | 41.668 | 56.549 | 6.623 | 1.00 | 88.85 | A | N |
| ATOM | 501 | CA | HIS | A | 190 | 42.181 | 55.652 | 5.617 | 1.00 | 86.54 | A | C |
| ATOM | 502 | CB | HIS | A | 190 | 43.578 | 55.184 | 5.980 | 1.00 | 91.63 | A | C |
| ATOM | 503 | CG | HIS | A | 190 | 44.218 | 54.335 | 4.926 | 1.00 | 94.39 | A | C |
| ATOM | 504 | CD2 | HIS | A | 190 | 44.282 | 52.991 | 4.777 | 1.00 | 93.98 | A | C |
| ATOM | 505 | ND1 | HIS | A | 190 | 44.873 | 54.870 | 3.840 | 1.00 | 97.55 | A | N |
| ATOM | 506 | CE1 | HIS | A | 190 | 45.318 | 53.892 | 3.069 | 1.00 | 97.31 | A | C |
| ATOM | 507 | NE2 | HIS | A | 190 | 44.971 | 52.741 | 3.615 | 1.00 | 94.82 | A | N |
| ATOM | 508 | C | HIS | A | 190 | 41.300 | 54.440 | 5.478 | 1.00 | 84.36 | A | C |
| ATOM | 509 | O | HIS | A | 190 | 40.763 | 53.929 | 6.476 | 1.00 | 77.53 | A | O |
| ATOM | 510 | N | PRO | A | 191 | 41.153 | 53.952 | 4.229 | 1.00 | 84.67 | A | N |
| ATOM | 511 | CD | PRO | A | 191 | 41.714 | 54.513 | 2.988 | 1.00 | 83.01 | A | C |
| ATOM | 512 | CA | PRO | A | 191 | 40.336 | 52.781 | 3.919 | 1.00 | 87.77 | A | C |
| ATOM | 513 | CB | PRO | A | 191 | 40.522 | 52.621 | 2.398 | 1.00 | 84.89 | A | C |
| ATOM | 514 | CG | PRO | A | 191 | 41.795 | 53.298 | 2.118 | 1.00 | 82.71 | A | C |
| ATOM | 515 | C | PRO | A | 191 | 40.716 | 51.530 | 4.720 | 1.00 | 90.77 | A | C |
| ATOM | 516 | O | PRO | A | 191 | 39.853 | 50.829 | 5.273 | 1.00 | 94.15 | A | O |
| ATOM | 517 | N | ASN | A | 192 | 42.012 | 51.259 | 4.801 | 1.00 | 90.49 | A | N |
| ATOM | 518 | CA | ASN | A | 192 | 42.491 | 50.089 | 5.535 | 1.00 | 86.62 | A | C |
| ATOM | 519 | CB | ASN | A | 192 | 43.714 | 49.506 | 4.810 | 1.00 | 79.06 | A | C |
| ATOM | 520 | CG | ASN | A | 192 | 43.427 | 49.194 | 3.361 | 1.00 | 69.42 | A | C |
| ATOM | 521 | OD1 | ASN | A | 192 | 44.104 | 49.684 | 2.469 | 1.00 | 65.15 | A | O |
| ATOM | 522 | ND2 | ASN | A | 192 | 42.415 | 48.381 | 3.123 | 1.00 | 64.64 | A | N |
| ATOM | 523 | C | ASN | A | 192 | 42.798 | 50.377 | 7.025 | 1.00 | 86.18 | A | C |
| ATOM | 524 | O | ASN | A | 192 | 43.580 | 49.672 | 7.674 | 1.00 | 86.54 | A | O |
| ATOM | 525 | N | ILE | A | 193 | 42.172 | 51.417 | 7.561 | 1.00 | 85.26 | A | N |
| ATOM | 526 | CA | ILE | A | 193 | 42.362 | 51.753 | 8.954 | 1.00 | 84.63 | A | C |
| ATOM | 527 | CB | ILE | A | 193 | 43.082 | 53.049 | 9.124 | 1.00 | 83.29 | A | C |
| ATOM | 528 | CG2 | ILE | A | 193 | 43.041 | 53.456 | 10.592 | 1.00 | 83.02 | A | C |
| ATOM | 529 | CG1 | ILE | A | 193 | 44.501 | 52.894 | 8.603 | 1.00 | 82.02 | A | C |
| ATOM | 530 | CD1 | ILE | A | 193 | 45.320 | 54.132 | 8.753 | 1.00 | 84.53 | A | C |
| ATOM | 531 | C | ILE | A | 193 | 41.009 | 51.912 | 9.564 | 1.00 | 87.33 | A | C |
| ATOM | 532 | O | ILE | A | 193 | 40.235 | 52.776 | 9.137 | 1.00 | 88.42 | A | O |
| ATOM | 533 | N | LEU | A | 194 | 40.724 | 51.083 | 10.561 | 1.00 | 89.72 | A | N |

Figure 4I

| ATOM | 534 | CA | LEU A 194 | 39.435 | 51.135 | 11.211 | 1.00 | 94.32 | A | C |
|---|---|---|---|---|---|---|---|---|---|---|
| ATOM | 535 | CB | LEU A 194 | 39.359 | 50.097 | 12.314 | 1.00 | 91.61 | A | C |
| ATOM | 536 | CG | LEU A 194 | 37.933 | 49.841 | 12.780 | 1.00 | 90.30 | A | C |
| ATOM | 537 | CD1 | LEU A 194 | 37.135 | 49.261 | 11.642 | 1.00 | 88.09 | A | C |
| ATOM | 538 | CD2 | LEU A 194 | 37.943 | 48.895 | 13.964 | 1.00 | 89.26 | A | C |
| ATOM | 539 | C | LEU A 194 | 39.273 | 52.522 | 11.790 | 1.00 | 98.98 | A | C |
| ATOM | 540 | O | LEU A 194 | 40.005 | 52.900 | 12.709 | 1.00 | 99.57 | A | O |
| ATOM | 541 | N | ARG A 195 | 38.317 | 53.274 | 11.239 | 1.00 | 103.51 | A | N |
| ATOM | 542 | CA | ARG A 195 | 38.034 | 54.655 | 11.664 | 1.00 | 108.42 | A | C |
| ATOM | 543 | CB | ARG A 195 | 37.096 | 55.343 | 10.648 | 1.00 | 110.99 | A | C |
| ATOM | 544 | CG | ARG A 195 | 36.791 | 56.839 | 10.951 | 1.00 | 115.51 | A | C |
| ATOM | 545 | CD | ARG A 195 | 35.895 | 57.528 | 9.886 | 1.00 | 116.54 | A | C |
| ATOM | 546 | NE | ARG A 195 | 35.720 | 58.962 | 10.154 | 1.00 | 119.15 | A | N |
| ATOM | 547 | CZ | ARG A 195 | 35.023 | 59.801 | 9.389 | 1.00 | 120.38 | A | C |
| ATOM | 548 | NH1 | ARG A 195 | 34.939 | 61.087 | 9.743 | 1.00 | 120.69 | A | N |
| ATOM | 549 | NH2 | ARG A 195 | 34.416 | 59.364 | 8.276 | 1.00 | 119.07 | A | N |
| ATOM | 550 | C | ARG A 195 | 37.424 | 54.777 | 13.072 | 1.00 | 109.46 | A | C |
| ATOM | 551 | O | ARG A 195 | 36.866 | 53.818 | 13.607 | 1.00 | 110.11 | A | O |
| ATOM | 552 | N | LEU A 196 | 37.534 | 55.970 | 13.658 | 1.00 | 109.48 | A | N |
| ATOM | 553 | CA | LEU A 196 | 36.994 | 56.239 | 14.986 | 1.00 | 108.61 | A | C |
| ATOM | 554 | CB | LEU A 196 | 38.131 | 56.458 | 15.973 | 1.00 | 112.89 | A | C |
| ATOM | 555 | CG | LEU A 196 | 37.760 | 57.019 | 17.349 | 1.00 | 116.91 | A | C |
| ATOM | 556 | CD1 | LEU A 196 | 36.516 | 56.329 | 17.942 | 1.00 | 118.75 | A | C |
| ATOM | 557 | CD2 | LEU A 196 | 38.994 | 56.849 | 18.242 | 1.00 | 119.73 | A | C |
| ATOM | 558 | C | LEU A 196 | 36.086 | 57.457 | 14.962 | 1.00 | 106.22 | A | C |
| ATOM | 559 | O | LEU A 196 | 36.445 | 58.541 | 15.412 | 1.00 | 103.26 | A | O |
| ATOM | 560 | N | TYR A 197 | 34.894 | 57.255 | 14.429 | 1.00 | 106.33 | A | N |
| ATOM | 561 | CA | TYR A 197 | 33.933 | 58.327 | 14.317 | 1.00 | 106.90 | A | C |
| ATOM | 562 | CB | TYR A 197 | 32.519 | 57.760 | 14.192 | 1.00 | 110.15 | A | C |
| ATOM | 563 | CG | TYR A 197 | 32.399 | 56.820 | 13.041 | 1.00 | 113.34 | A | C |
| ATOM | 564 | CD1 | TYR A 197 | 32.296 | 55.447 | 13.249 | 1.00 | 116.56 | A | C |
| ATOM | 565 | CE1 | TYR A 197 | 32.258 | 54.553 | 12.182 | 1.00 | 120.68 | A | C |
| ATOM | 566 | CD2 | TYR A 197 | 32.459 | 57.293 | 11.742 | 1.00 | 114.33 | A | C |
| ATOM | 567 | CE2 | TYR A 197 | 32.425 | 56.420 | 10.660 | 1.00 | 120.50 | A | C |
| ATOM | 568 | CZ | TYR A 197 | 32.324 | 55.039 | 10.877 | 1.00 | 122.27 | A | C |
| ATOM | 569 | OH | TYR A 197 | 32.296 | 54.153 | 9.796 | 1.00 | 126.22 | A | O |
| ATOM | 570 | C | TYR A 197 | 34.012 | 59.296 | 15.478 | 1.00 | 106.04 | A | C |
| ATOM | 571 | O | TYR A 197 | 34.231 | 60.485 | 15.268 | 1.00 | 106.77 | A | O |
| ATOM | 572 | N | GLY A 198 | 33.863 | 58.809 | 16.700 | 1.00 | 105.93 | A | N |
| ATOM | 573 | CA | GLY A 198 | 33.909 | 59.732 | 17.809 | 1.00 | 109.51 | A | C |
| ATOM | 574 | C | GLY A 198 | 34.061 | 59.077 | 19.152 | 1.00 | 112.38 | A | C |
| ATOM | 575 | O | GLY A 198 | 34.355 | 57.879 | 19.247 | 1.00 | 114.66 | A | O |
| ATOM | 576 | N | TYR A 199 | 33.868 | 59.877 | 20.196 | 1.00 | 114.31 | A | N |
| ATOM | 577 | CA | TYR A 199 | 33.984 | 59.379 | 21.553 | 1.00 | 115.53 | A | C |
| ATOM | 578 | CB | TYR A 199 | 35.457 | 59.232 | 21.939 | 1.00 | 119.01 | A | C |
| ATOM | 579 | CG | TYR A 199 | 35.834 | 60.032 | 23.165 | 1.00 | 123.04 | A | C |
| ATOM | 580 | CD1 | TYR A 199 | 36.428 | 61.306 | 23.046 | 1.00 | 123.81 | A | C |
| ATOM | 581 | CE1 | TYR A 199 | 36.743 | 62.070 | 24.194 | 1.00 | 127.39 | A | C |
| ATOM | 582 | CD2 | TYR A 199 | 35.562 | 59.533 | 24.456 | 1.00 | 124.45 | A | C |
| ATOM | 583 | CE2 | TYR A 199 | 35.868 | 60.284 | 25.608 | 1.00 | 128.90 | A | C |
| ATOM | 584 | CZ | TYR A 199 | 36.460 | 61.555 | 25.474 | 1.00 | 129.45 | A | C |
| ATOM | 585 | OH | TYR A 199 | 36.763 | 62.308 | 26.601 | 1.00 | 129.54 | A | O |
| ATOM | 586 | C | TYR A 199 | 33.296 | 60.285 | 22.560 | 1.00 | 114.23 | A | C |
| ATOM | 587 | O | TYR A 199 | 33.279 | 61.518 | 22.417 | 1.00 | 113.15 | A | O |
| ATOM | 588 | N | PHE A 200 | 32.738 | 59.653 | 23.584 | 1.00 | 113.27 | A | N |
| ATOM | 589 | CA | PHE A 200 | 32.084 | 60.369 | 24.658 | 1.00 | 113.90 | A | C |
| ATOM | 590 | CB | PHE A 200 | 30.565 | 60.539 | 24.385 | 1.00 | 113.63 | A | C |
| ATOM | 591 | CG | PHE A 200 | 29.833 | 59.270 | 23.992 | 1.00 | 113.39 | A | C |
| ATOM | 592 | CD1 | PHE A 200 | 30.095 | 58.630 | 22.780 | 1.00 | 114.27 | A | C |
| ATOM | 593 | CD2 | PHE A 200 | 28.839 | 58.749 | 24.825 | 1.00 | 114.10 | A | C |
| ATOM | 594 | CE1 | PHE A 200 | 29.379 | 57.496 | 22.402 | 1.00 | 115.44 | A | C |

Figure 4J

```
ATOM    595  CE2 PHE A 200      28.120  57.620  24.459  1.00  115.32      A    C
ATOM    596  CZ  PHE A 200      28.391  56.993  23.240  1.00  115.92      A    C
ATOM    597  C   PHE A 200      32.375  59.554  25.904  1.00  115.10      A    C
ATOM    598  O   PHE A 200      33.196  58.634  25.845  1.00  113.50      A    O
ATOM    599  N   HIS A 201      31.736  59.889  27.024  1.00  118.53      A    N
ATOM    600  CA  HIS A 201      31.965  59.158  28.278  1.00  122.57      A    C
ATOM    601  CB  HIS A 201      33.407  59.387  28.749  1.00  128.03      A    C
ATOM    602  CG  HIS A 201      33.757  60.836  28.965  1.00  134.01      A    C
ATOM    603  CD2 HIS A 201      34.488  61.700  28.213  1.00  135.47      A    C
ATOM    604  ND1 HIS A 201      33.330  61.558  30.064  1.00  134.63      A    N
ATOM    605  CE1 HIS A 201      33.785  62.798  29.978  1.00  134.21      A    C
ATOM    606  NE2 HIS A 201      34.490  62.911  28.865  1.00  134.60      A    N
ATOM    607  C   HIS A 201      31.024  59.504  29.436  1.00  121.46      A    C
ATOM    608  O   HIS A 201      30.802  60.680  29.727  1.00  121.52      A    O
ATOM    609  N   ASP A 202      30.457  58.489  30.088  1.00  120.64      A    N
ATOM    610  CA  ASP A 202      29.600  58.764  31.235  1.00  120.41      A    C
ATOM    611  CB  ASP A 202      28.317  57.883  31.260  1.00  122.35      A    C
ATOM    612  CG  ASP A 202      28.601  56.386  31.348  1.00  125.06      A    C
ATOM    613  OD1 ASP A 202      29.272  55.941  32.307  1.00  129.74      A    O
ATOM    614  OD2 ASP A 202      28.127  55.648  30.458  1.00  122.75      A    O
ATOM    615  C   ASP A 202      30.481  58.541  32.463  1.00  118.89      A    C
ATOM    616  O   ASP A 202      31.685  58.266  32.337  1.00  118.27      A    O
ATOM    617  N   ALA A 203      29.891  58.688  33.641  1.00  116.54      A    N
ATOM    618  CA  ALA A 203      30.620  58.531  34.889  1.00  112.60      A    C
ATOM    619  CB  ALA A 203      29.621  58.512  36.059  1.00  114.00      A    C
ATOM    620  C   ALA A 203      31.485  57.274  34.920  1.00  109.64      A    C
ATOM    621  O   ALA A 203      32.710  57.319  34.731  1.00  104.91      A    O
ATOM    622  N   THR A 204      30.803  56.161  35.169  1.00  109.33      A    N
ATOM    623  CA  THR A 204      31.402  54.843  35.279  1.00  110.76      A    C
ATOM    624  CB  THR A 204      30.276  53.756  35.573  1.00  111.06      A    C
ATOM    625  OG1 THR A 204      30.828  52.434  35.493  1.00  113.32      A    O
ATOM    626  CG2 THR A 204      29.113  53.868  34.587  1.00  109.92      A    C
ATOM    627  C   THR A 204      32.243  54.412  34.074  1.00  111.24      A    C
ATOM    628  O   THR A 204      33.434  54.091  34.204  1.00  111.24      A    O
ATOM    629  N   ARG A 205      31.617  54.435  32.904  1.00  110.48      A    N
ATOM    630  CA  ARG A 205      32.246  53.992  31.674  1.00  108.21      A    C
ATOM    631  CB  ARG A 205      31.377  52.866  31.085  1.00  112.04      A    C
ATOM    632  CG  ARG A 205      29.859  53.011  31.371  1.00  115.23      A    C
ATOM    633  CD  ARG A 205      29.077  51.691  31.143  1.00  120.66      A    C
ATOM    634  NE  ARG A 205      27.624  51.861  31.268  1.00  123.06      A    N
ATOM    635  CZ  ARG A 205      26.709  50.962  30.892  1.00  123.80      A    C
ATOM    636  NH1 ARG A 205      27.072  49.789  30.359  1.00  123.56      A    N
ATOM    637  NH2 ARG A 205      25.415  51.259  31.021  1.00  123.10      A    N
ATOM    638  C   ARG A 205      32.543  55.047  30.608  1.00  105.44      A    C
ATOM    639  O   ARG A 205      32.236  56.229  30.754  1.00  104.27      A    O
ATOM    640  N   VAL A 206      33.170  54.588  29.535  1.00  102.74      A    N
ATOM    641  CA  VAL A 206      33.517  55.424  28.392  1.00   99.73      A    C
ATOM    642  CB  VAL A 206      35.031  55.749  28.381  1.00   99.36      A    C
ATOM    643  CG1 VAL A 206      35.699  55.098  29.590  1.00   98.06      A    C
ATOM    644  CG2 VAL A 206      35.676  55.289  27.068  1.00   97.31      A    C
ATOM    645  C   VAL A 206      33.115  54.680  27.104  1.00   97.73      A    C
ATOM    646  O   VAL A 206      32.818  53.477  27.123  1.00   97.60      A    O
ATOM    647  N   TYR A 207      33.098  55.382  25.979  1.00   94.68      A    N
ATOM    648  CA  TYR A 207      32.690  54.725  24.755  1.00   92.15      A    C
ATOM    649  CB  TYR A 207      31.188  54.874  24.578  1.00   94.55      A    C
ATOM    650  CG  TYR A 207      30.387  54.596  25.837  1.00   95.95      A    C
ATOM    651  CD1 TYR A 207      30.229  55.574  26.831  1.00   92.90      A    C
ATOM    652  CE1 TYR A 207      29.483  55.327  27.969  1.00   94.47      A    C
ATOM    653  CD2 TYR A 207      29.777  53.358  26.023  1.00   98.62      A    C
ATOM    654  CE2 TYR A 207      29.026  53.098  27.160  1.00  100.49      A    C
ATOM    655  CZ  TYR A 207      28.881  54.090  28.131  1.00   99.10      A    C
```

Figure 4K

```
ATOM    656  OH  TYR A 207      28.111  53.842  29.247  1.00  99.87      A  O
ATOM    657  C   TYR A 207      33.390  55.178  23.495  1.00  91.09      A  C
ATOM    658  O   TYR A 207      33.609  56.369  23.246  1.00  88.43      A  O
ATOM    659  N   LEU A 208      33.724  54.182  22.697  1.00  92.14      A  N
ATOM    660  CA  LEU A 208      34.405  54.393  21.447  1.00  94.34      A  C
ATOM    661  CB  LEU A 208      35.606  53.463  21.329  1.00  96.20      A  C
ATOM    662  CG  LEU A 208      36.776  53.619  22.297  1.00  96.89      A  C
ATOM    663  CD1 LEU A 208      37.662  52.367  22.221  1.00  95.76      A  C
ATOM    664  CD2 LEU A 208      37.560  54.897  21.959  1.00  94.63      A  C
ATOM    665  C   LEU A 208      33.440  54.054  20.353  1.00  95.05      A  C
ATOM    666  O   LEU A 208      32.954  52.919  20.262  1.00  96.97      A  O
ATOM    667  N   ILE A 209      33.158  55.043  19.523  1.00  94.42      A  N
ATOM    668  CA  ILE A 209      32.263  54.839  18.401  1.00  93.86      A  C
ATOM    669  CB  ILE A 209      31.454  56.092  18.112  1.00  97.36      A  C
ATOM    670  CG2 ILE A 209      30.483  55.816  16.959  1.00  98.91      A  C
ATOM    671  CG1 ILE A 209      30.738  56.537  19.396  1.00  98.47      A  C
ATOM    672  CD1 ILE A 209      30.042  57.869  19.278  1.00 101.03      A  C
ATOM    673  C   ILE A 209      33.157  54.539  17.220  1.00  90.33      A  C
ATOM    674  O   ILE A 209      34.011  55.346  16.863  1.00  89.00      A  O
ATOM    675  N   LEU A 210      32.962  53.383  16.606  1.00  88.74      A  N
ATOM    676  CA  LEU A 210      33.826  53.020  15.502  1.00  88.57      A  C
ATOM    677  CB  LEU A 210      34.976  52.159  16.047  1.00  92.54      A  C
ATOM    678  CG  LEU A 210      35.730  52.557  17.333  1.00  92.49      A  C
ATOM    679  CD1 LEU A 210      34.958  52.088  18.567  1.00  91.36      A  C
ATOM    680  CD2 LEU A 210      37.121  51.909  17.321  1.00  93.40      A  C
ATOM    681  C   LEU A 210      33.193  52.317  14.290  1.00  86.56      A  C
ATOM    682  O   LEU A 210      32.058  51.836  14.327  1.00  86.13      A  O
ATOM    683  N   GLU A 211      33.965  52.272  13.212  1.00  84.75      A  N
ATOM    684  CA  GLU A 211      33.563  51.634  11.973  1.00  83.90      A  C
ATOM    685  CB  GLU A 211      34.683  51.781  10.945  1.00  85.78      A  C
ATOM    686  CG  GLU A 211      34.603  50.856   9.732  1.00  90.03      A  C
ATOM    687  CD  GLU A 211      35.684  51.155   8.683  1.00  89.97      A  C
ATOM    688  OE1 GLU A 211      36.839  51.473   9.062  1.00  85.49      A  O
ATOM    689  OE2 GLU A 211      35.371  51.056   7.475  1.00  88.84      A  O
ATOM    690  C   GLU A 211      33.310  50.178  12.251  1.00  83.19      A  C
ATOM    691  O   GLU A 211      34.046  49.542  12.996  1.00  83.10      A  O
ATOM    692  N   TYR A 212      32.271  49.634  11.648  1.00  82.36      A  N
ATOM    693  CA  TYR A 212      31.979  48.242  11.882  1.00  80.86      A  C
ATOM    694  CB  TYR A 212      30.469  48.069  11.986  1.00  81.34      A  C
ATOM    695  CG  TYR A 212      30.078  46.645  12.168  1.00  84.50      A  C
ATOM    696  CD1 TYR A 212      30.413  45.961  13.323  1.00  85.54      A  C
ATOM    697  CE1 TYR A 212      30.183  44.607  13.436  1.00  89.83      A  C
ATOM    698  CD2 TYR A 212      29.486  45.941  11.131  1.00  88.05      A  C
ATOM    699  CE2 TYR A 212      29.252  44.586  11.233  1.00  92.80      A  C
ATOM    700  CZ  TYR A 212      29.610  43.922  12.387  1.00  92.59      A  C
ATOM    701  OH  TYR A 212      29.443  42.559  12.470  1.00  98.40      A  O
ATOM    702  C   TYR A 212      32.578  47.347  10.784  1.00  79.51      A  C
ATOM    703  O   TYR A 212      32.398  47.612   9.592  1.00  80.50      A  O
ATOM    704  N   ALA A 213      33.303  46.302  11.202  1.00  78.31      A  N
ATOM    705  CA  ALA A 213      33.954  45.334  10.295  1.00  78.11      A  C
ATOM    706  CB  ALA A 213      35.417  45.245  10.610  1.00  76.93      A  C
ATOM    707  C   ALA A 213      33.325  43.934  10.369  1.00  77.49      A  C
ATOM    708  O   ALA A 213      33.774  43.059  11.113  1.00  75.06      A  O
ATOM    709  N   PRO A 214      32.304  43.703   9.539  1.00  79.91      A  N
ATOM    710  CD  PRO A 214      32.056  44.624   8.414  1.00  81.27      A  C
ATOM    711  CA  PRO A 214      31.492  42.494   9.381  1.00  82.31      A  C
ATOM    712  CB  PRO A 214      30.620  42.830   8.180  1.00  85.18      A  C
ATOM    713  CG  PRO A 214      31.518  43.693   7.372  1.00  84.46      A  C
ATOM    714  C   PRO A 214      32.138  41.133   9.225  1.00  82.71      A  C
ATOM    715  O   PRO A 214      31.616  40.135   9.721  1.00  81.38      A  O
ATOM    716  N   LEU A 215      33.261  41.072   8.535  1.00  85.17      A  N
```

Figure 4L

| ATOM | 717 | CA  | LEU A 215 | 33.876 | 39.778 | 8.320  | 1.00 | 88.45  | A | C |
| ATOM | 718 | CB  | LEU A 215 | 34.612 | 39.789 | 6.991  | 1.00 | 94.16  | A | C |
| ATOM | 719 | CG  | LEU A 215 | 33.563 | 39.723 | 5.874  | 1.00 | 98.56  | A | C |
| ATOM | 720 | CD1 | LEU A 215 | 34.219 | 39.842 | 4.487  | 1.00 | 101.23 | A | C |
| ATOM | 721 | CD2 | LEU A 215 | 32.787 | 38.392 | 6.022  | 1.00 | 102.41 | A | C |
| ATOM | 722 | C   | LEU A 215 | 34.757 | 39.238 | 9.424  | 1.00 | 87.82  | A | C |
| ATOM | 723 | O   | LEU A 215 | 35.517 | 38.293 | 9.221  | 1.00 | 84.90  | A | O |
| ATOM | 724 | N   | GLY A 216 | 34.621 | 39.825 | 10.606 | 1.00 | 88.96  | A | N |
| ATOM | 725 | CA  | GLY A 216 | 35.393 | 39.371 | 11.741 | 1.00 | 90.57  | A | C |
| ATOM | 726 | C   | GLY A 216 | 36.884 | 39.620 | 11.620 | 1.00 | 89.46  | A | C |
| ATOM | 727 | O   | GLY A 216 | 37.329 | 40.452 | 10.818 | 1.00 | 88.85  | A | O |
| ATOM | 728 | N   | THR A 217 | 37.647 | 38.866 | 12.414 | 1.00 | 87.40  | A | N |
| ATOM | 729 | CA  | THR A 217 | 39.103 | 38.973 | 12.494 | 1.00 | 83.89  | A | C |
| ATOM | 730 | CB  | THR A 217 | 39.553 | 38.771 | 13.985 | 1.00 | 81.48  | A | C |
| ATOM | 731 | OG1 | THR A 217 | 40.750 | 39.508 | 14.242 | 1.00 | 82.04  | A | O |
| ATOM | 732 | CG2 | THR A 217 | 39.812 | 37.318 | 14.288 | 1.00 | 80.94  | A | C |
| ATOM | 733 | C   | THR A 217 | 39.862 | 38.005 | 11.572 | 1.00 | 82.48  | A | C |
| ATOM | 734 | O   | THR A 217 | 39.467 | 36.859 | 11.393 | 1.00 | 82.47  | A | O |
| ATOM | 735 | N   | VAL A 218 | 40.948 | 38.485 | 10.978 | 1.00 | 82.00  | A | N |
| ATOM | 736 | CA  | VAL A 218 | 41.773 | 37.669 | 10.094 | 1.00 | 85.16  | A | C |
| ATOM | 737 | CB  | VAL A 218 | 42.983 | 38.458 | 9.570  | 1.00 | 84.81  | A | C |
| ATOM | 738 | CG1 | VAL A 218 | 44.141 | 37.527 | 9.284  | 1.00 | 84.29  | A | C |
| ATOM | 739 | CG2 | VAL A 218 | 42.599 | 39.187 | 8.314  | 1.00 | 85.91  | A | C |
| ATOM | 740 | C   | VAL A 218 | 42.277 | 36.478 | 10.873 | 1.00 | 86.16  | A | C |
| ATOM | 741 | O   | VAL A 218 | 42.370 | 35.375 | 10.351 | 1.00 | 84.77  | A | O |
| ATOM | 742 | N   | TYR A 219 | 42.633 | 36.732 | 12.125 | 1.00 | 89.86  | A | N |
| ATOM | 743 | CA  | TYR A 219 | 43.105 | 35.693 | 13.021 | 1.00 | 94.02  | A | C |
| ATOM | 744 | CB  | TYR A 219 | 42.934 | 36.154 | 14.472 | 1.00 | 95.00  | A | C |
| ATOM | 745 | CG  | TYR A 219 | 43.115 | 35.065 | 15.508 | 1.00 | 96.94  | A | C |
| ATOM | 746 | CD1 | TYR A 219 | 44.257 | 34.256 | 15.494 | 1.00 | 99.08  | A | C |
| ATOM | 747 | CE1 | TYR A 219 | 44.481 | 33.300 | 16.486 | 1.00 | 99.09  | A | C |
| ATOM | 748 | CD2 | TYR A 219 | 42.183 | 34.885 | 16.545 | 1.00 | 97.62  | A | C |
| ATOM | 749 | CE2 | TYR A 219 | 42.399 | 33.930 | 17.546 | 1.00 | 99.19  | A | C |
| ATOM | 750 | CZ  | TYR A 219 | 43.556 | 33.149 | 17.506 | 1.00 | 99.96  | A | C |
| ATOM | 751 | OH  | TYR A 219 | 43.828 | 32.253 | 18.504 | 1.00 | 100.03 | A | O |
| ATOM | 752 | C   | TYR A 219 | 42.182 | 34.535 | 12.755 | 1.00 | 97.03  | A | C |
| ATOM | 753 | O   | TYR A 219 | 42.614 | 33.436 | 12.390 | 1.00 | 97.16  | A | O |
| ATOM | 754 | N   | ARG A 220 | 40.895 | 34.818 | 12.938 | 1.00 | 100.19 | A | N |
| ATOM | 755 | CA  | ARG A 220 | 39.851 | 33.841 | 12.721 | 1.00 | 102.88 | A | C |
| ATOM | 756 | CB  | ARG A 220 | 38.466 | 34.472 | 12.946 | 1.00 | 106.18 | A | C |
| ATOM | 757 | CG  | ARG A 220 | 38.163 | 34.785 | 14.408 | 1.00 | 108.69 | A | C |
| ATOM | 758 | CD  | ARG A 220 | 38.242 | 33.518 | 15.227 | 1.00 | 111.32 | A | C |
| ATOM | 759 | NE  | ARG A 220 | 38.455 | 33.773 | 16.643 | 1.00 | 112.72 | A | N |
| ATOM | 760 | CZ  | ARG A 220 | 37.616 | 34.463 | 17.400 | 1.00 | 113.87 | A | C |
| ATOM | 761 | NH1 | ARG A 220 | 37.889 | 34.640 | 18.686 | 1.00 | 113.70 | A | N |
| ATOM | 762 | NH2 | ARG A 220 | 36.510 | 34.979 | 16.865 | 1.00 | 114.57 | A | N |
| ATOM | 763 | C   | ARG A 220 | 39.985 | 33.322 | 11.299 | 1.00 | 102.35 | A | C |
| ATOM | 764 | O   | ARG A 220 | 40.264 | 32.141 | 11.097 | 1.00 | 102.75 | A | O |
| ATOM | 765 | N   | GLU A 221 | 39.819 | 34.204 | 10.316 | 1.00 | 101.44 | A | N |
| ATOM | 766 | CA  | GLU A 221 | 39.924 | 33.779 | 8.924  | 1.00 | 101.27 | A | C |
| ATOM | 767 | CB  | GLU A 221 | 40.037 | 34.971 | 7.962  | 1.00 | 104.47 | A | C |
| ATOM | 768 | CG  | GLU A 221 | 38.779 | 35.195 | 7.114  | 1.00 | 108.08 | A | C |
| ATOM | 769 | CD  | GLU A 221 | 38.448 | 34.033 | 6.155  | 1.00 | 110.40 | A | C |
| ATOM | 770 | OE1 | GLU A 221 | 38.768 | 32.865 | 6.462  | 1.00 | 112.62 | A | O |
| ATOM | 771 | OE2 | GLU A 221 | 37.842 | 34.281 | 5.090  | 1.00 | 111.59 | A | O |
| ATOM | 772 | C   | GLU A 221 | 41.137 | 32.913 | 8.764  | 1.00 | 99.64  | A | C |
| ATOM | 773 | O   | GLU A 221 | 41.122 | 31.926 | 8.030  | 1.00 | 98.98  | A | O |
| ATOM | 774 | N   | LEU A 222 | 42.186 | 33.287 | 9.479  | 1.00 | 99.29  | A | N |
| ATOM | 775 | CA  | LEU A 222 | 43.432 | 32.565 | 9.415  | 1.00 | 101.55 | A | C |
| ATOM | 776 | CB  | LEU A 222 | 44.534 | 33.350 | 10.120 | 1.00 | 102.80 | A | C |
| ATOM | 777 | CG  | LEU A 222 | 45.916 | 32.672 | 10.091 | 1.00 | 106.84 | A | C |

Figure 4M

| ATOM | 778 | CD1 | LEU | A | 222 | 46.246 | 32.146 | 8.675 | 1.00 | 108.35 | A | C |
|------|-----|-----|-----|---|-----|--------|--------|-------|------|--------|---|---|
| ATOM | 779 | CD2 | LEU | A | 222 | 46.974 | 33.670 | 10.575 | 1.00 | 105.63 | A | C |
| ATOM | 780 | C | LEU | A | 222 | 43.347 | 31.166 | 9.990 | 1.00 | 102.22 | A | C |
| ATOM | 781 | O | LEU | A | 222 | 43.865 | 30.219 | 9.396 | 1.00 | 104.96 | A | O |
| ATOM | 782 | N | GLN | A | 223 | 42.704 | 31.017 | 11.138 | 1.00 | 101.75 | A | N |
| ATOM | 783 | CA | GLN | A | 223 | 42.608 | 29.696 | 11.723 | 1.00 | 101.94 | A | C |
| ATOM | 784 | CB | GLN | A | 223 | 42.270 | 29.813 | 13.190 | 1.00 | 105.44 | A | C |
| ATOM | 785 | CG | GLN | A | 223 | 40.964 | 30.524 | 13.423 | 1.00 | 117.72 | A | C |
| ATOM | 786 | CD | GLN | A | 223 | 40.603 | 30.588 | 14.891 | 1.00 | 123.20 | A | C |
| ATOM | 787 | OE1 | GLN | A | 223 | 39.498 | 31.012 | 15.264 | 1.00 | 126.90 | A | O |
| ATOM | 788 | NE2 | GLN | A | 223 | 41.540 | 30.162 | 15.744 | 1.00 | 125.88 | A | N |
| ATOM | 789 | C | GLN | A | 223 | 41.588 | 28.802 | 11.013 | 1.00 | 99.95 | A | C |
| ATOM | 790 | O | GLN | A | 223 | 41.614 | 27.594 | 11.196 | 1.00 | 98.20 | A | O |
| ATOM | 791 | N | LYS | A | 224 | 40.703 | 29.387 | 10.201 | 1.00 | 100.07 | A | N |
| ATOM | 792 | CA | LYS | A | 224 | 39.691 | 28.605 | 9.463 | 1.00 | 101.75 | A | C |
| ATOM | 793 | CB | LYS | A | 224 | 38.405 | 29.434 | 9.204 | 1.00 | 101.69 | A | C |
| ATOM | 794 | CG | LYS | A | 224 | 37.353 | 29.392 | 10.352 | 1.00 | 99.75 | A | C |
| ATOM | 795 | CD | LYS | A | 224 | 36.088 | 30.272 | 10.140 | 1.00 | 98.17 | A | C |
| ATOM | 796 | CE | LYS | A | 224 | 35.204 | 29.825 | 8.960 | 1.00 | 96.45 | A | C |
| ATOM | 797 | NZ | LYS | A | 224 | 33.927 | 30.620 | 8.826 | 1.00 | 92.43 | A | N |
| ATOM | 798 | C | LYS | A | 224 | 40.202 | 28.026 | 8.131 | 1.00 | 103.93 | A | C |
| ATOM | 799 | O | LYS | A | 224 | 39.833 | 26.900 | 7.767 | 1.00 | 106.49 | A | O |
| ATOM | 800 | N | LEU | A | 225 | 41.032 | 28.783 | 7.404 | 1.00 | 104.30 | A | N |
| ATOM | 801 | CA | LEU | A | 225 | 41.594 | 28.316 | 6.122 | 1.00 | 103.38 | A | C |
| ATOM | 802 | CB | LEU | A | 225 | 41.702 | 29.464 | 5.106 | 1.00 | 102.20 | A | C |
| ATOM | 803 | CG | LEU | A | 225 | 40.464 | 29.703 | 4.235 | 1.00 | 101.53 | A | C |
| ATOM | 804 | CD1 | LEU | A | 225 | 39.316 | 30.238 | 5.096 | 1.00 | 103.59 | A | C |
| ATOM | 805 | CD2 | LEU | A | 225 | 40.797 | 30.678 | 3.123 | 1.00 | 100.48 | A | C |
| ATOM | 806 | C | LEU | A | 225 | 42.964 | 27.675 | 6.304 | 1.00 | 101.97 | A | C |
| ATOM | 807 | O | LEU | A | 225 | 43.581 | 27.218 | 5.343 | 1.00 | 102.41 | A | O |
| ATOM | 808 | N | SER | A | 226 | 43.420 | 27.649 | 7.551 | 1.00 | 100.20 | A | N |
| ATOM | 809 | CA | SER | A | 226 | 44.706 | 27.069 | 7.919 | 1.00 | 98.06 | A | C |
| ATOM | 810 | CB | SER | A | 226 | 44.813 | 25.633 | 7.398 | 1.00 | 98.55 | A | C |
| ATOM | 811 | OG | SER | A | 226 | 46.098 | 25.092 | 7.672 | 1.00 | 97.22 | A | O |
| ATOM | 812 | C | SER | A | 226 | 45.894 | 27.864 | 7.408 | 1.00 | 95.51 | A | C |
| ATOM | 813 | O | SER | A | 226 | 46.874 | 28.070 | 8.118 | 1.00 | 93.79 | A | O |
| ATOM | 814 | N | LYS | A | 227 | 45.793 | 28.312 | 6.170 | 1.00 | 94.01 | A | N |
| ATOM | 815 | CA | LYS | A | 227 | 46.866 | 29.045 | 5.545 | 1.00 | 93.52 | A | C |
| ATOM | 816 | CB | LYS | A | 227 | 47.971 | 28.042 | 5.213 | 1.00 | 95.86 | A | C |
| ATOM | 817 | CG | LYS | A | 227 | 48.910 | 28.466 | 4.113 | 1.00 | 104.38 | A | C |
| ATOM | 818 | CD | LYS | A | 227 | 49.007 | 27.397 | 3.000 | 1.00 | 111.96 | A | C |
| ATOM | 819 | CE | LYS | A | 227 | 49.762 | 27.914 | 1.743 | 1.00 | 116.43 | A | C |
| ATOM | 820 | NZ | LYS | A | 227 | 49.764 | 26.966 | 0.571 | 1.00 | 117.83 | A | N |
| ATOM | 821 | C | LYS | A | 227 | 46.317 | 29.732 | 4.284 | 1.00 | 93.17 | A | C |
| ATOM | 822 | O | LYS | A | 227 | 45.631 | 29.100 | 3.472 | 1.00 | 93.00 | A | O |
| ATOM | 823 | N | PHE | A | 228 | 46.608 | 31.026 | 4.129 | 1.00 | 92.35 | A | N |
| ATOM | 824 | CA | PHE | A | 228 | 46.134 | 31.811 | 2.978 | 1.00 | 93.02 | A | C |
| ATOM | 825 | CB | PHE | A | 228 | 46.225 | 33.323 | 3.248 | 1.00 | 88.79 | A | C |
| ATOM | 826 | CG | PHE | A | 228 | 45.472 | 33.783 | 4.459 | 1.00 | 83.75 | A | C |
| ATOM | 827 | CD1 | PHE | A | 228 | 44.427 | 33.032 | 4.975 | 1.00 | 87.00 | A | C |
| ATOM | 828 | CD2 | PHE | A | 228 | 45.777 | 34.993 | 5.060 | 1.00 | 79.34 | A | C |
| ATOM | 829 | CE1 | PHE | A | 228 | 43.691 | 33.486 | 6.079 | 1.00 | 89.01 | A | C |
| ATOM | 830 | CE2 | PHE | A | 228 | 45.052 | 35.452 | 6.158 | 1.00 | 80.98 | A | C |
| ATOM | 831 | CZ | PHE | A | 228 | 44.006 | 34.700 | 6.670 | 1.00 | 85.15 | A | C |
| ATOM | 832 | C | PHE | A | 228 | 46.919 | 31.543 | 1.705 | 1.00 | 95.50 | A | C |
| ATOM | 833 | O | PHE | A | 228 | 48.123 | 31.323 | 1.758 | 1.00 | 94.62 | A | O |
| ATOM | 834 | N | ASP | A | 229 | 46.241 | 31.594 | 0.558 | 1.00 | 100.44 | A | N |
| ATOM | 835 | CA | ASP | A | 229 | 46.897 | 31.383 | -0.741 | 1.00 | 102.57 | A | C |
| ATOM | 836 | CB | ASP | A | 229 | 45.881 | 31.295 | -1.887 | 1.00 | 103.03 | A | C |
| ATOM | 837 | CG | ASP | A | 229 | 45.139 | 32.612 | -2.113 | 1.00 | 103.52 | A | C |
| ATOM | 838 | OD1 | ASP | A | 229 | 44.204 | 32.929 | -1.334 | 1.00 | 104.72 | A | O |

Figure 4N

```
ATOM   839  OD2 ASP A 229      45.501  33.337  -3.065  1.00 103.54      A    O
ATOM   840  C   ASP A 229      47.792  32.580  -0.995  1.00 102.24      A    C
ATOM   841  O   ASP A 229      47.902  33.482  -0.159  1.00 101.16      A    O
ATOM   842  N   GLU A 230      48.408  32.602  -2.164  1.00 100.71      A    N
ATOM   843  CA  GLU A 230      49.292  33.702  -2.486  1.00 100.33      A    C
ATOM   844  CB  GLU A 230      50.312  33.235  -3.520  1.00 102.96      A    C
ATOM   845  CG  GLU A 230      51.266  32.185  -2.972  1.00 105.87      A    C
ATOM   846  CD  GLU A 230      52.372  31.839  -3.948  1.00 106.22      A    C
ATOM   847  OE1 GLU A 230      53.072  32.762  -4.436  1.00 104.14      A    O
ATOM   848  OE2 GLU A 230      52.535  30.631  -4.215  1.00 108.49      A    O
ATOM   849  C   GLU A 230      48.612  35.000  -2.949  1.00  98.19      A    C
ATOM   850  O   GLU A 230      49.175  36.084  -2.819  1.00  98.47      A    O
ATOM   851  N   GLN A 231      47.407  34.909  -3.489  1.00  95.67      A    N
ATOM   852  CA  GLN A 231      46.734  36.116  -3.932  1.00  92.93      A    C
ATOM   853  CB  GLN A 231      45.496  35.764  -4.697  1.00  99.07      A    C
ATOM   854  CG  GLN A 231      45.775  34.877  -5.862  1.00 111.26      A    C
ATOM   855  CD  GLN A 231      44.493  34.319  -6.451  1.00 118.61      A    C
ATOM   856  OE1 GLN A 231      44.469  33.876  -7.608  1.00 123.69      A    O
ATOM   857  NE2 GLN A 231      43.413  34.331  -5.655  1.00 120.75      A    N
ATOM   858  C   GLN A 231      46.318  36.895  -2.731  1.00  88.61      A    C
ATOM   859  O   GLN A 231      46.735  38.021  -2.525  1.00  87.86      A    O
ATOM   860  N   ARG A 232      45.475  36.260  -1.942  1.00  85.50      A    N
ATOM   861  CA  ARG A 232      44.946  36.842  -0.738  1.00  85.80      A    C
ATOM   862  CB  ARG A 232      44.116  35.783  -0.021  1.00  91.03      A    C
ATOM   863  CG  ARG A 232      43.336  36.303   1.148  1.00  97.43      A    C
ATOM   864  CD  ARG A 232      42.335  35.277   1.651  1.00 101.69      A    C
ATOM   865  NE  ARG A 232      41.736  35.709   2.919  1.00 107.49      A    N
ATOM   866  CZ  ARG A 232      40.738  35.083   3.546  1.00 109.73      A    C
ATOM   867  NH1 ARG A 232      40.200  33.978   3.016  1.00 112.75      A    N
ATOM   868  NH2 ARG A 232      40.297  35.552   4.718  1.00 105.91      A    N
ATOM   869  C   ARG A 232      46.001  37.435   0.204  1.00  82.33      A    C
ATOM   870  O   ARG A 232      45.813  38.528   0.724  1.00  79.93      A    O
ATOM   871  N   THR A 233      47.106  36.732   0.426  1.00  79.80      A    N
ATOM   872  CA  THR A 233      48.161  37.227   1.328  1.00  77.93      A    C
ATOM   873  CB  THR A 233      49.192  36.115   1.648  1.00  75.42      A    C
ATOM   874  OG1 THR A 233      50.337  36.679   2.306  1.00  71.75      A    O
ATOM   875  CG2 THR A 233      49.633  35.440   0.384  1.00  74.11      A    C
ATOM   876  C   THR A 233      48.945  38.450   0.832  1.00  78.02      A    C
ATOM   877  O   THR A 233      49.245  39.371   1.595  1.00  76.40      A    O
ATOM   878  N   ALA A 234      49.286  38.445  -0.451  1.00  77.84      A    N
ATOM   879  CA  ALA A 234      50.045  39.536  -1.062  1.00  75.29      A    C
ATOM   880  CB  ALA A 234      50.353  39.202  -2.515  1.00  77.15      A    C
ATOM   881  C   ALA A 234      49.256  40.823  -0.993  1.00  73.65      A    C
ATOM   882  O   ALA A 234      49.747  41.853  -0.539  1.00  70.31      A    O
ATOM   883  N   THR A 235      48.022  40.751  -1.464  1.00  73.53      A    N
ATOM   884  CA  THR A 235      47.170  41.907  -1.450  1.00  74.15      A    C
ATOM   885  CB  THR A 235      45.786  41.559  -2.045  1.00  73.72      A    C
ATOM   886  OG1 THR A 235      44.836  42.565  -1.676  1.00  78.18      A    O
ATOM   887  CG2 THR A 235      45.320  40.189  -1.573  1.00  73.17      A    C
ATOM   888  C   THR A 235      47.056  42.422  -0.016  1.00  74.46      A    C
ATOM   889  O   THR A 235      47.271  43.605   0.256  1.00  71.96      A    O
ATOM   890  N   TYR A 236      46.748  41.530   0.913  1.00  75.19      A    N
ATOM   891  CA  TYR A 236      46.615  41.962   2.289  1.00  74.89      A    C
ATOM   892  CB  TYR A 236      46.441  40.755   3.238  1.00  80.36      A    C
ATOM   893  CG  TYR A 236      44.997  40.226   3.398  1.00  86.01      A    C
ATOM   894  CD1 TYR A 236      43.895  40.936   2.890  1.00  88.47      A    C
ATOM   895  CE1 TYR A 236      42.578  40.476   3.074  1.00  89.70      A    C
ATOM   896  CD2 TYR A 236      44.736  39.035   4.098  1.00  86.66      A    C
ATOM   897  CE2 TYR A 236      43.420  38.570   4.290  1.00  88.13      A    C
ATOM   898  CZ  TYR A 236      42.352  39.296   3.774  1.00  89.77      A    C
ATOM   899  OH  TYR A 236      41.062  38.843   3.946  1.00  88.66      A    O
```

Figure 40

```
ATOM    900  C    TYR A 236      47.859  42.757   2.630  1.00  70.33      A    C
ATOM    901  O    TYR A 236      47.774  43.870   3.121  1.00  71.27      A    O
ATOM    902  N    ILE A 237      49.016  42.203   2.315  1.00  67.78      A    N
ATOM    903  CA   ILE A 237      50.263  42.878   2.618  1.00  64.43      A    C
ATOM    904  CB   ILE A 237      51.456  42.082   2.120  1.00  62.05      A    C
ATOM    905  CG2  ILE A 237      52.707  42.907   2.261  1.00  63.48      A    C
ATOM    906  CG1  ILE A 237      51.593  40.799   2.927  1.00  57.60      A    C
ATOM    907  CD1  ILE A 237      51.858  41.042   4.405  1.00  52.01      A    C
ATOM    908  C    ILE A 237      50.336  44.260   2.017  1.00  63.37      A    C
ATOM    909  O    ILE A 237      50.860  45.183   2.634  1.00  57.56      A    O
ATOM    910  N    THR A 238      49.824  44.404   0.802  1.00  65.31      A    N
ATOM    911  CA   THR A 238      49.865  45.706   0.163  1.00  68.82      A    C
ATOM    912  CB   THR A 238      49.598  45.645  -1.386  1.00  71.04      A    C
ATOM    913  OG1  THR A 238      48.794  46.768  -1.786  1.00  73.52      A    O
ATOM    914  CG2  THR A 238      48.945  44.348  -1.787  1.00  70.75      A    C
ATOM    915  C    THR A 238      48.876  46.638   0.827  1.00  69.62      A    C
ATOM    916  O    THR A 238      49.217  47.774   1.145  1.00  70.51      A    O
ATOM    917  N    GLU A 239      47.658  46.169   1.051  1.00  68.63      A    N
ATOM    918  CA   GLU A 239      46.683  47.016   1.702  1.00  69.12      A    C
ATOM    919  CB   GLU A 239      45.440  46.208   2.069  1.00  71.32      A    C
ATOM    920  CG   GLU A 239      44.651  45.685   0.873  1.00  80.08      A    C
ATOM    921  CD   GLU A 239      43.338  44.991   1.263  1.00  82.50      A    C
ATOM    922  OE1  GLU A 239      42.603  44.552   0.355  1.00  83.13      A    O
ATOM    923  OE2  GLU A 239      43.040  44.881   2.473  1.00  84.93      A    O
ATOM    924  C    GLU A 239      47.328  47.561   2.975  1.00  69.14      A    C
ATOM    925  O    GLU A 239      47.325  48.772   3.238  1.00  69.47      A    O
ATOM    926  N    LEU A 240      47.910  46.643   3.743  1.00  67.54      A    N
ATOM    927  CA   LEU A 240      48.553  46.948   5.019  1.00  61.62      A    C
ATOM    928  CB   LEU A 240      49.116  45.657   5.607  1.00  60.79      A    C
ATOM    929  CG   LEU A 240      49.114  45.487   7.123  1.00  59.67      A    C
ATOM    930  CD1  LEU A 240      47.817  45.963   7.731  1.00  64.22      A    C
ATOM    931  CD2  LEU A 240      49.331  44.027   7.431  1.00  65.44      A    C
ATOM    932  C    LEU A 240      49.650  47.978   4.861  1.00  58.31      A    C
ATOM    933  O    LEU A 240      49.671  49.007   5.529  1.00  55.60      A    O
ATOM    934  N    ALA A 241      50.567  47.687   3.963  1.00  55.82      A    N
ATOM    935  CA   ALA A 241      51.657  48.587   3.711  1.00  54.67      A    C
ATOM    936  CB   ALA A 241      52.378  48.142   2.456  1.00  56.06      A    C
ATOM    937  C    ALA A 241      51.166  50.036   3.572  1.00  55.10      A    C
ATOM    938  O    ALA A 241      51.668  50.928   4.241  1.00  52.52      A    O
ATOM    939  N    ASN A 242      50.177  50.269   2.716  1.00  55.96      A    N
ATOM    940  CA   ASN A 242      49.675  51.622   2.495  1.00  52.11      A    C
ATOM    941  CB   ASN A 242      48.605  51.638   1.427  1.00  56.23      A    C
ATOM    942  CG   ASN A 242      49.133  51.182   0.097  1.00  63.76      A    C
ATOM    943  OD1  ASN A 242      48.426  51.192  -0.895  1.00  69.76      A    O
ATOM    944  ND2  ASN A 242      50.388  50.768   0.070  1.00  69.13      A    N
ATOM    945  C    ASN A 242      49.116  52.180   3.739  1.00  46.29      A    C
ATOM    946  O    ASN A 242      49.445  53.283   4.131  1.00  39.64      A    O
ATOM    947  N    ALA A 243      48.242  51.411   4.354  1.00  47.62      A    N
ATOM    948  CA   ALA A 243      47.659  51.852   5.590  1.00  57.54      A    C
ATOM    949  CB   ALA A 243      46.981  50.707   6.296  1.00  59.78      A    C
ATOM    950  C    ALA A 243      48.849  52.311   6.383  1.00  63.58      A    C
ATOM    951  O    ALA A 243      48.797  53.310   7.082  1.00  63.45      A    O
ATOM    952  N    LEU A 244      49.942  51.578   6.247  1.00  72.95      A    N
ATOM    953  CA   LEU A 244      51.151  51.920   6.972  1.00  78.61      A    C
ATOM    954  CB   LEU A 244      52.116  50.737   6.938  1.00  80.04      A    C
ATOM    955  CG   LEU A 244      52.220  49.827   8.173  1.00  82.33      A    C
ATOM    956  CD1  LEU A 244      51.096  50.068   9.190  1.00  83.92      A    C
ATOM    957  CD2  LEU A 244      52.219  48.389   7.681  1.00  84.36      A    C
ATOM    958  C    LEU A 244      51.800  53.173   6.396  1.00  81.09      A    C
ATOM    959  O    LEU A 244      52.269  54.041   7.141  1.00  80.56      A    O
ATOM    960  N    SER A 245      51.807  53.271   5.069  1.00  84.23      A    N
```

Figure 4P

| ATOM | 961 | CA | SER A 245 | 52.400 | 54.422 | 4.397 | 1.00 | 88.57 | A | C |
|---|---|---|---|---|---|---|---|---|---|---|
| ATOM | 962 | CB | SER A 245 | 52.261 | 54.314 | 2.892 | 1.00 | 90.30 | A | C |
| ATOM | 963 | OG | SER A 245 | 52.546 | 55.581 | 2.301 | 1.00 | 92.04 | A | O |
| ATOM | 964 | C | SER A 245 | 51.760 | 55.725 | 4.808 | 1.00 | 90.49 | A | C |
| ATOM | 965 | O | SER A 245 | 52.446 | 56.692 | 5.112 | 1.00 | 91.94 | A | O |
| ATOM | 966 | N | TYR A 246 | 50.438 | 55.759 | 4.751 | 1.00 | 91.95 | A | N |
| ATOM | 967 | CA | TYR A 246 | 49.691 | 56.933 | 5.153 | 1.00 | 92.95 | A | C |
| ATOM | 968 | CB | TYR A 246 | 48.204 | 56.651 | 4.938 | 1.00 | 92.76 | A | C |
| ATOM | 969 | CG | TYR A 246 | 47.252 | 57.519 | 5.722 | 1.00 | 94.43 | A | C |
| ATOM | 970 | CD1 | TYR A 246 | 46.672 | 58.642 | 5.149 | 1.00 | 94.86 | A | C |
| ATOM | 971 | CE1 | TYR A 246 | 45.803 | 59.459 | 5.892 | 1.00 | 96.16 | A | C |
| ATOM | 972 | CD2 | TYR A 246 | 46.942 | 57.222 | 7.055 | 1.00 | 95.64 | A | C |
| ATOM | 973 | CE2 | TYR A 246 | 46.079 | 58.028 | 7.807 | 1.00 | 95.23 | A | C |
| ATOM | 974 | CZ | TYR A 246 | 45.515 | 59.147 | 7.227 | 1.00 | 95.36 | A | C |
| ATOM | 975 | OH | TYR A 246 | 44.708 | 59.960 | 8.005 | 1.00 | 93.14 | A | O |
| ATOM | 976 | C | TYR A 246 | 50.011 | 57.204 | 6.641 | 1.00 | 94.96 | A | C |
| ATOM | 977 | O | TYR A 246 | 49.968 | 58.346 | 7.090 | 1.00 | 95.18 | A | O |
| ATOM | 978 | N | CYS A 247 | 50.357 | 56.151 | 7.386 | 1.00 | 96.00 | A | N |
| ATOM | 979 | CA | CYS A 247 | 50.689 | 56.256 | 8.810 | 1.00 | 97.84 | A | C |
| ATOM | 980 | CB | CYS A 247 | 50.789 | 54.879 | 9.444 | 1.00 | 98.48 | A | C |
| ATOM | 981 | SG | CYS A 247 | 49.268 | 54.278 | 10.131 | 1.00 | 105.20 | A | S |
| ATOM | 982 | C | CYS A 247 | 51.999 | 56.941 | 9.057 | 1.00 | 99.79 | A | C |
| ATOM | 983 | O | CYS A 247 | 52.127 | 57.817 | 9.898 | 1.00 | 100.00 | A | O |
| ATOM | 984 | N | HIS A 248 | 52.999 | 56.492 | 8.333 | 1.00 | 103.34 | A | N |
| ATOM | 985 | CA | HIS A 248 | 54.319 | 57.052 | 8.479 | 1.00 | 106.72 | A | C |
| ATOM | 986 | CB | HIS A 248 | 55.290 | 56.277 | 7.581 | 1.00 | 113.25 | A | C |
| ATOM | 987 | CG | HIS A 248 | 55.765 | 54.976 | 8.173 | 1.00 | 117.98 | A | C |
| ATOM | 988 | CD2 | HIS A 248 | 56.968 | 54.349 | 8.100 | 1.00 | 118.99 | A | C |
| ATOM | 989 | ND1 | HIS A 248 | 54.962 | 54.174 | 8.960 | 1.00 | 119.15 | A | N |
| ATOM | 990 | CE1 | HIS A 248 | 55.650 | 53.113 | 9.349 | 1.00 | 120.21 | A | C |
| ATOM | 991 | NE2 | HIS A 248 | 56.870 | 53.196 | 8.841 | 1.00 | 120.93 | A | N |
| ATOM | 992 | C | HIS A 248 | 54.318 | 58.529 | 8.133 | 1.00 | 105.90 | A | C |
| ATOM | 993 | O | HIS A 248 | 54.797 | 59.358 | 8.893 | 1.00 | 104.00 | A | O |
| ATOM | 994 | N | SER A 249 | 53.766 | 58.850 | 6.977 | 1.00 | 108.07 | A | N |
| ATOM | 995 | CA | SER A 249 | 53.702 | 60.231 | 6.523 | 1.00 | 112.32 | A | C |
| ATOM | 996 | CB | SER A 249 | 52.757 | 60.352 | 5.314 | 1.00 | 113.30 | A | C |
| ATOM | 997 | OG | SER A 249 | 51.419 | 59.958 | 5.623 | 1.00 | 113.57 | A | O |
| ATOM | 998 | C | SER A 249 | 53.211 | 61.156 | 7.624 | 1.00 | 114.04 | A | C |
| ATOM | 999 | O | SER A 249 | 53.878 | 62.117 | 8.020 | 1.00 | 115.06 | A | O |
| ATOM | 1000 | N | LYS A 250 | 52.022 | 60.855 | 8.111 | 1.00 | 115.15 | A | N |
| ATOM | 1001 | CA | LYS A 250 | 51.409 | 61.654 | 9.140 | 1.00 | 117.05 | A | C |
| ATOM | 1002 | CB | LYS A 250 | 49.933 | 61.252 | 9.211 | 1.00 | 121.24 | A | C |
| ATOM | 1003 | CG | LYS A 250 | 49.225 | 61.429 | 10.525 | 1.00 | 129.31 | A | C |
| ATOM | 1004 | CD | LYS A 250 | 49.381 | 60.188 | 11.423 | 1.00 | 136.73 | A | C |
| ATOM | 1005 | CE | LYS A 250 | 49.805 | 58.902 | 10.661 | 1.00 | 140.50 | A | C |
| ATOM | 1006 | NZ | LYS A 250 | 49.033 | 58.595 | 9.407 | 1.00 | 139.90 | A | N |
| ATOM | 1007 | C | LYS A 250 | 52.183 | 61.445 | 10.435 | 1.00 | 116.65 | A | C |
| ATOM | 1008 | O | LYS A 250 | 51.791 | 61.908 | 11.505 | 1.00 | 115.99 | A | O |
| ATOM | 1009 | N | ARG A 251 | 53.315 | 60.763 | 10.305 | 1.00 | 116.10 | A | N |
| ATOM | 1010 | CA | ARG A 251 | 54.200 | 60.486 | 11.425 | 1.00 | 116.43 | A | C |
| ATOM | 1011 | CB | ARG A 251 | 54.944 | 61.767 | 11.842 | 1.00 | 119.51 | A | C |
| ATOM | 1012 | CG | ARG A 251 | 56.140 | 62.111 | 10.934 | 1.00 | 122.96 | A | C |
| ATOM | 1013 | CD | ARG A 251 | 56.974 | 63.251 | 11.513 | 1.00 | 127.32 | A | C |
| ATOM | 1014 | NE | ARG A 251 | 58.205 | 63.495 | 10.756 | 1.00 | 129.97 | A | N |
| ATOM | 1015 | CZ | ARG A 251 | 59.050 | 64.499 | 11.001 | 1.00 | 131.96 | A | C |
| ATOM | 1016 | NH1 | ARG A 251 | 58.803 | 65.368 | 11.985 | 1.00 | 132.26 | A | N |
| ATOM | 1017 | NH2 | ARG A 251 | 60.153 | 64.632 | 10.268 | 1.00 | 132.44 | A | N |
| ATOM | 1018 | C | ARG A 251 | 53.554 | 59.826 | 12.642 | 1.00 | 114.26 | A | C |
| ATOM | 1019 | O | ARG A 251 | 53.264 | 60.466 | 13.653 | 1.00 | 113.40 | A | O |
| ATOM | 1020 | N | VAL A 252 | 53.344 | 58.526 | 12.523 | 1.00 | 112.60 | A | N |
| ATOM | 1021 | CA | VAL A 252 | 52.773 | 57.729 | 13.585 | 1.00 | 113.78 | A | C |

Figure 4Q

```
ATOM   1022  CB   VAL A 252      51.263  57.696  13.534  1.00  111.99      A    C
ATOM   1023  CG1  VAL A 252      50.753  56.444  14.230  1.00  110.43      A    C
ATOM   1024  CG2  VAL A 252      50.720  58.920  14.217  1.00  112.20      A    C
ATOM   1025  C    VAL A 252      53.265  56.345  13.329  1.00  116.92      A    C
ATOM   1026  O    VAL A 252      53.151  55.851  12.213  1.00  118.09      A    O
ATOM   1027  N    ILE A 253      53.815  55.717  14.359  1.00  121.61      A    N
ATOM   1028  CA   ILE A 253      54.336  54.362  14.214  1.00  126.11      A    C
ATOM   1029  CB   ILE A 253      55.862  54.289  14.618  1.00  127.90      A    C
ATOM   1030  CG2  ILE A 253      56.359  52.838  14.574  1.00  126.98      A    C
ATOM   1031  CG1  ILE A 253      56.723  55.139  13.657  1.00  129.64      A    C
ATOM   1032  CD1  ILE A 253      56.494  56.666  13.735  1.00  131.81      A    C
ATOM   1033  C    ILE A 253      53.508  53.379  15.054  1.00  127.68      A    C
ATOM   1034  O    ILE A 253      53.477  53.466  16.295  1.00  128.33      A    O
ATOM   1035  N    HIS A 254      52.833  52.458  14.355  1.00  128.83      A    N
ATOM   1036  CA   HIS A 254      51.982  51.430  14.978  1.00  128.27      A    C
ATOM   1037  CB   HIS A 254      50.877  50.966  13.996  1.00  127.67      A    C
ATOM   1038  CG   HIS A 254      49.529  51.552  14.280  1.00  127.76      A    C
ATOM   1039  CD2  HIS A 254      48.637  52.174  13.471  1.00  129.26      A    C
ATOM   1040  ND1  HIS A 254      48.962  51.539  15.537  1.00  128.83      A    N
ATOM   1041  CE1  HIS A 254      47.780  52.132  15.492  1.00  129.37      A    C
ATOM   1042  NE2  HIS A 254      47.558  52.526  14.250  1.00  129.06      A    N
ATOM   1043  C    HIS A 254      52.724  50.183  15.507  1.00  127.13      A    C
ATOM   1044  O    HIS A 254      53.510  50.262  16.473  1.00  127.02      A    O
ATOM   1045  N    ARG A 255      52.449  49.051  14.846  1.00  124.83      A    N
ATOM   1046  CA   ARG A 255      52.974  47.720  15.170  1.00  121.48      A    C
ATOM   1047  CB   ARG A 255      54.218  47.791  16.071  1.00  120.05      A    C
ATOM   1054  C    ARG A 255      51.827  46.988  15.894  1.00  119.17      A    C
ATOM   1055  O    ARG A 255      50.662  47.445  15.869  1.00  117.57      A    O
ATOM   1056  N    ASP A 256      52.154  45.869  16.541  1.00  116.17      A    N
ATOM   1057  CA   ASP A 256      51.148  45.065  17.232  1.00  113.90      A    C
ATOM   1058  CB   ASP A 256      50.402  45.916  18.274  1.00  111.74      A    C
ATOM   1062  C    ASP A 256      50.161  44.522  16.177  1.00  111.95      A    C
ATOM   1063  O    ASP A 256      49.281  43.708  16.490  1.00  114.67      A    O
ATOM   1064  N    ILE A 257      50.337  44.968  14.930  1.00  106.47      A    N
ATOM   1065  CA   ILE A 257      49.489  44.586  13.807  1.00  101.04      A    C
ATOM   1066  CB   ILE A 257      49.819  45.450  12.584  1.00  100.47      A    C
ATOM   1067  CG2  ILE A 257      49.460  46.887  12.875  1.00  103.75      A    C
ATOM   1068  CG1  ILE A 257      51.314  45.372  12.270  1.00  100.84      A    C
ATOM   1069  CD1  ILE A 257      51.615  44.782  10.921  1.00  100.91      A    C
ATOM   1070  C    ILE A 257      49.575  43.115  13.420  1.00   97.73      A    C
ATOM   1071  O    ILE A 257      50.102  42.761  12.369  1.00   99.79      A    O
ATOM   1072  N    LYS A 258      49.038  42.259  14.274  1.00   92.64      A    N
ATOM   1073  CA   LYS A 258      49.045  40.843  14.016  1.00   86.17      A    C
ATOM   1074  CB   LYS A 258      49.656  40.128  15.203  1.00   87.21      A    C
ATOM   1075  CG   LYS A 258      49.328  40.792  16.519  1.00   87.58      A    C
ATOM   1076  CD   LYS A 258      50.166  40.214  17.624  1.00   91.32      A    C
ATOM   1077  CE   LYS A 258      49.847  40.857  18.946  1.00   93.01      A    C
ATOM   1078  NZ   LYS A 258      50.707  40.246  19.994  1.00   99.26      A    N
ATOM   1079  C    LYS A 258      47.617  40.416  13.784  1.00   83.42      A    C
ATOM   1080  O    LYS A 258      46.683  41.187  14.001  1.00   79.92      A    O
ATOM   1081  N    PRO A 259      47.424  39.175  13.344  1.00   82.25      A    N
ATOM   1082  CD   PRO A 259      48.419  38.093  13.295  1.00   78.57      A    C
ATOM   1083  CA   PRO A 259      46.082  38.658  13.077  1.00   83.46      A    C
ATOM   1084  CB   PRO A 259      46.286  37.150  13.166  1.00   81.70      A    C
ATOM   1085  CG   PRO A 259      47.655  36.988  12.625  1.00   79.81      A    C
ATOM   1086  C    PRO A 259      44.996  39.170  14.034  1.00   84.33      A    C
ATOM   1087  O    PRO A 259      43.942  39.639  13.624  1.00   81.49      A    O
ATOM   1088  N    GLU A 260      45.283  39.083  15.318  1.00   87.71      A    N
ATOM   1089  CA   GLU A 260      44.367  39.486  16.371  1.00   89.95      A    C
ATOM   1090  CB   GLU A 260      45.042  39.290  17.736  1.00   94.80      A    C
ATOM   1091  CG   GLU A 260      45.668  37.899  17.956  1.00  102.92      A    C
```

Figure 4R

```
ATOM   1092  CD  GLU A 260      46.877  37.579  17.035  1.00 108.44      A    C
ATOM   1093  OE1 GLU A 260      47.399  36.444  17.128  1.00 111.46      A    O
ATOM   1094  OE2 GLU A 260      47.318  38.435  16.222  1.00 110.35      A    O
ATOM   1095  C   GLU A 260      43.913  40.925  16.240  1.00  87.92      A    C
ATOM   1096  O   GLU A 260      42.758  41.244  16.513  1.00  87.60      A    O
ATOM   1097  N   ASN A 261      44.821  41.792  15.819  1.00  86.43      A    N
ATOM   1098  CA  ASN A 261      44.487  43.197  15.707  1.00  88.09      A    C
ATOM   1099  CB  ASN A 261      45.578  44.056  16.344  1.00  88.60      A    C
ATOM   1100  CG  ASN A 261      45.857  43.665  17.777  1.00  88.74      A    C
ATOM   1101  OD1 ASN A 261      44.938  43.403  18.545  1.00  85.96      A    O
ATOM   1102  ND2 ASN A 261      47.130  43.627  18.147  1.00  89.76      A    N
ATOM   1103  C   ASN A 261      44.222  43.680  14.297  1.00  88.99      A    C
ATOM   1104  O   ASN A 261      44.409  44.861  13.992  1.00  88.63      A    O
ATOM   1105  N   LEU A 262      43.787  42.776  13.431  1.00  88.70      A    N
ATOM   1106  CA  LEU A 262      43.456  43.155  12.057  1.00  87.76      A    C
ATOM   1107  CB  LEU A 262      44.495  42.561  11.101  1.00  80.83      A    C
ATOM   1108  CG  LEU A 262      45.934  42.996  11.384  1.00  71.05      A    C
ATOM   1109  CD1 LEU A 262      46.878  42.303  10.437  1.00  63.69      A    C
ATOM   1110  CD2 LEU A 262      46.040  44.499  11.242  1.00  63.59      A    C
ATOM   1111  C   LEU A 262      42.024  42.658  11.738  1.00  89.15      A    C
ATOM   1112  O   LEU A 262      41.703  41.492  11.978  1.00  93.37      A    O
ATOM   1113  N   LEU A 263      41.160  43.534  11.224  1.00  86.92      A    N
ATOM   1114  CA  LEU A 263      39.785  43.140  10.930  1.00  84.68      A    C
ATOM   1115  CB  LEU A 263      38.837  44.041  11.704  1.00  84.62      A    C
ATOM   1116  CG  LEU A 263      38.970  43.946  13.221  1.00  81.46      A    C
ATOM   1117  CD1 LEU A 263      38.111  45.008  13.883  1.00  81.72      A    C
ATOM   1118  CD2 LEU A 263      38.546  42.563  13.666  1.00  83.91      A    C
ATOM   1119  C   LEU A 263      39.420  43.139   9.443  1.00  85.16      A    C
ATOM   1120  O   LEU A 263      40.139  43.711   8.627  1.00  85.56      A    O
ATOM   1121  N   LEU A 264      38.298  42.502   9.101  1.00  84.94      A    N
ATOM   1122  CA  LEU A 264      37.868  42.397   7.714  1.00  85.38      A    C
ATOM   1123  CB  LEU A 264      37.654  40.925   7.363  1.00  91.08      A    C
ATOM   1124  CG  LEU A 264      38.914  40.049   7.504  1.00  96.47      A    C
ATOM   1125  CD1 LEU A 264      38.580  38.566   7.331  1.00  98.05      A    C
ATOM   1126  CD2 LEU A 264      39.964  40.491   6.471  1.00  99.24      A    C
ATOM   1127  C   LEU A 264      36.617  43.182   7.401  1.00  83.76      A    C
ATOM   1128  O   LEU A 264      35.687  43.205   8.193  1.00  85.03      A    O
ATOM   1129  N   GLY A 265      36.605  43.812   6.231  1.00  82.44      A    N
ATOM   1130  CA  GLY A 265      35.459  44.599   5.807  1.00  85.90      A    C
ATOM   1131  C   GLY A 265      34.570  43.892   4.792  1.00  88.44      A    C
ATOM   1132  O   GLY A 265      34.836  42.751   4.428  1.00  88.85      A    O
ATOM   1133  N   SER A 266      33.522  44.581   4.330  1.00  91.40      A    N
ATOM   1134  CA  SER A 266      32.545  44.042   3.364  1.00  92.48      A    C
ATOM   1135  CB  SER A 266      31.747  45.201   2.707  1.00  91.85      A    C
ATOM   1136  OG  SER A 266      30.959  45.972   3.620  1.00  88.12      A    O
ATOM   1137  C   SER A 266      33.147  43.162   2.254  1.00  93.41      A    C
ATOM   1138  O   SER A 266      32.752  42.003   2.039  1.00  91.15      A    O
ATOM   1139  N   ALA A 267      34.106  43.732   1.546  1.00  95.25      A    N
ATOM   1140  CA  ALA A 267      34.750  43.037   0.451  1.00 100.59      A    C
ATOM   1141  CB  ALA A 267      35.233  44.058  -0.534  1.00 103.37      A    C
ATOM   1142  C   ALA A 267      35.911  42.116   0.861  1.00 103.14      A    C
ATOM   1143  O   ALA A 267      36.648  41.600   0.010  1.00 104.32      A    O
ATOM   1144  N   GLY A 268      36.076  41.896   2.159  1.00 103.71      A    N
ATOM   1145  CA  GLY A 268      37.171  41.052   2.601  1.00 102.54      A    C
ATOM   1146  C   GLY A 268      38.414  41.907   2.596  1.00 102.47      A    C
ATOM   1147  O   GLY A 268      39.526  41.424   2.355  1.00 103.00      A    O
ATOM   1148  N   GLU A 269      38.187  43.197   2.851  1.00 101.81      A    N
ATOM   1149  CA  GLU A 269      39.224  44.223   2.906  1.00 101.15      A    C
ATOM   1150  CB  GLU A 269      38.619  45.598   2.574  1.00 105.01      A    C
ATOM   1151  CG  GLU A 269      37.079  45.634   2.406  1.00 107.45      A    C
ATOM   1152  CD  GLU A 269      36.438  46.972   2.837  1.00 109.25      A    C
```

Figure 4S

```
ATOM   1153  OE1 GLU A 269      36.854  48.061   2.367  1.00 110.56     A    O
ATOM   1154  OE2 GLU A 269      35.497  46.932   3.658  1.00 110.09     A    O
ATOM   1155  C   GLU A 269      39.829  44.264   4.311  1.00  98.60     A    C
ATOM   1156  O   GLU A 269      39.190  43.825   5.271  1.00 100.18     A    O
ATOM   1157  N   LEU A 270      41.039  44.819   4.428  1.00  94.11     A    N
ATOM   1158  CA  LEU A 270      41.753  44.911   5.713  1.00  89.94     A    C
ATOM   1159  CB  LEU A 270      43.243  44.711   5.469  1.00  95.33     A    C
ATOM   1160  CG  LEU A 270      44.037  44.185   6.661  1.00 100.63     A    C
ATOM   1161  CD1 LEU A 270      43.391  42.895   7.183  1.00 104.12     A    C
ATOM   1162  CD2 LEU A 270      45.477  43.915   6.224  1.00  99.41     A    C
ATOM   1163  C   LEU A 270      41.548  46.205   6.519  1.08  84.15     A    C
ATOM   1164  O   LEU A 270      41.466  47.291   5.961  1.00  84.52     A    O
ATOM   1165  N   LYS A 271      41.482  46.082   7.838  1.00  77.12     A    N
ATOM   1166  CA  LYS A 271      41.271  47.236   8.685  1.00  73.34     A    C
ATOM   1167  CB  LYS A 271      39.816  47.318   9.131  1.00  73.45     A    C
ATOM   1168  CG  LYS A 271      38.787  47.325   8.025  1.00  75.19     A    C
ATOM   1169  CD  LYS A 271      38.711  48.665   7.362  1.00  74.17     A    C
ATOM   1170  CE  LYS A 271      37.499  48.722   6.473  1.00  76.05     A    C
ATOM   1171  NZ  LYS A 271      37.387  50.052   5.834  1.00  82.53     A    N
ATOM   1172  C   LYS A 271      42.122  47.079   9.908  1.00  73.07     A    C
ATOM   1173  O   LYS A 271      41.920  46.167  10.683  1.00  72.96     A    O
ATOM   1174  N   ILE A 272      43.104  47.945  10.137  1.00  75.11     A    N
ATOM   1175  CA  ILE A 272      43.903  47.784  11.360  1.00  76.99     A    C
ATOM   1176  CB  ILE A 272      45.307  48.400  11.233  1.00  75.36     A    C
ATOM   1177  CG2 ILE A 272      45.867  48.116   9.857  1.00  74.11     A    C
ATOM   1178  CG1 ILE A 272      45.257  49.910  11.512  1.00  74.33     A    C
ATOM   1179  CD1 ILE A 272      45.249  50.317  13.026  1.00  78.74     A    C
ATOM   1180  C   ILE A 272      43.193  48.435  12.553  1.00  81.17     A    C
ATOM   1181  O   ILE A 272      42.602  49.512  12.431  1.00  82.69     A    O
ATOM   1182  N   ALA A 273      43.253  47.787  13.709  1.00  85.70     A    N
ATOM   1183  CA  ALA A 273      42.604  48.317  14.902  1.00  90.36     A    C
ATOM   1184  CB  ALA A 273      41.333  47.527  15.184  1.00  90.04     A    C
ATOM   1185  C   ALA A 273      43.536  48.255  16.114  1.00  93.56     A    C
ATOM   1186  O   ALA A 273      43.527  47.269  16.855  1.00  94.38     A    O
ATOM   1187  N   ASP A 274      44.334  49.303  16.323  1.00  95.36     A    N
ATOM   1188  CA  ASP A 274      45.257  49.316  17.453  1.00  94.75     A    C
ATOM   1189  CB  ASP A 274      46.638  49.750  17.024  1.00  94.28     A    C
ATOM   1190  CG  ASP A 274      47.281  48.762  16.091  1.00  96.71     A    C
ATOM   1191  OD1 ASP A 274      48.441  48.991  15.678  1.00  96.24     A    O
ATOM   1192  OD2 ASP A 274      46.620  47.749  15.767  1.00  97.76     A    O
ATOM   1193  C   ASP A 274      44.817  50.211  18.561  1.00  94.31     A    C
ATOM   1194  O   ASP A 274      44.949  51.434  18.460  1.00  93.97     A    O
ATOM   1195  N   PHE A 275      44.295  49.574  19.617  1.00  80.18     A    N
ATOM   1196  CA  PHE A 275      43.788  50.239  20.853  1.00  80.18     A    C
ATOM   1197  CB  PHE A 275      42.245  50.439  20.775  1.00  80.18     A    C
ATOM   1198  CG  PHE A 275      41.758  50.973  19.439  1.00  80.18     A    C
ATOM   1199  CD1 PHE A 275      41.601  50.110  18.338  1.00  80.18     A    C
ATOM   1200  CD2 PHE A 275      41.522  52.349  19.260  1.00  80.18     A    C
ATOM   1201  CE1 PHE A 275      41.216  50.607  17.072  1.00  80.18     A    C
ATOM   1202  CE2 PHE A 275      41.135  52.862  17.996  1.00  80.18     A    C
ATOM   1203  CZ  PHE A 275      40.987  51.982  16.899  1.08  80.18     A    C
ATOM   1204  C   PHE A 275      44.145  49.478  22.193  1.00  80.19     A    C
ATOM   1205  O   PHE A 275      45.065  48.626  22.227  1.00  80.17     A    O
ATOM   1206  N   GLY A 276      43.430  49.795  23.284  1.00  80.17     A    N
ATOM   1207  CA  GLY A 276      43.683  49.135  24.567  1.00  80.19     A    C
ATOM   1208  C   GLY A 276      43.212  47.678  24.638  1.00  80.18     A    C
ATOM   1209  O   GLY A 276      44.043  46.763  24.805  1.00  80.18     A    O
ATOM   1210  N   TRP A 277      41.885  47.482  24.546  1.00  80.18     A    N
ATOM   1211  CA  TRP A 277      41.212  46.160  24.552  1.00  80.19     A    C
ATOM   1212  CB  TRP A 277      41.903  45.220  23.566  1.00  80.19     A    C
ATOM   1213  CG  TRP A 277      41.011  44.873  22.467  1.00  80.19     A    C
```

Figure 4T

```
ATOM   1214  CD2 TRP A 277      41.129  45.318  21.106  1.00  80.18      A    C
ATOM   1215  CE2 TRP A 277      39.970  44.862  20.417  1.00  80.18      A    C
ATOM   1216  CE3 TRP A 277      42.101  46.069  20.396  1.00  80.18      A    C
ATOM   1217  CD1 TRP A 277      39.830  44.178  22.554  1.00  80.18      A    C
ATOM   1218  NE1 TRP A 277      39.197  44.174  21.327  1.00  80.18      A    N
ATOM   1219  CZ2 TRP A 277      39.753  45.134  19.034  1.00  80.18      A    C
ATOM   1220  CZ3 TRP A 277      41.887  46.345  19.018  1.00  80.18      A    C
ATOM   1221  CH2 TRP A 277      40.721  45.875  18.358  1.00  80.19      A    C
ATOM   1222  C   TRP A 277      40.945  45.341  25.834  1.00  80.19      A    C
ATOM   1223  O   TRP A 277      40.039  45.667  26.622  1.00  80.18      A    O
ATOM   1224  N   SER A 278      41.702  44.234  25.970  1.00  80.18      A    N
ATOM   1225  CA  SER A 278      41.623  43.278  27.102  1.00  80.19      A    C
ATOM   1226  CB  SER A 278      40.443  42.280  26.891  1.00  80.19      A    C
ATOM   1227  OG  SER A 278      40.430  41.668  25.587  1.00  80.18      A    O
ATOM   1228  C   SER A 278      42.939  42.492  27.344  1.00  80.18      A    C
ATOM   1229  O   SER A 278      43.921  42.601  26.591  1.00  80.19      A    O
ATOM   1230  N   LEU A 289      51.160  29.641  23.909  1.00  91.98      A    N
ATOM   1231  CA  LEU A 289      51.175  30.617  22.828  1.00  95.69      A    C
ATOM   1232  CB  LEU A 289      49.776  31.212  22.620  1.00  93.34      A    C
ATOM   1236  C   LEU A 289      52.161  31.735  23.145  1.00  98.98      A    C
ATOM   1237  O   LEU A 289      51.884  32.604  23.988  1.00  97.51      A    O
ATOM   1238  N   CYS A 290      53.316  31.702  22.473  1.00 103.16      A    N
ATOM   1239  CA  CYS A 290      54.365  32.716  22.655  1.00 104.77      A    C
ATOM   1240  CB  CYS A 290      55.750  32.135  22.327  1.00 103.06      A    C
ATOM   1242  C   CYS A 290      54.063  33.893  21.730  1.00 106.10      A    C
ATOM   1243  O   CYS A 290      54.973  34.581  21.251  1.00 106.69      A    O
ATOM   1244  N   GLY A 291      52.767  34.101  21.488  1.00 106.60      A    N
ATOM   1245  CA  GLY A 291      52.301  35.178  20.630  1.00 103.83      A    C
ATOM   1246  C   GLY A 291      52.674  36.555  21.142  1.00 101.87      A    C
ATOM   1247  O   GLY A 291      52.645  37.535  20.388  1.00  99.74      A    O
ATOM   1248  N   THR A 292      53.017  36.621  22.429  1.00 100.88      A    N
ATOM   1249  CA  THR A 292      53.433  37.866  23.070  1.00  98.35      A    C
ATOM   1250  CB  THR A 292      53.746  37.608  24.584  1.00  98.64      A    C
ATOM   1251  OG1 THR A 292      52.681  36.840  25.163  1.00  95.90      A    O
ATOM   1252  CG2 THR A 292      53.872  38.919  25.354  1.00  97.26      A    C
ATOM   1253  C   THR A 292      54.682  38.418  22.325  1.00  95.62      A    C
ATOM   1254  O   THR A 292      54.658  39.529  21.776  1.00  93.74      A    O
ATOM   1255  N   LEU A 293      55.757  37.633  22.293  1.00  90.33      A    N
ATOM   1256  CA  LEU A 293      56.976  38.032  21.606  1.00  84.73      A    C
ATOM   1257  CB  LEU A 293      58.146  37.209  22.112  1.00  83.59      A    C
ATOM   1258  CG  LEU A 293      58.623  37.507  23.519  1.00  85.32      A    C
ATOM   1259  CD1 LEU A 293      59.534  36.398  24.008  1.00  87.94      A    C
ATOM   1260  CD2 LEU A 293      59.345  38.832  23.510  1.00  83.42      A    C
ATOM   1261  C   LEU A 293      56.838  37.804  20.108  1.00  81.88      A    C
ATOM   1262  O   LEU A 293      57.289  38.604  19.299  1.00  81.32      A    O
ATOM   1263  N   ASP A 294      56.207  36.696  19.757  1.00  79.52      A    N
ATOM   1264  CA  ASP A 294      56.027  36.309  18.381  1.00  77.99      A    C
ATOM   1265  CB  ASP A 294      54.721  35.570  18.228  1.00  79.09      A    C
ATOM   1266  CG  ASP A 294      54.879  34.096  18.487  1.00  80.00      A    C
ATOM   1267  OD1 ASP A 294      53.849  33.393  18.606  1.00  82.79      A    O
ATOM   1268  OD2 ASP A 294      56.045  33.645  18.562  1.00  75.58      A    O
ATOM   1269  C   ASP A 294      56.107  37.384  17.353  1.00  77.27      A    C
ATOM   1270  O   ASP A 294      56.602  37.135  16.261  1.00  77.40      A    O
ATOM   1271  N   TYR A 295      55.644  38.578  17.683  1.00  76.56      A    N
ATOM   1272  CA  TYR A 295      55.688  39.637  16.701  1.00  80.01      A    C
ATOM   1273  CB  TYR A 295      54.291  40.207  16.540  1.00  84.15      A    C
ATOM   1274  CG  TYR A 295      53.456  39.290  15.692  1.00  89.76      A    C
ATOM   1275  CD1 TYR A 295      53.024  38.061  16.190  1.00  89.96      A    C
ATOM   1276  CE1 TYR A 295      52.383  37.145  15.365  1.00  92.84      A    C
ATOM   1277  CD2 TYR A 295      53.213  39.587  14.341  1.00  92.30      A    C
ATOM   1278  CE2 TYR A 295      52.575  38.679  13.510  1.00  93.08      A    C
```

Figure 4U

```
ATOM   1279  CZ   TYR A 295      52.169  37.460  14.031  1.00  94.56      A    C
ATOM   1280  OH   TYR A 295      51.583  36.539  13.210  1.00  98.62      A    O
ATOM   1281  C    TYR A 295      56.699  40.753  16.875  1.00  80.02      A    C
ATOM   1282  O    TYR A 295      57.086  41.417  15.911  1.00  78.60      A    O
ATOM   1283  N    LEU A 296      57.145  40.945  18.102  1.00  82.28      A    N
ATOM   1284  CA   LEU A 296      58.099  41.995  18.404  1.00  81.54      A    C
ATOM   1285  CB   LEU A 296      58.348  42.001  19.917  1.00  83.52      A    C
ATOM   1286  CG   LEU A 296      57.067  41.911  20.773  1.00  84.63      A    C
ATOM   1287  CD1  LEU A 296      57.382  41.633  22.243  1.00  84.58      A    C
ATOM   1288  CD2  LEU A 296      56.294  43.202  20.634  1.00  86.07      A    C
ATOM   1289  C    LEU A 296      59.418  41.840  17.631  1.00  81.11      A    C
ATOM   1290  O    LEU A 296      59.843  40.727  17.312  1.00  79.86      A    O
ATOM   1291  N    PRO A 297      60.058  42.970  17.289  1.00  80.13      A    N
ATOM   1292  CD   PRO A 297      59.451  44.308  17.260  1.00  80.77      A    C
ATOM   1293  CA   PRO A 297      61.324  42.995  16.563  1.00  76.50      A    C
ATOM   1294  CB   PRO A 297      61.190  44.234  15.710  1.00  75.65      A    C
ATOM   1295  CG   PRO A 297      60.564  45.155  16.661  1.00  79.46      A    C
ATOM   1296  C    PRO A 297      62.498  43.099  17.545  1.00  74.40      A    C
ATOM   1297  O    PRO A 297      62.374  43.668  18.641  1.00  69.70      A    O
ATOM   1298  N    PRO A 298      63.659  42.554  17.150  1.00  72.29      A    N
ATOM   1299  CD   PRO A 298      63.953  41.933  15.841  1.00  70.95      A    C
ATOM   1300  CA   PRO A 298      64.854  42.573  17.982  1.00  68.01      A    C
ATOM   1301  CB   PRO A 298      65.953  42.233  16.989  1.00  70.34      A    C
ATOM   1302  CG   PRO A 298      65.268  41.228  16.095  1.00  69.45      A    C
ATOM   1303  C    PRO A 298      65.066  43.895  18.678  1.00  64.87      A    C
ATOM   1304  O    PRO A 298      65.144  43.965  19.889  1.00  61.59      A    O
ATOM   1305  N    GLU A 299      65.138  44.957  17.912  1.00  64.86      A    N
ATOM   1306  CA   GLU A 299      65.355  46.241  18.516  1.00  68.46      A    C
ATOM   1307  CB   GLU A 299      65.241  47.334  17.455  1.00  73.05      A    C
ATOM   1308  CG   GLU A 299      63.995  47.281  16.542  1.00  80.25      A    C
ATOM   1309  CD   GLU A 299      64.227  46.502  15.242  1.00  82.05      A    C
ATOM   1310  OE1  GLU A 299      63.593  46.813  14.204  1.00  80.07      A    O
ATOM   1311  OE2  GLU A 299      65.047  45.566  15.259  1.00  86.62      A    O
ATOM   1312  C    GLU A 299      64.449  46.557  19.707  1.00  69.06      A    C
ATOM   1313  O    GLU A 299      64.823  47.348  20.568  1.00  67.71      A    O
ATOM   1314  N    MET A 300      63.268  45.953  19.787  1.00  72.06      A    N
ATOM   1315  CA   MET A 300      62.408  46.269  20.924  1.00  76.56      A    C
ATOM   1316  CB   MET A 300      60.933  46.348  20.502  1.00  83.02      A    C
ATOM   1317  CG   MET A 300      60.053  47.203  21.469  1.00  93.18      A    C
ATOM   1318  SD   MET A 300      58.715  46.384  22.483  1.00 103.55      A    S
ATOM   1319  CE   MET A 300      59.475  46.110  24.098  1.00  99.95      A    C
ATOM   1320  C    MET A 300      62.559  45.284  22.080  1.00  74.61      A    C
ATOM   1321  O    MET A 300      62.724  45.682  23.236  1.00  73.66      A    O
ATOM   1322  N    ILE A 301      62.497  44.000  21.777  1.00  72.18      A    N
ATOM   1323  CA   ILE A 301      62.631  43.009  22.824  1.00  72.56      A    C
ATOM   1324  CB   ILE A 301      62.549  41.624  22.237  1.00  71.85      A    C
ATOM   1325  CG2  ILE A 301      61.387  41.565  21.291  1.00  73.11      A    C
ATOM   1326  CG1  ILE A 301      63.821  41.318  21.449  1.00  73.91      A    C
ATOM   1327  CD1  ILE A 301      63.873  39.922  20.845  1.00  71.55      A    C
ATOM   1328  C    ILE A 301      63.967  43.171  23.540  1.00  74.53      A    C
ATOM   1329  O    ILE A 301      64.081  42.851  24.720  1.00  73.44      A    O
ATOM   1330  N    GLU A 302      64.969  43.658  22.803  1.00  79.91      A    N
ATOM   1331  CA   GLU A 302      66.324  43.892  23.325  1.00  86.02      A    C
ATOM   1332  CB   GLU A 302      67.370  43.936  22.186  1.00  85.05      A    C
ATOM   1333  CG   GLU A 302      67.502  42.655  21.334  1.00  88.94      A    C
ATOM   1334  CD   GLU A 302      68.565  42.751  20.214  1.00  87.29      A    C
ATOM   1335  OE1  GLU A 302      68.589  43.779  19.496  1.00  84.07      A    O
ATOM   1336  OE2  GLU A 302      69.363  41.791  20.042  1.00  88.65      A    O
ATOM   1337  C    GLU A 302      66.351  45.233  24.074  1.00  91.02      A    C
ATOM   1338  O    GLU A 302      67.412  45.692  24.530  1.00  90.32      A    O
ATOM   1339  N    GLY A 303      65.175  45.857  24.178  1.00  95.75      A    N
```

Figure 4V

```
ATOM   1340  CA   GLY A 303      65.041  47.124  24.873  1.00   97.96      A    C
ATOM   1341  C    GLY A 303      65.794  48.256  24.223  1.00  101.02      A    C
ATOM   1342  O    GLY A 303      65.876  49.340  24.762  1.00   99.37      A    O
ATOM   1343  N    ARG A 304      66.350  48.015  23.052  1.00  105.96      A    N
ATOM   1344  CA   ARG A 304      67.096  49.054  22.371  1.00  112.23      A    C
ATOM   1345  CB   ARG A 304      67.909  48.438  21.226  1.00  114.86      A    C
ATOM   1346  CG   ARG A 304      68.981  47.440  21.707  1.00  120.66      A    C
ATOM   1347  CD   ARG A 304      69.629  46.633  20.555  1.00  125.80      A    C
ATOM   1348  NE   ARG A 304      70.172  47.477  19.490  1.00  131.93      A    N
ATOM   1349  CZ   ARG A 304      71.023  48.482  19.693  1.00  137.20      A    C
ATOM   1350  NH1  ARG A 304      71.437  48.774  20.932  1.00  140.05      A    N
ATOM   1351  NH2  ARG A 304      71.451  49.209  18.660  1.00  139.00      A    N
ATOM   1352  C    ARG A 304      66.141  50.115  21.849  1.00  115.07      A    C
ATOM   1353  O    ARG A 304      64.948  50.100  22.166  1.00  113.97      A    O
ATOM   1354  N    MET A 305      66.683  51.033  21.053  1.00  120.70      A    N
ATOM   1355  CA   MET A 305      65.915  52.128  20.454  1.00  126.96      A    C
ATOM   1356  CB   MET A 305      66.803  53.360  20.165  1.00  133.41      A    C
ATOM   1357  CG   MET A 305      67.985  53.615  21.131  1.00  140.92      A    C
ATOM   1358  SD   MET A 305      69.402  52.352  21.129  1.00  150.00      A    S
ATOM   1359  CE   MET A 305      69.892  52.292  19.331  1.00  150.00      A    C
ATOM   1360  C    MET A 305      65.298  51.670  19.129  1.00  127.16      A    C
ATOM   1361  O    MET A 305      66.004  51.253  18.196  1.00  128.67      A    O
ATOM   1362  N    HIS A 306      63.980  51.770  19.047  1.00  127.09      A    N
ATOM   1363  CA   HIS A 306      63.252  51.379  17.851  1.00  126.89      A    C
ATOM   1364  CB   HIS A 306      62.156  50.365  18.262  1.00  133.59      A    C
ATOM   1365  CG   HIS A 306      61.138  50.914  19.233  1.00  140.10      A    C
ATOM   1366  CD2  HIS A 306      59.800  51.113  19.102  1.00  142.87      A    C
ATOM   1367  ND1  HIS A 306      61.466  51.373  20.496  1.00  141.79      A    N
ATOM   1368  CE1  HIS A 306      60.378  51.833  21.095  1.00  142.27      A    C
ATOM   1369  NE2  HIS A 306      59.353  51.687  20.271  1.00  143.92      A    N
ATOM   1370  C    HIS A 306      62.637  52.664  17.243  1.00  123.55      A    C
ATOM   1371  O    HIS A 306      62.684  53.731  17.877  1.00  124.15      A    O
ATOM   1372  N    ASP A 307      62.106  52.575  16.018  1.00  116.91      A    N
ATOM   1373  CA   ASP A 307      61.419  53.699  15.379  1.00  107.68      A    C
ATOM   1374  CB   ASP A 307      62.165  55.023  15.598  1.00  108.47      A    C
ATOM   1375  CG   ASP A 307      61.353  56.029  16.464  1.00  111.28      A    C
ATOM   1376  OD1  ASP A 307      61.072  55.750  17.657  1.00  110.33      A    O
ATOM   1377  OD2  ASP A 307      60.985  57.110  15.949  1.00  111.11      A    O
ATOM   1378  C    ASP A 307      61.162  53.492  13.907  1.00  101.08      A    C
ATOM   1379  O    ASP A 307      62.101  53.352  13.127  1.00  101.13      A    O
ATOM   1380  N    GLU A 308      59.875  53.443  13.553  1.00   94.88      A    N
ATOM   1381  CA   GLU A 308      59.417  53.286  12.169  1.00   90.59      A    C
ATOM   1382  CB   GLU A 308      59.888  54.510  11.380  1.00   91.73      A    C
ATOM   1383  CG   GLU A 308      60.630  54.228  10.101  1.00   96.57      A    C
ATOM   1384  CD   GLU A 308      61.568  55.368   9.716  1.00   98.44      A    C
ATOM   1385  OE1  GLU A 308      62.544  55.636  10.454  1.00   95.55      A    O
ATOM   1386  OE2  GLU A 308      61.330  56.003   8.670  1.00  103.60      A    O
ATOM   1387  C    GLU A 308      59.789  51.975  11.439  1.00   85.52      A    C
ATOM   1388  O    GLU A 308      58.916  51.245  10.957  1.00   84.71      A    O
ATOM   1389  N    LYS A 309      61.081  51.682  11.358  1.00   79.53      A    N
ATOM   1390  CA   LYS A 309      61.539  50.487  10.694  1.00   71.62      A    C
ATOM   1391  CB   LYS A 309      63.025  50.303  10.977  1.00   71.18      A    C
ATOM   1396  C    LYS A 309      60.746  49.278  11.174  1.00   67.62      A    C
ATOM   1397  O    LYS A 309      60.363  48.420  10.395  1.00   67.83      A    O
ATOM   1398  N    VAL A 310      60.478  49.230  12.463  1.00   62.80      A    N
ATOM   1399  CA   VAL A 310      59.753  48.119  13.052  1.00   62.03      A    C
ATOM   1400  CB   VAL A 310      59.240  48.508  14.407  1.00   59.23      A    C
ATOM   1401  CG1  VAL A 310      60.398  48.910  15.291  1.00   61.76      A    C
ATOM   1402  CG2  VAL A 310      58.262  49.647  14.265  1.00   57.08      A    C
ATOM   1403  C    VAL A 310      58.576  47.570  12.267  1.00   62.27      A    C
ATOM   1404  O    VAL A 310      58.380  46.356  12.176  1.00   62.69      A    O
```

Figure 4W

```
ATOM   1405  N    ASP A 311      57.783  48.460  11.701  1.00  62.41      A    N
ATOM   1406  CA   ASP A 311      56.614  48.026  10.970  1.00  66.15      A    C
ATOM   1407  CB   ASP A 311      55.834  49.231  10.495  1.00  70.56      A    C
ATOM   1408  CG   ASP A 311      55.203  49.974  11.642  1.00  78.33      A    C
ATOM   1409  OD1  ASP A 311      54.604  49.295  12.515  1.00  81.15      A    O
ATOM   1410  OD2  ASP A 311      55.302  51.220  11.674  1.00  81.93      A    O
ATOM   1411  C    ASP A 311      56.909  47.111   9.819  1.00  65.13      A    C
ATOM   1412  O    ASP A 311      56.112  46.239   9.491  1.00  65.71      A    O
ATOM   1413  N    LEU A 312      58.061  47.302   9.203  1.00  67.42      A    N
ATOM   1414  CA   LEU A 312      58.446  46.462   8.081  1.00  70.14      A    C
ATOM   1415  CB   LEU A 312      59.689  47.050   7.398  1.00  71.43      A    C
ATOM   1416  CG   LEU A 312      59.587  48.404   6.654  1.00  70.53      A    C
ATOM   1417  CD1  LEU A 312      58.737  48.278   5.389  1.00  69.99      A    C
ATOM   1418  CD2  LEU A 312      59.011  49.466   7.578  1.00  70.24      A    C
ATOM   1419  C    LEU A 312      58.711  45.039   8.586  1.00  69.19      A    C
ATOM   1420  O    LEU A 312      58.462  44.047   7.890  1.00  68.91      A    O
ATOM   1421  N    TRP A 313      59.198  44.957   9.820  1.00  65.94      A    N
ATOM   1422  CA   TRP A 313      59.497  43.685  10.454  1.00  63.75      A    C
ATOM   1423  CB   TRP A 313      60.282  43.905  11.736  1.00  69.81      A    C
ATOM   1424  CG   TRP A 313      60.358  42.697  12.588  1.00  71.86      A    C
ATOM   1425  CD2  TRP A 313      61.434  41.767  12.636  1.00  70.53      A    C
ATOM   1426  CE2  TRP A 313      61.069  40.751  13.548  1.00  70.88      A    C
ATOM   1427  CE3  TRP A 313      62.677  41.691  11.996  1.00  68.84      A    C
ATOM   1428  CD1  TRP A 313      59.404  42.229  13.448  1.00  72.58      A    C
ATOM   1429  NE1  TRP A 313      59.824  41.057  14.032  1.00  71.89      A    N
ATOM   1430  CZ2  TRP A 313      61.902  39.673  13.832  1.00  68.34      A    C
ATOM   1431  CZ3  TRP A 313      63.503  40.623  12.280  1.00  67.31      A    C
ATOM   1432  CH2  TRP A 313      63.113  39.626  13.189  1.00  68.13      A    C
ATOM   1433  C    TRP A 313      58.205  43.016  10.787  1.00  60.84      A    C
ATOM   1434  O    TRP A 313      57.972  41.872  10.429  1.00  59.96      A    O
ATOM   1435  N    SER A 314      57.373  43.733  11.514  1.00  59.53      A    N
ATOM   1436  CA   SER A 314      56.092  43.191  11.862  1.00  63.39      A    C
ATOM   1437  CB   SER A 314      55.218  44.268  12.490  1.00  63.41      A    C
ATOM   1439  C    SER A 314      55.497  42.743  10.539  1.00  66.14      A    C
ATOM   1440  O    SER A 314      54.939  41.656  10.435  1.00  69.63      A    O
ATOM   1441  N    LEU A 315      55.646  43.580   9.518  1.00  66.11      A    N
ATOM   1442  CA   LEU A 315      55.111  43.276   8.194  1.00  66.22      A    C
ATOM   1443  CB   LEU A 315      55.370  44.438   7.238  1.00  68.82      A    C
ATOM   1444  CG   LEU A 315      54.716  44.329   5.860  1.00  73.34      A    C
ATOM   1445  CD1  LEU A 315      53.206  44.295   6.005  1.00  74.73      A    C
ATOM   1446  CD2  LEU A 315      55.127  45.506   5.003  1.00  75.61      A    C
ATOM   1447  C    LEU A 315      55.743  42.009   7.652  1.00  63.01      A    C
ATOM   1448  O    LEU A 315      55.144  41.274   6.869  1.00  61.40      A    O
ATOM   1449  N    GLY A 316      56.969  41.759   8.076  1.00  62.54      A    N
ATOM   1450  CA   GLY A 316      57.637  40.556   7.638  1.00  63.17      A    C
ATOM   1451  C    GLY A 316      56.933  39.346   8.226  1.00  62.44      A    C
ATOM   1452  O    GLY A 316      56.319  38.553   7.509  1.00  66.48      A    O
ATOM   1453  N    VAL A 317      57.005  39.205   9.543  1.00  58.54      A    N
ATOM   1454  CA   VAL A 317      56.375  38.082  10.210  1.00  57.24      A    C
ATOM   1455  CB   VAL A 317      56.160  38.386  11.688  1.00  57.91      A    C
ATOM   1456  CG1  VAL A 317      55.630  37.149  12.385  1.00  63.70      A    C
ATOM   1457  CG2  VAL A 317      57.455  38.879  12.316  1.00  54.44      A    C
ATOM   1458  C    VAL A 317      55.022  37.771   9.588  1.00  58.00      A    C
ATOM   1459  O    VAL A 317      54.786  36.681   9.072  1.00  61.25      A    O
ATOM   1460  N    LEU A 318      54.142  38.758   9.636  1.00  55.23      A    N
ATOM   1461  CA   LEU A 318      52.798  38.642   9.115  1.00  54.58      A    C
ATOM   1462  CB   LEU A 318      52.217  40.033   8.973  1.00  60.38      A    C
ATOM   1463  CG   LEU A 318      50.715  40.158   9.174  1.00  72.66      A    C
ATOM   1464  CD1  LEU A 318      50.247  39.363  10.408  1.00  74.60      A    C
ATOM   1465  CD2  LEU A 318      50.392  41.635   9.331  1.00  72.45      A    C
ATOM   1466  C    LEU A 318      52.752  37.931   7.786  1.00  51.19      A    C
```

Figure 4X

| ATOM | 1467 | O | LEU | A | 318 | 52.196 | 36.851 | 7.648 | 1.00 | 52.65 | A | O |
|---|---|---|---|---|---|---|---|---|---|---|---|---|
| ATOM | 1468 | N | CYS | A | 319 | 53.343 | 38.551 | 6.792 | 1.00 | 47.74 | A | N |
| ATOM | 1469 | CA | CYS | A | 319 | 53.348 | 37.948 | 5.496 | 1.00 | 48.42 | A | C |
| ATOM | 1470 | CB | CYS | A | 319 | 54.330 | 38.660 | 4.602 | 1.00 | 51.03 | A | C |
| ATOM | 1471 | SG | CYS | A | 319 | 54.602 | 37.776 | 3.086 | 1.00 | 61.23 | A | S |
| ATOM | 1472 | C | CYS | A | 319 | 53.744 | 36.502 | 5.615 | 1.00 | 47.44 | A | C |
| ATOM | 1473 | O | CYS | A | 319 | 53.332 | 35.670 | 4.832 | 1.00 | 45.04 | A | O |
| ATOM | 1474 | N | TYR | A | 320 | 54.554 | 36.202 | 6.605 | 1.00 | 50.53 | A | N |
| ATOM | 1475 | CA | TYR | A | 320 | 54.982 | 34.846 | 6.780 | 1.00 | 57.47 | A | C |
| ATOM | 1476 | CB | TYR | A | 320 | 56.153 | 34.787 | 7.717 | 1.00 | 59.47 | A | C |
| ATOM | 1477 | CG | TYR | A | 320 | 56.644 | 33.393 | 7.958 | 1.00 | 64.22 | A | C |
| ATOM | 1478 | CD1 | TYR | A | 320 | 57.706 | 32.886 | 7.233 | 1.00 | 65.78 | A | C |
| ATOM | 1479 | CE1 | TYR | A | 320 | 58.219 | 31.618 | 7.478 | 1.00 | 66.03 | A | C |
| ATOM | 1480 | CD2 | TYR | A | 320 | 56.081 | 32.590 | 8.941 | 1.00 | 67.36 | A | C |
| ATOM | 1481 | CE2 | TYR | A | 320 | 56.583 | 31.311 | 9.195 | 1.00 | 69.47 | A | C |
| ATOM | 1482 | CZ | TYR | A | 320 | 57.665 | 30.834 | 8.456 | 1.00 | 67.05 | A | C |
| ATOM | 1483 | OH | TYR | A | 320 | 58.235 | 29.600 | 8.717 | 1.00 | 66.22 | A | O |
| ATOM | 1484 | C | TYR | A | 320 | 53.879 | 33.997 | 7.355 | 1.00 | 62.98 | A | C |
| ATOM | 1485 | O | TYR | A | 320 | 53.491 | 33.012 | 6.756 | 1.00 | 66.11 | A | O |
| ATOM | 1486 | N | GLU | A | 321 | 53.381 | 34.360 | 8.532 | 1.00 | 65.81 | A | N |
| ATOM | 1487 | CA | GLU | A | 321 | 52.330 | 33.567 | 9.161 | 1.00 | 67.09 | A | C |
| ATOM | 1488 | CB | GLU | A | 321 | 51.771 | 34.252 | 10.419 | 1.00 | 70.57 | A | C |
| ATOM | 1489 | CG | GLU | A | 321 | 51.379 | 33.237 | 11.505 | 1.00 | 79.40 | A | C |
| ATOM | 1490 | CD | GLU | A | 321 | 50.308 | 33.690 | 12.504 | 1.00 | 82.26 | A | C |
| ATOM | 1491 | OE1 | GLU | A | 321 | 50.437 | 34.761 | 13.122 | 1.00 | 79.01 | A | O |
| ATOM | 1492 | OE2 | GLU | A | 321 | 49.312 | 32.941 | 12.694 | 1.00 | 84.31 | A | O |
| ATOM | 1493 | C | GLU | A | 321 | 51.214 | 33.380 | 8.156 | 1.00 | 66.48 | A | C |
| ATOM | 1494 | O | GLU | A | 321 | 50.558 | 32.345 | 8.108 | 1.00 | 63.93 | A | O |
| ATOM | 1495 | N | PHE | A | 322 | 51.002 | 34.393 | 7.341 | 1.00 | 65.78 | A | N |
| ATOM | 1496 | CA | PHE | A | 322 | 49.966 | 34.297 | 6.352 | 1.00 | 67.34 | A | C |
| ATOM | 1497 | CB | PHE | A | 322 | 49.973 | 35.541 | 5.479 | 1.00 | 66.67 | A | C |
| ATOM | 1498 | CG | PHE | A | 322 | 49.413 | 36.743 | 6.155 | 1.00 | 67.10 | A | C |
| ATOM | 1499 | CD1 | PHE | A | 322 | 48.448 | 36.606 | 7.145 | 1.00 | 70.05 | A | C |
| ATOM | 1500 | CD2 | PHE | A | 322 | 49.786 | 38.012 | 5.756 | 1.00 | 64.93 | A | C |
| ATOM | 1501 | CE1 | PHE | A | 322 | 47.859 | 37.714 | 7.721 | 1.00 | 71.21 | A | C |
| ATOM | 1502 | CE2 | PHE | A | 322 | 49.204 | 39.123 | 6.322 | 1.00 | 62.96 | A | C |
| ATOM | 1503 | CZ | PHE | A | 322 | 48.236 | 38.974 | 7.307 | 1.00 | 68.48 | A | C |
| ATOM | 1504 | C | PHE | A | 322 | 50.158 | 33.069 | 5.488 | 1.00 | 68.77 | A | C |
| ATOM | 1505 | O | PHE | A | 322 | 49.311 | 32.173 | 5.453 | 1.00 | 69.04 | A | O |
| ATOM | 1506 | N | LEU | A | 323 | 51.292 | 33.037 | 4.803 | 1.00 | 69.52 | A | N |
| ATOM | 1507 | CA | LEU | A | 323 | 51.625 | 31.954 | 3.893 | 1.00 | 69.64 | A | C |
| ATOM | 1508 | CB | LEU | A | 323 | 52.809 | 32.372 | 3.038 | 1.00 | 64.99 | A | C |
| ATOM | 1509 | CG | LEU | A | 323 | 52.582 | 33.609 | 2.179 | 1.00 | 60.38 | A | C |
| ATOM | 1510 | CD1 | LEU | A | 323 | 53.902 | 34.106 | 1.625 | 1.00 | 56.40 | A | C |
| ATOM | 1511 | CD2 | LEU | A | 323 | 51.629 | 33.248 | 1.068 | 1.00 | 60.63 | A | C |
| ATOM | 1512 | C | LEU | A | 323 | 51.929 | 30.610 | 4.533 | 1.00 | 70.69 | A | C |
| ATOM | 1513 | O | LEU | A | 323 | 51.982 | 29.604 | 3.835 | 1.00 | 74.73 | A | O |
| ATOM | 1514 | N | VAL | A | 324 | 52.120 | 30.582 | 5.848 | 1.00 | 70.16 | A | N |
| ATOM | 1515 | CA | VAL | A | 324 | 52.444 | 29.328 | 6.517 | 1.00 | 67.98 | A | C |
| ATOM | 1516 | CB | VAL | A | 324 | 53.796 | 29.435 | 7.238 | 1.00 | 63.48 | A | C |
| ATOM | 1517 | CG1 | VAL | A | 324 | 54.169 | 28.095 | 7.803 | 1.00 | 61.67 | A | C |
| ATOM | 1518 | CG2 | VAL | A | 324 | 54.862 | 29.906 | 6.284 | 1.00 | 54.87 | A | C |
| ATOM | 1519 | C | VAL | A | 324 | 51.401 | 28.783 | 7.505 | 1.00 | 70.07 | A | C |
| ATOM | 1520 | O | VAL | A | 324 | 51.130 | 27.584 | 7.517 | 1.00 | 72.92 | A | O |
| ATOM | 1521 | N | GLY | A | 325 | 50.822 | 29.639 | 8.338 | 1.00 | 69.11 | A | N |
| ATOM | 1522 | CA | GLY | A | 325 | 49.830 | 29.145 | 9.278 | 1.00 | 68.96 | A | C |
| ATOM | 1523 | C | GLY | A | 325 | 50.276 | 29.368 | 10.698 | 1.00 | 67.27 | A | C |
| ATOM | 1524 | O | GLY | A | 325 | 49.560 | 29.073 | 11.659 | 1.00 | 65.21 | A | O |
| ATOM | 1525 | N | LYS | A | 326 | 51.483 | 29.896 | 10.812 | 1.00 | 67.06 | A | N |
| ATOM | 1526 | CA | LYS | A | 326 | 52.052 | 30.193 | 12.097 | 1.00 | 67.54 | A | C |
| ATOM | 1527 | CB | LYS | A | 326 | 52.558 | 28.929 | 12.765 | 1.00 | 75.55 | A | C |

Figure 4Y

```
ATOM 1528  CG   LYS A 326    53.570  28.159  11.959  1.00   83.17  A  C
ATOM 1529  CD   LYS A 326    54.111  26.997  12.784  1.00   91.62  A  C
ATOM 1530  CE   LYS A 326    54.986  26.073  11.956  1.00   98.25  A  C
ATOM 1531  NZ   LYS A 326    54.178  25.426  10.888  1.00  106.04  A  N
ATOM 1532  C    LYS A 326    53.181  31.160  11.912  1.00   62.90  A  C
ATOM 1533  O    LYS A 326    53.756  31.266  10.847  1.00   57.40  A  O
ATOM 1534  N    PRO A 327    53.487  31.915  12.953  1.00   64.20  A  N
ATOM 1535  CD   PRO A 327    52.984  31.846  14.329  1.00   65.35  A  C
ATOM 1536  CA   PRO A 327    54.569  32.874  12.843  1.00   66.03  A  C
ATOM 1537  CB   PRO A 327    54.569  33.552  14.199  1.00   67.53  A  C
ATOM 1538  CG   PRO A 327    54.118  32.454  15.096  1.00   68.78  A  C
ATOM 1539  C    PRO A 327    55.834  32.118  12.575  1.00   65.27  A  C
ATOM 1540  O    PRO A 327    55.881  30.892  12.695  1.00   61.89  A  O
ATOM 1541  N    PRO A 328    56.878  32.846  12.200  1.00   66.25  A  N
ATOM 1542  CD   PRO A 328    56.768  34.246  11.772  1.00   62.51  A  C
ATOM 1543  CA   PRO A 328    58.198  32.321  11.883  1.00   71.53  A  C
ATOM 1544  CB   PRO A 328    58.740  33.371  10.943  1.00   68.37  A  C
ATOM 1545  CG   PRO A 328    58.187  34.600  11.512  1.00   65.64  A  C
ATOM 1546  C    PRO A 328    59.107  32.092  13.070  1.00   75.99  A  C
ATOM 1547  O    PRO A 328    60.180  31.497  12.952  1.00   76.72  A  O
ATOM 1548  N    PHE A 329    58.688  32.550  14.230  1.00   80.01  A  N
ATOM 1549  CA   PHE A 329    59.542  32.361  15.379  1.00   86.19  A  C
ATOM 1550  CB   PHE A 329    60.072  33.722  15.805  1.00   87.46  A  C
ATOM 1551  CG   PHE A 329    60.808  34.461  14.695  1.00   87.41  A  C
ATOM 1552  CD1  PHE A 329    61.971  33.933  14.132  1.00   86.40  A  C
ATOM 1553  CD2  PHE A 329    60.343  35.692  14.224  1.00   87.36  A  C
ATOM 1554  CE1  PHE A 329    62.656  34.623  13.124  1.00   83.92  A  C
ATOM 1555  CE2  PHE A 329    61.027  36.379  13.217  1.00   84.25  A  C
ATOM 1556  CZ   PHE A 329    62.181  35.842  12.672  1.00   81.51  A  C
ATOM 1557  C    PHE A 329    58.819  31.635  16.507  1.00   90.30  A  C
ATOM 1558  O    PHE A 329    59.247  31.631  17.660  1.00   93.36  A  O
ATOM 1559  N    GLU A 330    57.715  31.000  16.138  1.00   91.24  A  N
ATOM 1560  CA   GLU A 330    56.906  30.229  17.060  1.00   89.33  A  C
ATOM 1561  CB   GLU A 330    55.685  29.687  16.329  1.00   85.78  A  C
ATOM 1562  CG   GLU A 330    54.864  28.712  17.121  1.00   82.49  A  C
ATOM 1563  CD   GLU A 330    53.638  28.289  16.361  1.00   80.36  A  C
ATOM 1564  OE1  GLU A 330    52.826  29.170  16.019  1.00   80.43  A  O
ATOM 1565  OE2  GLU A 330    53.487  27.082  16.099  1.00   77.20  A  O
ATOM 1566  C    GLU A 330    57.718  29.075  17.621  1.00   91.13  A  C
ATOM 1567  O    GLU A 330    58.377  28.329  16.887  1.00   89.13  A  O
ATOM 1568  N    ALA A 331    57.667  28.939  18.936  1.00   94.97  A  N
ATOM 1569  CA   ALA A 331    58.388  27.875  19.602  1.00   99.70  A  C
ATOM 1570  CB   ALA A 331    59.885  28.106  19.479  1.00   98.91  A  C
ATOM 1571  C    ALA A 331    57.992  27.735  21.070  1.00  102.25  A  C
ATOM 1572  O    ALA A 331    57.314  28.595  21.644  1.00  101.05  A  O
ATOM 1573  N    ASN A 332    58.425  26.621  21.652  1.00  106.38  A  N
ATOM 1574  CA   ASN A 332    58.176  26.265  23.049  1.00  108.08  A  C
ATOM 1575  CB   ASN A 332    58.666  24.826  23.278  1.00  109.70  A  C
ATOM 1576  CG   ASN A 332    60.021  24.557  22.595  1.00  111.15  A  C
ATOM 1577  OD1  ASN A 332    60.107  24.457  21.358  1.00  108.81  A  O
ATOM 1578  ND2  ASN A 332    61.085  24.466  23.399  1.00  112.08  A  N
ATOM 1579  C    ASN A 332    58.894  27.227  24.013  1.00  108.12  A  C
ATOM 1580  O    ASN A 332    60.134  27.250  24.087  1.00  109.65  A  O
ATOM 1581  N    THR A 333    58.107  28.019  24.739  1.00  106.99  A  N
ATOM 1582  CA   THR A 333    58.610  28.989  25.725  1.00  104.58  A  C
ATOM 1583  CB   THR A 333    59.710  28.363  26.662  1.00  103.30  A  C
ATOM 1584  OG1  THR A 333    59.598  28.974  27.956  1.00  101.27  A  O
ATOM 1585  CG2  THR A 333    61.149  28.570  26.100  1.00   95.97  A  C
ATOM 1586  C    THR A 333    59.134  30.309  25.157  1.00  102.26  A  C
ATOM 1587  O    THR A 333    59.538  30.388  24.004  1.00  101.90  A  O
ATOM 1588  N    TYR A 334    59.099  31.344  25.990  1.00   99.25  A  N
```

Figure 4Z

| ATOM | 1589 | CA | TYR | A | 334 | 59.567 | 32.673 | 25.628 | 1.00 | 95.68 | A | C |
|---|---|---|---|---|---|---|---|---|---|---|---|---|
| ATOM | 1590 | CB | TYR | A | 334 | 59.289 | 33.615 | 26.776 | 1.00 | 96.99 | A | C |
| ATOM | 1591 | CG | TYR | A | 334 | 57.857 | 34.008 | 26.906 | 1.00 | 100.15 | A | C |
| ATOM | 1592 | CD1 | TYR | A | 334 | 57.195 | 34.615 | 25.846 | 1.00 | 103.75 | A | C |
| ATOM | 1593 | CE1 | TYR | A | 334 | 55.898 | 35.125 | 25.988 | 1.00 | 109.32 | A | C |
| ATOM | 1594 | CD2 | TYR | A | 334 | 57.193 | 33.894 | 28.121 | 1.00 | 103.89 | A | C |
| ATOM | 1595 | CE2 | TYR | A | 334 | 55.890 | 34.400 | 28.283 | 1.00 | 109.09 | A | C |
| ATOM | 1596 | CZ | TYR | A | 334 | 55.249 | 35.020 | 27.208 | 1.00 | 111.05 | A | C |
| ATOM | 1597 | OH | TYR | A | 334 | 53.979 | 35.558 | 27.341 | 1.00 | 113.89 | A | O |
| ATOM | 1598 | C | TYR | A | 334 | 61.054 | 32.749 | 25.295 | 1.00 | 94.32 | A | C |
| ATOM | 1599 | O | TYR | A | 334 | 61.440 | 33.426 | 24.359 | 1.00 | 92.37 | A | O |
| ATOM | 1600 | N | GLN | A | 335 | 61.878 | 32.075 | 26.092 | 1.00 | 95.70 | A | N |
| ATOM | 1601 | CA | GLN | A | 335 | 63.331 | 32.040 | 25.922 | 1.00 | 96.60 | A | C |
| ATOM | 1602 | CB | GLN | A | 335 | 63.927 | 31.002 | 26.863 | 1.00 | 98.70 | A | C |
| ATOM | 1603 | CG | GLN | A | 335 | 63.684 | 31.357 | 28.324 | 1.00 | 104.56 | A | C |
| ATOM | 1604 | CD | GLN | A | 335 | 62.197 | 31.547 | 28.662 | 1.00 | 108.41 | A | C |
| ATOM | 1605 | OE1 | GLN | A | 335 | 61.823 | 32.386 | 29.498 | 1.00 | 109.98 | A | O |
| ATOM | 1606 | NE2 | GLN | A | 335 | 61.346 | 30.754 | 28.020 | 1.00 | 112.33 | A | N |
| ATOM | 1607 | C | GLN | A | 335 | 63.686 | 31.722 | 24.485 | 1.00 | 97.70 | A | C |
| ATOM | 1608 | O | GLN | A | 335 | 64.270 | 32.558 | 23.793 | 1.00 | 97.45 | A | O |
| ATOM | 1609 | N | GLU | A | 336 | 63.362 | 30.510 | 24.034 | 1.00 | 99.72 | A | N |
| ATOM | 1610 | CA | GLU | A | 336 | 63.596 | 30.163 | 22.638 | 1.00 | 100.18 | A | C |
| ATOM | 1611 | CB | GLU | A | 336 | 63.107 | 28.741 | 22.362 | 1.00 | 105.13 | A | C |
| ATOM | 1612 | CG | GLU | A | 336 | 63.904 | 27.628 | 23.054 | 1.00 | 110.81 | A | C |
| ATOM | 1613 | CD | GLU | A | 336 | 65.030 | 27.045 | 22.175 | 1.00 | 114.62 | A | C |
| ATOM | 1614 | OE1 | GLU | A | 336 | 65.814 | 26.217 | 22.687 | 1.00 | 116.38 | A | O |
| ATOM | 1615 | OE2 | GLU | A | 336 | 65.141 | 27.392 | 20.974 | 1.00 | 115.00 | A | O |
| ATOM | 1616 | C | GLU | A | 336 | 62.682 | 31.197 | 21.971 | 1.00 | 98.85 | A | C |
| ATOM | 1617 | O | GLU | A | 336 | 61.865 | 31.809 | 22.658 | 1.00 | 102.56 | A | O |
| ATOM | 1618 | N | THR | A | 337 | 62.789 | 31.398 | 20.666 | 1.00 | 94.24 | A | N |
| ATOM | 1619 | CA | THR | A | 337 | 61.968 | 32.403 | 19.975 | 1.00 | 92.56 | A | C |
| ATOM | 1620 | CB | THR | A | 337 | 60.548 | 32.602 | 20.591 | 1.00 | 94.81 | A | C |
| ATOM | 1621 | OG1 | THR | A | 337 | 59.780 | 31.397 | 20.462 | 1.00 | 100.57 | A | O |
| ATOM | 1622 | CG2 | THR | A | 337 | 59.814 | 33.729 | 19.875 | 1.00 | 96.19 | A | C |
| ATOM | 1623 | C | THR | A | 337 | 62.743 | 33.691 | 20.132 | 1.00 | 88.02 | A | C |
| ATOM | 1624 | O | THR | A | 337 | 63.220 | 34.255 | 19.158 | 1.00 | 85.69 | A | O |
| ATOM | 1625 | N | TYR | A | 338 | 62.869 | 34.166 | 21.363 | 1.00 | 85.47 | A | N |
| ATOM | 1626 | CA | TYR | A | 338 | 63.652 | 35.362 | 21.580 | 1.00 | 81.53 | A | C |
| ATOM | 1627 | CB | TYR | A | 338 | 63.960 | 35.548 | 23.062 | 1.00 | 85.45 | A | C |
| ATOM | 1628 | CG | TYR | A | 338 | 64.939 | 36.661 | 23.307 | 1.00 | 92.06 | A | C |
| ATOM | 1629 | CD1 | TYR | A | 338 | 64.500 | 37.963 | 23.545 | 1.00 | 97.39 | A | C |
| ATOM | 1630 | CE1 | TYR | A | 338 | 65.404 | 39.034 | 23.669 | 1.00 | 99.84 | A | C |
| ATOM | 1631 | CD2 | TYR | A | 338 | 66.310 | 36.438 | 23.202 | 1.00 | 97.04 | A | C |
| ATOM | 1632 | CE2 | TYR | A | 338 | 67.233 | 37.498 | 23.319 | 1.00 | 102.58 | A | C |
| ATOM | 1633 | CZ | TYR | A | 338 | 66.767 | 38.799 | 23.550 | 1.00 | 102.63 | A | C |
| ATOM | 1634 | OH | TYR | A | 338 | 67.645 | 39.868 | 23.636 | 1.00 | 102.55 | A | O |
| ATOM | 1635 | C | TYR | A | 338 | 64.905 | 34.910 | 20.879 | 1.00 | 76.58 | A | C |
| ATOM | 1636 | O | TYR | A | 338 | 65.380 | 35.506 | 19.915 | 1.00 | 74.36 | A | O |
| ATOM | 1637 | N | LYS | A | 339 | 65.398 | 33.791 | 21.370 | 1.00 | 73.01 | A | N |
| ATOM | 1638 | CA | LYS | A | 339 | 66.577 | 33.209 | 20.826 | 1.00 | 71.11 | A | C |
| ATOM | 1639 | CB | LYS | A | 339 | 66.637 | 31.724 | 21.181 | 1.00 | 75.49 | A | C |
| ATOM | 1640 | CG | LYS | A | 339 | 67.863 | 31.003 | 20.620 | 1.00 | 83.83 | A | C |
| ATOM | 1641 | CD | LYS | A | 339 | 68.089 | 29.622 | 21.242 | 1.00 | 93.15 | A | C |
| ATOM | 1642 | CE | LYS | A | 339 | 68.414 | 29.728 | 22.745 | 1.00 | 99.04 | A | C |
| ATOM | 1643 | NZ | LYS | A | 339 | 68.866 | 28.434 | 23.386 | 1.00 | 106.61 | A | N |
| ATOM | 1644 | C | LYS | A | 339 | 66.469 | 33.390 | 19.345 | 1.00 | 68.72 | A | C |
| ATOM | 1645 | O | LYS | A | 339 | 67.242 | 34.110 | 18.743 | 1.00 | 65.80 | A | O |
| ATOM | 1646 | N | ARG | A | 340 | 65.451 | 32.787 | 18.769 | 1.00 | 69.97 | A | N |
| ATOM | 1647 | CA | ARG | A | 340 | 65.298 | 32.847 | 17.337 | 1.00 | 73.20 | A | C |
| ATOM | 1648 | CB | ARG | A | 340 | 64.279 | 31.774 | 16.886 | 1.00 | 81.85 | A | C |
| ATOM | 1649 | CG | ARG | A | 340 | 64.711 | 30.290 | 17.207 | 1.00 | 88.83 | A | C |

Figure 4AA

```
ATOM  1650  CD   ARG A 340      63.640  29.187  16.861  1.00   93.29      A   C
ATOM  1651  NE   ARG A 340      63.974  27.848  17.395  1.00   94.45      A   N
ATOM  1652  CZ   ARG A 340      63.154  26.792  17.402  1.00   90.40      A   C
ATOM  1653  NH1  ARG A 340      61.928  26.886  16.900  1.00   91.39      A   N
ATOM  1654  NH2  ARG A 340      63.555  25.639  17.924  1.00   84.42      A   N
ATOM  1655  C    ARG A 340      64.963  34.222  16.767  1.00   69.38      A   C
ATOM  1656  O    ARG A 340      65.327  34.529  15.643  1.00   70.49      A   O
ATOM  1657  N    ILE A 341      64.305  35.074  17.528  1.00   63.88      A   N
ATOM  1658  CA   ILE A 341      63.959  36.379  16.999  1.00   60.27      A   C
ATOM  1659  CB   ILE A 341      63.019  37.123  17.936  1.00   60.92      A   C
ATOM  1660  CG2  ILE A 341      62.864  38.547  17.482  1.00   63.49      A   C
ATOM  1661  CG1  ILE A 341      61.661  36.444  17.965  1.00   62.67      A   C
ATOM  1662  CD1  ILE A 341      60.668  37.149  18.831  1.00   62.60      A   C
ATOM  1663  C    ILE A 341      65.196  37.219  16.815  1.00   59.49      A   C
ATOM  1664  O    ILE A 341      65.522  37.653  15.722  1.00   55.44      A   O
ATOM  1665  N    SER A 342      65.880  37.453  17.917  1.00   63.88      A   N
ATOM  1666  CA   SER A 342      67.085  38.253  17.907  1.00   71.06      A   C
ATOM  1667  CB   SER A 342      67.603  38.415  19.324  1.00   69.66      A   C
ATOM  1668  OG   SER A 342      67.702  37.148  19.931  1.00   71.99      A   O
ATOM  1669  C    SER A 342      68.150  37.597  17.055  1.00   76.21      A   C
ATOM  1670  O    SER A 342      68.897  38.260  16.356  1.00   81.00      A   O
ATOM  1671  N    ARG A 343      68.238  36.283  17.117  1.00   78.92      A   N
ATOM  1672  CA   ARG A 343      69.237  35.588  16.323  1.00   79.63      A   C
ATOM  1673  CB   ARG A 343      69.465  34.198  16.945  1.00   85.90      A   C
ATOM  1674  CG   ARG A 343      70.373  33.233  16.185  1.00   94.40      A   C
ATOM  1675  CD   ARG A 343      69.566  32.209  15.342  1.00  101.87      A   C
ATOM  1676  NE   ARG A 343      69.843  30.803  15.694  1.00  111.15      A   N
ATOM  1677  CZ   ARG A 343      69.131  30.061  16.553  1.00  116.33      A   C
ATOM  1678  NH1  ARG A 343      68.073  30.566  17.168  1.00  120.46      A   N
ATOM  1679  NH2  ARG A 343      69.481  28.802  16.815  1.00  119.07      A   N
ATOM  1680  C    ARG A 343      68.761  35.511  14.860  1.00   76.83      A   C
ATOM  1681  O    ARG A 343      69.547  35.244  13.956  1.00   76.06      A   O
ATOM  1682  N    VAL A 344      67.476  35.789  14.648  1.00   75.06      A   N
ATOM  1683  CA   VAL A 344      66.876  35.736  13.312  1.00   74.54      A   C
ATOM  1684  CB   VAL A 344      67.577  36.670  12.357  1.00   70.64      A   C
ATOM  1685  CG1  VAL A 344      66.862  36.686  11.046  1.00   64.52      A   C
ATOM  1686  CG2  VAL A 344      67.613  38.047  12.939  1.00   69.18      A   C
ATOM  1687  C    VAL A 344      66.962  34.318  12.783  1.00   79.63      A   C
ATOM  1688  O    VAL A 344      67.491  34.059  11.712  1.00   75.82      A   O
ATOM  1689  N    GLU A 345      66.420  33.405  13.573  1.00   88.50      A   N
ATOM  1690  CA   GLU A 345      66.393  31.979  13.285  1.00   97.17      A   C
ATOM  1691  CB   GLU A 345      66.652  31.207  14.575  1.00  103.20      A   C
ATOM  1692  CG   GLU A 345      66.495  29.715  14.442  1.00  115.88      A   C
ATOM  1693  CD   GLU A 345      67.310  29.187  13.285  1.00  124.81      A   C
ATOM  1694  OE1  GLU A 345      68.492  29.611  13.177  1.00  129.03      A   O
ATOM  1695  OE2  GLU A 345      66.774  28.361  12.493  1.00  130.44      A   O
ATOM  1696  C    GLU A 345      65.060  31.514  12.701  1.00   98.90      A   C
ATOM  1697  O    GLU A 345      64.131  31.165  13.446  1.00   97.90      A   O
ATOM  1698  N    PHE A 346      64.974  31.475  11.374  1.00  101.67      A   N
ATOM  1699  CA   PHE A 346      63.732  31.058  10.716  1.00  105.15      A   C
ATOM  1700  CB   PHE A 346      62.853  32.285  10.486  1.00  101.46      A   C
ATOM  1701  CG   PHE A 346      63.165  33.008   9.229  1.00   94.81      A   C
ATOM  1702  CD1  PHE A 346      62.542  32.654   8.039  1.00   94.94      A   C
ATOM  1703  CD2  PHE A 346      64.118  34.003   9.217  1.00   92.92      A   C
ATOM  1704  CE1  PHE A 346      62.866  33.283   6.858  1.00   95.84      A   C
ATOM  1705  CE2  PHE A 346      64.452  34.640   8.036  1.00   93.74      A   C
ATOM  1706  CZ   PHE A 346      63.827  34.281   6.852  1.00   94.47      A   C
ATOM  1707  C    PHE A 346      63.932  30.313   9.377  1.00  108.68      A   C
ATOM  1708  O    PHE A 346      64.828  30.648   8.582  1.00  108.29      A   O
ATOM  1709  N    THR A 347      63.071  29.327   9.118  1.00  112.47      A   N
ATOM  1710  CA   THR A 347      63.183  28.539   7.896  1.00  115.77      A   C
```

Figure 4BB

```
ATOM   1711  CB  THR A 347      63.741  27.124   8.205  1.00 116.22      A    C
ATOM   1712  OG1 THR A 347      64.212  26.527   6.990  1.00 115.60      A    O
ATOM   1713  CG2 THR A 347      62.647  26.237   8.853  1.00 113.91      A    C
ATOM   1714  C   THR A 347      61.860  28.394   7.139  1.00 117.77      A    C
ATOM   1715  O   THR A 347      60.768  28.532   7.729  1.00 120.13      A    O
ATOM   1716  N   PHE A 348      61.989  28.091   5.839  1.00 117.75      A    N
ATOM   1717  CA  PHE A 348      60.864  27.922   4.905  1.00 114.46      A    C
ATOM   1718  CB  PHE A 348      61.191  28.546   3.536  1.00 115.32      A    C
ATOM   1719  CG  PHE A 348      61.323  30.051   3.544  1.00 115.42      A    C
ATOM   1720  CD1 PHE A 348      60.205  30.875   3.674  1.00 113.37      A    C
ATOM   1721  CD2 PHE A 348      62.570  30.639   3.406  1.00 115.78      A    C
ATOM   1722  CE1 PHE A 348      60.332  32.264   3.668  1.00 112.89      A    C
ATOM   1723  CE2 PHE A 348      62.705  32.020   3.400  1.00 116.22      A    C
ATOM   1724  CZ  PHE A 348      61.583  32.836   3.531  1.00 114.67      A    C
ATOM   1725  C   PHE A 348      60.451  26.479   4.628  1.00 111.19      A    C
ATOM   1726  O   PHE A 348      61.301  25.601   4.457  1.00 109.14      A    O
ATOM   1727  N   PRO A 349      59.129  26.235   4.545  1.00 108.80      A    N
ATOM   1728  CD  PRO A 349      58.022  27.167   4.848  1.00 108.30      A    C
ATOM   1729  CA  PRO A 349      58.602  24.906   4.271  1.00 107.30      A    C
ATOM   1730  CB  PRO A 349      57.163  25.001   4.771  1.00 106.96      A    C
ATOM   1731  CG  PRO A 349      56.792  26.393   4.383  1.00 107.53      A    C
ATOM   1732  C   PRO A 349      58.693  24.594   2.767  1.00 105.98      A    C
ATOM   1733  O   PRO A 349      58.922  25.465   1.908  1.00 103.92      A    O
ATOM   1734  N   ASP A 350      58.497  23.325   2.467  1.00 104.94      A    N
ATOM   1735  CA  ASP A 350      58.578  22.842   1.111  1.00 103.42      A    C
ATOM   1736  CB  ASP A 350      58.632  21.319   1.132  1.00 108.05      A    C
ATOM   1737  CG  ASP A 350      59.959  20.774   0.623  1.00 110.77      A    C
ATOM   1738  OD1 ASP A 350      61.025  21.331   0.991  1.00 109.18      A    O
ATOM   1739  OD2 ASP A 350      59.929  19.778  -0.138  1.00 114.39      A    O
ATOM   1740  C   ASP A 350      57.467  23.288   0.189  1.00  99.93      A    C
ATOM   1741  O   ASP A 350      56.615  22.471  -0.186  1.00  98.20      A    O
ATOM   1742  N   PHE A 351      57.471  24.567  -0.180  1.00  94.59      A    N
ATOM   1743  CA  PHE A 351      56.461  25.042  -1.103  1.00  92.87      A    C
ATOM   1744  CB  PHE A 351      55.087  24.453  -0.777  1.00  89.57      A    C
ATOM   1745  CG  PHE A 351      54.391  25.140   0.340  1.00  90.46      A    C
ATOM   1746  CD1 PHE A 351      53.801  26.386   0.153  1.00  90.98      A    C
ATOM   1747  CD2 PHE A 351      54.350  24.556   1.592  1.00  91.77      A    C
ATOM   1748  CE1 PHE A 351      53.184  27.036   1.199  1.00  93.77      A    C
ATOM   1749  CE2 PHE A 351      53.736  25.191   2.651  1.00  95.52      A    C
ATOM   1750  CZ  PHE A 351      53.151  26.435   2.460  1.00  96.07      A    C
ATOM   1751  C   PHE A 351      56.313  26.531  -1.190  1.00  94.12      A    C
ATOM   1752  O   PHE A 351      55.638  27.027  -2.088  1.00  96.72      A    O
ATOM   1753  N   VAL A 352      56.895  27.272  -0.267  1.00  93.66      A    N
ATOM   1754  CA  VAL A 352      56.710  28.708  -0.375  1.00  92.97      A    C
ATOM   1755  CB  VAL A 352      57.179  29.459   0.852  1.00  93.04      A    C
ATOM   1756  CG1 VAL A 352      57.087  30.963   0.596  1.00  88.93      A    C
ATOM   1757  CG2 VAL A 352      56.323  29.065   2.045  1.00  92.84      A    C
ATOM   1758  C   VAL A 352      57.477  29.218  -1.594  1.00  93.26      A    C
ATOM   1759  O   VAL A 352      58.677  28.993  -1.673  1.00  92.69      A    O
ATOM   1760  N   THR A 353      56.766  29.908  -2.429  1.00  94.47      A    N
ATOM   1761  CA  THR A 353      57.373  30.452  -3.625  1.00  96.66      A    C
ATOM   1762  CB  THR A 353      56.436  31.434  -4.328  1.00  97.68      A    C
ATOM   1763  OG1 THR A 353      57.158  32.119  -5.359  1.00  99.14      A    O
ATOM   1764  CG2 THR A 353      55.866  32.433  -3.329  1.00  97.94      A    C
ATOM   1765  C   THR A 353      58.647  31.174  -3.265  1.00  97.92      A    C
ATOM   1766  O   THR A 353      58.762  31.761  -2.195  1.00  99.25      A    O
ATOM   1767  N   GLU A 354      59.613  31.126  -4.161  1.00  99.61      A    N
ATOM   1768  CA  GLU A 354      60.865  31.784  -3.902  1.00 100.44      A    C
ATOM   1769  CB  GLU A 354      61.845  31.405  -4.958  1.00 107.39      A    C
ATOM   1770  CG  GLU A 354      63.099  32.164  -4.855  1.00 117.96      A    C
ATOM   1771  CD  GLU A 354      63.979  31.818  -6.003  1.00 127.17      A    C
```

Figure 4CC

```
ATOM   1772  OE1 GLU A 354      63.474  31.906  -7.171  1.00 132.51      A    O
ATOM   1773  OE2 GLU A 354      65.155  31.451  -5.726  1.00 132.47      A    O
ATOM   1774  C   GLU A 354      60.707  33.288  -3.883  1.00  97.47      A    C
ATOM   1775  O   GLU A 354      61.472  33.985  -3.215  1.00  97.39      A    O
ATOM   1776  N   GLY A 355      59.724  33.784  -4.632  1.00  94.87      A    N
ATOM   1777  CA  GLY A 355      59.464  35.218  -4.670  1.00  92.69      A    C
ATOM   1778  C   GLY A 355      59.085  35.743  -3.296  1.00  88.92      A    C
ATOM   1779  O   GLY A 355      59.300  36.907  -2.962  1.00  86.52      A    O
ATOM   1780  N   ALA A 356      58.499  34.858  -2.503  1.00  88.39      A    N
ATOM   1781  CA  ALA A 356      58.096  35.181  -1.150  1.00  87.48      A    C
ATOM   1782  CB  ALA A 356      56.997  34.201  -0.679  1.00  91.52      A    C
ATOM   1783  C   ALA A 356      59.357  35.006  -0.321  1.00  84.55      A    C
ATOM   1784  O   ALA A 356      59.771  35.897   0.426  1.00  82.86      A    O
ATOM   1785  N   ARG A 357      59.973  33.843  -0.487  1.00  80.83      A    N
ATOM   1786  CA  ARG A 357      61.176  33.513   0.226  1.00  79.07      A    C
ATOM   1787  CB  ARG A 357      61.831  32.293  -0.401  1.00  76.36      A    C
ATOM   1788  CG  ARG A 357      61.232  31.007   0.090  1.00  74.75      A    C
ATOM   1789  CD  ARG A 357      61.470  29.896  -0.885  1.00  76.91      A    C
ATOM   1790  NE  ARG A 357      61.200  28.588  -0.295  1.00  79.47      A    N
ATOM   1791  CZ  ARG A 357      62.003  27.995   0.581  1.00  81.41      A    C
ATOM   1792  NH1 ARG A 357      63.115  28.610   0.953  1.00  81.89      A    N
ATOM   1793  NH2 ARG A 357      61.707  26.792   1.077  1.00  82.39      A    N
ATOM   1794  C   ARG A 357      62.146  34.667   0.275  1.00  80.64      A    C
ATOM   1795  O   ARG A 357      62.978  34.720   1.153  1.00  82.71      A    O
ATOM   1796  N   ASP A 358      62.052  35.611  -0.647  1.00  82.32      A    N
ATOM   1797  CA  ASP A 358      62.984  36.736  -0.606  1.00  81.54      A    C
ATOM   1798  CB  ASP A 358      63.688  36.913  -1.961  1.00  86.19      A    C
ATOM   1799  CG  ASP A 358      62.905  37.791  -2.924  1.00  87.91      A    C
ATOM   1800  OD1 ASP A 358      61.888  37.331  -3.485  1.00  90.46      A    O
ATOM   1801  OD2 ASP A 358      63.313  38.954  -3.114  1.00  88.23      A    O
ATOM   1802  C   ASP A 358      62.300  38.040  -0.200  1.00  78.10      A    C
ATOM   1803  O   ASP A 358      62.921  38.929   0.374  1.00  79.03      A    O
ATOM   1804  N   LEU A 359      61.018  38.159  -0.506  1.00  75.12      A    N
ATOM   1805  CA  LEU A 359      60.298  39.358  -0.145  1.00  72.85      A    C
ATOM   1806  CB  LEU A 359      58.847  39.274  -0.620  1.00  70.08      A    C
ATOM   1807  CG  LEU A 359      57.819  40.322  -0.175  1.00  68.28      A    C
ATOM   1808  CD1 LEU A 359      57.328  39.971   1.210  1.00  67.60      A    C
ATOM   1809  CD2 LEU A 359      58.411  41.719  -0.215  1.00  67.07      A    C
ATOM   1810  C   LEU A 359      60.360  39.423   1.355  1.00  74.04      A    C
ATOM   1811  O   LEU A 359      60.572  40.481   1.929  1.00  75.69      A    O
ATOM   1812  N   ILE A 360      60.192  38.276   1.993  1.00  75.88      A    N
ATOM   1813  CA  ILE A 360      60.240  38.237   3.438  1.00  79.14      A    C
ATOM   1814  CB  ILE A 360      59.557  36.965   3.962  1.00  79.80      A    C
ATOM   1815  CG2 ILE A 360      60.239  35.752   3.398  1.00  73.30      A    C
ATOM   1816  CG1 ILE A 360      59.562  36.966   5.492  1.00  83.77      A    C
ATOM   1817  CD1 ILE A 360      58.753  35.845   6.119  1.00  88.60      A    C
ATOM   1818  C   ILE A 360      61.693  38.330   3.941  1.00  80.74      A    C
ATOM   1819  O   ILE A 360      61.987  39.080   4.868  1.00  82.77      A    O
ATOM   1820  N   SER A 361      62.610  37.589   3.329  1.00  79.31      A    N
ATOM   1821  CA  SER A 361      64.007  37.648   3.753  1.00  77.82      A    C
ATOM   1822  CB  SER A 361      64.910  36.909   2.786  1.00  77.89      A    C
ATOM   1823  OG  SER A 361      64.693  35.527   2.875  1.00  81.50      A    O
ATOM   1824  C   SER A 361      64.410  39.082   3.726  1.00  79.23      A    C
ATOM   1825  O   SER A 361      65.306  39.496   4.449  1.00  78.87      A    O
ATOM   1826  N   ARG A 362      63.739  39.821   2.852  1.00  83.07      A    N
ATOM   1827  CA  ARG A 362      63.989  41.231   2.665  1.00  87.72      A    C
ATOM   1828  CB  ARG A 362      63.637  41.656   1.248  1.00  87.31      A    C
ATOM   1829  CG  ARG A 362      64.134  43.028   0.953  1.00  91.26      A    C
ATOM   1830  CD  ARG A 362      65.317  42.942   0.055  1.00  99.16      A    C
ATOM   1831  NE  ARG A 362      64.884  43.068  -1.327  1.00 107.85      A    N
ATOM   1832  CZ  ARG A 362      64.469  44.215  -1.866  1.00 113.06      A    C
```

Figure 4DD

```
ATOM   1833  NH1 ARG A 362      64.442  45.328  -1.125  1.00 112.65      A    N
ATOM   1834  NH2 ARG A 362      64.079  44.251  -3.145  1.00 116.84      A    N
ATOM   1835  C   ARG A 362      63.165  42.058   3.622  1.00  90.36      A    C
ATOM   1836  O   ARG A 362      63.189  43.280   3.549  1.00  93.67      A    O
ATOM   1837  N   LEU A 363      62.428  41.400   4.511  1.00  91.62      A    N
ATOM   1838  CA  LEU A 363      61.593  42.114   5.473  1.00  93.79      A    C
ATOM   1839  CB  LEU A 363      60.135  41.757   5.262  1.00  92.63      A    C
ATOM   1840  CG  LEU A 363      59.238  42.973   5.100  1.00  91.15      A    C
ATOM   1841  CD1 LEU A 363      59.961  44.079   4.361  1.00  90.29      A    C
ATOM   1842  CD2 LEU A 363      58.022  42.548   4.339  1.00  95.75      A    C
ATOM   1843  C   LEU A 363      61.973  41.849   6.915  1.00  97.98      A    C
ATOM   1844  O   LEU A 363      61.681  42.634   7.811  1.00  99.90      A    O
ATOM   1845  N   LEU A 364      62.618  40.728   7.145  1.00 102.21      A    N
ATOM   1846  CA  LEU A 364      63.041  40.434   8.482  1.00 106.04      A    C
ATOM   1847  CB  LEU A 364      62.478  39.067   8.914  1.00 108.42      A    C
ATOM   1848  CG  LEU A 364      63.110  37.739   8.461  1.00 112.73      A    C
ATOM   1849  CD1 LEU A 364      63.398  37.756   6.966  1.00 114.72      A    C
ATOM   1850  CD2 LEU A 364      64.410  37.490   9.238  1.00 114.36      A    C
ATOM   1851  C   LEU A 364      64.581  40.485   8.495  1.00 107.46      A    C
ATOM   1852  O   LEU A 364      65.258  39.661   7.868  1.00 107.13      A    O
ATOM   1853  N   LYS A 365      65.123  41.506   9.162  1.00 111.08      A    N
ATOM   1854  CA  LYS A 365      66.575  41.672   9.299  1.00 115.83      A    C
ATOM   1855  CB  LYS A 365      67.158  42.466   8.137  1.00 118.34      A    C
ATOM   1856  CG  LYS A 365      68.588  42.078   7.828  1.00 122.84      A    C
ATOM   1857  CD  LYS A 365      68.665  40.680   7.170  1.00 126.91      A    C
ATOM   1858  CE  LYS A 365      70.053  39.999   7.351  1.00 128.43      A    C
ATOM   1859  NZ  LYS A 365      70.441  39.708   8.787  1.00 126.93      A    N
ATOM   1860  C   LYS A 365      66.938  42.359  10.623  1.00 117.43      A    C
ATOM   1861  O   LYS A 365      66.311  43.361  11.024  1.00 117.04      A    O
ATOM   1862  N   HIS A 366      67.950  41.804  11.296  1.00 120.22      A    N
ATOM   1863  CA  HIS A 366      68.402  42.306  12.596  1.00 122.56      A    C
ATOM   1864  CB  HIS A 366      69.726  41.660  13.013  1.00 126.19      A    C
ATOM   1865  CG  HIS A 366      70.053  41.842  14.464  1.00 129.99      A    C
ATOM   1866  CD2 HIS A 366      70.645  42.865  15.125  1.00 132.30      A    C
ATOM   1867  ND1 HIS A 366      69.759  40.891  15.421  1.00 133.57      A    N
ATOM   1868  CE1 HIS A 366      70.158  41.317  16.609  1.00 134.32      A    C
ATOM   1869  NE2 HIS A 366      70.700  42.513  16.457  1.00 135.34      A    N
ATOM   1870  C   HIS A 366      68.592  43.802  12.555  1.00 122.17      A    C
ATOM   1871  O   HIS A 366      68.029  44.543  13.376  1.00 122.56      A    O
ATOM   1872  N   ASN A 367      69.402  44.232  11.592  1.00 120.69      A    N
ATOM   1873  CA  ASN A 367      69.678  45.640  11.406  1.00 119.19      A    C
ATOM   1874  CB  ASN A 367      70.770  45.805  10.360  1.00 119.34      A    C
ATOM   1875  CG  ASN A 367      71.582  47.057  10.578  1.00 122.59      A    C
ATOM   1876  OD1 ASN A 367      71.038  48.141  10.810  1.00 124.09      A    O
ATOM   1877  ND2 ASN A 367      72.894  46.921  10.511  1.00 125.24      A    N
ATOM   1878  C   ASN A 367      68.403  46.376  10.951  1.00 118.22      A    C
ATOM   1879  O   ASN A 367      67.942  46.172   9.831  1.00 118.01      A    O
ATOM   1880  N   PRO A 368      67.820  47.236  11.818  1.00 117.67      A    N
ATOM   1881  CD  PRO A 368      68.189  47.530  13.213  1.00 117.09      A    C
ATOM   1882  CA  PRO A 368      66.607  47.971  11.458  1.00 119.21      A    C
ATOM   1883  CB  PRO A 368      66.357  48.841  12.685  1.00 116.57      A    C
ATOM   1884  CG  PRO A 368      66.892  48.021  13.786  1.00 115.01      A    C
ATOM   1885  C   PRO A 368      66.772  48.812  10.195  1.00 123.08      A    C
ATOM   1886  O   PRO A 368      65.799  49.044   9.467  1.00 125.04      A    O
ATOM   1887  N   SER A 369      67.999  49.270   9.939  1.00 126.13      A    N
ATOM   1888  CA  SER A 369      68.292  50.112   8.768  1.00 127.05      A    C
ATOM   1889  CB  SER A 369      69.603  50.886   8.973  1.00 125.63      A    C
ATOM   1890  OG  SER A 369      70.728  50.028   8.891  1.00 124.92      A    O
ATOM   1891  C   SER A 369      68.361  49.375   7.429  1.00 127.83      A    C
ATOM   1892  O   SER A 369      68.001  49.943   6.395  1.00 129.60      A    O
ATOM   1893  N   GLN A 370      68.815  48.124   7.436  1.00 127.59      A    N
```

Figure 4EE

```
ATOM  1894  CA   GLN A 370      68.924  47.362   6.191  1.00  126.82      A    C
ATOM  1895  CB   GLN A 370      69.787  46.107   6.422  1.00  129.90      A    C
ATOM  1896  CG   GLN A 370      71.210  46.370   6.928  1.00  133.53      A    C
ATOM  1897  CD   GLN A 370      72.159  45.166   6.750  1.00  136.39      A    C
ATOM  1898  OE1  GLN A 370      73.276  45.168   7.268  1.00  138.16      A    O
ATOM  1899  NE2  GLN A 370      71.721  44.147   6.009  1.00  138.57      A    N
ATOM  1900  C    GLN A 370      67.574  46.959   5.533  1.00  125.03      A    C
ATOM  1901  O    GLN A 370      67.573  46.332   4.462  1.00  123.43      A    O
ATOM  1902  N    ARG A 371      66.441  47.334   6.152  1.00  123.37      A    N
ATOM  1903  CA   ARG A 371      65.095  46.978   5.639  1.00  119.21      A    C
ATOM  1904  CB   ARG A 371      64.126  46.665   6.810  1.00  127.12      A    C
ATOM  1905  CG   ARG A 371      64.514  45.440   7.721  1.00  134.84      A    C
ATOM  1906  CD   ARG A 371      64.668  44.070   6.962  1.00  141.58      A    C
ATOM  1907  NE   ARG A 371      65.713  44.073   5.910  1.00  145.04      A    N
ATOM  1908  CZ   ARG A 371      66.127  43.013   5.197  1.00  143.97      A    C
ATOM  1909  NH1  ARG A 371      67.078  43.168   4.275  1.00  143.01      A    N
ATOM  1910  NH2  ARG A 371      65.613  41.798   5.399  1.00  143.52      A    N
ATOM  1911  C    ARG A 371      64.451  47.992   4.674  1.00  111.56      A    C
ATOM  1912  O    ARG A 371      64.511  49.211   4.872  1.00  107.85      A    O
ATOM  1913  N    PRO A 372      63.796  47.477   3.623  1.00  107.05      A    N
ATOM  1914  CD   PRO A 372      63.295  46.095   3.515  1.00  105.70      A    C
ATOM  1915  CA   PRO A 372      63.157  48.322   2.622  1.00  104.97      A    C
ATOM  1916  CB   PRO A 372      62.465  47.314   1.715  1.00  104.32      A    C
ATOM  1917  CG   PRO A 372      62.051  46.266   2.672  1.00  103.50      A    C
ATOM  1918  C    PRO A 372      62.192  49.286   3.230  1.00  103.88      A    C
ATOM  1919  O    PRO A 372      61.743  49.108   4.357  1.00  105.02      A    O
ATOM  1920  N    MET A 373      61.883  50.327   2.480  1.00  102.54      A    N
ATOM  1921  CA   MET A 373      60.935  51.291   2.965  1.00  100.05      A    C
ATOM  1922  CB   MET A 373      61.338  52.703   2.534  1.00   97.86      A    C
ATOM  1923  CG   MET A 373      61.216  53.765   3.632  1.00   92.64      A    C
ATOM  1924  SD   MET A 373      59.518  54.116   4.143  1.00   91.01      A    S
ATOM  1925  CE   MET A 373      59.679  54.352   5.900  1.00   81.46      A    C
ATOM  1926  C    MET A 373      59.637  50.877   2.316  1.00   99.17      A    C
ATOM  1927  O    MET A 373      59.577  49.924   1.548  1.00   96.25      A    O
ATOM  1928  N    LEU A 374      58.593  51.591   2.663  1.00  100.83      A    N
ATOM  1929  CA   LEU A 374      57.284  51.358   2.118  1.00  104.81      A    C
ATOM  1930  CB   LEU A 374      56.496  52.677   2.238  1.00  108.29      A    C
ATOM  1931  CG   LEU A 374      57.255  54.012   2.020  1.00  109.79      A    C
ATOM  1932  CD1  LEU A 374      57.278  54.413   0.522  1.00  108.76      A    C
ATOM  1933  CD2  LEU A 374      56.589  55.112   2.861  1.00  107.21      A    C
ATOM  1934  C    LEU A 374      57.293  50.854   0.663  1.00  106.77      A    C
ATOM  1935  O    LEU A 374      57.089  49.671   0.399  1.00  104.15      A    O
ATOM  1936  N    ARG A 375      57.550  51.772  -0.267  1.00  111.39      A    N
ATOM  1937  CA   ARG A 375      57.545  51.508  -1.708  1.00  114.73      A    C
ATOM  1938  CB   ARG A 375      58.239  52.675  -2.451  1.00  121.24      A    C
ATOM  1939  CG   ARG A 375      58.221  52.540  -3.995  1.00  129.96      A    C
ATOM  1940  CD   ARG A 375      59.022  53.641  -4.753  1.00  136.60      A    C
ATOM  1941  NE   ARG A 375      60.448  53.336  -4.980  1.00  142.14      A    N
ATOM  1942  CZ   ARG A 375      61.406  53.443  -4.055  1.00  144.03      A    C
ATOM  1943  NH1  ARG A 375      62.674  53.140  -4.361  1.00  144.67      A    N
ATOM  1944  NH2  ARG A 375      61.098  53.860  -2.822  1.00  146.67      A    N
ATOM  1945  C    ARG A 375      58.120  50.177  -2.207  1.00  112.06      A    C
ATOM  1946  O    ARG A 375      57.495  49.479  -3.015  1.00  110.66      A    O
ATOM  1947  N    GLU A 376      59.302  49.820  -1.735  1.00  111.32      A    N
ATOM  1948  CA   GLU A 376      59.913  48.601  -2.219  1.00  111.63      A    C
ATOM  1949  CB   GLU A 376      61.149  48.258  -1.374  1.00  115.45      A    C
ATOM  1950  CG   GLU A 376      62.172  47.331  -2.100  1.00  120.42      A    C
ATOM  1951  CD   GLU A 376      62.663  47.855  -3.494  1.00  121.42      A    C
ATOM  1952  OE1  GLU A 376      63.310  48.929  -3.552  1.00  118.90      A    O
ATOM  1953  OE2  GLU A 376      62.409  47.185  -4.533  1.00  121.36      A    O
ATOM  1954  C    GLU A 376      58.943  47.417  -2.316  1.00  108.94      A    C
```

Figure 4FF

```
ATOM  1955  O    GLU A 376    58.748  46.881  -3.408  1.00  109.31  A  O
ATOM  1956  N    VAL A 377    58.315  47.018  -1.211  1.00  106.15  A  N
ATOM  1957  CA   VAL A 377    57.388  45.883  -1.259  1.00  103.77  A  C
ATOM  1958  CB   VAL A 377    56.791  45.536   0.122  1.00  104.15  A  C
ATOM  1959  CG1  VAL A 377    57.851  44.919   1.013  1.00  105.26  A  C
ATOM  1960  CG2  VAL A 377    56.189  46.785   0.757  1.00  107.73  A  C
ATOM  1961  C    VAL A 377    56.221  46.138  -2.193  1.00  101.71  A  C
ATOM  1962  O    VAL A 377    55.892  45.290  -3.032  1.00  101.04  A  O
ATOM  1963  N    LEU A 378    55.590  47.301  -2.038  1.00   99.52  A  N
ATOM  1964  CA   LEU A 378    54.459  47.663  -2.879  1.00   97.29  A  C
ATOM  1965  CB   LEU A 378    54.082  49.125  -2.667  1.00   96.55  A  C
ATOM  1966  CG   LEU A 378    52.752  49.385  -1.959  1.00   98.02  A  C
ATOM  1967  CD1  LEU A 378    52.570  48.431  -0.793  1.00   96.23  A  C
ATOM  1968  CD2  LEU A 378    52.723  50.822  -1.478  1.00  101.23  A  C
ATOM  1969  C    LEU A 378    54.868  47.440  -4.316  1.00   97.23  A  C
ATOM  1970  O    LEU A 378    54.041  47.107  -5.164  1.00   96.30  A  O
ATOM  1971  N    GLU A 379    56.168  47.603  -4.556  1.00   97.66  A  N
ATOM  1972  CA   GLU A 379    56.768  47.441  -5.871  1.00   96.85  A  C
ATOM  1973  CB   GLU A 379    57.680  48.643  -6.171  1.00  100.81  A  C
ATOM  1974  CG   GLU A 379    58.097  48.800  -7.646  1.00  106.97  A  C
ATOM  1975  CD   GLU A 379    59.523  48.320  -7.934  1.00  109.48  A  C
ATOM  1976  OE1  GLU A 379    59.916  48.340  -9.124  1.00  109.75  A  O
ATOM  1977  OE2  GLU A 379    60.241  47.931  -6.977  1.00  109.57  A  O
ATOM  1978  C    GLU A 379    57.578  46.147  -5.930  1.00   94.08  A  C
ATOM  1979  O    GLU A 379    58.433  45.972  -6.790  1.00   98.02  A  O
ATOM  1980  N    HIS A 380    57.319  45.226  -5.022  1.00   87.94  A  N
ATOM  1981  CA   HIS A 380    58.086  44.012  -5.057  1.00   82.56  A  C
ATOM  1982  CB   HIS A 380    58.115  43.358  -3.692  1.00   82.26  A  C
ATOM  1983  CG   HIS A 380    58.890  42.083  -3.666  1.00   82.11  A  C
ATOM  1984  CD2  HIS A 380    60.048  41.756  -3.049  1.00   81.03  A  C
ATOM  1985  ND1  HIS A 380    58.490  40.957  -4.355  1.00   82.96  A  N
ATOM  1986  CE1  HIS A 380    59.368  39.990  -4.161  1.00   82.13  A  C
ATOM  1987  NE2  HIS A 380    60.323  40.449  -3.371  1.00   83.50  A  N
ATOM  1988  C    HIS A 380    57.512  43.065  -6.075  1.00   81.77  A  C
ATOM  1989  O    HIS A 380    56.299  42.965  -6.227  1.00   76.43  A  O
ATOM  1990  N    PRO A 381    58.394  42.359  -6.797  1.00   85.35  A  N
ATOM  1991  CD   PRO A 381    59.862  42.517  -6.709  1.00   88.70  A  C
ATOM  1992  CA   PRO A 381    58.045  41.384  -7.836  1.00   87.28  A  C
ATOM  1993  CB   PRO A 381    59.394  40.734  -8.163  1.00   89.44  A  C
ATOM  1994  CG   PRO A 381    60.351  41.874  -8.008  1.00   89.30  A  C
ATOM  1995  C    PRO A 381    57.004  40.366  -7.385  1.00   85.70  A  C
ATOM  1996  O    PRO A 381    56.473  39.596  -8.175  1.00   85.32  A  O
ATOM  1997  N    TRP A 382    56.698  40.356  -6.110  1.00   84.08  A  N
ATOM  1998  CA   TRP A 382    55.728  39.409  -5.666  1.00   82.35  A  C
ATOM  1999  CB   TRP A 382    56.207  38.778  -4.395  1.00   86.28  A  C
ATOM  2000  CG   TRP A 382    55.528  37.506  -4.138  1.00   93.30  A  C
ATOM  2001  CD2  TRP A 382    54.759  37.165  -2.973  1.00   94.03  A  C
ATOM  2002  CE2  TRP A 382    54.346  35.816  -3.124  1.00   96.26  A  C
ATOM  2003  CE3  TRP A 382    54.381  37.865  -1.816  1.00   90.54  A  C
ATOM  2004  CD1  TRP A 382    55.545  36.386  -4.935  1.00   97.22  A  C
ATOM  2005  NE1  TRP A 382    54.836  35.364  -4.327  1.00   98.14  A  N
ATOM  2006  CZ2  TRP A 382    53.577  35.156  -2.152  1.00   95.12  A  C
ATOM  2007  CZ3  TRP A 382    53.618  37.209  -0.855  1.00   88.54  A  C
ATOM  2008  CH2  TRP A 382    53.226  35.870  -1.029  1.00   91.88  A  C
ATOM  2009  C    TRP A 382    54.403  40.100  -5.451  1.00   81.95  A  C
ATOM  2010  O    TRP A 382    53.381  39.672  -5.967  1.00   81.84  A  O
ATOM  2011  N    ILE A 383    54.420  41.178  -4.684  1.00   81.87  A  N
ATOM  2012  CA   ILE A 383    53.199  41.933  -4.427  1.00   82.97  A  C
ATOM  2013  CB   ILE A 383    53.521  43.351  -3.917  1.00   84.29  A  C
ATOM  2014  CG2  ILE A 383    52.270  44.241  -4.004  1.00   84.19  A  C
ATOM  2015  CG1  ILE A 383    54.058  43.272  -2.483  1.00   83.30  A  C
```

Figure 4GG

```
ATOM 2016  CD1  ILE A 383      55.353  42.486  -2.319  1.00   80.07  A  C
ATOM 2017  C    ILE A 383      52.465  42.061  -5.740  1.00   82.79  A  C
ATOM 2018  O    ILE A 383      51.281  41.784  -5.874  1.00   79.23  A  O
ATOM 2019  N    THR A 384      53.212  42.493  -6.724  1.00   84.74  A  N
ATOM 2020  CA   THR A 384      52.664  42.663  -8.035  1.00   87.97  A  C
ATOM 2021  CB   THR A 384      53.586  43.585  -8.817  1.00   89.41  A  C
ATOM 2022  OG1  THR A 384      54.912  43.035  -8.818  1.00   91.34  A  O
ATOM 2023  CG2  THR A 384      53.637  44.956  -8.143  1.00   89.54  A  C
ATOM 2024  C    THR A 384      52.553  41.288  -8.693  1.00   90.25  A  C
ATOM 2025  O    THR A 384      53.473  40.471  -8.589  1.00   91.06  A  O
ATOM 2026  N    ALA A 385      51.417  41.050  -9.349  1.00   93.14  A  N
ATOM 2027  CA   ALA A 385      51.109  39.799 -10.053  1.00   95.90  A  C
ATOM 2028  CB   ALA A 385      52.380  38.978 -10.303  1.00   96.67  A  C
ATOM 2029  C    ALA A 385      50.137  39.025  -9.182  1.00   97.63  A  C
ATOM 2030  O    ALA A 385      48.932  39.288  -9.213  1.00   96.06  A  O
ATOM 2031  N    ASN A 386      50.658  38.060  -8.425  1.00  100.68  A  N
ATOM 2032  CA   ASN A 386      49.819  37.302  -7.514  1.00  101.83  A  C
ATOM 2033  CB   ASN A 386      50.599  36.164  -6.830  1.00  100.85  A  C
ATOM 2034  CG   ASN A 386      52.090  36.428  -6.773  1.00  101.11  A  C
ATOM 2035  OD1  ASN A 386      52.516  37.488  -6.319  1.00  102.88  A  O
ATOM 2036  ND2  ASN A 386      52.893  35.465  -7.233  1.00   98.39  A  N
ATOM 2037  C    ASN A 386      49.468  38.399  -6.534  1.00  102.28  A  C
ATOM 2038  O    ASN A 386      50.257  38.760  -5.666  1.00  100.95  A  O
ATOM 2039  N    SER A 387      48.288  38.964  -6.732  1.00  103.93  A  N
ATOM 2040  CA   SER A 387      47.801  40.056  -5.916  1.00  105.55  A  C
ATOM 2041  CB   SER A 387      48.691  41.282  -6.108  1.00  103.48  A  C
ATOM 2042  OG   SER A 387      48.125  42.430  -5.495  1.00  104.49  A  O
ATOM 2043  C    SER A 387      46.408  40.370  -6.422  1.00  108.91  A  C
ATOM 2044  O    SER A 387      46.300  40.367  -7.667  1.00  112.21  A  O
TER  2046       SER A 387                                           A
ATOM 2047  O5'  ADN B   1      37.122  43.331  20.396  1.00  110.17  B  O
ATOM 2048  C5'  ADN B   1      36.390  42.153  20.753  1.00  112.35  B  C
ATOM 2049  C4'  ADN B   1      35.872  41.464  19.511  1.00  112.18  B  C
ATOM 2050  O4'  ADN B   1      34.847  42.283  18.886  1.00  111.86  B  O
ATOM 2051  C1'  ADN B   1      34.942  42.172  17.472  1.00  110.02  B  C
ATOM 2052  N9   ADN B   1      35.095  43.513  16.891  1.00  106.02  B  N
ATOM 2053  C4   ADN B   1      34.668  43.897  15.637  1.00  103.78  B  C
ATOM 2054  N3   ADN B   1      34.090  43.122  14.693  1.00  103.70  B  N
ATOM 2055  C2   ADN B   1      33.783  43.846  13.620  1.00  102.28  B  C
ATOM 2056  N1   ADN B   1      33.968  45.162  13.398  1.00   98.04  B  N
ATOM 2057  C6   ADN B   1      34.548  45.910  14.365  1.00   95.63  B  C
ATOM 2058  N6   ADN B   1      34.711  47.216  14.152  1.00   90.44  B  N
ATOM 2059  C5   ADN B   1      34.936  45.257  15.549  1.00   98.62  B  C
ATOM 2060  N7   ADN B   1      35.560  45.711  16.703  1.00   97.18  B  N
ATOM 2061  C8   ADN B   1      35.640  44.642  17.462  1.00  100.81  B  C
ATOM 2062  C2'  ADN B   1      36.072  41.192  17.150  1.00  112.86  B  C
ATOM 2063  O2'  ADN B   1      35.501  39.925  16.877  1.00  116.91  B  O
ATOM 2064  C3'  ADN B   1      36.916  41.256  18.426  1.00  113.20  B  C
ATOM 2065  O3'  ADN B   1      37.655  40.060  18.676  1.00  113.89  B  O
TER  2066       ADN B   1                                           B
END
```

CRYSTAL STRUCTURE OF AURORA-2 PROTEIN AND BINDING POCKETS THEREOF

This application is a divisional of U.S. patent application Ser. No. 12/070,054, filed Feb. 13, 2008, which is a divisional of U.S. patent application Ser. No. 10/979,375, filed Nov. 1, 2004, now U.S. Pat. No. 7,361,492 (patented); which is a continuation of PCT Application No. PCT/US03/13605, filed May 1, 2003 (expired), which claims benefit of U.S. Provisional Application 60/377,510, filed May 1, 2002 (expired), the disclosures of which are incorporated by reference.

TECHNICAL FIELD OF THE INVENTION

The present invention provides crystalline molecules or molecular complexes which comprise binding pockets of Aurora-2 or its homologues. The present invention also provides crystals comprising Aurora-2. This invention also provides methods of using the structure coordinates to solve the structure of homologous proteins or protein complexes. In addition, this invention provides methods of using the structure coordinates to design compounds, including inhibitory compounds and antibodies, that bind to Aurora-2 or homologues thereof.

BACKGROUND OF THE INVENTION

Protein kinases mediate intracellular signal transduction by causing a phosphoryl transfer from a nucleoside triphosphate to a protein acceptor involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, $H_2O_2$), cytokines (e.g., interleukin-1 (IL-1) and tumor necrosis factor-α (TNF-α)), growth factors (e.g., granulocyte macrophage-colony-stimulating factor (GM-CSF), and fibroblast growth factor (FGF). An extracellular stimulus may affect one or more cellular responses related to cell growth, migration, differentiation, secretion of hormones, activation of transcription factors, muscle contraction, glucose metabolism, control of protein synthesis and regulation of cell cycle.

Many disease states are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease and hormone-related diseases. Thus, an understanding of the structure, function, and inhibition of kinase activity could lead to useful human therapeutics.

Among medically important kinases are the serine/threonine kinases. The serine/threonine kinase family include the mammalian mitogen-activated protein (MAP) kinases. MAP kinases are activated by dual phosphorylation of threonine and tyrosine at the Thr-X-Tyr segment in the activation loop. Members of the MAP kinase family also share sequence similarity and conserved structural domains, and include the extracellular-signal regulated kinases (ERKs), Jun N-terminal kinases (JNKs) and p38 kinases. MAP kinases also phosphorylate various substrates including transcription factors, which in turn regulate the expression of specific sets of genes and mediate a specific response to the stimulus.

Another important group in the serine/threonine kinase family includes a subgroup of three closely related serine/threonine protein kinases, the Aurora kinases. The Aurora kinases play a key role in protein phosphorylation events that regulate the mitotic phase of the cell cycle. Aurora-2, for example, is up-regulated during the M phase of the cell cycle and localizes to the spindle pole during mitosis, suggesting a possible involvement in centrosomal functions. The Aurora kinases share a common structure, including a highly-conserved catalytic domain, and a very short N-terminal domain that varies in size (R. Giet and C. Prigent, *J. Cell Sci.*, 112, pp. 3591-'3601 (1999)). The N-terminal domains do not share any sequence similarity. The Aurora kinases are overexpressed in various types of cancer, such as colon, breast and other solid tumors (for a review see T. M. Goepfert and B. R. Brinkley, *Curr. Top. Dev. Biol.*, 49, pp. 331-342 (2000)). Even more importantly, both the Aurora-1 and -2 genes are amplified in breast and colorectal cancers whereas the Aurora-3 gene is located in a region that is rearranged or deleted in several cancer cells. Overexpression of Aurora-2 in rodent fibroblasts induces transformation, indicating that Aurora-2 is oncogenic. Recently, Aurora-2 mRNA expression has been linked to chromosomal instability in human breast cancers (Y. Miyoshi et al., *Int. J. Cancer*, 92, pp. 370-373 (2001)).

Accordingly, there has been an interest in finding inhibitors of Aurora-1, Aurora-2 or Aurora-3 that are effective as therapeutic agents. A challenge has been to find protein kinase inhibitors that act in a selective manner for the Aurora family kinases. Since there are numerous protein kinases involved in a variety of cellular responses, non-selective inhibitors may lead to undesirable side effects. In this regard, the three-dimensional structure of the kinase would assist in the rational design of inhibitors. The determination of the amino acid residues in Aurora-2 binding pockets and the determination of the shape of those binding pockets would allow one to design selective inhibitors that bind favorably to this class of enzymes. The determination of the amino acid residues in Aurora-2 binding pockets and the determination of the shape of those binding pockets would also allow one to design inhibitors that can bind selectively to Aurora-1, Aurora-2 or Aurora-3, or any combination thereof.

Despite the fact that the genes for various Aurora-1, Aurora-2 and Aurora-3 have been isolated and the amino acid sequences of Aurora-1, Aurora-2 and Aurora-3 proteins are known, the X-ray crystal structural coordinate information of Aurora-1, Aurora-2 or Aurora-3 protein has not yet been described. Such information would be useful in identifying and designing therapeutic inhibitors of the Aurora kinases or homologues thereof.

SUMMARY OF THE INVENTION

Applicants have solved this problem by providing, for the first time, the crystal structures of Aurora-2-inhibitor complexes and the crystal structure of Aurora-2 bound to adenosine. The present invention provides crystalline molecules or molecular complexes comprising Aurora-2 binding pockets, or Aurora-2-like binding pockets that have similar three-dimensional shapes. In one embodiment, the molecules or molecular complexes are Aurora-2 proteins or homologues, or Aurora-2 protein complexes or homologues thereof. In another embodiment, the molecules or molecular complexes are Aurora-2 kinase domains or homologues thereof, or Aurora-2 kinase domain complexes or homologues thereof.

The invention also provides crystal compositions comprising Aurora-2 protein, Aurora-2 kinase domain or homologues thereof in the presence or absence of a chemical entity. The invention also provides a method of crystallizing Aurora-2 protein, Aurora-2 protein complex, or homologues thereof.

The invention further provides a computer comprising a data storage medium which comprises the structure coordinates of molecules and molecular complexes comprising all or part of the Aurora-2 binding pockets or Aurora-2-like binding pockets. Such storage medium, when read and utilized by a computer programmed with appropriate software, displays on a computer screen or similar viewing device, a three-dimensional graphical representation of a molecule or molecular complex comprising such binding pockets.

The invention provides methods for screening, designing, optimizing, evaluating and identifying compounds which bind to the molecules or molecular complexes or their binding pockets. Such compounds are potential inhibitors of Aurora-2 or its homologues. Such methods can be used to identify agonist or antagonist of Aurora-2 and its homologues.

The invention also provides a method for determining at least a portion of the three-dimensional structure of molecules or molecular complexes which contain at least some structurally similar features to Aurora-2, particularly Aurora-2 homologues. This is achieved by using at least some of the structure coordinates obtained from the Aurora-2 complexes.

BRIEF DESCRIPTION OF THE DRAWINGS

The following abbreviations are used in FIGS. 1-4:

"Atom type" refers to the element whose coordinates are measured. The first letter in the column defines the element.

"Resid" refers to the amino acid residue identity in the molecular model.

"X, Y, Z" define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in the molecules.

"Mol" refers to the molecule in the asymmetric unit.

FIG. 1A to 1HH lists the atomic structure coordinates (Aurora-2 amino acid residues 127-278 and 290-390 of SEQ ID NO:1) for the Aurora-2-(5-Cyclopropyl-2H-pyrazol-3-yl)-(2-phenyl-quinazolin-4-yl)-amine inhibitor complex as derived by X-ray diffraction from the crystal.

FIG. 2A to 2HH lists the atomic structure coordinates (Aurora-2 amino acid residues 120-279 and 287-388 of SEQ ID NO:1, wherein Lys153 is Ala153, Gln154 is Ala154 and Lys156 is Ala156) for the Aurora-2-(5-Methylthiazol-2-yl)-(2-phenyl-quinazolin-4-yl)-amine inhibitor complex as derived by X-ray diffraction from the crystal.

FIG. 3A to 3GG lists the atomic structure coordinates (Aurora-2 amino acid residues 128-277 and 291-388 of SEQ ID NO:1, wherein Lys153 is Ala153, Gln154 is Ala154 and Lys156 is Ala156) for the Aurora-2-(5-Methyl-2H-pyrazol-3-yl)-(2-(pyridin-3-ylmethylamino)-quinazolin-4-yl)-amine inhibitor complex as derived by X-ray diffraction from the crystal.

FIG. 4A to 4GG lists the atomic structure coordinates (Aurora-2 amino acid residues 128-278 and 289-387 of SEQ ID NO:1, wherein Lys153 is Ala153, Gln154 is Ala154 and Lys156 is Ala156) for the Aurora-2-adenosine complex as derived by X-ray diffraction from the crystal.

Figure 5:
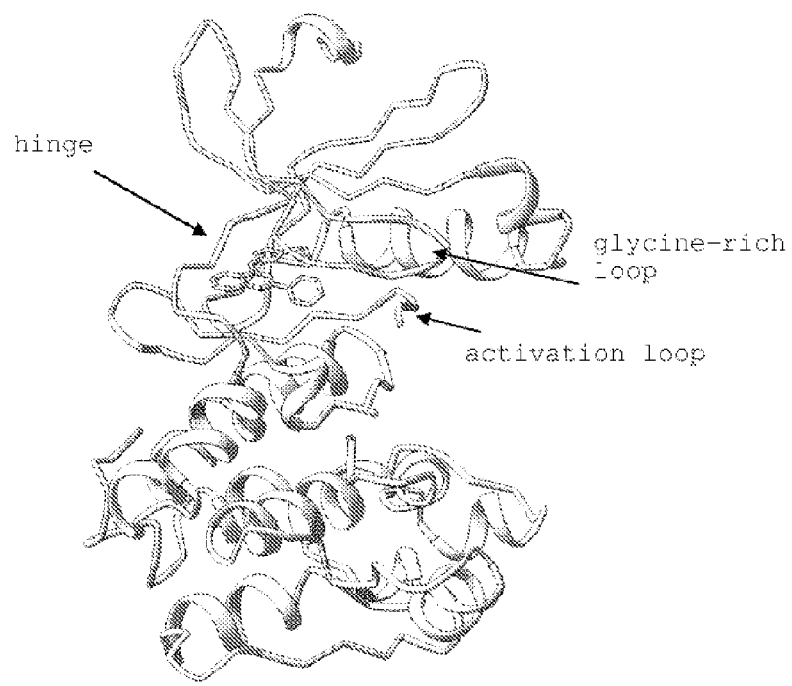

FIG. 5 depicts a ribbon diagram of the overall fold of Aurora-2-(5-Cyclopropyl-2H-pyrazol-3-yl)-(2-phenyl-quinazolin-4-yl)-amine complex. The N-terminal lobe of the Aurora-2 catalytic domain corresponds to the β-strand sub-domain and encompasses amino acid residues 127 to 215. The α-helical sub-domain corresponds to amino acid residues 216 to 390. Key features of the kinase-fold such as the hinge (approximately amino acid residues 132 to 135), glycine rich loop (approximately amino acid residues 140 to 149) and activation loop or phosphorylation lip (approximately amino acid residues 272 to 289) are indicated. In each of the Aurora-2 crystal structures some of the amino acid residues at the N-terminus (~107-126), C-terminus (~391-403) and activation loop (~279-289) were disordered. They exhibited only weak electron density and could not be fitted.

Figure 6:
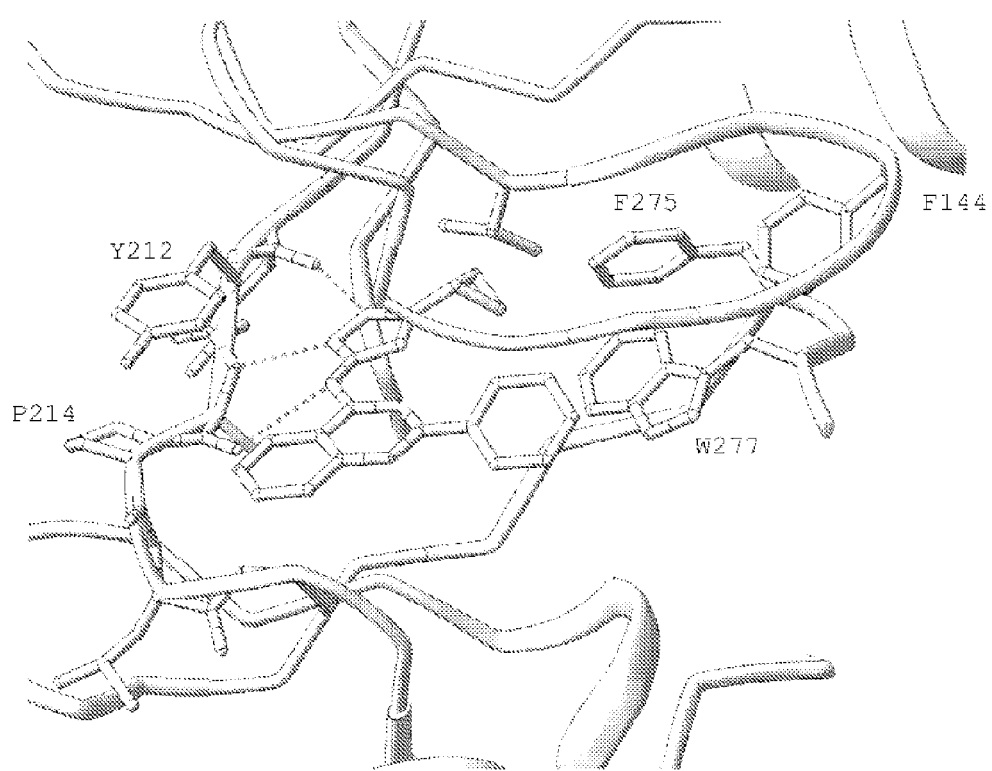

FIG. 6 shows a detailed representation of pockets in the catalytic active site of the Aurora-2-(5-Cyclopropyl-2H-pyrazol-3-yl)-(2-phenyl-quinazolin-4-yl)-amine complex.

Figure 7:
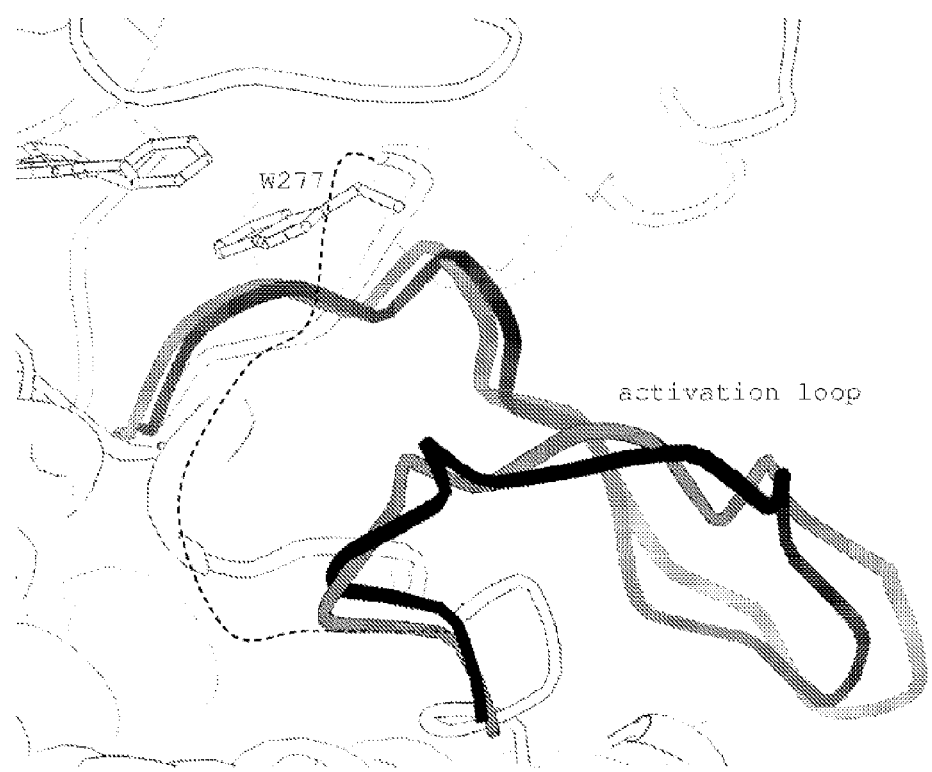

FIG. 7 shows a comparison between the activation loops of Aurora-2-(5-Cyclopropyl-2H-pyrazol-3-yl)-(2-phenyl-quinazolin-4-yl)-amine complex in white, unphosphorylated GSK-3β in grey (ter Haar, E. et al., *Nat. Struct. Biol.* 8, 593-596 (2001)), and activated substrate-bound human CDK2 in black (PDB Accession number 1B38).

Figure 8:
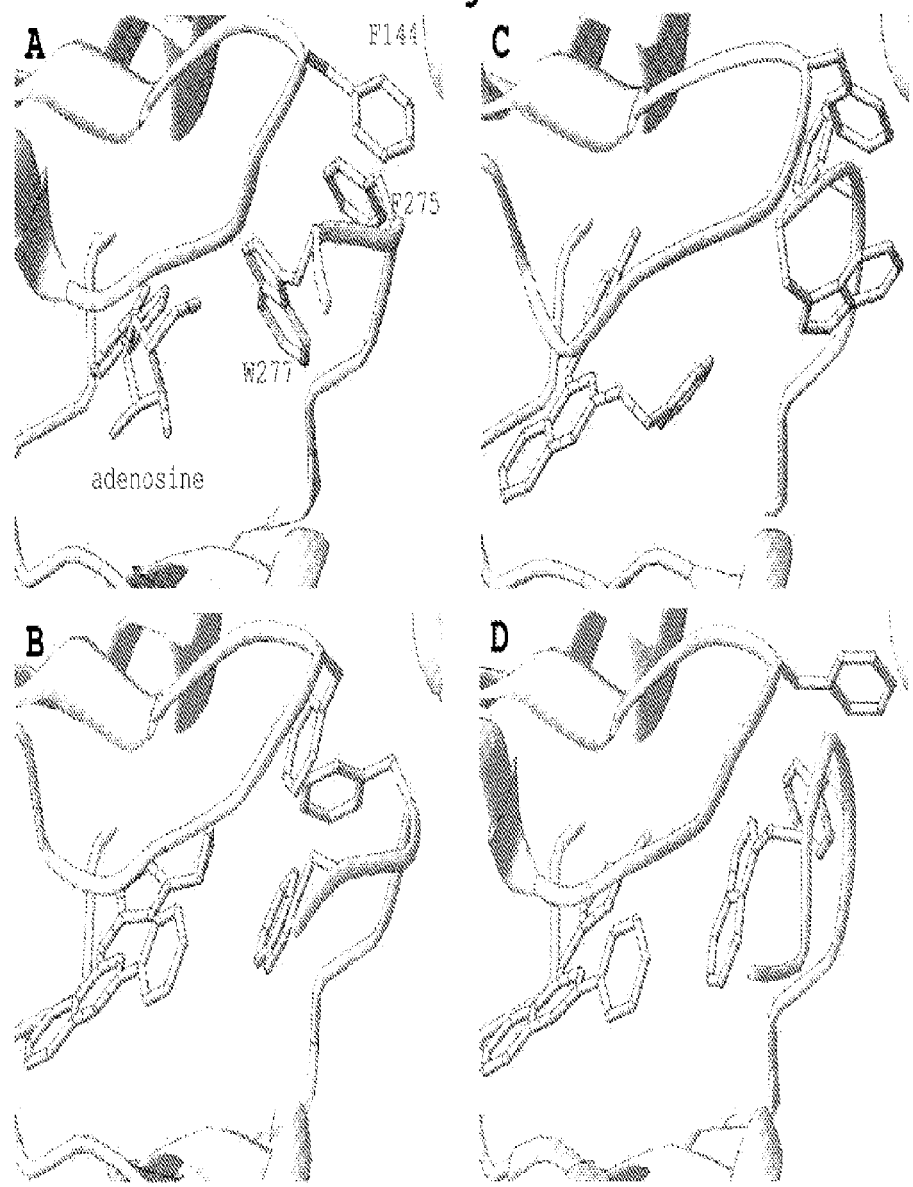

FIG. 8 shows that in each of the Aurora-2-inhibitor crystal structures, the Aurora-2 catalytic active site is partially occupied by the activation loop region (residues 275-279) which forms a unique hydrophobic pocket in the Aurora-2 catalytic active site. In comparison (see FIG. 7) the activation loops of other kinases adopt a more extended and "open" conformation. Residue W277 is conserved in the Aurora-1, Aurora-2 and Aurora-3 catalytic active sites and plays an important role in forming this unique hydrophobic pocket. FIGS. 8A, B, C and D represent the Aurora-2-adenosine, Aurora-2-(5-Cyclopropyl-2H-pyrazol-3-yl)-(2-phenyl-quinazolin-4-yl)-amine, Aurora-2-(5-Methyl-2H-pyrazol-3-yl)-[2-(pyridin-3-ylmethylamino)-quinazolin-4-yl]-amine, Aurora-2-(5-Methylthiazol-2-yl)-(2-phenyl-quinazolin-4-yl)-amine complexes, respectively.

Figure 9:
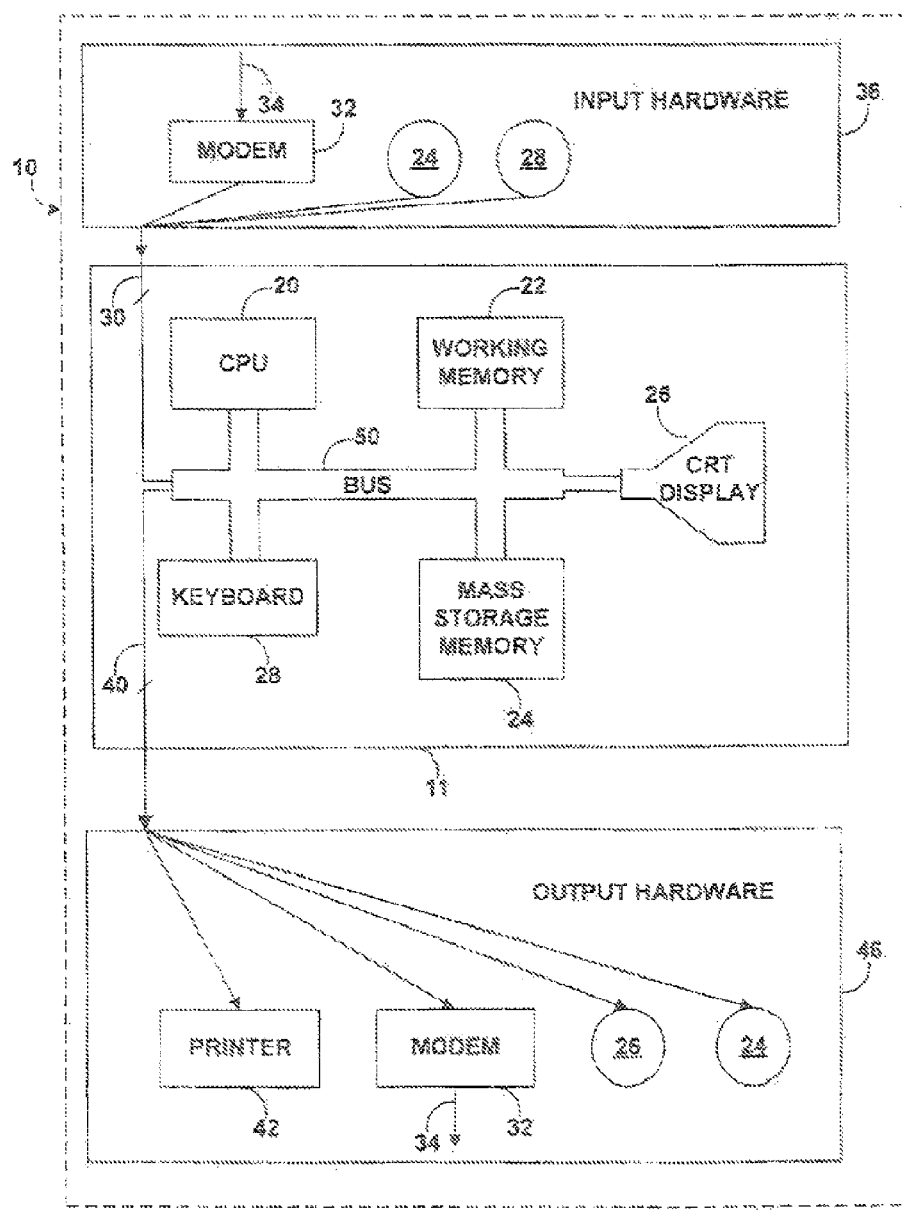
Figure 10:
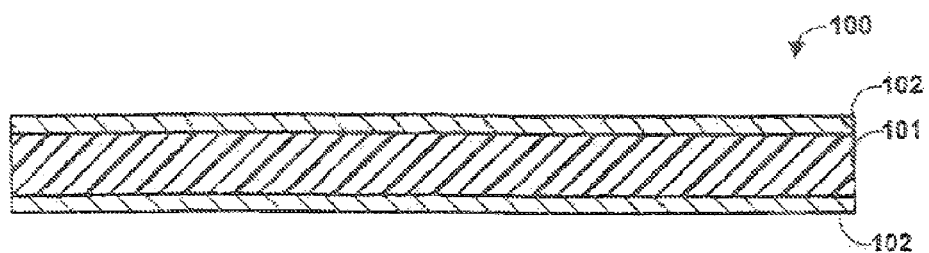
Figure 11:
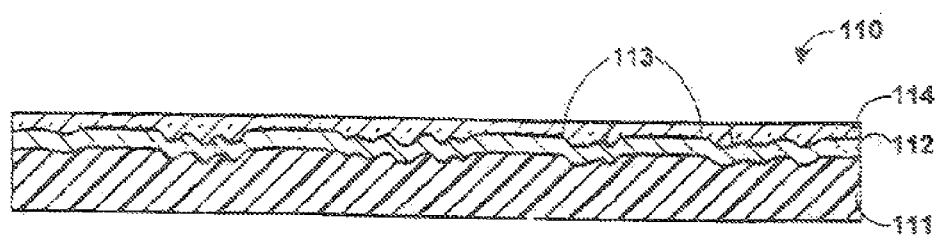

FIG. 9 shows a diagram of a system used to carry out the instructions encoded by the storage medium of FIGS. 10 and 11.

FIG. 10 shows a cross section of a magnetic storage medium.

FIG. 11 shows a cross section of an optically-readable data storage medium.

DETAILED DESCRIPTION OF THE INVENTION

In order that the invention described herein may be more fully understood, the following detailed description is set forth.

Throughout the specification, the word "comprise", or variations such as "comprises" or "comprising" will be understood to imply the inclusion of a stated integer or groups of integers but not exclusion of any other integer or groups of integers.

The following abbreviations are used throughout the application:

A=Ala=Alanine T=Thr=Threonine
V=Val=Valine C=Cys=Cysteine
L=Leu=Leucine Y=Tyr=Tyrosine
I=Ile=Isoleucine N=Asn=Asparagine
P=Pro=Proline Q=Gln=Glutamine
F=Phe=Phenylalanine D=Asp=Aspartic Acid
W=Trp=Tryptophan E=Glu=Glutamic Acid
M=Met=Methionine K=Lys=Lysine
G=Gly=Glycine R=Arg=Arginine
S=Ser=Serine H=His=Histidine As used herein, the following definitions shall apply unless otherwise indicated.

The term "about" when used in the context of RMSD values takes into consideration the standard error of the RMSD value, which is ±0.1 Å.

The term "associating with" refers to a condition of proximity between a chemical entity or compound, or portions thereof, and a binding pocket or binding site on a protein. The association may be non-covalent—wherein the juxtaposition is energetically favored by hydrogen bonding or van der Waals or electrostatic interactions—or it may be covalent.

The term "ATP analogue" refers to a compound derived from adenosine-5'-triphosphate (ATP). The compound can be ADP, or a non-hydrolyzable analogue, such as, but not limited to adenylyl imidodiphosphate (AMPPNP). The analogue may be in complex with magnesium or manganese ions.

The term "Aurora protein" refers to kinases from the Aurora kinase family. Examples of this family of kinases include but are not limited to Aurora-1, Aurora-2, and Aurora-3.

The "Aurora-2 ATP-binding pocket" refers to a binding pocket of a molecule or molecular complex defined by the structure coordinates of a certain set of amino acid residues present in the Aurora-2 structure, as described below. In general, the ligand for the ATP-binding pocket is a nucleotide such as ATP. This binding pocket is in the catalytic active site of the kinase domain. In the protein kinase family, the ATP-binding pocket is generally located at the interface of the α-helical and β-strand sub-domains, and is bordered by the glycine rich loop and the hinge (See, Xie et al., *Structure*, 6, pp. 983-991 (1998), incorporated herein by reference).

The term "Aurora-2 kinase domain" or "Aurora-2-like kinase domain" refers to the catalytic domain of Aurora-2 or Aurora-2-like kinase, respectively. The kinase domain includes, for example, the catalytic active site which comprises the catalytic residues, the activation loop or phosphorylation lip, the DFGWSxxxxxxxRxTxCGTxDYLPPE (SEQ ID NO:2 or DFG motif, and the glycine-rich phosphate anchor or glycine-rich loop (See, Xie et al., Structure, 6, pp. 983-991 (1998); R. Giet and C. Prigent, J. Cell Sci., 112, pp. 3591-3601 (1999), incorporated herein by reference). The kinase domain in the Aurora-2 protein comprises amino acid residues selected from the group consisting of amino acids residues 107-403, 127-403, 107-387, and 127-387 according to SEQ ID NO:1.

The term "Aurora-2-like" refers to all or a portion of a molecule or molecular complex that has a commonality of shape to all or a portion of the Aurora-2 protein. For example, in the Aurora-2-like ATP-binding pocket, the commonality of shape is defined by a root mean square deviation of the structure coordinates of the backbone atoms between the amino acids in the Aurora-2-like ATP-binding pocket and the amino acids in the Aurora-2 ATP-binding pocket (as set forth in FIG. 1, 2, 3 or 4). Compared to an amino acid in the Aurora-2 ATP-binding pocket, the corresponding amino acids in the Aurora-2-like ATP-binding pocket may or may not be identical. Depending on the Aurora-2 amino acid residues that define the Aurora-2-ATP binding pocket, one skilled in the art would be able to locate the corresponding amino acid residues that define an Aurora-2-like-ATP binding pocket in a protein based upon sequence and structural homology.

The term "Aurora-2 protein complex" or "Aurora-2 homologue complex" refers to a molecular complex formed by associating the Aurora-2 protein or Aurora-2 homologue with a chemical entity, for example, a ligand, a substrate, nucleotide triphosphate, nucleotide diphosphate, phosphate, an agonist or antagonist, inhibitor, antibody, drug or compound. In one embodiment, the chemical entity is selected from the group consisting of ATP, an ATP analogue, a nucleotide triphosphate and ATP-binding pocket inhibitor. In another embodiment, the inhibitor is an ATP analogue such as MgAMP-PNP (adenylyl imidodiphosphate), adenosine, (5-Methyl-2H-pyrazol-3-yl)-(2-(pyridin-3-ylmethylamino)-quinazolin-4-yl)-amine, (5-Cyclopropyl-2H-pyrazol-3-yl)-(2-phenyl-quinazolin-4-yl)-amine or (5-Methylthiazol-2-yl)-(2-phenyl-quinazolin-4-yl)-amine.

The term "binding pocket" refers to a region of a molecule or molecular complex, that, as a result of its shape and charge, favorably associates with another chemical entity or compound. The term "pocket" includes, but is not limited to, cleft, channel or site. Aurora-2 or Aurora-2-like molecules may have binding pockets which include, but are not limited to, peptide or substrate binding, ATP-binding and antibody binding sites.

The term "catalytic active site" or "active site" refers to the portion of the protein kinase to which nucleotide substrates bind. For example, the catalytic active site of Aurora-2 is at the interface between the N-terminal, β-strand sub-domain and the C-terminal, α-helical sub-domain, and is bordered by the glycine rich loop and the hinge (See, Xie et al., *Structure*, 6, pp. 983-991 (1998).

The term "chemical entity" refers to chemical compounds, complexes of at least two chemical compounds, and fragments of such compounds or complexes. The chemical entity may be, for example, a ligand, a substrate, a nucleotide triphosphate, a nucleotide diphosphate, phosphate, a nucleotide, an agonist, antagonist, inhibitor, antibody, drug, peptide, protein or compound.

"Conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., *Atlas of Protein Sequence and Structure*, 5, pp. 345-352 (1978 & Supp.), which is incorporated herein by reference. Examples of conservative substitutions are substitutions including but not limited to the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

The term "corresponding amino acid" or "residue which corresponds to" refers to a particular amino acid or analogue thereof in an Aurora-2 protein or Aurora-2 homologue that is identical or functionally equivalent to an amino acid in Aurora-2 according to SEQ ID NO: 1.

Methods for identifying a corresponding amino acid are known in the art and are based upon sequence, structural alignment, its functional position or a combination thereof as compared to the Aurora-2 kinase. For example, corresponding amino acids may be identified by superimposing the backbone atoms of the amino acids in Aurora-2 and the Aurora-2 homologue using well known software applications, such as QUANTA (Accelrys, San Diego, Calif. ©2001, 2002). The corresponding amino acids may also be identified using sequence alignment programs such as the "bestfit" program available from the Genetics Computer Group which uses the local homology algorithm described by Smith and Waterman in *Advances in Applied Mathematics* 2, 482 (1981), which is incorporated herein by reference.

The term "crystallization solution" refers to a solution which promotes crystallization comprising at least one agent including a buffer, one or more salts, a precipitating agent, one or more detergents, sugars or organic compounds, lanthanide ions, a poly-ionic compound, and/or stabilizer.

The term "domain" refers to a portion of the Aurora-2 protein or homologue that can be separated based on its biological function, for example, catalysis. The domain may comprise a binding pocket, a sequence or a structural motif.

The term "fitting operation" refers to an operation that utilizes the structure coordinates of a chemical entity, binding pocket, molecule or molecular complex, or portion thereof, to associate the chemical entity with the binding pocket, molecule or molecular complex, or portion thereof. This may be achieved by positioning, rotating or translating the chemical entity in the binding pocket to match the shape and electrostatic complementarity of the binding pocket. Covalent interactions, non-covalent interactions such as hydrogen bond, electrostatic, hydrophobic, van der Waals interactions, and non-complementary electrostatic interactions such as repulsive charge-charge, dipole-dipole and charge-dipole interactions may be optimized. Alternatively, one may minimize the deformation energy of binding of the chemical entity to the binding pocket.

The term "generating a three-dimensional structure" or "generating a three-dimensional representation" refers to converting the lists of structure coordinates into structural models or graphical representation in three-dimensional space. This can be achieved through commercially or publicly available software. The three-dimensional structure may be displayed or used to perform computer modeling or fitting operations. In addition, the structure coordinates themselves may be used to perform computer modeling and fitting operations.

The term "homology model" refers to a structural model derived from known three-dimensional structure(s). Generation of the homology model, termed "homology modeling", can include sequence alignment, residue replacement, residue conformation adjustment through energy minimization, or a combination thereof.

The term "homologue of Aurora-2" or "Aurora-2 homologue" refers to a molecule that is homologous to Aurora-2 by structure or sequence, but retains the kinase activity of an Aurora protein. Examples of homologues include but are not limited to human Aurora-2 and Aurora-2 from another species with conservative substitutions, additions, deletions or a combination thereof; or another member of the Aurora family of protein kinases including, but not limited to, Aurora-1 and Aurora-3, with conservative substitutions, additions, deletions or a combination thereof.

The term "homologue of Aurora-2 kinase domain" or "Aurora-2 kinase domain homologue" refers to a molecule having amino acids which correspond to the amino acids in the Aurora-2 kinase domain. Examples of homologues include but are not limited to the kinase domain of human Aurora-2 and Aurora-2 from another species with conservative substitutions; or the kinase domain of another member of the Aurora family of protein kinases including, but not limited to, Aurora-1 and Aurora-3, or with conservative substitutions.

The term "molecular complex" or "complex" refers to a molecule associated with at least one chemical entity.

The term "motif" refers to a portion of the Aurora-2 protein or homologue that defines a structural compartment or carries out a function in the protein, for example, catalysis, structural stabilization, or phosphorylation. The motif may be conserved in sequence, structure and function. The motif can be contiguous in primary sequence or three-dimensional space. Examples of a motif include but are not limited to the phosphorylation lip or activation loop, the glycine-rich phosphate anchor loop, the catalytic loop, the DFG or DFG-WSxxxxxxxxRxTxCGTxDYLPPE loop (SEQ ID NO:2) (See, Xie et al., Structure, 6, pp. 983-991 (1998); R. Giet and C. Prigent, J. Cell Sci., 112, pp. 3591-3601 (1999)), and the degradation box.

The term "part of a binding pocket" refers to less than all of the amino acid residues that define the binding pocket. For example, the structure coordinates of residues that constitute part of a binding pocket may be specific for defining the chemical environment of the binding pocket, or useful in designing fragments of an inhibitor that may interact with those residues. For example, the portion of residues may be key residues that play a role in ligand binding, or may be residues that are spatially related and define a three-dimensional compartment of the binding pocket. The residues may be contiguous or non-contiguous in primary sequence.

The term "part of an Aurora-2 kinase domain" or "part of an Aurora-2-like kinase domain" refers to less than all of the Aurora-2 or Aurora-2-like catalytic domain, respectively. The structure coordinates of residues that constitute part of an Aurora-2 or Aurora-2-like kinase domain may be specific for defining the chemical environment of the domain, or useful in designing fragments of an inhibitor that interact with those residues. For example, the portion of residues may be residues that play a role in ligand binding, or may be residues that are spatially related and define a three-dimensional compartment of the domain. The residues may be contiguous or non-contiguous in primary sequence. For example, part of an Aurora-2 kinase domain can be the active site, the DFG or DFGWSxxxxxxxRxTxCGTxDYLPPE motif SEQ ID NO:2), the glycine-rich loop, the activation loop, or the catalytic loop (see Xie et al., supra).

The term "part of an Aurora-2 protein" or "part of an Aurora-2 homologue" refers to less than all of the amino acid residues of an Aurora-2 protein or homologue. In one embodiment, part of an Aurora-2 protein or homologue defines the binding pockets, domains, sub-domains, and motifs of the protein or homologue. The structure coordinates of residues that constitute part of an Aurora-2 protein or homologue may be specific for defining the chemical environment of the protein, or useful in designing fragments of an inhibitor that may interact with those residues. The portion of residues may also be residues that are spatially related and define a three-dimensional compartment of a binding pocket, motif or domain. The residues may be contiguous or non-contiguous in primary sequence. For example, the portion of residues may be key residues that play a role in ligand or substrate binding, peptide binding, antibody binding, catalysis, structural stabilization or degradation.

The term "root mean square deviation" or "RMSD" means the square root of the arithmetic mean of the squares of the deviations from the mean. It is a way to express the deviation or variation from a trend or object. For purposes of this invention, the "root mean square deviation" defines the variation in the backbone of a protein from the backbone of Aurora-2, a binding pocket, a motif, a domain, or portion thereof, as defined by the structure coordinates of Aurora-2 described herein. It would be apparent to the skilled worker that the calculation of RMSD involves a standard error.

The term "soaked" refers to a process in which the crystal is transferred to a solution containing a compound of interest.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

The term "sub-domain" refers to a portion of the domain as defined above in the Aurora-2 protein or homologue. The catalytic kinase domain (amino acid residues selected from the group consisting of amino acids residues 107-403, 127-403, 107-387 and 127-387 according to SEQ ID NO: 1) of Aurora-2 is a bi-lobal structure consisting of an N-terminal, β-strand sub-domain (amino acid residues 127 to 215) and a C-terminal, α-helical sub-domain (amino acid residues 216 to 390).

The term "sufficiently homologous to Aurora-2" refers to a protein that has a sequence homology of at least 20% compared to Aurora-2 protein. In one embodiment, the sequence homology is at least 40%.

The term "three-dimensional structural information" refers to information obtained from the structure coordinates. Structural information generated can include the three-dimensional structure or graphical representation of the structure. Structural information can also be generated when subtracting distances between atoms in the structure coordinates, calculating chemical energies for an Aurora-2 molecule or molecular complex or homologues thereof, calculating or minimizing energies for an association of an Aurora-2 molecule or molecular complex or homologues thereof to a chemical entity.

Crystallizable Compositions and Crystals of Aurora-2 Protein and Protein Complexes According to one embodiment, the invention provides a crystallizable composition or crystal comprising Aurora-2 kinase domain or Aurora-2 kinase domain homologue in the presence or absence of a chemical entity. The Aurora-2 kinase domain may be phosphorylated or unphosphorylated. Preferably, the chemical entity is an ATP analogue, nucleotide triphosphate, nucleotide diphosphate, phosphate, or an ATP-binding pocket inhibitor. More preferably, the chemical entity is MgAMP-PNP (adenylyl imidodiphosphate), adenosine, (5-Methyl-2H-pyrazol-3-yl)-(2-(pyridin-3-ylmethylamino)-quinazolin-4-yl)-amine, (5-Cyclopropyl-2H-pyrazol-3-yl)-(2-phenyl-quinazolin-4-yl)-amine or (5-Methylthiazol-2-yl)-(2-phenyl-quinazolin-4-yl)-amine. In another embodiment, the crystal has a unit cell dimension of a=b=87 Å, c=76 Å, α=β=90°, γ=120° and belongs to space group P3$_2$21. It will be readily apparent to those skilled in the art that the unit cells of the crystal compositions may deviate ±1-2 Å from the above cell dimensions depending on the deviation in the unit cell calculations.

The Aurora-2 protein or its homologue may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products. In a preferred embodiment, the protein is overexpressed in a baculovirus system or an E. coli system. In a more preferred embodiment, the protein is overexpressed in a baculovirus system.

The invention also provides a method of making crystals of Aurora-2 protein or a homologue thereof in the presence or absence of a chemical entity. Such methods comprise the steps of:

a. producing and purifying Aurora-2 protein;
b. combining said Aurora-2 protein, or a homologue thereof in the presence or absence of a chemical entity with a crystallization solution to produce a crystallizable composition; and
c. subjecting said crystallizable composition to, conditions which promote crystallization.

The crystallization solution may include, but is not limited to, polyethylene glycol (PEG) at between about 10% to 30% v/v, 100-300 mM ammonium sulphate and a buffer that maintains pH at between about 4.0 and 8.0. In one embodiment, the crystallization solution comprises 25% PEG 3350, 50 mM 2-(N-morpholino) ethanesulfonic acid (MES) at pH 6.0 and 200 mM ammonium sulphate.

According to one embodiment, the crystallizable composition comprises Aurora-2 protein or a homologue thereof in the presence or absence of a chemical entity. In another embodiment, the crystallizable composition comprises Aurora-2 protein and a chemical entity. In one embodiment, the crystallizable composition further comprises a precipitant, polyethylene glycol (PEG) at between about 10 to 30% v/v, 100-300 mM ammonium sulphate and a buffer that maintains pH at between about 4.0 and 8.0, and optionally a reducing agent, such as dithiothreitol (DTT) at between about 1 to 20 mM. The Aurora-2 protein may be phosphorylated or unphosphorylated. The Aurora-2 protein or complex is preferably 85-100% pure prior to forming the composition. More preferably, the Aurora-2 protein or complex is 90-100% pure. Even more preferably, the Aurora-2 protein or complex is 95-100% pure.

In a preferred embodiment, the crystallizable composition comprises unphosphorylated Aurora-2 protein kinase domain, 25% PEG 3350, 50 mM 2-(N-morpholino)ethanesulfonic acid (MES) at pH 6.0, and 200 mM ammonium sulphate. In a more preferred embodiment, the crystallizable composition comprises unphosphorylated Aurora-2 protein kinase domain, 25% PEG 3350, 50 mM 2-(N-morpholino) ethanesulfonic acid (MES) at pH 6.0, 200 mM ammonium sulphate and a chemical entity selected from the group consisting of an inhibitor and substrate analogue.

In another embodiment, the method of making crystals of Aurora-2 proteins or a homologue thereof in the presence or absence of a chemical entity includes the use of a device for promoting crystallizations. Devices for promoting crystallization can include but are not limited to the hanging-drop, sitting-drop, sandwich-drop, dialysis, microbatch or microtube batch devices (U.S. Pat. Nos. 4,886,646, 5,096,676, 5,130,105, 5,221,410 and 5,400,741; Pav et al., *Proteins: Structure, Function, and Genetics,* 20, pp. 98-102 (1994); Chayen, *Acta. Cryst.,* D54, pp. 8-15 (1998), Chayen, *Structure,* 5, pp. 1269-1274 (1997), D'Arcy et al., J. Cryst. Growth, 168, pp. 175-180 (1996) and Chayen, *J. Appl. Cryst.,* 30, pp. 198-202 (1997), incorporated herein by reference). The hanging-drop, sitting-drop and some adaptations of the microbatch methods (D'Arcy et al., J. Cryst. Growth, 168, pp. 175-180 (1996) and Chayen, *J. Appl. Cryst.,* 30, pp. 198-202 (1997)) produce crystals by vapor diffusion. The hanging drop and sitting drop containing the crystallizable composition is equilibrated against a reservoir containing a higher or lower concentration of precipitant. As the drop approaches equilibrium with the reservoir, the saturation of protein in the solution leads to the formation of crystals.

Microseeding may be used to increase the size and quality of crystals. In this instance, micro-crystals are crushed to yield a stock seed solution. The stock seed solution is diluted in series. Using a needle, glass rod or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

It would be readily apparent to one of skill in the art to vary the crystallization conditions disclosed above to identify other crystallization conditions that would produce crystals of Aurora-2 protein or a homologue thereof in the presence or absence of a chemical entity. Such variations include, but are not limited to, adjusting pH, protein concentration and/or crystallization temperature, changing the identity or concentration of salt and/or precipitant used, using a different method for crystallization, or introducing additives such as detergents (e.g., TWEEN® 20 (monolaurate), LDOA, BRIJ® 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

Binding Pockets of Aurora-2 Protein, Protein Complexes or Homologues Thereof.

As disclosed above, applicants have provided the three-dimensional X-ray crystal structures of three Aurora-2-inhibitor complexes and an Aurora-2-adenosine complex. The crystal structures of Aurora-2 presented here are the first reported within the Aurora subfamily. The invention will be useful for inhibitor design and to study the role of Aurora-1, Aurora-2 and Aurora-3 in cell signaling. The atomic coordinate data is presented in FIGS. 1-4.

In order to use the structure coordinates generated for Aurora-2, its complexes, one of its binding pockets, or an Aurora-2-like binding pocket thereof, it is often times necessary to convert the structure coordinates into a three-dimensional shape. This is achieved through the use of commercially available software that is capable of generating three-dimensional graphical representations of molecules or portions thereof from a set of structure coordinates.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The ATP and substrate binding pockets of this invention will be important for drug design.

In one embodiment, part of binding pocket is at least two amino acid residues, preferably, E211 and A213. In another embodiment, the ATP-binding pocket comprises amino acids of L139, L194, L210, E211, A213, L263 and W277 according to any one of FIGS. 1-4. These were common residues found in the ATP-binding pockets of each of the protein complexes described in the present invention.

In another embodiment, the ATP-binding pocket comprises amino acids L139, G140, F144, V147, A160, K162, L194, L210, E211, Y212, A213, P214, L215, T217, R220, L263, A273, and W277 according to the structure of Aurora-2-(5-Methyl-2H-pyrazol-3-yl)-(2-(pyridin-3-ylmethylamino)-quinazolin-4-yl)-amine complex in FIG. 3. In another embodiment, the ATP-binding pocket comprises amino acids L139, G140, F144, V147, A160, K162, L194, L210, E211, Y212, A213, P214, L215, T217, R220, L263, A273, W277 and S278 according to the structure of Aurora-2-(5-Cyclopropyl-2H-pyrazol-3-yl)-(2-phenyl-quinazolin-4-yl)-amine complex in FIG. 1, or Aurora-2-adenosine complex in FIG. 4. In yet another embodiment, the ATP-binding pocket comprises amino acids L139, G140, F144, V147, A160, K162, L194, L210, E211, Y212, A213, P214, L215, T217, R220, L263, A273, W277, S278, and V279 according to the structure of Aurora-2-(5-Methylthiazol-2-yl)-(2-phenyl-quinazolin-4-yl)-amine complex in FIG. 2. The above-identified amino acid residues were within 5 Å ("5 Å sphere amino acids") of the inhibitor bound in the ATP-binding pockets. These residues were identified using the program QUANTA (Molecular Simulations, Inc., San Diego, Calif. ©1998, 2000), O (T. A. Jones et al., Acta Cryst., A47, pp. 110-119 (1991)) and RIBBONS (Carson, J. Appi. Cryst., 24, pp. 958-961 (1991)), which allow the display and output of all residues within 5 Å from the inhibitor.

In another embodiment, the ATP-binding pocket comprises amino acids 8137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275 and W277 according to the structure of Aurora-2-(5-Methyl-2H-pyrazol-3-yl)-(2-(pyridin-3-ylmethylamino)-quinazolin-4-yl)-amine complex in FIG. 3. In another embodiment, the ATP-binding pocket comprises amino acids R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, and 5278 according to the structure of Aurora-2-(5-Cyclopropyl-2H-pyrazol-3-yl)-(2-phenyl-quinazolin-4-yl)-amine complex in FIG. 1, or Aurora-2-adenosine complex in FIG. 4. In yet another embodiment, the ATP-binding pocket comprises amino acids R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, S278, and V279 according to the structure of Aurora-2-(5-Methylthiazol-2-yl)-(2-phenyl-quinazolin-4-yl)-amine complex in FIG. 2. These amino acids residues were within 8 Å ("8 Å sphere amino acids") of the inhibitor bound in the ATP-binding pockets. These residues were identified using the programs QUANTA, O and RIBBONS, supra.

Using a multiple alignment program to compare each Aurora-2 structure and structures of other members of the protein kinase family (Gerstein et al., J. Mol. Biol., 251, pp. 161-175 (1995), incorporated herein by reference), the above amino acids were identified as the ATP-binding pocket. For the comparison, first, a sequence alignment between members of the protein kinase family including GSK-3β (PDB Accession number 1IO9), p38 (K. P. Wilson et al., J. Biol. Chem., 271, pp. 27696-27700 (1996); Z. Wang et al., Proc. Natl. Acad. Sci. U.S.A., 94, pp. 2327-32 (1997)), cdk2 (PDB Accession number 1B38), SRC (Xu, W., et al., Cell 3, pp. 629-638 (1999); PDB Accession number 2SRC), MAPKAP2 (U.S. Provisional application 60/337,513), and ERK2 (Zhang et al., Nature, 367, pp. 704-711 (1994); PDB Accession number 1ERK) is performed. Second, a putative core is constructed by superimposing a series of corresponding structures in the protein kinase family. Third, residues of high spatial variation are discarded, and the core alignment is iteratively refined. The amino acids that make up the final core structure have low structural variance and have the same local and global conformation relative to the corresponding residues in the protein family.

Therefore, in another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275 and W277 according to the structure of the Aurora-2-(5-Methyl-2H-pyrazol-3-yl)-(2-(pyridin-3-ylmethylamino)-quinazolin-4-yl)-amine complex in FIG. 3.

In another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277 and S278 according to the structure of the Aurora-2-(5-Cyclopropyl-2H-pyrazol-3-yl)-(2-phenyl-quinazolin-4-yl)-amine complex in FIG. 1 or Aurora-2-adenosine complex in FIG. 4.

In another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278 and V279 according to the structure of the Aurora-2-(5-Methylthiazol-2-yl)-(2-phenyl-quinazolin-4-yl)-amine complex in FIG. 2.

It will be readily apparent to those of skill in the art that the numbering of amino acids in other homologues of Aurora-2 may be different than that set forth for Aurora-2. Corresponding amino acids in homologues of Aurora-2 are easily identified by visual inspection of the amino acid sequences or by using commercially available sequence homology, structural homology or structure superimposition software programs.

Those of skill in the art understand that a set of structure coordinates for a molecule or a molecular-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated as a result of mathematical manipulations of the Aurora-2 structure coordinates. For example, the structure coordinates set forth in FIG. 1, 2, 3 or 4 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within a certain root mean square deviation as compared to the original coordinates, the resulting three-dimensional shape is considered encompassed by this invention. Thus, for example, a ligand that binds to the binding pocket of Aurora-2 would also be expected to bind to another binding pocket whose structure coordinates define a shape that falls within the acceptable root mean square deviation.

Various computational analyses may be necessary to determine whether a binding pocket, motif, domain or portion thereof of a molecule or molecular complex is sufficiently similar to the binding pocket, motif, domain or portion thereof of Aurora-2. Such analyses may be carried out using well known software applications, such as ProFit (A. C. R. Martin, SciTech Software, ProFit version 1.8, University College London, www.bioinf.org.uk/software), Swiss-Pdb Viewer (Guex et al., *Electrophoresis,* 18, pp. 2714-2723 (1997)), the Molecular Similarity application of QUANTA (Molecular Simulations Inc., San Diego, Calif. © 1998, 2000) and as described in the accompanying User's Guide, which are incorporated herein by reference.

The above programs permit comparisons between different structures, different conformations of the same structure, and different parts of the same structure. The procedure used in QUANTA (Molecular Simulations, Inc., San Diego, Calif. ©1998, 2000) and Swiss-Pdb Viewer to compare structures is divided into four steps: 1) load the structures to be compared; 2) define the atom equivalences in these structures; 3) perform a fitting operation on the structures; and 4) analyze the results.

The procedure used in ProFit to compare structures includes the following steps: 1) load the structures to be compared; 2) specify selected residues of interest; 3) define the atom equivalences in the selected residues; 4) perform a fitting operation on the selected residues; and 5) analyze the results.

Each structure in the comparison is identified by a name. One structure is identified as the target (i.e., the fixed structure); all remaining structures are working structures (i.e., moving structures). Since atom equivalency within the above programs is defined by user input, for the purpose of this invention we will define equivalent atoms as protein backbone atoms (N, Cα, C and O) for Aurora-2 amino acids and corresponding amino acids in the structures being compared.

The corresponding amino acids may be identified by sequence alignment programs such as the "bestfit" program available from the Genetics Computer Group which uses the local homology algorithm described by Smith and Waterman in *Advances in Applied Mathematics* 2, 482 (1981), which is incorporated herein by reference. A suitable amino acid sequence alignment will require that the proteins being aligned share minimum percentage of identical amino acids. Generally, a first protein being aligned with a second protein should share in excess of about 35% identical amino acids [Hanks et al., *Science,* 241, 42 (1988); Hanks and Quinn, *Methods in Enzymology,* 200, 38 (1991)]. The identification of equivalent residues can also be assisted by secondary structure alignment, for example, aligning the α-helices, β-sheets in the structure. The program Swiss-Pdb Viewer has its own best fit algorithm that is based on secondary sequence alignment.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by the above programs. The Swiss-Pdb Viewer program sets an RMSD cutoff for eliminating pairs of equivalent atoms that have high RMSD values. An RMSD cutoff value can be used to exclude pairs of equivalent atoms with extreme individual RMSD values. In the program ProFit, the RMSD cutoff value can be specified by the user.

The rigid fitting between structures was performed by QUANTA and then inputted into the program ProFit, from which the RMSD values were determined. For the 5 Å and 8 Å sphere amino acids, the RMSD values of the ATP-binding pocket between the Aurora-2-adenosine complex and the Aurora-2-inhibitor complexes are 0.61-0.77 Å and 0.58-0.64 Å, respectively. The comparison of the entire kinase domain between the Aurora-2 structures in the present invention yields RMSD values in the range of 0.61-0.77 Å using Aurora-2-adenosine as a reference. The RMSD values are averages of individual RMSD values calculated for the backbone atoms (C, O, N and Cα) of all residues in the kinase or ATP-binding pocket between the reference structure and the other Aurora-2-inhibitor complex structures.

For the purpose of this invention, any molecule, molecular complex, binding pocket, motif, domain thereof or portion thereof that is within a root mean square deviation for backbone atoms (N, Cα, C, O) when superimposed on the relevant backbone atoms described by structure coordinates listed in FIGS. 1-4 are encompassed by this invention.

Therefore, one embodiment of this invention provides a molecule or molecular complex comprising all or part of an Aurora-2 ATP-binding pocket defined by structure coordinates of a set of amino acid residues that correspond to Aurora-2 amino acid residues L139, L194, L210, E211, A213, L263, and W277 according to any one of FIGS. 1-4, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, and W277 according to FIG. 3, wherein the root mean square-deviation (RMSD) of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, W277, and 5278 according to FIG. 1 or 4, wherein the root mean square deviation (RMSD) of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, W277, S278, and V279 according to FIG. 2, wherein the root mean square deviation (RMSD) of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, and W277 according to FIG. 3, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277 and 5278 according to FIG. 1 or 4, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, S278, and V279 according to FIG. 2, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, 5245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, and W277 according to FIG. 3, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, v182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, 5245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, and S278 according to FIG. 1 or 4, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, V182, E183, Q185, H190, N192, I193, L194, 8195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, 5249, K250, R251, V252, I253, H254, R255, D256, I257, K258, P259, E260, N261, L262, L263, L264, G265, S266, G268, E269, L270, K271, I272, A273, D274, F275, W277, S278, and V279 according to FIG. 2, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising a protein defined by structure coordinates of a set of amino acid residues which correspond to Aurora-2 amino acid residues according to FIG. 1, 2, 3 or 4, wherein the root mean square deviation between said set of amino acid residues of said molecule or molecular complex and said Aurora-2 amino acid residues is not more than about 5 Å. In one embodiment, the RMSD is not greater than about 4 Å. In one embodiment, the RMSD is not greater than about 3 Å. In one embodiment, the RMSD is not greater than about 2 Å. In one embodiment, the RMSD is not greater than about 1.5 Å. In another embodiment, the RMSD is not greater than about 1 Å. In one embodiment, the RMSD is not greater than about 0.8 Å. In one embodiment, the RMSD is not greater than about 0.5 Å.

In one embodiment, the above molecules or molecular complexes are in crystalline form.

Computer Systems

According to another embodiment, this invention provided a machine-readable data storage medium, comprising a data storage material encoded with machine-readable data, wherein said data defines the above-mentioned molecules or molecular complexes. In one embodiment, the data defines the above-mentioned binding pockets by comprising the structure coordinates of said amino acid residues according to any one of FIG. 1-4. To use the structure coordinates generated for Aurora-2, homologues thereof, or one of its binding pockets, it is at times necessary to convert them into a three-dimensional shape. This is achieved through the use of commercially or publicly available software that is capable of generating a three-dimensional structure of molecules or portions thereof from a set of structure coordinates. The three-dimensional structure may be displayed as a graphical representation.

Therefore, according to another embodiment, this invention provides a machine-readable data storage medium comprising a data storage material encoded with machine readable data. In one embodiment, a machine programmed with instructions for using said data, is capable of generating a three-dimensional structure of any of the molecule or molecular complexes, or binding pockets thereof, that are described herein.

This invention also provides a computer comprising:
(a) a machine-readable data storage medium comprising a data storage material encoded with machine-readable data, wherein said data defines any one of the above molecules or molecular complexes;
(b) a working memory for storing instructions for processing said machine-readable data;
(c) a central processing unit (CPU) coupled to said working memory and to said machine-readable data storage medium for processing said machine readable data and means for generating three-dimensional structural information of said molecule or molecular complex; and
(d) output hardware coupled to said central processing unit for outputting three-dimensional structural information of said molecule or molecular complex, or information produced using said three-dimensional structural information of said molecule or molecular complex.

In one embodiment, the data defines the binding pocket or protein of the molecule or molecular complex.

Three-dimensional data generation may be provided by an instruction or set of instructions such as a computer program or commands for generating a three-dimensional structure or graphical representation from structure coordinates, or by subtracting distances between atoms, calculating chemical energies for an Aurora-2 molecule or molecular complex or homologues thereof, or calculating or minimizing energies for an association of an Aurora-2 molecule or molecular complex or homologues thereof to a chemical entity. The graphical representation can be generated or displayed by commercially available software programs. Examples of software programs include but are not limited to QUANTA [Accelrys ©2001, 2002], O [Jones et al., *Acta Crystallogr. A*47, pp. 110-119 (1991)] and RIBBONS [Carson, *J. Appl. Crystallogr.*, 24, pp. 9589-961 (1991)], which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described in the Rational Drug Design section.

In one embodiment, the computer is executing an instruction such as a computer program for three dimensional data generation.

Information of said binding pocket or information produced by using said binding pocket can be outputted through display terminals, touchscreens, facsimile machines, modems, CD-ROMs printers or disk drives. The information can be in graphical or alphanumeric form.

FIG. 9 demonstrates one version of these embodiments. System (10) includes a computer (11) comprising a central processing unit ("CPU") (20), a working memory (22) which may be, e.g., RAM (random-access memory) or "core" memory, mass storage memory (24) (such as one or more disk drives or CD-ROM drives), one or more cathode-ray tube ("CRT") display terminals (26), one or more keyboards (28), one or more input lines (30), and one or more output lines (40), all of which are, interconnected by a conventional bi-directional system bus (50).

Input hardware (36), coupled to computer (11) by input lines (30), may be implemented in a variety of ways. Machine-readable data of this invention may be inputted via the use of a modem or modems (32) connected by a telephone line or dedicated data line (34). Alternatively or additionally, the input hardware (36) may comprise CD-ROM drives or disk drives (24). In conjunction with display terminal (26), keyboard (28) may also be used as an input device.

Output hardware (46), coupled to computer (11) by output lines (40), may similarly be implemented by conventional devices. By way of example, output hardware (46) may include CRT display terminal (26) for displaying a graphical representation of a binding pocket of this invention using a program such as QUANTA as described herein. Output hardware may also include a printer (42), so that hard copy output may be produced, or a disk drive (24), to store system output for later use. Output hardware may also include a CD or DVD recorder, ZIP™ or JAZ™ drive, or other machine-readable data storage device.

In operation, CPU (20) coordinates the use of the various input and output devices (36), (46), coordinates data accesses from mass storage (24) and accesses to and from working memory (22), and determines the sequence of data processing steps. A number of programs may be used to process the machine-readable data of this invention. Such programs are discussed in reference to the computational methods of drug discovery as described herein. Specific references to components of the hardware system (10) are included as appropriate throughout the following description of the data storage medium.

FIG. 10 shows a cross section of a magnetic data storage medium (100) which can be encoded with a machine-readable data that can be carried out by a system such as system (10) of FIG. 9. Medium (100) can be a conventional floppy diskette or hard disk, having a suitable substrate (101), which may be conventional, and a suitable coating (102), which may be conventional, on one or both sides, containing magnetic domains (not visible) whose polarity or orientation can be altered magnetically. Medium (100) may also have an opening (not shown) for receiving the spindle of a disk drive or other data storage device (24).

The magnetic domains of coating (102) of medium (100) are polarized or oriented so as to encode in manner which may be conventional, machine readable data such as that described herein, for execution by a system such as system (10) of FIG. 9.

FIG. 11 shows a cross section of an optically-readable data storage medium (110) which also can be encoded with such a machine-readable data, or set of instructions, which can be carried out by a system such as system (10) of FIG. 9. Medium (110) can be a conventional compact disk read only memory (CD-ROM) or a rewritable medium such as a magneto-optical disk which is optically readable and magneto-optically writable. Medium (100) preferably has a suitable substrate (111), which may be conventional, and a suitable coating (112), which may be conventional, usually of one side of substrate (111).

In the case of CD-ROM, as is well known, coating (112) is reflective and is impressed with a plurality of pits (113) to encode the machine-readable data. The arrangement of pits is read by reflecting laser light off the surface of coating (112). A protective coating (114), which preferably is substantially transparent, is provided on top of coating (112).

In the case of a magneto-optical disk, as is well known, coating (112) has no pits (113), but has a plurality of magnetic domains whose polarity or orientation can be changed magnetically when heated above a certain temperature, as by a laser (not shown). The orientation of the domains can be read by measuring the polarization of laser light reflected from coating (112). The arrangement of the domains encodes the data as described above.

In one embodiment, the structure coordinates of said molecules or molecular complexes are produced by homology modeling of at least a portion of the structure coordinates of FIG. 1, 2, 3 or 4. Homology modeling can be used to generate structural models of Aurora-2 homologues or other homologous proteins based on the known structure of Aurora-2. This can be achieved by performing one or more of the following steps: performing sequence alignment between the amino acid sequence of an unknown molecule against the amino acid sequence of Aurora-2; identifying conserved and variable regions by sequence or structure; generating structure co-ordinates for structurally conserved residues of the unknown structure from those of Aurora-2; generating conformations for the structurally variable residues in the unknown structure; replacing the non-conserved residues of Aurora-2 with residues in the unknown structure; building side chain conformations; and refining and/or evaluating the unknown structure.

For example, since the protein sequence of the catalytic domains of Aurora-2 and Aurora-1 or Aurora-3 can be aligned relative to each other, it is possible to construct models of the structures of Aurora-1 or Aurora-3, particularly in the regions of the active site, using the Aurora-2 structure. Software programs that are useful in homology modeling include XALIGN [Wishart, D. S. et al., *Comput. Appl. Biosci.*, 10, pp. 687-88 (1994)] and CLUSTAL W Alignment Tool [Higgins D. G. et al., *Methods Enzymol.*, 266, pp. 383-402 (1996)]. See also, U.S. Pat. No. 5,884,230. Thege references are incorporated herein by reference.

To perform the sequence alignment, programs such as the "bestfit" program available from the Genetics Computer Group [Waterman in *Advances in Applied Mathematics* 2, 482 (1981), which is incorporated herein by reference] and CLUSTAL W Alignment Tool [Higgins D. G. et al., *Methods Enzymol.*, 266, pp. 383-402 (1996), which is incorporated by reference] can be used. To model the amino acid side chains of Aurora-1 or Aurora-3, the amino acid residues in Aurora-2 can be replaced, using a computer graphics program such as "O" [Jones et al, (1991) *Acta Cryst. Sect. A*, 47: 110-119], by those of the homologous protein, where they differ. The same orientation or a different orientation of the amino acid can be used. Insertions and deletions of amino acid residues may be necessary where gaps occur in the sequence alignment. However, certain portions of the active site of Aurora-2 and its homologues are highly conserved with essentially no insertions and deletions.

Homology modeling can be performed using, for example, the computer programs SWISS-MODEL available through Glaxo Wellcome Experimental Research in Geneva, Switzerland; WHATIF available on EMBL servers; Schnare et al., *J. Mol. Biol*, 256: 701-719 (1996); Blundell et al., *Nature* 326: 347-352 (1987); Fetrow and Bryant, *Bio/Technology* 11:479-484 (1993); Greer, *Methods in Enzymology* 202: 239-252 (1991); and Johnson et al, *Crit. Rev. Biochem. Mol. Biol.* 29:1-68 (1994). An example of homology modeling can be found, for example, in Szklarz G. D., *Life Sci.* 61: 2507-2520 (1997). These references are incorporated herein by reference.

Thus, in accordance with the present invention, data capable of generating the three dimensional structure of the above molecules or molecular complexes, or binding pockets thereof, can be stored in a machine-readable storage medium, which is capable of displaying a graphical three-dimensional representation of the structure.

Rational Drug Design

The Aurora-2 structure coordinates or the three-dimensional graphical representation generated from these coordinates may be used in conjunction with a computer for a variety of purposes, including drug discovery.

For example, the structure encoded by the data may be computationally evaluated for its ability to associate with chemical entities. Chemical entities that associate with Aurora-2 may inhibit Aurora-2 or its homologues, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention provides a method for designing, selecting and/or optimizing a chemical entity that binds to all or part of the molecule or molecular complex comprising the steps of:
 (a) providing the structure coordinates of said molecule or molecular complex on a computer comprising the means for generating three-dimensional structural information of all or part of said molecule or molecular complex from said structure coordinates; and
 (b) designing, selecting and/or optimizing said chemical entity by employing means for performing a fitting operation between said chemical entity and said three-dimensional structural information of all or part of said molecule or molecular complex.

In one embodiment, the method is for designing, selecting and or optimizing a chemical entity that binds with the binding pocket of a molecule or molecular complex. In one embodiment, the above method further comprises the following steps before step (a):
 (c) producing a crystal of a molecule or molecular complex comprising Aurora-2 or homologue thereof;
 (d) determining the three-dimensional structure coordinates of the molecule or molecular complex by X-ray diffraction of the crystal; and
 (e) identifying all or part of said binding pocket.

Three-dimensional structural information in step (a) may be generated by instructions such as a computer program or commands that can generate a three-dimensional structure or graphical representation; subtract distances between atoms; calculate chemical energies for an Aurora-2 molecule, molecular complex or homologues thereof; or calculate or minimize energies of an association of Aurora-2 molecule, molecular complex or homologues thereof to a chemical entity. These types of computer programs are known in the art. The graphical representation can be generated or displayed by commercially available software programs. Examples of software programs include but are not limited to QUANTA [Accelrys ©2001, 2002], O [Jones et al., *Acta Crystallogr.* A47, pp. 110-119 (1991)] and RIBBONS [Carson, *J. Appl. Crystallogr.*, 24, pp. 9589-961 (1991)], which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described below.

Thus, according to another embodiment, the invention provides a method for evaluating the potential of a chemical entity to associate with all or part of a molecule or molecular complex as described previously in the different embodiments.

This method comprises the steps of: (a) employing computational means to perform a fitting operation between the chemical entity and all or part of the molecule or molecular complex described before; (b) analyzing the results of said fitting operation to quantify the association between the chemical entity and all or part of the molecule or molecular complex; and optionally (c) outputting said quantified association to a suitable output hardware, such as a CRT display terminal, a CD or DVD recorder, ZIP™ or JAZ™ drive, a disk drive, or other machine-readable data storage device, as described previously. The method may further comprise generating a three-dimensional structure, graphical representation thereof, or both of all or part of the molecule or molecular complex prior to step (a). In one embodiment, the method is for evaluating the ability of a chemical entity to associate with all or part of the binding pocket of a molecule or molecular complex.

In another embodiment, the invention provides a method for screening a plurality of chemical entities to associate at a deformation energy of binding of less than −7 kcal/mol with said binding pocket:
   (a) employing computational means, which utilize said structure coordinates to perform a fitting operation between one of said chemical entities from the plurality of chemical entities and said binding pocket;
   (b) quantifying the deformation energy of binding between the chemical entity and the binding pocket;
   (c) repeating steps (a) and (b) for each remaining chemical entity; and
   (d) outputting a set of chemical entities that associate with the binding pocket at a deformation energy of binding of less than −7 kcal/mol to a suitable output hardware.

In another embodiment, the method comprises the steps of:
   (a) constructing a computer model of a binding pocket of the molecule or molecular complex;
   (b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of an Aurora-2 protein or homologue thereof;
   (c) employing computational means to perform a fitting operation between computer models of said chemical entity to be evaluated and said binding pocket in order to provide an energy-minimized configuration of said chemical entity in the binding pocket; and
   (d) evaluating the results of said fitting operation to quantify the association between said chemical entity and the binding pocket model, whereby evaluating the ability of said chemical entity to associate with said binding pocket.

In another embodiment, the invention provides a method of using a computer for evaluating the ability of a chemical entity to associate with all or part of the molecule or molecular complex, wherein said computer comprises a machine-readable data storage medium comprising a data storage material encoded with said structure coordinates defining said binding pocket and means for generating a three-dimensional graphical representation of the binding pocket, and wherein said method comprises the steps of:
   (a) positioning a first chemical entity within all or part of said binding pocket using a graphical three-dimensional representation of the structure of the chemical entity and the binding pocket;
   (b) performing a fitting operation between said chemical entity and said binding pocket by employing computational means;
   (c) analyzing the results of said fitting operation to quantitate the association between said chemical entity and all or part of the binding pocket; and
   (d) outputting said quantitated association to a suitable output hardware.

The above method may further comprise the steps of:
   (e) repeating steps (a) through (d) with a second chemical entity; and
   (f) selecting at least one of said first or second chemical entity that associates with all or part of said binding pocket based on said quantitated association of said first or second chemical entity.

Alternatively, the structure coordinates of the Aurora-2 binding pockets may be utilized in a method for identifying an agonist or antagonist of a molecule comprising a binding pocket of Aurora-2. This method comprises the steps of:
   (a) using a three-dimensional structure of the molecule or molecular complex to design or select a chemical entity;
   (b) contacting the chemical entity with the molecule and molecular complex;
   (c) monitoring the activity of the molecule or molecular complex; and
   (d) classifying the chemical entity as an agonist or antagonist based on the effect of the chemical entity on the activity of the molecule or molecular complex.

In one embodiment, step (a) is using a three-dimensional structure of the binding pocket of the molecule or molecular complex. In another embodiment, the three-dimensional structure is displayed as a graphical representation.

In another embodiment, the method comprises the steps of:
   (a) constructing a computer model of a binding pocket of the molecule or molecular complex;
   (b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of an Aurora-2 protein or homologue thereof;
   (c) employing computational means to perform a fitting operation between computer models of said chemical entity to be evaluated and said binding pocket in order to provide an energy-minimized configuration of said chemical entity in the binding pocket; and
   (d) evaluating the results of said fitting operation to quantify the association between said chemical entity and the binding pocket model, whereby evaluating the ability of said chemical entity to associate with said binding pocket;
   (e) synthesizing said chemical entity; and
   (f) contacting said chemical entity with said molecule or molecular complex to determine the ability of said compound to activate or inhibit said molecule.

In one embodiment, the invention provides a method of designing a compound or complex that associates with all or part of the binding pocket comprising the steps of:
   (a) providing the structure coordinates of said binding pocket or protein on a computer comprising the means for generating three-dimensional structural information from said structure coordinates; and (b) using the computer to perform a fitting operation to associate a first chemical entity with all or part of the binding pocket;

(c) performing a fitting operation to associate at least a second chemical entity with all or part of the binding pocket;

(d) quantifying the association between the first and second chemical entity and all or part of the binding pocket;

(e) optionally repeating steps (b) to (d) with another first and second chemical entity, selecting a first and a second chemical entity based on said quantified association of all of said first and second chemical entity;

(f) optionally, visually inspecting the relationship of the first and second chemical entity to each other in relation to the binding pocket on a computer screen using the three-dimensional graphical representation of the binding pocket and said first and second chemical entity; and (g) assembling the first and second chemical entity into a compound or complex that associates with all or part of said binding pocket by model building.

For the first time, the present invention permits the use of molecular design techniques to identify, select and design chemical entities, including inhibitory compounds, capable of binding to Aurora-2 or Aurora-2-like binding pockets, motifs and domains.

Applicants' elucidation of binding pockets on Aurora-2 provides the necessary information for designing new chemical entities and compounds that may interact with Aurora-2 substrate or ATP-binding pockets or Aurora-2-like substrate or ATP-binding pockets, in whole or in part. Due to the homology in the kinase core between Aurora-2, Aurora-1 and Aurora-3, compounds that inhibit Aurora-2 are also expected to inhibit Aurora-1 and Aurora-3, especially those compounds that bind the ATP-binding pocket.

Throughout this section, discussions about the ability of a chemical entity to bind to, associate with or inhibit Aurora-2 binding pockets refer to features of the entity alone. Assays to determine if a compound binds to Aurora-2 are well known in the art and are exemplified below.

The design of compounds that bind to or inhibit Aurora-2 binding pockets according to this invention generally involves consideration of two factors. First, the chemical entity must be capable of physically and structurally associating with parts or all of the Aurora-2 binding pockets. Non-covalent molecular interactions important in this association include hydrogen bonding, van der Waals interactions, hydrophobic interactions and electrostatic interactions.

Second, the chemical entity must be able to assume a conformation that allows it to associate with the Aurora-2 binding pockets directly. Although certain portions of the chemical entity will not directly participate in these associations, those portions of the chemical entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of a chemical entity comprising several chemical entities that directly interact with the Aurora-2 or Aurora-2-like binding pockets.

The potential inhibitory or binding effect of a chemical entity on Aurora-2 binding pockets may be analyzed prior to its actual synthesis and testing by the use of computer modeling techniques. If the theoretical structure of the given entity suggests insufficient interaction and association between it and the Aurora-2 binding pockets, testing of the entity is obviated. However, if computer modeling indicates a strong interaction, the molecule may then be synthesized and tested for its ability to bind to an Aurora-2 binding pocket. This may be achieved by testing the ability of the molecule to inhibit Aurora-2 using the assays described in Example 8. In this manner, synthesis of inoperative compounds may be avoided.

A potential inhibitor of an Aurora-2 binding pocket may be computationally evaluated by means of a series of steps in which chemical entities or fragments are screened and selected for their ability to associate with the Aurora-2 binding pockets.

One skilled in the art may use one of several methods to screen chemical entities or fragments for their ability to associate with an Aurora-2 binding pocket. This process may begin by visual inspection of, for example, an Aurora-2 binding pocket on the computer screen based on the Aurora-2 structure coordinates in any of FIGS. 1-4 or other coordinates which define a similar shape generated from the machine-readable storage medium. Selected fragments or chemical entities may then be positioned in a variety of orientations, or docked, within that binding pocket as defined supra. Docking may be accomplished using software such as QUANTA (Molecular Simulations, Inc., San Diego, Calif. ©1998, 2000) and Sybyl (Tripos Associates, St. Louis, Mo.), followed by energy minimization and molecular dynamics with standard molecular mechanics force fields, such as CHARMM and AMBER.

Specialized computer programs may also assist in the process of selecting fragments or chemical entities. These include:

1. GRID (P. J. Goodford, "A Computational Procedure for Determining Energetically Favorable Binding Sites on Biologically Important Macromolecules", *J. Med. Chem.*, 28, pp. 849-857 (1985)). GRID is available from Oxford University, Oxford, UK.

2. MCSS (A. Miranker et al., "Functionality Maps of Binding Sites: A Multiple Copy Simultaneous Search Method." *Proteins: Structure, Function and Genetics*, 11, pp. 29-34 (1991)). MCSS is available from Molecular Simulations, San Diego, Calif.

3. AUTODOCK (D. S. Goodsell et al., "Automated Docking of Substrates to Proteins by Simulated Annealing", *Proteins: Structure, Function, and Genetics*, 8, pp. 195-202 (1990)). AUTODOCK is available from Scripps Research Institute, La Jolla, Calif.

4. DOCK (I. D. Kuntz et al., "A Geometric Approach to Macromolecule-Ligand Interactions", *J. Mol. Biol.*, 161, pp. 269-288 (1982)). DOCK is available from University of California, San Francisco, Calif.

Once suitable chemical, entities or fragments have been selected, they can be assembled into a single compound or complex. Assembly may be preceded by visual inspection of the relationship of the fragments to each other on the three-dimensional image displayed on a computer screen in relation to the structure coordinates of Aurora-2. This would be followed by manual model building using software such as QUANTA (Molecular Simulations, Inc., San Diego, Calif. ©1998, 2000) or Sybyl (Tripos Associates, St. Louis, Mo.).

Useful programs to aid one of skill in the art in connecting the individual chemical entities or fragments include:

1. CAVEAT (P. A. Bartlett et al., "CAVEAT: A Program to Facilitate the Structure-Derived Design of Biologically Active Molecules", in *Molecular Recognition in Chemical and Biological Problems*, Special Pub., Royal Chem. Soc., 78, pp. 182-196 (1989); G. Lauri and P. A. Bartlett, "CAVEAT: a Program to Facilitate the Design of Organic Molecules", *J. Comput. Aided Mol. Des.,* 8, pp. 51-66 (1994)). CAVEAT is available from the University of California, Berkeley, Calif.

2. 3D Database systems such as ISIS (MDL Information Systems, San Leandro, Calif.). This area is reviewed in Y. C. Martin, "3D Database Searching in Drug Design", J. Med. Chem., 35, pp. 2145-2154 (1992).

3. HOOK (M. B. Eisen et al., "HOOK: A Program for Finding Novel Molecular Architectures that Satisfy the Chemical and Steric Requirements of a Macromolecule Binding Site", *Proteins: Struct., Funct., Genet.,* 19, pp. 199-221 (1994)). HOOK is available from Molecular Simulations, San Diego, Calif.

Instead of proceeding to build an inhibitor of an Aurora-2 binding pocket in a step-wise fashion one fragment or chemical entity at a time as described above, inhibitory or other Aurora-2 binding compounds may be designed as a whole or "de novo" using either an empty binding pocket or optionally including some portion(s) of a known inhibitor(s). There are many de novo ligand design methods including:

1. LUDI (H.-J. Bohm, "The Computer Program LUDI: A New Method for the De Novo Design of Enzyme Inhibitors", *J. Comp. Aid. Molec. Design,* 6, pp. 61-78 (1992)). LUDI is available from Molecular Simulations Incorporated, San Diego, Calif.

2. LEGEND (Y. Nishibata et al., *Tetrahedron,* 47, p. 8985 (1991)). LEGEND is available from Molecular Simulations Incorporated, San Diego, Calif.

3. LeapFrog (available from Tripos Associates, St. Louis, Mo.).

4. SPROUT (V. Gillet et al., "SPROUT: A Program for Structure Generation)", *J. Comput. Aided Mol. Design,* 7, pp. 127-153 (1993)). SPROUT is available from the University of Leeds, UK.

Other molecular modeling techniques may also be employed in accordance with this invention (see, e.g., N. C. Cohen et al., "Molecular Modeling Software and Methods for Medicinal Chemistry", *J. Med. Chem.,* 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", *Curr. Opin. Struct. Biology,* 4, pp. 777-781 (1994)).

Once a chemical entity has been designed or selected by the above methods, the efficiency with which that chemical entity may bind to an Aurora-2 binding pocket may be tested and optimized by computational evaluation. For example, an effective Aurora-2 binding pocket inhibitor must preferably demonstrate a relatively small difference in energy between its bound and free states (i.e., a small deformation energy of binding). Thus, the most efficient Aurora-2 binding pocket inhibitors should preferably be designed with a deformation energy of binding of not greater than about 10 kcal/mole, more preferably, not greater than 7 kcal/mole. Aurora-2 binding pocket inhibitors may interact with the binding pocket in more than one conformation that is similar in overall binding energy. In those cases, the deformation energy of binding is taken to be the difference between the energy of the free chemical entity and the average energy of the conformations observed when the inhibitor binds to the protein.

A chemical entity designed or selected as binding to an Aurora-2 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Molecular Simulations, Inc., San Diego, Calif. ©1998, 2000); Insight II/Discover (Molecular Simulations, Inc., San Diego, Calif. ©1998); DelPhi (Molecular Simulations, Inc., San Diego, Calif. ©1998); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention, is the computational screening of small molecule databases for chemical entities or compounds that can bind in whole, or in part, to an Aurora-2 binding pocket. In this screening, the quality of fit of such entities to the binding pocket may be judged either by shape complementarity or by estimated interaction energy (E. C. Meng et al., *J. Comp. Chem.,* 13, pp. 505-524 (1992)).

According to another embodiment, the invention provides compounds which associate with an Aurora-2 binding pocket produced or identified by the method set forth above.

Another particularly useful drug design technique enabled by this invention is iterative drug design. Iterative drug design is a method for optimizing associations between a protein and a compound by determining and evaluating the three-dimensional structures of successive sets of protein/compound complexes.

In iterative drug design, crystals of a series of protein or protein complexes are obtained and then the three-dimensional structures of each crystal is solved.

Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. High throughput crystallization assays may be used to find a new crystallization condition or to optimize the original protein or complex crystallization condition for the new complex. Alternatively, a pre-formed protein crystal may be soaked in the presence of an inhibitor, thereby forming a protein/compound complex and obviating the need to crystallize each individual protein/compound complex.

Structure Determination of Other Molecules

The structure coordinates set forth in FIGS. 1-4 can also be used to aid in obtaining structural information about other crystallized molecules or molecular complexes. This may be achieved by any of a number of well-known techniques, including molecular replacement.

According to an alternate embodiment, the machine-readable data storage medium comprises a data storage material encoded with a first set of machine readable data which comprises the Fourier transform of at least a portion of the structure coordinates set forth in FIGS. 1-4 or homology model thereof, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex, wherein said computer comprises:
  (a) a machine-readable data storage medium comprising a data storage material encoded with machine-readable data, wherein said data comprises at least a portion of the structure coordinates of Aurora-2 according to any one of FIGS. 1-4 or homology model thereof;
  (b) a machine-readable data storage medium comprising a data storage material encoded with machine-readable data, wherein said data comprises X-ray diffraction data obtained from said molecule or molecular complex; and
  (c) instructions for performing a Fourier transform of the machine-readable data of (a) and for processing said machine-readable data of (b) into structure coordinates.

For example, the Fourier transform of at least a portion of the structure coordinates set forth in any one of FIGS. 1-4 or homology model thereof may be used to determine at least a portion of the structure coordinates of Aurora-2 homologues. In one embodiment, the molecule is an Aurora-2 homologue. In another embodiment, the molecular complex is selected from the group consisting of Aurora-2 complex and Aurora-2 homologue complex.

Therefore, in another embodiment this invention provides a method of utilizing molecular replacement to obtain structural information about a molecule or a molecular complex of unknown structure wherein the molecule or molecular complex is sufficiently homologous to Aurora-2, comprising the steps of:
  (a) crystallizing said molecule or molecular complex of unknown structure;
  (b) generating an X-ray diffraction pattern from said crystallized molecule or molecular complex;
  (c) applying at least a portion of the Aurora-2 structure coordinates set forth in one of FIGS. 1-4 or a homology model thereof to the X-ray diffraction pattern to generate a three-dimensional electron density map of at least a portion of the molecule or molecular complex whose structure is unknown; and
  (d) generating a structural model of the molecule or molecular complex from the three-dimensional electron density map.

In one embodiment, the method is performed using a computer. In another embodiment, the molecule is selected from the group consisting of Aurora-2 and Aurora-2 homologues. In another embodiment, the molecule is an Aurora molecular complex or homologue thereof.

By using molecular replacement, all or part of the structure coordinates of the Aurora-2 as provided by this invention or homology model thereof (and set forth in any one of FIGS. 1-4) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of the Aurora-2 according to any one of FIGS. 1-4 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions", in *Meth. Enzymol.*, 115, pp. 55-77 (1985); M. G. Rossmann, ed., "The Molecular Replacement Method", Int. Sci. Rev. Ser., No. 13, Gordon & Breach, New York (1972)).

The structure of any portion of any crystallized molecule or molecular complex that is sufficiently homologous to any portion of the Aurora-2 can be resolved by this method.

In one embodiment, the method of molecular replacement is utilized to obtain structural information about an Aurora-2 homologue. The structure coordinates of Aurora-2 as provided by this invention are particularly useful in solving the structure of Aurora-2 complexes that are bound by ligands, substrates and inhibitors.

Furthermore, the structure coordinates of Aurora-2 as provided by this invention are useful in solving the structure of Aurora-2 proteins that have amino acid substitutions, additions and/or deletions (referred to collectively as "Aurora-2 mutants", as compared to naturally occurring Aurora-2). These Aurora-2 mutants may optionally be crystallized in co-complex with a chemical entity, such as a non-hydrolyzable ATP analogue or a suicide substrate. The crystal structures of a series of such complexes may then be solved by molecular replacement and compared with that of wild-type Aurora-2. Potential sites for modification within the various binding pockets of the enzyme may thus be identified. This information provides an additional tool for determining the most efficient binding interactions, for example, increased hydrophobic interactions, between Aurora-2 and a chemical entity or compound.

The structure coordinates are also particularly useful in solving the structure of crystals of Aurora-2 or Aurora-2 homologues co-complexed with a variety of chemical entities. This approach enables the determination of the optimal sites for interaction between chemical entities, including candidate Aurora-2 inhibitors. For example, high resolution X-ray diffraction data collected from crystals exposed to different types of solvent allows the determination of where each type of solvent molecule resides. Small molecules that bind tightly to those sites can then be designed and synthesized and tested for their Aurora-2 inhibition activity.

All of the complexes referred to above may be studied using well-known X-ray diffraction techniques and may be refined using 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)) or CNS (Brunger et al., *Acta Cryst.*, D54, pp. 905-921, (1998)).

In order that this invention be more fully understood, the following examples are set forth. These examples are for the purpose of illustration only and are not to be construed as limiting the scope of the invention in any way.

EXAMPLE 1

Expression and Purification of Aurora-2

The expression of Aurora-2 was carried out using standard procedures known in the art. A truncated Aurora-2 (amino acid residues 107-403) (full length sequence: GenBank AF011468; SEQ ID NO: 1) with an N-terminal hexa-histidine tag and a thrombin cleavage site was overexpressed in a baculovirus expression system.

Aurora-2 was purified using Ni/NTA agarose metal affinity chromatography (Qiagen, Hilden, Germany) followed by size-exclusion on a Superdex 200 column (Amersham Pharmacia Biotech, Uppsala, Sweden). The hexa-histidine tag was removed by incubation with thrombin (Calbiochem, La Jolla, Calif.). Incubation overnight incubation at 4° C. with 5 units/mg thrombin produced more than 90% Aurora-2 (amino acid residues 107-403), which was used for crystallographic studies. The reaction was quenched with PMSF (phenylmethylsulfonyl fluoride or α-toluenesulfonyl fluoride) and thrombin was removed with benzamidine sepharose (Pharmacia, Uppsala, Sweden). The protein was applied to a MonoS 10/10 column (Pharmacia, Uppsala, Sweden) equilibrated in 20 mM HEPES, pH 7.3, 10% Glycerol (v/v), 2 mM DTT, and eluted with a linear gradient from 0 to 500 mM NaCl in 80 column volumes. Unphosphorylated Aurora-2 (107-403) eluted at 148 mM NaCl. The protein was dialyzed against 25 mM Tris pH 8.0 containing 200 mM NaCl and 2 mM DTT at 4° C., concentrated to 15 mg/ml, and centrifuged at 100,000×g prior to crystallization. All protein molecular weights were confirmed by electrospray mass spectrometry.

EXAMPLE 2

Formation of Aurora-2-Inhibitor Complex for Crystallization

Crystals of Aurora-2-inhibitor complex crystals were formed by co-crystallizing the protein with the inhibitors or with adenosine. The inhibitor was added to the Aurora-2 protein solution immediately after the final Mono-S purification step and prior to protein concentration (Example 1). Alternatively, inhibitor may be added to the concentrated Aurora-2 protein solution immediately before setting up the crystallization drop.

EXAMPLE 3

Crystallization of Aurora-2 and Aurora-2-Inhibitor Complexes

Crystallization of Aurora-2 was carried out using the hanging drop vapor diffusion technique. The Aurora-2 formed diamond shaped or hexagonal plate-like crystals over a reservoir containing 25% PEG 3350, 50 mM MES pH 6.0, 200 mM ammonium sulphate. The crystallization droplet contained 1 μl of 15 mg ml$^{-1}$ protein solution and 1 μl of reservoir solution. Crystals formed in less than 48 hours.

The formed crystals were transferred to a reservoir solution containing 15% glycerol. After soaking the crystals in 15% glycerol for less than 2 minutes, the crystals were scooped up with a cryo-loop, frozen in liquid nitrogen and stored for data collection.

EXAMPLE 4

X-Ray Data Collection and Structure Determination

The Aurora-2-inhibitor complex structures and the Aurora-2-adenosine structure were solved by molecular replacement using X-ray diffraction data collected either (i) at beam line 5.0.2 of the Advanced Light Source Lawrence Berkeley Laboratory, Berkeley, Calif., USA, (ii) at beam line 14.2 of the CCLRC Synchrotron Radiation Source, Daresbury, Cheshire, UK, or (iii) at beamline X31, DESY, EMBL Outstation, Hamburg, Germany. The diffraction images were processed with the program MOSFLM (A. G. Leslie, *Acta Cryst.*, D55, pp. 1696-1702 (1999)) and the data was scaled using SCALA (Collaborative Computational Project, N., *Acta Cryst.*, D50, pp. 760-763 (1994)).

The data statistics, unit cell parameters and spacegroup of the Aurora-2-(5-Cyclopropyl-2H-pyrazol-3-yl)-(2-phenyl-quinazolin-4-yl)-amine crystal structure is given in Table 1. The starting phases for the Aurora-2 complexes were obtained by molecular replacement using coordinates of GSK-3β (PDB Accession number 1I09) (E. ter Haar, et al., *Nat. Struct. Biol.*, 8, pp. 593-596 (2001)) as a search model in the program AMoRe (J. Navaza, *Acta. Cryst. A*, 50, pp. 157-163 (1994)). The asymmetric unit contained a single Aurora-2 complex. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 127 to 279 and residues 288 to 390. The refined model has a crystallographic R-factor of 26.3% and R-free of 33.2%.

The data statistics, unit cell parameters and spacegroup of the Aurora-2-(5-Methylthiazol-2-yl)-(2-phenyl-quinazolin-4-yl)-amine crystal structure is given in Table 2. The starting phases were obtained by molecular replacement using coordinates of the Aurora-2-(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 120 to 279 and residues 287 to 388. The refined model has a crystallographic R-factor of 25.9% and R-free of 32.8%.

The data statistics, unit cell parameters and spacegroup of the Aurora-2-(5-Methyl-2H-pyrazol-3-yl)-(2-(pyridin-3-yl-methylamino)-quinazolin-4-yl)-amine crystal structure is given in Table 3. The starting phases were obtained by molecular replacement using coordinates of the Aurora-2-(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 128 to 277 and residues 291 to 388. The refined model has a crystallographic R-factor of 23.6% and R-free of 29.1%.

The data statistics, unit cell parameters and spacegroup of the Aurora-2-adenosine crystal structure is given in Table 4. The starting phases were obtained by molecular replacement using coordinates of the Aurora-2-(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 127 to 278 and residues 289 to 387. The refined model has a crystallographic R-factor of 26.4% and R-free of 31.7%.

In the above models, disordered residues were not included in the model. Alanine or glycine residues were used in the model if the side chains of certain residues could not be located in the electron density.

EXAMPLE 5

Overall Structure of Aurora-2

Aurora-2 has the typical bi-lobal catalytic kinase fold or structural domain (S. K. Hanks, et al., *Science,* 241, pp. 42-52 (1988); Hanks, S. K. and A. M. Quinn, *Meth. Enzymol.,* 200, pp. 38-62 (1991)) with a β-strand sub-domain (residues 127-215) at the N-terminal end and an α-helical sub-domain at the C-terminal end (residues 216-385) (FIG. 5). The ATP-binding pocket is at the interface of the α-helical and β-strand domains, and is bordered by the glycine rich loop and the hinge. The activation loop runs along the surface of the catalytic active site. The β-strand domain consists of five anti-parallel β-strands that form a β-barrel structure.
Comparison of the Aurora-2 Structure with Other Kinases Comparison with other kinases such as GSK-3β, CDK2 and p38 revealed that the structure of Aurora-2 closely resembles the substrate-bound activated, form of a kinase. However, a unique feature that is present in all four Aurora-2 crystal structures is the unusual conformation of the activation loop (amino acid residues 273-292). Amino acid residues 275-290 act like a flexible flap that partially occludes the catalytic active site and creates a novel hydrophobic binding pocket in the catalytic active site (FIG. 6). This hydrophobic pocket is unique in that it partially overlaps with the triphosphate binding pocket of the catalytic active site. Comparison of the activation loops of GSK-3β (PDB Accession number 1IO9) (E. ter Haar, et al., *Nat. Struct. Biol.,* 8, pp. 593-596 (2001)), P38 (PDB Accession number 1CM8) (Bellon, S., et al., *Struct. Fold Des.,* 7, pp. 1057-65 (1999)) and substrate-bound activated CDK2 (PDB Accession number 1B38) (N. R. Brown et al., *J. Biol. Chem.,* 274, pp. 8746-8756 (1999)) shows that in other closely related kinases, the activation loop adopts a more extended conformation, irrespective of whether activated protein was used in the crystal structure determination (FIG. 7).

EXAMPLE 6

Catalytic Active Site of Aurora-2-Inhibitor Complexes

The inhibitor (5-Cyclopropyl-2H-pyrazol-3-yl)-(2-phenyl-quinazolin-4-yl)-amine is bound in the deep cleft of the catalytic active site in the Aurora-2 structure (FIG. 6). The inhibitor forms three hydrogen bonds with the hinge portion of the ATP-binding pocket (dotted lines). The 1H pyrazole nitrogen shares a proton with the E211 backbone carbonyl. The other pyrazole nitrogen (position 2) accepts a proton from the A213 backbone nitrogen. Comparison with the adenosine-bound crystal structure reveals that the pyrazole mimics the binding of adenosine, a constituent of the natural ATP substrate.

The side chains of L210 and K162 are positioned inside the ATP-binding pocket. K162 is a catalytically important residue and is unable to make a salt bridge with D274 due to the formation of a unique hydrophobic binding pocket in the Aurora-2 catalytic active site. This lysine-glutamic acid salt bridge is seen in other kinase crystal structures.

FIG. 8 represents the binding pockets for each Aurora-2 complex in the present invention.

EXAMPLE 7

The Use of Aurora-2 Coordinates for Inhibitor Design

The coordinates of any one of FIGS. 1-4 are used to design compounds, including inhibitory compounds, that associate with Aurora-1, Aurora-2, Aurora-3, or homologues of Aurora-1, Aurora-2 or Aurora-3. This process may be aided by using a computer comprising a machine-readable data storage medium encoded with a set of machine-executable instructions, wherein the recorded instructions are capable of displaying a three-dimensional representation of the Aurora-2 or a portion thereof. The graphical representation is used according to the methods described herein to design compounds. Such compounds associate with the Aurora-2 at the ATP-binding pocket or substrate binding pocket.

EXAMPLE 8

Aurora-2 Activity Inhibition Assay

Compounds were screened for their ability to inhibit full length Aurora-2 (AA 1-403) activity using a standard coupled enzyme system (Fox et al., *Protein Sci.,* 7, pp. 2249 (1998)). Reactions were carried out in a solution containing 100 mM HEPES (pH 7.5), 10 mM $MgCl_2$, 25 mM NaCl, 300 µM NADH, 1 mM DTT and 3% DMSO. Final substrate concentrations in the assay were 200 µM ATP (Sigma Chemicals, St Louis, Mo.) and 800 µM peptide (LRRASLG, American Peptide, Sunnyvale, Calif.). Reactions were carried out at 30° C. and with 35 nM Aurora-2. Final concentrations of the components of the coupled enzyme system were 2.5 mM phosphoenolpyruvate, 200 µM NADH, 60 µg/ml pyruvate kinase and 20 µg/ml lactate dehydrogenase.

An assay stock buffer solution was prepared containing all of the reagents listed above with the exception of ATP and the test compound of interest. The assay stock buffer solution (60 µl) was incubated in a 96 well plate with 2 µl of the test compound of interest at final concentrations spanning 0.002 µM to 30 µM at 30° C. for 10 min. Typically, a 12 point titration was conducted by preparing serial dilutions (from 1 mM compound stocks) with DMSO of the test compounds in daughter plates. The reaction was initiated by the addition of 5 µl of ATP (final concentration 200 µM). Rates of reaction were obtained using a Molecular Devices Spectramax plate reader (Sunnyvale, Calif.) over 10 min at 30° C. The Ki values were determined from the rate data as a function of inhibitor concentration using computerized nonlinear regression (Prism 3.0, Graphpad Software, San Diego, Calif.).

EXAMPLE 9

The Use of Aurora-2 Coordinates in the Design of Aurora-Specific Antibodies

The atomic coordinates in any one of FIGS. 1-4 also define, in great detail, the external solvent-accessible, hydrophilic, and mobile surface regions of the Aurora-2 catalytic kinase domain. Anti-peptide antibodies are known to react strongly against highly mobile regions but do not react with well-ordered regions of proteins. Mobility is therefore a major factor in the recognition of proteins by anti-peptide antibodies (J. A. Tainer et al., *Nature*, 312, pp. 127-134 (1984))

One skilled in the art would therefore be able to use the X-ray crystallography data to determine possible antigenic sites in the Aurora-2 kinase domain. Possible antigenic sites are exposed, small and mobile regions on the kinase surface which have atomic B-factors of greater than about 80 $Å^2$ in FIGS. 1, 2, 3 and 4. This information can be used in conjunction with data from immunological studies to design and produce specific monoclonal or polyclonal antibodies.

This process, may be aided by using a computer comprising a machine-readable data storage medium encoded with a set of machine-executable instructions, wherein the recorded instructions are capable of displaying a three-dimensional representation of the Aurora-2 or a portion thereof.

TABLE 1

Summary of data collection for
Aurora-2-(5-Cyclopropyl-2H-pyrazol-3-yl)-
(2-phenyl-quinazolin-4-yl)-amine complex Space Group: $P3_221$
Unit Cell: $a = b = 87 Å, c = 76 Å; \alpha = \beta = 90°, \gamma = 120°$

| | |
|---|---|
| Source | ALS 5.0.2 |
| Wavelength (Å) | 1.1 |
| Resolution (Å) | 2.7 |
| No. of Reflections (measured/unique) | 62,585/9,773 |
| Completeness (%) (overall/outer shell) | 99.4/99.4 |
| I/σ(I) (overall/outer shell) | 23.1/1.9 |
| $R_{merge}$* (%) (overall/outer shell) | 4.9/39 |
| Molecules per asymmetric unit | 1 |
| Structure refinement | |
| Resolution (Å) | 30-2.7 |
| No. of reflections | 7381 |
| R factor | 26.3 |
| Free R factor † | 33.2 |
| RMSD values Bond lengths/angles | 0.005/2.5° |

*$R_{merge} = 100 \times \Sigma_h\Sigma_i @I_{hi} - <I_h> @/\Sigma_h\Sigma_iI_{hi}$.
† The Free R factor was calculated with 7.9% of the data.

TABLE 2

Summary of data collection for
Aurora-2-(5-Methylthiazol-2-yl)-
(2-phenyl-quinazolin-4-yl)-amine complex Space Group: $P3_221$
Unit Cell: $a = b = 87 Å, c = 76 Å; \alpha = \beta = 90°, \gamma = 120°$

| | |
|---|---|
| Source | Daresbury SRS 14.2 |
| Wavelength (Å) | 0.98 |
| Resolution (Å) | 2.5 |

TABLE 2-continued

Summary of data collection for
Aurora-2-(5-Methylthiazol-2-yl)-
(2-phenyl-quinazolin-4-yl)-amine complex

| | |
|---|---|
| No. of Reflections (measured/unique) | 113,308/12,094 |
| Completeness (%) (overall/outer shell) | 99.8/99.8 |
| I/σ(I) (overall/outer shell) | 18.2/1.5 |
| $R_{merge}$* (%) (overall/outer shell) | 8.2/46 |
| Molecules per asymmetric unit | 1 |
| Structure refinement | |
| Resolution (Å) | 30-2.5 |
| No. of reflections | 9318 |
| R factor | 25.9 |
| Free R factor †† | 32.8 |
| RMSD values Bond lengths/angles | 0.011/1.9° |

*$R_{merge} = 100 \times \Sigma_h\Sigma_i @I_{hi} - <I_h> @/\Sigma_h\Sigma_iI_{hi}$.
†† The Free R factor was calculated with 8.1% of the data.

TABLE 3

Summary of data collection for
Aurora-2-(5-Methyl-2H-pyrazol-3-yl)-
(2-(pyridin-3-ylmethylamino)-quinazolin-4-yl)-amine complex Space Group: $P3_221$
Unit Cell: $a = b = 87 Å, c = 76 Å; \alpha = \beta = 90°, \gamma = 120°$

| | |
|---|---|
| Source | Daresbury SRS 14.2 |
| Wavelength (Å) | 0.98 |
| Resolution (Å) | 3.1 |
| No. of Reflections (measured/unique) | 23,387/5,359 |
| Completeness (%) (overall/outer shell) | 99.8/99.8 |
| I/σ(I) (overall, shell) | 15.9/2.5 |
| $R_{merge}$* (%) (overall/outer shell) | 8.6/41 |
| Molecules per asymmetric unit | 1 |
| Structure refinement | |
| Resolution (Å) | 30-3.3 |
| No. of reflections | 4409 |
| R factor | 23.6 |
| Free R factor ††† | 29.1 |
| RMSD values Bond lengths/angles | 0.011/1.78° |

*$R_{merge} = 100 \times \Sigma_h\Sigma_i @I_{hi} - <I_h> @/\Sigma_h\Sigma_iI_{hi}$.
††† The Free R factor was calculated with 4.3% of the data.

TABLE 4

Summary of data collection for Aurora-2-adenosine complex

Space Group: $P3_221$
Unit Cell: $a = b = 87 Å, c = 76 Å; \alpha = \beta = 90°, \gamma = 120°$

| | |
|---|---|
| Source | EMBL Hamburg X31 |
| Wavelength (Å) | 0.8 |
| Resolution (Å) | 3.2 |
| No. of Reflections (measured/unique) | 12,545/5,355 |
| Completeness (%) (overall/outer shell) | 96.5/96.5 |
| I/σ(I) (overall/outer shell) | 14.5/1.2 |
| $R_{merge}$* (%) (overall/outer shell) | 5.0/46.8 |
| Molecules per asymmetric unit | 1 |

TABLE 4-continued

Summary of data collection for Aurora-2-adenosine complex

Structure refinement

| | |
|---|---|
| Resolution (Å) | 20-3.2 |
| No. of reflections | 4016 |
| R factor | 26.4 |
| Free R factor ††† | 31.7 |

TABLE 4-continued

Summary of data collection for Aurora-2-adenosine complex

| | |
|---|---|
| RMSD values Bond lengths/angles | 0.013/1.65° |

*$R_{merge} = 100 \times \Sigma_h \Sigma_i @I_{hi} - <I_h> @/\Sigma_h \Sigma_i I_{hi}$.

††† The Free R factor was calculated with 4.0% of the data.

We claim:

1. A crystalline composition comprising amino acid residues 107-403 of SEQ ID NO:1, and a ligand, wherein said crystalline composition is characterized with space group P3$_2$21 and has unit cell parameters a=b=87±2Å; c=76±2Å; α,β=90° and γ=120°.

2. The crystalline composition according to claim 1, wherein said ligand is selected from the group consisting of: (5-Methyl-2H-pyrazol-3-yl)-(2-(pyridin-3-ylmethylamino)-quinazolin-4-yl)-amine; (5-Cyclopropyl-2H-pyrazol-3-yl)-(2-phenyl-quinazolin-4-yl)-amine; (5-Methylthiazol-2-yl)-(2-phenyl-quinazolin-4-yl)-amine; and adenosine.

3. A molecular complex comprising:
   amino acid residues 107-403 of SEQ ID NO:1, and a ligand,
   wherein said molecular complex forms a crystalline composition characterized with space group P3$_2$21 and unit cell parameters a=b=87±2Å; c=76±2Å; α,β=90° and γ=120° when crystallized from a crystallization solution,
   wherein said crystallization solution is buffered at between pH. 4.0-8.0 and comprises 10-30% PEG and 100-300 mM ammonium sulphate.

4. The molecular complex according to claim 3, wherein said ligand is selected from the group consisting of: (5-Methyl-2H-pyrazol-3-yl)-(2-(pyridin-3-ylmethylamino)-quinazolin-4-yl)-amine; (5-Cyclopropyl-2H-pyrazol-3-yl)-(2-phenyl-quinazolin-4-yl)-amine; (5-Methylthiazol-2-yl)-(2-phenyl-quinazolin-4-yl)-amine; and adenosine.

* * * * *

SEQUENCE LISTING

<160> NUMBER OF SEQ ID NOS: 2

<210> SEQ ID NO 1
<211> LENGTH: 403
<212> TYPE: PRT
<213> ORGANISM: Homo sapiens

<400> SEQUENCE: 1

```
Met Asp Arg Ser Lys Glu Asn Cys Ile Ser Gly Pro Val Lys Ala Thr
 1               5                  10                  15

Ala Pro Val Gly Gly Pro Lys Arg Val Leu Val Thr Gln Gln Ile Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Val Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
           100                 105                 110

Glu Leu Ala Ser Lys Gln Lys Asn Glu Glu Ser Lys Lys Arg Gln Trp
       115                 120                 125

Ala Leu Glu Asp Phe Glu Ile Gly Arg Pro Leu Gly Lys Gly Lys Phe
   130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
               165                 170                 175

Gln Leu Arg Arg Glu Val Glu Ile Gln Ser His Leu Arg His Pro Asn
           180                 185                 190

Ile Leu Arg Leu Tyr Gly Tyr Phe His Asp Ala Thr Arg Val Tyr Leu
       195                 200                 205

Ile Leu Glu Tyr Ala Pro Leu Gly Thr Val Tyr Arg Glu Leu Gln Lys
   210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
               245                 250                 255

Ile Lys Pro Glu Asn Leu Leu Leu Gly Ser Ala Gly Glu Leu Lys Ile
           260                 265                 270

Ala Asp Phe Gly Trp Ser Val His Ala Pro Ser Ser Arg Arg Thr Thr
       275                 280                 285

Leu Cys Gly Thr Leu Asp Tyr Leu Pro Pro Glu Met Ile Glu Gly Arg
```

```
                290                 295                 300
Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
                340                 345                 350

Thr Glu Gly Ala Arg Asp Leu Ile Ser Arg Leu Leu Lys His Asn Pro
                355                 360                 365

Ser Gln Arg Pro Met Leu Arg Glu Val Leu Glu His Pro Trp Ile Thr
        370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 2
<211> LENGTH: 26
<212> TYPE: PRT
<213> ORGANISM: human
<220> FEATURE:
<221> NAME/KEY: misc_feature
<222> LOCATION: (6)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 2

Asp Phe Gly Trp Ser Xaa Xaa Xaa Xaa Xaa Xaa Xaa Arg Xaa Thr Xaa
1               5                   10                  15

Cys Gly Thr Xaa Asp Tyr Leu Pro Pro Glu
                20                  25
```